United States Patent
Cravatt et al.

(10) Patent No.: US 11,535,597 B2
(45) Date of Patent: Dec. 27, 2022

(54) PHOTOREACTIVE LIGANDS AND USES THEREOF

(71) Applicant: The Scripps Research Institute, La Jolla, CA (US)

(72) Inventors: Benjamin F. Cravatt, La Jolla, CA (US); Christopher G. Parker, San Diego, CA (US); Bruno Correia, Bremblens (CH)

(73) Assignee: The Scripps Research Institute, La Jolla, CA (US)

( * ) Notice: Subject to any disclaimer, the term of this patent is extended or adjusted under 35 U.S.C. 154(b) by 0 days.

(21) Appl. No.: 16/478,444

(22) PCT Filed: Jan. 17, 2018

(86) PCT No.: PCT/US2018/014104
§ 371 (c)(1),
(2) Date: Jul. 16, 2019

(87) PCT Pub. No.: WO2018/136555
PCT Pub. Date: Jul. 26, 2018

(65) Prior Publication Data
US 2020/0071277 A1 Mar. 5, 2020

Related U.S. Application Data

(60) Provisional application No. 62/447,882, filed on Jan. 18, 2017.

(51) Int. Cl.
*C07D 229/02* (2006.01)
*C07D 223/06* (2006.01)
(Continued)

(52) U.S. Cl.
CPC .......... *C07D 229/02* (2013.01); *C07C 233/06* (2013.01); *C07D 295/10* (2013.01);
(Continued)

(58) Field of Classification Search
CPC .. C07D 405/12; C07D 229/02; C07D 401/10; C07D 295/10; C07D 409/12;
(Continued)

(56) References Cited

U.S. PATENT DOCUMENTS 4,469,863 A 9/1984 Ts'o et al.
5,034,506 A 7/1991 Summerton et al.
(Continued)

FOREIGN PATENT DOCUMENTS

JP 2011517315 A 6/2011
WO WO-0077184 A1 12/2000
(Continued)

OTHER PUBLICATIONS

Abegg et al. Proteome-Wide Profiling of Targets of Cysteine reactive Small molecules by Using Ethynyl Benziodoxolone Reagents. Angewandte Chemie International Edition 54:10852-10857 (2015).
(Continued)

*Primary Examiner* — Shafiqul Haq
(74) *Attorney, Agent, or Firm* — Jennifer Kisko; Thomas Fitting

(57) ABSTRACT

Disclosed herein are methods for identifying proteins as targets for interaction with a small molecule ligand. Also disclosed herein are small molecule ligands and compositions for use in profiling druggable proteins.

3 Claims, 69 Drawing Sheets

Specification includes a Sequence Listing.

(51) Int. Cl.

| | |
|---|---|
| C07C 233/06 | (2006.01) |
| C07D 295/10 | (2006.01) |
| C07D 317/46 | (2006.01) |
| C07D 401/10 | (2006.01) |
| C07D 403/12 | (2006.01) |
| C07D 405/12 | (2006.01) |
| C07D 409/12 | (2006.01) |
| G01N 1/28 | (2006.01) |
| G01N 1/44 | (2006.01) |
| G01N 33/68 | (2006.01) |

(52) U.S. Cl.
CPC ......... *C07D 317/46* (2013.01); *C07D 401/10* (2013.01); *C07D 403/12* (2013.01); *C07D 405/12* (2013.01); *C07D 409/12* (2013.01); *G01N 1/28* (2013.01); *G01N 1/44* (2013.01); *G01N 33/6848* (2013.01)

(58) Field of Classification Search
CPC .. C07D 401/12; C07D 401/06; C07D 317/46; C07D 403/12; G01N 1/28; G01N 33/6848; G01N 1/44; C07C 233/06; C40B 30/06

See application file for complete search history.

(56) References Cited

U.S. PATENT DOCUMENTS

| | | | |
|---|---|---|---|
| 5,216,141 | A | 6/1993 | Benner |
| 5,235,033 | A | 8/1993 | Summerton et al. |
| 5,386,023 | A | 1/1995 | Sanghvi et al. |
| 5,602,240 | A | 2/1997 | Mesmaeker et al. |
| 5,637,684 | A | 6/1997 | Cook et al. |
| 5,644,048 | A | 7/1997 | Yau et al. |
| 6,344,330 | B1 | 2/2002 | Ellman et al. |
| 7,348,437 | B2 | 3/2008 | Cravatt et al. |
| 8,669,065 | B1 | 3/2014 | Hansen et al. |
| 8,778,302 | B2 | 7/2014 | Tai et al. |
| 10,168,342 | B2 | 1/2019 | Cravatt et al. |
| 2009/0068107 | A1 | 3/2009 | Cravatt et al. |
| 2010/0021950 | A1 | 1/2010 | Lammert et al. |
| 2010/0179118 | A1 | 7/2010 | Ozawa et al. |
| 2010/0184661 | A1 | 7/2010 | Luo et al. |
| 2010/0203647 | A1 | 8/2010 | Hang et al. |
| 2011/0020837 | A1 | 1/2011 | Haberkant et al. |
| 2011/0195527 | A1 | 8/2011 | O'Neill et al. |
| 2012/0225434 | A1 | 9/2012 | Ciufolini et al. |
| 2013/0165337 | A1 | 6/2013 | Robinson et al. |
| 2014/0243430 | A1 | 8/2014 | Geho et al. |
| 2014/0357512 | A1 | 12/2014 | Yang et al. |
| 2015/0157686 | A1 | 6/2015 | Janssen-Heininger et al. |
| 2016/0252509 | A1 | 9/2016 | Cravatt et al. |
| 2017/0115303 | A1 | 4/2017 | Cravatt et al. |
| 2020/0292555 | A1 | 9/2020 | Cravatt et al. |

FOREIGN PATENT DOCUMENTS

| | | |
|---|---|---|
| WO | WO-0242773 A2 | 5/2002 |
| WO | WO-2005118833 A2 | 12/2005 |
| WO | WO-2006112841 A1 | 10/2006 |
| WO | WO-2009142678 A1 | 11/2009 |
| WO | WO-2015023724 A1 | 2/2015 |
| WO | WO-2016029037 A1 | 2/2016 |
| WO | WO-2017070611 A1 | 4/2017 |
| WO | WO-2018136555 A2 | 7/2018 |

OTHER PUBLICATIONS

Ahmad et al. Structure Based Molecular Inhibition of Caspase-8 For Treatment of Multi-Neurodegenerative Disease Using Known Natural Compounds. Bioinformatics 10(4):191-195 (2014).

Aldini et al. Identification of actin as a 15-deoxy-Delta12,14-prostaglandin J2 target in neuroblastoma cells: mass spectrometric, computational, and functional approaches to investigate the effect on cytoskeletal derangement. Biochemistry 46:2707-2718 (2007).

Bachovchin et al. Academic cross-fertilization by public screening yields a remarkable class of protein phosphatase methylesterase-1 inhibitors. PNAS USA 108:6811-6816 (2011).

Bachovchin et al. The Pharmacological Landscape and Therapeutic Potential of Serine Hydrolases. Nature Reviews 11:52-68 (2012).

Backus et al. Proteome-wide covalent ligand discovery in native biological systems. Nature 534(7608):570-574 (2016).

Ban et al. Tyrosine bioconjugation through aqueous ene-type reactions: a click-like reaction for tyrosine. J Am Chem Soc 132:1523-1525 (2010).

Barelier et al. Discovery of Fragment Molecules That Bind The Human Peroxiredoxin 5 Active Site. PLoS One 5(3):e9744 (2010).

Beaucage, et al. The functionalization of oligonucleotides via phosphoramidite derivative. Tetrahedron. 1993;49(10):1925-63.

Bennaars-Eiden et al. Covalent modification of epithelial fatty acid-binding protein by 4-hydroxynonenal in vitro and in vivo. Evidence for a role in antioxidant biology. J Biol Chem 277:50693-50702 (2002).

Bischoff et al. Amino Acids: Chemistry, Functionality and Selected Non-Enzymatic Post-Translational Modifications. J Proteomics 75:2275-2296 (2012).

Bloem et al. Tissue distribution and functional expression of a cDNA encoding a novel mixed lineage kinase. J Mol Cell Cardiol 33:1739-1750 (2001).

Brill et al. Synthesis of oligodeoxynucleoside phosphorodithioates via thioamidites. J. Am. Chem. Soc. 111:2321-2322 (1989).

Carbone et al. Inhibition of Hsp72-mediated protein refolding by 4-hydroxy-2-nonenal. Chem Res Toxicol 17:1459-1467 (2004).

Carbone et al. Modification of heat shock protein 90 by 4-hydroxynonenal in a rat model of chronic alcoholic liver disease. J Pharmacol Exp Ther 315:8-15 (2005).

Carlsson et al. Screening for genetic mutations. Nature 380(6571):207 (1996).

Chalker et al. Chemical modification of proteins at cysteine: opportunities in chemistry and biology. Chem Asian J 4(5):630-640 (2009).

Chaudhary et al. Probing the phosphoinositide 4,5-bisphosphate binding site of human profilin I. Chemistry & Biology 5(5):273-281 (1998).

Chipuk et al. Sphingolipid metabolism cooperates with BAK and BAX to promote the mitochondrial pathway of apoptosis. Cell 148:988-1000 (2012).

Codreanu et al. Global analysis of protein damage by the lipid electrophile 4-hydroxy-2-nonenal. Mol Cell Proteomics 8:670-680 (2009).

Cohen et al. Structural bioinformatics-based design of selective, irreversible kinase inhibitors. Science 308:1318-1321 (2005).

De Mesmaeker et al. Comparison of Rigid and Flexible Backbones in Antisense Oligonucleotides Bioorg Med Chem Lett 4(3):395-398 (1994).

Dempcy et al. Synthesis of a thymidyl pentamer of deoxyribonucleic guanidine and binding studies with DNA homopolynucleotides PNAS USa 92:6097-6101 (1995).

Deng et al. Proteome-wide Quantification and Characterization of Oxidation-Sensitive Cysteines in Pathogenic Bacteria. Cell Host Microbe 13:358-370 (2013).

Derakhshan et al. Unbiased Identification of Cyteine S-Nitrosylation Sites on Proteins. Nat Protocol 2(7):1685-1691 (2007).

Doorn et al. Covalent modification of amino acid nucleophiles by the lipid peroxidation products 4-hydroxy-2-nonenal and 4-oxo-2-nonenal. Chem Res Toxicol 15:1445-1450 (2002).

Dubinina et al. Role of 4-hydroxy-trans-2-nonenal in cell functions. Biochemistry (Most) 75:1069-1087 (2010).

Egholm et al. Peptide nucleic acids (PNA) oligonucleotide analogues with an achiral peptide backbone. J Am Chem Soc 114:1895-1897 (1992).

Erlanson et al. Tethering: Fragment-Based Drug Discovery. Annu Rev Biophys Biomol Structure 33:199-223 (2004).

(56) References Cited

OTHER PUBLICATIONS

Forman. Reactive oxygen species and alpha,beta-unsaturated aldehydes as second messengers in signal transduction. Ann N Y Acad Sci 1203:35-44 (2010).
Frei et al. Fast and Highly Chemoselective Alkynylation of Thiols with Hypervalent Iodine Reagents Enabled through a Low Energy Barrier Concerted Mechanism. J Am Chem Soc 136:16563-16573 (2014).
Fritz et al. An overview of the chemistry and biology of reactive aldehydes. Free Radic Biol Med 59:85-91 (2012).
Fritz et al. Exploring the biology of lipid peroxidation-derived protein carbonylation. Chem Res Toxicol 24:1411-1419 (2011).
Fujishima et al. Ligand-directed acyl imidazole chemistry for labeling of membrane-bound proteins on live cells. J Am Chem Soc 134:3961-3964 (2012).
Gao et al. Unusual conformation of a 3'-thioformacetal linkage in a DNA duplex. J. Biomolecular NMR.34:17-34 (1994).
Giron et al. Cysteine Tagging for MS-based Proteomics. Mass spectrometry Reviews 30:366-395 (2011).
Gotoh et al. Identification and characterization of a novel MAP kinase kinase kinase, MLTK. J Biol Chem 276:4276-4286 (2001).
Gubbens et al. Photocrosslinking and click chemistry enable the specific detection of proteins interacting with phospholipids at the membrane interface. Chem Biol. 16(1):3-14 (2009).
Gubbens et al. Proteome-wide detection of phospholipid-protein interactions in mitochondria by photocrosslinking and click chemistry. Mol Biosyst 6(10):1751-1759 (2010).
Gueraud et al. Chemistry and biochemistry of lipid peroxidation products. Free Radic Res 44:1098-1124 (2010).
Gushwa et al. Selective targeting of distinct active site nucleophiles by irreversible SRC-family kinase inhibitors. J Am Chem Soc 134:20214-20217 (2012).
Haberkant et al. Protein-lipid interactions: paparazzi hunting for snap-shots. Biol Chem 390:795-803 (2009).
Han et al. A comparative 'bottom up' proteomics strategy for the site-specific identification and quantification of protein modifications by electrophilic lipids. J Proteomics 75:5724-5733 (2012).
Hang et al. Exploring protein lipidation with chemical biology. Chem Rev 111:6341-6358 (2011).
Higdon et al. Methods for imaging and detecting modification of proteins by reactive lipid species. Free Radic Biol Med 47:201-212 (2009.
Horn et al. Oligonucleotides with alternating anionic and cationic phosphoramidate linkages: Synthesis and hybridization of stereo-uniform isomers. Tetrahedron Lett 37:743-746 (1996).
Huang et al. Crystal structure of an inactive Akt2 kinase domain. Structure 11:21-30 (2003).
Hulce et al. Proteome-wide mapping of cholesterol-interacting proteins in mammalian cells. Nat Methods 10(3):259-264 (2013).
Jacob et al. Control of Oxidative Posttranslational Cysteine Modifications: From Intricate Chemistry to Widespread Biological and Medical Applications. Chem Res Toxicol 25:588-604 (2012).
Jacobs et al. Heat shock factor 1 attenuates 4-Hydroxynonenal mediated apoptosis: critical role for heat shock protein 70 induction and stabilization of Bcl-XL. J Biol Chem 282:33412-33420 (2007).
Jacobs et al. Systems analysis of protein modification and cellular responses induced by electrophile stress. Acc Chem Res. 43(5):673-683 (2010).
Jenkins et al. The Biosynthesis of Carbocyclic Nucleosides Chem Soc Re 24:169-176 (1995).
Jung et al. Hybridization of Alternating Cationic/Anionic Oligonucleotides to RNA Segments. Nucleosides & Nucleotides 13(6 &7):1597-1605 (1994).
Kambe et al. Supporting Information—Mapping the Protein Interaction Landscape for Fully Functionalized Small-Molecule Probes in Human Cells. J Am Chem Soc 136(30):10777-10782 (2014).
Keshet et al. Chapter 1: The MAP kinase signaling cascades: a system of hundreds of components regulates a diverse array of physiological functions. Methods Mol Biol 661:3-38 (2010).

Kiedrowshi et al. Parabolic Growth of a Self-Replicating Hexadeoxynucleotide Bearing a 3'-5'-Phosphoamidate Linkage Angew. Chem. Intl. Ed. English 30(4):423-426 (1991).
Kim et al. An azido-biotin reagent for use in the isolation of protein adducts of lipid-derived electrophiles by streptavidin catch and photorelease. Mol Cell Proteomics 8:2080-2089 (2009).
Knight et al. Features of selective kinase inhibitors. Chem Biol 12:621-637 (2005).
Koshkin et al. LNA (locked nucleic acids): An RNA mimic forming exceedingly stable LNA: LNA duplexes. J Am Chem Soc 120:13252-13253 (1998).
Kumagai et al. CERT Mediates Intermembrane Transfer of Various Molecular Species of Ceramides. JBC 280:6488-6495 (2005).
Kutuk et al. Apoptosis signalling by 4-hydroxynonenal: a role for JNK-c-Jun/AP-1 pathway. Redox Rep 12:30-34 (2007).
Leitner et al. Chemistry meets proteomics: the use of chemical tagging reactions for MS-based proteomics. Proteomics 6:5418-5434 (2006).
Leonard et al. Chemical 'omics' approaches for understanding protein cysteine oxidation in biology. Curr Opin Chem Biol 15:88-102 (2011).
Leonarduzzi et al. Signaling kinases modulated by 4-hydroxynonenal. Free Radic Biol Med 37:1694-1702 (2004).
Letsinger et al. Cationic Oligonucleotides J Am Chem Soc 110:4470-4471 (1988).
Letsinger et al. Effects of pendant groups at phosphorus on binding properties of d-ApA analogues. Nucl Acids Res14(8):3487-3499 (1986).
Letsinger et al. Phosphoramidate Analogs of Oligonucleotides J Org Chem 35(11):3800-3803 (1970).
Liu et al. Developing irreversible inhibitors of the protein kinase cysteinome. Chem Biol 20:146-159 (2013).
Long et al. The Metabolic Serine Hydrolases and Their Functions in Mammalian Physiology and Disease. Chemical Reviews 111:6022-6063 (2011).
Lopachin et al. Molecular mechanisms of 4-hydroxy-2-nonenal and acrolein toxicity: nucleophilic targets and adduct formation. Chem Res Toxicol 22:1499-1508 (2009).
Mag et al. Synthesis and selective cleavage of an oligodeoxynucleotide containing a bridged internucleotide 5'-phosphorothioate linkage. Nucleic Acids Res 19(7):1437-1441 (1991).
Marino et al. Proteomics: mapping reactive cysteines. Nat Chem Biol. 7(2):72-73 (2011).
Meier et al. Peptide Nucleic Acids (PNAs)—Unusual Properties of Nonionic Oligonucleotide Analogues. Angew. Chem. Int. Ed. Engl. 31(8):1008-1010 (1992).
Ngo et al. Mutant methionyl-tRNA synthetase from bacteria enables site-selective N-terminal labeling of proteins expressed in mammalian cells. PNAS USA 110:4992-4997 (2013).
Niphakis et al. A Global Map of Lipid-Binding Proteins and Their Ligandability in Cells. Cell 161(7):1668-1680 (2015).
Pace et al. Diverse functional roles of reactive cysteines. ACS Chem Biol 8(2):283-296 (2013).
Parker et al. Ligand and Target Discovery by Fragment-Based Screening in Human Cells. Cell 168(3):527-541 (2017).
Parola et al. HNE interacts directly with JNK isoforms in human hepatic stellate cells. J Clin Invest 102:1942-1950 (1998).
Patricelli et al. Functional interrogation of the kinome using nucleotide acyl phosphates. Biochemistry 46:350-358 (2007).
Pauwels et al. Biological activity of new 2-5A analogues. Chemica Scripta 26:141-149 (1986).
PCT/US2014/050828 International Preliminary Report on Patentability dated Feb. 25, 2016.
PCT/US2014/050828 International Search Report and Written Opinion dated Dec. 12, 2014.
PCT/US2016/024148 International Preliminary Report on Patentability dated Oct. 12, 2017.
PCT/US2016/024148 International Search Report and Written Opinion dated Jul. 25, 2016.
PCT/US2016/058308 International Preliminary Report on Patentability dated May 3, 2018.
PCT/US2016/058308 International Search Report and Written Opinion dated Jan. 17, 2017.

(56) References Cited

OTHER PUBLICATIONS

PCT/US2018/014104 International Preliminary Report on Patentability dated Aug. 1, 2019.
PCT/US2018/14104 International Search Report and Written Opinion dated Jul. 26, 2018.
PCT/US2018/14104 Invitation to Pay Additional Fees dated May 31, 2018.
Peng et al. Turning the spotlight on protein-lipid interactions in cells. Curr Opin Chem Biol 21:144-153 (2014).
Perluigi et al. 4-Hydroxy-2-nonenal, a reactive product of lipid peroxidation, and neurodegenerative diseases: a toxic combination illuminated by redox proteomics studies. Antioxid Redox Signal 17:1590-1609 (2012).
Prescher et al. Chemistry in living systems. Nat Chem Biol. 1(1):13-21 (2005).
Rawls, Rebecca L. Optimistic about antisense. Promising clinical results and chemical strategies for further improvements delight antisense drug researchers. C & E News. 35-59 (Jun. 2, 1997).
Roe et al. Proteomic mapping of 4-hydroxynonenal protein modification sites by solid-phase hydrazide chemistry and mass spectrometry. Anal Chem 79:3747-3756 (2007).
Rostovtsev et al. A stepwise huisgen cycloaddition process: copper (i)-catalyzed regioselective "ligation" of azides and terminal alkynes. Angew. Chem. Int. Ed. Engl. 41(14):2596-2599 (2002).
Rudolph et al. Transduction of redox signaling by electrophile-protein reactions. Sci Signal 2:re7 (2009).
Sadaghiani et al. Tagging and detection strategies for activity-based proteomics. Curr Opin Chem Biol. 11(1):20-28 (2007).
Saghatelian et al. Assignment of endogenous substrates to enzymes by global metabolite profiling. Biochemistry 43:14332-14339 (2004).
Sawai et al. Synthesis and Properties of Oligoadenylic Acids Containing 2'-5' Phosphoramide Linkage. Chem. Lett. 13(5):805-808 (1984).
Scotcher et al. Identification of Two Reactive Cysteine Residues in the Tumor Suppressor Protein p53 Using Top-Down FTICR Mass Spectrometry. 22:888-897 (2011).
Shearn et al. Modification of Akt2 by 4-hydroxynonenal inhibits insulin-dependent Akt signaling in HepG2 cells. Biochemistry 50:3984-3996 (2011).
Shen et al. JNK signaling pathway is a key modulator in cell death mediated by reactive oxygen and nitrogen species. Free Radic Biol Med 40:928-939 (2006).
Simon et al. Determining target engagement in living systems. Nat Chem Biol 9(4):200-205 (2013).
Singh et al. The resurgence of covalent drugs. Nat Rev Drug Discov 10(4):307-317 (2011).
Speers et al. Activity-based protein profiling in vivo using a copper(i)-catalyzed azide-alkyne [3+2] cycloaddition. J Am Chem Soc. 125(16):4686-4687 (2003).
Sprinzel et al. Enzymatic incorporation of ATP and CTP analogues into the 3' end of tRNA. Eur J Biochem 81(3):579-589 (1977).
Surh et al. 15-Deoxy-Δ(12,14)-prostaglandin J(2), an electrophilic lipid mediator of anti-inflammatory and pro-resolving signaling. Biochem Pharmacol 82:1335-1351 (2011).
Tate. Recent advances in chemical proteomics: exploring the post-translational proteome. J Chem Biol 1:17-26 (2008).
U.S. Appl. No. 14/911,316 Office Action dated Jan. 12, 2018.
U.S. Appl. No. 14/911,316 Office Action dated Mar. 27, 2019.
U.S. Appl. No. 15/080,767 Office Action dated Dec. 19, 2017.
U.S. Appl. No. 15/080,767 Office Action dated May 17, 2017.
U.S. Appl. No. 15/080,767 Office Action dated Oct. 28, 2016.
U.S. Appl. No. 15/331,745 Office Action dated Apr. 22, 2019.
U.S. Appl. No. 15/331,745 Office Action dated Dec. 29, 2017.
U.S. Appl. No. 15/331,745 Office Action dated Jul. 17, 2017.
U.S. Appl. No. 15/331,745 Office Action dated Jun. 12, 2018.
U.S. Appl. No. 15/331,745 Office Action dated Oct. 9, 2018.
Uchida. 4-Hydroxy-2-nonenal: a product and mediator of oxidative stress. Prog Lipid Res 42:318-343 (2003).
Vila et al. Identification of protein targets of 4-hydroxynonenal using click chemistry for ex vivo biotinylation of azido and alkynyl derivatives. Chem Res Toxicol. 21(2):432-444 (2008).
Wang et al. A chemoproteomic platform to quantitatively map targets of lipid-derived electrophiles. Nat Methods. 11(1):79-85 (2014).
Wang et al. Complete inhibition of anisomycin and UV radiation but not cytokine induced JNK and p38 activation by an aryl-substituted dihydropyrrolopyrazole quinoline and mixed lineage kinase 7 small interfering RNA. J Biol Chem 280:19298-19305 (2005).
Wang et al. Exploring post-translational arginine modification using chemically synthesized methylglyoxal hydroimidazolones (MG-Hs). J Am Chem Soc 134:8958-8967 (2012).
Washburn et al. Large-scale analysis of the yeast proteome by multidimensional protein identification technology. Nat Biotechnol 19(3):242-247 (2001).
Weerapana et al. Disparate proteome reactivity profiles of carbon electrophiles. Nat Chem Biol 4:405-407 (2008).
Weerapana et al. Quantitative reactivity profiling predicts functional cysteines in proteomes. Nature 468:790-795 (2010).
Wong et al. Small molecule kinase inhibitors block the ZAK-dependent inflammatory effects of doxorubicin. Cancer Biol Ther. 14(1):56-63 (2013).
Xia et al. Photoactivatable lipid probes for studying biomembranes by photoaffinity labeling. Chem Rev. 113(10):7880-7929 (2013).
Yang et al. ZAK inhibits human lung cancer cell growth via ERK and JNK activation in an AP-1-dependent manner. Cancer Sci 101:1374-1381 (2010).
Yu et al. Effect of C-terminal truncations on MLK7 catalytic activity and JNK activation. Biochem Biophys Res Commun 310:452-457 (2003).
Zhou et al. A structure-guided approach to creating covalent FGFR inhibitors. Chem Biol 17:285-295 (2010).
Fu et al. Accelerated cellular on- and off-target screening of bioactive compounds using microarrays. Org Biomol Chem 14(1):59-64 (2015).
Li et al. Design and Synthesis of Minimalist Terminal Alkyne-Containing Diazirine Photo-Crosslinkers and Their Incorporation into Kinase Inhibitors for Cell- and Tissue-Based Proteome Profiling. Angewandte Chemie 125(33):8713-8718 (2103).
Li et al. Minimalist Cyclopropene-Containing Photo-Cross-Linkers Suitable for Live-Cell Imaging and Affinity-Based Protein Labeling. J Am Chem Soc 136(28):9990-9998 (2014).
U.S. Appl. No. 14/911,316 Office Action dated Oct. 4, 2019.
Wang et al. Fluorescein Derivatives as Bifunctional Molecules for the Simultaneous Inhibiting and Labeling of FTO Protein. J Am Chem Soc 137(43):13736-13739 (2015).
Weerapana et al. Supplementary Information, Quantitative reactivity profiling predicts functional cysteines in proteomes. Nature 468:1-263 (2010).
Xie et al. Fluorescent Probes for Single-Step Detection and Proteomic Profiling of Histone Deacetylases. J Am Chem Soc 138(48):15596-15604 (2016).

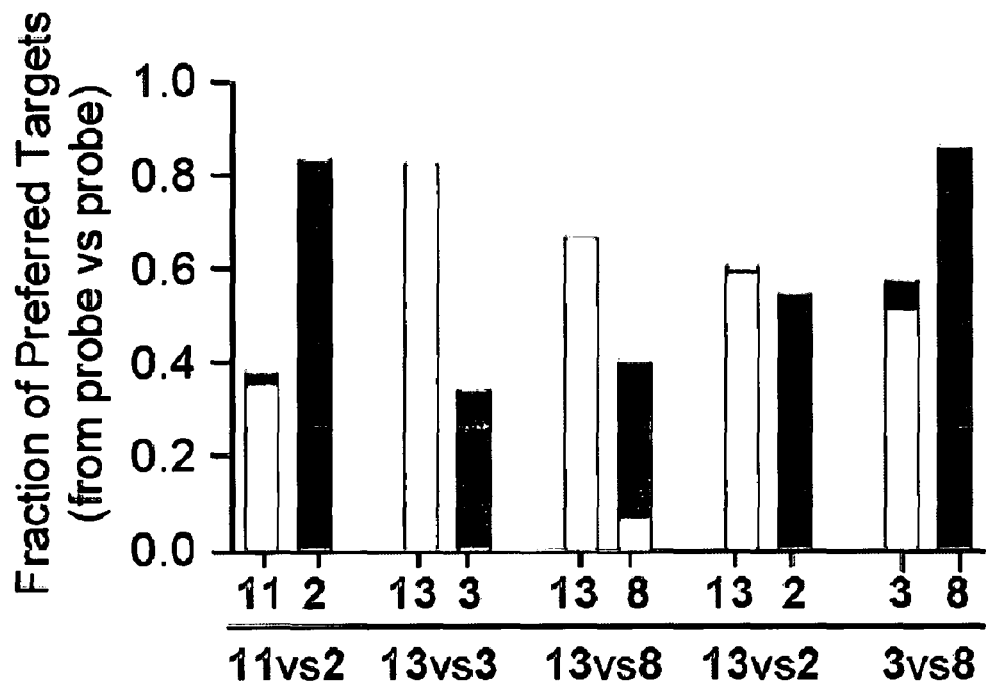
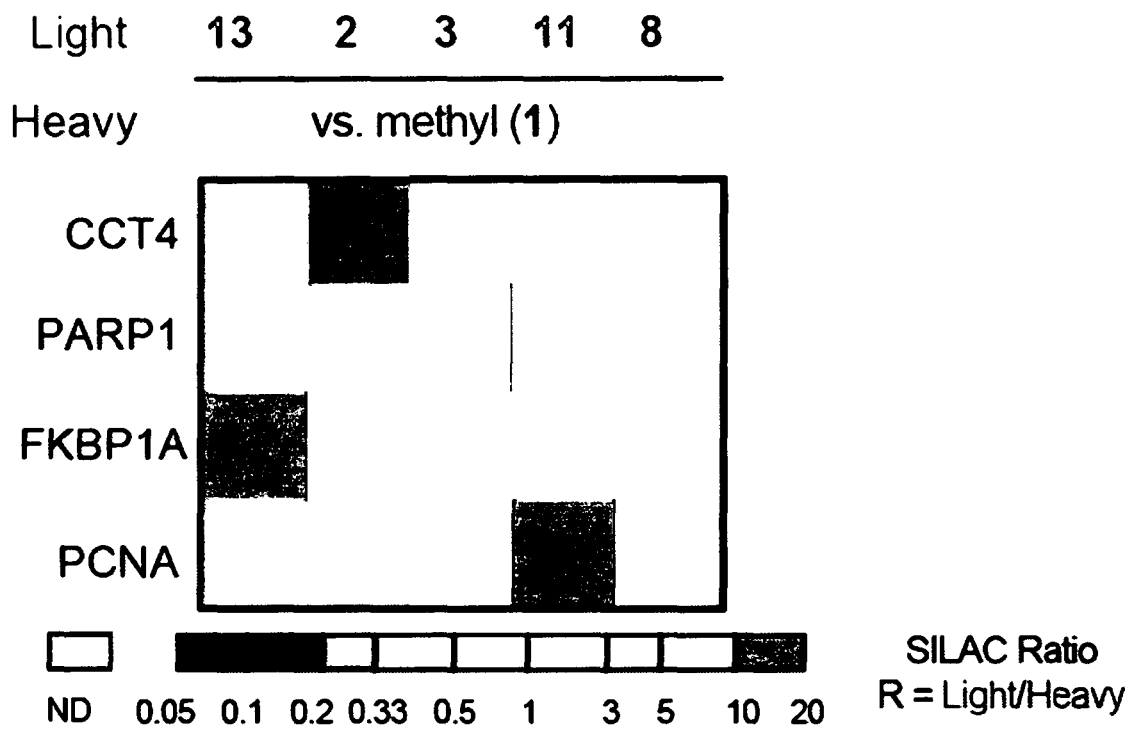

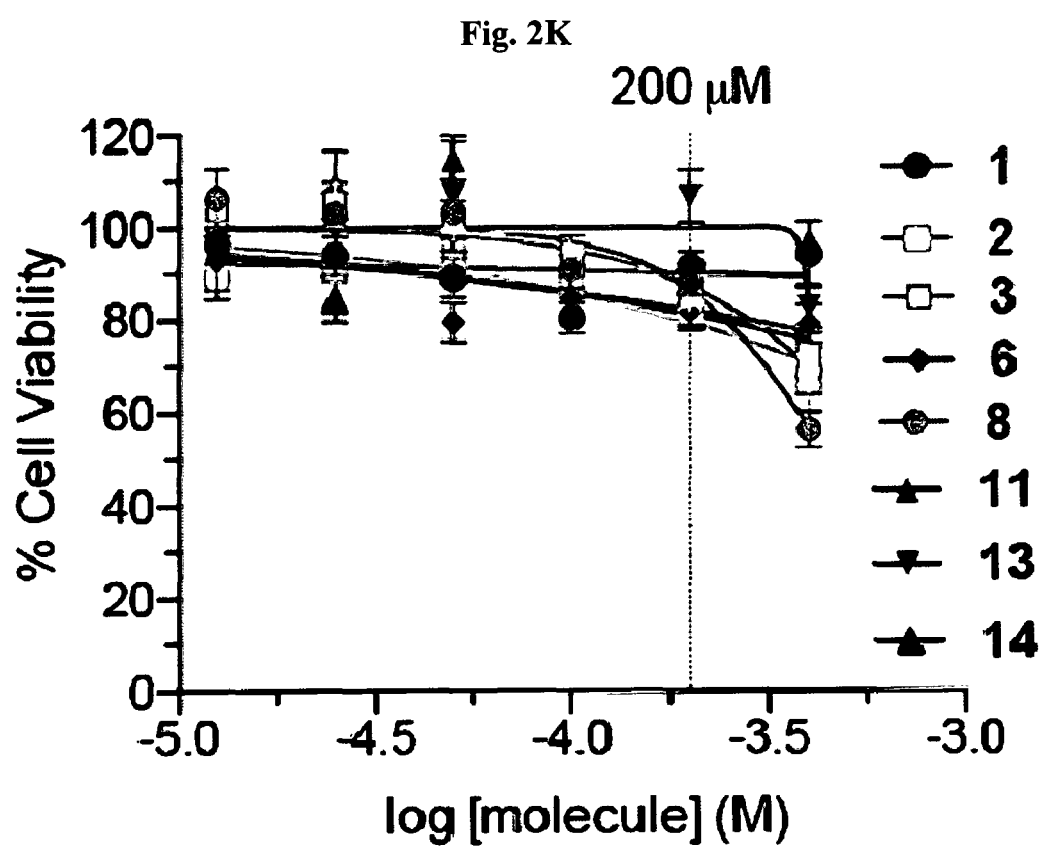

Overlap with predicted pocket residues

■ Overlapped
☐ Not Overlapped

Functional Site Overlap

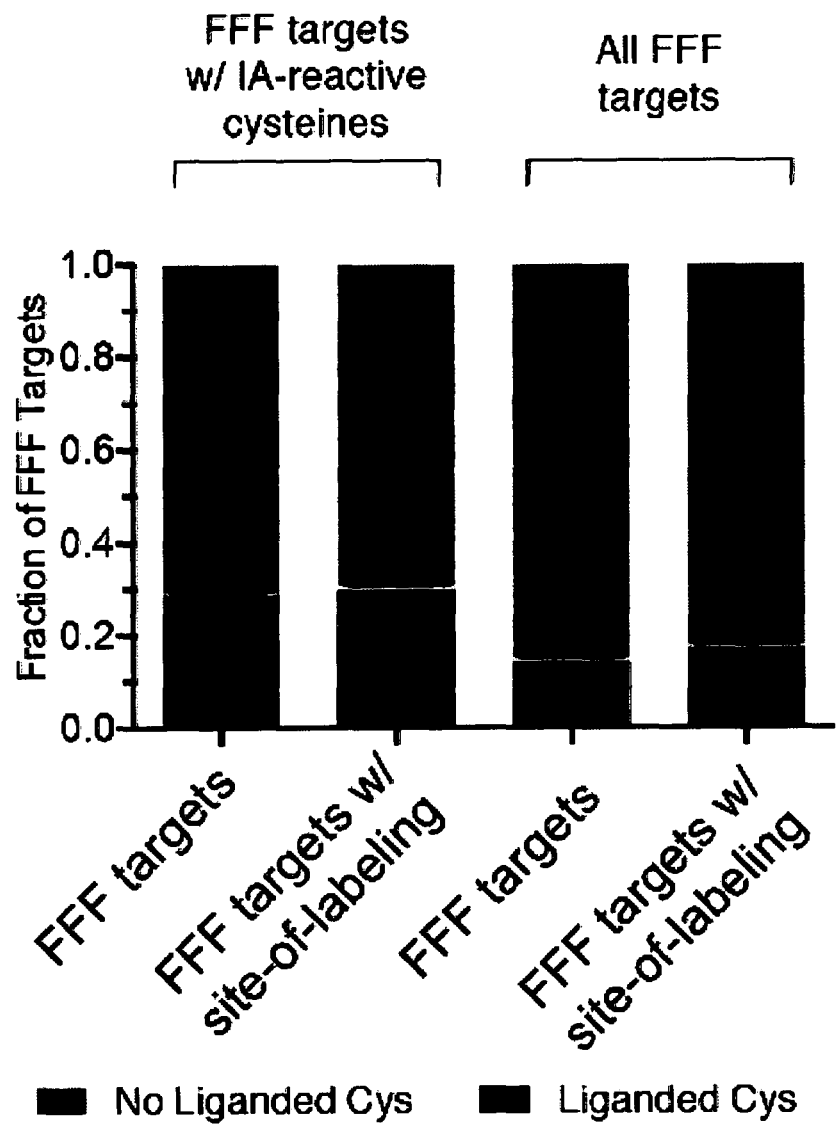

8 + 20

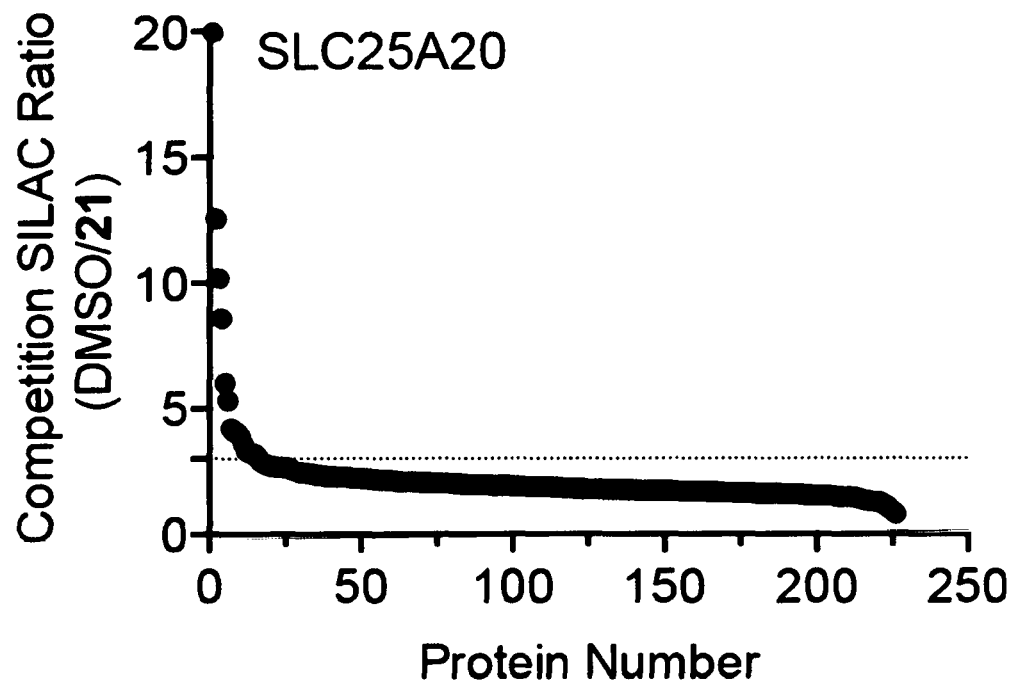

20-competed peptides

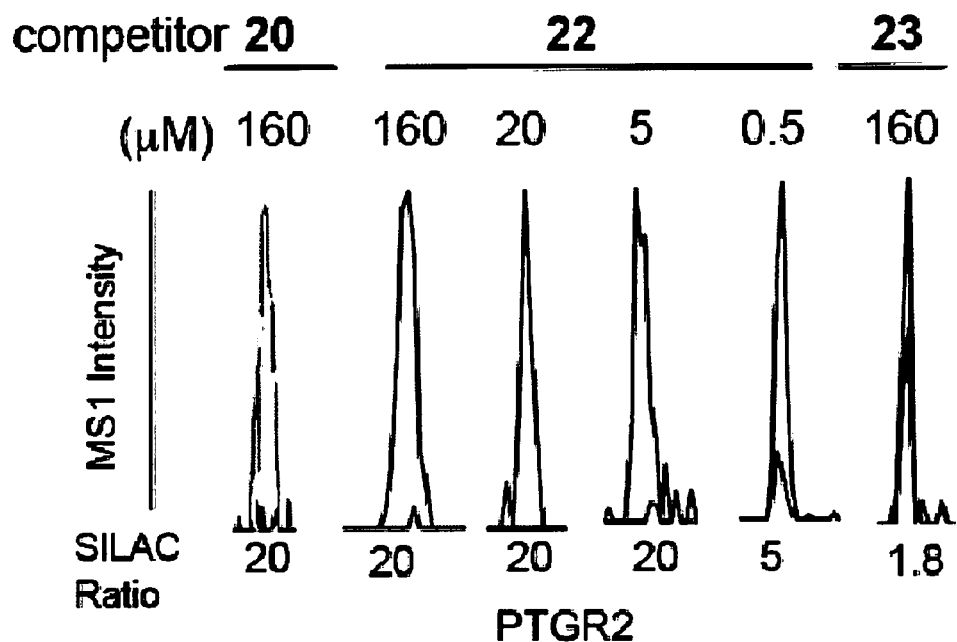
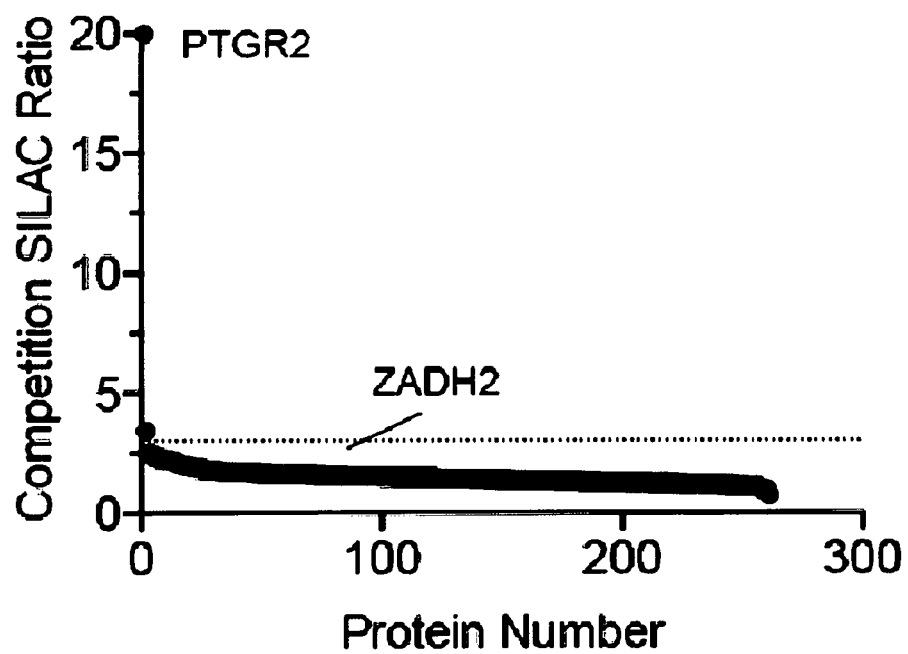

Palmitate Oxidation Assay

ABCUS 11,535,597 B2

SEQUENCE LISTING

<160> NUMBER OF SEQ ID NOS: 925

<210> SEQ ID NO 1
<211> LENGTH: 18
<212> TYPE: PRT
<213> ORGANISM: Homo sapiens

<400> SEQUENCE: 1

Val Asp Ser Ala Ala Thr Ser Gly Tyr Glu Ile Gly Asn Pro Pro Asp

```
                 1               5                   10                  15

Tyr Arg

<210> SEQ ID NO 2
<211> LENGTH: 19
<212> TYPE: PRT
<213> ORGANISM: Homo sapiens

<400> SEQUENCE: 2

Leu Gly Gln Met Leu Ser Ile Gln Asp Asp Ala Phe Ile Asn Pro His
 1               5                   10                  15

Leu Ala Lys

<210> SEQ ID NO 3
<211> LENGTH: 16
<212> TYPE: PRT
<213> ORGANISM: Homo sapiens

<400> SEQUENCE: 3

Ile Phe Thr Leu Asn Leu Ser Ala Pro Phe Ile Ser Gln Phe Tyr Lys
 1               5                   10                  15

<210> SEQ ID NO 4
<211> LENGTH: 11
<212> TYPE: PRT
<213> ORGANISM: Homo sapiens

<400> SEQUENCE: 4

Phe Ile Glu Asp Glu Leu Gln Ile Pro Val Lys
 1               5                   10

<210> SEQ ID NO 5
<211> LENGTH: 36
<212> TYPE: PRT
<213> ORGANISM: Homo sapiens

<400> SEQUENCE: 5

Pro Tyr Trp His Gln Ser Met Phe Trp Ser Asp Leu Gly Pro Asp Val
 1               5                   10                  15

Gly Tyr Glu Ala Ile Gly Leu Val Asp Ser Ser Leu Pro Thr Val Gly
                20                  25                  30

Val Phe Ala Lys
            35

<210> SEQ ID NO 6
<211> LENGTH: 24
<212> TYPE: PRT
<213> ORGANISM: Homo sapiens

<400> SEQUENCE: 6

Ile Leu Val Glu Gly Val Gly Glu Val Gln Glu Tyr Val Asp Ile Cys
 1               5                   10                  15

Asp Tyr Ala Val Gly Leu Ser Arg
                20

<210> SEQ ID NO 7
<211> LENGTH: 21
<212> TYPE: PRT
<213> ORGANISM: Homo sapiens

<400> SEQUENCE: 7

Leu Gly Glu Ile Val Thr Thr Ile Pro Thr Ile Gly Phe Asn Val Glu
```

```
                1               5                   10                  15
Thr Val Glu Tyr Lys
            20

<210> SEQ ID NO 8
<211> LENGTH: 21
<212> TYPE: PRT
<213> ORGANISM: Homo sapiens

<400> SEQUENCE: 8

Leu Gly Glu Ile Val Thr Thr Ile Pro Thr Ile Gly Phe Asn Val Glu
1               5                   10                  15

Thr Val Glu Tyr Lys
            20

<210> SEQ ID NO 9
<211> LENGTH: 16
<212> TYPE: PRT
<213> ORGANISM: Homo sapiens

<400> SEQUENCE: 9

Gly Thr Gly Leu Asp Glu Ala Met Glu Trp Leu Val Glu Thr Leu Lys
1               5                   10                  15

<210> SEQ ID NO 10
<211> LENGTH: 23
<212> TYPE: PRT
<213> ORGANISM: Homo sapiens

<400> SEQUENCE: 10

Leu Gln Val Gly Glu Val Val Thr Thr Ile Pro Thr Ile Gly Phe Asn
1               5                   10                  15

Val Glu Thr Val Thr Tyr Lys
            20

<210> SEQ ID NO 11
<211> LENGTH: 17
<212> TYPE: PRT
<213> ORGANISM: Homo sapiens

<400> SEQUENCE: 11

Ala Phe Thr His Thr Ala Gln Tyr Asp Glu Ala Ile Ser Asp Tyr Phe
1               5                   10                  15

Arg

<210> SEQ ID NO 12
<211> LENGTH: 14
<212> TYPE: PRT
<213> ORGANISM: Homo sapiens

<400> SEQUENCE: 12

Cys Tyr Phe Phe Leu Ser Ala Phe Val Asp Thr Ala Gln Arg
1               5                   10

<210> SEQ ID NO 13
<211> LENGTH: 16
<212> TYPE: PRT
<213> ORGANISM: Homo sapiens

<400> SEQUENCE: 13

Gly Glu Ile Ser Ala Thr Gln Asp Val Met Met Glu Glu Ile Phe Arg
1               5                   10                  15
```

<210> SEQ ID NO 14
<211> LENGTH: 29
<212> TYPE: PRT
<213> ORGANISM: Homo sapiens

<400> SEQUENCE: 14

Ser Gly Thr Ile Phe Asp Asn Phe Leu Ile Thr Asn Asp Glu Ala Tyr
1               5                   10                  15

Ala Glu Glu Phe Gly Asn Glu Thr Trp Gly Val Thr Lys
            20                  25

<210> SEQ ID NO 15
<211> LENGTH: 13
<212> TYPE: PRT
<213> ORGANISM: Homo sapiens

<400> SEQUENCE: 15

His Glu Gln Asn Ile Asp Cys Gly Gly Gly Tyr Val Lys
1               5                   10

<210> SEQ ID NO 16
<211> LENGTH: 19
<212> TYPE: PRT
<213> ORGANISM: Homo sapiens

<400> SEQUENCE: 16

Leu Val Phe Val His Ser Ala Glu Gly Asn Glu Phe Trp Ser Ala Leu
1               5                   10                  15

Leu Glu Lys

<210> SEQ ID NO 17
<211> LENGTH: 19
<212> TYPE: PRT
<213> ORGANISM: Homo sapiens

<400> SEQUENCE: 17

Phe Pro Ala Glu Asp Glu Phe Pro Asp Leu Ser Ala His Asn Asn His
1               5                   10                  15

Met Ala Lys

<210> SEQ ID NO 18
<211> LENGTH: 16
<212> TYPE: PRT
<213> ORGANISM: Homo sapiens

<400> SEQUENCE: 18

Leu Ala Val Glu Ala Leu Ser Ser Leu Asp Gly Asp Leu Ala Gly Arg
1               5                   10                  15

<210> SEQ ID NO 19
<211> LENGTH: 13
<212> TYPE: PRT
<213> ORGANISM: Homo sapiens

<400> SEQUENCE: 19

Thr Phe Leu Val Trp Val Asn Glu Glu Asp His Leu Arg
1               5                   10

<210> SEQ ID NO 20
<211> LENGTH: 13
<212> TYPE: PRT
<213> ORGANISM: Homo sapiens

```
<400> SEQUENCE: 20

Phe Cys Thr Gly Leu Thr Gln Ile Glu Thr Leu Phe Lys
1               5                   10

<210> SEQ ID NO 21
<211> LENGTH: 17
<212> TYPE: PRT
<213> ORGANISM: Homo sapiens

<400> SEQUENCE: 21

Leu Gly Phe Ser Glu Val Glu Leu Val Gln Met Val Val Asp Gly Val
1               5                   10                  15

Lys

<210> SEQ ID NO 22
<211> LENGTH: 15
<212> TYPE: PRT
<213> ORGANISM: Homo sapiens

<400> SEQUENCE: 22

Leu Glu Gln Gly Gln Ala Ile Asp Asp Leu Met Pro Ala Gln Lys
1               5                   10                  15

<210> SEQ ID NO 23
<211> LENGTH: 13
<212> TYPE: PRT
<213> ORGANISM: Homo sapiens

<400> SEQUENCE: 23

Ser Phe Leu Ile Trp Val Asn Glu Glu Asp His Thr Arg
1               5                   10

<210> SEQ ID NO 24
<211> LENGTH: 12
<212> TYPE: PRT
<213> ORGANISM: Homo sapiens

<400> SEQUENCE: 24

Gln Ser Leu Gln Val Ile Glu Ser Ala Met Glu Arg
1               5                   10

<210> SEQ ID NO 25
<211> LENGTH: 23
<212> TYPE: PRT
<213> ORGANISM: Homo sapiens

<400> SEQUENCE: 25

Asp Tyr Asn Val Leu Val Met Asp Leu Leu Gly Pro Ser Leu Glu Asp
1               5                   10                  15

Leu Phe Asn Phe Cys Ser Arg
            20

<210> SEQ ID NO 26
<211> LENGTH: 23
<212> TYPE: PRT
<213> ORGANISM: Homo sapiens

<400> SEQUENCE: 26

Val Tyr Cys Glu Asn Gln Pro Met Leu Pro Ile Gly Leu Ser Asp Ile
1               5                   10                  15

Pro Gly Glu Ala Met Val Lys
            20
```

```
<210> SEQ ID NO 27
<211> LENGTH: 17
<212> TYPE: PRT
<213> ORGANISM: Homo sapiens

<400> SEQUENCE: 27

Gly Gln Asp His Cys Gly Ile Glu Ser Glu Val Val Ala Gly Ile Pro
1               5                   10                  15

Arg

<210> SEQ ID NO 28
<211> LENGTH: 18
<212> TYPE: PRT
<213> ORGANISM: Homo sapiens

<400> SEQUENCE: 28

Asp Pro Asp Ala Gln Pro Gly Gly Glu Leu Met Leu Gly Gly Thr Asp
1               5                   10                  15

Ser Lys

<210> SEQ ID NO 29
<211> LENGTH: 22
<212> TYPE: PRT
<213> ORGANISM: Homo sapiens

<400> SEQUENCE: 29

Glu Gly Cys Glu Ala Ile Val Asp Thr Gly Thr Ser Leu Met Val Gly
1               5                   10                  15

Pro Val Asp Glu Val Arg
            20

<210> SEQ ID NO 30
<211> LENGTH: 18
<212> TYPE: PRT
<213> ORGANISM: Homo sapiens

<400> SEQUENCE: 30

Ala Ile Gly Ala Val Pro Leu Ile Gln Gly Glu Tyr Met Ile Pro Cys
1               5                   10                  15

Glu Lys

<210> SEQ ID NO 31
<211> LENGTH: 7
<212> TYPE: PRT
<213> ORGANISM: Homo sapiens

<400> SEQUENCE: 31

Leu Trp Tyr Thr Leu Asp Arg
1               5

<210> SEQ ID NO 32
<211> LENGTH: 17
<212> TYPE: PRT
<213> ORGANISM: Homo sapiens

<400> SEQUENCE: 32

Phe Asp Gly Gly Glu Glu Val Leu Ile Ser Gly Glu Phe Asn Asp Leu
1               5                   10                  15

Arg

<210> SEQ ID NO 33
```

<211> LENGTH: 9
<212> TYPE: PRT
<213> ORGANISM: Homo sapiens

<400> SEQUENCE: 33

Ile Ser Ala Val Ser Val Ala Glu Arg
1               5

<210> SEQ ID NO 34
<211> LENGTH: 33
<212> TYPE: PRT
<213> ORGANISM: Homo sapiens

<400> SEQUENCE: 34

Val Leu Gly Ala His Ile Leu Gly Pro Gly Ala Gly Glu Met Val Asn
1               5                   10                  15

Glu Ala Ala Leu Ala Leu Glu Tyr Gly Ala Ser Cys Glu Asp Ile Ala
            20                  25                  30

Arg

<210> SEQ ID NO 35
<211> LENGTH: 19
<212> TYPE: PRT
<213> ORGANISM: Homo sapiens

<400> SEQUENCE: 35

Met Phe Thr Ala Gly Ile Asp Leu Met Asp Met Ala Ser Asp Ile Leu
1               5                   10                  15

Gln Pro Lys

<210> SEQ ID NO 36
<211> LENGTH: 10
<212> TYPE: PRT
<213> ORGANISM: Homo sapiens

<400> SEQUENCE: 36

Tyr Gln Glu Thr Phe Asn Val Ile Glu Arg
1               5                   10

<210> SEQ ID NO 37
<211> LENGTH: 15
<212> TYPE: PRT
<213> ORGANISM: Homo sapiens

<400> SEQUENCE: 37

Glu Val Asp Val Gly Leu Ala Asp Val Gly Thr Leu Gln Arg
1               5                   10                  15

<210> SEQ ID NO 38
<211> LENGTH: 13
<212> TYPE: PRT
<213> ORGANISM: Homo sapiens

<400> SEQUENCE: 38

Met Phe Val Leu Asp Glu Ala Asp Glu Met Leu Ser Arg
1               5                   10

<210> SEQ ID NO 39
<211> LENGTH: 14
<212> TYPE: PRT
<213> ORGANISM: Homo sapiens

<400> SEQUENCE: 39

Gly Tyr Asp Val Ile Ala Gln Ala Gln Ser Gly Thr Gly Lys
1               5                   10

<210> SEQ ID NO 40
<211> LENGTH: 14
<212> TYPE: PRT
<213> ORGANISM: Homo sapiens

<400> SEQUENCE: 40

Gly Tyr Asp Val Ile Ala Gln Ala Gln Ser Gly Thr Gly Lys
1               5                   10

<210> SEQ ID NO 41
<211> LENGTH: 16
<212> TYPE: PRT
<213> ORGANISM: Homo sapiens

<400> SEQUENCE: 41

His Ser Met Asn Pro Phe Cys Glu Ile Ala Val Glu Glu Ala Val Arg
1               5                   10                  15

<210> SEQ ID NO 42
<211> LENGTH: 19
<212> TYPE: PRT
<213> ORGANISM: Homo sapiens

<400> SEQUENCE: 42

Ser Glu Val Val Ile Leu Phe Ser Ala His Ser Leu Pro Met Ser Val
1               5                   10                  15

Val Asn Arg

<210> SEQ ID NO 43
<211> LENGTH: 12
<212> TYPE: PRT
<213> ORGANISM: Homo sapiens

<400> SEQUENCE: 43

Ser Ile Leu Asp Trp Thr Ser Phe Asn Gln Glu Arg
1               5                   10

<210> SEQ ID NO 44
<211> LENGTH: 18
<212> TYPE: PRT
<213> ORGANISM: Homo sapiens

<400> SEQUENCE: 44

Phe Met Cys Asn Leu Asp Cys Gln Glu Glu Pro Asp Ser Cys Ile Ser
1               5                   10                  15

Glu Lys

<210> SEQ ID NO 45
<211> LENGTH: 15
<212> TYPE: PRT
<213> ORGANISM: Homo sapiens

<400> SEQUENCE: 45

Leu Phe Met Glu Met Ala Glu Leu Met Val Ser Glu Gly Trp Lys
1               5                   10                  15

<210> SEQ ID NO 46
<211> LENGTH: 14
<212> TYPE: PRT
<213> ORGANISM: Homo sapiens

```
<400> SEQUENCE: 46

Thr Glu Ala Val Ala Ser Ser Leu Tyr Asp Ile Leu Ala Arg
1               5                   10

<210> SEQ ID NO 47
<211> LENGTH: 20
<212> TYPE: PRT
<213> ORGANISM: Homo sapiens

<400> SEQUENCE: 47

Gly Leu Ala Phe Ile Gln Asp Pro Asp Gly Tyr Trp Ile Glu Ile Leu
1               5                   10                  15

Asn Pro Asn Lys
            20

<210> SEQ ID NO 48
<211> LENGTH: 11
<212> TYPE: PRT
<213> ORGANISM: Homo sapiens

<400> SEQUENCE: 48

Tyr Ser Thr Asp Val Ser Val Asp Glu Val Lys
1               5                   10

<210> SEQ ID NO 49
<211> LENGTH: 16
<212> TYPE: PRT
<213> ORGANISM: Homo sapiens

<400> SEQUENCE: 49

His Gly Gly Thr Ile Pro Ile Val Pro Thr Ala Glu Phe Gln Asp Arg
1               5                   10                  15

<210> SEQ ID NO 50
<211> LENGTH: 16
<212> TYPE: PRT
<213> ORGANISM: Homo sapiens

<400> SEQUENCE: 50

Glu Gly Tyr Thr Ser Phe Trp Asn Asp Cys Ile Ser Ser Gly Leu Arg
1               5                   10                  15

<210> SEQ ID NO 51
<211> LENGTH: 16
<212> TYPE: PRT
<213> ORGANISM: Homo sapiens

<400> SEQUENCE: 51

Phe Gln Asp Gly Asp Leu Thr Leu Tyr Gln Ser Asn Thr Ile Leu Arg
1               5                   10                  15

<210> SEQ ID NO 52
<211> LENGTH: 15
<212> TYPE: PRT
<213> ORGANISM: Homo sapiens

<400> SEQUENCE: 52

Val Gly Ala His Ala Gly Glu Tyr Gly Ala Glu Ala Leu Glu Arg
1               5                   10                  15

<210> SEQ ID NO 53
<211> LENGTH: 7
<212> TYPE: PRT
<213> ORGANISM: Homo sapiens
```

-continued

<400> SEQUENCE: 53

Val Asp Pro Val Asn Phe Lys
1               5

<210> SEQ ID NO 54
<211> LENGTH: 11
<212> TYPE: PRT
<213> ORGANISM: Homo sapiens

<400> SEQUENCE: 54

Leu Thr Ser Asp Leu Thr Phe Ala Tyr Glu Arg
1               5                   10

<210> SEQ ID NO 55
<211> LENGTH: 8
<212> TYPE: PRT
<213> ORGANISM: Homo sapiens

<400> SEQUENCE: 55

Ala Glu Asn Thr Gln Phe Val Lys
1               5

<210> SEQ ID NO 56
<211> LENGTH: 19
<212> TYPE: PRT
<213> ORGANISM: Homo sapiens

<400> SEQUENCE: 56

Leu Ala Thr Thr Ala Leu Tyr Phe Thr Tyr Ser Ala Leu Glu Glu
1               5                   10                  15

Met Glu Arg

<210> SEQ ID NO 57
<211> LENGTH: 15
<212> TYPE: PRT
<213> ORGANISM: Homo sapiens

<400> SEQUENCE: 57

Leu Gly Leu Leu Gly Leu Ala Asn Ser Leu Ala Ile Glu Gly Arg
1               5                   10                  15

<210> SEQ ID NO 58
<211> LENGTH: 19
<212> TYPE: PRT
<213> ORGANISM: Homo sapiens

<400> SEQUENCE: 58

Val Phe Ile Met Asp Ser Cys Asp Glu Leu Ile Pro Glu Tyr Leu Asn
1               5                   10                  15

Phe Ile Arg

<210> SEQ ID NO 59
<211> LENGTH: 20
<212> TYPE: PRT
<213> ORGANISM: Homo sapiens

<400> SEQUENCE: 59

Gly Phe Glu Val Val Tyr Met Thr Glu Pro Ile Asp Glu Tyr Cys Val
1               5                   10                  15

Gln Gln Leu Lys
            20

```
<210> SEQ ID NO 60
<211> LENGTH: 19
<212> TYPE: PRT
<213> ORGANISM: Homo sapiens

<400> SEQUENCE: 60

Leu Ile Ser Leu Thr Asp Glu Asn Ala Leu Ser Gly Asn Glu Glu Leu
1               5                   10                  15

Thr Val Lys

<210> SEQ ID NO 61
<211> LENGTH: 15
<212> TYPE: PRT
<213> ORGANISM: Homo sapiens

<400> SEQUENCE: 61

Tyr Ser Gln Phe Ile Asn Phe Pro Ile Tyr Val Trp Ser Ser Lys
1               5                   10                  15

<210> SEQ ID NO 62
<211> LENGTH: 14
<212> TYPE: PRT
<213> ORGANISM: Homo sapiens

<400> SEQUENCE: 62

Ser Phe Tyr Pro Glu Glu Val Ser Ser Met Val Leu Thr Lys
1               5                   10

<210> SEQ ID NO 63
<211> LENGTH: 15
<212> TYPE: PRT
<213> ORGANISM: Homo sapiens

<400> SEQUENCE: 63

Tyr Glu Gln Gly Phe Ile Thr Asp Pro Val Val Leu Ser Pro Lys
1               5                   10                  15

<210> SEQ ID NO 64
<211> LENGTH: 15
<212> TYPE: PRT
<213> ORGANISM: Homo sapiens

<400> SEQUENCE: 64

Asp Leu Ala Asp Glu Leu Ala Leu Val Asp Val Ile Glu Asp Lys
1               5                   10                  15

<210> SEQ ID NO 65
<211> LENGTH: 11
<212> TYPE: PRT
<213> ORGANISM: Homo sapiens

<400> SEQUENCE: 65

Met Val Val Glu Ser Ala Tyr Glu Val Ile Lys
1               5                   10

<210> SEQ ID NO 66
<211> LENGTH: 17
<212> TYPE: PRT
<213> ORGANISM: Homo sapiens

<400> SEQUENCE: 66

Asp Tyr Thr Gly Glu Asp Val Thr Pro Gln Asn Phe Leu Ala Val Leu
1               5                   10                  15
```

Arg

<210> SEQ ID NO 67
<211> LENGTH: 21
<212> TYPE: PRT
<213> ORGANISM: Homo sapiens

<400> SEQUENCE: 67

Leu Val Val Asp Leu Thr Asp Ile Asp Pro Asp Val Ala Tyr Ser Ser
1               5                   10                  15

Val Pro Tyr Glu Lys
            20

<210> SEQ ID NO 68
<211> LENGTH: 15
<212> TYPE: PRT
<213> ORGANISM: Homo sapiens

<400> SEQUENCE: 68

Tyr Leu Leu Glu Thr Ser Gly Asn Leu Asp Gly Leu Glu Tyr Lys
1               5                   10                  15

<210> SEQ ID NO 69
<211> LENGTH: 19
<212> TYPE: PRT
<213> ORGANISM: Homo sapiens

<400> SEQUENCE: 69

Asp Glu Leu His Ile Val Glu Ala Glu Ala Met Asn Tyr Glu Gly Ser
1               5                   10                  15

Pro Ile Lys

<210> SEQ ID NO 70
<211> LENGTH: 21
<212> TYPE: PRT
<213> ORGANISM: Homo sapiens

<400> SEQUENCE: 70

Met Ser Val Gln Pro Thr Val Ser Leu Gly Gly Phe Glu Ile Thr Pro
1               5                   10                  15

Pro Val Val Leu Arg
            20

<210> SEQ ID NO 71
<211> LENGTH: 19
<212> TYPE: PRT
<213> ORGANISM: Homo sapiens

<400> SEQUENCE: 71

Leu Ile Leu Pro Val Gly Pro Ala Gly Gly Asn Gln Met Leu Glu Gln
1               5                   10                  15

Tyr Asp Lys

<210> SEQ ID NO 72
<211> LENGTH: 16
<212> TYPE: PRT
<213> ORGANISM: Homo sapiens

<400> SEQUENCE: 72

Val Phe Leu Leu Gly Glu Glu Val Ala Gln Tyr Asp Gly Ala Tyr Lys
1               5                   10                  15

```
<210> SEQ ID NO 73
<211> LENGTH: 18
<212> TYPE: PRT
<213> ORGANISM: Homo sapiens

<400> SEQUENCE: 73

Gln Ile Val Trp Asn Gly Pro Val Gly Val Phe Glu Trp Glu Ala Phe
1               5                   10                  15

Ala Arg

<210> SEQ ID NO 74
<211> LENGTH: 13
<212> TYPE: PRT
<213> ORGANISM: Homo sapiens

<400> SEQUENCE: 74

Ile Tyr Val Asp Asp Gly Leu Ile Ser Leu Gln Val Lys
1               5                   10

<210> SEQ ID NO 75
<211> LENGTH: 22
<212> TYPE: PRT
<213> ORGANISM: Homo sapiens

<400> SEQUENCE: 75

Leu Ala Pro Ile Thr Ser Asp Pro Thr Glu Ala Thr Ala Val Gly Ala
1               5                   10                  15

Val Glu Ala Ser Phe Lys
            20

<210> SEQ ID NO 76
<211> LENGTH: 14
<212> TYPE: PRT
<213> ORGANISM: Homo sapiens

<400> SEQUENCE: 76

Thr Ala Leu Thr Tyr Tyr Leu Asp Ile Thr Asn Pro Pro Arg
1               5                   10

<210> SEQ ID NO 77
<211> LENGTH: 9
<212> TYPE: PRT
<213> ORGANISM: Homo sapiens

<400> SEQUENCE: 77

Ile Tyr Gly Phe Tyr Asp Glu Cys Lys
1               5

<210> SEQ ID NO 78
<211> LENGTH: 9
<212> TYPE: PRT
<213> ORGANISM: Homo sapiens

<400> SEQUENCE: 78

Ile Tyr Gly Phe Tyr Asp Glu Cys Lys
1               5

<210> SEQ ID NO 79
<211> LENGTH: 17
<212> TYPE: PRT
<213> ORGANISM: Homo sapiens

<400> SEQUENCE: 79

Glu Ile Phe Leu Ser Gln Pro Ile Leu Leu Glu Leu Glu Ala Pro Leu
```

<210> SEQ ID NO 80
<211> LENGTH: 27
<212> TYPE: PRT
<213> ORGANISM: Homo sapiens

<400> SEQUENCE: 80

Thr Leu Met Glu Asp Val Glu Asn Ser Phe Phe Leu Asn Val Asn Ser
1               5                   10                  15

Gln Val Thr Thr Val Cys Gln Ala Leu Ala Lys
            20                  25

<210> SEQ ID NO 81
<211> LENGTH: 8
<212> TYPE: PRT
<213> ORGANISM: Homo sapiens

<400> SEQUENCE: 81

Thr Asp Glu Gly Ile Ala Tyr Arg
1               5

<210> SEQ ID NO 82
<211> LENGTH: 20
<212> TYPE: PRT
<213> ORGANISM: Homo sapiens

<400> SEQUENCE: 82

Phe Glu Gly Gly Val Val Ile Ala Ala Asp Met Leu Gly Ser Tyr Gly
1               5                   10                  15

Ser Leu Ala Arg
            20

<210> SEQ ID NO 83
<211> LENGTH: 10
<212> TYPE: PRT
<213> ORGANISM: Homo sapiens

<400> SEQUENCE: 83

Leu Leu Ala Asn Met Val Tyr Gln Tyr Lys
1               5                   10

<210> SEQ ID NO 84
<211> LENGTH: 14
<212> TYPE: PRT
<213> ORGANISM: Homo sapiens

<400> SEQUENCE: 84

Asp Ala Tyr Ser Gly Gly Ala Val Asn Leu Tyr His Val Arg
1               5                   10

<210> SEQ ID NO 85
<211> LENGTH: 39
<212> TYPE: PRT
<213> ORGANISM: Homo sapiens

<400> SEQUENCE: 85

Ser Gly Ser Ala Ala Asp Thr Gln Ala Val Ala Asp Ala Val Thr Tyr
1               5                   10                  15

Gln Leu Gly Phe His Ser Ile Glu Leu Asn Glu Pro Pro Leu Val His
            20                  25                  30

Thr Ala Ala Ser Leu Phe Lys
        35

<210> SEQ ID NO 86
<211> LENGTH: 10
<212> TYPE: PRT
<213> ORGANISM: Homo sapiens

<400> SEQUENCE: 86

Asp Glu Phe Leu Ile Gln Ala Ser Pro Arg
1               5                   10

<210> SEQ ID NO 87
<211> LENGTH: 16
<212> TYPE: PRT
<213> ORGANISM: Homo sapiens

<400> SEQUENCE: 87

Ala Leu Glu Ser Asp Met Ala Pro Val Leu Ile Met Ala Thr Asn Arg
1               5                   10                  15

<210> SEQ ID NO 88
<211> LENGTH: 11
<212> TYPE: PRT
<213> ORGANISM: Homo sapiens

<400> SEQUENCE: 88

Asp Gln Tyr Cys Phe Glu Cys Asp Cys Phe Arg
1               5                   10

<210> SEQ ID NO 89
<211> LENGTH: 38
<212> TYPE: PRT
<213> ORGANISM: Homo sapiens

<400> SEQUENCE: 89

Gly Cys His Glu Ser Cys Leu Asp Glu Glu Val Glu Gly Gln Gly Phe
1               5                   10                  15

Cys Ser Gly Pro Gly Trp Asp Pro Val Thr Gly Trp Gly Thr Pro Asn
            20                  25                  30

Phe Pro Ala Leu Leu Lys
        35

<210> SEQ ID NO 90
<211> LENGTH: 14
<212> TYPE: PRT
<213> ORGANISM: Homo sapiens

<400> SEQUENCE: 90

Tyr Glu Glu Val Ser Val Ser Gly Phe Glu Glu Phe His Arg
1               5                   10

<210> SEQ ID NO 91
<211> LENGTH: 11
<212> TYPE: PRT
<213> ORGANISM: Homo sapiens

<400> SEQUENCE: 91

Glu Ala Ala Glu Asn Ser Leu Val Ala Tyr Lys
1               5                   10

<210> SEQ ID NO 92
<211> LENGTH: 19
<212> TYPE: PRT

```
<213> ORGANISM: Homo sapiens

<400> SEQUENCE: 92

Ala Ala Phe Asp Asp Ala Ile Ala Glu Leu Asp Thr Leu Ser Glu Glu
1               5                   10                  15

Ser Tyr Lys

<210> SEQ ID NO 93
<211> LENGTH: 19
<212> TYPE: PRT
<213> ORGANISM: Homo sapiens

<400> SEQUENCE: 93

Thr Ala Phe Asp Glu Ala Ile Ala Glu Leu Asp Thr Leu Asn Glu Asp
1               5                   10                  15

Ser Tyr Lys

<210> SEQ ID NO 94
<211> LENGTH: 19
<212> TYPE: PRT
<213> ORGANISM: Homo sapiens

<400> SEQUENCE: 94

Thr Ala Phe Asp Glu Ala Ile Ala Glu Leu Asp Thr Leu Ser Glu Glu
1               5                   10                  15

Ser Tyr Lys

<210> SEQ ID NO 95
<211> LENGTH: 22
<212> TYPE: PRT
<213> ORGANISM: Homo sapiens

<400> SEQUENCE: 95

Ser Gln Gly Val Asp Cys Leu Val Ala Pro Tyr Glu Ala Asp Ala Gln
1               5                   10                  15

Leu Ala Tyr Leu Asn Lys
            20

<210> SEQ ID NO 96
<211> LENGTH: 15
<212> TYPE: PRT
<213> ORGANISM: Homo sapiens

<400> SEQUENCE: 96

Met Gln Gln Gln Leu Asp Glu Tyr Gln Glu Leu Leu Asp Ile Lys
1               5                   10                  15

<210> SEQ ID NO 97
<211> LENGTH: 16
<212> TYPE: PRT
<213> ORGANISM: Homo sapiens

<400> SEQUENCE: 97

Ala Asp Ile Gln Leu Leu Val Tyr Thr Ile Asp Asp Leu Ile Asp Lys
1               5                   10                  15

<210> SEQ ID NO 98
<211> LENGTH: 15
<212> TYPE: PRT
<213> ORGANISM: Homo sapiens

<400> SEQUENCE: 98
```

Tyr Ser Glu Glu Gly Val Tyr Asn Val Gln Tyr Ser Phe Ile Lys
1               5                   10                  15

<210> SEQ ID NO 99
<211> LENGTH: 19
<212> TYPE: PRT
<213> ORGANISM: Homo sapiens

<400> SEQUENCE: 99

Val Ala Met Ser His Phe Glu Pro Asn Glu Tyr Ile His Tyr Asp Leu
1               5                   10                  15

Leu Glu Lys

<210> SEQ ID NO 100
<211> LENGTH: 16
<212> TYPE: PRT
<213> ORGANISM: Homo sapiens

<400> SEQUENCE: 100

Ser Tyr Glu Leu Pro Asp Gly Gln Val Ile Thr Ile Gly Asn Glu Arg
1               5                   10                  15

<210> SEQ ID NO 101
<211> LENGTH: 16
<212> TYPE: PRT
<213> ORGANISM: Homo sapiens

<400> SEQUENCE: 101

Tyr Pro Ile Glu His Gly Ile Ile Thr Asn Trp Asp Asp Met Glu Lys
1               5                   10                  15

<210> SEQ ID NO 102
<211> LENGTH: 16
<212> TYPE: PRT
<213> ORGANISM: Homo sapiens

<400> SEQUENCE: 102

Ser Tyr Glu Leu Pro Asp Gly Gln Val Ile Thr Ile Gly Asn Glu Arg
1               5                   10                  15

<210> SEQ ID NO 103
<211> LENGTH: 16
<212> TYPE: PRT
<213> ORGANISM: Homo sapiens

<400> SEQUENCE: 103

Tyr Pro Ile Glu His Gly Ile Ile Thr Asn Trp Asp Asp Met Glu Lys
1               5                   10                  15

<210> SEQ ID NO 104
<211> LENGTH: 30
<212> TYPE: PRT
<213> ORGANISM: Homo sapiens

<400> SEQUENCE: 104

Thr Thr Gly Ile Val Met Asp Ser Gly Asp Gly Val Thr His Thr Val
1               5                   10                  15

Pro Ile Tyr Glu Gly Tyr Ala Leu Pro His Ala Ile Leu Arg
            20                  25                  30

<210> SEQ ID NO 105
<211> LENGTH: 10
<212> TYPE: PRT
<213> ORGANISM: Homo sapiens

```
<400> SEQUENCE: 105

Gly Tyr Ser Phe Thr Thr Thr Ala Glu Arg
1               5                   10

<210> SEQ ID NO 106
<211> LENGTH: 23
<212> TYPE: PRT
<213> ORGANISM: Homo sapiens

<400> SEQUENCE: 106

Leu Cys Tyr Val Ala Leu Asp Phe Glu Gln Glu Met Ala Thr Ala Ala
1               5                   10                  15

Ser Ser Ser Ser Leu Glu Lys
            20

<210> SEQ ID NO 107
<211> LENGTH: 16
<212> TYPE: PRT
<213> ORGANISM: Homo sapiens

<400> SEQUENCE: 107

Ser Tyr Glu Leu Pro Asp Gly Gln Val Ile Thr Ile Gly Asn Glu Arg
1               5                   10                  15

<210> SEQ ID NO 108
<211> LENGTH: 18
<212> TYPE: PRT
<213> ORGANISM: Homo sapiens

<400> SEQUENCE: 108

Val Ala Pro Glu Glu His Pro Val Leu Leu Thr Glu Ala Pro Leu Asn
1               5                   10                  15

Pro Lys

<210> SEQ ID NO 109
<211> LENGTH: 16
<212> TYPE: PRT
<213> ORGANISM: Homo sapiens

<400> SEQUENCE: 109

Ser Tyr Glu Leu Pro Asp Gly Gln Val Ile Thr Ile Gly Asn Glu Arg
1               5                   10                  15

<210> SEQ ID NO 110
<211> LENGTH: 18
<212> TYPE: PRT
<213> ORGANISM: Homo sapiens

<400> SEQUENCE: 110

Val Ala Pro Asp Glu His Pro Ile Leu Leu Thr Glu Ala Pro Leu Asn
1               5                   10                  15

Pro Lys

<210> SEQ ID NO 111
<211> LENGTH: 10
<212> TYPE: PRT
<213> ORGANISM: Homo sapiens

<400> SEQUENCE: 111

Ala Gly Tyr Ala Gly Glu Asp Cys Pro Lys
1               5                   10
```

<210> SEQ ID NO 112
<211> LENGTH: 18
<212> TYPE: PRT
<213> ORGANISM: Homo sapiens

<400> SEQUENCE: 112

Ala Ile Met Thr Tyr Val Ser Ser Phe Tyr His Ala Phe Ser Gly Ala
1               5                   10                  15

Gln Lys

<210> SEQ ID NO 113
<211> LENGTH: 11
<212> TYPE: PRT
<213> ORGANISM: Homo sapiens

<400> SEQUENCE: 113

Gly Tyr Glu Glu Trp Leu Leu Asn Glu Ile Arg
1               5                   10

<210> SEQ ID NO 114
<211> LENGTH: 18
<212> TYPE: PRT
<213> ORGANISM: Homo sapiens

<400> SEQUENCE: 114

Ala Ile Met Thr Tyr Val Ser Ser Phe Tyr His Ala Phe Ser Gly Ala
1               5                   10                  15

Gln Lys

<210> SEQ ID NO 115
<211> LENGTH: 11
<212> TYPE: PRT
<213> ORGANISM: Homo sapiens

<400> SEQUENCE: 115

Gly Tyr Glu Glu Trp Leu Leu Asn Glu Ile Arg
1               5                   10

<210> SEQ ID NO 116
<211> LENGTH: 25
<212> TYPE: PRT
<213> ORGANISM: Homo sapiens

<400> SEQUENCE: 116

Val Glu Gln Ile Ala Ala Ile Ala Gln Glu Leu Asn Glu Leu Asp Tyr
1               5                   10                  15

Tyr Asp Ser His Asn Val Asn Thr Arg
            20                  25

<210> SEQ ID NO 117
<211> LENGTH: 14
<212> TYPE: PRT
<213> ORGANISM: Homo sapiens

<400> SEQUENCE: 117

Ala Cys Leu Ile Ser Leu Gly Tyr Asp Val Glu Asn Asp Arg
1               5                   10

<210> SEQ ID NO 118
<211> LENGTH: 22
<212> TYPE: PRT
<213> ORGANISM: Homo sapiens

```
<400> SEQUENCE: 118

Leu Ala Ser Tyr Trp Ala Gln Pro Gln Asp Ala Leu Ser Gln Glu Val
1               5                   10                  15

Ser Pro Glu Val Trp Lys
            20

<210> SEQ ID NO 119
<211> LENGTH: 17
<212> TYPE: PRT
<213> ORGANISM: Homo sapiens

<400> SEQUENCE: 119

Gly Ile Ser Asp Pro Leu Thr Val Phe Glu Gln Thr Glu Ala Ala Ala
1               5                   10                  15

Arg

<210> SEQ ID NO 120
<211> LENGTH: 12
<212> TYPE: PRT
<213> ORGANISM: Homo sapiens

<400> SEQUENCE: 120

Gly Ile Val Glu Glu Ser Val Thr Gly Val His Arg
1               5                   10

<210> SEQ ID NO 121
<211> LENGTH: 12
<212> TYPE: PRT
<213> ORGANISM: Homo sapiens

<400> SEQUENCE: 121

Gly Ile Val Glu Glu Ser Val Thr Gly Val His Arg
1               5                   10

<210> SEQ ID NO 122
<211> LENGTH: 22
<212> TYPE: PRT
<213> ORGANISM: Homo sapiens

<400> SEQUENCE: 122

Val Phe Thr Thr Gln Glu Leu Val Gln Ala Phe Thr His Ala Pro Ala
1               5                   10                  15

Thr Leu Glu Ala Asp Arg
            20

<210> SEQ ID NO 123
<211> LENGTH: 7
<212> TYPE: PRT
<213> ORGANISM: Homo sapiens

<400> SEQUENCE: 123

Tyr Tyr Phe Glu Gly Ile Lys
1               5

<210> SEQ ID NO 124
<211> LENGTH: 13
<212> TYPE: PRT
<213> ORGANISM: Homo sapiens

<400> SEQUENCE: 124

Phe Ala Ser Tyr Leu Thr Phe Ser Pro Ser Glu Val Lys
1               5                   10
```

-continued

<210> SEQ ID NO 125
<211> LENGTH: 21
<212> TYPE: PRT
<213> ORGANISM: Homo sapiens

<400> SEQUENCE: 125

Ala Gly Phe Ser Val Phe Trp Ala Asp Asp Gly Leu Asp Thr Gly Pro
1               5                   10                  15

Ile Leu Leu Gln Arg
            20

<210> SEQ ID NO 126
<211> LENGTH: 18
<212> TYPE: PRT
<213> ORGANISM: Homo sapiens

<400> SEQUENCE: 126

Leu Asp Cys Tyr Glu Gly Leu Ile Glu Cys Tyr Leu Ala Ser Asn Ser
1               5                   10                  15

Ile Arg

<210> SEQ ID NO 127
<211> LENGTH: 16
<212> TYPE: PRT
<213> ORGANISM: Homo sapiens

<400> SEQUENCE: 127

Ser Leu Asp Leu Phe Asn Cys Glu Val Thr Asn Leu Asn Asp Tyr Arg
1               5                   10                  15

<210> SEQ ID NO 128
<211> LENGTH: 16
<212> TYPE: PRT
<213> ORGANISM: Homo sapiens

<400> SEQUENCE: 128

Ser Leu Asp Leu Phe Asn Cys Glu Val Thr Asn Leu Asn Asp Tyr Arg
1               5                   10                  15

<210> SEQ ID NO 129
<211> LENGTH: 12
<212> TYPE: PRT
<213> ORGANISM: Homo sapiens

<400> SEQUENCE: 129

Leu Thr Asn Gly Ile Trp Val Leu Ala Glu Leu Arg
1               5                   10

<210> SEQ ID NO 130
<211> LENGTH: 15
<212> TYPE: PRT
<213> ORGANISM: Homo sapiens

<400> SEQUENCE: 130

Val Leu Glu Asp Val Thr Gly Glu Glu Phe Val Leu Phe Met Lys
1               5                   10                  15

<210> SEQ ID NO 131
<211> LENGTH: 18
<212> TYPE: PRT
<213> ORGANISM: Homo sapiens

<400> SEQUENCE: 131

-continued

```
Gly Thr Leu Gly Gly Leu Phe Ser Gln Ile Leu Gln Gly Glu Asp Ile
1               5                   10                  15

Val Arg

<210> SEQ ID NO 132
<211> LENGTH: 27
<212> TYPE: PRT
<213> ORGANISM: Homo sapiens

<400> SEQUENCE: 132

Gln Gln Leu Val Glu Leu Val Ala Glu Gln Ala Asp Leu Glu Gln Thr
1               5                   10                  15

Phe Asn Pro Ser Asp Pro Asp Cys Val Asp Arg
            20                  25

<210> SEQ ID NO 133
<211> LENGTH: 10
<212> TYPE: PRT
<213> ORGANISM: Homo sapiens

<400> SEQUENCE: 133

Gly Tyr Ile Val Ile Glu Asp Leu Trp Lys
1               5                   10

<210> SEQ ID NO 134
<211> LENGTH: 23
<212> TYPE: PRT
<213> ORGANISM: Homo sapiens

<400> SEQUENCE: 134

Met Met Gln Glu Ala Met Ser Ala Phe Pro Gly Ile Asp Glu Ala Met
1               5                   10                  15

Ser Tyr Ala Glu Val Met Arg
            20

<210> SEQ ID NO 135
<211> LENGTH: 8
<212> TYPE: PRT
<213> ORGANISM: Homo sapiens

<400> SEQUENCE: 135

Ala Phe Val Thr Asp Trp Asp Lys
1               5

<210> SEQ ID NO 136
<211> LENGTH: 18
<212> TYPE: PRT
<213> ORGANISM: Homo sapiens

<400> SEQUENCE: 136

Asn Leu Glu Ala Val Glu Thr Leu Gly Ser Thr Ser Thr Ile Cys Ser
1               5                   10                  15

Asp Lys

<210> SEQ ID NO 137
<211> LENGTH: 18
<212> TYPE: PRT
<213> ORGANISM: Homo sapiens

<400> SEQUENCE: 137

Trp Ile Asn Asp Val Glu Asp Ser Tyr Gly Gln Gln Trp Thr Tyr Glu
1               5                   10                  15
```

Gln Arg

<210> SEQ ID NO 138
<211> LENGTH: 18
<212> TYPE: PRT
<213> ORGANISM: Homo sapiens

<400> SEQUENCE: 138

Ser Leu Pro Ser Val Glu Thr Leu Gly Cys Thr Ser Val Ile Cys Ser
1               5                   10                  15

Asp Lys

<210> SEQ ID NO 139
<211> LENGTH: 17
<212> TYPE: PRT
<213> ORGANISM: Homo sapiens

<400> SEQUENCE: 139

Glu Ala Ser Asp Ile Ile Leu Thr Asp Asp Asn Phe Thr Ser Ile Val
1               5                   10                  15

Lys

<210> SEQ ID NO 140
<211> LENGTH: 17
<212> TYPE: PRT
<213> ORGANISM: Homo sapiens

<400> SEQUENCE: 140

Glu Ala Ser Asp Ile Ile Leu Thr Asp Asp Asn Phe Thr Ser Ile Val
1               5                   10                  15

Lys

<210> SEQ ID NO 141
<211> LENGTH: 20
<212> TYPE: PRT
<213> ORGANISM: Homo sapiens

<400> SEQUENCE: 141

Gly Met Ser Leu Asn Leu Glu Pro Asp Asn Val Gly Val Val Val Phe
1               5                   10                  15

Gly Asn Asp Lys
            20

<210> SEQ ID NO 142
<211> LENGTH: 22
<212> TYPE: PRT
<213> ORGANISM: Homo sapiens

<400> SEQUENCE: 142

Glu Val Ala Ala Phe Ala Gln Phe Gly Ser Asp Leu Asp Ala Ala Thr
1               5                   10                  15

Gln Gln Leu Leu Ser Arg
            20

<210> SEQ ID NO 143
<211> LENGTH: 12
<212> TYPE: PRT
<213> ORGANISM: Homo sapiens

<400> SEQUENCE: 143

Ile Met Asn Val Ile Gly Glu Pro Ile Asp Glu Arg
1               5                   10

<210> SEQ ID NO 144
<211> LENGTH: 14
<212> TYPE: PRT
<213> ORGANISM: Homo sapiens

<400> SEQUENCE: 144

Ala His Gly Gly Tyr Ser Val Phe Ala Gly Val Gly Glu Arg
1               5                   10

<210> SEQ ID NO 145
<211> LENGTH: 18
<212> TYPE: PRT
<213> ORGANISM: Homo sapiens

<400> SEQUENCE: 145

Glu Gly Asn Asp Leu Tyr His Glu Met Ile Glu Ser Gly Val Ile Asn
1               5                   10                  15

Leu Lys

<210> SEQ ID NO 146
<211> LENGTH: 16
<212> TYPE: PRT
<213> ORGANISM: Homo sapiens

<400> SEQUENCE: 146

Asp Gln Glu Gly Gln Asp Val Leu Leu Phe Ile Asp Asn Ile Phe Arg
1               5                   10                  15

<210> SEQ ID NO 147
<211> LENGTH: 36
<212> TYPE: PRT
<213> ORGANISM: Homo sapiens

<400> SEQUENCE: 147

Gly Ser Ile Thr Ser Val Gln Ala Ile Tyr Val Pro Ala Asp Asp Leu
1               5                   10                  15

Thr Asp Pro Ala Pro Ala Thr Thr Phe Ala His Leu Asp Ala Thr Thr
                20                  25                  30

Val Leu Ser Arg
            35

<210> SEQ ID NO 148
<211> LENGTH: 19
<212> TYPE: PRT
<213> ORGANISM: Homo sapiens

<400> SEQUENCE: 148

Ala Ile Ala Glu Leu Gly Ile Tyr Pro Ala Val Asp Pro Leu Asp Ser
1               5                   10                  15

Thr Ser Arg

<210> SEQ ID NO 149
<211> LENGTH: 16
<212> TYPE: PRT
<213> ORGANISM: Homo sapiens

<400> SEQUENCE: 149

Ile Met Asp Pro Asn Ile Val Gly Ser Glu His Tyr Asp Val Ala Arg
1               5                   10                  15

<210> SEQ ID NO 150

```
<211> LENGTH: 19
<212> TYPE: PRT
<213> ORGANISM: Homo sapiens

<400> SEQUENCE: 150

Ser Leu Gln Asp Ile Ile Ala Ile Leu Gly Met Asp Glu Leu Ser Glu
1               5                   10                  15

Glu Asp Lys

<210> SEQ ID NO 151
<211> LENGTH: 18
<212> TYPE: PRT
<213> ORGANISM: Homo sapiens

<400> SEQUENCE: 151

Phe Leu Ser Gln Pro Phe Gln Val Ala Glu Val Phe Thr Gly His Met
1               5                   10                  15

Gly Lys

<210> SEQ ID NO 152
<211> LENGTH: 15
<212> TYPE: PRT
<213> ORGANISM: Homo sapiens

<400> SEQUENCE: 152

Leu Val Leu Glu Val Ala Gln His Leu Gly Glu Ser Thr Val Arg
1               5                   10                  15

<210> SEQ ID NO 153
<211> LENGTH: 11
<212> TYPE: PRT
<213> ORGANISM: Homo sapiens

<400> SEQUENCE: 153

Ser Glu Val Ala Thr Leu Thr Ala Ala Gly Lys
1               5                   10

<210> SEQ ID NO 154
<211> LENGTH: 11
<212> TYPE: PRT
<213> ORGANISM: Homo sapiens

<400> SEQUENCE: 154

Tyr Gly Pro Phe Val Ala Asp Phe Ala Asp Lys
1               5                   10

<210> SEQ ID NO 155
<211> LENGTH: 15
<212> TYPE: PRT
<213> ORGANISM: Homo sapiens

<400> SEQUENCE: 155

Tyr Gly Leu Ile Pro Glu Glu Phe Phe Gln Phe Leu Tyr Pro Lys
1               5                   10                  15

<210> SEQ ID NO 156
<211> LENGTH: 20
<212> TYPE: PRT
<213> ORGANISM: Homo sapiens

<400> SEQUENCE: 156

Thr Gly Val Thr Gly Pro Tyr Val Leu Gly Thr Gly Leu Ile Leu Tyr
1               5                   10                  15
```

```
Ala Leu Ser Lys
        20

<210> SEQ ID NO 157
<211> LENGTH: 21
<212> TYPE: PRT
<213> ORGANISM: Homo sapiens

<400> SEQUENCE: 157

Ala Val Val Gly Glu Glu Ala Leu Thr Ser Asp Asp Leu Leu Tyr Leu
1               5                   10                  15

Glu Phe Leu Gln Lys
        20

<210> SEQ ID NO 158
<211> LENGTH: 11
<212> TYPE: PRT
<213> ORGANISM: Homo sapiens

<400> SEQUENCE: 158

Ser Gly Gln Val Leu Glu Val Ser Gly Ser Lys
1               5                   10

<210> SEQ ID NO 159
<211> LENGTH: 13
<212> TYPE: PRT
<213> ORGANISM: Homo sapiens

<400> SEQUENCE: 159

Leu Asp Leu Ile Ala Gln Gln Met Met Pro Glu Val Arg
1               5                   10

<210> SEQ ID NO 160
<211> LENGTH: 13
<212> TYPE: PRT
<213> ORGANISM: Homo sapiens

<400> SEQUENCE: 160

Leu Leu Gly Asn Thr Phe Val Ala Leu Ser Asp Leu Arg
1               5                   10

<210> SEQ ID NO 161
<211> LENGTH: 13
<212> TYPE: PRT
<213> ORGANISM: Homo sapiens

<400> SEQUENCE: 161

Ile Gly Asp Glu Leu Asp Ser Asn Met Glu Leu Gln Arg
1               5                   10

<210> SEQ ID NO 162
<211> LENGTH: 15
<212> TYPE: PRT
<213> ORGANISM: Homo sapiens

<400> SEQUENCE: 162

Val Tyr Asn Glu Asn Leu Val His Met Ile Glu His Ala Gln Lys
1               5                   10                  15

<210> SEQ ID NO 163
<211> LENGTH: 18
<212> TYPE: PRT
<213> ORGANISM: Homo sapiens

<400> SEQUENCE: 163
```

Ser Glu Leu His Ile Glu Asn Leu Asn Met Glu Ala Asp Pro Gly Gln
1               5                   10                  15

Tyr Arg

<210> SEQ ID NO 164
<211> LENGTH: 16
<212> TYPE: PRT
<213> ORGANISM: Homo sapiens

<400> SEQUENCE: 164

Ser Ser Glu His Ile Asn Glu Gly Glu Thr Ala Met Leu Val Cys Lys
1               5                   10                  15

<210> SEQ ID NO 165
<211> LENGTH: 18
<212> TYPE: PRT
<213> ORGANISM: Homo sapiens

<400> SEQUENCE: 165

Leu Leu Leu Asp Glu Phe Leu Gly Tyr Asp Asp Ile Leu Met Ser Ser
1               5                   10                  15

Val Lys

<210> SEQ ID NO 166
<211> LENGTH: 30
<212> TYPE: PRT
<213> ORGANISM: Homo sapiens

<400> SEQUENCE: 166

Gly Val Asp Asn Thr Phe Ala Asp Glu Leu Val Glu Leu Ser Thr Ala
1               5                   10                  15

Leu Glu His Gln Glu Tyr Ile Thr Phe Leu Glu Asp Leu Lys
            20                  25                  30

<210> SEQ ID NO 167
<211> LENGTH: 20
<212> TYPE: PRT
<213> ORGANISM: Homo sapiens

<400> SEQUENCE: 167

Val Glu Glu Gln Glu Pro Glu Leu Thr Ser Thr Pro Asn Phe Val Val
1               5                   10                  15

Glu Val Ile Lys
            20

<210> SEQ ID NO 168
<211> LENGTH: 15
<212> TYPE: PRT
<213> ORGANISM: Homo sapiens

<400> SEQUENCE: 168

Met Ser Gly Gly Trp Glu Leu Glu Leu Asn Gly Thr Glu Ala Lys
1               5                   10                  15

<210> SEQ ID NO 169
<211> LENGTH: 27
<212> TYPE: PRT
<213> ORGANISM: Homo sapiens

<400> SEQUENCE: 169

Ala Leu Val Leu Asp Cys His Tyr Pro Glu Asp Glu Val Gly Gln Glu
1               5                   10                  15

Asp Glu Ala Glu Ser Asp Ile Phe Ser Ile Arg
            20                  25

<210> SEQ ID NO 170
<211> LENGTH: 11
<212> TYPE: PRT
<213> ORGANISM: Homo sapiens

<400> SEQUENCE: 170

Ala Phe Val Asp Phe Leu Ser Asp Glu Ile Lys
1               5                   10

<210> SEQ ID NO 171
<211> LENGTH: 26
<212> TYPE: PRT
<213> ORGANISM: Homo sapiens

<400> SEQUENCE: 171

Ile Thr Val Thr Phe Asn Ile Asn Asn Ser Ile Pro Pro Thr Phe Asp
1               5                   10                  15

Gly Glu Glu Glu Pro Ser Gln Gly Gln Lys
            20                  25

<210> SEQ ID NO 172
<211> LENGTH: 13
<212> TYPE: PRT
<213> ORGANISM: Homo sapiens

<400> SEQUENCE: 172

Glu Val Ser Phe Gln Ser Thr Gly Glu Ser Glu Trp Lys
1               5                   10

<210> SEQ ID NO 173
<211> LENGTH: 22
<212> TYPE: PRT
<213> ORGANISM: Homo sapiens

<400> SEQUENCE: 173

Glu Ala Asp Ile Asp Gly Asp Gly Gln Val Asn Tyr Glu Glu Phe Val
1               5                   10                  15

Gln Met Met Thr Ala Lys
            20

<210> SEQ ID NO 174
<211> LENGTH: 37
<212> TYPE: PRT
<213> ORGANISM: Homo sapiens

<400> SEQUENCE: 174

Ser Leu Gly Gln Asn Pro Thr Glu Ala Glu Leu Gln Asp Met Ile Asn
1               5                   10                  15

Glu Val Asp Ala Asp Gly Asn Gly Thr Ile Asp Phe Pro Glu Phe Leu
            20                  25                  30

Thr Met Met Ala Arg
        35

<210> SEQ ID NO 175
<211> LENGTH: 40
<212> TYPE: PRT
<213> ORGANISM: Homo sapiens

<400> SEQUENCE: 175

```
Thr His Leu Tyr Thr Leu Ile Leu Asn Pro Asp Asn Ser Phe Glu Ile
 1               5                  10                  15

Leu Val Asp Gln Ser Val Val Asn Ser Gly Asn Leu Asn Asp Met
             20                  25                  30

Thr Pro Pro Val Asn Pro Ser Arg
         35                  40

<210> SEQ ID NO 176
<211> LENGTH: 22
<212> TYPE: PRT
<213> ORGANISM: Homo sapiens

<400> SEQUENCE: 176

Asn Leu Glu Ala Leu Ala Leu Asp Leu Met Glu Pro Glu Gln Ala Val
 1               5                  10                  15

Asp Leu Thr Leu Pro Lys
             20

<210> SEQ ID NO 177
<211> LENGTH: 16
<212> TYPE: PRT
<213> ORGANISM: Homo sapiens

<400> SEQUENCE: 177

Leu Asn Gln Glu Asn Glu His Ile Tyr Asn Leu Trp Cys Ser Gly Arg
 1               5                  10                  15

<210> SEQ ID NO 178
<211> LENGTH: 18
<212> TYPE: PRT
<213> ORGANISM: Homo sapiens

<400> SEQUENCE: 178

Asp Met Glu Ala Leu Leu Pro Leu Met Asn Met Val Ile Tyr Ser Ile
 1               5                  10                  15

Asp Lys

<210> SEQ ID NO 179
<211> LENGTH: 11
<212> TYPE: PRT
<213> ORGANISM: Homo sapiens

<400> SEQUENCE: 179

Tyr Glu Glu Phe Val Gly Leu Asn Glu Val Arg
 1               5                  10

<210> SEQ ID NO 180
<211> LENGTH: 29
<212> TYPE: PRT
<213> ORGANISM: Homo sapiens

<400> SEQUENCE: 180

Gln Leu Ile Tyr Asn Tyr Pro Glu Gln Leu Phe Gly Ala Ala Gly Val
 1               5                  10                  15

Met Ala Ile Glu His Ala Asp Phe Ala Gly Val Glu Arg
             20                  25

<210> SEQ ID NO 181
<211> LENGTH: 15
<212> TYPE: PRT
<213> ORGANISM: Homo sapiens

<400> SEQUENCE: 181
```

Gln Val Leu Leu Ser Ala Ala Glu Ala Glu Val Ile Leu Arg
1               5                   10                  15

<210> SEQ ID NO 182
<211> LENGTH: 22
<212> TYPE: PRT
<213> ORGANISM: Homo sapiens

<400> SEQUENCE: 182

Val Gln Asp Asp Glu Val Gly Asp Gly Thr Thr Ser Val Thr Val Leu
1               5                   10                  15

Ala Ala Glu Leu Leu Arg
            20

<210> SEQ ID NO 183
<211> LENGTH: 11
<212> TYPE: PRT
<213> ORGANISM: Homo sapiens

<400> SEQUENCE: 183

Ala Val Ala Gln Ala Leu Glu Val Ile Pro Arg
1               5                   10

<210> SEQ ID NO 184
<211> LENGTH: 42
<212> TYPE: PRT
<213> ORGANISM: Homo sapiens

<400> SEQUENCE: 184

Thr Gln Asp Glu Glu Val Gly Asp Gly Thr Thr Ser Val Ile Ile Leu
1               5                   10                  15

Ala Gly Glu Met Leu Ser Val Ala Glu His Phe Leu Glu Gln Gln Met
            20                  25                  30

His Pro Thr Val Val Ile Ser Ala Tyr Arg
            35                  40

<210> SEQ ID NO 185
<211> LENGTH: 19
<212> TYPE: PRT
<213> ORGANISM: Homo sapiens

<400> SEQUENCE: 185

Val Val Ser Gln Tyr Ser Ser Leu Leu Ser Pro Met Ser Val Asn Ala
1               5                   10                  15

Val Met Lys

<210> SEQ ID NO 186
<211> LENGTH: 29
<212> TYPE: PRT
<213> ORGANISM: Homo sapiens

<400> SEQUENCE: 186

Ala Phe Ala Asp Ala Met Glu Val Ile Pro Ser Thr Leu Ala Glu Asn
1               5                   10                  15

Ala Gly Leu Asn Pro Ile Ser Thr Val Thr Glu Leu Arg
            20                  25

<210> SEQ ID NO 187
<211> LENGTH: 30
<212> TYPE: PRT
<213> ORGANISM: Homo sapiens

```
<400> SEQUENCE: 187

Glu Thr Gly Ala Asn Leu Ala Ile Cys Gln Trp Gly Phe Asp Asp Glu
1               5                   10                  15

Ala Asn His Leu Leu Gln Asn Asn Leu Pro Ala Val Arg
            20                  25                  30

<210> SEQ ID NO 188
<211> LENGTH: 17
<212> TYPE: PRT
<213> ORGANISM: Homo sapiens

<400> SEQUENCE: 188

Trp Val Gly Gly Pro Glu Ile Glu Leu Ile Ala Ile Ala Thr Gly Gly
1               5                   10                  15

Arg

<210> SEQ ID NO 189
<211> LENGTH: 29
<212> TYPE: PRT
<213> ORGANISM: Homo sapiens

<400> SEQUENCE: 189

Ala Phe Ala Asp Ala Leu Glu Val Ile Pro Met Ala Leu Ser Glu Asn
1               5                   10                  15

Ser Gly Met Asn Pro Ile Gln Thr Met Thr Glu Val Arg
            20                  25

<210> SEQ ID NO 190
<211> LENGTH: 30
<212> TYPE: PRT
<213> ORGANISM: Homo sapiens

<400> SEQUENCE: 190

Ser Gln Asp Asp Glu Ile Gly Asp Gly Thr Thr Gly Val Val Val Leu
1               5                   10                  15

Ala Gly Ala Leu Leu Glu Glu Ala Glu Gln Leu Leu Asp Arg
            20                  25                  30

<210> SEQ ID NO 191
<211> LENGTH: 25
<212> TYPE: PRT
<213> ORGANISM: Homo sapiens

<400> SEQUENCE: 191

Asn Ala Ile Asp Asp Gly Cys Val Val Pro Gly Ala Gly Ala Val Glu
1               5                   10                  15

Val Ala Met Ala Glu Ala Leu Ile Lys
            20                  25

<210> SEQ ID NO 192
<211> LENGTH: 22
<212> TYPE: PRT
<213> ORGANISM: Homo sapiens

<400> SEQUENCE: 192

Ser Gln Asp Ala Glu Val Gly Asp Gly Thr Thr Ser Val Thr Leu Leu
1               5                   10                  15

Ala Ala Glu Phe Leu Lys
            20

<210> SEQ ID NO 193
```

-continued

```
<211> LENGTH: 10
<212> TYPE: PRT
<213> ORGANISM: Homo sapiens

<400> SEQUENCE: 193

Phe Ala Glu Ala Phe Glu Ala Ile Pro Arg
1               5                   10

<210> SEQ ID NO 194
<211> LENGTH: 21
<212> TYPE: PRT
<213> ORGANISM: Homo sapiens

<400> SEQUENCE: 194

Leu Gly Pro Gly Gly Leu Asp Pro Val Glu Val Tyr Glu Ser Leu Pro
1               5                   10                  15

Glu Glu Leu Gln Lys
            20

<210> SEQ ID NO 195
<211> LENGTH: 17
<212> TYPE: PRT
<213> ORGANISM: Homo sapiens

<400> SEQUENCE: 195

Asn Gln Phe Leu Asp Glu Leu Met Glu Leu Glu Ile Phe Leu Ala Gln
1               5                   10                  15

Arg

<210> SEQ ID NO 196
<211> LENGTH: 15
<212> TYPE: PRT
<213> ORGANISM: Homo sapiens

<400> SEQUENCE: 196

Ser Thr Leu Gln Thr Met Glu Ser Asp Ile Tyr Thr Glu Val Arg
1               5                   10                  15

<210> SEQ ID NO 197
<211> LENGTH: 23
<212> TYPE: PRT
<213> ORGANISM: Homo sapiens

<400> SEQUENCE: 197

Tyr Thr Phe Cys Pro Thr Gly Ser Pro Ile Pro Val Met Glu Gly Asp
1               5                   10                  15

Asp Asp Ile Glu Val Phe Arg
            20

<210> SEQ ID NO 198
<211> LENGTH: 21
<212> TYPE: PRT
<213> ORGANISM: Homo sapiens

<400> SEQUENCE: 198

Val Val Asn Gln Leu Ala Ala Ala Tyr Glu Gln Asp Leu Leu Pro Gly
1               5                   10                  15

Gly Cys Thr Leu Arg
            20

<210> SEQ ID NO 199
<211> LENGTH: 22
<212> TYPE: PRT
```

-continued

<213> ORGANISM: Homo sapiens

<400> SEQUENCE: 199

Ser Pro Trp Asn Phe Leu Gly Asp Glu Leu Tyr Glu Gln Ser Asp Glu
1               5                   10                  15

Glu Gln Asp Ser Val Lys
            20

<210> SEQ ID NO 200
<211> LENGTH: 15
<212> TYPE: PRT
<213> ORGANISM: Homo sapiens

<400> SEQUENCE: 200

Ala Leu Asn Thr Phe Ile Asp Asp Leu Phe Ala Phe Val Ile Lys
1               5                   10                  15

<210> SEQ ID NO 201
<211> LENGTH: 18
<212> TYPE: PRT
<213> ORGANISM: Homo sapiens

<400> SEQUENCE: 201

Tyr Glu Ala Ala Gly Thr Leu Val Thr Leu Ser Ser Ala Pro Thr Ala
1               5                   10                  15

Ile Lys

<210> SEQ ID NO 202
<211> LENGTH: 17
<212> TYPE: PRT
<213> ORGANISM: Homo sapiens

<400> SEQUENCE: 202

Leu Tyr Leu Glu Asp Asp Asp Pro Val Gln Ala Glu Ala Tyr Ile Asn
1               5                   10                  15

Arg

<210> SEQ ID NO 203
<211> LENGTH: 22
<212> TYPE: PRT
<213> ORGANISM: Homo sapiens

<400> SEQUENCE: 203

Leu Tyr Asp Leu Tyr Ser Phe Gln Val Ile Pro Val Leu Gly Glu Val
1               5                   10                  15

Ile Ala Gly Asp Trp Lys
            20

<210> SEQ ID NO 204
<211> LENGTH: 18
<212> TYPE: PRT
<213> ORGANISM: Homo sapiens

<400> SEQUENCE: 204

Met Gly Glu Ser Trp Ile Pro Glu Asp Leu Phe Thr Phe Ser Pro Ile
1               5                   10                  15

Leu Arg

<210> SEQ ID NO 205
<211> LENGTH: 15
<212> TYPE: PRT
<213> ORGANISM: Homo sapiens

```
<400> SEQUENCE: 205

Gly Ile Asn Thr Leu Val Thr Tyr Asp Met Val Pro Glu Pro Lys
1               5                   10                  15

<210> SEQ ID NO 206
<211> LENGTH: 20
<212> TYPE: PRT
<213> ORGANISM: Homo sapiens

<400> SEQUENCE: 206

Asp Gly Ser Thr Ala Val His Phe Glu His Ser Trp Gly Asp Gly Val
1               5                   10                  15

Ala Val Leu Arg
            20

<210> SEQ ID NO 207
<211> LENGTH: 18
<212> TYPE: PRT
<213> ORGANISM: Homo sapiens

<400> SEQUENCE: 207

Gln Tyr Gly Gln Thr Val Ala Thr Tyr Glu Ser Cys Ser Thr Ala Ala
1               5                   10                  15

Phe Lys

<210> SEQ ID NO 208
<211> LENGTH: 12
<212> TYPE: PRT
<213> ORGANISM: Homo sapiens

<400> SEQUENCE: 208

Gln Asn Trp Phe Glu Ala Phe Glu Ile Leu Asp Lys
1               5                   10

<210> SEQ ID NO 209
<211> LENGTH: 12
<212> TYPE: PRT
<213> ORGANISM: Homo sapiens

<400> SEQUENCE: 209

Cys Thr Glu Pro Glu Asp Gln Leu Tyr Tyr Val Lys
1               5                   10

<210> SEQ ID NO 210
<211> LENGTH: 14
<212> TYPE: PRT
<213> ORGANISM: Homo sapiens

<400> SEQUENCE: 210

Asn Asn Asp Phe Tyr Val Thr Gly Glu Ser Tyr Ala Gly Lys
1               5                   10

<210> SEQ ID NO 211
<211> LENGTH: 21
<212> TYPE: PRT
<213> ORGANISM: Homo sapiens

<400> SEQUENCE: 211

Phe Leu Glu Ser Val Glu Gly Asn Gln Asn Tyr Pro Leu Leu Leu Leu
1               5                   10                  15

Thr Leu Leu Glu Lys
            20
```

-continued

```
<210> SEQ ID NO 212
<211> LENGTH: 23
<212> TYPE: PRT
<213> ORGANISM: Homo sapiens

<400> SEQUENCE: 212

Phe Phe Glu Gly Pro Val Thr Gly Ile Phe Ser Gly Tyr Val Asn Ser
1               5                   10                  15

Met Leu Gln Glu Tyr Ala Lys
            20

<210> SEQ ID NO 213
<211> LENGTH: 25
<212> TYPE: PRT
<213> ORGANISM: Homo sapiens

<400> SEQUENCE: 213

Tyr Gly Asp Ile Pro Glu Tyr Val Leu Ala Tyr Ile Asp Tyr Leu Ser
1               5                   10                  15

His Leu Asn Glu Asp Asn Asn Thr Arg
            20                  25

<210> SEQ ID NO 214
<211> LENGTH: 12
<212> TYPE: PRT
<213> ORGANISM: Homo sapiens

<400> SEQUENCE: 214

Leu Phe Ser Asp Glu Ala Ala Asn Ile Tyr Glu Arg
1               5                   10

<210> SEQ ID NO 215
<211> LENGTH: 14
<212> TYPE: PRT
<213> ORGANISM: Homo sapiens

<400> SEQUENCE: 215

Asn Glu Gly Val Ala Thr Tyr Ala Ala Ala Val Leu Phe Arg
1               5                   10

<210> SEQ ID NO 216
<211> LENGTH: 7
<212> TYPE: PRT
<213> ORGANISM: Homo sapiens

<400> SEQUENCE: 216

Tyr Tyr Thr Ser Glu Ser Lys
1               5

<210> SEQ ID NO 217
<211> LENGTH: 17
<212> TYPE: PRT
<213> ORGANISM: Homo sapiens

<400> SEQUENCE: 217

Thr Phe Ser Ser Leu Gly Phe Ser Gly Thr Gln Glu Cys Pro Glu Leu
1               5                   10                  15

Arg

<210> SEQ ID NO 218
<211> LENGTH: 15
<212> TYPE: PRT
```

<213> ORGANISM: Homo sapiens

<400> SEQUENCE: 218

Gly Val Tyr Pro Asp Leu Leu Ala Thr Ser Gly Asp Tyr Leu Arg
1               5                   10                  15

<210> SEQ ID NO 219
<211> LENGTH: 16
<212> TYPE: PRT
<213> ORGANISM: Homo sapiens

<400> SEQUENCE: 219

Glu Asn Leu Ala Thr Val Glu Gly Asn Phe Ala Ser Ile Asp Glu Arg
1               5                   10                  15

<210> SEQ ID NO 220
<211> LENGTH: 20
<212> TYPE: PRT
<213> ORGANISM: Homo sapiens

<400> SEQUENCE: 220

Ala Ala Leu Gln Glu Glu Leu Ser Asp Val Leu Ile Tyr Leu Val Ala
1               5                   10                  15

Leu Ala Ala Arg
            20

<210> SEQ ID NO 221
<211> LENGTH: 12
<212> TYPE: PRT
<213> ORGANISM: Homo sapiens

<400> SEQUENCE: 221

Leu Ile Gln Leu Met Glu Glu Ile Met Ala Glu Lys
1               5                   10

<210> SEQ ID NO 222
<211> LENGTH: 12
<212> TYPE: PRT
<213> ORGANISM: Homo sapiens

<400> SEQUENCE: 222

Val Leu Glu Glu Ala Asn Gln Ala Ile Asn Pro Lys
1               5                   10

<210> SEQ ID NO 223
<211> LENGTH: 19
<212> TYPE: PRT
<213> ORGANISM: Homo sapiens

<400> SEQUENCE: 223

Ser Ile Phe Trp Glu Leu Gln Asp Ile Ile Pro Phe Gly Asn Asn Pro
1               5                   10                  15

Ile Phe Arg

<210> SEQ ID NO 224
<211> LENGTH: 17
<212> TYPE: PRT
<213> ORGANISM: Homo sapiens

<400> SEQUENCE: 224

Gly Asn Glu Ala Glu Leu Tyr Ile Asp Ile Gly Ala Tyr Gly Glu Pro
1               5                   10                  15

Arg

<210> SEQ ID NO 225
<211> LENGTH: 17
<212> TYPE: PRT
<213> ORGANISM: Homo sapiens

<400> SEQUENCE: 225

Ser Asp His Leu Thr Val Val Asn Ala Phe Glu Gly Trp Glu Glu Ala
1               5                   10                  15

Arg

<210> SEQ ID NO 226
<211> LENGTH: 21
<212> TYPE: PRT
<213> ORGANISM: Homo sapiens

<400> SEQUENCE: 226

Ala Glu Asn Asn Ser Glu Val Gly Ala Ser Gly Tyr Gly Val Pro Gly
1               5                   10                  15

Pro Thr Trp Asp Arg
            20

<210> SEQ ID NO 227
<211> LENGTH: 17
<212> TYPE: PRT
<213> ORGANISM: Homo sapiens

<400> SEQUENCE: 227

Met Asn Ser Glu Glu Glu Asp Glu Val Trp Gln Val Ile Ile Gly Ala
1               5                   10                  15

Arg

<210> SEQ ID NO 228
<211> LENGTH: 20
<212> TYPE: PRT
<213> ORGANISM: Homo sapiens

<400> SEQUENCE: 228

Gly Trp Gly Glu Leu Glu Phe Gly Ala Gly Asp Leu Gln Gly Pro Leu
1               5                   10                  15

Phe Gly Leu Lys
            20

<210> SEQ ID NO 229
<211> LENGTH: 30
<212> TYPE: PRT
<213> ORGANISM: Homo sapiens

<400> SEQUENCE: 229

Gln Leu Thr Tyr Thr Tyr Pro Trp Val Tyr Asn Tyr Gln Leu Glu Gly
1               5                   10                  15

Ile Phe Ala Gln Glu Phe Pro Asp Leu Glu Asn Val Val Lys
            20                  25                  30

<210> SEQ ID NO 230
<211> LENGTH: 20
<212> TYPE: PRT
<213> ORGANISM: Homo sapiens

<400> SEQUENCE: 230

Phe Cys Val Ser Asp Thr Glu Asn Asn Leu Gly Phe Ala Leu Gly Pro
1               5                   10                  15

```
Met Phe Val Lys
            20

<210> SEQ ID NO 231
<211> LENGTH: 12
<212> TYPE: PRT
<213> ORGANISM: Homo sapiens

<400> SEQUENCE: 231

Glu Leu Tyr Leu Glu Glu Ala Leu Gln Asn Glu Arg
1               5                   10

<210> SEQ ID NO 232
<211> LENGTH: 12
<212> TYPE: PRT
<213> ORGANISM: Homo sapiens

<400> SEQUENCE: 232

Glu His Ala Leu Leu Ala Tyr Thr Leu Gly Val Lys
1               5                   10

<210> SEQ ID NO 233
<211> LENGTH: 22
<212> TYPE: PRT
<213> ORGANISM: Homo sapiens

<400> SEQUENCE: 233

Gly Gln Glu Leu Ala Phe Pro Leu Ser Pro Asp Trp Gln Val Asp Tyr
1               5                   10                  15

Glu Ser Tyr Thr Trp Arg
            20

<210> SEQ ID NO 234
<211> LENGTH: 28
<212> TYPE: PRT
<213> ORGANISM: Homo sapiens

<400> SEQUENCE: 234

Val Pro Ala Phe Glu Gly Asp Asp Gly Phe Cys Val Phe Glu Ser Asn
1               5                   10                  15

Ala Ile Ala Tyr Tyr Val Ser Asn Glu Glu Leu Arg
            20                  25

<210> SEQ ID NO 235
<211> LENGTH: 25
<212> TYPE: PRT
<213> ORGANISM: Homo sapiens

<400> SEQUENCE: 235

Tyr Val Glu Pro Ile Glu Asp Val Pro Cys Gly Asn Ile Val Gly Leu
1               5                   10                  15

Val Gly Val Asp Gln Phe Leu Val Lys
            20                  25

<210> SEQ ID NO 236
<211> LENGTH: 26
<212> TYPE: PRT
<213> ORGANISM: Homo sapiens

<400> SEQUENCE: 236

Leu Met Glu Pro Ile Tyr Leu Val Glu Ile Gln Cys Pro Glu Gln Val
1               5                   10                  15
```

Val Gly Gly Ile Tyr Gly Val Leu Asn Arg
            20              25

<210> SEQ ID NO 237
<211> LENGTH: 18
<212> TYPE: PRT
<213> ORGANISM: Homo sapiens

<400> SEQUENCE: 237

Gly His Val Phe Glu Glu Ser Gln Val Ala Gly Thr Pro Met Phe Val
1               5                   10                  15

Val Lys

<210> SEQ ID NO 238
<211> LENGTH: 19
<212> TYPE: PRT
<213> ORGANISM: Homo sapiens

<400> SEQUENCE: 238

Leu Ala Ser Glu Ile Leu Met Gln Asn Trp Asp Ala Ala Met Glu Asp
1               5                   10                  15

Leu Thr Arg

<210> SEQ ID NO 239
<211> LENGTH: 18
<212> TYPE: PRT
<213> ORGANISM: Homo sapiens

<400> SEQUENCE: 239

Glu Ala Pro Asn Pro Ile His Leu Thr Val Asp Thr Ser Leu Gln Asn
1               5                   10                  15

Gly Arg

<210> SEQ ID NO 240
<211> LENGTH: 19
<212> TYPE: PRT
<213> ORGANISM: Homo sapiens

<400> SEQUENCE: 240

Ile Gln Asp Ala Leu Ser Thr Val Leu Gln Tyr Ala Glu Asp Val Leu
1               5                   10                  15

Ser Gly Lys

<210> SEQ ID NO 241
<211> LENGTH: 14
<212> TYPE: PRT
<213> ORGANISM: Homo sapiens

<400> SEQUENCE: 241

Asn Ser His Leu Ile Asn Val Leu Met Trp Glu Leu Glu Lys
1               5                   10

<210> SEQ ID NO 242
<211> LENGTH: 16
<212> TYPE: PRT
<213> ORGANISM: Homo sapiens

<400> SEQUENCE: 242

Gly Asp Pro Gln Val Tyr Glu Glu Leu Phe Ser Tyr Ser Cys Pro Lys
1               5                   10                  15

<210> SEQ ID NO 243

```
<211> LENGTH: 20
<212> TYPE: PRT
<213> ORGANISM: Homo sapiens

<400> SEQUENCE: 243

Gln Leu Glu Val Tyr Thr Ser Gly Gly Asp Pro Glu Ser Val Ala Gly
1               5                   10                  15

Glu Tyr Gly Arg
            20

<210> SEQ ID NO 244
<211> LENGTH: 13
<212> TYPE: PRT
<213> ORGANISM: Homo sapiens

<400> SEQUENCE: 244

Glu Ala Leu Thr Tyr Asp Gly Ala Leu Leu Gly Asp Arg
1               5                   10

<210> SEQ ID NO 245
<211> LENGTH: 15
<212> TYPE: PRT
<213> ORGANISM: Homo sapiens

<400> SEQUENCE: 245

Ala Met Gly Pro Leu Val Leu Thr Glu Val Leu Phe Asn Glu Lys
1               5                   10                  15

<210> SEQ ID NO 246
<211> LENGTH: 18
<212> TYPE: PRT
<213> ORGANISM: Homo sapiens

<400> SEQUENCE: 246

Thr Asn Leu Ile Val Asn Tyr Leu Pro Gln Asn Met Thr Gln Asp Glu
1               5                   10                  15

Leu Arg

<210> SEQ ID NO 247
<211> LENGTH: 17
<212> TYPE: PRT
<213> ORGANISM: Homo sapiens

<400> SEQUENCE: 247

Ala Phe Asp Asp Glu Ile Asn Ala Phe Leu Asp Asn Met Phe Gly Pro
1               5                   10                  15

Arg

<210> SEQ ID NO 248
<211> LENGTH: 10
<212> TYPE: PRT
<213> ORGANISM: Homo sapiens

<400> SEQUENCE: 248

Ala Pro Gly Ala Gly Leu Gly Gln Asp Arg
1               5                   10

<210> SEQ ID NO 249
<211> LENGTH: 15
<212> TYPE: PRT
<213> ORGANISM: Homo sapiens

<400> SEQUENCE: 249
```

-continued

Gly Tyr Asn Asp Asp Tyr Glu Glu Ser Tyr Phe Thr Thr Arg
1               5                   10                  15

<210> SEQ ID NO 250
<211> LENGTH: 10
<212> TYPE: PRT
<213> ORGANISM: Homo sapiens

<400> SEQUENCE: 250

Phe Ser Thr Trp Thr Asn Thr Glu Phe Arg
1               5                   10

<210> SEQ ID NO 251
<211> LENGTH: 17
<212> TYPE: PRT
<213> ORGANISM: Homo sapiens

<400> SEQUENCE: 251

Thr Tyr Ala Asp Tyr Glu Ser Val Asn Glu Cys Met Glu Gly Val Cys
1               5                   10                  15

Lys

<210> SEQ ID NO 252
<211> LENGTH: 24
<212> TYPE: PRT
<213> ORGANISM: Homo sapiens

<400> SEQUENCE: 252

Gln Asp His Pro Ser Ser Met Gly Val Tyr Gly Gln Glu Ser Gly Gly
1               5                   10                  15

Phe Ser Gly Pro Gly Glu Asn Arg
            20

<210> SEQ ID NO 253
<211> LENGTH: 29
<212> TYPE: PRT
<213> ORGANISM: Homo sapiens

<400> SEQUENCE: 253

Leu Glu Gly Leu Ile Gln Pro Asp Asp Leu Ile Asn Gln Leu Thr Phe
1               5                   10                  15

Ile Met Asp Ala Asn Gln Thr Tyr Leu Val Ser Glu Arg
            20                  25

<210> SEQ ID NO 254
<211> LENGTH: 12
<212> TYPE: PRT
<213> ORGANISM: Homo sapiens

<400> SEQUENCE: 254

Trp Glu Tyr Val Pro Leu Gly Pro Phe Leu Gly Lys
1               5                   10

<210> SEQ ID NO 255
<211> LENGTH: 13
<212> TYPE: PRT
<213> ORGANISM: Homo sapiens

<400> SEQUENCE: 255

Thr Met Asp Val Ile Ala Glu Gly Asp Pro Gly Phe Lys
1               5                   10

<210> SEQ ID NO 256

```
<211> LENGTH: 11
<212> TYPE: PRT
<213> ORGANISM: Homo sapiens

<400> SEQUENCE: 256

Tyr Asp Leu Leu Cys Leu Glu Gly Leu Val Arg
1               5                   10

<210> SEQ ID NO 257
<211> LENGTH: 13
<212> TYPE: PRT
<213> ORGANISM: Homo sapiens

<400> SEQUENCE: 257

Ile Met Gln Leu Leu Asp Val Pro Pro Gly Glu Asp Lys
1               5                   10

<210> SEQ ID NO 258
<211> LENGTH: 34
<212> TYPE: PRT
<213> ORGANISM: Homo sapiens

<400> SEQUENCE: 258

Gly His Pro Leu Gly Asp Ile Val Ala Phe Leu Thr Ser Thr Glu Pro
1               5                   10                  15

Gln Tyr Gly Gln Gly Ile Leu Ser Gln Asp Ala Trp Glu Ser Leu Phe
            20                  25                  30

Ser Arg

<210> SEQ ID NO 259
<211> LENGTH: 15
<212> TYPE: PRT
<213> ORGANISM: Homo sapiens

<400> SEQUENCE: 259

Ala Leu Asp Thr Leu Glu Asp Asp Met Thr Ile Ser Val Glu Lys
1               5                   10                  15

<210> SEQ ID NO 260
<211> LENGTH: 12
<212> TYPE: PRT
<213> ORGANISM: Homo sapiens

<400> SEQUENCE: 260

Ala Ala Val Phe Leu Ala Leu Glu Glu Gln Glu Lys
1               5                   10

<210> SEQ ID NO 261
<211> LENGTH: 15
<212> TYPE: PRT
<213> ORGANISM: Homo sapiens

<400> SEQUENCE: 261

Gly Gly Thr Tyr Asp Thr Tyr Val Gly Ser Gly Trp Leu Ile Lys
1               5                   10                  15

<210> SEQ ID NO 262
<211> LENGTH: 17
<212> TYPE: PRT
<213> ORGANISM: Homo sapiens

<400> SEQUENCE: 262

Phe Glu Ile Gly Glu Gly Glu Asn Leu Asp Leu Pro Tyr Gly Leu Glu
1               5                   10                  15
```

Arg

<210> SEQ ID NO 263
<211> LENGTH: 28
<212> TYPE: PRT
<213> ORGANISM: Homo sapiens

<400> SEQUENCE: 263

Met Gly Gln Ala Val Pro Ala Pro Thr Gly Ala Pro Pro Gly Gly Gln
1               5                   10                  15

Pro Asp Tyr Ser Ala Ala Trp Ala Glu Tyr Tyr Arg
            20                  25

<210> SEQ ID NO 264
<211> LENGTH: 13
<212> TYPE: PRT
<213> ORGANISM: Homo sapiens

<400> SEQUENCE: 264

Ile Gly Gly Asn Glu Gly Ile Asp Val Pro Ile Pro Arg
1               5                   10

<210> SEQ ID NO 265
<211> LENGTH: 14
<212> TYPE: PRT
<213> ORGANISM: Homo sapiens

<400> SEQUENCE: 265

Gly Glu Ala Thr Val Ser Phe Asp Asp Pro Pro Ser Ala Lys
1               5                   10

<210> SEQ ID NO 266
<211> LENGTH: 16
<212> TYPE: PRT
<213> ORGANISM: Homo sapiens

<400> SEQUENCE: 266

Gly Glu Leu Phe Trp Asp Asp Gly Glu Ser Leu Glu Val Leu Glu Arg
1               5                   10                  15

<210> SEQ ID NO 267
<211> LENGTH: 19
<212> TYPE: PRT
<213> ORGANISM: Homo sapiens

<400> SEQUENCE: 267

Val Pro Ser Thr Glu Ala Glu Ala Leu Ala Ser Ser Leu Met Gly Leu
1               5                   10                  15

Phe Glu Lys

<210> SEQ ID NO 268
<211> LENGTH: 19
<212> TYPE: PRT
<213> ORGANISM: Homo sapiens

<400> SEQUENCE: 268

Ser Pro Tyr Leu Tyr Pro Leu Tyr Gly Leu Gly Glu Leu Pro Gln Gly
1               5                   10                  15

Phe Ala Arg

<210> SEQ ID NO 269
<211> LENGTH: 23

```
<212> TYPE: PRT
<213> ORGANISM: Homo sapiens

<400> SEQUENCE: 269

Ala Ala Trp Tyr Thr Ala Gly Ile Val Gly Gly Leu Ser Thr Val Ala
1               5                   10                  15

Met Cys Ala Pro Ser Glu Lys
            20

<210> SEQ ID NO 270
<211> LENGTH: 26
<212> TYPE: PRT
<213> ORGANISM: Homo sapiens

<400> SEQUENCE: 270

Thr Met Val Gly Phe Gly Pro Glu Asp His Phe Val Ala Glu Leu
1               5                   10                  15

Thr Tyr Asn Tyr Gly Val Gly Asp Tyr Lys
            20                  25

<210> SEQ ID NO 271
<211> LENGTH: 16
<212> TYPE: PRT
<213> ORGANISM: Homo sapiens

<400> SEQUENCE: 271

Leu Leu Gln Val Val Glu Glu Pro Gln Ala Leu Ala Ala Phe Leu Arg
1               5                   10                  15

<210> SEQ ID NO 272
<211> LENGTH: 25
<212> TYPE: PRT
<213> ORGANISM: Homo sapiens

<400> SEQUENCE: 272

Ser Val Glu Asp Leu Gln Trp Ser Pro Thr Glu Asn Thr Val Phe Ala
1               5                   10                  15

Ser Cys Ser Ala Asp Ala Ser Ile Arg
            20                  25

<210> SEQ ID NO 273
<211> LENGTH: 29
<212> TYPE: PRT
<213> ORGANISM: Homo sapiens

<400> SEQUENCE: 273

Val Gly Ala Thr Ala Ala Val Tyr Ser Ala Ala Ile Leu Glu Tyr Leu
1               5                   10                  15

Thr Ala Glu Val Leu Glu Leu Ala Gly Asn Ala Ser Lys
            20                  25

<210> SEQ ID NO 274
<211> LENGTH: 22
<212> TYPE: PRT
<213> ORGANISM: Homo sapiens

<400> SEQUENCE: 274

Leu Gly Ala Gly Tyr Pro Met Gly Pro Phe Glu Leu Leu Asp Tyr Val
1               5                   10                  15

Gly Leu Asp Thr Thr Lys
            20
```

```
<210> SEQ ID NO 275
<211> LENGTH: 14
<212> TYPE: PRT
<213> ORGANISM: Homo sapiens

<400> SEQUENCE: 275

Thr Leu Gln Glu Val Thr Gln Leu Ser Gln Glu Ala Gln Arg
1               5                   10

<210> SEQ ID NO 276
<211> LENGTH: 24
<212> TYPE: PRT
<213> ORGANISM: Homo sapiens

<400> SEQUENCE: 276

Glu Phe Tyr Gln Cys Asp Phe Asp Ile Ala Gly Asn Phe Asp Pro Met
1               5                   10                  15

Ile Pro Asp Ala Glu Cys Leu Lys
            20

<210> SEQ ID NO 277
<211> LENGTH: 15
<212> TYPE: PRT
<213> ORGANISM: Homo sapiens

<400> SEQUENCE: 277

Tyr Leu Asn Ala Leu Val Asp Ser Ala Val Ala Leu Glu Thr Lys
1               5                   10                  15

<210> SEQ ID NO 278
<211> LENGTH: 17
<212> TYPE: PRT
<213> ORGANISM: Homo sapiens

<400> SEQUENCE: 278

Met Asp Ile Leu Val Thr Glu Thr Glu Leu Ala Glu Asn Ile Leu
1               5                   10                  15

Lys

<210> SEQ ID NO 279
<211> LENGTH: 11
<212> TYPE: PRT
<213> ORGANISM: Homo sapiens

<400> SEQUENCE: 279

Ser Trp Met Gly Tyr Glu Leu Pro Phe Asp Arg
1               5                   10

<210> SEQ ID NO 280
<211> LENGTH: 27
<212> TYPE: PRT
<213> ORGANISM: Homo sapiens

<400> SEQUENCE: 280

Ser Phe Ser Ala Thr Ala Leu Asn Met Leu Glu Ser Ala Leu Leu Ser
1               5                   10                  15

Pro Val Ser Ser Met Glu Ser Leu Leu Leu Lys
            20                  25

<210> SEQ ID NO 281
<211> LENGTH: 15
<212> TYPE: PRT
<213> ORGANISM: Homo sapiens
```

<400> SEQUENCE: 281

Glu Asn Ile Ala Ser Val Leu Glu Asn Tyr His Thr Glu Ser Lys
1               5                   10                  15

<210> SEQ ID NO 282
<211> LENGTH: 11
<212> TYPE: PRT
<213> ORGANISM: Homo sapiens

<400> SEQUENCE: 282

Ala Leu Ala Ala Ala Gly Tyr Asp Val Glu Lys
1               5                   10

<210> SEQ ID NO 283
<211> LENGTH: 14
<212> TYPE: PRT
<213> ORGANISM: Homo sapiens

<400> SEQUENCE: 283

Phe Ile Ala Val Gly Tyr Val Asp Asp Thr Gln Phe Val Arg
1               5                   10

<210> SEQ ID NO 284
<211> LENGTH: 12
<212> TYPE: PRT
<213> ORGANISM: Homo sapiens

<400> SEQUENCE: 284

Asn Ala Ser Asp Met Pro Glu Thr Ile Thr Ser Arg
1               5                   10

<210> SEQ ID NO 285
<211> LENGTH: 18
<212> TYPE: PRT
<213> ORGANISM: Homo sapiens

<400> SEQUENCE: 285

Asn Gln Gly Gly Tyr Gly Gly Ser Ser Ser Ser Ser Tyr Gly Ser
1               5                   10                  15

Gly Arg

<210> SEQ ID NO 286
<211> LENGTH: 14
<212> TYPE: PRT
<213> ORGANISM: Homo sapiens

<400> SEQUENCE: 286

Ser Ser Gly Pro Tyr Gly Gly Gly Gln Tyr Phe Ala Lys
1               5                   10

<210> SEQ ID NO 287
<211> LENGTH: 20
<212> TYPE: PRT
<213> ORGANISM: Homo sapiens

<400> SEQUENCE: 287

Gly Phe Gly Phe Val Thr Tyr Ala Thr Val Glu Glu Val Asp Ala Ala
1               5                   10                  15

Met Asn Ala Arg
            20

<210> SEQ ID NO 288
<211> LENGTH: 33

```
<212> TYPE: PRT
<213> ORGANISM: Homo sapiens

<400> SEQUENCE: 288

Gly Gly Gly Gly Tyr Gly Gly Ser Gly Asp Gly Tyr Asn Gly Phe Gly
1               5                   10                  15

Asn Asp Gly Gly Tyr Gly Gly Gly Pro Gly Tyr Ser Gly Gly Ser
            20                  25                  30

Arg

<210> SEQ ID NO 289
<211> LENGTH: 16
<212> TYPE: PRT
<213> ORGANISM: Homo sapiens

<400> SEQUENCE: 289

Leu Phe Ile Gly Gly Leu Ser Phe Glu Thr Thr Asp Glu Ser Leu Arg
1               5                   10                  15

<210> SEQ ID NO 290
<211> LENGTH: 10
<212> TYPE: PRT
<213> ORGANISM: Homo sapiens

<400> SEQUENCE: 290

Ile Glu Val Ile Glu Ile Met Thr Asp Arg
1               5                   10

<210> SEQ ID NO 291
<211> LENGTH: 14
<212> TYPE: PRT
<213> ORGANISM: Homo sapiens

<400> SEQUENCE: 291

Ser Ser Gly Pro Tyr Gly Gly Gly Gly Gln Tyr Phe Ala Lys
1               5                   10

<210> SEQ ID NO 292
<211> LENGTH: 10
<212> TYPE: PRT
<213> ORGANISM: Homo sapiens

<400> SEQUENCE: 292

Ile Glu Val Ile Glu Ile Met Thr Asp Arg
1               5                   10

<210> SEQ ID NO 293
<211> LENGTH: 16
<212> TYPE: PRT
<213> ORGANISM: Homo sapiens

<400> SEQUENCE: 293

Leu Phe Ile Gly Gly Leu Ser Phe Glu Thr Thr Asp Glu Ser Leu Arg
1               5                   10                  15

<210> SEQ ID NO 294
<211> LENGTH: 8
<212> TYPE: PRT
<213> ORGANISM: Homo sapiens

<400> SEQUENCE: 294

Asp Tyr Phe Glu Glu Tyr Gly Lys
1               5
```

<210> SEQ ID NO 295
<211> LENGTH: 10
<212> TYPE: PRT
<213> ORGANISM: Homo sapiens

<400> SEQUENCE: 295

Ile Asp Thr Ile Glu Ile Ile Thr Asp Arg
1               5                   10

<210> SEQ ID NO 296
<211> LENGTH: 10
<212> TYPE: PRT
<213> ORGANISM: Homo sapiens

<400> SEQUENCE: 296

Gln Glu Met Gln Glu Val Gln Ser Ser Arg
1               5                   10

<210> SEQ ID NO 297
<211> LENGTH: 10
<212> TYPE: PRT
<213> ORGANISM: Homo sapiens

<400> SEQUENCE: 297

Gly Gly Ser Asp Gly Tyr Gly Ser Gly Arg
1               5                   10

<210> SEQ ID NO 298
<211> LENGTH: 28
<212> TYPE: PRT
<213> ORGANISM: Homo sapiens

<400> SEQUENCE: 298

Gly Phe Gly Asp Gly Tyr Asn Gly Tyr Gly Gly Pro Gly Gly Gly
1               5                   10                  15

Asn Phe Gly Gly Ser Pro Gly Tyr Gly Gly Arg
                20                  25

<210> SEQ ID NO 299
<211> LENGTH: 16
<212> TYPE: PRT
<213> ORGANISM: Homo sapiens

<400> SEQUENCE: 299

Leu Phe Ile Gly Gly Leu Ser Phe Glu Thr Thr Glu Glu Ser Leu Arg
1               5                   10                  15

<210> SEQ ID NO 300
<211> LENGTH: 51
<212> TYPE: PRT
<213> ORGANISM: Homo sapiens

<400> SEQUENCE: 300

Gly Gly Tyr Gly Gly Gly Pro Gly Tyr Asn Gln Gly Gly
1               5                   10                  15

Tyr Gly Gly Gly Tyr Asp Asn Tyr Gly Gly Asn Tyr Gly Ser Gly
                20                  25                  30

Asn Tyr Asn Asp Phe Gly Asn Tyr Asn Gln Gln Pro Ser Asn Tyr Gly
                35                  40                  45

Pro Met Lys
    50

```
<210> SEQ ID NO 301
<211> LENGTH: 25
<212> TYPE: PRT
<213> ORGANISM: Homo sapiens

<400> SEQUENCE: 301

Asn Met Gly Gly Pro Tyr Gly Gly Asn Tyr Gly Pro Gly Gly Ser
1               5                   10                  15

Gly Gly Ser Gly Gly Tyr Gly Gly Arg
            20                  25

<210> SEQ ID NO 302
<211> LENGTH: 9
<212> TYPE: PRT
<213> ORGANISM: Homo sapiens

<400> SEQUENCE: 302

Thr Leu Glu Thr Val Pro Leu Glu Arg
1               5

<210> SEQ ID NO 303
<211> LENGTH: 10
<212> TYPE: PRT
<213> ORGANISM: Homo sapiens

<400> SEQUENCE: 303

Ile Glu Thr Ile Glu Val Met Glu Asp Arg
1               5                   10

<210> SEQ ID NO 304
<211> LENGTH: 22
<212> TYPE: PRT
<213> ORGANISM: Homo sapiens

<400> SEQUENCE: 304

Ser Ser Gly Ser Pro Tyr Gly Gly Tyr Gly Ser Gly Gly Ser
1               5                   10                  15

Gly Gly Tyr Gly Ser Arg
            20

<210> SEQ ID NO 305
<211> LENGTH: 16
<212> TYPE: PRT
<213> ORGANISM: Homo sapiens

<400> SEQUENCE: 305

Leu Phe Ile Gly Gly Leu Ser Phe Glu Thr Thr Asp Asp Ser Leu Arg
1               5                   10                  15

<210> SEQ ID NO 306
<211> LENGTH: 31
<212> TYPE: PRT
<213> ORGANISM: Homo sapiens

<400> SEQUENCE: 306

Ser Ala Ala Glu Met Tyr Gly Ser Val Thr Glu His Pro Ser Pro Ser
1               5                   10                  15

Pro Leu Leu Ser Ser Ser Phe Asp Leu Asp Tyr Asp Phe Gln Arg
            20                  25                  30

<210> SEQ ID NO 307
<211> LENGTH: 7
<212> TYPE: PRT
```

<400> SEQUENCE: 307

Met Tyr Ser Tyr Pro Ala Arg
1               5

<210> SEQ ID NO 308
<211> LENGTH: 11
<212> TYPE: PRT
<213> ORGANISM: Homo sapiens

<400> SEQUENCE: 308

Gly Phe Ala Phe Val Gln Tyr Val Asn Glu Arg
1               5                   10

<210> SEQ ID NO 309
<211> LENGTH: 9
<212> TYPE: PRT
<213> ORGANISM: Homo sapiens

<400> SEQUENCE: 309

Ala Ala Val Ala Gly Glu Asp Gly Arg
1               5

<210> SEQ ID NO 310
<211> LENGTH: 16
<212> TYPE: PRT
<213> ORGANISM: Homo sapiens

<400> SEQUENCE: 310

Met Ile Ala Gly Gln Val Leu Asp Ile Asn Leu Ala Ala Glu Pro Lys
1               5                   10                  15

<210> SEQ ID NO 311
<211> LENGTH: 14
<212> TYPE: PRT
<213> ORGANISM: Homo sapiens

<400> SEQUENCE: 311

Ile Phe Val Gly Gly Leu Ser Pro Asp Thr Pro Glu Glu Lys
1               5                   10

<210> SEQ ID NO 312
<211> LENGTH: 17
<212> TYPE: PRT
<213> ORGANISM: Homo sapiens

<400> SEQUENCE: 312

Ile Thr Gly Glu Ala Phe Val Gln Phe Ala Ser Gln Glu Leu Ala Glu
1               5                   10                  15

Lys

<210> SEQ ID NO 313
<211> LENGTH: 16
<212> TYPE: PRT
<213> ORGANISM: Homo sapiens

<400> SEQUENCE: 313

Gln Ser Gly Glu Ala Phe Val Glu Leu Gly Ser Glu Asp Asp Val Lys
1               5                   10                  15

<210> SEQ ID NO 314
<211> LENGTH: 16
<212> TYPE: PRT
<213> ORGANISM: Homo sapiens

```
<400> SEQUENCE: 314

His Ser Gly Pro Asn Ser Ala Asp Ser Ala Asn Asp Gly Phe Val Arg
1               5                   10                  15

<210> SEQ ID NO 315
<211> LENGTH: 26
<212> TYPE: PRT
<213> ORGANISM: Homo sapiens

<400> SEQUENCE: 315

Glu Glu Ile Val Gln Phe Phe Ser Gly Leu Glu Ile Val Pro Asn Gly
1               5                   10                  15

Ile Thr Leu Pro Val Asp Pro Glu Gly Lys
            20                  25

<210> SEQ ID NO 316
<211> LENGTH: 17
<212> TYPE: PRT
<213> ORGANISM: Homo sapiens

<400> SEQUENCE: 316

Ala Thr Glu Asn Asp Ile Tyr Asn Phe Phe Ser Pro Leu Asn Pro Val
1               5                   10                  15

Arg

<210> SEQ ID NO 317
<211> LENGTH: 10
<212> TYPE: PRT
<213> ORGANISM: Homo sapiens

<400> SEQUENCE: 317

Val His Ile Glu Ile Gly Pro Asp Gly Arg
1               5                   10

<210> SEQ ID NO 318
<211> LENGTH: 26
<212> TYPE: PRT
<213> ORGANISM: Homo sapiens

<400> SEQUENCE: 318

Glu Glu Ile Val Gln Phe Phe Ser Gly Leu Glu Ile Val Pro Asn Gly
1               5                   10                  15

Ile Thr Leu Pro Val Asp Phe Gln Gly Arg
            20                  25

<210> SEQ ID NO 319
<211> LENGTH: 17
<212> TYPE: PRT
<213> ORGANISM: Homo sapiens

<400> SEQUENCE: 319

Ser Thr Gly Glu Ala Phe Val Gln Phe Ala Ser Gln Glu Ile Ala Glu
1               5                   10                  15

Lys

<210> SEQ ID NO 320
<211> LENGTH: 26
<212> TYPE: PRT
<213> ORGANISM: Homo sapiens

<400> SEQUENCE: 320
```

Gly Ala Tyr Gly Gly Tyr Gly Gly Tyr Asp Asp Tyr Asn Gly Tyr
1               5                   10                  15

Asn Asp Gly Tyr Gly Phe Gly Ser Asp Arg
            20                  25

<210> SEQ ID NO 321
<211> LENGTH: 13
<212> TYPE: PRT
<213> ORGANISM: Homo sapiens

<400> SEQUENCE: 321

Asp Leu Asn Tyr Cys Phe Ser Gly Met Ser Asp His Arg
1               5                   10

<210> SEQ ID NO 322
<211> LENGTH: 19
<212> TYPE: PRT
<213> ORGANISM: Homo sapiens

<400> SEQUENCE: 322

Tyr Gly Asp Gly Gly Ser Thr Phe Gln Ser Thr Thr Gly His Cys Val
1               5                   10                  15

His Met Arg

<210> SEQ ID NO 323
<211> LENGTH: 17
<212> TYPE: PRT
<213> ORGANISM: Homo sapiens

<400> SEQUENCE: 323

Ala Thr Glu Asn Asp Ile Tyr Asn Phe Phe Ser Pro Leu Asn Pro Val
1               5                   10                  15

Arg

<210> SEQ ID NO 324
<211> LENGTH: 10
<212> TYPE: PRT
<213> ORGANISM: Homo sapiens

<400> SEQUENCE: 324

Val His Ile Glu Ile Gly Pro Asp Gly Arg
1               5                   10

<210> SEQ ID NO 325
<211> LENGTH: 20
<212> TYPE: PRT
<213> ORGANISM: Homo sapiens

<400> SEQUENCE: 325

Tyr Val Glu Leu Phe Leu Asn Ser Thr Ala Gly Ala Ser Gly Gly Ala
1               5                   10                  15

Tyr Glu His Arg
            20

<210> SEQ ID NO 326
<211> LENGTH: 16
<212> TYPE: PRT
<213> ORGANISM: Homo sapiens

<400> SEQUENCE: 326

His Thr Gly Pro Asn Ser Pro Asp Thr Ala Asn Asp Gly Phe Val Arg
1               5                   10                  15

<210> SEQ ID NO 327
<211> LENGTH: 17
<212> TYPE: PRT
<213> ORGANISM: Homo sapiens

<400> SEQUENCE: 327

Ser Thr Gly Glu Ala Phe Val Gln Phe Ala Ser Gln Glu Ile Ala Glu
1               5                   10                  15

Lys

<210> SEQ ID NO 328
<211> LENGTH: 26
<212> TYPE: PRT
<213> ORGANISM: Homo sapiens

<400> SEQUENCE: 328

Gly Ala Tyr Gly Gly Tyr Gly Gly Tyr Asp Asp Tyr Gly Gly Tyr
1               5                   10                  15

Asn Asp Gly Tyr Gly Phe Gly Ser Asp Arg
            20                  25

<210> SEQ ID NO 329
<211> LENGTH: 13
<212> TYPE: PRT
<213> ORGANISM: Homo sapiens

<400> SEQUENCE: 329

Asp Leu Asn Tyr Cys Phe Ser Gly Met Ser Asp His Arg
1               5                   10

<210> SEQ ID NO 330
<211> LENGTH: 17
<212> TYPE: PRT
<213> ORGANISM: Homo sapiens

<400> SEQUENCE: 330

Ala Thr Glu Asn Asp Ile Tyr Asn Phe Phe Ser Pro Leu Asn Pro Met
1               5                   10                  15

Arg

<210> SEQ ID NO 331
<211> LENGTH: 10
<212> TYPE: PRT
<213> ORGANISM: Homo sapiens

<400> SEQUENCE: 331

Val His Ile Glu Ile Gly Pro Asp Gly Arg
1               5                   10

<210> SEQ ID NO 332
<211> LENGTH: 16
<212> TYPE: PRT
<213> ORGANISM: Homo sapiens

<400> SEQUENCE: 332

His Thr Gly Pro Asn Ser Pro Asp Thr Ala Asn Asp Gly Phe Val Arg
1               5                   10                  15

<210> SEQ ID NO 333
<211> LENGTH: 31
<212> TYPE: PRT
<213> ORGANISM: Homo sapiens -continued

<400> SEQUENCE: 333

Gly Gly Asp Gly Tyr Asp Gly Tyr Gly Phe Asp Asp Tyr Gly
1               5                   10                  15
Gly Tyr Asn Asn Tyr Gly Tyr Gly Asn Asp Gly Phe Asp Asp Arg
            20                  25                  30

<210> SEQ ID NO 334
<211> LENGTH: 17
<212> TYPE: PRT
<213> ORGANISM: Homo sapiens

<400> SEQUENCE: 334

Ala Thr Glu Asn Asp Ile Ala Asn Phe Phe Ser Pro Leu Asn Pro Ile
1               5                   10                  15
Arg

<210> SEQ ID NO 335
<211> LENGTH: 26
<212> TYPE: PRT
<213> ORGANISM: Homo sapiens

<400> SEQUENCE: 335

Tyr Ile Glu Leu Phe Leu Asn Ser Thr Pro Gly Gly Ser Gly Met
1               5                   10                  15
Gly Gly Ser Gly Met Gly Gly Tyr Gly Arg
            20                  25

<210> SEQ ID NO 336
<211> LENGTH: 14
<212> TYPE: PRT
<213> ORGANISM: Homo sapiens

<400> SEQUENCE: 336

Asp Gly Met Asp Asn Gln Gly Gly Tyr Gly Ser Val Gly Arg
1               5                   10

<210> SEQ ID NO 337
<211> LENGTH: 20
<212> TYPE: PRT
<213> ORGANISM: Homo sapiens

<400> SEQUENCE: 337

Gly Gly Gly Gly Ser Gly Gly Tyr Tyr Gly Gln Gly Met Ser Gly
1               5                   10                  15
Gly Gly Trp Arg
            20

<210> SEQ ID NO 338
<211> LENGTH: 12
<212> TYPE: PRT
<213> ORGANISM: Homo sapiens

<400> SEQUENCE: 338

Ser Thr Gly Glu Ala Phe Val Gln Phe Ala Ser Lys
1               5                   10

<210> SEQ ID NO 339
<211> LENGTH: 11
<212> TYPE: PRT
<213> ORGANISM: Homo sapiens

<400> SEQUENCE: 339

```
Ile Asp Glu Pro Leu Glu Gly Ser Glu Asp Arg
1               5                   10

<210> SEQ ID NO 340
<211> LENGTH: 9
<212> TYPE: PRT
<213> ORGANISM: Homo sapiens

<400> SEQUENCE: 340

Asp Leu Ala Gly Ser Ile Ile Gly Lys
1               5

<210> SEQ ID NO 341
<211> LENGTH: 8
<212> TYPE: PRT
<213> ORGANISM: Homo sapiens

<400> SEQUENCE: 341

His Glu Ser Gly Ala Ser Ile Lys
1               5

<210> SEQ ID NO 342
<211> LENGTH: 23
<212> TYPE: PRT
<213> ORGANISM: Homo sapiens

<400> SEQUENCE: 342

Ile Ile Thr Ile Thr Gly Thr Gln Asp Gln Ile Gln Asn Ala Gln Tyr
1               5                   10                  15

Leu Leu Gln Asn Ser Val Lys
            20

<210> SEQ ID NO 343
<211> LENGTH: 17
<212> TYPE: PRT
<213> ORGANISM: Homo sapiens

<400> SEQUENCE: 343

Thr Asp Tyr Asn Ala Ser Val Ser Val Pro Asp Ser Ser Gly Pro Glu
1               5                   10                  15

Arg

<210> SEQ ID NO 344
<211> LENGTH: 16
<212> TYPE: PRT
<213> ORGANISM: Homo sapiens

<400> SEQUENCE: 344

Ile Leu Ser Ile Ser Ala Asp Ile Glu Thr Ile Gly Glu Ile Leu Lys
1               5                   10                  15

<210> SEQ ID NO 345
<211> LENGTH: 36
<212> TYPE: PRT
<213> ORGANISM: Homo sapiens

<400> SEQUENCE: 345

Ile Ile Pro Thr Leu Glu Glu Gly Leu Gln Leu Pro Ser Pro Thr Ala
1               5                   10                  15

Thr Ser Gln Leu Pro Leu Glu Ser Asp Ala Val Glu Cys Leu Asn Tyr
            20                  25                  30

Gln His Tyr Lys
        35
```

<210> SEQ ID NO 346
<211> LENGTH: 12
<212> TYPE: PRT
<213> ORGANISM: Homo sapiens

<400> SEQUENCE: 346

Leu Phe Gln Glu Cys Cys Pro His Ser Thr Asp Arg
1               5                   10

<210> SEQ ID NO 347
<211> LENGTH: 12
<212> TYPE: PRT
<213> ORGANISM: Homo sapiens

<400> SEQUENCE: 347

Ile Ile Leu Asp Leu Ile Ser Glu Ser Pro Ile Lys
1               5                   10

<210> SEQ ID NO 348
<211> LENGTH: 25
<212> TYPE: PRT
<213> ORGANISM: Homo sapiens

<400> SEQUENCE: 348

Ala Gln Pro Tyr Asp Pro Asn Phe Tyr Asp Glu Thr Tyr Asp Tyr Gly
1               5                   10                  15

Gly Phe Thr Met Met Phe Asp Asp Arg
            20                  25

<210> SEQ ID NO 349
<211> LENGTH: 8
<212> TYPE: PRT
<213> ORGANISM: Homo sapiens

<400> SEQUENCE: 349

Asp Tyr Asp Asp Met Ser Pro Arg
1               5

<210> SEQ ID NO 350
<211> LENGTH: 9
<212> TYPE: PRT
<213> ORGANISM: Homo sapiens

<400> SEQUENCE: 350

Gly Gly Asp Leu Met Ala Tyr Asp Arg
1               5

<210> SEQ ID NO 351
<211> LENGTH: 19
<212> TYPE: PRT
<213> ORGANISM: Homo sapiens

<400> SEQUENCE: 351

Gly Ser Tyr Gly Asp Leu Gly Gly Pro Ile Ile Thr Thr Gln Val Thr
1               5                   10                  15

Ile Pro Lys

<210> SEQ ID NO 352
<211> LENGTH: 29
<212> TYPE: PRT
<213> ORGANISM: Homo sapiens

<400> SEQUENCE: 352

```
Gly Leu Ile Asp Gly Val Val Glu Ala Asp Leu Val Glu Ala Leu Gln
1               5                   10                  15

Glu Phe Gly Pro Ile Ser Tyr Val Val Met Pro Lys
            20                  25
```

<210> SEQ ID NO 353
<211> LENGTH: 13
<212> TYPE: PRT
<213> ORGANISM: Homo sapiens

<400> SEQUENCE: 353

```
Val Phe Asn Val Phe Cys Leu Tyr Gly Asn Val Glu Lys
1               5                   10
```

<210> SEQ ID NO 354
<211> LENGTH: 10
<212> TYPE: PRT
<213> ORGANISM: Homo sapiens

<400> SEQUENCE: 354

```
Tyr Tyr Gly Gly Gly Ser Glu Gly Gly Arg
1               5                   10
```

<210> SEQ ID NO 355
<211> LENGTH: 17
<212> TYPE: PRT
<213> ORGANISM: Homo sapiens

<400> SEQUENCE: 355

```
Met Gly Gly Met Glu Gly Pro Phe Gly Gly Met Glu Asn Met Gly
1               5                   10                  15

Arg
```

<210> SEQ ID NO 356
<211> LENGTH: 12
<212> TYPE: PRT
<213> ORGANISM: Homo sapiens

<400> SEQUENCE: 356

```
Met Val Pro Ala Gly Met Gly Ala Gly Leu Glu Arg
1               5                   10
```

<210> SEQ ID NO 357
<211> LENGTH: 13
<212> TYPE: PRT
<213> ORGANISM: Homo sapiens

<400> SEQUENCE: 357

```
Leu Gly Ser Thr Val Phe Val Ala Asn Leu Asp Tyr Lys
1               5                   10
```

<210> SEQ ID NO 358
<211> LENGTH: 23
<212> TYPE: PRT
<213> ORGANISM: Homo sapiens

<400> SEQUENCE: 358

```
Gly Ile Gly Met Gly Asn Ile Gly Pro Ala Gly Met Gly Met Glu Gly
1               5                   10                  15

Ile Gly Phe Gly Ile Asn Lys
            20
```

```
<210> SEQ ID NO 359
<211> LENGTH: 7
<212> TYPE: PRT
<213> ORGANISM: Homo sapiens

<400> SEQUENCE: 359

Met Gly Leu Val Met Asp Arg
1               5

<210> SEQ ID NO 360
<211> LENGTH: 15
<212> TYPE: PRT
<213> ORGANISM: Homo sapiens

<400> SEQUENCE: 360

Met Gly Pro Leu Gly Leu Asp His Met Ala Ser Ser Ile Glu Arg
1               5                   10                  15

<210> SEQ ID NO 361
<211> LENGTH: 7
<212> TYPE: PRT
<213> ORGANISM: Homo sapiens

<400> SEQUENCE: 361

Met Gly Pro Val Met Asp Arg
1               5

<210> SEQ ID NO 362
<211> LENGTH: 7
<212> TYPE: PRT
<213> ORGANISM: Homo sapiens

<400> SEQUENCE: 362

Met Ala Thr Gly Leu Glu Arg
1               5

<210> SEQ ID NO 363
<211> LENGTH: 8
<212> TYPE: PRT
<213> ORGANISM: Homo sapiens

<400> SEQUENCE: 363

Met Gly Ala Asn Ser Leu Glu Arg
1               5

<210> SEQ ID NO 364
<211> LENGTH: 15
<212> TYPE: PRT
<213> ORGANISM: Homo sapiens

<400> SEQUENCE: 364

Met Gly Pro Ala Met Gly Pro Ala Leu Gly Ala Gly Ile Glu Arg
1               5                   10                  15

<210> SEQ ID NO 365
<211> LENGTH: 9
<212> TYPE: PRT
<213> ORGANISM: Homo sapiens

<400> SEQUENCE: 365

Phe Glu Ser Pro Glu Val Ala Glu Arg
1               5

<210> SEQ ID NO 366
<211> LENGTH: 16
```

<212> TYPE: PRT
<213> ORGANISM: Homo sapiens

<400> SEQUENCE: 366

Val Gly Glu Val Thr Tyr Val Glu Leu Leu Met Asp Ala Glu Gly Lys
1               5                   10                  15

<210> SEQ ID NO 367
<211> LENGTH: 8
<212> TYPE: PRT
<213> ORGANISM: Homo sapiens

<400> SEQUENCE: 367

Gly Cys Ala Val Val Glu Phe Lys
1               5

<210> SEQ ID NO 368
<211> LENGTH: 11
<212> TYPE: PRT
<213> ORGANISM: Homo sapiens

<400> SEQUENCE: 368

Met Gly Ala Gly Met Gly Phe Gly Leu Glu Arg
1               5                   10

<210> SEQ ID NO 369
<211> LENGTH: 25
<212> TYPE: PRT
<213> ORGANISM: Homo sapiens

<400> SEQUENCE: 369

Tyr Gly Gly Pro Pro Asp Ser Val Tyr Ser Gly Val Gln Pro Gly
1               5                   10                  15

Ile Gly Thr Glu Val Phe Val Gly Lys
            20                  25

<210> SEQ ID NO 370
<211> LENGTH: 24
<212> TYPE: PRT
<213> ORGANISM: Homo sapiens

<400> SEQUENCE: 370

Val Trp Gly Asn Val Val Thr Val Glu Trp Ala Asp Pro Val Glu Glu
1               5                   10                  15

Pro Asp Pro Glu Val Met Ala Lys
            20

<210> SEQ ID NO 371
<211> LENGTH: 13
<212> TYPE: PRT
<213> ORGANISM: Homo sapiens

<400> SEQUENCE: 371

Asn Leu Ala Thr Thr Val Thr Glu Glu Ile Leu Glu Lys
1               5                   10

<210> SEQ ID NO 372
<211> LENGTH: 14
<212> TYPE: PRT
<213> ORGANISM: Homo sapiens

<400> SEQUENCE: 372

Ser Thr Ala Tyr Glu Asp Tyr Tyr Tyr His Pro Pro Pro Arg
1               5                   10

```
<210> SEQ ID NO 373
<211> LENGTH: 20
<212> TYPE: PRT
<213> ORGANISM: Homo sapiens

<400> SEQUENCE: 373

Gly Leu Val Ala Val Ile Thr Gly Gly Ala Ser Gly Leu Gly Leu Ala
1               5                   10                  15

Thr Ala Glu Arg
            20

<210> SEQ ID NO 374
<211> LENGTH: 25
<212> TYPE: PRT
<213> ORGANISM: Homo sapiens

<400> SEQUENCE: 374

Gly Ala Ile Leu Asn Ile Ser Ser Gly Ser Gly Met Leu Pro Val Pro
1               5                   10                  15

Leu Leu Thr Ile Tyr Ser Ala Thr Lys
            20                  25

<210> SEQ ID NO 375
<211> LENGTH: 29
<212> TYPE: PRT
<213> ORGANISM: Homo sapiens

<400> SEQUENCE: 375

Val Trp Gly Val Gly Asn Glu Ala Gly Val Gly Pro Gly Leu Gly Glu
1               5                   10                  15

Trp Ala Val Val Thr Gly Ser Thr Asp Gly Ile Gly Lys
            20                  25

<210> SEQ ID NO 376
<211> LENGTH: 19
<212> TYPE: PRT
<213> ORGANISM: Homo sapiens

<400> SEQUENCE: 376

Ser Met Met Gly Gly Gly Leu Ala Glu Ile Pro Gly Leu Ser Ile Asn
1               5                   10                  15

Phe Ala Lys

<210> SEQ ID NO 377
<211> LENGTH: 12
<212> TYPE: PRT
<213> ORGANISM: Homo sapiens

<400> SEQUENCE: 377

Leu Gln Ser Thr Phe Val Phe Glu Glu Ile Gly Arg
1               5                   10

<210> SEQ ID NO 378
<211> LENGTH: 19
<212> TYPE: PRT
<213> ORGANISM: Homo sapiens

<400> SEQUENCE: 378

Val Phe Ile Met Asp Asn Cys Glu Glu Leu Ile Pro Glu Tyr Leu Asn
1               5                   10                  15

Phe Ile Arg
```

<210> SEQ ID NO 379
<211> LENGTH: 15
<212> TYPE: PRT
<213> ORGANISM: Homo sapiens

<400> SEQUENCE: 379

Asn Pro Asp Asp Ile Thr Asn Glu Glu Tyr Gly Glu Phe Tyr Lys
1               5                   10                  15

<210> SEQ ID NO 380
<211> LENGTH: 21
<212> TYPE: PRT
<213> ORGANISM: Homo sapiens

<400> SEQUENCE: 380

His Gly Leu Glu Val Ile Tyr Met Ile Glu Pro Ile Asp Glu Tyr Cys
1               5                   10                  15

Val Gln Gln Leu Lys
            20

<210> SEQ ID NO 381
<211> LENGTH: 34
<212> TYPE: PRT
<213> ORGANISM: Homo sapiens

<400> SEQUENCE: 381

Leu Gly Leu Gly Ile Asp Glu Asp Glu Val Ala Ala Glu Glu Pro Asn
1               5                   10                  15

Ala Ala Val Pro Asp Glu Ile Pro Pro Leu Glu Gly Asp Glu Asp Ala
            20                  25                  30

Ser Arg

<210> SEQ ID NO 382
<211> LENGTH: 8
<212> TYPE: PRT
<213> ORGANISM: Homo sapiens

<400> SEQUENCE: 382

Ala Gln Ala Tyr Gln Thr Gly Lys
1               5

<210> SEQ ID NO 383
<211> LENGTH: 10
<212> TYPE: PRT
<213> ORGANISM: Homo sapiens

<400> SEQUENCE: 383

Leu Gly Val Ile Glu Asp His Ser Asn Arg
1               5                   10

<210> SEQ ID NO 384
<211> LENGTH: 16
<212> TYPE: PRT
<213> ORGANISM: Homo sapiens

<400> SEQUENCE: 384

Glu Glu Glu Ala Ile Gln Leu Asp Gly Leu Asn Ala Ser Gln Ile Arg
1               5                   10                  15

<210> SEQ ID NO 385
<211> LENGTH: 14
<212> TYPE: PRT

```
<213> ORGANISM: Homo sapiens

<400> SEQUENCE: 385

Ala Phe Tyr Pro Glu Glu Ile Ser Ser Met Val Leu Thr Lys
1               5                   10

<210> SEQ ID NO 386
<211> LENGTH: 16
<212> TYPE: PRT
<213> ORGANISM: Homo sapiens

<400> SEQUENCE: 386

Ile Ile Asn Glu Pro Thr Ala Ala Ala Ile Ala Tyr Gly Leu Asp Arg
1               5                   10                  15

<210> SEQ ID NO 387
<211> LENGTH: 23
<212> TYPE: PRT
<213> ORGANISM: Homo sapiens

<400> SEQUENCE: 387

Ser Ile Asn Pro Asp Glu Ala Val Ala Tyr Gly Ala Ala Val Gln Ala
1               5                   10                  15

Ala Ile Leu Met Gly Asp Lys
            20

<210> SEQ ID NO 388
<211> LENGTH: 24
<212> TYPE: PRT
<213> ORGANISM: Homo sapiens

<400> SEQUENCE: 388

Gln Thr Gln Ile Phe Thr Thr Tyr Ser Asp Asn Gln Pro Gly Val Leu
1               5                   10                  15

Ile Gln Val Tyr Glu Gly Glu Arg
            20

<210> SEQ ID NO 389
<211> LENGTH: 31
<212> TYPE: PRT
<213> ORGANISM: Homo sapiens

<400> SEQUENCE: 389

Glu Leu Glu Gln Val Cys Asn Pro Ile Ile Ser Gly Leu Tyr Gln Gly
1               5                   10                  15

Ala Gly Gly Pro Gly Pro Gly Gly Phe Gly Ala Gln Gly Pro Lys
            20                  25                  30

<210> SEQ ID NO 390
<211> LENGTH: 16
<212> TYPE: PRT
<213> ORGANISM: Homo sapiens

<400> SEQUENCE: 390

Ile Glu Trp Leu Glu Ser His Gln Asp Ala Asp Ile Glu Asp Phe Lys
1               5                   10                  15

<210> SEQ ID NO 391
<211> LENGTH: 15
<212> TYPE: PRT
<213> ORGANISM: Homo sapiens

<400> SEQUENCE: 391
```

Asn Gln Leu Thr Ser Asn Pro Glu Asn Thr Val Phe Asp Ala Lys
1               5                   10                  15

<210> SEQ ID NO 392
<211> LENGTH: 18
<212> TYPE: PRT
<213> ORGANISM: Homo sapiens

<400> SEQUENCE: 392

Asp Asn His Leu Leu Gly Thr Phe Asp Leu Thr Gly Ile Pro Pro Ala
1               5                   10                  15

Pro Arg

<210> SEQ ID NO 393
<211> LENGTH: 14
<212> TYPE: PRT
<213> ORGANISM: Homo sapiens

<400> SEQUENCE: 393

Ile Thr Pro Ser Tyr Val Ala Phe Thr Pro Glu Gly Glu Arg
1               5                   10

<210> SEQ ID NO 394
<211> LENGTH: 24
<212> TYPE: PRT
<213> ORGANISM: Homo sapiens

<400> SEQUENCE: 394

Gln Thr Gln Thr Phe Thr Thr Tyr Ser Asp Asn Gln Pro Gly Val Leu
1               5                   10                  15

Ile Gln Val Tyr Glu Gly Glu Arg
                20

<210> SEQ ID NO 395
<211> LENGTH: 19
<212> TYPE: PRT
<213> ORGANISM: Homo sapiens

<400> SEQUENCE: 395

Ser Thr Asn Gly Asp Thr Phe Leu Gly Gly Glu Asp Phe Asp Gln Ala
1               5                   10                  15

Leu Leu Arg

<210> SEQ ID NO 396
<211> LENGTH: 8
<212> TYPE: PRT
<213> ORGANISM: Homo sapiens

<400> SEQUENCE: 396

Val Gly Glu Val Ile Val Thr Lys
1               5

<210> SEQ ID NO 397
<211> LENGTH: 13
<212> TYPE: PRT
<213> ORGANISM: Homo sapiens

<400> SEQUENCE: 397

Thr Leu Asn Asp Glu Leu Glu Ile Ile Glu Gly Met Lys
1               5                   10

<210> SEQ ID NO 398
<211> LENGTH: 12

<212> TYPE: PRT
<213> ORGANISM: Homo sapiens

<400> SEQUENCE: 398

Gly Tyr Ile Ser Pro Tyr Phe Ile Asn Thr Ser Lys
1               5                   10

<210> SEQ ID NO 399
<211> LENGTH: 18
<212> TYPE: PRT
<213> ORGANISM: Homo sapiens

<400> SEQUENCE: 399

Ile Ser Ser Ile Gln Ser Ile Val Pro Ala Leu Glu Ile Ala Asn Ala
1               5                   10                  15

His Arg

<210> SEQ ID NO 400
<211> LENGTH: 17
<212> TYPE: PRT
<213> ORGANISM: Homo sapiens

<400> SEQUENCE: 400

Ile Gln Glu Ile Ile Glu Gln Leu Asp Val Thr Thr Ser Glu Tyr Glu
1               5                   10                  15

Lys

<210> SEQ ID NO 401
<211> LENGTH: 23
<212> TYPE: PRT
<213> ORGANISM: Homo sapiens

<400> SEQUENCE: 401

Ile Met Gln Ser Ser Ser Glu Val Gly Tyr Asp Ala Met Ala Gly Asp
1               5                   10                  15

Phe Val Asn Met Val Glu Lys
            20

<210> SEQ ID NO 402
<211> LENGTH: 25
<212> TYPE: PRT
<213> ORGANISM: Homo sapiens

<400> SEQUENCE: 402

Leu Val Gln Asp Val Ala Asn Asn Thr Asn Glu Glu Ala Gly Asp Gly
1               5                   10                  15

Thr Thr Thr Ala Thr Val Leu Ala Arg
            20                  25

<210> SEQ ID NO 403
<211> LENGTH: 15
<212> TYPE: PRT
<213> ORGANISM: Homo sapiens

<400> SEQUENCE: 403

Ser Cys Gln Thr Ala Leu Val Glu Ile Leu Asp Val Ile Val Arg
1               5                   10                  15

<210> SEQ ID NO 404
<211> LENGTH: 11
<212> TYPE: PRT
<213> ORGANISM: Homo sapiens

```
<400> SEQUENCE: 404

Glu Leu Ser Asn Phe Tyr Phe Ser Ile Ile Lys
1               5                   10

<210> SEQ ID NO 405
<211> LENGTH: 13
<212> TYPE: PRT
<213> ORGANISM: Homo sapiens

<400> SEQUENCE: 405

Asn Leu Tyr Val Thr Phe Pro Ile Pro Asp Leu Gln Lys
1               5                   10

<210> SEQ ID NO 406
<211> LENGTH: 8
<212> TYPE: PRT
<213> ORGANISM: Homo sapiens

<400> SEQUENCE: 406

Trp Pro Leu Tyr Met Ser Thr Lys
1               5

<210> SEQ ID NO 407
<211> LENGTH: 29
<212> TYPE: PRT
<213> ORGANISM: Homo sapiens

<400> SEQUENCE: 407

Val Glu Ala Cys Val Leu Asp Glu Leu Asp Met Glu Leu Ala Phe Leu
1               5                   10                  15

Thr Ile Val Cys Met Glu Glu Phe Glu Asp Met Glu Arg
                20                  25

<210> SEQ ID NO 408
<211> LENGTH: 17
<212> TYPE: PRT
<213> ORGANISM: Homo sapiens

<400> SEQUENCE: 408

Thr Val Asn Glu Leu Gln Asn Leu Thr Ala Ala Glu Val Val Val Pro
1               5                   10                  15

Arg

<210> SEQ ID NO 409
<211> LENGTH: 28
<212> TYPE: PRT
<213> ORGANISM: Homo sapiens

<400> SEQUENCE: 409

Ile Leu Gly Gln Glu Gly Asp Ala Ser Tyr Leu Ala Ser Glu Ile Ser
1               5                   10                  15

Thr Trp Asp Gly Val Ile Val Thr Pro Ser Glu Lys
                20                  25

<210> SEQ ID NO 410
<211> LENGTH: 23
<212> TYPE: PRT
<213> ORGANISM: Homo sapiens

<400> SEQUENCE: 410

Ile Asn Asn Val Ile Asp Asn Leu Ile Val Ala Pro Gly Thr Phe Glu
1               5                   10                  15
```

Val Gln Ile Glu Glu Val Arg
            20

<210> SEQ ID NO 411
<211> LENGTH: 21
<212> TYPE: PRT
<213> ORGANISM: Homo sapiens

<400> SEQUENCE: 411

Glu Gln Val Pro Ser Leu Gly Ser Asn Val Ala Cys Gly Leu Ala Tyr
1               5                   10                  15

Thr Asp Tyr His Lys
            20

<210> SEQ ID NO 412
<211> LENGTH: 9
<212> TYPE: PRT
<213> ORGANISM: Homo sapiens

<400> SEQUENCE: 412

Val Gln Ala Ala Gln Ser Glu Ala Lys
1               5

<210> SEQ ID NO 413
<211> LENGTH: 19
<212> TYPE: PRT
<213> ORGANISM: Homo sapiens

<400> SEQUENCE: 413

Leu Ser Gln Glu Gln Val Asp Asn Phe Thr Leu Asp Ile Asn Thr Ala
1               5                   10                  15

Tyr Ala Arg

<210> SEQ ID NO 414
<211> LENGTH: 17
<212> TYPE: PRT
<213> ORGANISM: Homo sapiens

<400> SEQUENCE: 414

Gly Ile Glu Gln Ala Val Gln Ser His Ala Val Ala Glu Glu Ala
1               5                   10                  15

Arg

<210> SEQ ID NO 415
<211> LENGTH: 20
<212> TYPE: PRT
<213> ORGANISM: Homo sapiens

<400> SEQUENCE: 415

Leu Leu Asn Glu Thr Leu Gly Glu Val Gly Ser Pro Gly Leu Leu Phe
1               5                   10                  15

Tyr Ser Leu Arg
            20

<210> SEQ ID NO 416
<211> LENGTH: 15
<212> TYPE: PRT
<213> ORGANISM: Homo sapiens

<400> SEQUENCE: 416

Val Ala Ala Ala Glu Ser Met Pro Leu Leu Leu Glu Cys Ala Arg
1               5                   10                  15

<210> SEQ ID NO 417
<211> LENGTH: 17
<212> TYPE: PRT
<213> ORGANISM: Homo sapiens

<400> SEQUENCE: 417

Thr Met Gly Phe Cys Tyr Gln Ile Leu Thr Glu Pro Asn Ala Asp Pro
1               5                   10                  15

Arg

<210> SEQ ID NO 418
<211> LENGTH: 26
<212> TYPE: PRT
<213> ORGANISM: Homo sapiens

<400> SEQUENCE: 418

Val Leu Glu Val Thr Glu Glu Phe Gly Val His Leu Ala Glu Leu Thr
1               5                   10                  15

Val Asp Pro Gln Gly Ala Leu Ala Ile Arg
            20                  25

<210> SEQ ID NO 419
<211> LENGTH: 12
<212> TYPE: PRT
<213> ORGANISM: Homo sapiens

<400> SEQUENCE: 419

Leu Cys Leu Thr Asp Glu Glu Val Val Phe Val Arg
1               5                   10

<210> SEQ ID NO 420
<211> LENGTH: 18
<212> TYPE: PRT
<213> ORGANISM: Homo sapiens

<400> SEQUENCE: 420

Ile Gly Gln Gln Pro Gln Pro Gly Ala Pro Pro Gln Gln Asp Tyr
1               5                   10                  15

Thr Lys

<210> SEQ ID NO 421
<211> LENGTH: 24
<212> TYPE: PRT
<213> ORGANISM: Homo sapiens

<400> SEQUENCE: 421

Val Ser Leu Leu Glu Ile Tyr Asn Glu Glu Leu Phe Asp Leu Leu Asn
1               5                   10                  15

Pro Ser Ser Asp Val Ser Glu Arg
            20

<210> SEQ ID NO 422
<211> LENGTH: 25
<212> TYPE: PRT
<213> ORGANISM: Homo sapiens

<400> SEQUENCE: 422

Tyr Gly Ala Val Asp Pro Leu Leu Ala Leu Leu Ala Val Pro Asp Met
1               5                   10                  15

Ser Ser Leu Ala Cys Gly Tyr Leu Arg
            20                  25

<210> SEQ ID NO 423
<211> LENGTH: 15
<212> TYPE: PRT
<213> ORGANISM: Homo sapiens

<400> SEQUENCE: 423

Leu Leu Gly Ala Ser Glu Leu Pro Ile Val Thr Pro Ala Leu Arg
1               5                   10                  15

<210> SEQ ID NO 424
<211> LENGTH: 16
<212> TYPE: PRT
<213> ORGANISM: Homo sapiens

<400> SEQUENCE: 424

Gly Ala Leu Gln Tyr Leu Val Pro Ile Leu Thr Gln Thr Leu Thr Lys
1               5                   10                  15

<210> SEQ ID NO 425
<211> LENGTH: 15
<212> TYPE: PRT
<213> ORGANISM: Homo sapiens

<400> SEQUENCE: 425

Ala Ala Val Glu Asn Leu Pro Thr Phe Leu Val Glu Leu Ser Arg
1               5                   10                  15

<210> SEQ ID NO 426
<211> LENGTH: 12
<212> TYPE: PRT
<213> ORGANISM: Homo sapiens

<400> SEQUENCE: 426

Ser Ser Ala Tyr Glu Ser Leu Met Glu Ile Val Lys
1               5                   10

<210> SEQ ID NO 427
<211> LENGTH: 12
<212> TYPE: PRT
<213> ORGANISM: Homo sapiens

<400> SEQUENCE: 427

Gly Ile Leu Thr Val Asp Glu Leu Leu Ala Ile Arg
1               5                   10

<210> SEQ ID NO 428
<211> LENGTH: 11
<212> TYPE: PRT
<213> ORGANISM: Homo sapiens

<400> SEQUENCE: 428

Ile Leu Asp Leu Gln Leu Glu Phe Asp Glu Lys
1               5                   10

<210> SEQ ID NO 429
<211> LENGTH: 12
<212> TYPE: PRT
<213> ORGANISM: Homo sapiens

<400> SEQUENCE: 429

Val Ala Glu Val Glu Gly Glu Gln Val Asp Asn Lys
1               5                   10

<210> SEQ ID NO 430

<211> LENGTH: 20
<212> TYPE: PRT
<213> ORGANISM: Homo sapiens

<400> SEQUENCE: 430

Ala Leu Met Leu Cys Glu Gly Leu Phe Val Ala Asp Val Thr Asp Phe
1               5                   10                  15

Glu Gly Trp Lys
            20

<210> SEQ ID NO 431
<211> LENGTH: 16
<212> TYPE: PRT
<213> ORGANISM: Homo sapiens

<400> SEQUENCE: 431

Glu Leu Cys Gly Asn Leu Cys Phe Leu Leu Cys Gly Phe Asn Glu Arg
1               5                   10                  15

<210> SEQ ID NO 432
<211> LENGTH: 10
<212> TYPE: PRT
<213> ORGANISM: Homo sapiens

<400> SEQUENCE: 432

Ile Thr Glu Ser Glu Glu Val Val Ser Arg
1               5                   10

<210> SEQ ID NO 433
<211> LENGTH: 9
<212> TYPE: PRT
<213> ORGANISM: Homo sapiens

<400> SEQUENCE: 433

Leu Glu Ala Ala Leu Gly Glu Ala Lys
1               5

<210> SEQ ID NO 434
<211> LENGTH: 8
<212> TYPE: PRT
<213> ORGANISM: Homo sapiens

<400> SEQUENCE: 434

Asn Ile Tyr Ser Glu Glu Leu Arg
1               5

<210> SEQ ID NO 435
<211> LENGTH: 16
<212> TYPE: PRT
<213> ORGANISM: Homo sapiens

<400> SEQUENCE: 435

Asn Ser Asn Leu Val Gly Ala Ala His Glu Glu Leu Gln Gln Ser Arg
1               5                   10                  15

<210> SEQ ID NO 436
<211> LENGTH: 10
<212> TYPE: PRT
<213> ORGANISM: Homo sapiens

<400> SEQUENCE: 436

Ile Gln Glu Leu Glu Asp Leu Leu Ala Lys
1               5                   10

<210> SEQ ID NO 437
<211> LENGTH: 11
<212> TYPE: PRT
<213> ORGANISM: Homo sapiens

<400> SEQUENCE: 437

Ala Leu Tyr Glu Thr Glu Leu Ala Asp Ala Arg
1               5                   10

<210> SEQ ID NO 438
<211> LENGTH: 17
<212> TYPE: PRT
<213> ORGANISM: Homo sapiens

<400> SEQUENCE: 438

Asp Gln Met Gln Gln Gln Leu Asn Asp Tyr Glu Gln Leu Leu Asp Val
1               5                   10                  15

Lys

<210> SEQ ID NO 439
<211> LENGTH: 11
<212> TYPE: PRT
<213> ORGANISM: Homo sapiens

<400> SEQUENCE: 439

Ser Met Tyr Glu Glu Glu Ile Asn Glu Thr Arg
1               5                   10

<210> SEQ ID NO 440
<211> LENGTH: 16
<212> TYPE: PRT
<213> ORGANISM: Homo sapiens

<400> SEQUENCE: 440

Ser Leu Glu Thr Glu Asn Ser Ala Leu Gln Leu Gln Val Thr Glu Arg
1               5                   10                  15

<210> SEQ ID NO 441
<211> LENGTH: 8
<212> TYPE: PRT
<213> ORGANISM: Homo sapiens

<400> SEQUENCE: 441

Ala Glu Leu Asp Glu Val Asn Lys
1               5

<210> SEQ ID NO 442
<211> LENGTH: 11
<212> TYPE: PRT
<213> ORGANISM: Homo sapiens

<400> SEQUENCE: 442

Ala Leu Tyr Glu Ser Glu Leu Ala Asp Ala Arg
1               5                   10

<210> SEQ ID NO 443
<211> LENGTH: 12
<212> TYPE: PRT
<213> ORGANISM: Homo sapiens

<400> SEQUENCE: 443

Ser Glu Val Glu Leu Ala Ala Ala Leu Ser Asp Lys
1               5                   10

```
<210> SEQ ID NO 444
<211> LENGTH: 35
<212> TYPE: PRT
<213> ORGANISM: Homo sapiens

<400> SEQUENCE: 444

Gly Tyr Gln Gly Asp Pro Ser Ser Ala Leu Leu Glu Leu Leu Asp Pro
1               5                   10                  15

Glu Gln Asn Ala Asn Phe Leu Asp His Tyr Leu Asp Val Pro Val Asp
            20                  25                  30

Leu Ser Lys
        35

<210> SEQ ID NO 445
<211> LENGTH: 25
<212> TYPE: PRT
<213> ORGANISM: Homo sapiens

<400> SEQUENCE: 445

Val Thr Glu Leu Gln Gln Gln Pro Leu Cys Thr Ser Val Asn Thr Ile
1               5                   10                  15

Tyr Asp Asn Ala Val Gln Gly Leu Arg
            20                  25

<210> SEQ ID NO 446
<211> LENGTH: 15
<212> TYPE: PRT
<213> ORGANISM: Homo sapiens

<400> SEQUENCE: 446

Glu Leu Val Asp Tyr Phe Leu Asn Val Ala Thr Ala Gln Gly Arg
1               5                   10                  15

<210> SEQ ID NO 447
<211> LENGTH: 25
<212> TYPE: PRT
<213> ORGANISM: Homo sapiens

<400> SEQUENCE: 447

Ala Thr Phe Asp Pro Asp Thr Gly Leu Leu Met Glu Ile Met Asn Met
1               5                   10                  15

Asn Gln Gln Leu Leu Leu Pro Val Arg
            20                  25

<210> SEQ ID NO 448
<211> LENGTH: 23
<212> TYPE: PRT
<213> ORGANISM: Homo sapiens

<400> SEQUENCE: 448

Ala Ala Val Pro Ala Trp Glu Ala Val Glu Met Glu Ile Val Ala Gly
1               5                   10                  15

Gln Leu Val Thr Glu Ile Arg
            20

<210> SEQ ID NO 449
<211> LENGTH: 19
<212> TYPE: PRT
<213> ORGANISM: Homo sapiens

<400> SEQUENCE: 449

Asn Ile Glu Leu Ile Cys Gln Glu Asn Glu Gly Glu Asn Asp Pro Val
1               5                   10                  15
```

Leu Gln Arg

<210> SEQ ID NO 450
<211> LENGTH: 24
<212> TYPE: PRT
<213> ORGANISM: Homo sapiens

<400> SEQUENCE: 450

Glu Glu Gly Ser Glu Gln Ala Pro Leu Met Ser Glu Asp Glu Leu Ile
1               5                   10                  15

Asn Ile Ile Asp Gly Val Leu Arg
            20

<210> SEQ ID NO 451
<211> LENGTH: 11
<212> TYPE: PRT
<213> ORGANISM: Homo sapiens

<400> SEQUENCE: 451

Val Met Leu Glu Ser Phe Ile Asp Thr Gln Lys
1               5                   10

<210> SEQ ID NO 452
<211> LENGTH: 15
<212> TYPE: PRT
<213> ORGANISM: Homo sapiens

<400> SEQUENCE: 452

Ala Glu Ile Asn Ile Leu Leu Cys Gly Asp Pro Gly Thr Ser Lys
1               5                   10                  15

<210> SEQ ID NO 453
<211> LENGTH: 13
<212> TYPE: PRT
<213> ORGANISM: Homo sapiens

<400> SEQUENCE: 453

Ser Gln Leu Leu Gln Tyr Val Tyr Asn Leu Val Pro Arg
1               5                   10

<210> SEQ ID NO 454
<211> LENGTH: 27
<212> TYPE: PRT
<213> ORGANISM: Homo sapiens

<400> SEQUENCE: 454

Asn Thr Leu Val Val Ser Phe Val Asp Leu Glu Gln Phe Asn Gln Gln
1               5                   10                  15

Leu Ser Thr Thr Ile Gln Glu Glu Phe Tyr Arg
            20                  25

<210> SEQ ID NO 455
<211> LENGTH: 15
<212> TYPE: PRT
<213> ORGANISM: Homo sapiens

<400> SEQUENCE: 455

Thr Leu Met Met Phe Val Thr Val Ser Gly Ser Pro Thr Glu Lys
1               5                   10                  15

<210> SEQ ID NO 456
<211> LENGTH: 12
<212> TYPE: PRT

-continued

<213> ORGANISM: Homo sapiens

<400> SEQUENCE: 456

Val Thr Cys Ile Asp Pro Asn Pro Asn Phe Glu Lys
1               5                   10

<210> SEQ ID NO 457
<211> LENGTH: 12
<212> TYPE: PRT
<213> ORGANISM: Homo sapiens

<400> SEQUENCE: 457

Ser Gly Ala Ser Glu Ala Asn Leu Ile Val Ala Lys
1               5                   10

<210> SEQ ID NO 458
<211> LENGTH: 9
<212> TYPE: PRT
<213> ORGANISM: Homo sapiens

<400> SEQUENCE: 458

Gln Asp Gly Ser Thr Ile His Ile Arg
1               5

<210> SEQ ID NO 459
<211> LENGTH: 24
<212> TYPE: PRT
<213> ORGANISM: Homo sapiens

<400> SEQUENCE: 459

Ala Leu Glu Leu Glu Glu Phe Gln Tyr Ile Gly Glu Ser Gln Gly Tyr
1               5                   10                  15

Asp Ile Met Glu Pro Ala Ala Lys
            20

<210> SEQ ID NO 460
<211> LENGTH: 10
<212> TYPE: PRT
<213> ORGANISM: Homo sapiens

<400> SEQUENCE: 460

Val Val Leu Pro Ile Glu Ala Pro Ile Arg
1               5                   10

<210> SEQ ID NO 461
<211> LENGTH: 9
<212> TYPE: PRT
<213> ORGANISM: Homo sapiens

<400> SEQUENCE: 461

Trp Ala Ile Ile Glu Glu Phe Thr Lys
1               5

<210> SEQ ID NO 462
<211> LENGTH: 39
<212> TYPE: PRT
<213> ORGANISM: Homo sapiens

<400> SEQUENCE: 462

Met Asp Gly Gly Ser Gly Gly Leu Gly Ser Gly Asp Asn Ala Pro Thr
1               5                   10                  15

Thr Glu Ala Leu Phe Val Ala Leu Gly Ala Gly Val Thr Ala Leu Ser
            20                  25                  30

His Pro Leu Leu Tyr Val Lys
        35

<210> SEQ ID NO 463
<211> LENGTH: 16
<212> TYPE: PRT
<213> ORGANISM: Homo sapiens

<400> SEQUENCE: 463

Ser Trp Gln Asp Glu Leu Ala Gln Gln Ala Glu Glu Gly Ser Ala Arg
1               5                   10                  15

<210> SEQ ID NO 464
<211> LENGTH: 12
<212> TYPE: PRT
<213> ORGANISM: Homo sapiens

<400> SEQUENCE: 464

Thr Glu Leu Gly Leu Asp Leu Gly Leu Glu Pro Lys
1               5                   10

<210> SEQ ID NO 465
<211> LENGTH: 13
<212> TYPE: PRT
<213> ORGANISM: Homo sapiens

<400> SEQUENCE: 465

Tyr Leu Gly Tyr Ala Asn Glu Val Gly Glu Ala Phe Arg
1               5                   10

<210> SEQ ID NO 466
<211> LENGTH: 14
<212> TYPE: PRT
<213> ORGANISM: Homo sapiens

<400> SEQUENCE: 466

Val Cys Ala Ala Ser Leu Tyr Val Leu Gly Thr Ala Thr Arg
1               5                   10

<210> SEQ ID NO 467
<211> LENGTH: 20
<212> TYPE: PRT
<213> ORGANISM: Homo sapiens

<400> SEQUENCE: 467

Ile His Phe Gly Gly Leu Ile Glu Glu Asp Val Ile Leu Leu Ala
1               5                   10                  15

Ala Ala Leu Arg
            20

<210> SEQ ID NO 468
<211> LENGTH: 15
<212> TYPE: PRT
<213> ORGANISM: Homo sapiens

<400> SEQUENCE: 468

Gln Gly Ala Asp Thr Leu Ala Phe Met Ser Leu Leu Glu Glu Lys
1               5                   10                  15

<210> SEQ ID NO 469
<211> LENGTH: 17
<212> TYPE: PRT
<213> ORGANISM: Homo sapiens

<400> SEQUENCE: 469

-continued

Thr Gln Leu Glu Glu Leu Glu Asp Glu Leu Gln Ala Thr Glu Asp Ala
1               5                   10                  15

Lys

<210> SEQ ID NO 470
<211> LENGTH: 18
<212> TYPE: PRT
<213> ORGANISM: Homo sapiens

<400> SEQUENCE: 470

Ser Leu Glu Ala Glu Ile Leu Gln Leu Gln Glu Glu Leu Ala Ser Ser
1               5                   10                  15

Glu Arg

<210> SEQ ID NO 471
<211> LENGTH: 21
<212> TYPE: PRT
<213> ORGANISM: Homo sapiens

<400> SEQUENCE: 471

Ile Ala Gln Leu Glu Glu Glu Leu Glu Glu Gln Ser Asn Met Glu
1               5                   10                  15

Leu Leu Asn Asp Arg
            20

<210> SEQ ID NO 472
<211> LENGTH: 9
<212> TYPE: PRT
<213> ORGANISM: Homo sapiens

<400> SEQUENCE: 472

Ala Thr Ile Ser Ala Leu Glu Ala Lys
1               5

<210> SEQ ID NO 473
<211> LENGTH: 21
<212> TYPE: PRT
<213> ORGANISM: Homo sapiens

<400> SEQUENCE: 473

Ile Asn Phe Asp Val Thr Gly Tyr Ile Val Gly Ala Asn Ile Glu Thr
1               5                   10                  15

Tyr Leu Leu Glu Lys
            20

<210> SEQ ID NO 474
<211> LENGTH: 21
<212> TYPE: PRT
<213> ORGANISM: Homo sapiens

<400> SEQUENCE: 474

Asn Ile Leu Ala Glu Gln Leu Gln Ala Glu Thr Glu Leu Phe Ala Glu
1               5                   10                  15

Ala Glu Glu Met Arg
            20

<210> SEQ ID NO 475
<211> LENGTH: 17
<212> TYPE: PRT
<213> ORGANISM: Homo sapiens

<400> SEQUENCE: 475

```
Thr Gln Leu Glu Glu Leu Glu Asp Glu Leu Gln Ala Thr Glu Asp Ala
1               5                   10                  15

Lys

<210> SEQ ID NO 476
<211> LENGTH: 18
<212> TYPE: PRT
<213> ORGANISM: Homo sapiens

<400> SEQUENCE: 476

Ser Met Glu Ala Glu Met Ile Gln Leu Gln Glu Glu Leu Ala Ala Ala
1               5                   10                  15

Glu Arg

<210> SEQ ID NO 477
<211> LENGTH: 21
<212> TYPE: PRT
<213> ORGANISM: Homo sapiens

<400> SEQUENCE: 477

Asn Leu Gln Thr Cys Met Glu Val Leu Glu Ala Leu Tyr Asp Gly Ser
1               5                   10                  15

Leu Gly Asp Cys Lys
            20

<210> SEQ ID NO 478
<211> LENGTH: 15
<212> TYPE: PRT
<213> ORGANISM: Homo sapiens

<400> SEQUENCE: 478

Gln Ala Val Gln Glu Leu Val Ser Leu Tyr Tyr Glu Glu Ala Arg
1               5                   10                  15

<210> SEQ ID NO 479
<211> LENGTH: 22
<212> TYPE: PRT
<213> ORGANISM: Homo sapiens

<400> SEQUENCE: 479

Ala Gly Gly Val Leu Ala Tyr Glu Leu Leu Pro Ala Leu Asp Glu Val
1               5                   10                  15

Leu Ala Ser Asp Ser Arg
            20

<210> SEQ ID NO 480
<211> LENGTH: 10
<212> TYPE: PRT
<213> ORGANISM: Homo sapiens

<400> SEQUENCE: 480

Phe Tyr Glu Glu Val His Asp Leu Glu Arg
1               5                   10

<210> SEQ ID NO 481
<211> LENGTH: 18
<212> TYPE: PRT
<213> ORGANISM: Homo sapiens

<400> SEQUENCE: 481

Asn Val Asp Leu Leu Ser Asp Met Val Gln Glu His Asp Glu Pro Ile
1               5                   10                  15
```

Leu Lys

<210> SEQ ID NO 482
<211> LENGTH: 17
<212> TYPE: PRT
<213> ORGANISM: Homo sapiens

<400> SEQUENCE: 482

Leu Asp Gly Leu Val Glu Thr Pro Thr Gly Tyr Ile Glu Ser Leu Pro
1               5                   10                  15

Arg

<210> SEQ ID NO 483
<211> LENGTH: 10
<212> TYPE: PRT
<213> ORGANISM: Homo sapiens

<400> SEQUENCE: 483

Phe Tyr Glu Glu Val His Asp Leu Glu Arg
1               5                   10

<210> SEQ ID NO 484
<211> LENGTH: 24
<212> TYPE: PRT
<213> ORGANISM: Homo sapiens

<400> SEQUENCE: 484

Ser Leu Gln Glu Asn Glu Glu Glu Ile Gly Asn Leu Glu Leu Ala
1               5                   10                  15

Trp Asp Met Leu Asp Leu Ala Lys
            20

<210> SEQ ID NO 485
<211> LENGTH: 17
<212> TYPE: PRT
<213> ORGANISM: Homo sapiens

<400> SEQUENCE: 485

Tyr Gly Glu Thr Ala Asn Glu Cys Gly Glu Ala Phe Phe Phe Tyr Gly
1               5                   10                  15

Lys

<210> SEQ ID NO 486
<211> LENGTH: 26
<212> TYPE: PRT
<213> ORGANISM: Homo sapiens

<400> SEQUENCE: 486

Ala Ser Gly Asp Leu Ile Pro Trp Thr Val Ser Glu Gln Phe Gln Asp
1               5                   10                  15

Pro Asp Phe Gly Gly Leu Ser Gly Gly Arg
            20                  25

<210> SEQ ID NO 487
<211> LENGTH: 24
<212> TYPE: PRT
<213> ORGANISM: Homo sapiens

<400> SEQUENCE: 487

Ser Ala Cys Ser Leu Glu Ser Asn Leu Glu Gly Leu Ala Gly Val Leu
1               5                   10                  15

Glu Ala Asp Leu Pro Asn Tyr Lys
            20

<210> SEQ ID NO 488
<211> LENGTH: 14
<212> TYPE: PRT
<213> ORGANISM: Homo sapiens

<400> SEQUENCE: 488

Gly Leu Leu Thr Tyr Thr Ser Trp Glu Asp Ala Leu Ser Arg
1               5                   10

<210> SEQ ID NO 489
<211> LENGTH: 10
<212> TYPE: PRT
<213> ORGANISM: Homo sapiens

<400> SEQUENCE: 489

Gly Ala Pro Tyr Asn Ala Leu Thr Gly Lys
1               5                   10

<210> SEQ ID NO 490
<211> LENGTH: 12
<212> TYPE: PRT
<213> ORGANISM: Homo sapiens

<400> SEQUENCE: 490

Gln Gln Ile Gln Ser Ile Gln Gln Ser Ile Glu Arg
1               5                   10

<210> SEQ ID NO 491
<211> LENGTH: 14
<212> TYPE: PRT
<213> ORGANISM: Homo sapiens

<400> SEQUENCE: 491

Gly Trp Asp Glu Asn Val Tyr Tyr Thr Val Pro Leu Val Arg
1               5                   10

<210> SEQ ID NO 492
<211> LENGTH: 16
<212> TYPE: PRT
<213> ORGANISM: Homo sapiens

<400> SEQUENCE: 492

Val Ser Phe Gly Val Ser Glu Gln Gln Ala Val Glu Ala Trp Glu Lys
1               5                   10                  15

<210> SEQ ID NO 493
<211> LENGTH: 9
<212> TYPE: PRT
<213> ORGANISM: Homo sapiens

<400> SEQUENCE: 493

Val Glu Leu Asp Asn Met Pro Leu Arg
1               5

<210> SEQ ID NO 494
<211> LENGTH: 14
<212> TYPE: PRT
<213> ORGANISM: Homo sapiens

<400> SEQUENCE: 494

Phe Ala Gln Pro Gly Ser Phe Glu Tyr Glu Tyr Ala Met Arg
1               5                   10

```
<210> SEQ ID NO 495
<211> LENGTH: 9
<212> TYPE: PRT
<213> ORGANISM: Homo sapiens

<400> SEQUENCE: 495

Leu Glu Met Glu Met Glu Ala Ala Arg
1               5

<210> SEQ ID NO 496
<211> LENGTH: 23
<212> TYPE: PRT
<213> ORGANISM: Homo sapiens

<400> SEQUENCE: 496

Asn Leu Pro Gln Tyr Val Ser Asn Glu Leu Leu Glu Glu Ala Phe Ser
1               5                   10                  15

Val Phe Gly Gln Val Glu Arg
            20

<210> SEQ ID NO 497
<211> LENGTH: 8
<212> TYPE: PRT
<213> ORGANISM: Homo sapiens

<400> SEQUENCE: 497

Ala Val Val Ile Val Asp Asp Arg
1               5

<210> SEQ ID NO 498
<211> LENGTH: 11
<212> TYPE: PRT
<213> ORGANISM: Homo sapiens

<400> SEQUENCE: 498

Met Glu Glu Leu His Asn Gln Glu Val Gln Lys
1               5                   10

<210> SEQ ID NO 499
<211> LENGTH: 22
<212> TYPE: PRT
<213> ORGANISM: Homo sapiens

<400> SEQUENCE: 499

Phe Gly Gln Ala Ala Thr Met Glu Gly Ile Gly Ala Ile Gly Gly Thr
1               5                   10                  15

Pro Pro Ala Phe Asn Arg
            20

<210> SEQ ID NO 500
<211> LENGTH: 14
<212> TYPE: PRT
<213> ORGANISM: Homo sapiens

<400> SEQUENCE: 500

Met Thr Asp Gln Glu Ala Ile Gln Asp Leu Trp Gln Trp Arg
1               5                   10

<210> SEQ ID NO 501
<211> LENGTH: 13
<212> TYPE: PRT
<213> ORGANISM: Homo sapiens
```

<400> SEQUENCE: 501

Val Asp Asn Asp Glu Asn Glu His Gln Leu Ser Leu Arg
1               5                   10

<210> SEQ ID NO 502
<211> LENGTH: 16
<212> TYPE: PRT
<213> ORGANISM: Homo sapiens

<400> SEQUENCE: 502

Leu Ala Gln Glu Gly Ile Tyr Thr Leu Tyr Pro Phe Ile Asn Ser Arg
1               5                   10                  15

<210> SEQ ID NO 503
<211> LENGTH: 19
<212> TYPE: PRT
<213> ORGANISM: Homo sapiens

<400> SEQUENCE: 503

Asp Asn Met Ala Gln Glu Gly Val Ile Leu Asp Asp Val Asp Ser Ser
1               5                   10                  15

Val Cys Arg

<210> SEQ ID NO 504
<211> LENGTH: 16
<212> TYPE: PRT
<213> ORGANISM: Homo sapiens

<400> SEQUENCE: 504

Tyr Leu Gln Glu Val Ile Asp Val Leu Glu Thr Asp Gly His Phe Arg
1               5                   10                  15

<210> SEQ ID NO 505
<211> LENGTH: 10
<212> TYPE: PRT
<213> ORGANISM: Homo sapiens

<400> SEQUENCE: 505

Gln Val Ile Asp Val Leu Glu Thr Asp Lys
1               5                   10

<210> SEQ ID NO 506
<211> LENGTH: 24
<212> TYPE: PRT
<213> ORGANISM: Homo sapiens

<400> SEQUENCE: 506

Glu Ser His Pro Ala Thr Val Phe Ile Leu Phe Ser Asp Leu Asn Pro
1               5                   10                  15

Leu Val Thr Leu Gly Gly Asn Lys
            20

<210> SEQ ID NO 507
<211> LENGTH: 30
<212> TYPE: PRT
<213> ORGANISM: Homo sapiens

<400> SEQUENCE: 507

Glu Pro Pro Pro Val Tyr Pro Asp Leu Ala Glu Val Val Gly Tyr Gln
1               5                   10                  15

Trp Ser Ser Pro Ser Glu Ala Thr Glu Ser Phe Leu Ser Lys
            20                  25                  30

```
<210> SEQ ID NO 508
<211> LENGTH: 17
<212> TYPE: PRT
<213> ORGANISM: Homo sapiens

<400> SEQUENCE: 508

His Gly Glu Pro Glu Glu Asp Ile Val Gly Leu Gln Ala Phe Gln Glu
1               5                   10                  15

Arg

<210> SEQ ID NO 509
<211> LENGTH: 24
<212> TYPE: PRT
<213> ORGANISM: Homo sapiens

<400> SEQUENCE: 509

Ala Ala Glu Gln Ile Leu Glu Asp Met Ile Thr Ile Asp Val Glu Asn
1               5                   10                  15

Val Met Glu Asp Ile Cys Ser Lys
            20

<210> SEQ ID NO 510
<211> LENGTH: 18
<212> TYPE: PRT
<213> ORGANISM: Homo sapiens

<400> SEQUENCE: 510

Val Leu Val Ala Glu Val Asn Ala Leu Gln Gly Met Ala Ala Ile Gly
1               5                   10                  15

Gln Arg

<210> SEQ ID NO 511
<211> LENGTH: 14
<212> TYPE: PRT
<213> ORGANISM: Homo sapiens

<400> SEQUENCE: 511

Thr Thr Leu Leu Glu Gly Phe Ala Gly Val Glu Glu Ala Arg
1               5                   10

<210> SEQ ID NO 512
<211> LENGTH: 15
<212> TYPE: PRT
<213> ORGANISM: Homo sapiens

<400> SEQUENCE: 512

Glu Gly Gln Glu Ile Ala Ser Val Ser Asp Asp His Thr Cys Arg
1               5                   10                  15

<210> SEQ ID NO 513
<211> LENGTH: 7
<212> TYPE: PRT
<213> ORGANISM: Homo sapiens

<400> SEQUENCE: 513

Phe Glu Ser Thr Asp Pro Arg
1               5

<210> SEQ ID NO 514
<211> LENGTH: 16
<212> TYPE: PRT
<213> ORGANISM: Homo sapiens
```

<400> SEQUENCE: 514

Ala Asp Glu Asp Pro Ile Met Gly Phe His Gln Met Phe Leu Leu Lys
1               5                   10                  15

<210> SEQ ID NO 515
<211> LENGTH: 20
<212> TYPE: PRT
<213> ORGANISM: Homo sapiens

<400> SEQUENCE: 515

Asp Tyr Thr Asn Leu Pro Glu Ala Ala Pro Leu Leu Thr Ile Leu Asp
1               5                   10                  15

Met Ser Ala Arg
            20

<210> SEQ ID NO 516
<211> LENGTH: 14
<212> TYPE: PRT
<213> ORGANISM: Homo sapiens

<400> SEQUENCE: 516

Thr Val Gln Gly Pro Pro Thr Ser Asp Asp Ile Phe Glu Arg
1               5                   10

<210> SEQ ID NO 517
<211> LENGTH: 20
<212> TYPE: PRT
<213> ORGANISM: Homo sapiens

<400> SEQUENCE: 517

Val Ala Ile Ala Ala Leu Glu Val Leu Glu Glu Asn Leu Ala Glu
1               5                   10                  15

Asn Ala Asp Lys
            20

<210> SEQ ID NO 518
<211> LENGTH: 13
<212> TYPE: PRT
<213> ORGANISM: Homo sapiens

<400> SEQUENCE: 518

Val Phe Ala Glu Cys Asn Asp Glu Ser Phe Trp Phe Arg
1               5                   10

<210> SEQ ID NO 519
<211> LENGTH: 18
<212> TYPE: PRT
<213> ORGANISM: Homo sapiens

<400> SEQUENCE: 519

Cys Asn Glu Glu His Pro Ala Tyr Leu Ala Ser Asp Glu Ile Thr Thr
1               5                   10                  15

Val Arg

<210> SEQ ID NO 520
<211> LENGTH: 30
<212> TYPE: PRT
<213> ORGANISM: Homo sapiens

<400> SEQUENCE: 520

Thr Gly Pro Ala Ala Thr Thr Leu Pro Asp Gly Ala Ala Ala Glu Ser
1               5                   10                  15

-continued

Leu Val Glu Ser Ser Glu Val Ala Val Ile Gly Phe Phe Lys
            20                  25                  30

<210> SEQ ID NO 521
<211> LENGTH: 25
<212> TYPE: PRT
<213> ORGANISM: Homo sapiens

<400> SEQUENCE: 521

Gln Phe Leu Gln Ala Ala Glu Ala Ile Asp Asp Ile Pro Phe Gly Ile
1               5                   10                  15

Thr Ser Asn Ser Asp Val Phe Ser Lys
            20                  25

<210> SEQ ID NO 522
<211> LENGTH: 17
<212> TYPE: PRT
<213> ORGANISM: Homo sapiens

<400> SEQUENCE: 522

His Asn Gln Leu Pro Leu Val Ile Glu Phe Thr Glu Gln Thr Ala Pro
1               5                   10                  15

Lys

<210> SEQ ID NO 523
<211> LENGTH: 16
<212> TYPE: PRT
<213> ORGANISM: Homo sapiens

<400> SEQUENCE: 523

Ala Leu Tyr Asp Thr Phe Ser Ala Phe Gly Asn Ile Leu Ser Cys Lys
1               5                   10                  15

<210> SEQ ID NO 524
<211> LENGTH: 17
<212> TYPE: PRT
<213> ORGANISM: Homo sapiens

<400> SEQUENCE: 524

Ser Leu Gly Tyr Ala Tyr Val Asn Phe Gln Gln Pro Ala Asp Ala Glu
1               5                   10                  15

Arg

<210> SEQ ID NO 525
<211> LENGTH: 24
<212> TYPE: PRT
<213> ORGANISM: Homo sapiens

<400> SEQUENCE: 525

Ile Thr Gly Met Leu Leu Glu Ile Asp Asn Ser Glu Leu Leu His Met
1               5                   10                  15

Leu Glu Ser Pro Glu Ser Leu Arg
            20

<210> SEQ ID NO 526
<211> LENGTH: 17
<212> TYPE: PRT
<213> ORGANISM: Homo sapiens

<400> SEQUENCE: 526

Ser Leu Gly Tyr Ala Tyr Val Asn Phe Gln Gln Pro Ala Asp Ala Glu
1               5                   10                  15

Arg

<210> SEQ ID NO 527
<211> LENGTH: 24
<212> TYPE: PRT
<213> ORGANISM: Homo sapiens

<400> SEQUENCE: 527

Ile Thr Gly Met Leu Leu Glu Ile Asp Asn Ser Glu Leu Leu His Met
1               5                   10                  15

Leu Glu Ser Pro Glu Ser Leu Arg
            20

<210> SEQ ID NO 528
<211> LENGTH: 16
<212> TYPE: PRT
<213> ORGANISM: Homo sapiens

<400> SEQUENCE: 528

Ala Leu Tyr Asp Thr Phe Ser Ala Phe Gly Asn Ile Leu Ser Cys Lys
1               5                   10                  15

<210> SEQ ID NO 529
<211> LENGTH: 18
<212> TYPE: PRT
<213> ORGANISM: Homo sapiens

<400> SEQUENCE: 529

Val Glu Met Leu Asp Asn Leu Leu Asp Ile Glu Val Ala Tyr Ser Leu
1               5                   10                  15

Leu Arg

<210> SEQ ID NO 530
<211> LENGTH: 47
<212> TYPE: PRT
<213> ORGANISM: Homo sapiens

<400> SEQUENCE: 530

Thr Thr Pro Asp Pro Ser Ala Asn Ile Ser Leu Asp Gly Val Asp Val
1               5                   10                  15

Pro Leu Gly Thr Gly Ile Ser Ser Gly Val Asn Asp Thr Ser Leu Leu
            20                  25                  30

Tyr Asn Glu Tyr Ile Val Tyr Asp Ile Ala Gln Val Asn Leu Lys
        35                  40                  45

<210> SEQ ID NO 531
<211> LENGTH: 17
<212> TYPE: PRT
<213> ORGANISM: Homo sapiens

<400> SEQUENCE: 531

Glu Ile Ile Ser Phe Gly Ser Gly Tyr Gly Gly Asn Ser Leu Leu Gly
1               5                   10                  15

Lys

<210> SEQ ID NO 532
<211> LENGTH: 21
<212> TYPE: PRT
<213> ORGANISM: Homo sapiens

<400> SEQUENCE: 532

Leu Met Asp Leu Asp Val Glu Gln Leu Gly Ile Pro Glu Gln Glu Tyr
1               5                   10                  15

```
1               5                   10                  15
Ser Cys Val Val Lys
            20

<210> SEQ ID NO 533
<211> LENGTH: 14
<212> TYPE: PRT
<213> ORGANISM: Homo sapiens

<400> SEQUENCE: 533

Ser Asn Leu Ile Ser Gly Ser Val Met Tyr Ile Glu Glu Lys
1               5                   10

<210> SEQ ID NO 534
<211> LENGTH: 13
<212> TYPE: PRT
<213> ORGANISM: Homo sapiens

<400> SEQUENCE: 534

Met Tyr Glu Val Val Tyr Gln Ile Gly Thr Glu Thr Arg
1               5                   10

<210> SEQ ID NO 535
<211> LENGTH: 11
<212> TYPE: PRT
<213> ORGANISM: Homo sapiens

<400> SEQUENCE: 535

Met His Met Trp Val Glu Asp Val Leu Asp Lys
1               5                   10

<210> SEQ ID NO 536
<211> LENGTH: 18
<212> TYPE: PRT
<213> ORGANISM: Homo sapiens

<400> SEQUENCE: 536

Ile Ala Ile Ile Gly Ala Gly Ile Gly Gly Thr Ser Ala Ala Tyr Tyr
1               5                   10                  15

Leu Arg

<210> SEQ ID NO 537
<211> LENGTH: 11
<212> TYPE: PRT
<213> ORGANISM: Homo sapiens

<400> SEQUENCE: 537

Asp Leu Pro Glu Leu Ala Leu Asp Thr Pro Arg
1               5                   10

<210> SEQ ID NO 538
<211> LENGTH: 14
<212> TYPE: PRT
<213> ORGANISM: Homo sapiens

<400> SEQUENCE: 538

Phe Ala Met Glu Pro Glu Glu Phe Asp Ser Asp Thr Leu Arg
1               5                   10

<210> SEQ ID NO 539
<211> LENGTH: 20
<212> TYPE: PRT
<213> ORGANISM: Homo sapiens
```

-continued

<400> SEQUENCE: 539

Ser Ile Glu Gly Thr Ala Asp Asp Glu Glu Gly Val Ser Pro Asp
1               5                   10                  15

Thr Ala Ile Arg
            20

<210> SEQ ID NO 540
<211> LENGTH: 18
<212> TYPE: PRT
<213> ORGANISM: Homo sapiens

<400> SEQUENCE: 540

Asn Gln Leu Asp Gln Glu Val Glu Phe Leu Ser Thr Ser Ile Ala Gln
1               5                   10                  15

Leu Lys

<210> SEQ ID NO 541
<211> LENGTH: 16
<212> TYPE: PRT
<213> ORGANISM: Homo sapiens

<400> SEQUENCE: 541

Thr Phe Val Asn Ile Thr Pro Ala Glu Val Gly Val Leu Val Gly Lys
1               5                   10                  15

<210> SEQ ID NO 542
<211> LENGTH: 14
<212> TYPE: PRT
<213> ORGANISM: Homo sapiens

<400> SEQUENCE: 542

Asp Ser Leu Leu Gln Asp Gly Glu Phe Ser Met Asp Leu Arg
1               5                   10

<210> SEQ ID NO 543
<211> LENGTH: 14
<212> TYPE: PRT
<213> ORGANISM: Homo sapiens

<400> SEQUENCE: 543

Phe Tyr Gly Pro Glu Gly Pro Tyr Gly Val Phe Ala Gly Arg
1               5                   10

<210> SEQ ID NO 544
<211> LENGTH: 20
<212> TYPE: PRT
<213> ORGANISM: Homo sapiens

<400> SEQUENCE: 544

Gly Asp Gln Pro Ala Ala Ser Gly Asp Ser Asp Asp Glu Pro Pro
1               5                   10                  15

Pro Leu Pro Arg
            20

<210> SEQ ID NO 545
<211> LENGTH: 14
<212> TYPE: PRT
<213> ORGANISM: Homo sapiens

<400> SEQUENCE: 545

Phe Tyr Gly Pro Ala Gly Pro Tyr Gly Ile Phe Ala Gly Arg
1               5                   10

<210> SEQ ID NO 546
<211> LENGTH: 20
<212> TYPE: PRT
<213> ORGANISM: Homo sapiens

<400> SEQUENCE: 546

Ala Ala Glu Leu Ile Ala Asn Ser Leu Ala Thr Ala Gly Asp Gly Leu
1               5                   10                  15

Ile Glu Leu Arg
            20

<210> SEQ ID NO 547
<211> LENGTH: 13
<212> TYPE: PRT
<213> ORGANISM: Homo sapiens

<400> SEQUENCE: 547

Leu Glu Ala Ala Glu Asp Ile Ala Tyr Gln Leu Ser Arg
1               5                   10

<210> SEQ ID NO 548
<211> LENGTH: 7
<212> TYPE: PRT
<213> ORGANISM: Homo sapiens

<400> SEQUENCE: 548

Val Phe Glu Ser Ile Gly Lys
1               5

<210> SEQ ID NO 549
<211> LENGTH: 11
<212> TYPE: PRT
<213> ORGANISM: Homo sapiens

<400> SEQUENCE: 549

Glu Ser Val Phe Thr Val Glu Gly Gly His Arg
1               5                   10

<210> SEQ ID NO 550
<211> LENGTH: 17
<212> TYPE: PRT
<213> ORGANISM: Homo sapiens

<400> SEQUENCE: 550

Ile Gly Gly Val Gln Gln Asp Thr Ile Leu Ala Glu Gly Leu His Phe
1               5                   10                  15

Arg

<210> SEQ ID NO 551
<211> LENGTH: 12
<212> TYPE: PRT
<213> ORGANISM: Homo sapiens

<400> SEQUENCE: 551

Ile Val Gln Ala Glu Gly Glu Ala Glu Ala Ala Lys
1               5                   10

<210> SEQ ID NO 552
<211> LENGTH: 14
<212> TYPE: PRT
<213> ORGANISM: Homo sapiens

<400> SEQUENCE: 552

Cys Gly Glu Glu Ile Ala Val Gln Phe Val Asp Met Val Lys
1               5                   10

<210> SEQ ID NO 553
<211> LENGTH: 13
<212> TYPE: PRT
<213> ORGANISM: Homo sapiens

<400> SEQUENCE: 553

Asn Glu Thr Gly Gly Gly Glu Gly Ile Glu Val Leu Lys
1               5                   10

<210> SEQ ID NO 554
<211> LENGTH: 22
<212> TYPE: PRT
<213> ORGANISM: Homo sapiens

<400> SEQUENCE: 554

Ala Leu Ile Glu Ser Gly Leu Gly Thr Asp Phe Ser Pro Asp Val Gly
1               5                   10                  15

Tyr Asn Gly Tyr Thr Arg
            20

<210> SEQ ID NO 555
<211> LENGTH: 29
<212> TYPE: PRT
<213> ORGANISM: Homo sapiens

<400> SEQUENCE: 555

Ala Thr Tyr Ile Gly Thr Ser Asn Trp Ser Gly Asn Tyr Phe Thr Glu
1               5                   10                  15

Thr Ala Gly Thr Ser Leu Leu Val Thr Gln Asn Gly Arg
            20                  25

<210> SEQ ID NO 556
<211> LENGTH: 14
<212> TYPE: PRT
<213> ORGANISM: Homo sapiens

<400> SEQUENCE: 556

Ile Ser Phe Asp Glu Phe Val Tyr Ile Phe Gln Glu Val Lys
1               5                   10

<210> SEQ ID NO 557
<211> LENGTH: 9
<212> TYPE: PRT
<213> ORGANISM: Homo sapiens

<400> SEQUENCE: 557

Pro Val Ile Phe Glu Asp Val Gly Arg
1               5

<210> SEQ ID NO 558
<211> LENGTH: 19
<212> TYPE: PRT
<213> ORGANISM: Homo sapiens

<400> SEQUENCE: 558

Thr Asn Met Leu Leu Gln Leu Asp Gly Ser Thr Pro Ile Cys Glu Asp
1               5                   10                  15

Ile Gly Arg

<210> SEQ ID NO 559

<211> LENGTH: 34
<212> TYPE: PRT
<213> ORGANISM: Homo sapiens

<400> SEQUENCE: 559

Ala Leu Tyr Ala Ile Pro Gly Leu Asp Tyr Val Ser His Glu Asp Ile
1               5                   10                  15

Leu Pro Tyr Thr Ser Thr Asp Gln Val Pro Ile Gln His Glu Leu Phe
            20                  25                  30

Glu Arg

<210> SEQ ID NO 560
<211> LENGTH: 21
<212> TYPE: PRT
<213> ORGANISM: Homo sapiens

<400> SEQUENCE: 560

Met Leu Leu Gln Val Leu Gln Ala Leu Pro Ala Gln Gly Glu Ser Phe
1               5                   10                  15

Thr Thr Leu Ala Arg
            20

<210> SEQ ID NO 561
<211> LENGTH: 17
<212> TYPE: PRT
<213> ORGANISM: Homo sapiens

<400> SEQUENCE: 561

Ile Trp Ser Glu Pro Phe Tyr Gln Glu Thr Tyr Leu Pro Tyr Met Ile
1               5                   10                  15

Arg

<210> SEQ ID NO 562
<211> LENGTH: 25
<212> TYPE: PRT
<213> ORGANISM: Homo sapiens

<400> SEQUENCE: 562

Leu Gly Leu Ser Tyr Thr Pro Leu Ala Glu Val Gly Leu Asn Ala Leu
1               5                   10                  15

Glu Glu Trp Ser Ile Tyr Ile Asp Arg
            20                  25

<210> SEQ ID NO 563
<211> LENGTH: 12
<212> TYPE: PRT
<213> ORGANISM: Homo sapiens

<400> SEQUENCE: 563

Asp Val Asp Phe Met Tyr Val Glu Leu Ile Gln Arg
1               5                   10

<210> SEQ ID NO 564
<211> LENGTH: 11
<212> TYPE: PRT
<213> ORGANISM: Homo sapiens

<400> SEQUENCE: 564

Ala Thr Leu Tyr Val Thr Ala Ile Glu Asp Arg
1               5                   10

<210> SEQ ID NO 565

-continued

```
<211> LENGTH: 17
<212> TYPE: PRT
<213> ORGANISM: Homo sapiens

<400> SEQUENCE: 565

Ala Leu Gln Asp Glu Trp Asp Ala Val Met Leu His Ser Phe Thr Leu
1               5                   10                  15

Arg

<210> SEQ ID NO 566
<211> LENGTH: 15
<212> TYPE: PRT
<213> ORGANISM: Homo sapiens

<400> SEQUENCE: 566

Glu Ile Val Asp Ser Tyr Leu Pro Val Ile Leu Asp Ile Ile Lys
1               5                   10                  15

<210> SEQ ID NO 567
<211> LENGTH: 13
<212> TYPE: PRT
<213> ORGANISM: Homo sapiens

<400> SEQUENCE: 567

Glu Ile Cys Ala Leu Val Gly Phe Cys Asp Glu Val Lys
1               5                   10

<210> SEQ ID NO 568
<211> LENGTH: 13
<212> TYPE: PRT
<213> ORGANISM: Homo sapiens

<400> SEQUENCE: 568

Ser Asp Val Tyr Cys Glu Val Cys Glu Phe Leu Val Lys
1               5                   10

<210> SEQ ID NO 569
<211> LENGTH: 9
<212> TYPE: PRT
<213> ORGANISM: Homo sapiens

<400> SEQUENCE: 569

Gln Glu Ile Leu Ala Ala Leu Glu Lys
1               5

<210> SEQ ID NO 570
<211> LENGTH: 11
<212> TYPE: PRT
<213> ORGANISM: Homo sapiens

<400> SEQUENCE: 570

Gly Cys Ser Phe Leu Pro Asp Pro Tyr Gln Lys
1               5                   10

<210> SEQ ID NO 571
<211> LENGTH: 29
<212> TYPE: PRT
<213> ORGANISM: Homo sapiens

<400> SEQUENCE: 571

Gln Cys Asp Gln Phe Val Ala Glu Tyr Glu Pro Val Leu Ile Glu Ile
1               5                   10                  15

Leu Val Glu Val Met Asp Pro Ser Phe Val Cys Leu Lys
                20                  25
```

-continued

<210> SEQ ID NO 572
<211> LENGTH: 11
<212> TYPE: PRT
<213> ORGANISM: Homo sapiens

<400> SEQUENCE: 572

Asp Val Val Thr Ala Ala Gly Asp Met Leu Lys
1               5                   10

<210> SEQ ID NO 573
<211> LENGTH: 16
<212> TYPE: PRT
<213> ORGANISM: Homo sapiens

<400> SEQUENCE: 573

Pro Tyr Leu Phe Gln Ser Asp Pro Ser Gly Ala Tyr Phe Ala Trp Lys
1               5                   10                  15

<210> SEQ ID NO 574
<211> LENGTH: 21
<212> TYPE: PRT
<213> ORGANISM: Homo sapiens

<400> SEQUENCE: 574

Leu Val Gln Ile Glu Tyr Ala Leu Ala Ala Val Ala Gly Gly Ala Pro
1               5                   10                  15

Ser Val Gly Ile Lys
            20

<210> SEQ ID NO 575
<211> LENGTH: 24
<212> TYPE: PRT
<213> ORGANISM: Homo sapiens

<400> SEQUENCE: 575

Leu Asn Glu Asp Met Ala Cys Ser Val Ala Gly Ile Thr Ser Asp Ala
1               5                   10                  15

Asn Val Leu Thr Asn Glu Leu Arg
            20

<210> SEQ ID NO 576
<211> LENGTH: 18
<212> TYPE: PRT
<213> ORGANISM: Homo sapiens

<400> SEQUENCE: 576

Phe Phe Pro Tyr Tyr Val Tyr Asn Ile Ile Gly Gly Leu Asp Glu Glu
1               5                   10                  15

Gly Lys

<210> SEQ ID NO 577
<211> LENGTH: 31
<212> TYPE: PRT
<213> ORGANISM: Homo sapiens

<400> SEQUENCE: 577

Thr Pro Tyr His Val Asn Leu Leu Leu Ala Gly Tyr Asp Glu His Glu
1               5                   10                  15

Gly Pro Ala Leu Tyr Tyr Met Asp Tyr Leu Ala Ala Leu Ala Lys
            20                  25                  30

<210> SEQ ID NO 578
<211> LENGTH: 21
<212> TYPE: PRT
<213> ORGANISM: Homo sapiens

<400> SEQUENCE: 578

Ile Leu Leu Leu Cys Val Gly Glu Ala Gly Asp Thr Val Gln Phe Ala
1               5                   10                  15

Glu Tyr Ile Gln Lys
            20

<210> SEQ ID NO 579
<211> LENGTH: 16
<212> TYPE: PRT
<213> ORGANISM: Homo sapiens

<400> SEQUENCE: 579

Phe Gly Pro Tyr Tyr Thr Glu Pro Val Ile Ala Gly Leu Asp Pro Lys
1               5                   10                  15

<210> SEQ ID NO 580
<211> LENGTH: 12
<212> TYPE: PRT
<213> ORGANISM: Homo sapiens

<400> SEQUENCE: 580

Ala Leu Leu Val Glu Val Gln Leu Leu Glu Ser Lys
1               5                   10

<210> SEQ ID NO 581
<211> LENGTH: 20
<212> TYPE: PRT
<213> ORGANISM: Homo sapiens

<400> SEQUENCE: 581

Thr Ala Tyr Ser Tyr Phe Tyr Glu Ala Phe Glu Gly Tyr Asp Ser Ile
1               5                   10                  15

Asp Ser Pro Lys
            20

<210> SEQ ID NO 582
<211> LENGTH: 7
<212> TYPE: PRT
<213> ORGANISM: Homo sapiens

<400> SEQUENCE: 582

Ser Leu Ala Asp Phe Glu Lys
1               5

<210> SEQ ID NO 583
<211> LENGTH: 15
<212> TYPE: PRT
<213> ORGANISM: Homo sapiens

<400> SEQUENCE: 583

His Asp Ala Asp Gly Gln Ala Thr Leu Leu Asn Leu Leu Leu Arg
1               5                   10                  15

<210> SEQ ID NO 584
<211> LENGTH: 15
<212> TYPE: PRT
<213> ORGANISM: Homo sapiens

<400> SEQUENCE: 584

```
Leu Gln Leu Asp Ser Pro Glu Asp Ala Glu Phe Ile Val Ala Lys
1               5                   10                  15
```

<210> SEQ ID NO 585
<211> LENGTH: 14
<212> TYPE: PRT
<213> ORGANISM: Homo sapiens

<400> SEQUENCE: 585

```
Ile Glu Asp Gly Asn Asp Phe Gly Val Ala Ile Gln Glu Lys
1               5                   10
```

<210> SEQ ID NO 586
<211> LENGTH: 20
<212> TYPE: PRT
<213> ORGANISM: Homo sapiens

<400> SEQUENCE: 586

```
Ile Glu Asp Gly Asn Asn Phe Gly Val Ser Ile Gln Glu Glu Thr Val
1               5                   10                  15

Ala Glu Leu Arg
            20
```

<210> SEQ ID NO 587
<211> LENGTH: 15
<212> TYPE: PRT
<213> ORGANISM: Homo sapiens

<400> SEQUENCE: 587

```
Thr Val Glu Ser Glu Ala Ala Ser Tyr Leu Asp Gln Ile Ser Arg
1               5                   10                  15
```

<210> SEQ ID NO 588
<211> LENGTH: 15
<212> TYPE: PRT
<213> ORGANISM: Homo sapiens

<400> SEQUENCE: 588

```
Ile Thr Ser Glu Ala Glu Asp Leu Val Ala Asn Phe Phe Pro Lys
1               5                   10                  15
```

<210> SEQ ID NO 589
<211> LENGTH: 19
<212> TYPE: PRT
<213> ORGANISM: Homo sapiens

<400> SEQUENCE: 589

```
Pro Val Ile Val Glu Pro Met Glu Gln Phe Asp Glu Asp Gly Leu
1               5                   10                  15

Pro Glu Lys
```

<210> SEQ ID NO 590
<211> LENGTH: 20
<212> TYPE: PRT
<213> ORGANISM: Homo sapiens

<400> SEQUENCE: 590

```
Asn Asn Gln Phe Gln Ala Leu Leu Gln Tyr Ala Asp Pro Val Ser Ala
1               5                   10                  15

Gln His Ala Lys
            20
```

<210> SEQ ID NO 591

```
<211> LENGTH: 8
<212> TYPE: PRT
<213> ORGANISM: Homo sapiens

<400> SEQUENCE: 591

Phe Ile Ile Asn Ser Tyr Pro Lys
1               5

<210> SEQ ID NO 592
<211> LENGTH: 14
<212> TYPE: PRT
<213> ORGANISM: Homo sapiens

<400> SEQUENCE: 592

Gly Asp Phe Val Thr Ser Phe Tyr Trp Pro Trp Gln Thr Lys
1               5                   10

<210> SEQ ID NO 593
<211> LENGTH: 17
<212> TYPE: PRT
<213> ORGANISM: Homo sapiens

<400> SEQUENCE: 593

Asp Val Pro Tyr Pro Pro Pro Leu Ser Pro Ala Ile Glu Ala Ile Gln
1               5                   10                  15

Lys

<210> SEQ ID NO 594
<211> LENGTH: 14
<212> TYPE: PRT
<213> ORGANISM: Homo sapiens

<400> SEQUENCE: 594

Leu Glu Ser Glu Gly Ser Pro Glu Thr Leu Thr Asn Leu Arg
1               5                   10

<210> SEQ ID NO 595
<211> LENGTH: 16
<212> TYPE: PRT
<213> ORGANISM: Homo sapiens

<400> SEQUENCE: 595

Asp Ile Asp Asp Asp Leu Glu Gly Glu Val Thr Glu Glu Cys Gly Lys
1               5                   10                  15

<210> SEQ ID NO 596
<211> LENGTH: 22
<212> TYPE: PRT
<213> ORGANISM: Homo sapiens

<400> SEQUENCE: 596

Gly Ser Val Ala Gly Gly Ala Val Tyr Leu Val Tyr Asp Gln Glu Leu
1               5                   10                  15

Leu Gly Pro Ser Asp Lys
            20

<210> SEQ ID NO 597
<211> LENGTH: 14
<212> TYPE: PRT
<213> ORGANISM: Homo sapiens

<400> SEQUENCE: 597

Met Gln Leu Met Glu Leu Ala Ile Leu Asn Gly Thr Tyr Arg
1               5                   10
```

```
<210> SEQ ID NO 598
<211> LENGTH: 14
<212> TYPE: PRT
<213> ORGANISM: Homo sapiens

<400> SEQUENCE: 598

Tyr Glu His Ala Ser Phe Ile Pro Ser Cys Thr Pro Asp Arg
1               5                   10

<210> SEQ ID NO 599
<211> LENGTH: 20
<212> TYPE: PRT
<213> ORGANISM: Homo sapiens

<400> SEQUENCE: 599

Ser Ala Leu Thr Leu Gln Phe Met Tyr Asp Glu Phe Val Glu Asp Tyr
1               5                   10                  15

Glu Pro Thr Lys
            20

<210> SEQ ID NO 600
<211> LENGTH: 13
<212> TYPE: PRT
<213> ORGANISM: Homo sapiens

<400> SEQUENCE: 600

Gly Asn Thr Ala Ala Tyr Leu Leu Tyr Ala Phe Thr Arg
1               5                   10

<210> SEQ ID NO 601
<211> LENGTH: 15
<212> TYPE: PRT
<213> ORGANISM: Homo sapiens

<400> SEQUENCE: 601

Ala Ser Tyr Val Ala Pro Leu Thr Ala Gln Pro Ala Thr Tyr Arg
1               5                   10                  15

<210> SEQ ID NO 602
<211> LENGTH: 8
<212> TYPE: PRT
<213> ORGANISM: Homo sapiens

<400> SEQUENCE: 602

Ala Leu Val Val Glu Met Ser Arg
1               5

<210> SEQ ID NO 603
<211> LENGTH: 32
<212> TYPE: PRT
<213> ORGANISM: Homo sapiens

<400> SEQUENCE: 603

Leu Phe Val Gly Gly Leu Asn Phe Asn Thr Asp Glu Gln Ala Leu Glu
1               5                   10                  15

Asp His Phe Ser Ser Phe Gly Pro Ile Ser Glu Val Val Val Val Lys
                20                  25                  30

<210> SEQ ID NO 604
<211> LENGTH: 19
<212> TYPE: PRT
<213> ORGANISM: Homo sapiens
```

<400> SEQUENCE: 604

Gly Gly His Met Asp Asp Gly Gly Tyr Ser Met Asn Phe Asn Met Ser
1               5                   10                  15

Ser Ser Arg

<210> SEQ ID NO 605
<211> LENGTH: 8
<212> TYPE: PRT
<213> ORGANISM: Homo sapiens

<400> SEQUENCE: 605

Ala Leu Glu Ala Val Phe Gly Lys
1               5

<210> SEQ ID NO 606
<211> LENGTH: 8
<212> TYPE: PRT
<213> ORGANISM: Homo sapiens

<400> SEQUENCE: 606

Asp Tyr Gly His Ser Ser Ser Arg
1               5

<210> SEQ ID NO 607
<211> LENGTH: 10
<212> TYPE: PRT
<213> ORGANISM: Homo sapiens

<400> SEQUENCE: 607

Asp Ser Tyr Glu Ser Tyr Gly Asn Ser Arg
1               5                   10

<210> SEQ ID NO 608
<211> LENGTH: 11
<212> TYPE: PRT
<213> ORGANISM: Homo sapiens

<400> SEQUENCE: 608

Gly Pro Pro Pro Ser Tyr Gly Gly Ser Ser Arg
1               5                   10

<210> SEQ ID NO 609
<211> LENGTH: 8
<212> TYPE: PRT
<213> ORGANISM: Homo sapiens

<400> SEQUENCE: 609

Ser Asp Leu Tyr Ser Ser Gly Arg
1               5

<210> SEQ ID NO 610
<211> LENGTH: 14
<212> TYPE: PRT
<213> ORGANISM: Homo sapiens

<400> SEQUENCE: 610

Gly Phe Ala Phe Val Thr Phe Glu Ser Pro Ala Asp Ala Lys
1               5                   10

<210> SEQ ID NO 611
<211> LENGTH: 11
<212> TYPE: PRT
<213> ORGANISM: Homo sapiens

```
<400> SEQUENCE: 611

Gly Pro Pro Pro Ser Tyr Gly Gly Ser Ser Arg
1               5                   10

<210> SEQ ID NO 612
<211> LENGTH: 14
<212> TYPE: PRT
<213> ORGANISM: Homo sapiens

<400> SEQUENCE: 612

Gly Phe Ala Phe Val Thr Phe Glu Ser Pro Ala Asp Ala Lys
1               5                   10

<210> SEQ ID NO 613
<211> LENGTH: 8
<212> TYPE: PRT
<213> ORGANISM: Homo sapiens

<400> SEQUENCE: 613

Asp Tyr Gly His Ser Ser Ser Arg
1               5

<210> SEQ ID NO 614
<211> LENGTH: 10
<212> TYPE: PRT
<213> ORGANISM: Homo sapiens

<400> SEQUENCE: 614

Asp Ser Tyr Glu Ser Tyr Gly Asn Ser Arg
1               5                   10

<210> SEQ ID NO 615
<211> LENGTH: 19
<212> TYPE: PRT
<213> ORGANISM: Homo sapiens

<400> SEQUENCE: 615

Gly Gly His Met Asp Asp Gly Gly Tyr Ser Met Asn Phe Asn Met Ser
1               5                   10                  15

Ser Ser Arg

<210> SEQ ID NO 616
<211> LENGTH: 15
<212> TYPE: PRT
<213> ORGANISM: Homo sapiens

<400> SEQUENCE: 616

Ile Asp Asn Asp Gly Asp Gly Phe Val Thr Thr Glu Glu Leu Lys
1               5                   10                  15

<210> SEQ ID NO 617
<211> LENGTH: 23
<212> TYPE: PRT
<213> ORGANISM: Homo sapiens

<400> SEQUENCE: 617

Leu Ser Glu Glu Glu Ile Leu Glu Asn Pro Asp Leu Phe Leu Thr Ser
1               5                   10                  15

Glu Ala Thr Asp Tyr Gly Arg
                20

<210> SEQ ID NO 618
<211> LENGTH: 19
```

```
<212> TYPE: PRT
<213> ORGANISM: Homo sapiens

<400> SEQUENCE: 618

Val Ile Asp Phe Asp Glu Asn Thr Ala Leu Asp Asp Ala Glu Glu Glu
1               5                   10                  15

Ser Phe Arg

<210> SEQ ID NO 619
<211> LENGTH: 16
<212> TYPE: PRT
<213> ORGANISM: Homo sapiens

<400> SEQUENCE: 619

Trp Asp Pro Thr Ala Asn Glu Asp Pro Glu Trp Ile Leu Val Glu Lys
1               5                   10                  15

<210> SEQ ID NO 620
<211> LENGTH: 8
<212> TYPE: PRT
<213> ORGANISM: Homo sapiens

<400> SEQUENCE: 620

His Tyr Ala Met Gln Glu Ala Lys
1               5

<210> SEQ ID NO 621
<211> LENGTH: 40
<212> TYPE: PRT
<213> ORGANISM: Homo sapiens

<400> SEQUENCE: 621

Ala Asn Gln Asp Ser Gly Pro Gly Leu Ser Leu Glu Glu Phe Ile Ala
1               5                   10                  15

Phe Glu His Pro Glu Glu Val Asp Tyr Met Thr Glu Phe Val Ile Gln
                20                  25                  30

Glu Ala Leu Glu Glu His Asp Lys
        35                  40

<210> SEQ ID NO 622
<211> LENGTH: 20
<212> TYPE: PRT
<213> ORGANISM: Homo sapiens

<400> SEQUENCE: 622

Val Pro Tyr Thr Asp Asp Gly Leu Glu Ala Ile Ile Phe Thr Ala Gln
1               5                   10                  15

Gly Asp Met Arg
            20

<210> SEQ ID NO 623
<211> LENGTH: 11
<212> TYPE: PRT
<213> ORGANISM: Homo sapiens

<400> SEQUENCE: 623

Ser Glu Ile Glu Tyr Tyr Ala Met Leu Ala Lys
1               5                   10

<210> SEQ ID NO 624
<211> LENGTH: 16
<212> TYPE: PRT
<213> ORGANISM: Homo sapiens
```

```
<400> SEQUENCE: 624

Ala Ser Gly Asn Tyr Ala Thr Val Ile Ser His Asn Pro Glu Thr Lys
1               5                   10                  15

<210> SEQ ID NO 625
<211> LENGTH: 12
<212> TYPE: PRT
<213> ORGANISM: Homo sapiens

<400> SEQUENCE: 625

Asn Ile Glu Asp Val Ile Ala Gln Gly Ile Gly Lys
1               5                   10

<210> SEQ ID NO 626
<211> LENGTH: 18
<212> TYPE: PRT
<213> ORGANISM: Homo sapiens

<400> SEQUENCE: 626

Gln Phe Val Val Phe Glu Gly Asn His Tyr Phe Tyr Ser Pro Tyr Pro
1               5                   10                  15

Thr Lys

<210> SEQ ID NO 627
<211> LENGTH: 25
<212> TYPE: PRT
<213> ORGANISM: Homo sapiens

<400> SEQUENCE: 627

Thr His Tyr Ile Val Gly Tyr Asn Leu Pro Ser Tyr Glu Tyr Leu Tyr
1               5                   10                  15

Asn Leu Gly Asp Gln Tyr Ala Leu Lys
            20                  25

<210> SEQ ID NO 628
<211> LENGTH: 12
<212> TYPE: PRT
<213> ORGANISM: Homo sapiens

<400> SEQUENCE: 628

Ala Leu Thr Ser Glu Ile Ala Leu Leu Gln Ser Arg
1               5                   10

<210> SEQ ID NO 629
<211> LENGTH: 24
<212> TYPE: PRT
<213> ORGANISM: Homo sapiens

<400> SEQUENCE: 629

Glu Glu Thr Val Leu Ala Thr Val Gln Ala Leu Gln Thr Ala Ser His
1               5                   10                  15

Leu Ser Gln Gln Ala Asp Leu Arg
            20

<210> SEQ ID NO 630
<211> LENGTH: 12
<212> TYPE: PRT
<213> ORGANISM: Homo sapiens

<400> SEQUENCE: 630

Ser Ile Val Glu Glu Ile Glu Asp Leu Val Ala Arg
1               5                   10
```

<210> SEQ ID NO 631
<211> LENGTH: 14
<212> TYPE: PRT
<213> ORGANISM: Homo sapiens

<400> SEQUENCE: 631

Thr Gly Gln Glu Val Val Phe Val Ala Glu Pro Asp Asn Lys
1               5                   10

<210> SEQ ID NO 632
<211> LENGTH: 15
<212> TYPE: PRT
<213> ORGANISM: Homo sapiens

<400> SEQUENCE: 632

Asp Tyr Leu His Leu Pro Pro Glu Ile Val Pro Ala Thr Leu Arg
1               5                   10                  15

<210> SEQ ID NO 633
<211> LENGTH: 22
<212> TYPE: PRT
<213> ORGANISM: Homo sapiens

<400> SEQUENCE: 633

Phe Val Asp Gly Leu Met Ile His Ser Gly Asp Pro Val Asn Tyr Tyr
1               5                   10                  15

Val Asp Thr Ala Val Arg
            20

<210> SEQ ID NO 634
<211> LENGTH: 13
<212> TYPE: PRT
<213> ORGANISM: Homo sapiens

<400> SEQUENCE: 634

Glu Leu Ala Glu Asp Gly Tyr Ser Gly Val Glu Val Arg
1               5                   10

<210> SEQ ID NO 635
<211> LENGTH: 9
<212> TYPE: PRT
<213> ORGANISM: Homo sapiens

<400> SEQUENCE: 635

Thr Glu Ile Ile Ile Leu Ala Thr Arg
1               5

<210> SEQ ID NO 636
<211> LENGTH: 14
<212> TYPE: PRT
<213> ORGANISM: Homo sapiens

<400> SEQUENCE: 636

Phe Gly Phe Pro Glu Gly Ser Val Glu Leu Tyr Ala Glu Lys
1               5                   10

<210> SEQ ID NO 637
<211> LENGTH: 13
<212> TYPE: PRT
<213> ORGANISM: Homo sapiens

<400> SEQUENCE: 637

Ile Ser Ser Leu Leu Glu Glu Gln Phe Gln Gln Gly Lys

```
<210> SEQ ID NO 638
<211> LENGTH: 16
<212> TYPE: PRT
<213> ORGANISM: Homo sapiens

<400> SEQUENCE: 638

Ala Tyr Leu Glu Ser Glu Val Ala Ile Ser Glu Glu Leu Val Gln Lys
1               5                   10                  15

<210> SEQ ID NO 639
<211> LENGTH: 16
<212> TYPE: PRT
<213> ORGANISM: Homo sapiens

<400> SEQUENCE: 639

Ala Leu Glu Ser Ser Ile Ala Pro Ile Val Ile Phe Ala Ser Asn Arg
1               5                   10                  15

<210> SEQ ID NO 640
<211> LENGTH: 17
<212> TYPE: PRT
<213> ORGANISM: Homo sapiens

<400> SEQUENCE: 640

Val Pro Phe Cys Pro Met Val Gly Ser Glu Val Tyr Ser Thr Glu Ile
1               5                   10                  15

Lys

<210> SEQ ID NO 641
<211> LENGTH: 21
<212> TYPE: PRT
<213> ORGANISM: Homo sapiens

<400> SEQUENCE: 641

Leu Thr Gly Ser Tyr Asn Thr Met Val Gly Asn Asn Glu Gly Ser Met
1               5                   10                  15

Val Leu Gly Leu Lys
            20

<210> SEQ ID NO 642
<211> LENGTH: 23
<212> TYPE: PRT
<213> ORGANISM: Homo sapiens

<400> SEQUENCE: 642

Gly Val Tyr Ile Ile Gly Ser Ser Gly Phe Asp Ser Ile Pro Ala Asp
1               5                   10                  15

Leu Gly Val Ile Tyr Thr Arg
            20

<210> SEQ ID NO 643
<211> LENGTH: 20
<212> TYPE: PRT
<213> ORGANISM: Homo sapiens

<400> SEQUENCE: 643

Ala Glu Met Ile Ile Glu Gln Asn Thr Asp Gly Val Asn Phe Tyr Asn
1               5                   10                  15

Ile Leu Thr Lys
            20
```

<210> SEQ ID NO 644
<211> LENGTH: 32
<212> TYPE: PRT
<213> ORGANISM: Homo sapiens

<400> SEQUENCE: 644

Ile Pro Asn Phe Trp Val Thr Thr Phe Val Asn His Pro Gln Val Ser
1               5                   10                  15
Ala Leu Leu Gly Glu Glu Asp Glu Glu Ala Leu His Tyr Leu Thr Arg
            20                  25                  30

<210> SEQ ID NO 645
<211> LENGTH: 23
<212> TYPE: PRT
<213> ORGANISM: Homo sapiens

<400> SEQUENCE: 645

Asn Leu Ser Pro Tyr Val Ser Asn Glu Leu Leu Glu Glu Ala Phe Ser
1               5                   10                  15
Gln Phe Gly Pro Ile Glu Arg
            20

<210> SEQ ID NO 646
<211> LENGTH: 19
<212> TYPE: PRT
<213> ORGANISM: Homo sapiens

<400> SEQUENCE: 646

Pro Val Ile Val Glu Pro Leu Glu Gln Leu Asp Asp Glu Asp Gly Leu
1               5                   10                  15
Pro Glu Lys

<210> SEQ ID NO 647
<211> LENGTH: 13
<212> TYPE: PRT
<213> ORGANISM: Homo sapiens

<400> SEQUENCE: 647

Asn Ile Leu Leu Thr Asn Glu Gln Leu Glu Ser Ala Arg
1               5                   10

<210> SEQ ID NO 648
<211> LENGTH: 34
<212> TYPE: PRT
<213> ORGANISM: Homo sapiens

<400> SEQUENCE: 648

Ser Gly Asp Ala Pro Leu Thr Val Asn Glu Leu Gly Thr Ala Tyr Val
1               5                   10                  15
Ser Ala Thr Thr Gly Ala Val Ala Thr Ala Leu Gly Leu Asn Ala Leu
            20                  25                  30
Thr Lys

<210> SEQ ID NO 649
<211> LENGTH: 15
<212> TYPE: PRT
<213> ORGANISM: Homo sapiens

<400> SEQUENCE: 649

Gln Gly Ile Val Pro Pro Gly Leu Thr Glu Asn Glu Leu Trp Arg
1               5                   10                  15

```
<210> SEQ ID NO 650
<211> LENGTH: 20
<212> TYPE: PRT
<213> ORGANISM: Homo sapiens

<400> SEQUENCE: 650

Met Ser Ala Gln Val Pro Met Asn Met Thr Ile Thr Gly Cys Met Met
1               5                   10                  15

Thr Phe Tyr Arg
            20

<210> SEQ ID NO 651
<211> LENGTH: 20
<212> TYPE: PRT
<213> ORGANISM: Homo sapiens

<400> SEQUENCE: 651

Ile Leu Met Ala Ala Pro Gly Met Ala Ile Pro Pro Phe Ile Met Asn
1               5                   10                  15

Thr Leu Glu Lys
            20

<210> SEQ ID NO 652
<211> LENGTH: 24
<212> TYPE: PRT
<213> ORGANISM: Homo sapiens

<400> SEQUENCE: 652

Phe Leu Gln Trp Thr Glu Leu Leu Asp Pro Thr Asn Val Phe Ile Ser
1               5                   10                  15

Val Glu Ser Ile Glu Asn Ser Arg
            20

<210> SEQ ID NO 653
<211> LENGTH: 15
<212> TYPE: PRT
<213> ORGANISM: Homo sapiens

<400> SEQUENCE: 653

Ala Phe Glu Pro Tyr Leu Glu Ile Leu Glu Val Tyr Ser Thr Lys
1               5                   10                  15

<210> SEQ ID NO 654
<211> LENGTH: 8
<212> TYPE: PRT
<213> ORGANISM: Homo sapiens

<400> SEQUENCE: 654

Ala Val Gln Phe Thr Glu Glu Lys
1               5

<210> SEQ ID NO 655
<211> LENGTH: 17
<212> TYPE: PRT
<213> ORGANISM: Homo sapiens

<400> SEQUENCE: 655

Tyr Tyr Gly Gly Ala Glu Val Val Asp Glu Ile Glu Leu Leu Cys Gln
1               5                   10                  15

Arg

<210> SEQ ID NO 656
```

```
<211> LENGTH: 16
<212> TYPE: PRT
<213> ORGANISM: Homo sapiens

<400> SEQUENCE: 656

Gly Ala Leu Val Thr Val Gly Gln Leu Ser Cys Tyr Asp Gln Ala Lys
1               5                   10                  15

<210> SEQ ID NO 657
<211> LENGTH: 24
<212> TYPE: PRT
<213> ORGANISM: Homo sapiens

<400> SEQUENCE: 657

Tyr Gly Gln Val Thr Pro Leu Glu Ile Asp Ile Leu Tyr Gln Leu Ala
1               5                   10                  15

Asp Leu Tyr Asn Ala Ser Gly Arg
            20

<210> SEQ ID NO 658
<211> LENGTH: 12
<212> TYPE: PRT
<213> ORGANISM: Homo sapiens

<400> SEQUENCE: 658

Leu Ala Thr Ala Thr Phe Ala Gly Ile Glu Asn Lys
1               5                   10

<210> SEQ ID NO 659
<211> LENGTH: 18
<212> TYPE: PRT
<213> ORGANISM: Homo sapiens

<400> SEQUENCE: 659

Ile Ala Pro Leu Glu Glu Gly Thr Leu Pro Phe Asn Leu Ala Glu Ala
1               5                   10                  15

Gln Arg

<210> SEQ ID NO 660
<211> LENGTH: 22
<212> TYPE: PRT
<213> ORGANISM: Homo sapiens

<400> SEQUENCE: 660

Phe Gly Gln Val Thr Pro Met Glu Val Asp Ile Leu Phe Gln Leu Ala
1               5                   10                  15

Asp Leu Tyr Glu Pro Arg
            20

<210> SEQ ID NO 661
<211> LENGTH: 12
<212> TYPE: PRT
<213> ORGANISM: Homo sapiens

<400> SEQUENCE: 661

Leu Ala Val Ala Thr Phe Ala Gly Ile Glu Asn Lys
1               5                   10

<210> SEQ ID NO 662
<211> LENGTH: 16
<212> TYPE: PRT
<213> ORGANISM: Homo sapiens

<400> SEQUENCE: 662
```

```
Val Leu Pro Ala Val Gly Ile Ser Tyr Val Val Tyr Glu Asn Met Lys
1               5                   10                  15

<210> SEQ ID NO 663
<211> LENGTH: 16
<212> TYPE: PRT
<213> ORGANISM: Homo sapiens

<400> SEQUENCE: 663

Val Leu Tyr Ser Asn Met Leu Gly Glu Glu Asn Thr Tyr Leu Trp Arg
1               5                   10                  15

<210> SEQ ID NO 664
<211> LENGTH: 26
<212> TYPE: PRT
<213> ORGANISM: Homo sapiens

<400> SEQUENCE: 664

Thr Ser Leu Tyr Leu Ala Ala Ser Ala Ser Ala Glu Phe Phe Ala Asp
1               5                   10                  15

Ile Ala Leu Ala Pro Met Glu Ala Ala Lys
            20                  25

<210> SEQ ID NO 665
<211> LENGTH: 28
<212> TYPE: PRT
<213> ORGANISM: Homo sapiens

<400> SEQUENCE: 665

Leu Glu Ala Thr Glu Tyr Leu Val Ser Ala Ala Glu Ala Gly Ala Met
1               5                   10                  15

Thr Leu Cys Ile Thr Asn Pro Leu Trp Val Thr Lys
            20                  25

<210> SEQ ID NO 666
<211> LENGTH: 11
<212> TYPE: PRT
<213> ORGANISM: Homo sapiens

<400> SEQUENCE: 666

Ala Ala Tyr Phe Gly Val Tyr Asp Thr Ala Lys
1               5                   10

<210> SEQ ID NO 667
<211> LENGTH: 17
<212> TYPE: PRT
<213> ORGANISM: Homo sapiens

<400> SEQUENCE: 667

Leu Gly Glu Asn Glu Thr Cys Ile Pro Ile Val Ala Gly Ile Val Ala
1               5                   10                  15

Arg

<210> SEQ ID NO 668
<211> LENGTH: 13
<212> TYPE: PRT
<213> ORGANISM: Homo sapiens

<400> SEQUENCE: 668

Asp Phe Leu Ala Gly Gly Val Ala Ala Ala Ile Ser Lys
1               5                   10
```

```
<210> SEQ ID NO 669
<211> LENGTH: 11
<212> TYPE: PRT
<213> ORGANISM: Homo sapiens

<400> SEQUENCE: 669

Ala Ala Tyr Phe Gly Ile Tyr Asp Thr Ala Lys
1               5                   10

<210> SEQ ID NO 670
<211> LENGTH: 13
<212> TYPE: PRT
<213> ORGANISM: Homo sapiens

<400> SEQUENCE: 670

Asp Phe Leu Ala Gly Gly Ile Ala Ala Ala Ile Ser Lys
1               5                   10

<210> SEQ ID NO 671
<211> LENGTH: 11
<212> TYPE: PRT
<213> ORGANISM: Homo sapiens

<400> SEQUENCE: 671

Ala Ala Tyr Phe Gly Val Tyr Asp Thr Ala Lys
1               5                   10

<210> SEQ ID NO 672
<211> LENGTH: 34
<212> TYPE: PRT
<213> ORGANISM: Homo sapiens

<400> SEQUENCE: 672

Glu Asp Asn Ser Gly Ser Asp Val Leu Ile Gly Asp Ile Leu Val Leu
1               5                   10                  15

Leu Gly Ala Ser Leu Tyr Ala Ile Ser Asn Val Cys Glu Glu Tyr Ile
            20                  25                  30

Val Lys

<210> SEQ ID NO 673
<211> LENGTH: 21
<212> TYPE: PRT
<213> ORGANISM: Homo sapiens

<400> SEQUENCE: 673

Asp Leu Asn Pro Glu Asp Phe Trp Glu Ile Ile Gly Glu Leu Gly Asp
1               5                   10                  15

Gly Ala Phe Gly Lys
            20

<210> SEQ ID NO 674
<211> LENGTH: 12
<212> TYPE: PRT
<213> ORGANISM: Homo sapiens

<400> SEQUENCE: 674

Ser Leu Val Ala Leu Leu Val Glu Thr Gln Met Lys
1               5                   10

<210> SEQ ID NO 675
<211> LENGTH: 17
<212> TYPE: PRT
<213> ORGANISM: Homo sapiens
```

```
<400> SEQUENCE: 675

Phe Asn Ala Cys Phe Glu Ser Val Ala Thr Asn Ile Asp Glu Ile Tyr
1               5                   10                  15

Lys

<210> SEQ ID NO 676
<211> LENGTH: 28
<212> TYPE: PRT
<213> ORGANISM: Homo sapiens

<400> SEQUENCE: 676

Gly His Ala Asp Ser Val Thr Gly Leu Ser Leu Ser Ser Glu Gly Ser
1               5                   10                  15

Tyr Leu Leu Ser Asn Ala Met Asp Asn Thr Val Arg
            20                  25

<210> SEQ ID NO 677
<211> LENGTH: 20
<212> TYPE: PRT
<213> ORGANISM: Homo sapiens

<400> SEQUENCE: 677

Tyr Phe Ile Leu Pro Asp Ser Leu Pro Leu Asp Thr Leu Leu Val Asp
1               5                   10                  15

Val Glu Pro Lys
            20

<210> SEQ ID NO 678
<211> LENGTH: 29
<212> TYPE: PRT
<213> ORGANISM: Homo sapiens

<400> SEQUENCE: 678

Ser Leu Gly Tyr Asp Leu Pro Met Val Glu Glu Gly Glu Pro Asp Pro
1               5                   10                  15

Glu Phe Glu Ala Ile Leu Asp Thr Val Asp Pro Asn Arg
            20                  25

<210> SEQ ID NO 679
<211> LENGTH: 12
<212> TYPE: PRT
<213> ORGANISM: Homo sapiens

<400> SEQUENCE: 679

Glu Val Asp Asp Leu Glu Gln Trp Ile Ala Glu Arg
1               5                   10

<210> SEQ ID NO 680
<211> LENGTH: 22
<212> TYPE: PRT
<213> ORGANISM: Homo sapiens

<400> SEQUENCE: 680

Ile Phe Leu Leu Gly Leu Ala Asp Asn Glu Ala Ala Ile Val Gln Ala
1               5                   10                  15

Glu Ser Glu Glu Thr Lys
            20

<210> SEQ ID NO 681
<211> LENGTH: 15
<212> TYPE: PRT
```

<400> SEQUENCE: 681

Ser Gly Asp Ser Glu Val Tyr Gln Leu Gly Asp Val Ser Gln Lys
1               5                   10                  15

<210> SEQ ID NO 682
<211> LENGTH: 18
<212> TYPE: PRT
<213> ORGANISM: Homo sapiens

<400> SEQUENCE: 682

Glu Leu Gln Glu Asn Gln Asp Glu Ile Glu Asn Met Met Asn Ala Ile
1               5                   10                  15

Phe Lys

<210> SEQ ID NO 683
<211> LENGTH: 14
<212> TYPE: PRT
<213> ORGANISM: Homo sapiens

<400> SEQUENCE: 683

Asp Cys Glu Glu Cys Ile Gln Leu Glu Pro Thr Phe Ile Lys
1               5                   10

<210> SEQ ID NO 684
<211> LENGTH: 15
<212> TYPE: PRT
<213> ORGANISM: Homo sapiens

<400> SEQUENCE: 684

Ile Leu Glu Pro Gly Leu Asn Ile Leu Ile Pro Val Leu Asp Arg
1               5                   10                  15

<210> SEQ ID NO 685
<211> LENGTH: 17
<212> TYPE: PRT
<213> ORGANISM: Homo sapiens

<400> SEQUENCE: 685

Asn Thr Val Val Leu Phe Val Pro Gln Gln Glu Ala Trp Val Val Glu
1               5                   10                  15

Arg

<210> SEQ ID NO 686
<211> LENGTH: 21
<212> TYPE: PRT
<213> ORGANISM: Homo sapiens

<400> SEQUENCE: 686

Ala Ser Tyr Gly Val Glu Asp Pro Glu Tyr Ala Val Thr Gln Leu Ala
1               5                   10                  15

Gln Thr Thr Met Arg
            20

<210> SEQ ID NO 687
<211> LENGTH: 11
<212> TYPE: PRT
<213> ORGANISM: Homo sapiens

<400> SEQUENCE: 687

Phe Tyr Ser Leu Leu Asp Pro Ser Tyr Ala Lys
1               5                   10

<210> SEQ ID NO 688
<211> LENGTH: 9
<212> TYPE: PRT
<213> ORGANISM: Homo sapiens

<400> SEQUENCE: 688

Phe Leu Ala Glu Glu Gly Phe Tyr Lys
1               5

<210> SEQ ID NO 689
<211> LENGTH: 19
<212> TYPE: PRT
<213> ORGANISM: Homo sapiens

<400> SEQUENCE: 689

Asp Phe Glu Leu Asp Val Leu Glu Glu Ala Tyr Thr Thr Glu His Trp
1               5                   10                  15

Leu Val Arg

<210> SEQ ID NO 690
<211> LENGTH: 24
<212> TYPE: PRT
<213> ORGANISM: Homo sapiens

<400> SEQUENCE: 690

Glu Leu Asp Val Ser Tyr Val Leu Val Ile Phe Gly Gly Leu Thr Gly
1               5                   10                  15

Tyr Ser Ser Asp Asp Ile Asn Lys
            20

<210> SEQ ID NO 691
<211> LENGTH: 12
<212> TYPE: PRT
<213> ORGANISM: Homo sapiens

<400> SEQUENCE: 691

Glu Ser Asp Tyr Phe Thr Pro Gln Gly Glu Phe Arg
1               5                   10

<210> SEQ ID NO 692
<211> LENGTH: 24
<212> TYPE: PRT
<213> ORGANISM: Homo sapiens

<400> SEQUENCE: 692

Thr Leu Asp Val Asp Tyr Val Leu Val Ile Phe Gly Gly Val Ile Gly
1               5                   10                  15

Tyr Ser Gly Asp Asp Ile Asn Lys
            20

<210> SEQ ID NO 693
<211> LENGTH: 10
<212> TYPE: PRT
<213> ORGANISM: Homo sapiens

<400> SEQUENCE: 693

Glu Thr Tyr Leu Ala Ile Leu Met Asp Arg
1               5                   10

<210> SEQ ID NO 694
<211> LENGTH: 13
<212> TYPE: PRT
<213> ORGANISM: Homo sapiens

```
<400> SEQUENCE: 694

Leu Cys Leu Ile Ser Thr Phe Leu Glu Asp Gly Ile Arg
1               5                   10

<210> SEQ ID NO 695
<211> LENGTH: 13
<212> TYPE: PRT
<213> ORGANISM: Homo sapiens

<400> SEQUENCE: 695

Asn Leu Ala Asn Thr Val Thr Glu Glu Ile Leu Glu Lys
1               5                   10

<210> SEQ ID NO 696
<211> LENGTH: 14
<212> TYPE: PRT
<213> ORGANISM: Homo sapiens

<400> SEQUENCE: 696

Gly Glu Ala Thr Val Ser Phe Asp Asp Pro Pro Ser Ala Lys
1               5                   10

<210> SEQ ID NO 697
<211> LENGTH: 9
<212> TYPE: PRT
<213> ORGANISM: Homo sapiens

<400> SEQUENCE: 697

Ser Gly Gly Gly Tyr Gly Gly Asp Arg
1               5

<210> SEQ ID NO 698
<211> LENGTH: 12
<212> TYPE: PRT
<213> ORGANISM: Homo sapiens

<400> SEQUENCE: 698

Ala Ala Leu Glu Ala Leu Leu Pro Tyr Thr Glu Arg
1               5                   10

<210> SEQ ID NO 699
<211> LENGTH: 13
<212> TYPE: PRT
<213> ORGANISM: Homo sapiens

<400> SEQUENCE: 699

Ala Leu Ala Asp Val Glu Val Thr Tyr Thr Val Gln Arg
1               5                   10

<210> SEQ ID NO 700
<211> LENGTH: 11
<212> TYPE: PRT
<213> ORGANISM: Homo sapiens

<400> SEQUENCE: 700

Leu Ser Glu Phe Asp Val Glu Met Ser Met Arg
1               5                   10

<210> SEQ ID NO 701
<211> LENGTH: 22
<212> TYPE: PRT
<213> ORGANISM: Homo sapiens

<400> SEQUENCE: 701
```

Asp Phe Val Glu Ala Pro Ser Gln Met Leu Glu Asn Trp Val Trp Glu
1               5                   10                  15

Gln Glu Pro Leu Leu Arg
            20

<210> SEQ ID NO 702
<211> LENGTH: 19
<212> TYPE: PRT
<213> ORGANISM: Homo sapiens

<400> SEQUENCE: 702

Ala Gln Gln Leu Ala Ala Glu Leu Glu Val Glu Met Met Ala Asp Met
1               5                   10                  15

Tyr Asn Arg

<210> SEQ ID NO 703
<211> LENGTH: 23
<212> TYPE: PRT
<213> ORGANISM: Homo sapiens

<400> SEQUENCE: 703

Ile Val Asp Asp Cys Gly Gly Ala Phe Thr Met Gly Thr Ile Gly Gly
1               5                   10                  15

Gly Ile Phe Gln Ala Ile Lys
            20

<210> SEQ ID NO 704
<211> LENGTH: 23
<212> TYPE: PRT
<213> ORGANISM: Homo sapiens

<400> SEQUENCE: 704

Ile Val Asp Asp Cys Gly Gly Ala Phe Thr Met Gly Val Ile Gly Gly
1               5                   10                  15

Gly Val Phe Gln Ala Ile Lys
            20

<210> SEQ ID NO 705
<211> LENGTH: 12
<212> TYPE: PRT
<213> ORGANISM: Homo sapiens

<400> SEQUENCE: 705

Asp Gln Asp Glu Leu Asn Pro Tyr Ala Ala Trp Arg
1               5                   10

<210> SEQ ID NO 706
<211> LENGTH: 16
<212> TYPE: PRT
<213> ORGANISM: Homo sapiens

<400> SEQUENCE: 706

Leu Glu Asp Leu Ser Glu Ser Ile Val Asn Asp Phe Ala Tyr Met Lys
1               5                   10                  15

<210> SEQ ID NO 707
<211> LENGTH: 17
<212> TYPE: PRT
<213> ORGANISM: Homo sapiens

<400> SEQUENCE: 707

Cys Phe Ile Glu Glu Ile Pro Asp Glu Thr Met Val Ile Gly Asn Tyr

-continued

```
1               5                   10                  15

Arg

<210> SEQ ID NO 708
<211> LENGTH: 21
<212> TYPE: PRT
<213> ORGANISM: Homo sapiens

<400> SEQUENCE: 708

Cys Phe Val Ser Phe Pro Leu Asn Thr Gly Asp Leu Asp Cys Glu Thr
1               5                   10                  15

Cys Thr Ile Thr Arg
            20

<210> SEQ ID NO 709
<211> LENGTH: 17
<212> TYPE: PRT
<213> ORGANISM: Homo sapiens

<400> SEQUENCE: 709

Thr Tyr Asp Ala Ala Ser Tyr Ile Cys Glu Ala Ala Phe Asp Glu Val
1               5                   10                  15

Lys

<210> SEQ ID NO 710
<211> LENGTH: 26
<212> TYPE: PRT
<213> ORGANISM: Homo sapiens

<400> SEQUENCE: 710

Thr Gln Asp Gln Asp Glu Asn Val Ala Leu Glu Ala Cys Glu Phe Trp
1               5                   10                  15

Leu Thr Leu Ala Glu Gln Pro Ile Cys Lys
            20                  25

<210> SEQ ID NO 711
<211> LENGTH: 20
<212> TYPE: PRT
<213> ORGANISM: Homo sapiens

<400> SEQUENCE: 711

Leu Glu Gln Leu Asn Gln Tyr Pro Asp Phe Asn Asn Tyr Leu Ile Phe
1               5                   10                  15

Val Leu Thr Lys
            20

<210> SEQ ID NO 712
<211> LENGTH: 12
<212> TYPE: PRT
<213> ORGANISM: Homo sapiens

<400> SEQUENCE: 712

Leu Gln Met Glu Gln Gln Gln Leu Gln Gln Arg
1               5                   10

<210> SEQ ID NO 713
<211> LENGTH: 16
<212> TYPE: PRT
<213> ORGANISM: Homo sapiens

<400> SEQUENCE: 713

Ser Ala Ala Gly Ala Thr Phe Asp Leu Ser Leu Phe Val Ala Gln Lys
```

-continued

```
1               5                   10                  15
```

<210> SEQ ID NO 714
<211> LENGTH: 16
<212> TYPE: PRT
<213> ORGANISM: Homo sapiens

<400> SEQUENCE: 714

```
Ala Ser Asp Gln Leu Gln Val Gly Val Glu Phe Glu Ala Ser Thr Arg
1               5                   10                  15
```

<210> SEQ ID NO 715
<211> LENGTH: 20
<212> TYPE: PRT
<213> ORGANISM: Homo sapiens

<400> SEQUENCE: 715

```
Cys Ala Glu Gly Tyr Ala Leu Tyr Ala Gln Ala Leu Thr Asp Gln Gln
1               5                   10                  15

Gln Phe Gly Lys
            20
```

<210> SEQ ID NO 716
<211> LENGTH: 8
<212> TYPE: PRT
<213> ORGANISM: Homo sapiens

<400> SEQUENCE: 716

```
Ser Leu Glu Ala Ala Ser Glu Lys
1               5
```

<210> SEQ ID NO 717
<211> LENGTH: 19
<212> TYPE: PRT
<213> ORGANISM: Homo sapiens

<400> SEQUENCE: 717

```
Asp Leu Leu Glu Gln Met Met Ala Glu Met Ile Gly Glu Phe Pro Asp
1               5                   10                  15

Leu His Arg
```

<210> SEQ ID NO 718
<211> LENGTH: 17
<212> TYPE: PRT
<213> ORGANISM: Homo sapiens

<400> SEQUENCE: 718

```
Leu Asp Thr His Pro Ala Met Val Thr Val Leu Glu Met Gly Ala Ala
1               5                   10                  15

Arg
```

<210> SEQ ID NO 719
<211> LENGTH: 11
<212> TYPE: PRT
<213> ORGANISM: Homo sapiens

<400> SEQUENCE: 719

```
Val Glu Glu Val Val Tyr Asp Leu Ser Ile Arg
1               5                   10
```

<210> SEQ ID NO 720
<211> LENGTH: 16
<212> TYPE: PRT

-continued

<213> ORGANISM: Homo sapiens

<400> SEQUENCE: 720

Ala Ile Thr Tyr Thr Tyr Asp Leu Met Ala Asn Leu Ala Phe Ile Arg
1               5                   10                  15

<210> SEQ ID NO 721
<211> LENGTH: 34
<212> TYPE: PRT
<213> ORGANISM: Homo sapiens

<400> SEQUENCE: 721

Cys Met Leu Leu Pro Trp Ala Pro Thr Asp Met Leu Asp Leu Ser Ser
1               5                   10                  15

Cys Thr Pro Glu Pro Pro Ala Glu His Tyr Gln Ala Ile Leu Glu Glu
            20                  25                  30

Asn Lys

<210> SEQ ID NO 722
<211> LENGTH: 18
<212> TYPE: PRT
<213> ORGANISM: Homo sapiens

<400> SEQUENCE: 722

Val Gly Ile Asn Tyr Gln Pro Pro Thr Val Pro Gly Gly Asp Leu
1               5                   10                  15

Ala Lys

<210> SEQ ID NO 723
<211> LENGTH: 21
<212> TYPE: PRT
<213> ORGANISM: Homo sapiens

<400> SEQUENCE: 723

Phe Asp Gly Ala Leu Asn Val Asp Leu Thr Glu Phe Gln Thr Asn Leu
1               5                   10                  15

Val Pro Tyr Pro Arg
            20

<210> SEQ ID NO 724
<211> LENGTH: 24
<212> TYPE: PRT
<213> ORGANISM: Homo sapiens

<400> SEQUENCE: 724

Ala Tyr His Glu Gln Leu Ser Val Ala Glu Ile Thr Asn Ala Cys Phe
1               5                   10                  15

Glu Pro Ala Asn Gln Met Val Lys
            20

<210> SEQ ID NO 725
<211> LENGTH: 17
<212> TYPE: PRT
<213> ORGANISM: Homo sapiens

<400> SEQUENCE: 725

Ala Val Cys Met Leu Ser Asn Thr Thr Ala Ile Ala Glu Ala Trp Ala
1               5                   10                  15

Arg

<210> SEQ ID NO 726

```
<211> LENGTH: 15
<212> TYPE: PRT
<213> ORGANISM: Homo sapiens

<400> SEQUENCE: 726

Ala Val Phe Val Asp Leu Glu Pro Thr Val Ile Asp Glu Val Arg
1               5                   10                  15

<210> SEQ ID NO 727
<211> LENGTH: 20
<212> TYPE: PRT
<213> ORGANISM: Homo sapiens

<400> SEQUENCE: 727

Ala Phe Val His Trp Tyr Val Gly Glu Gly Met Glu Glu Gly Glu Phe
1               5                   10                  15

Ser Glu Ala Arg
            20

<210> SEQ ID NO 728
<211> LENGTH: 20
<212> TYPE: PRT
<213> ORGANISM: Homo sapiens

<400> SEQUENCE: 728

Thr Ile Gly Gly Gly Asp Asp Ser Phe Asn Thr Phe Phe Ser Glu Thr
1               5                   10                  15

Gly Ala Gly Lys
            20

<210> SEQ ID NO 729
<211> LENGTH: 21
<212> TYPE: PRT
<213> ORGANISM: Homo sapiens

<400> SEQUENCE: 729

Phe Asp Gly Ala Leu Asn Val Asp Leu Thr Glu Phe Gln Thr Asn Leu
1               5                   10                  15

Val Pro Tyr Pro Arg
            20

<210> SEQ ID NO 730
<211> LENGTH: 24
<212> TYPE: PRT
<213> ORGANISM: Homo sapiens

<400> SEQUENCE: 730

Ala Tyr His Glu Gln Leu Ser Val Ala Glu Ile Thr Asn Ala Cys Phe
1               5                   10                  15

Glu Pro Ala Asn Gln Met Val Lys
            20

<210> SEQ ID NO 731
<211> LENGTH: 20
<212> TYPE: PRT
<213> ORGANISM: Homo sapiens

<400> SEQUENCE: 731

Thr Ile Gly Gly Gly Asp Asp Ser Phe Asn Thr Phe Phe Ser Glu Thr
1               5                   10                  15

Gly Ala Gly Lys
            20
```

<210> SEQ ID NO 732
<211> LENGTH: 21
<212> TYPE: PRT
<213> ORGANISM: Homo sapiens

<400> SEQUENCE: 732

Phe Asp Gly Ala Leu Asn Val Asp Leu Thr Glu Phe Gln Thr Asn Leu
1               5                   10                  15

Val Pro Tyr Pro Arg
            20

<210> SEQ ID NO 733
<211> LENGTH: 24
<212> TYPE: PRT
<213> ORGANISM: Homo sapiens

<400> SEQUENCE: 733

Ala Tyr His Glu Gln Leu Ser Val Ala Glu Ile Thr Asn Ala Cys Phe
1               5                   10                  15

Glu Pro Ala Asn Gln Met Val Lys
            20

<210> SEQ ID NO 734
<211> LENGTH: 13
<212> TYPE: PRT
<213> ORGANISM: Homo sapiens

<400> SEQUENCE: 734

Ser Ile Gln Phe Val Asp Trp Cys Pro Thr Gly Phe Lys
1               5                   10

<210> SEQ ID NO 735
<211> LENGTH: 21
<212> TYPE: PRT
<213> ORGANISM: Homo sapiens

<400> SEQUENCE: 735

Phe Asp Gly Ala Leu Asn Val Asp Leu Thr Glu Phe Gln Thr Asn Leu
1               5                   10                  15

Val Pro Tyr Pro Arg
            20

<210> SEQ ID NO 736
<211> LENGTH: 18
<212> TYPE: PRT
<213> ORGANISM: Homo sapiens

<400> SEQUENCE: 736

Gly His Tyr Thr Glu Gly Ala Glu Leu Val Asp Ser Val Leu Asp Val
1               5                   10                  15

Val Arg

<210> SEQ ID NO 737
<211> LENGTH: 39
<212> TYPE: PRT
<213> ORGANISM: Homo sapiens

<400> SEQUENCE: 737

Val Ser Asp Thr Val Val Glu Pro Tyr Asn Ala Thr Leu Ser Val His
1               5                   10                  15

Gln Leu Val Glu Asn Thr Asp Glu Thr Tyr Cys Ile Asp Asn Glu Ala
            20                  25                  30

-continued

Leu Tyr Asp Ile Cys Phe Arg
        35

<210> SEQ ID NO 738
<211> LENGTH: 27
<212> TYPE: PRT
<213> ORGANISM: Homo sapiens

<400> SEQUENCE: 738

Phe Trp Glu Val Ile Ser Asp Glu His Gly Ile Asp Pro Thr Gly Thr
1               5                   10                  15

Tyr His Gly Asp Ser Asp Leu Gln Leu Asp Arg
            20                  25

<210> SEQ ID NO 739
<211> LENGTH: 25
<212> TYPE: PRT
<213> ORGANISM: Homo sapiens

<400> SEQUENCE: 739

Leu Thr Thr Pro Thr Tyr Gly Asp Leu Asn His Leu Val Ser Ala Thr
1               5                   10                  15

Met Ser Gly Val Thr Thr Cys Leu Arg
            20                  25

<210> SEQ ID NO 740
<211> LENGTH: 15
<212> TYPE: PRT
<213> ORGANISM: Homo sapiens

<400> SEQUENCE: 740

Ala Leu Thr Val Pro Glu Leu Thr Gln Gln Val Phe Asp Ala Lys
1               5                   10                  15

<210> SEQ ID NO 741
<211> LENGTH: 9
<212> TYPE: PRT
<213> ORGANISM: Homo sapiens

<400> SEQUENCE: 741

Tyr Leu Thr Val Ala Ala Val Phe Arg
1               5

<210> SEQ ID NO 742
<211> LENGTH: 14
<212> TYPE: PRT
<213> ORGANISM: Homo sapiens

<400> SEQUENCE: 742

Asn Ser Ser Tyr Phe Val Glu Trp Ile Pro Asn Asn Val Lys
1               5                   10

<210> SEQ ID NO 743
<211> LENGTH: 10
<212> TYPE: PRT
<213> ORGANISM: Homo sapiens

<400> SEQUENCE: 743

Ile Ser Glu Gln Phe Thr Ala Met Phe Arg
1               5                   10

<210> SEQ ID NO 744
<211> LENGTH: 12

```
<212> TYPE: PRT
<213> ORGANISM: Homo sapiens

<400> SEQUENCE: 744

Ile Ser Val Tyr Tyr Asn Glu Ala Thr Gly Gly Lys
1               5                   10

<210> SEQ ID NO 745
<211> LENGTH: 15
<212> TYPE: PRT
<213> ORGANISM: Homo sapiens

<400> SEQUENCE: 745

Ala Ile Leu Val Asp Leu Glu Pro Gly Thr Met Asp Ser Val Arg
1               5                   10                  15

<210> SEQ ID NO 746
<211> LENGTH: 10
<212> TYPE: PRT
<213> ORGANISM: Homo sapiens

<400> SEQUENCE: 746

Ile Ser Glu Gln Phe Thr Ala Met Phe Arg
1               5                   10

<210> SEQ ID NO 747
<211> LENGTH: 15
<212> TYPE: PRT
<213> ORGANISM: Homo sapiens

<400> SEQUENCE: 747

Ala Ile Leu Val Asp Leu Glu Pro Gly Thr Met Asp Ser Val Arg
1               5                   10                  15

<210> SEQ ID NO 748
<211> LENGTH: 39
<212> TYPE: PRT
<213> ORGANISM: Homo sapiens

<400> SEQUENCE: 748

Val Ser Asp Thr Val Val Glu Pro Tyr Asn Ala Thr Leu Ser Val His
1               5                   10                  15

Gln Leu Val Glu Asn Thr Asp Glu Thr Tyr Cys Ile Asp Asn Glu Ala
            20                  25                  30

Leu Tyr Asp Ile Cys Phe Arg
            35

<210> SEQ ID NO 749
<211> LENGTH: 14
<212> TYPE: PRT
<213> ORGANISM: Homo sapiens

<400> SEQUENCE: 749

Asn Ser Ser Tyr Phe Val Glu Trp Ile Pro Asn Asn Val Lys
1               5                   10

<210> SEQ ID NO 750
<211> LENGTH: 18
<212> TYPE: PRT
<213> ORGANISM: Homo sapiens

<400> SEQUENCE: 750

Gly His Tyr Thr Glu Gly Ala Glu Leu Val Asp Ser Val Leu Asp Val
1               5                   10                  15
```

Val Arg

<210> SEQ ID NO 751
<211> LENGTH: 25
<212> TYPE: PRT
<213> ORGANISM: Homo sapiens

<400> SEQUENCE: 751

Leu Thr Thr Pro Thr Tyr Gly Asp Leu Asn His Leu Val Ser Ala Thr
1               5                   10                  15

Met Ser Gly Val Thr Thr Cys Leu Arg
            20                  25

<210> SEQ ID NO 752
<211> LENGTH: 18
<212> TYPE: PRT
<213> ORGANISM: Homo sapiens

<400> SEQUENCE: 752

Gly His Tyr Thr Glu Gly Ala Glu Leu Val Asp Ser Val Leu Asp Val
1               5                   10                  15

Val Arg

<210> SEQ ID NO 753
<211> LENGTH: 14
<212> TYPE: PRT
<213> ORGANISM: Homo sapiens

<400> SEQUENCE: 753

Asn Ser Ser Tyr Phe Val Glu Trp Ile Pro Asn Asn Val Lys
1               5                   10

<210> SEQ ID NO 754
<211> LENGTH: 15
<212> TYPE: PRT
<213> ORGANISM: Homo sapiens

<400> SEQUENCE: 754

Ala Ile Leu Val Asp Leu Glu Pro Gly Thr Met Asp Ser Val Arg
1               5                   10                  15

<210> SEQ ID NO 755
<211> LENGTH: 18
<212> TYPE: PRT
<213> ORGANISM: Homo sapiens

<400> SEQUENCE: 755

Gly His Tyr Thr Glu Gly Ala Glu Leu Val Asp Ser Val Leu Asp Val
1               5                   10                  15

Val Arg

<210> SEQ ID NO 756
<211> LENGTH: 39
<212> TYPE: PRT
<213> ORGANISM: Homo sapiens

<400> SEQUENCE: 756

Val Ser Asp Thr Val Val Glu Pro Tyr Asn Ala Thr Leu Ser Val His
1               5                   10                  15

Gln Leu Val Glu Asn Thr Asp Glu Thr Tyr Cys Ile Asp Asn Glu Ala
            20                  25                  30

Leu Tyr Asp Ile Cys Phe Arg
            35

<210> SEQ ID NO 757
<211> LENGTH: 25
<212> TYPE: PRT
<213> ORGANISM: Homo sapiens

<400> SEQUENCE: 757

Leu Thr Thr Pro Thr Tyr Gly Asp Leu Asn His Leu Val Ser Ala Thr
1               5                   10                  15

Met Ser Gly Val Thr Thr Cys Leu Arg
            20                  25

<210> SEQ ID NO 758
<211> LENGTH: 9
<212> TYPE: PRT
<213> ORGANISM: Homo sapiens

<400> SEQUENCE: 758

Tyr Leu Thr Val Ala Ala Val Phe Arg
1               5

<210> SEQ ID NO 759
<211> LENGTH: 14
<212> TYPE: PRT
<213> ORGANISM: Homo sapiens

<400> SEQUENCE: 759

Asn Ser Ser Tyr Phe Val Glu Trp Ile Pro Asn Asn Val Lys
1               5                   10

<210> SEQ ID NO 760
<211> LENGTH: 10
<212> TYPE: PRT
<213> ORGANISM: Homo sapiens

<400> SEQUENCE: 760

Ile Ser Glu Gln Phe Thr Ala Met Phe Arg
1               5                   10

<210> SEQ ID NO 761
<211> LENGTH: 25
<212> TYPE: PRT
<213> ORGANISM: Homo sapiens

<400> SEQUENCE: 761

Leu Thr Thr Pro Thr Tyr Gly Asp Leu Asn His Leu Val Ser Ala Thr
1               5                   10                  15

Met Ser Gly Val Thr Thr Ser Leu Arg
            20                  25

<210> SEQ ID NO 762
<211> LENGTH: 39
<212> TYPE: PRT
<213> ORGANISM: Homo sapiens

<400> SEQUENCE: 762

Val Ser Asp Thr Val Val Glu Pro Tyr Asn Ala Thr Leu Ser Val His
1               5                   10                  15

Gln Leu Val Glu Asn Thr Asp Glu Thr Tyr Cys Ile Asp Asn Glu Ala
            20                  25                  30

Leu Tyr Asp Ile Cys Phe Arg

<210> SEQ ID NO 763
<211> LENGTH: 14
<212> TYPE: PRT
<213> ORGANISM: Homo sapiens

<400> SEQUENCE: 763

Asn Ser Ser Tyr Phe Val Glu Trp Ile Pro Asn Asn Val Lys
1               5                   10

<210> SEQ ID NO 764
<211> LENGTH: 18
<212> TYPE: PRT
<213> ORGANISM: Homo sapiens

<400> SEQUENCE: 764

Ala Asp Ala Val Gln Asp Ser Glu Met Val Glu Leu Val Glu Leu Glu
1               5                   10                  15

Ile Arg

<210> SEQ ID NO 765
<211> LENGTH: 14
<212> TYPE: PRT
<213> ORGANISM: Homo sapiens

<400> SEQUENCE: 765

Leu Leu Asp Ala Val Asp Thr Tyr Ile Pro Val Pro Ala Arg
1               5                   10

<210> SEQ ID NO 766
<211> LENGTH: 10
<212> TYPE: PRT
<213> ORGANISM: Homo sapiens

<400> SEQUENCE: 766

Gly Thr Val Val Thr Gly Thr Leu Glu Arg
1               5                   10

<210> SEQ ID NO 767
<211> LENGTH: 19
<212> TYPE: PRT
<213> ORGANISM: Homo sapiens

<400> SEQUENCE: 767

Thr Ala Thr Glu Glu Trp Gly Thr Glu Asp Trp Asn Glu Asp Leu Ser
1               5                   10                  15

Glu Thr Lys

<210> SEQ ID NO 768
<211> LENGTH: 19
<212> TYPE: PRT
<213> ORGANISM: Homo sapiens

<400> SEQUENCE: 768

Asn Ala Leu Val Ser His Leu Asp Gly Thr Thr Pro Val Cys Glu Asp
1               5                   10                  15

Ile Gly Arg

<210> SEQ ID NO 769
<211> LENGTH: 22
<212> TYPE: PRT
<213> ORGANISM: Homo sapiens -continued

<400> SEQUENCE: 769

Gly Ala Leu Val Leu Gly Tyr Glu Gly Trp Leu Ala Gly Tyr Gln Met
1               5                   10                  15

Asn Phe Glu Thr Ala Lys
            20

<210> SEQ ID NO 770
<211> LENGTH: 19
<212> TYPE: PRT
<213> ORGANISM: Homo sapiens

<400> SEQUENCE: 770

Glu His Ile Asn Leu Gly Cys Asp Met Asp Phe Asp Ile Ala Gly Pro
1               5                   10                  15

Ser Ile Arg

<210> SEQ ID NO 771
<211> LENGTH: 19
<212> TYPE: PRT
<213> ORGANISM: Homo sapiens

<400> SEQUENCE: 771

Trp Asn Thr Asp Asn Thr Leu Gly Thr Glu Ile Thr Val Glu Asp Gln
1               5                   10                  15

Leu Ala Arg

<210> SEQ ID NO 772
<211> LENGTH: 11
<212> TYPE: PRT
<213> ORGANISM: Homo sapiens

<400> SEQUENCE: 772

Val Thr Gln Ser Asn Phe Ala Val Gly Tyr Lys
1               5                   10

<210> SEQ ID NO 773
<211> LENGTH: 11
<212> TYPE: PRT
<213> ORGANISM: Homo sapiens

<400> SEQUENCE: 773

Trp Thr Glu Tyr Gly Leu Thr Phe Thr Glu Lys
1               5                   10

<210> SEQ ID NO 774
<211> LENGTH: 19
<212> TYPE: PRT
<213> ORGANISM: Homo sapiens

<400> SEQUENCE: 774

Ser Glu Asn Gly Leu Glu Phe Thr Ser Ser Gly Ser Ala Asn Thr Glu
1               5                   10                  15

Thr Thr Lys

<210> SEQ ID NO 775
<211> LENGTH: 23
<212> TYPE: PRT
<213> ORGANISM: Homo sapiens

<400> SEQUENCE: 775

Thr Asp Glu Phe Gln Leu His Thr Asn Val Asn Asp Gly Thr Glu Phe

-continued

```
                1               5                  10                  15

Gly Gly Ser Ile Tyr Gln Lys
            20

<210> SEQ ID NO 776
<211> LENGTH: 12
<212> TYPE: PRT
<213> ORGANISM: Homo sapiens

<400> SEQUENCE: 776

Tyr Gln Ile Asp Pro Asp Ala Cys Phe Ser Ala Lys
1               5                  10

<210> SEQ ID NO 777
<211> LENGTH: 22
<212> TYPE: PRT
<213> ORGANISM: Homo sapiens

<400> SEQUENCE: 777

Trp Asn Thr Asp Asn Thr Leu Gly Thr Glu Ile Ala Ile Glu Asp Gln
1               5                  10                  15

Ile Cys Gln Gly Leu Lys
            20

<210> SEQ ID NO 778
<211> LENGTH: 8
<212> TYPE: PRT
<213> ORGANISM: Homo sapiens

<400> SEQUENCE: 778

Asn Asn Phe Ala Val Gly Tyr Arg
1               5

<210> SEQ ID NO 779
<211> LENGTH: 23
<212> TYPE: PRT
<213> ORGANISM: Homo sapiens

<400> SEQUENCE: 779

Thr Gly Asp Phe Gln Leu His Thr Asn Val Asn Asp Gly Thr Glu Phe
1               5                  10                  15

Gly Gly Ser Ile Tyr Gln Lys
            20

<210> SEQ ID NO 780
<211> LENGTH: 21
<212> TYPE: PRT
<213> ORGANISM: Homo sapiens

<400> SEQUENCE: 780

Val Cys Glu Asp Leu Asp Thr Ser Val Asn Leu Ala Trp Thr Ser Gly
1               5                  10                  15

Thr Asn Cys Thr Arg
            20

<210> SEQ ID NO 781
<211> LENGTH: 12
<212> TYPE: PRT
<213> ORGANISM: Homo sapiens

<400> SEQUENCE: 781

Tyr Gln Leu Asp Pro Thr Ala Ser Ile Ser Ala Lys
1               5                  10
```

```
<210> SEQ ID NO 782
<211> LENGTH: 11
<212> TYPE: PRT
<213> ORGANISM: Homo sapiens

<400> SEQUENCE: 782

Trp Cys Glu Tyr Gly Leu Thr Phe Thr Glu Lys
1               5                   10

<210> SEQ ID NO 783
<211> LENGTH: 11
<212> TYPE: PRT
<213> ORGANISM: Homo sapiens

<400> SEQUENCE: 783

Leu Ser Gln Asn Asn Phe Ala Leu Gly Tyr Lys
1               5                   10

<210> SEQ ID NO 784
<211> LENGTH: 10
<212> TYPE: PRT
<213> ORGANISM: Homo sapiens

<400> SEQUENCE: 784

Asn Leu Gln Glu Ala Glu Glu Trp Tyr Lys
1               5                   10

<210> SEQ ID NO 785
<211> LENGTH: 13
<212> TYPE: PRT
<213> ORGANISM: Homo sapiens

<400> SEQUENCE: 785

Gln Val Gln Ser Leu Thr Cys Glu Val Asp Ala Leu Lys
1               5                   10

<210> SEQ ID NO 786
<211> LENGTH: 9
<212> TYPE: PRT
<213> ORGANISM: Homo sapiens

<400> SEQUENCE: 786

Asp Asn Leu Ala Glu Asp Ile Met Arg
1               5

<210> SEQ ID NO 787
<211> LENGTH: 11
<212> TYPE: PRT
<213> ORGANISM: Homo sapiens

<400> SEQUENCE: 787

Glu Glu Ala Glu Asn Thr Leu Gln Ser Phe Arg
1               5                   10

<210> SEQ ID NO 788
<211> LENGTH: 10
<212> TYPE: PRT
<213> ORGANISM: Homo sapiens

<400> SEQUENCE: 788

Ile Leu Leu Ala Glu Leu Glu Gln Leu Lys
1               5                   10
```

```
<210> SEQ ID NO 789
<211> LENGTH: 8
<212> TYPE: PRT
<213> ORGANISM: Homo sapiens

<400> SEQUENCE: 789

Ser Tyr Val Thr Thr Ser Thr Arg
1               5

<210> SEQ ID NO 790
<211> LENGTH: 10
<212> TYPE: PRT
<213> ORGANISM: Homo sapiens

<400> SEQUENCE: 790

Leu Gly Asp Leu Tyr Glu Glu Glu Met Arg
1               5                   10

<210> SEQ ID NO 791
<211> LENGTH: 8
<212> TYPE: PRT
<213> ORGANISM: Homo sapiens

<400> SEQUENCE: 791

Ser Val Ser Ser Ser Ser Tyr Arg
1               5

<210> SEQ ID NO 792
<211> LENGTH: 8
<212> TYPE: PRT
<213> ORGANISM: Homo sapiens

<400> SEQUENCE: 792

Leu Gln Glu Glu Met Leu Gln Arg
1               5

<210> SEQ ID NO 793
<211> LENGTH: 9
<212> TYPE: PRT
<213> ORGANISM: Homo sapiens

<400> SEQUENCE: 793

Val Glu Leu Gln Glu Leu Asn Asp Arg
1               5

<210> SEQ ID NO 794
<211> LENGTH: 19
<212> TYPE: PRT
<213> ORGANISM: Homo sapiens

<400> SEQUENCE: 794

Leu Leu Gln Asp Ser Val Asp Phe Ser Leu Ala Asp Ala Ile Asn Thr
1               5                   10                  15

Glu Phe Lys

<210> SEQ ID NO 795
<211> LENGTH: 10
<212> TYPE: PRT
<213> ORGANISM: Homo sapiens

<400> SEQUENCE: 795

Phe Ala Asp Leu Ser Glu Ala Ala Asn Arg
1               5                   10
```

```
<210> SEQ ID NO 796
<211> LENGTH: 19
<212> TYPE: PRT
<213> ORGANISM: Homo sapiens

<400> SEQUENCE: 796

Glu Met Glu Glu Asn Phe Ala Val Glu Ala Ala Asn Tyr Gln Asp Thr
1               5                   10                  15
Ile Gly Arg

<210> SEQ ID NO 797
<211> LENGTH: 8
<212> TYPE: PRT
<213> ORGANISM: Homo sapiens

<400> SEQUENCE: 797

Gly Thr Asn Glu Ser Leu Glu Arg
1               5

<210> SEQ ID NO 798
<211> LENGTH: 7
<212> TYPE: PRT
<213> ORGANISM: Homo sapiens

<400> SEQUENCE: 798

Phe Ala Asn Tyr Ile Asp Lys
1               5

<210> SEQ ID NO 799
<211> LENGTH: 9
<212> TYPE: PRT
<213> ORGANISM: Homo sapiens

<400> SEQUENCE: 799

Leu Gln Asp Glu Ile Gln Asn Met Lys
1               5

<210> SEQ ID NO 800
<211> LENGTH: 9
<212> TYPE: PRT
<213> ORGANISM: Homo sapiens

<400> SEQUENCE: 800

Glu Tyr Gln Asp Leu Leu Asn Val Lys
1               5

<210> SEQ ID NO 801
<211> LENGTH: 14
<212> TYPE: PRT
<213> ORGANISM: Homo sapiens

<400> SEQUENCE: 801

Ser Leu Tyr Ala Ser Ser Pro Gly Gly Val Tyr Ala Thr Arg
1               5                   10

<210> SEQ ID NO 802
<211> LENGTH: 12
<212> TYPE: PRT
<213> ORGANISM: Homo sapiens

<400> SEQUENCE: 802

Val Glu Ser Leu Gln Glu Glu Ile Ala Phe Leu Lys
1               5                   10
```

-continued

```
<210> SEQ ID NO 803
<211> LENGTH: 30
<212> TYPE: PRT
<213> ORGANISM: Homo sapiens

<400> SEQUENCE: 803

Leu Ser Gly Ala Glu Pro Asp Asp Glu Tyr Gln Glu Phe Glu Glu
1               5                   10                  15

Met Leu Glu His Ala Glu Ser Ala Gln Asp Phe Ala Ser Arg
                20                  25                  30

<210> SEQ ID NO 804
<211> LENGTH: 30
<212> TYPE: PRT
<213> ORGANISM: Homo sapiens

<400> SEQUENCE: 804

Asn Val Asp Leu Leu Thr Pro Leu Ala Thr Gln Leu Thr Tyr Glu Gly
1               5                   10                  15

Leu Ile Asp Glu Ile Tyr Gly Ile Gln Asn Ser Tyr Val Lys
                20                  25                  30

<210> SEQ ID NO 805
<211> LENGTH: 22
<212> TYPE: PRT
<213> ORGANISM: Homo sapiens

<400> SEQUENCE: 805

Phe Val Ala Asp Glu Glu Leu Val His Leu Leu Leu Asp Glu Val Val
1               5                   10                  15

Ala Ser Ala Ala Leu Arg
                20

<210> SEQ ID NO 806
<211> LENGTH: 19
<212> TYPE: PRT
<213> ORGANISM: Homo sapiens

<400> SEQUENCE: 806

Val Leu Val Thr Val Ile Gln Gly Ala Val Glu Tyr Pro Asp Pro Ile
1               5                   10                  15

Ala Gln Lys

<210> SEQ ID NO 807
<211> LENGTH: 14
<212> TYPE: PRT
<213> ORGANISM: Homo sapiens

<400> SEQUENCE: 807

Ser Asp Ser Phe Glu Asn Pro Val Leu Gln Gln His Phe Arg
1               5                   10

<210> SEQ ID NO 808
<211> LENGTH: 22
<212> TYPE: PRT
<213> ORGANISM: Homo sapiens

<400> SEQUENCE: 808

Asn Leu Glu Ala Leu Ala Leu Asp Leu Met Glu Pro Glu Gln Ala Val
1               5                   10                  15

Asp Leu Thr Leu Pro Lys
                20
```

<210> SEQ ID NO 809
<211> LENGTH: 17
<212> TYPE: PRT
<213> ORGANISM: Homo sapiens

<400> SEQUENCE: 809

Ser Val Gly Asp Gly Glu Thr Val Glu Phe Asp Val Val Glu Gly Glu
1               5                   10                  15

Lys

<210> SEQ ID NO 810
<211> LENGTH: 12
<212> TYPE: PRT
<213> ORGANISM: Homo sapiens

<400> SEQUENCE: 810

Gly Ile Val Glu Glu Ser Val Thr Gly Val His Arg
1               5                   10

<210> SEQ ID NO 811
<211> LENGTH: 16
<212> TYPE: PRT
<213> ORGANISM: Homo sapiens

<400> SEQUENCE: 811

Ser Leu Asp Leu Phe Asn Cys Glu Val Thr Asn Leu Asn Asp Tyr Arg
1               5                   10                  15

<210> SEQ ID NO 812
<211> LENGTH: 15
<212> TYPE: PRT
<213> ORGANISM: Homo sapiens

<400> SEQUENCE: 812

Val Leu Glu Asp Val Thr Gly Glu Glu Phe Val Leu Phe Met Lys
1               5                   10                  15

<210> SEQ ID NO 813
<211> LENGTH: 18
<212> TYPE: PRT
<213> ORGANISM: Homo sapiens

<400> SEQUENCE: 813

Gly Thr Leu Gly Gly Leu Phe Ser Gln Ile Leu Gln Gly Glu Asp Ile
1               5                   10                  15

Val Arg

<210> SEQ ID NO 814
<211> LENGTH: 27
<212> TYPE: PRT
<213> ORGANISM: Homo sapiens

<400> SEQUENCE: 814

Gln Gln Leu Val Glu Leu Val Ala Glu Gln Ala Asp Leu Glu Gln Thr
1               5                   10                  15

Phe Asn Pro Ser Asp Pro Asp Cys Val Asp Arg
            20                  25

<210> SEQ ID NO 815
<211> LENGTH: 13
<212> TYPE: PRT
<213> ORGANISM: Homo sapiens

<400> SEQUENCE: 815

Ile Gly Asp Glu Leu Asp Ser Asn Met Glu Leu Gln Arg
1               5                   10

<210> SEQ ID NO 816
<211> LENGTH: 30
<212> TYPE: PRT
<213> ORGANISM: Homo sapiens

<400> SEQUENCE: 816

Gly Val Asp Asn Thr Phe Ala Asp Glu Leu Val Glu Leu Ser Thr Ala
1               5                   10                  15

Leu Glu His Gln Glu Tyr Ile Thr Phe Leu Glu Asp Leu Lys
            20                  25                  30

<210> SEQ ID NO 817
<211> LENGTH: 15
<212> TYPE: PRT
<213> ORGANISM: Homo sapiens

<400> SEQUENCE: 817

Met Ser Gly Gly Trp Glu Leu Glu Leu Asn Gly Thr Glu Ala Lys
1               5                   10                  15

<210> SEQ ID NO 818
<211> LENGTH: 37
<212> TYPE: PRT
<213> ORGANISM: Homo sapiens

<400> SEQUENCE: 818

Ser Leu Gly Gln Asn Pro Thr Glu Ala Glu Leu Gln Asp Met Ile Asn
1               5                   10                  15

Glu Val Asp Ala Asp Gly Asn Gly Thr Ile Asp Phe Pro Glu Phe Leu
            20                  25                  30

Thr Met Met Ala Arg
        35

<210> SEQ ID NO 819
<211> LENGTH: 17
<212> TYPE: PRT
<213> ORGANISM: Homo sapiens

<400> SEQUENCE: 819

Leu Tyr Leu Glu Asp Asp Asp Pro Val Gln Ala Glu Ala Tyr Ile Asn
1               5                   10                  15

Arg

<210> SEQ ID NO 820
<211> LENGTH: 14
<212> TYPE: PRT
<213> ORGANISM: Homo sapiens

<400> SEQUENCE: 820

Asn Glu Gly Val Ala Thr Tyr Ala Ala Ala Val Leu Phe Arg
1               5                   10

<210> SEQ ID NO 821
<211> LENGTH: 17
<212> TYPE: PRT
<213> ORGANISM: Homo sapiens

<400> SEQUENCE: 821

```
Met Asn Ser Glu Glu Glu Asp Glu Val Trp Gln Val Ile Ile Gly Ala
1               5                   10                  15

Arg

<210> SEQ ID NO 822
<211> LENGTH: 18
<212> TYPE: PRT
<213> ORGANISM: Homo sapiens

<400> SEQUENCE: 822

Thr Asn Leu Ile Val Asn Tyr Leu Pro Gln Asn Met Thr Gln Asp Glu
1               5                   10                  15

Leu Arg

<210> SEQ ID NO 823
<211> LENGTH: 17
<212> TYPE: PRT
<213> ORGANISM: Homo sapiens

<400> SEQUENCE: 823

Thr Tyr Ala Asp Tyr Glu Ser Val Asn Glu Cys Met Glu Gly Val Cys
1               5                   10                  15

Lys

<210> SEQ ID NO 824
<211> LENGTH: 11
<212> TYPE: PRT
<213> ORGANISM: Homo sapiens

<400> SEQUENCE: 824

Tyr Asp Leu Leu Cys Leu Glu Gly Leu Val Arg
1               5                   10

<210> SEQ ID NO 825
<211> LENGTH: 13
<212> TYPE: PRT
<213> ORGANISM: Homo sapiens

<400> SEQUENCE: 825

Ile Met Gln Leu Leu Asp Val Pro Pro Gly Glu Asp Lys
1               5                   10

<210> SEQ ID NO 826
<211> LENGTH: 15
<212> TYPE: PRT
<213> ORGANISM: Homo sapiens

<400> SEQUENCE: 826

Ala Leu Asp Thr Leu Glu Asp Asp Met Thr Ile Ser Val Glu Lys
1               5                   10                  15

<210> SEQ ID NO 827
<211> LENGTH: 17
<212> TYPE: PRT
<213> ORGANISM: Homo sapiens

<400> SEQUENCE: 827

Phe Glu Ile Gly Glu Gly Glu Asn Leu Asp Leu Pro Tyr Gly Leu Glu
1               5                   10                  15

Arg

<210> SEQ ID NO 828
```

```
<211> LENGTH: 29
<212> TYPE: PRT
<213> ORGANISM: Homo sapiens

<400> SEQUENCE: 828

Val Gly Ala Thr Ala Ala Val Tyr Ser Ala Ala Ile Leu Glu Tyr Leu
1               5                   10                  15

Thr Ala Glu Val Leu Glu Leu Ala Gly Asn Ala Ser Lys
            20                  25

<210> SEQ ID NO 829
<211> LENGTH: 22
<212> TYPE: PRT
<213> ORGANISM: Homo sapiens

<400> SEQUENCE: 829

Leu Gly Ala Gly Tyr Pro Met Gly Pro Phe Glu Leu Leu Asp Tyr Val
1               5                   10                  15

Gly Leu Asp Thr Thr Lys
            20

<210> SEQ ID NO 830
<211> LENGTH: 24
<212> TYPE: PRT
<213> ORGANISM: Homo sapiens

<400> SEQUENCE: 830

Glu Phe Tyr Gln Cys Asp Phe Asp Ile Ala Gly Asn Phe Asp Pro Met
1               5                   10                  15

Ile Pro Asp Ala Glu Cys Leu Lys
            20

<210> SEQ ID NO 831
<211> LENGTH: 14
<212> TYPE: PRT
<213> ORGANISM: Homo sapiens

<400> SEQUENCE: 831

Phe Ile Ala Val Gly Tyr Val Asp Asp Thr Gln Phe Val Arg
1               5                   10

<210> SEQ ID NO 832
<211> LENGTH: 20
<212> TYPE: PRT
<213> ORGANISM: Homo sapiens

<400> SEQUENCE: 832

Gly Phe Gly Phe Val Thr Tyr Ala Thr Val Glu Glu Val Asp Ala Ala
1               5                   10                  15

Met Asn Ala Arg
            20

<210> SEQ ID NO 833
<211> LENGTH: 16
<212> TYPE: PRT
<213> ORGANISM: Homo sapiens

<400> SEQUENCE: 833

Leu Phe Ile Gly Gly Leu Ser Phe Glu Thr Thr Asp Glu Ser Leu Arg
1               5                   10                  15

<210> SEQ ID NO 834
<211> LENGTH: 10
```

<212> TYPE: PRT
<213> ORGANISM: Homo sapiens

<400> SEQUENCE: 834

Ile Glu Val Ile Glu Ile Met Thr Asp Arg
1               5                   10

<210> SEQ ID NO 835
<211> LENGTH: 11
<212> TYPE: PRT
<213> ORGANISM: Homo sapiens

<400> SEQUENCE: 835

Ile Asp Glu Pro Leu Glu Gly Ser Glu Asp Arg
1               5                   10

<210> SEQ ID NO 836
<211> LENGTH: 9
<212> TYPE: PRT
<213> ORGANISM: Homo sapiens

<400> SEQUENCE: 836

Asp Leu Ala Gly Ser Ile Ile Gly Lys
1               5

<210> SEQ ID NO 837
<211> LENGTH: 8
<212> TYPE: PRT
<213> ORGANISM: Homo sapiens

<400> SEQUENCE: 837

His Glu Ser Gly Ala Ser Ile Lys
1               5

<210> SEQ ID NO 838
<211> LENGTH: 23
<212> TYPE: PRT
<213> ORGANISM: Homo sapiens

<400> SEQUENCE: 838

Ile Ile Thr Ile Thr Gly Thr Gln Asp Gln Ile Gln Asn Ala Gln Tyr
1               5                   10                  15

Leu Leu Gln Asn Ser Val Lys
            20

<210> SEQ ID NO 839
<211> LENGTH: 13
<212> TYPE: PRT
<213> ORGANISM: Homo sapiens

<400> SEQUENCE: 839

Val Phe Asn Val Phe Cys Leu Tyr Gly Asn Val Glu Lys
1               5                   10

<210> SEQ ID NO 840
<211> LENGTH: 20
<212> TYPE: PRT
<213> ORGANISM: Homo sapiens

<400> SEQUENCE: 840

Gly Leu Val Ala Val Ile Thr Gly Gly Ala Ser Gly Leu Gly Leu Ala
1               5                   10                  15

Thr Ala Glu Arg
            20

<210> SEQ ID NO 841
<211> LENGTH: 24
<212> TYPE: PRT
<213> ORGANISM: Homo sapiens

<400> SEQUENCE: 841

Gln Thr Gln Ile Phe Thr Thr Tyr Ser Asp Asn Gln Pro Gly Val Leu
1               5                   10                  15

Ile Gln Val Tyr Glu Gly Glu Arg
            20

<210> SEQ ID NO 842
<211> LENGTH: 16
<212> TYPE: PRT
<213> ORGANISM: Homo sapiens

<400> SEQUENCE: 842

Ile Glu Trp Leu Glu Ser His Gln Asp Ala Asp Ile Glu Asp Phe Lys
1               5                   10                  15

<210> SEQ ID NO 843
<211> LENGTH: 18
<212> TYPE: PRT
<213> ORGANISM: Homo sapiens

<400> SEQUENCE: 843

Asp Asn His Leu Leu Gly Thr Phe Asp Leu Thr Gly Ile Pro Pro Ala
1               5                   10                  15

Pro Arg

<210> SEQ ID NO 844
<211> LENGTH: 19
<212> TYPE: PRT
<213> ORGANISM: Homo sapiens

<400> SEQUENCE: 844

Ser Thr Asn Gly Asp Thr Phe Leu Gly Gly Glu Asp Phe Asp Gln Ala
1               5                   10                  15

Leu Leu Arg

<210> SEQ ID NO 845
<211> LENGTH: 13
<212> TYPE: PRT
<213> ORGANISM: Homo sapiens

<400> SEQUENCE: 845

Thr Leu Asn Asp Glu Leu Glu Ile Ile Glu Gly Met Lys
1               5                   10

<210> SEQ ID NO 846
<211> LENGTH: 12
<212> TYPE: PRT
<213> ORGANISM: Homo sapiens

<400> SEQUENCE: 846

Gly Tyr Ile Ser Pro Tyr Phe Ile Asn Thr Ser Lys
1               5                   10

<210> SEQ ID NO 847
<211> LENGTH: 18
<212> TYPE: PRT
<213> ORGANISM: Homo sapiens

<400> SEQUENCE: 847

Ile Ser Ser Ile Gln Ser Ile Val Pro Ala Leu Glu Ile Ala Asn Ala
1               5                   10                  15

His Arg

<210> SEQ ID NO 848
<211> LENGTH: 17
<212> TYPE: PRT
<213> ORGANISM: Homo sapiens

<400> SEQUENCE: 848

Ile Gln Glu Ile Ile Glu Gln Leu Asp Val Thr Thr Ser Glu Tyr Glu
1               5                   10                  15

Lys

<210> SEQ ID NO 849
<211> LENGTH: 23
<212> TYPE: PRT
<213> ORGANISM: Homo sapiens

<400> SEQUENCE: 849

Ile Met Gln Ser Ser Ser Glu Val Gly Tyr Asp Ala Met Ala Gly Asp
1               5                   10                  15

Phe Val Asn Met Val Glu Lys
            20

<210> SEQ ID NO 850
<211> LENGTH: 25
<212> TYPE: PRT
<213> ORGANISM: Homo sapiens

<400> SEQUENCE: 850

Leu Val Gln Asp Val Ala Asn Asn Thr Asn Glu Glu Ala Gly Asp Gly
1               5                   10                  15

Thr Thr Thr Ala Thr Val Leu Ala Arg
            20                  25

<210> SEQ ID NO 851
<211> LENGTH: 13
<212> TYPE: PRT
<213> ORGANISM: Homo sapiens

<400> SEQUENCE: 851

Asn Leu Tyr Val Thr Phe Pro Ile Pro Asp Leu Gln Lys
1               5                   10

<210> SEQ ID NO 852
<211> LENGTH: 17
<212> TYPE: PRT
<213> ORGANISM: Homo sapiens

<400> SEQUENCE: 852

Thr Val Asn Glu Leu Gln Asn Leu Thr Ala Ala Glu Val Val Val Pro
1               5                   10                  15

Arg

<210> SEQ ID NO 853
<211> LENGTH: 25
<212> TYPE: PRT
<213> ORGANISM: Homo sapiens

```
<400> SEQUENCE: 853

Tyr Gly Ala Val Asp Pro Leu Ala Leu Leu Ala Val Pro Asp Met
1               5                   10                  15

Ser Ser Leu Ala Cys Gly Tyr Leu Arg
            20                  25

<210> SEQ ID NO 854
<211> LENGTH: 15
<212> TYPE: PRT
<213> ORGANISM: Homo sapiens

<400> SEQUENCE: 854

Leu Leu Gly Ala Ser Glu Leu Pro Ile Val Thr Pro Ala Leu Arg
1               5                   10                  15

<210> SEQ ID NO 855
<211> LENGTH: 16
<212> TYPE: PRT
<213> ORGANISM: Homo sapiens

<400> SEQUENCE: 855

Gly Ala Leu Gln Tyr Leu Val Pro Ile Leu Thr Gln Thr Leu Thr Lys
1               5                   10                  15

<210> SEQ ID NO 856
<211> LENGTH: 15
<212> TYPE: PRT
<213> ORGANISM: Homo sapiens

<400> SEQUENCE: 856

Ala Ala Val Glu Asn Leu Pro Thr Phe Leu Val Glu Leu Ser Arg
1               5                   10                  15

<210> SEQ ID NO 857
<211> LENGTH: 12
<212> TYPE: PRT
<213> ORGANISM: Homo sapiens

<400> SEQUENCE: 857

Ser Ser Ala Tyr Glu Ser Leu Met Glu Ile Val Lys
1               5                   10

<210> SEQ ID NO 858
<211> LENGTH: 15
<212> TYPE: PRT
<213> ORGANISM: Homo sapiens

<400> SEQUENCE: 858

Gln Ala Val Gln Glu Leu Val Ser Leu Tyr Tyr Glu Glu Ala Arg
1               5                   10                  15

<210> SEQ ID NO 859
<211> LENGTH: 22
<212> TYPE: PRT
<213> ORGANISM: Homo sapiens

<400> SEQUENCE: 859

Ala Gly Gly Val Leu Ala Tyr Glu Leu Leu Pro Ala Leu Asp Glu Val
1               5                   10                  15

Leu Ala Ser Asp Ser Arg
            20

<210> SEQ ID NO 860
```

-continued

```
<211> LENGTH: 24
<212> TYPE: PRT
<213> ORGANISM: Homo sapiens

<400> SEQUENCE: 860

Ser Ala Cys Ser Leu Glu Ser Asn Leu Glu Gly Leu Ala Gly Val Leu
1               5                   10                  15

Glu Ala Asp Leu Pro Asn Tyr Lys
            20

<210> SEQ ID NO 861
<211> LENGTH: 12
<212> TYPE: PRT
<213> ORGANISM: Homo sapiens

<400> SEQUENCE: 861

Gln Gln Ile Gln Ser Ile Gln Gln Ser Ile Glu Arg
1               5                   10

<210> SEQ ID NO 862
<211> LENGTH: 9
<212> TYPE: PRT
<213> ORGANISM: Homo sapiens

<400> SEQUENCE: 862

Val Glu Leu Asp Asn Met Pro Leu Arg
1               5

<210> SEQ ID NO 863
<211> LENGTH: 14
<212> TYPE: PRT
<213> ORGANISM: Homo sapiens

<400> SEQUENCE: 863

Phe Ala Gln Pro Gly Ser Phe Glu Tyr Glu Tyr Ala Met Arg
1               5                   10

<210> SEQ ID NO 864
<211> LENGTH: 9
<212> TYPE: PRT
<213> ORGANISM: Homo sapiens

<400> SEQUENCE: 864

Leu Glu Met Glu Met Glu Ala Ala Arg
1               5

<210> SEQ ID NO 865
<211> LENGTH: 23
<212> TYPE: PRT
<213> ORGANISM: Homo sapiens

<400> SEQUENCE: 865

Asn Leu Pro Gln Tyr Val Ser Asn Glu Leu Leu Glu Glu Ala Phe Ser
1               5                   10                  15

Val Phe Gly Gln Val Glu Arg
            20

<210> SEQ ID NO 866
<211> LENGTH: 8
<212> TYPE: PRT
<213> ORGANISM: Homo sapiens

<400> SEQUENCE: 866

Ala Val Val Ile Val Asp Asp Arg
1               5
```

<210> SEQ ID NO 867
<211> LENGTH: 19
<212> TYPE: PRT
<213> ORGANISM: Homo sapiens

<400> SEQUENCE: 867

Asp Asn Met Ala Gln Glu Gly Val Ile Leu Asp Asp Val Asp Ser Ser
1               5                   10                  15

Val Cys Arg

<210> SEQ ID NO 868
<211> LENGTH: 20
<212> TYPE: PRT
<213> ORGANISM: Homo sapiens

<400> SEQUENCE: 868

Val Ala Ile Ala Ala Leu Glu Val Leu Glu Glu Glu Asn Leu Ala Glu
1               5                   10                  15

Asn Ala Asp Lys
            20

<210> SEQ ID NO 869
<211> LENGTH: 25
<212> TYPE: PRT
<213> ORGANISM: Homo sapiens

<400> SEQUENCE: 869

Gln Phe Leu Gln Ala Ala Glu Ala Ile Asp Asp Ile Pro Phe Gly Ile
1               5                   10                  15

Thr Ser Asn Ser Asp Val Phe Ser Lys
            20                  25

<210> SEQ ID NO 870
<211> LENGTH: 17
<212> TYPE: PRT
<213> ORGANISM: Homo sapiens

<400> SEQUENCE: 870

His Asn Gln Leu Pro Leu Val Ile Glu Phe Thr Glu Gln Thr Ala Pro
1               5                   10                  15

Lys

<210> SEQ ID NO 871
<211> LENGTH: 16
<212> TYPE: PRT
<213> ORGANISM: Homo sapiens

<400> SEQUENCE: 871

Ala Leu Tyr Asp Thr Phe Ser Ala Phe Gly Asn Ile Leu Ser Cys Lys
1               5                   10                  15

<210> SEQ ID NO 872
<211> LENGTH: 17
<212> TYPE: PRT
<213> ORGANISM: Homo sapiens

<400> SEQUENCE: 872

Ser Leu Gly Tyr Ala Tyr Val Asn Phe Gln Gln Pro Ala Asp Ala Glu
1               5                   10                  15

Arg

<210> SEQ ID NO 873
<211> LENGTH: 18
<212> TYPE: PRT
<213> ORGANISM: Homo sapiens

<400> SEQUENCE: 873

Val Glu Met Leu Asp Asn Leu Leu Asp Ile Glu Val Ala Tyr Ser Leu
1               5                   10                  15

Leu Arg

<210> SEQ ID NO 874
<211> LENGTH: 47
<212> TYPE: PRT
<213> ORGANISM: Homo sapiens

<400> SEQUENCE: 874

Thr Thr Pro Asp Pro Ser Ala Asn Ile Ser Leu Asp Gly Val Asp Val
1               5                   10                  15

Pro Leu Gly Thr Gly Ile Ser Ser Gly Val Asn Asp Thr Ser Leu Leu
            20                  25                  30

Tyr Asn Glu Tyr Ile Val Tyr Asp Ile Ala Gln Val Asn Leu Lys
        35                  40                  45

<210> SEQ ID NO 875
<211> LENGTH: 21
<212> TYPE: PRT
<213> ORGANISM: Homo sapiens

<400> SEQUENCE: 875

Leu Met Asp Leu Asp Val Glu Gln Leu Gly Ile Pro Glu Gln Glu Tyr
1               5                   10                  15

Ser Cys Val Val Lys
            20

<210> SEQ ID NO 876
<211> LENGTH: 11
<212> TYPE: PRT
<213> ORGANISM: Homo sapiens

<400> SEQUENCE: 876

Asp Leu Pro Glu Leu Ala Leu Asp Thr Pro Arg
1               5                   10

<210> SEQ ID NO 877
<211> LENGTH: 14
<212> TYPE: PRT
<213> ORGANISM: Homo sapiens

<400> SEQUENCE: 877

Phe Tyr Gly Pro Glu Gly Pro Tyr Gly Val Phe Ala Gly Arg
1               5                   10

<210> SEQ ID NO 878
<211> LENGTH: 16
<212> TYPE: PRT
<213> ORGANISM: Homo sapiens

<400> SEQUENCE: 878

Pro Tyr Leu Phe Gln Ser Asp Pro Ser Gly Ala Tyr Phe Ala Trp Lys
1               5                   10                  15

-continued

```
<210> SEQ ID NO 879
<211> LENGTH: 21
<212> TYPE: PRT
<213> ORGANISM: Homo sapiens

<400> SEQUENCE: 879

Leu Val Gln Ile Glu Tyr Ala Leu Ala Ala Val Ala Gly Gly Ala Pro
1               5                   10                  15

Ser Val Gly Ile Lys
            20

<210> SEQ ID NO 880
<211> LENGTH: 24
<212> TYPE: PRT
<213> ORGANISM: Homo sapiens

<400> SEQUENCE: 880

Leu Asn Glu Asp Met Ala Cys Ser Val Ala Gly Ile Thr Ser Asp Ala
1               5                   10                  15

Asn Val Leu Thr Asn Glu Leu Arg
            20

<210> SEQ ID NO 881
<211> LENGTH: 18
<212> TYPE: PRT
<213> ORGANISM: Homo sapiens

<400> SEQUENCE: 881

Phe Phe Pro Tyr Tyr Val Tyr Asn Ile Ile Gly Gly Leu Asp Glu Glu
1               5                   10                  15

Gly Lys

<210> SEQ ID NO 882
<211> LENGTH: 31
<212> TYPE: PRT
<213> ORGANISM: Homo sapiens

<400> SEQUENCE: 882

Thr Pro Tyr His Val Asn Leu Leu Ala Gly Tyr Asp Glu His Glu
1               5                   10                  15

Gly Pro Ala Leu Tyr Tyr Met Asp Tyr Leu Ala Ala Leu Ala Lys
            20                  25                  30

<210> SEQ ID NO 883
<211> LENGTH: 21
<212> TYPE: PRT
<213> ORGANISM: Homo sapiens

<400> SEQUENCE: 883

Ile Leu Leu Leu Cys Val Gly Glu Ala Gly Asp Thr Val Gln Phe Ala
1               5                   10                  15

Glu Tyr Ile Gln Lys
            20

<210> SEQ ID NO 884
<211> LENGTH: 16
<212> TYPE: PRT
<213> ORGANISM: Homo sapiens

<400> SEQUENCE: 884

Phe Gly Pro Tyr Tyr Thr Glu Pro Val Ile Ala Gly Leu Asp Pro Lys
1               5                   10                  15
```

```
<210> SEQ ID NO 885
<211> LENGTH: 19
<212> TYPE: PRT
<213> ORGANISM: Homo sapiens

<400> SEQUENCE: 885

Pro Val Ile Val Glu Pro Met Glu Gln Phe Asp Asp Glu Asp Gly Leu
1               5                   10                  15

Pro Glu Lys

<210> SEQ ID NO 886
<211> LENGTH: 14
<212> TYPE: PRT
<213> ORGANISM: Homo sapiens

<400> SEQUENCE: 886

Gly Asp Phe Val Thr Ser Phe Tyr Trp Pro Trp Gln Thr Lys
1               5                   10

<210> SEQ ID NO 887
<211> LENGTH: 17
<212> TYPE: PRT
<213> ORGANISM: Homo sapiens

<400> SEQUENCE: 887

Asp Val Pro Tyr Pro Pro Leu Ser Pro Ala Ile Glu Ala Ile Gln
1               5                   10                  15

Lys

<210> SEQ ID NO 888
<211> LENGTH: 13
<212> TYPE: PRT
<213> ORGANISM: Homo sapiens

<400> SEQUENCE: 888

Gly Asn Thr Ala Ala Tyr Leu Leu Tyr Ala Phe Thr Arg
1               5                   10

<210> SEQ ID NO 889
<211> LENGTH: 11
<212> TYPE: PRT
<213> ORGANISM: Homo sapiens

<400> SEQUENCE: 889

Ser Glu Ile Glu Tyr Tyr Ala Met Leu Ala Lys
1               5                   10

<210> SEQ ID NO 890
<211> LENGTH: 16
<212> TYPE: PRT
<213> ORGANISM: Homo sapiens

<400> SEQUENCE: 890

Ala Leu Glu Ser Ser Ile Ala Pro Ile Val Ile Phe Ala Ser Asn Arg
1               5                   10                  15

<210> SEQ ID NO 891
<211> LENGTH: 17
<212> TYPE: PRT
<213> ORGANISM: Homo sapiens

<400> SEQUENCE: 891

Val Pro Phe Cys Pro Met Val Gly Ser Glu Val Tyr Ser Thr Glu Ile
```

-continued

```
1               5                   10                  15

Lys

<210> SEQ ID NO 892
<211> LENGTH: 23
<212> TYPE: PRT
<213> ORGANISM: Homo sapiens

<400> SEQUENCE: 892

Asn Leu Ser Pro Tyr Val Ser Asn Glu Leu Leu Glu Glu Ala Phe Ser
1               5                   10                  15

Gln Phe Gly Pro Ile Glu Arg
            20

<210> SEQ ID NO 893
<211> LENGTH: 19
<212> TYPE: PRT
<213> ORGANISM: Homo sapiens

<400> SEQUENCE: 893

Pro Val Ile Val Glu Pro Leu Glu Gln Leu Asp Asp Glu Asp Gly Leu
1               5                   10                  15

Pro Glu Lys

<210> SEQ ID NO 894
<211> LENGTH: 24
<212> TYPE: PRT
<213> ORGANISM: Homo sapiens

<400> SEQUENCE: 894

Tyr Gly Gln Val Thr Pro Leu Glu Ile Asp Ile Leu Tyr Gln Leu Ala
1               5                   10                  15

Asp Leu Tyr Asn Ala Ser Gly Arg
            20

<210> SEQ ID NO 895
<211> LENGTH: 22
<212> TYPE: PRT
<213> ORGANISM: Homo sapiens

<400> SEQUENCE: 895

Phe Gly Gln Val Thr Pro Met Glu Val Asp Ile Leu Phe Gln Leu Ala
1               5                   10                  15

Asp Leu Tyr Glu Pro Arg
            20

<210> SEQ ID NO 896
<211> LENGTH: 12
<212> TYPE: PRT
<213> ORGANISM: Homo sapiens

<400> SEQUENCE: 896

Leu Ala Val Ala Thr Phe Ala Gly Ile Glu Asn Lys
1               5                   10

<210> SEQ ID NO 897
<211> LENGTH: 12
<212> TYPE: PRT
<213> ORGANISM: Homo sapiens

<400> SEQUENCE: 897

Glu Val Asp Asp Leu Glu Gln Trp Ile Ala Glu Arg
```

```
<210> SEQ ID NO 898
<211> LENGTH: 18
<212> TYPE: PRT
<213> ORGANISM: Homo sapiens

<400> SEQUENCE: 898

Glu Leu Gln Glu Asn Gln Asp Glu Ile Glu Asn Met Met Asn Ala Ile
1               5                   10                  15

Phe Lys

<210> SEQ ID NO 899
<211> LENGTH: 19
<212> TYPE: PRT
<213> ORGANISM: Homo sapiens

<400> SEQUENCE: 899

Ala Gln Gln Leu Ala Ala Glu Leu Glu Val Glu Met Met Ala Asp Met
1               5                   10                  15

Tyr Asn Arg

<210> SEQ ID NO 900
<211> LENGTH: 12
<212> TYPE: PRT
<213> ORGANISM: Homo sapiens

<400> SEQUENCE: 900

Asp Gln Asp Glu Leu Asn Pro Tyr Ala Ala Trp Arg
1               5                   10

<210> SEQ ID NO 901
<211> LENGTH: 26
<212> TYPE: PRT
<213> ORGANISM: Homo sapiens

<400> SEQUENCE: 901

Thr Gln Asp Gln Asp Glu Asn Val Ala Leu Glu Ala Cys Glu Phe Trp
1               5                   10                  15

Leu Thr Leu Ala Glu Gln Pro Ile Cys Lys
            20                  25

<210> SEQ ID NO 902
<211> LENGTH: 20
<212> TYPE: PRT
<213> ORGANISM: Homo sapiens

<400> SEQUENCE: 902

Leu Glu Gln Leu Asn Gln Tyr Pro Asp Phe Asn Asn Tyr Leu Ile Phe
1               5                   10                  15

Val Leu Thr Lys
            20

<210> SEQ ID NO 903
<211> LENGTH: 11
<212> TYPE: PRT
<213> ORGANISM: Homo sapiens

<400> SEQUENCE: 903

Val Glu Glu Val Val Tyr Asp Leu Ser Ile Arg
1               5                   10
```

-continued

```
<210> SEQ ID NO 904
<211> LENGTH: 22
<212> TYPE: PRT
<213> ORGANISM: Homo sapiens

<400> SEQUENCE: 904

Gly Ala Leu Val Leu Gly Tyr Glu Gly Trp Leu Ala Gly Tyr Gln Met
1               5                   10                  15

Asn Phe Glu Thr Ala Lys
            20

<210> SEQ ID NO 905
<211> LENGTH: 19
<212> TYPE: PRT
<213> ORGANISM: Homo sapiens

<400> SEQUENCE: 905

Glu His Ile Asn Leu Gly Cys Asp Met Asp Phe Asp Ile Ala Gly Pro
1               5                   10                  15

Ser Ile Arg

<210> SEQ ID NO 906
<211> LENGTH: 19
<212> TYPE: PRT
<213> ORGANISM: Homo sapiens

<400> SEQUENCE: 906

Trp Asn Thr Asp Asn Thr Leu Gly Thr Glu Ile Thr Val Glu Asp Gln
1               5                   10                  15

Leu Ala Arg

<210> SEQ ID NO 907
<211> LENGTH: 11
<212> TYPE: PRT
<213> ORGANISM: Homo sapiens

<400> SEQUENCE: 907

Val Thr Gln Ser Asn Phe Ala Val Gly Tyr Lys
1               5                   10

<210> SEQ ID NO 908
<211> LENGTH: 11
<212> TYPE: PRT
<213> ORGANISM: Homo sapiens

<400> SEQUENCE: 908

Trp Thr Glu Tyr Gly Leu Thr Phe Thr Glu Lys
1               5                   10

<210> SEQ ID NO 909
<211> LENGTH: 19
<212> TYPE: PRT
<213> ORGANISM: Homo sapiens

<400> SEQUENCE: 909

Ser Glu Asn Gly Leu Glu Phe Thr Ser Ser Gly Ser Ala Asn Thr Glu
1               5                   10                  15

Thr Thr Lys

<210> SEQ ID NO 910
<211> LENGTH: 23
<212> TYPE: PRT
<213> ORGANISM: Homo sapiens
```

```
<400> SEQUENCE: 910

Thr Asp Glu Phe Gln Leu His Thr Asn Val Asn Asp Gly Thr Glu Phe
1               5                   10                  15

Gly Gly Ser Ile Tyr Gln Lys
            20

<210> SEQ ID NO 911
<211> LENGTH: 12
<212> TYPE: PRT
<213> ORGANISM: Homo sapiens

<400> SEQUENCE: 911

Tyr Gln Ile Asp Pro Asp Ala Cys Phe Ser Ala Lys
1               5                   10

<210> SEQ ID NO 912
<211> LENGTH: 9
<212> TYPE: PRT
<213> ORGANISM: Homo sapiens

<400> SEQUENCE: 912

Asp Asn Leu Ala Glu Asp Ile Met Arg
1               5

<210> SEQ ID NO 913
<211> LENGTH: 11
<212> TYPE: PRT
<213> ORGANISM: Homo sapiens

<400> SEQUENCE: 913

Glu Glu Ala Glu Asn Thr Leu Gln Ser Phe Arg
1               5                   10

<210> SEQ ID NO 914
<211> LENGTH: 8
<212> TYPE: PRT
<213> ORGANISM: Homo sapiens

<400> SEQUENCE: 914

Leu Gln Glu Glu Met Leu Gln Arg
1               5

<210> SEQ ID NO 915
<211> LENGTH: 12
<212> TYPE: PRT
<213> ORGANISM: Homo sapiens

<400> SEQUENCE: 915

Val Glu Ser Leu Gln Glu Glu Ile Ala Phe Leu Lys
1               5                   10

<210> SEQ ID NO 916
<211> LENGTH: 30
<212> TYPE: PRT
<213> ORGANISM: Homo sapiens

<400> SEQUENCE: 916

Asn Val Asp Leu Leu Thr Pro Leu Ala Thr Gln Leu Thr Tyr Glu Gly
1               5                   10                  15

Leu Ile Asp Glu Ile Tyr Gly Ile Gln Asn Ser Tyr Val Lys
            20                  25                  30
```

```
<210> SEQ ID NO 917
<211> LENGTH: 14
<212> TYPE: PRT
<213> ORGANISM: Homo sapiens

<400> SEQUENCE: 917

Ser Asp Ser Phe Glu Asn Pro Val Leu Gln Gln His Phe Arg
1               5                   10

<210> SEQ ID NO 918
<211> LENGTH: 20
<212> TYPE: PRT
<213> ORGANISM: Homo sapiens

<400> SEQUENCE: 918

Lys Ala Ala Phe Asp Asp Ala Ile Ala Glu Leu Asp Thr Leu Ser Glu
1               5                   10                  15

Glu Ser Tyr Lys
            20

<210> SEQ ID NO 919
<211> LENGTH: 13
<212> TYPE: PRT
<213> ORGANISM: Homo sapiens

<400> SEQUENCE: 919

Ile Gly Asp Glu Leu Asp Ser Asn Met Glu Leu Gln Arg
1               5                   10

<210> SEQ ID NO 920
<211> LENGTH: 19
<212> TYPE: PRT
<213> ORGANISM: Homo sapiens

<400> SEQUENCE: 920

Arg Gly Gln Asp His Cys Gly Ile Glu Ser Glu Val Val Ala Gly Ile
1               5                   10                  15

Pro Arg Thr

<210> SEQ ID NO 921
<211> LENGTH: 14
<212> TYPE: PRT
<213> ORGANISM: Homo sapiens

<400> SEQUENCE: 921

Lys Ser Ile Leu Asp Trp Thr Ser Phe Asn Gln Glu Arg Ile
1               5                   10

<210> SEQ ID NO 922
<211> LENGTH: 20
<212> TYPE: PRT
<213> ORGANISM: Homo sapiens

<400> SEQUENCE: 922

Arg Phe Met Cys Asn Leu Asp Cys Gln Glu Glu Pro Asp Ser Cys Ile
1               5                   10                  15

Ser Glu Lys Leu
            20

<210> SEQ ID NO 923
<211> LENGTH: 19
<212> TYPE: PRT
<213> ORGANISM: Homo sapiens
```

```
<400> SEQUENCE: 923

Lys Asp Val Pro Tyr Pro Pro Pro Leu Ser Pro Ala Ile Glu Ala Ile
1               5                   10                  15

Gln Lys Glu

<210> SEQ ID NO 924
<211> LENGTH: 33
<212> TYPE: PRT
<213> ORGANISM: Homo sapiens

<400> SEQUENCE: 924

Arg Met Asn Glu Asp Thr Gly Thr Asp Tyr Ile Thr Pro Trp Gln Leu
1               5                   10                  15

Ser Gln Val Val Asp Gly Gly Gly Ile Gly Ile Ile Glu Glu Ser Lys
            20                  25                  30

His

<210> SEQ ID NO 925
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 925

Lys Asp Glu Leu
1
```

PHOTOREACTIVE LIGANDS AND USES THEREOF

CROSS-REFERENCE

This application is a U.S. National Phase of International Application No. PCT/US2018/014104, filed on Jan. 17, 2018, which claims the benefit of U.S. Provisional Application No. 62/447,882, filed Jan. 18, 2017, both of which are incorporated herein by reference in their entireties.

STATEMENT AS TO FEDERALLY SPONSORED RESEARCH

This invention was made with government support under grant numbers DK099810, CA132630 and 1S10OD16357 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Mar. 14, 2018, is named 48054-706_831_SL.txt and is 199,103 bytes in size.

BACKGROUND OF THE DISCLOSURE

Protein function assignment has been benefited from genetic methods, such as target gene disruption, RNA interference, and genome editing technologies, which selectively disrupt the expression of proteins in native biological systems. Chemical probes offer a complementary way to perturb proteins that have the advantages of producing graded (dose-dependent) gain- (agonism) or loss- (antagonism) of-function effects that are introduced acutely and reversibly in cells and organisms. Small molecules present an alternative method to selectively modulate proteins and to serve as leads for the development of novel therapeutics.

SUMMARY OF THE DISCLOSURE

Disclosed herein, in certain embodiments, is a method of identifying a protein capable of interacting with a small molecule ligand, comprising: (a) providing a cell sample; (b) exposing the cell sample to at least one potential small molecule ligand having a structure comprising at least a photoreactive diazirine group and a terminal alkyne group; (c) irradiating the cell sample with UV light; (d) performing lysis on the cell sample; (e) subjecting proteins in the post lysis material to fluorophore tagging; and (f) isolating at least one fluorophore-tagged protein.

Disclosed herein, in certain embodiments, is a method of identifying a protein capable of interacting with a small molecule ligand, comprising: (a) providing a cell sample; (b) exposing the cell sample to the small molecule ligand having a structure comprising at least a photoreactive diazirine group, and a terminal alkyne group; (c) irradiating the cell sample with UV light; (d) performing lysis on the cell sample; (e) subjecting the proteins in the post lysis material to tagging; and (f) isolating the tagged proteins for analysis to identify a protein capable of interacting with the small molecule ligand.

Disclosed herein, in certain embodiments, is a method of identifying a small molecule ligand binding site on an isolated protein, comprising: (a) providing an isolated protein; (b) exposing the protein to at least one of potential small molecule ligands having a structure comprising at least a photoreactive diazirine group and a terminal alkyne group; (c) irradiating the protein with UV light; (d) tagging the protein with biotin; (e) binding the biotin-tagged protein to solid phase beads; (f) digesting the protein to provide protein fragments; and (g) analyzing the protein fragments to determine the small molecule ligand binding site.

Disclosed herein, in certain embodiments, is a method of identifying a small molecule ligand capable of interacting with a cellular protein, comprising: (a) providing a cell which expresses the cellular protein; (b) exposing the cell to a first-small molecule ligand of predetermined affinity for the cellular protein and a second small molecule ligand, wherein the small molecule ligand of predetermined affinity has a structure comprising at least a photoreactive diazirine group and a terminal alkyne group; (c) irradiating the cell with UV light; (d) performing lysis on the cell; (e) subjecting proteins in the post lysis material to tagging of the first small molecule ligand; and (f) determining the level of tagging in the presence of the second small molecule ligand compared to the level of tagging in the absence of the second small molecule ligand.

Disclosed herein, in certain embodiments, is a small molecule ligand which is capable of binding to a binding site on a protein, in which the protein is selected from Tables 1-4. In some cases, the binding site is disclosed in Tables 1-3.

BRIEF DESCRIPTION OF THE DRAWINGS

Various aspects of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

FIG. 1A represents schematic depiction of fully functionalized fragment (FFF) probes and experimental workflow to identify FFF-protein interactions in cells by quantitative MS-based proteomics. Isotopically heavy and light amino acid-labeled cells are treated with distinct FFF probes for 30 min, followed by UV light exposure, lysis, conjugation to biotin azide by CuAAC, streptavidin enrichment of labeled proteins, tryptic digestion and subsequent analysis of tryptic peptides. FIG. 1B exemplifies structures of FFF probes. Shown are the 'constant' (containing the diazirine photoreactive group and clickable alkyne handle) and 'variable' (consisting of small-molecule fragments; enclosed in box) regions of probes. FIG. 1C exemplifies FFF probe-protein interactions in cells. HEK293T cells were treated with probes (20 µM) for 30 min, followed by photocrosslinking and analysis as described in FIG. 1D. Asterisk mark representative distinct probe-protein interactions. FIG. 1E exemplifies additional profiles of FFF probe-protein interactions. FIG. 1D exemplifies experimental workflow to visualize FFF probe-protein interactions in cells by SDS-PAGE coupled with in-gel fluorescence scanning. Cells are treated with indicated FFF probe for 30 min, followed by photocrosslinking, lysis, CuAAC conjugation to a rhodamine (TAMRA)-azide tag, separation by SDS-PAGE, and visualization by in-gel fluorescence scanning. FIG. 1E exemplifies FFF probe-protein interactions in cells. HEK293T cells were treated with FFF probes (20 µM) for 30 min in situ, followed by photocrosslinking, separation of soluble and membrane fractions and analysis. (FIG. 1F, FIG. 1G) Fragment probes show concentration-dependent labeling of proteins in HEK293T cells (FIG. 1F), with little to no further change in protein labeling when incubated in cells for 5 to 30 min prior to photocrosslinking (FIG. 1G). FIG. 1H exemplifies HEK293T cells were treated with FFF probes (20 µM) for 30 min, and the cells were then washed 1-2× with DPBS prior to photocrosslinking. Asterisks mark proteins that show similar extents of probe labeling before and after cell washing.

FIG. 2A exemplifies heatmap showing relative protein enrichment values of FFF probes (200 µM) versus control 1 in HEK293T cells. FIG. 2B also exemplifies proteins that were strongly enriched by both probes in probe-vs-control 1 experiments and proteins not enriched by either probe. FIG. 2C exemplifies that most proteins demonstrating preferential enrichment (>3-fold) in probe-vs-probe experiments show corresponding preferential enrichment by the same probe in probe-vs-1 experiments. Light gray portions of bars mark fractions of proteins that were strongly enriched by both probes in probe-vs-control 1 experiments. (FIG. 2D-FIG. 2F) Heatmaps (FIG. 2D, FIG. 2E) and extracted MS1 chromatograms of representative tryptic peptides (FIG. 2F) for four example proteins showing strong preferential enrichment by one FFF probe over control 1 (FIG. 2D) and the corresponding results for these proteins in probe-vs-probe experiments (FIG. 2E). FIG. 2K exemplifies that FFF probes show minimal toxicity in HEK293T cells when tested under conditions that mirror those used for mapping probe-protein interactions in cells (200 µM FFF probe, 45 min incubation). Viability was assessed by CellTiter-Glo luminescent assay. Data represent average values±SD. n=3 per group. FIG. 2T exemplifies confirmation of FFF probe interaction profiles for representative protein targets. Proteins were recombinantly expressed as FLAG-tagged forms in HEK293T cells, followed by treatment with the indicated FFF probes (20 µM), photocrosslinking and lysis, SDS-PAGE, and in-gel fluorescence scanning.

FIG. 3A-FIG. 3P exemplify types of proteins and sites on these proteins targeted by FFF probes. (FIG. 3A, FIG. 3B) Categorization of FFF probe targets based on presence or absence in DrugBank (FIG. 3A) and protein class distribution (FIG. 3B). FIG. 3E exemplifies that FFF 13-modified peptide (aa 197-215) in human YWHAE (gray, PDB 3UBW) overlaps with the binding cleft that interacts with myeloid leukemia factor 1 (MLF1-derived peptide shown in yellow). This pocket is also the target of fragment (3S)-pyrrolindin-3-ol shown in purple. FIG. 3E discloses SEQ ID NO: 918. FIG. 3F exemplifies that FFF 13-modified peptide (aa 66-79) in human BAX (gray, PDB 4ZIE) complexed with BH3 peptide of BIM (cyan). FIG. 3F discloses SEQ ID NO: 919. FIG. 3G exemplifies the ribbon structure of human CTSB (gray, PDB 1GMY) highlighting FFF 9-modified peptide (aa 315-332) that is competed when HEK293T cells are co-treated with 9 (200 µM) and CTSB inhibitor Z-FA-FMK. Represented in yellow is the catalytic cysteine C108 (red) bound to Z-FA-FMK. FIG. 3G discloses SEQ ID NO: 920. FIG. 3O discloses SEQ ID NOS 921-922, respectively, in order of appearance. FIG. 3P exemplifies overlap of protein targets of FFF probes with protein targets of cysteine-reactive fragments.

FIG. 4A-FIG. 4M exemplify ligand discovery by competitive profiling of elaborated fragment-based compounds. FIG. 4A exemplifies a schematic for competitive profiling experiments. Isotopically heavy and light amino acid-labeled cells are treated with DMSO or elaborated fragment competitor, respectively, and the corresponding FFF probe for 30 min, followed by UV light exposure, cell lysis, CuAAC conjugation to biotin azide, streptavidin enrichment of probe-labeled proteins, tryptic digestion, and quantitative MS analysis of tryptic peptides. Competed targets are defined as those showing >3-fold reductions in FFF probe labeling in the presence of competitor compound. FIG. 4B exemplifies structure of fragment cores (upper) with representative elaborated competitors (lower, where core fragments are depicted). (FIG. 4C, FIG. 4D) Heatmap of (FIG. 4C) and number of competitor compounds per (FIG. 4D) competed protein targets in experiments using 20 μM FFF and 160 μM competitor. FIG. 4E exemplifies categorization of competed targets based on presence or absence in DrugBank for experiments using either 20 μM FFF probes (+160 μM competitors) or 200 μM FFF probes (+200 μM competitors). Targets competed in both 20 and 200 μM data sets were excluded from the 200 μM groups for the pie chart analysis. FIG. 4F exemplifies the protein functional class distribution for competed targets compared to all FFF probe targets. (FIG. 4G, FIG. 4H) Representative SILAC ratio plots for competitive profiling experiments with FFF probes 8 (FIG. 4G) and 3 (FIG. 4H) (20 μM) and 8× competitors 20 and 21, respectively. PTGR2 (FIG. 4G) and SLC25A20 (FIG. 4H) were identified as the top competed targets for 20 and 21, respectively. Dotted lines indicate a three-fold ratio change threshold for designating competed targets. (FIG. 4I-FIG. 4K) Structures of elaborated fragment competitors with corresponding FFF probe used in competitive profiling experiments. Core fragment structure within each competitor compound is highlighted. FIG. 4L exemplifies the number of competed protein targets per competitor tested in HEK293T cells at 160 μM with 20 μM FFF probe. FIG. 4M exemplifies the total number of competed protein targets for five representative competitors (160-200 μM) evaluated in experiments with high (200 μM) or low (20 μM) concentrations of FFF probes.

FIG. 5A exemplifies structure of hPTGR2 (PDB 2ZB4, gray) highlighting FFF 8-modified tryptic peptides (aa 55-66, green; and aa 261-278, pink) near the active site (15-keto-PGE2 in yellow, NADP+ in blue) of PTGR2. Probe labeling (200 μM) of both tryptic peptides was blocked by 20 (200 μM), as shown with representative MS1 plots for each peptide. FIG. 5A discloses SEQ ID NOS 923-924, respectively, in order of appearance. FIG. 5K exemplifies extracted MS1 chromatograms and corresponding SILAC ratios for representative tryptic peptides of PTGR2 from competition experiments with the indicated compounds, in which isotopically light and heavy amino acid-labeled HEK293T cells were treated with FFF probe 8 (20 μM) and, respectively, DMSO (red) or competitor compound (blue) at the indicated concentrations. (FIG. 5L, FIG. 5M) Competition SILAC plots for optimized PTGR2 inhibitor 22 (60 μM, FIG. 5L) and inactive control 23 (160 μM, FIG. 5M) tested with FFF probe 8 (20 μM). FIG. 5S exemplify oxygen consumption rate (OCR) of HSC5 cells pre-treated for 40 min with 21 or 24 and then provided with exogenous palmitate. A concentration-dependent inhibition of basal and maximal respiration was observed for 21, but not 24. Data represent average values±SD; n=5 per group. Oligomycin is an inhibitor of ATP synthase; FCCP=carbonyl cyanide-4-(trifluoromethoxy)phenylhydrazone is an ionophore uncoupling reagent that collapses mitochondrial membrane potential, allowing maximal respiration; RAA=rotenone and antimycin A are complex I and complex III inhibitors that block mitochondrial respiration, enabling the calculation of non-mitochondrial respiration.

DETAILED DESCRIPTION OF THE DISCLOSURE

Figure 1A:
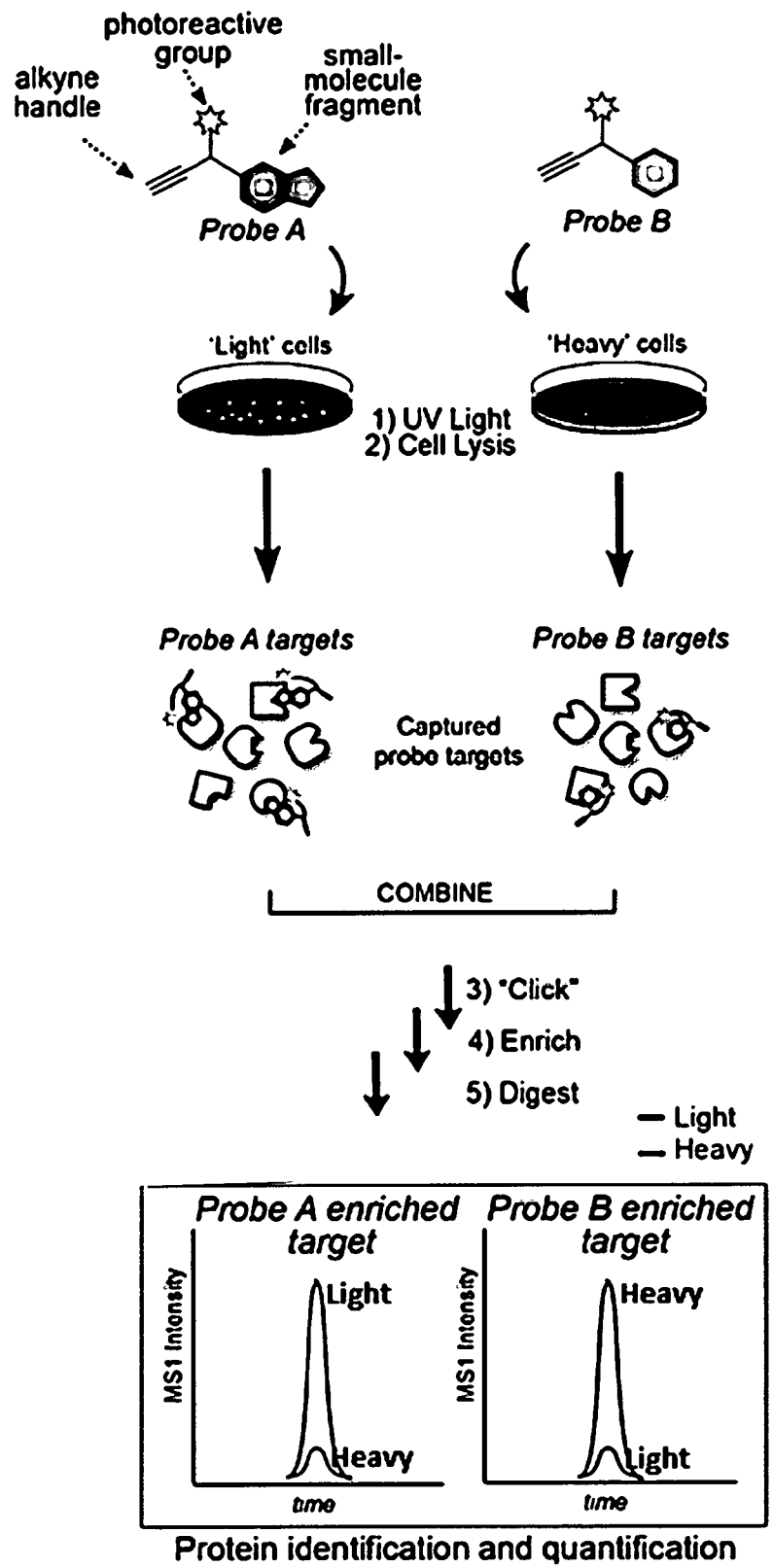
FIG. 1A-FIG. 1H exemplify a chemical proteomic strategy for mapping of fragment-protein interactions in cells.

Chemical probes can be discovered through multiple routes that can involve, for example, high-throughput screening (HTS) of individual proteins (target-based) or more complex cell and organismal systems (e.g., phenotype-based systems). In some instances, high-throughput screening, whether it is target- or phenotype-based, uses large chemical libraries (~$10^6$) composed of relatively high MW (300-500 Da) and structurally diverse compounds. In some cases, hit compounds from these libraries prove difficult to optimize due to their size, structural complexity, and suboptimal ligand efficiency. Target-based screens are furthermore generally performed with purified proteins and therefore do not provide direct information about the activity of ligands in more complex biological systems (e.g., cells), where factors that regulate protein structure and function, such as subcellular localization, post-translational modification, and protein-protein interactions can affect ligand-protein interactions. Alternatively, phenotype-based screening, for example, faces the challenge of identifying the molecular target(s) of active compounds, in particular, in cases where the screening hits display moderate-low potency.

Fragment-based ligand and drug discovery (FBLD) is an approach that utilizes smaller numbers (~$10^3$) of low molecular weight compounds (<300 Da), and typically screened at high concentrations (>100 M). In some instances, FBLD emphasizes the identification of structurally simple hit compounds that are then optimized into more potent ligands. In some cases, a tenet of FBLD is that, by limiting molecular size, a relatively small number of fragments can represent a large fraction of accessible chemical space.

In some embodiments, described herein is another method of identifying small molecule ligands for interaction with target proteins of interest. In some instances, this method allows for mapping of small molecule ligands for interaction with a target protein under native conditions, thereby allowing for accurate mapping of interaction with potential small molecule ligands. In some instances, the method allows for identification of novel proteins as druggable targets as the method eliminates the need of recombinant expression and purification.

In additional embodiments, described herein include small molecule ligands, compositions, cells and assays related to the method of identifying small molecule ligands for interaction with target proteins of interest.

Small Molecule Ligands

In some embodiments, disclosed herein are small molecule ligands in which each of the small molecule ligand comprises a photoreactive diazirine group and an alkyne group. In some instances, the alkyne group is a terminal alkyne group. In some instances, the small molecule ligand further comprises a small molecule fragment. In some embodiments, the small molecule fragments described herein comprise non-naturally occurring molecules. In some instances, the non-naturally occurring molecules do not include natural and/or non-natural peptide fragments, or small molecules that are produced naturally within the body of a mammal.

In some embodiments, a small molecule fragment described herein comprises a molecule weight of about 100 Dalton or higher. In some embodiments, the small molecule fragment comprises a molecule weight of about 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 500, 550, 600, 650, 700, 750, 800, 850, 900, 950, 1000 Dalton, or higher. In some instances, the molecule weight of the small molecule fragment is between about 150 and about 500, about 150 and about 450, about 150 and about 440, about 150 and about 430, about 150 and about 400, about 150 and about 350, about 150 and about 300, about 150 and about 250, about 170 and about 500, about 180 and about 450, about 190 and about 400, about 200 and about 350, about 130 and about 300, or about 120 and about 250 Dalton.

In some embodiments, the molecule weight of a small molecule fragment described herein is calculated based on the molecule weight of carbon and hydrogen atoms and optionally further based on nitrogen, oxygen and/or sulfur atoms of the small molecule fragment. In some cases, the molecule weight of the small molecule fragment is calculated without the molecular weight of one or more elements selected from a halogen, a nonmetal, a transition metal, or a combination thereof.

In some embodiments, a small molecule fragment described herein comprises micromolar or millimolar binding affinity. In some instances, the small molecule fragment comprises a binding affinity of about 100 nM, 200 nM, 300 nM, 400 nM, 500 nM, 1 μM, 10 μM, 100 μM, 500 μM, 1 mM, 10 mM, or higher.

In some embodiments, a small molecule fragment described herein has a high ligand efficiency (LE). Ligand efficiency is the measurement of the binding energy per atom of a ligand to its binding partner. In some instances, the ligand efficiency is defined as the ratio of the Gibbs free energy ($\Delta G$) to the number of non-hydrogen atoms of the compound (N):

$$LE=(\Delta G)/N.$$

In some cases, LE is also arranged as:

$$LE=1.4(-\log IC_{50})/N.$$

In some instances, the LE score is about 0.3 kcal $mol^{-1}HA^{-1}$, about 0.35 kcal $mol^{-1}HA^{-1}$, about 0.4 kcal $mol^{-1}HA^{-1}$, or higher.

In some embodiments, a small molecule fragment described herein is designed based on the Rule of 3. In some embodiments, the Rule of 3 comprises a non-polar solvent-polar solvent (e.g. octanol-water) partition coefficient log P of about 3 or less, a molecular mass of about 300 Daltons or less, about 3 hydrogen bond donors or less, about 3 hydrogen bond acceptors or less, and about 3 rotatable bonds or less.

In some embodiments, a small molecule fragment described herein comprises three cyclic rings or less.

In some embodiments, a small molecule fragment described herein binds to a binding site of a protein in which the protein is about 20 amino acid residues in length or more. In some instances, the small molecule fragment described herein binds to a binding site of a protein in which the protein is about 30, 35, 40, 45, 50, 55, 60, 65, 70, 75, 80, 85, 90, 95, 100, 150, 200, 250, 300, 350, 400, 450, 500, 600, 700, 800, 900, 1000 amino acid residues in length or more.

In some embodiments, a small molecule fragment described herein is obtained from a compound library. In some cases, the compound library comprises ChemBridge fragment library, Pyramid Platform Fragment-Based Drug Discovery, Maybridge fragment library, FRGx from AnalytiCon, TCI-Frag from AnCoreX, Bio Building Blocks from ASINEX, BioFocus 3D from Charles River, Fragments of Life (FOL) from Emerald Bio, Enamine Fragment Library, IOTA Diverse 1500, BIONET fragments library, Life Chemicals Fragments Collection, OTAVA fragment library, Prestwick fragment library, Selcia fragment library, TimTec fragment-based library, Allium from Vitas-M Laboratory, or Zenobia fragment library.

Figure 1B:
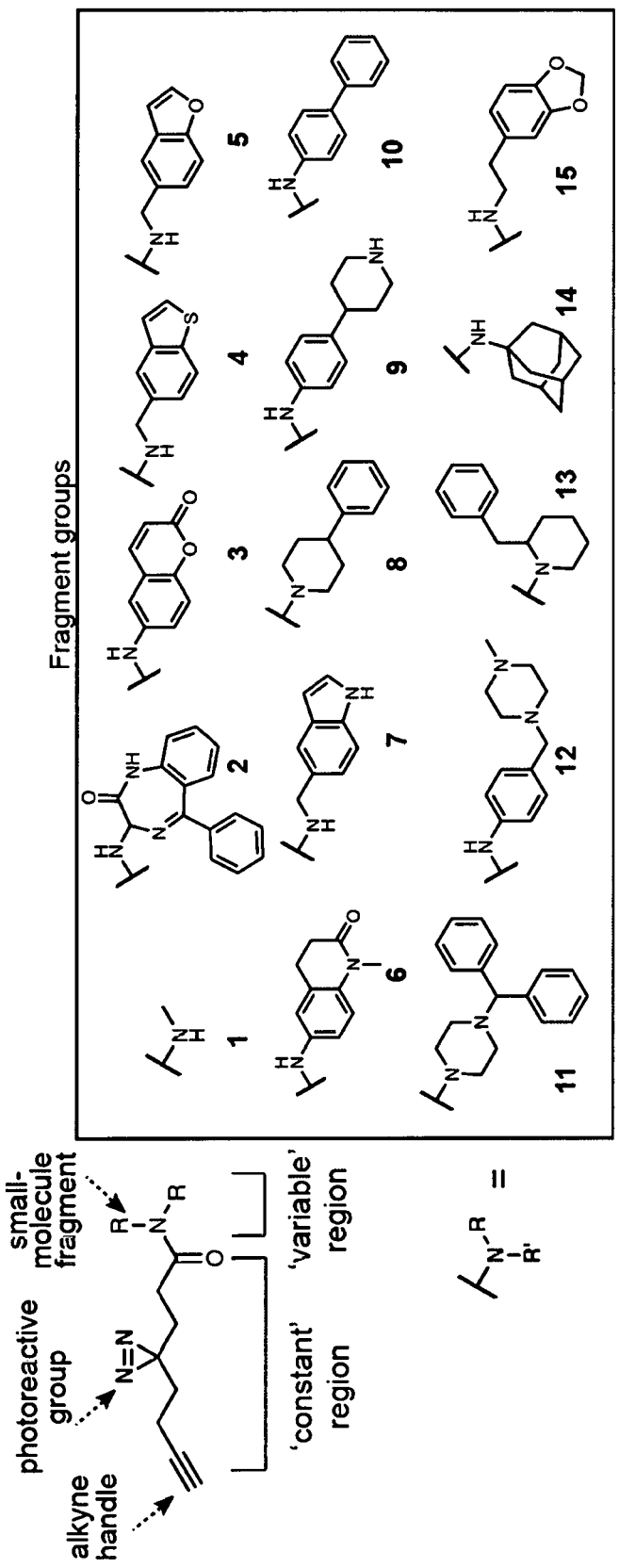

In some embodiments, a small molecule fragment comprises a structure illustrated in FIG. 1B, in which each fragment nomenclature (or probe nomenclature) is illustrated by a numerical number. For example, the small molecule fragment

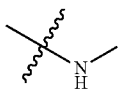

is assigned as probe 1.

In some embodiments, a small molecule ligand described herein has a structure represented by Formula (I):

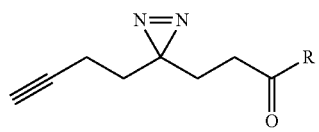

(I)

wherein R is selected from the groups provided below:

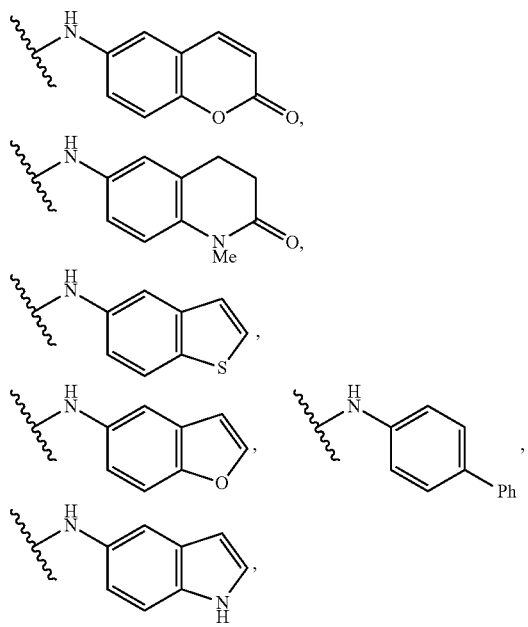

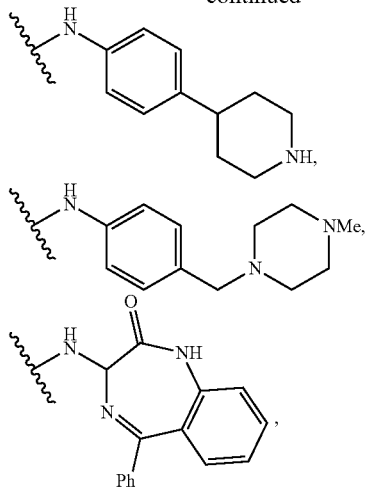

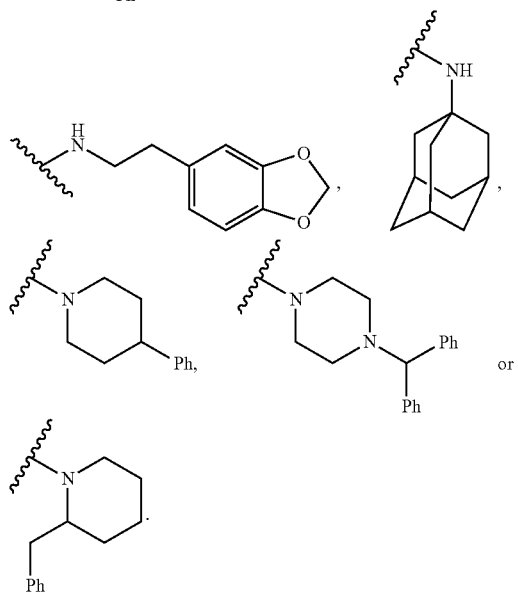

Protein Targets

In some embodiments, a protein target described herein is a soluble protein or a membrane protein. In some cases, a protein target described herein is involved in one or more of a biological process such as protein transport, lipid metabolism, apoptosis, transcription, electron transport, mRNA processing, or host-virus interaction. In some instances, the protein target is associated with one or more of diseases such as cancer or one or more disorders or conditions such as immune, metabolic, developmental, reproductive, neurological, psychiatric, renal, cardiovascular, or hematological disorders or conditions.

In some embodiments, the protein target comprises one or more functions of an enzyme, a transporter, a receptor, a channel protein, an adaptor protein, a chaperone, a signaling protein, a plasma protein, transcription related protein, translation related protein, mitochondrial protein, or cytoskeleton related protein. In some embodiments, the protein target is an enzyme, a transporter, a receptor, a channel protein, an adaptor protein, a chaperone, a signaling protein, a plasma protein, transcription related protein, translation related protein, mitochondrial protein, or cytoskeleton related protein. In some instances, the protein target has an uncategorized function.

In some embodiments, the protein target is an enzyme. An enzyme is a protein molecule that accelerates or catalyzes chemical reaction. In some embodiments, non-limiting examples of enzymes include kinases, proteases, or deubiquitinating enzymes.

In some instances, exemplary kinases include tyrosine kinases such as the TEC family of kinases such as Tec, Bruton's tyrosine kinase (Btk), interleukin-2-indicible T-cell kinase (Itk) (or Emt/Tsk), Bmx, and Txk/Rlk; spleen tyrosine kinase (Syk) family such as SYK and Zeta-chain-associated protein kinase 70 (ZAP-70); Src kinases such as Src, Yes, Fyn, Fgr, Lck, Hck, Blk, Lyn, and Frk; JAK kinases such as Janus kinase 1 (JAK1), Janus kinase 2 (JAK2), Janus kinase 3 (JAK3), and Tyrosine kinase 2 (TYK2); or ErbB family of kinases such as Her1 (EGFR, ErbB1), Her2 (Neu, ErbB2), Her3 (ErbB3), and Her4 (ErbB4).

In some embodiments, the protein target is a protease. In some embodiments, the protease is a caspase. In some instances, the caspase is an initiator (apical) caspase. In some instances, the caspase is an effector (executioner) caspase. Exemplary caspase includes CASP2, CASP8, CASP9, CASP10, CASP3, CASP6, CASP7, CASP4, and CASP5. In some instances, the cysteine protease is a cathepsin. Exemplary cathepsin includes Cathepsin B, Cathepsin C, Cathepsin F, Cathepsin H, Cathepsin K, Cathepsin L1, Cathepsin L2, Cathepsin O, Cathepsin S, Cathepsin W, or Cathepsin Z.

In some embodiments, the protein target is a deubiquitinating enzyme (DUB). In some embodiments, exemplary deubiquitinating enzymes include cysteine proteases DUBs or metalloproteases. Exemplary cysteine protease DUBs include ubiquitin-specific protease (USP/UBP) such as USP1, USP2, USP3, USP4, USP5, USP6, USP7, USP8, USP9X, USP9Y, USP10, USP11, USP12, USP13, USP14, USP15, USP16, USP17, USP17L2, USP17L3, USP17L4, USP17L5, USP17L7, USP17L8, USP18, USP19, USP20, USP21, USP22, USP23, USP24, USP25, USP26, USP27X, USP28, USP29, USP30, USP31, USP32, USP33, USP34, USP35, USP36, USP37, USP38, USP39, USP40, USP41, USP42, USP43, USP44, USP45, or USP46; ovarian tumor (OTU) proteases such as OTUB1 and OTUB2; Machado-Josephin domain (MJD) proteases such as ATXN3 and ATXN3L; and ubiquitin C-terminal hydrolase (UCH) proteases such as BAP1, UCHL1, UCHL3, and UCHL5. Exemplary metalloproteases include the Jab1/Mov34/Mpr1 Pad1 N-terminal+ (MPN+) (JAMM) domain proteases.

In some embodiments, exemplary proteins as enzymes include, but are not limited to, abhydrolase domain-containing protein 10, mitochondrial (ABHD10); aconitate hydratase, mitochondrial (ACO2); low molecular weight phosphotyrosine protein phosphatase (ACP1); chaperone activity of bcl complex-like, mitochondrial (ADCK3); adenosine kinase (ADK); adenylosuccinate synthetase isozyme 2 (ADSS); acylglycerol kinase, mitochondrial (AGK); alkyldihydroxyacetonephosphate synthase, peroxisomal (AGPS); apoptosis-inducing factor 1, mitochondrial (AIFM1); Delta-1-pyrroline-5-carboxylate synthase (ALDH18A1); mitochondrial 10-formyltetrahydrofolate dehydrogen (ALDH1L2); alpha-aminoadipic semialdehyde dehydrogenase (ALDH7A1); ATPase ASNAI (ASNAI); ATPase family AAA domain-containing protein 3A (ATAD3A); bifunctional purine biosynthesis protein PURH (ATIC); bleomycin hydrolase (BLMH); calpain-1 catalytic subunit (CAPN1); creatine kinase B-type (CKB); caseinolytic peptidase B protein homolog (CLPB); putative ATP-dependent Clp protease proteolytic subunit (CLPP); carnitine O-palmitoyltransferase 2, mitochondrial (CPT2); probable serine carboxypeptidase CPVL (CPVL); cathepsin B (CTSB); cathepsin D (CTSD); NADH-cytochrome b5 reductase 3 (CYB5R3); cytochrome P450 20A1 (CYP20A1); 2,4-dienoyl-CoA reductase, mitochondrial (DECR1); delta(24)-sterol reductase (DHCR24); dihydrolipoyl dehydrogenase, mitochondrial (DLD); deoxyribonuclease-2-alpha (DNASE2); endothelin-converting enzyme 1 (ECEI); Delta(3,5)-Delta(2,4)-dienoyl-CoA isomerase, mitochondrial (ECH1); eukaryotic translation initiation factor 3 subunit (EIF3F); elongation of very long chain fatty acids protein (ELOVL2); exonuclease 1 (EXO1); phenylalanine—tRNA ligase beta subunit (FARSB); fatty acid synthase (FASN); squalene synthase (FDFT1); ferrochelatase, mitochondrial (FECH); alpha-galactosidase A (GLA); beta-galactosidase (GLB1); lactoylglutathione lyase (GLO1); glutamate dehydrogenase 1, mitochondrial (GLUD1); hydroxyacyl-coenzyme A dehydrogenase, mitochondrial (HADH); trifunctional enzyme subunit alpha, mitochondrial (HADHA); histidine—tRNA ligase, cytoplasmic (HARS); minor histocompatibility antigen H13 (HM13); heme oxygenase 2 (HMOX2); estradiol 17-beta-dehydrogenase 12 (HSD17B12); peroxisomal multifunctional enzyme type 2 (HSD17B4); insulin-degrading enzyme (IDE); isocitrate dehydrogenase (IDH2); gamma-interferon-inducible lysosomal thiol reductase (IFI30); inosine-5-monophosphate dehydrogenase 2 (IMPDH2); leucine—tRNA ligase, cytoplasmic (LARS); L-lactate dehydrogenase A chain (LDHA); L-lactate dehydrogenase B chain (LDHB); legumain (LGMN); lysosomal acid lipase/cholesteryl ester hydrolase (LIPA); methyltransferase-like protein 7A (METTL7A); NADH-ubiquinone oxidoreductase chain 2 (MT-ND2); monofunctional C1-tetrahydrofolate synthase, mitochondrial (MTHFD1L); alpha-N-acetylglucosaminidase (NAGLU); peroxisomal NADH pyrophosphatase NUDT12 (NUDT12); nucleoside diphosphate-linked moiety X motif 19, mitochondrial (NUDT19); ornithine aminotransferase, mitochondrial (OAT); phosphoenolpyruvate carboxykinase (PCK2); protein-L-isoaspartate (D-aspartate)O-methyltransferase (PCMT1); prenylcysteine oxidase 1 (PCYOX1); presequence protease, mitochondrial (PITRM1); pyruvate kinase isozymes M1/M2 (PKM); peroxiredoxin-2 (PRDX2); DNA-dependent protein kinase catalytic subunit (PRKDC); proteasome subunit alpha type-2 (PSMA2); dolichyl-diphosphooligosaccharide—protein glycosyltransferase subnit 1 (RPN1); RuvB-like 1 (RUVBL1); thimet oligopeptidase (THOP1); or tripeptidyl-peptidase 1 (TPP1).

In some embodiments, the protein target is a transcription factor or regulator. Exemplary protein targets as transcription factors and regulators include, but are not limited to, actin-like protein 6A (ACTL6A); putative adenosylhomocysteinase 2 (AHCYL1); acidic leucine-rich nuclear phosphoprotein 32 family member A (ANP32A); complement component 1 Q subcomponent-binding protein (C1QBP); probable ATP-dependent RNA helicase DDX17 (DDX17); probable ATP-dependent RNA helicase DHX36 (DHX36); elongation factor 1-alpha 1 (EEF1A1); eukaryotic initiation factor 4A-I (EIF4A1); electron transfer flavoprotein subunit beta (ETFB); far upstream element-binding protein 1 (FUBP1); histone H1.2 (HIST1H1C); heterogeneous nuclear ribonucleoprotein K (HNRNPK); interleukin enhancer-binding factor 2 (ILF2); DNA replication licensing factor MCM2 (MCM2); DNA replication licensing factor MCM4 (MCM4); N-alpha-acetyltransferase 15, NatA auxiliary subunit (NAA15); non-POU domain-containing octamer-binding protein (NONO); nucleobindin-1 (UCB1); polyadenylate-binding protein 1 (PABPC1); paraspeckle component 1 (PSPC1); RNA-binding protein 14 (RBM14); putative RNA-binding protein 3 (RBM3); RNA-binding motif protein, X chromosome (RBMX); 40S ribosomal protein S3 (RPS3); X-ray repair cross-complementing protein 6 (XRCC6); nuclease-sensitive element-binding protein 1 (YBX1); prostaglandin reductase 2 (PTGR2); zinc binding alcohol dehydrogenase domain containing 2 (ZADH2); or lysophosphatidylcholine acetyltransferase 3 (LPCAT3).

In some embodiments, the protein target is a channel, transporter or receptor. Exemplary protein targets as channels, transporters, or receptors include, but are not limited to, alpha-actinin-4 (ACTN4); AP-1 complex subunit beta-1 (AP1B1); ADP-ribosylation factor 1 (ARF1); ADP-ribosylation factor 3 (ARF3); ADP-ribosylation factor 4 (ARF4); ADP-ribosylation factor 5 (ARF5); sodium/potassium-transporting ATPase subunit alpha (ATP1A1); sarcoplasmic/endoplasmic reticulum calcium ATPase (ATP2A2); plasma membrane calcium-transporting ATPase 1 (ATP2B1); plasma membrane calcium-transporting ATPase 4 (ATP2B4); ATP synthase subunit alpha, mitochondrial (ATP5A1); coatomer subunit beta (COPB1); exportin-2 (CSE1L); Electron transfer flavoprotein subunit beta (ETFB); heterogeneous nuclear ribonucleoprotein A1 (HNRNPA1); heterogeneous nuclear ribonucleoprotein A1-like 2 (HNRNPA1L2); importin-4 (IPO4); cytochrome c oxidase subunit 2 (MT-C02); nuclear autoantigenic sperm protein (NASP); nucleoporin Nup37 (NUP37); nuclear pore complex protein Nup93 (NUP93); nuclear transport factor 2 (NUTF2); membrane-associated progesterone receptor component (PGRMC2); prohibitin-2 (PHB2); protein quaking (QKI); sideroflexin-1 (SFXN1); ADP/ATP translocase 3 (SLC25A6); mitochondrial carnitine/acylcarnitine carrier protein (SLC25A20) or voltage-dependent anion-selective channel protein (VDAC3).

In some embodiments, the protein target is a chaperone. Exemplary protein targets as chaperones include, but are not limited to, acidic leucine-rich nuclear phosphoprotein 32 family member B (ANP32B); large proline-rich protein BAG6 (BAG6); T-complex protein 1 subunit beta (CCT2); peptidyl-prolyl cis-trans isomerase FKBP4 (FKBP4); heat shock protein HSP 90-beta (HSP90AB1); endoplasmin (HSP90B1); LDLR chaperone MESD (MESDC2); nucleophosmin (NPM1); or protein SET (SET).

In some embodiments, the protein target is an adapter, scaffolding or modulator protein. Exemplary protein targets as adapter, scaffolding, or modulator proteins include, but are not limited to, actin, alpha skeletal muscle (ACTA1); actin, cytoplasmic 1 (ACTB); cytoskeleton-associated protein 4 (CKAP4); cytochrome c oxidase subunit 5A, mitochondrial (COX5A); catenin beta-1 (CTNNB1); FGFR1 oncogene partner (FGFR1OP); HAUS augmin-like complex subunit 2 (HAUS2); hemoglobin subunit alpha (HBA2); kinesin-like protein KIF11 (KIF11); myosin-10 (MYH10); myosin-9 (MYH9); phosphatidylinositol transfer protein beta isoform (PITPNB); proactivator polypeptide (PSAP); endophilin-B1 (SH3GLB1); stomatin-like protein 2 (STOML2); tubulin beta-4B chain (TUBB4B); or tubulin beta-6 chain (TUBB6).

In some embodiments, a protein target comprises a protein illustrated in Tables 1-4. In some instances, a protein target comprises a protein illustrated in Table 1. In some embodiments, the protein target comprises a binding site denoted in Table 1. In some instances, a protein target comprises a protein illustrated in Table 2. In some embodiments, the protein target comprises a binding site denoted in Table 2. In some instances, a protein target comprises a protein illustrated in Table 3. In some embodiments, the protein target comprises a binding site denoted in Table 3. In some instances, a protein target comprises a protein illustrated in Table 4.

Methods of Use

In some embodiments, disclosed herein include a method of identifying a protein that is capable of interacting with a small molecule ligand. In some instances, the method comprises (a) providing a cell sample; (b) exposing the cell sample to a plurality of potential small molecule ligands having a structure comprising at least a photoreactive diazirine group and a terminal alkyne group; (c) irradiating the cell sample with UV light; (d) performing lysis on the cell sample; (e) subjecting proteins in the post lysis material to fluorophore tagging (e.g., rhodamine, fluorescein, and the like); and (f) isolating at least one fluorophore-tagged protein. In other instances, the method comprises (a) providing a cell sample; (b) exposing the cell sample to the small molecule ligand having a structure comprising at least a photoreactive diazirine group, and a terminal alkyne group; (c) irradiating the cell sample with UV light; (d) performing lysis on the cell sample; (e) subjecting the proteins in the post lysis material to tagging; and (f) isolating the tagged proteins for analysis to identify a protein capable of interacting with the small molecule ligand.

In some cases, the small molecule ligand has a structure represented by Formula (I):

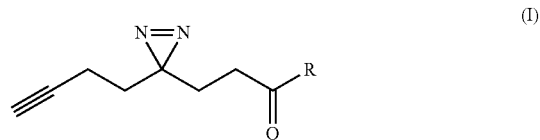

wherein R is selected from the groups provided below:

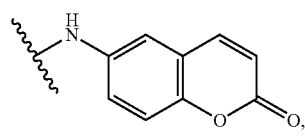

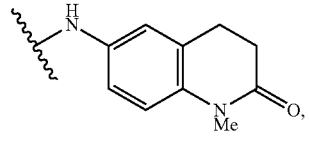

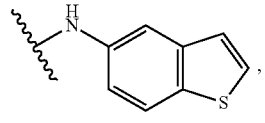

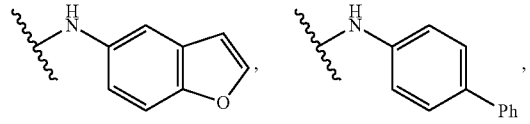

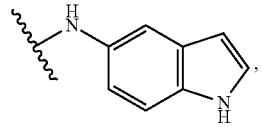

-continued

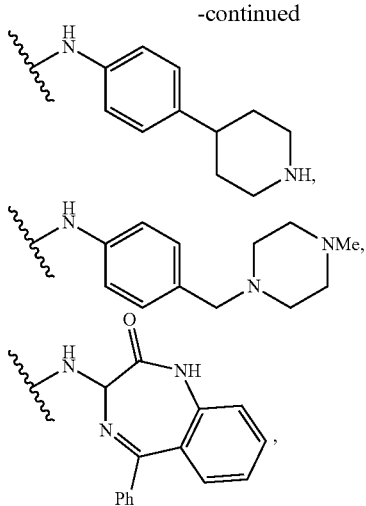

In some cases, the small molecule ligand has a structure represented by Formula (Ib):

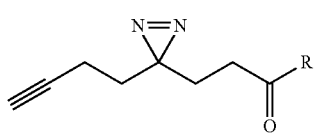

wherein R is an amide substituent bonded to the NH group of the amines provided in FIGS. 6A-J.

In some cases, the small molecule ligand has a structure represented by Formula (II):

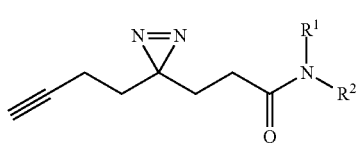

wherein $R^1$ is hydrogen and $R^2$ is selected from substituted alkyl, optionally substituted aryl, optionally substituted heteroaryl, optionally substituted cycloalkyl, optionally substituted heterocyclyl, optionally substituted heteroaryl, optionally substituted aralkyl, optionally substituted heteroarylalkyl, or optionally substituted heterocyclylalkyl; or $R^1$ and $R^2$ together with the nitrogen to which they are attached form an optionally substituted heterocyclyl ring.

In some cases, the small molecule ligand has a structure represented by Formula (III):

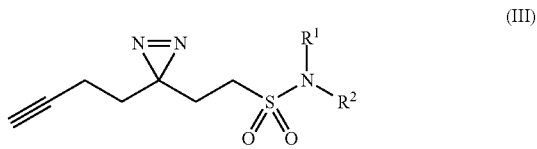

wherein $R^1$ is hydrogen and $R^2$ is selected from substituted alkyl, optionally substituted aryl, optionally substituted heteroaryl, optionally substituted cycloalkyl, optionally substituted heterocyclyl, optionally substituted heteroaryl, optionally substituted aralkyl, optionally substituted heteroarylalkyl, or optionally substituted heterocyclylalkyl; or $R^1$ and $R^2$ together with the nitrogen to which they are attached form an optionally substituted heterocyclyl ring.

In some cases, the small molecule ligand has a structure represented by Formula (III):

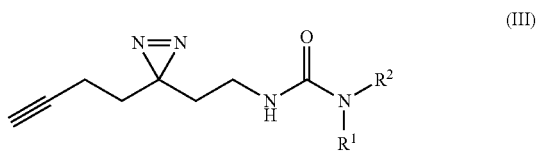

wherein $R^1$ is hydrogen and $R^2$ is selected from substituted alkyl, optionally substituted aryl, optionally substituted heteroaryl, optionally substituted cycloalkyl, optionally substituted heterocyclyl, optionally substituted heteroaryl, optionally substituted aralkyl, optionally substituted heteroarylalkyl, or optionally substituted heterocyclylalkyl; or $R^1$ and $R^2$ together with the nitrogen to which they are attached form an optionally substituted heterocyclyl ring.

In some cases, the small molecule ligand has a structure represented by Formula (IV):

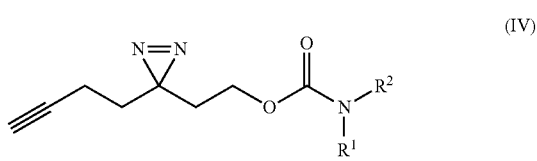

wherein $R^1$ is hydrogen and $R^2$ is selected from substituted alkyl, optionally substituted aryl, optionally substituted heteroaryl, optionally substituted cycloalkyl, optionally substituted heterocyclyl, optionally substituted heteroaryl, optionally substituted aralkyl, optionally substituted heteroarylalkyl, or optionally substituted heterocyclylalkyl; or $R^1$ and $R^2$ together with the nitrogen to which they are attached form an optionally substituted heterocyclyl ring.

In some cases, the small molecule ligand has a structure represented by Formula (V):

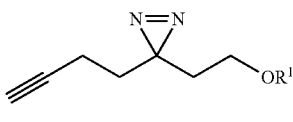

wherein $R^1$ is selected from substituted alkyl, optionally substituted aryl, optionally substituted heteroaryl, optionally substituted cycloalkyl, optionally substituted heterocyclyl, optionally substituted heteroaryl, optionally substituted aralkyl, optionally substituted heteroarylalkyl, or optionally substituted heterocyclylalkyl.

In some cases, the small molecule ligand has a structure represented by Formula (VI):

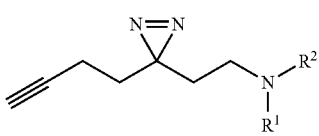

wherein $R^1$ is hydrogen and $R^2$ is selected from substituted alkyl, optionally substituted aryl, optionally substituted heteroaryl, optionally substituted cycloalkyl, optionally substituted heterocyclyl, optionally substituted heteroaryl, optionally substituted aralkyl, optionally substituted heteroarylalkyl, or optionally substituted heterocyclylalkyl; or $R^1$ and $R^2$ together with the nitrogen to which they are attached form an optionally substituted heterocyclyl ring.

In some cases, the tagging further comprises i) attaching the small molecule ligand-protein complex to a biotin moiety and ii) interacting the biotin moiety with a streptavidin-coupled bead.

In some instances, the analysis comprises a proteomic analysis.

In some instances, a cell from the cell sample is a mammalian cell. In some cases, a cell from the cell sample is obtained from HEK293T, K562, or HSC-5 cell lines. In some cases, a cell from the cell sample is a tumor cell.

In some cases, the method is an in situ method. In other cases, the method is an in vitro method.

In some embodiments, also disclosed herein include a method of identifying a small molecule ligand binding site on an isolated protein. In some cases, the method comprises (a) providing an isolated protein; (b) exposing the protein to a plurality of potential small molecule ligands having a structure comprising at least a photoreactive diazirine group and a terminal alkyne group; (c) irradiating the protein with UV light; (d) tagging the protein with biotin; (e) binding the biotin-tagged protein to solid phase beads; (f) digesting the protein to provide protein fragments; and (g) analyzing the protein fragments to determine the small molecule ligand binding site.

In some instances, the isolated protein is selected from Tables 1-3. In some cases, the isolated protein is selected from Table 1. In some cases, the isolated protein is selected from Table 2. In some cases, the isolated protein is selected from Table 3. In some cases, the isolated protein is a recombinant protein.

In some cases, the small molecule ligand has a structure represented by Formula (I):

wherein R is selected from the groups provided below:

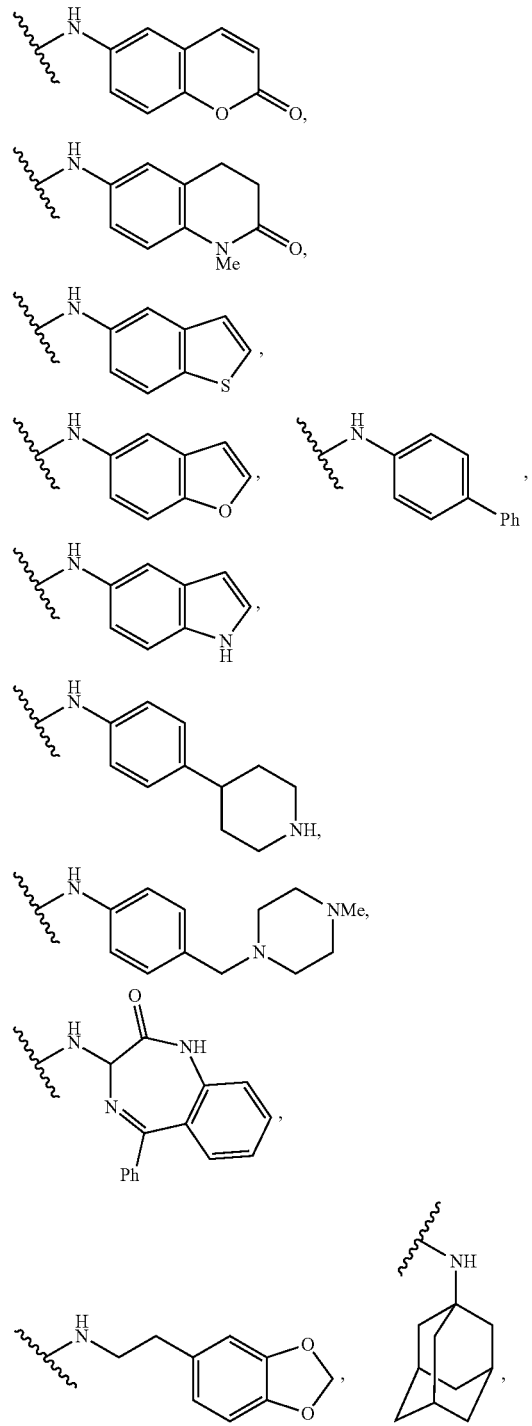

-continued

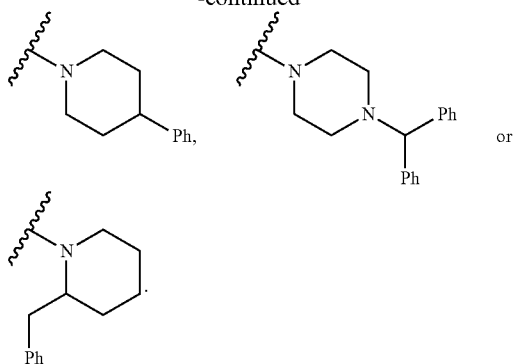

In some cases, the small molecule ligand has a structure represented by Formula (Ib):

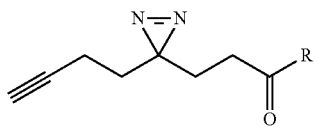

wherein R is an amide substituent bonded to the NH group of the amines provided in FIGS. 6A-J.

In some cases, the small molecule ligand has a structure represented by Formula (II):

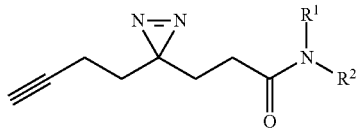

wherein $R^1$ is hydrogen and $R^2$ is selected from substituted alkyl, optionally substituted aryl, optionally substituted heteroaryl, optionally substituted cycloalkyl, optionally substituted heterocyclyl, optionally substituted heteroaryl, optionally substituted aralkyl, optionally substituted heteroarylalkyl, or optionally substituted heterocyclylalkyl; or $R^1$ and $R^2$ together with the nitrogen to which they are attached form an optionally substituted heterocyclyl ring.

In some cases, the small molecule ligand has a structure represented by Formula (III):

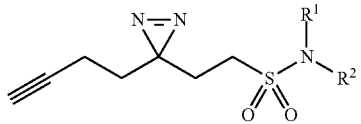

wherein $R^1$ is hydrogen and $R^2$ is selected from substituted alkyl, optionally substituted aryl, optionally substituted heteroaryl, optionally substituted cycloalkyl, optionally substituted heterocyclyl, optionally substituted heteroaryl, optionally substituted aralkyl, optionally substituted heteroarylalkyl, or optionally substituted heterocyclylalkyl; or $R^1$ and $R^2$ together with the nitrogen to which they are attached form an optionally substituted heterocyclyl ring.

In some cases, the small molecule ligand has a structure represented by Formula (III):

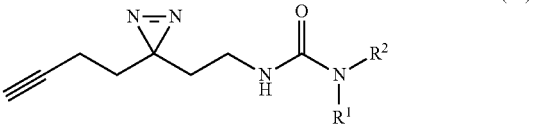

wherein $R^1$ is hydrogen and $R^2$ is selected from substituted alkyl, optionally substituted aryl, optionally substituted heteroaryl, optionally substituted cycloalkyl, optionally substituted heterocyclyl, optionally substituted heteroaryl, optionally substituted aralkyl, optionally substituted heteroarylalkyl, or optionally substituted heterocyclylalkyl; or $R^1$ and $R^2$ together with the nitrogen to which they are attached form an optionally substituted heterocyclyl ring.

In some cases, the small molecule ligand has a structure represented by Formula (IV):

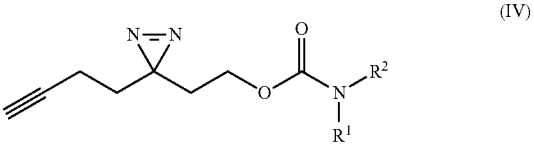

wherein $R^1$ is hydrogen and $R^2$ is selected from substituted alkyl, optionally substituted aryl, optionally substituted heteroaryl, optionally substituted cycloalkyl, optionally substituted heterocyclyl, optionally substituted heteroaryl, optionally substituted aralkyl, optionally substituted heteroarylalkyl, or optionally substituted heterocyclylalkyl; or $R^1$ and $R^2$ together with the nitrogen to which they are attached form an optionally substituted heterocyclyl ring.

In some cases, the small molecule ligand has a structure represented by Formula (V):

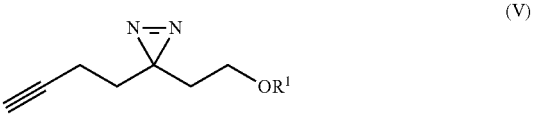

wherein $R^1$ is selected from substituted alkyl, optionally substituted aryl, optionally substituted heteroaryl, optionally substituted cycloalkyl, optionally substituted heterocyclyl, optionally substituted heteroaryl, optionally substituted aralkyl, optionally substituted heteroarylalkyl, or optionally substituted heterocyclylalkyl.

In some cases, the small molecule ligand has a structure represented by Formula (VI):

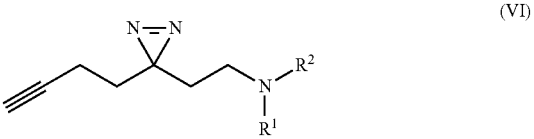

wherein $R^1$ is hydrogen and $R^2$ is selected from substituted alkyl, optionally substituted aryl, optionally substituted heteroaryl, optionally substituted cycloalkyl, optionally substituted heterocyclyl, optionally substituted heteroaryl, optionally substituted aralkyl, optionally substituted heteroarylalkyl, or optionally substituted heterocyclylalkyl; or $R^1$ and $R^2$ together with the nitrogen to which they are attached form an optionally substituted heterocyclyl ring.

In some instances, the analyzing comprises a proteomic analysis.

In some embodiments, tagging comprises labeling the protein with a labeling group for use in further analysis of the protein. In some instances, the labeling group comprises a fluorophore. In some instances, a fluorophore comprises rhodamine, rhodol, fluorescein, thiofluorescein, aminofluorescein, carboxyfluorescein, chlorofluorescein, methylfluorescein, sulfofluorescein, aminorhodol, carboxyrhodol, chlororhodol, methylrhodol, sulforhodol, aminorhodamine, carboxyrhodamine, chlororhodamine, methylrhodamine, sulforhodamine, thiorhodamine, cyanine, indocarbocyanine, oxacarbocyanine, thiacarbocyanine, merocyanine, cyanine 2, cyanine 3, cyanine 3.5, cyanine 5, cyanine 5.5, cyanine 7, oxadiazole derivatives, pyridyloxazole, nitrobenzoxadiazole, benzoxadiazole, pyren derivatives, cascade blue, oxazine derivatives, Nile red, Nile blue, cresyl violet, oxazine 170, acridine derivatives, proflavin, acridine orange, acridine yellow, arylmethine derivatives, auramine, crystal violet, malachite green, tetrapyrrole derivatives, porphin, phtalocyanine, bilirubin 1-dimethylaminonaphthyl-5-sulfonate, 1-anilino-8-naphthalene sulfonate, 2-p-touidinyl-6-naphthalene sulfonate, 3-phenyl-7-isocyanatocoumarin, N-(p-(2-benzoxazolyl)phenyl)maleimide, stilbenes, pyrenes, 6-FAM (Fluorescein), 6-FAM (NHS Ester), 5(6)-FAM, 5-FAM, Fluorescein dT, 5-TAMRA-cadavarine, 2-aminoacridone, HEX, JOE (NHS Ester), MAX, TET, ROX, TAMRA, TARMA™ (NHS Ester), TEX 615, ATTO™ 488, ATTO™ 532, ATTO™ 550, ATTO™ 565, ATTO™ Rho101, ATTO™ 590, ATTO™ 633, ATTO™ 647N, TYE™ 563, TYE™ 665, or TYE™ 705.

In some embodiments, the labeling group comprises a biotin, a streptavidin, bead, resin, a solid support, or a combination thereof. As used herein, a biotin described herein comprises biotin and biotin derivatives. Exemplary biotin derivatives include, but are not limited by, desthiobiotin, biotin alkyne or biotin azide. In some instances, a biotin described herein is desthiobiotin. In some cases, a biotin described herein is d-Desthiobiotin.

In some instances, the labeling group comprising biotin further comprises a linker. In some cases, the linker is about 5, 6, 7, 8, 9, 10, 11, 12, 13, 14, 15 or more residues in length. In some instances, the linker further comprises a cleavage site, such as a protease cleavage site (e.g., TEV cleavage site). In some cases, the biotin-linker moiety is further isotopically-labeled, for example, isotopically labeled with $^{13}$C and $^{15}$N atoms at one or more amino acid residue positions. In some cases, the biotin-linker moiety is a isotopically-labeled TEV-tag as described in Weerapana, et al., "Quantitative reactivity profiling predicts functional cysteines in proteomes," Nature 468(7325): 790-795.

In some cases, the labeling group comprising biotin further interacts with a streptavidin moiety. In some instances, the labeling group comprising biotin is further attached to a bead, such as a streptavidin-coupled bead. In some instances, the labeling group comprising biotin is further attached to a resin or a solid support, such as a streptavidin-coupled resin or a streptavidin-coupled solid support. In some instances, the solid support is a plate, a platform, a cover slide, a microfluidic channel, and the like.

In some cases, the method is a high-throughput method.

In some embodiments, disclosed herein also include proteins and their respective binding sites identified for interaction with one or more small molecule ligands. In some instances, the binding sites are disclosed in Tables 1-3. In some cases, the binding sites are disclosed in Table 3.

In some embodiments, disclosed herein is a small molecule ligand which binds to the ACP1 protein, wherein the small molecule ligand binds to one or more of the following residues: VDSAATSGYEIGNPPDYR (SEQ ID NO: 1) of the ACP1 protein having the UniProtKB accession number P24666. In some instances, also disclosed herein is a small molecule ligand which binds to the ACP1 protein, wherein the small molecule ligand binds a ligand binding site defined by the following residues: VDSAATSGYEIGNPPDYR (SEQ ID NO: 1) of the ACP1 protein having the UniProtKB accession number P24666. In some instances, the small molecule ligand is probe 13.

In some embodiments, disclosed herein is a small molecule ligand which binds to the ADCK3 protein, wherein the small molecule ligand binds to one or more of the following residues: LGQMLSIQDDAFINPHLAK (SEQ ID NO: 2) of the ADCK3 protein having the UniProtKB accession number Q8NI60. In some embodiments, also disclosed herein is a small molecule ligand which binds to the ADCK3 protein, wherein the small molecule ligand binds a ligand binding site defined by the following residues: LGQMLSIQDDAFINPHLAK (SEQ ID NO: 2) of the ADCK3 protein having the UniProtKB accession number Q8NI60. In some instances, the small molecule ligand is probe 14.

In some embodiments, disclosed herein is a small molecule ligand which binds to the ADK protein, wherein the small molecule ligand binds to one or more of the following residues: IFTLNLSAPFISQFYK (SEQ ID NO: 3) of the ADK protein having the UniProtKB accession number P55263. In some embodiments, also disclosed herein is a small molecule ligand which binds to the ADK protein, wherein the small molecule ligand binds a ligand binding site defined by the following residues: IFTLNLSAPFISQFYK (SEQ ID NO: 3) of the ADK protein having the UniProtKB accession number P55263. In some instances, the small molecule ligand is probe 2.

In some embodiments, disclosed herein is a small molecule ligand which binds to the ADSS protein, wherein the small molecule ligand binds to one or more of the following residues: FIEDELQIPVK (SEQ ID NO: 4) of the ADSS protein having the UniProtKB accession number P30520. In some embodiments, also disclosed herein is a small molecule ligand which binds to the ADSS protein, wherein the small molecule ligand binds a ligand binding site defined by the following residues: FIEDELQIPVK (SEQ ID NO: 4) of the ADSS protein having the UniProtKB accession number P30520. In some instances, the small molecule ligand is probe 14.

In some embodiments, disclosed herein is a small molecule ligand which binds to the AIFM1 protein, wherein the small molecule ligand binds to one or more of the following residues: PYWHQSMFWSDLGPDVGYEAIGLVDSSLPTVGVFAK (SEQ ID NO: 5) of the AIFM1 protein having the UniProtKB accession number O95831. In some embodiments, also disclosed herein is a small molecule ligand which binds to the AIFM1 protein, wherein the small molecule ligand binds a ligand binding site defined by the following residues: PYWHQSMFWSDLGPDVGYEAIGLVDSSLPTVGVFAK (SEQ ID NO: 5) of the AIFM1 protein having the UniProtKB accession number O95831. In some instances, the small molecule ligand is probe 2, 3, 4 or 6.

In some embodiments, disclosed herein is a small molecule ligand which binds to the ALDH7A1 protein, wherein the small molecule ligand binds to one or more of the following residues: ILVEGVGEVQEYVDICDYAVGLSR (SEQ ID NO: 6) of the ALDH7A1 protein having the UniProtKB accession number P49419. In some embodiments, also disclosed herein is a small molecule ligand which binds to the ALDH7A1 protein, wherein the small molecule ligand binds a ligand binding site defined by the following residues: ILVEGVGEVQEYVDICDYAVGLSR (SEQ ID NO: 6) of the ALDH7A1 protein having the UniProtKB accession number P49419. In some instances, the small molecule ligand is probe 8 or 13.

In some embodiments, disclosed herein is a small molecule ligand which binds to a protein selected from ARF4 or ARF5, wherein the small molecule ligand binds to one or more of the following residues: LGEIVTTIPTIGFNVETVEYK (SEQ ID NO: 7), corresponding to LGEIVTTIPTIGFNVETVEYK (SEQ ID NO: 7) of the ARF4 protein having the UniProtKB accession number P18085. In some embodiments, also disclosed herein is a small molecule ligand which binds to a protein selected from ARF4 or ARF5, wherein the small molecule ligand binds a ligand binding site defined by the following residues: LGEIVTTIPTIGFNVETVEYK (SEQ ID NO: 7), corresponding to LGEIVTTIPTIGFNVETVEYK (SEQ ID NO: 7) of the ARF4 protein having the UniProtKB accession number P18085. In some instances, the small molecule ligand is probe 2, 3, 4, 8 or 13.

In some embodiments, disclosed herein is a small molecule ligand which binds to the ARL1 protein, wherein the small molecule ligand binds to one or more residues of a ligand binding site selected from: GTGLDEAMEWLVETLK (SEQ ID NO: 9) and LQVGEVVTTIPTIGFNVETVTYK (SEQ ID NO: 10) of the ARL1 protein having the UniProtKB accession number P40616. In some embodiments, also disclosed herein is a small molecule ligand which binds to the ARL1 protein, wherein the small molecule ligand binds a ligand binding site defined by: GTGLDEAMEWLVETLK (SEQ ID NO: 9) or LQVGEVVTTIPTIGFNVETVTYK (SEQ ID NO: 10) of the ARL1 protein having the UniProtKB accession number P40616. In some instances, the small molecule ligand is probe 13 or 14.

In some embodiments, disclosed herein is a small molecule ligand which binds to the ATIC protein, wherein the small molecule ligand binds to one or more of the following residues: AFTHTAQYDEAISDYFR (SEQ ID NO: 11) of the ATIC protein having the UniProtKB accession number P31939. In some embodiments, also disclosed herein is a small molecule ligand which binds to the ATIC protein, wherein the small molecule ligand binds a ligand binding site defined by the following residues: AFTHTAQYDEAISDYFR (SEQ ID NO: 11) of the ATIC protein having the UniProtKB accession number P31939. In some instances, the small molecule ligand is probe 13.

In some embodiments, disclosed herein is a small molecule ligand which binds to the BLMH protein, wherein the small molecule ligand binds to one or more residues of a ligand binding site selected from: CYFFLSAFVDTAQR (SEQ ID NO: 12) and GEISATQDVMMEEIFR (SEQ ID NO: 13) of the BLMH protein having the UniProtKB accession number Q13867. In some embodiments, also disclosed herein is a small molecule ligand which binds to the BLMH protein, wherein the small molecule ligand binds a ligand binding site defined by: CYFFLSAFVDTAQR (SEQ ID NO: 12) or GEISATQDVMMEEIFR (SEQ ID NO: 13) of the BLMH protein having the UniProtKB accession number Q13867. In some instances, the small molecule ligand is probe 13 or 14.

In some embodiments, disclosed herein is a small molecule ligand which binds to the CALR protein, wherein the small molecule ligand binds to one or more residues of a ligand binding site selected from: SGTIFDNFLITNDEAYAEEFGNETWGVTK (SEQ ID NO: 14) and HEQNIDCGGGYVK (SEQ ID NO: 15) of the CALR protein having the UniProtKB accession number P27797. In some embodiments, also disclosed herein is a small molecule ligand which binds to the CALR protein, wherein the small molecule ligand binds a ligand binding site defined by: SGTIFDNFLITNDEAYAEEFGNETWGVTK (SEQ ID NO: 14) or HEQNIDCGGGYVK (SEQ ID NO: 15) of the CALR protein having the UniProtKB accession number P27797. In some instances, the small molecule ligand is probe 6, 9, or 13.

In some embodiments, disclosed herein is a small molecule ligand which binds to the CAPN1 protein, wherein the small molecule ligand binds to one or more of the following residues: LVFVHSAEGNEFWSALLEK (SEQ ID NO: 16) of the CAPN1 protein having the UniProtKB accession number P07384. In some embodiments, also disclosed herein is a small molecule ligand which binds to the CAPN1 protein, wherein the small molecule ligand binds a ligand binding site defined by the following residues: LVFVHSAEGNEFWSALLEK (SEQ ID NO: 16) of the CAPN1 protein having the UniProtKB accession number P07384. In some instances, the small molecule ligand is probe 14.

In some embodiments, disclosed herein is a small molecule ligand which binds to the CKB protein, wherein the small molecule ligand binds to one or more residues of a ligand binding site selected from: FPAEDEFPDLSAHNNHMAK (SEQ ID NO: 17), LAVEALSSLDGDLAGR (SEQ ID NO: 18), TFLVWVNEEDHLR (SEQ ID NO: 19), FCTGLTQIETLFK (SEQ ID NO: 20), LGFSEVELVQMVVDGVK (SEQ ID NO: 21) and LEQGQAIDDLMPAQK (SEQ ID NO: 22) of the CKB protein having the UniProtKB accession number P12277. In some embodiments, also disclosed herein is a small molecule ligand which binds to the CKB protein, wherein the small molecule ligand binds a ligand binding site defined by: FPAEDEFPDLSAHNNHMAK (SEQ ID NO: 17), LAVEALSSLDGDLAGR (SEQ ID NO: 18), TFLVWVNEEDHLR (SEQ ID NO: 19), FCTGLTQIETLFK (SEQ ID NO: 20), LGFSEVELVQMVVDGVK (SEQ ID NO: 21) or LEQGQAIDDLMPAQK (SEQ ID NO: 22) of the CKB protein having the UniProtKB accession number P12277. In some instances, the small molecule ligand is probe 3 or 13.

In some embodiments, disclosed herein is a small molecule ligand which binds to the CKMT1B protein, wherein the small molecule ligand binds to one or more of the following residues: SFLIWVNEEDHTR (SEQ ID NO: 23) of the CKMT1B protein having the UniProtKB accession number P12532. In some embodiments, disclosed herein is a small molecule ligand which binds to the CKMT1B protein, wherein the small molecule ligand binds a ligand binding site defined by the following residues: SFLIWVNEEDHTR (SEQ ID NO: 23) of the CKMT1B protein having the UniProtKB accession number P12532. In some instances, the small molecule ligand is probe 3.

In some embodiments, disclosed herein is a small molecule ligand which binds to the CLPP protein, wherein the small molecule ligand binds to one or more of the following residues: QSLQVIESAMER (SEQ ID NO: 24) of the CLPP protein having the UniProtKB accession number Q16740. In some embodiments, also disclosed herein is a small molecule ligand which binds to the CLPP protein, wherein the small molecule ligand binds a ligand binding site defined by the following residues: QSLQVIESAMER (SEQ ID NO: 24) of the CLPP protein having the UniProtKB accession number Q16740. In some instances, the small molecule ligand is probe 6.

In some embodiments, disclosed herein is a small molecule ligand which binds to the CSNK1A1 protein, wherein the small molecule ligand binds to one or more of the following residues: DYNVLVMDLLGPSLEDLFNFCSR (SEQ ID NO: 25) of the CSNK1A1 protein having the UniProtKB accession number P48729. In some embodiments, also disclosed herein is a small molecule ligand which binds to the CSNK1A1 protein, wherein the small molecule ligand binds a ligand binding site defined by the following residues: DYNVLVMDLLGPSLEDLFNFCSR (SEQ ID NO: 25) of the CSNK1A1 protein having the UniProtKB accession number P48729. In some instances, the small molecule ligand is probe 14.

In some embodiments, disclosed herein is a small molecule ligand which binds to the CSNK2B protein, wherein the small molecule ligand binds to one or more of the following residues: VYCENQPMLPIGLSDIPGEAMVK (SEQ ID NO: 26) of the CSNK2B protein having the UniProtKB accession number P67870. In some embodiments, also disclosed herein is a small molecule ligand which binds to the CSNK2B protein, wherein the small molecule ligand binds a ligand binding site defined by the following residues: VYCENQPMLPIGLSDIPGEAMVK (SEQ ID NO: 26) of the CSNK2B protein having the UniProtKB accession number P67870. In some instances, the small molecule ligand is probe 14.

In some embodiments, disclosed herein is a small molecule ligand which binds to the CTSB protein, wherein the small molecule ligand binds to one or more of the following residues: GQDHCGIESEVVAGIPR (SEQ ID NO: 27) of the CTSB protein having the UniProtKB accession number P07858. In some embodiments, also disclosed herein is a small molecule ligand which binds to the CTSB protein, wherein the small molecule ligand binds a ligand binding site defined by the following residues: GQDHCGIESEVVAGIPR (SEQ ID NO: 27) of the CTSB protein having the UniProtKB accession number P07858. In some cases, the small molecule ligand is probe 2, 4, 9 or 13.

In some embodiments, disclosed herein is a small molecule ligand which binds to the CTSD protein, wherein the small molecule ligand binds to one or more residues of a ligand binding site selected from: DPDAQPGGELMLGGTDSK (SEQ ID NO: 28), EGCEAIVDTGTSLMVGPVDEVR (SEQ ID NO: 29) and AIGAVPLIQGEYMIPCEK (SEQ ID NO: 30) of the CTSD protein having the UniProtKB accession number P07339. In some embodiments, also disclosed herein is a small molecule ligand which binds to the CTSD protein, wherein the small molecule ligand binds a ligand binding site defined by: DPDAQPGGELMLGGTDSK (SEQ ID NO: 28), EGCEAIVDTGTSLMVGPVDEVR (SEQ ID NO: 29) or AIGAVPLIQGEYMIPCEK (SEQ ID NO: 30) of the CTSD protein having the UniProtKB accession number P07339. In some cases, the small molecule ligand is probe 2, 3, 4, 6, 8, 9, 13, 14 or 15.

In some embodiments, disclosed herein is a small molecule ligand which binds to the CYB5R3 protein, wherein the small molecule ligand binds to one or more of the following residues: LWYTLDR (SEQ ID NO: 31) of the CYB5R3 protein having the UniProtKB accession number P00387. In some embodiments, also disclosed herein is a small molecule ligand which binds to the CYB5R3 protein, wherein the small molecule ligand binds a ligand binding site defined by the following residues: LWYTLDR (SEQ ID NO: 31) of the CYB5R3 protein having the UniProtKB accession number P00387. In some cases, the small molecule ligand is probe 3.

In some embodiments, disclosed herein is a small molecule ligand which binds to the DECR1 protein, wherein the small molecule ligand binds to one or more of the following residues: FDGGEEVLISGEFNDLR (SEQ ID NO: 32) of the DECR1 protein having the UniProtKB accession number Q16698. In some embodiments, also disclosed herein is a small molecule ligand which binds to the DECR1 protein, wherein the small molecule ligand binds a ligand binding site defined by the following residues: FDGGEEVLISGEFNDLR (SEQ ID NO: 32) of the DECR1 protein having the UniProtKB accession number Q16698. In some cases, the small molecule ligand is probe 6.

In some embodiments, disclosed herein is a small molecule ligand which binds to the DHX9 protein, wherein the small molecule ligand binds to one or more of the following residues: ISAVSVAER (SEQ ID NO: 33) of the DHX9 protein having the UniProtKB accession number Q08211. In some embodiments, also disclosed herein is a small molecule ligand which binds to the DHX9 protein, wherein the small molecule ligand binds a ligand binding site defined by the following residues: ISAVSVAER (SEQ ID NO: 33) of the DHX9 protein having the UniProtKB accession number Q08211. In some cases, the small molecule ligand is probe 3.

In some embodiments, disclosed herein is a small molecule ligand which binds to the DLD protein, wherein the small molecule ligand binds to one or more of the following residues: VLGAHILGPGAGEMVNEAALALEYGASCEDIAR (SEQ ID NO: 34) of the DLD protein having the UniProtKB accession number P09622. In some embodiments, also disclosed herein is a small molecule ligand which binds to the DLD protein, wherein the small molecule ligand binds a ligand binding site defined by the following residues: VLGAHILGPGAGEMVNEAALALEYGASCEDIAR (SEQ ID NO: 34) of the DLD protein having the UniProtKB accession number P09622. In some cases, the small molecule ligand is probe 4, 13 or 14.

In some embodiments, disclosed herein is a small molecule ligand which binds to the ECH1 protein, wherein the small molecule ligand binds to one or more residues of a ligand binding site selected from: MFTAGIDLMDMASDILQPK (SEQ ID NO: 35), YQETFNVIER (SEQ ID NO: 36) and EVDVGLAADVGTLQR (SEQ ID NO: 37) of the ECH1 protein having the UniProtKB accession number Q13011. In some embodiments, also disclosed herein is a small molecule ligand which binds to the ECH1 protein, wherein the small molecule ligand binds a ligand binding site defined by: MFTAGIDLMDMASDILQPK (SEQ ID NO: 35), YQETFNVIER (SEQ ID NO: 36) or EVDVGLAADVGTLQR (SEQ ID NO: 37) of the ECH1 protein having the UniProtKB accession number Q13011. In some cases, the small molecule ligand is probe 3, 4, 6, 8, 13, 14 or 15.

In some embodiments, disclosed herein is a small molecule ligand which binds to the EIF4A1 protein, wherein the small molecule ligand binds to one or more residues of a ligand binding site selected from: MFVLDEADEMLSR (SEQ ID NO: 38) and GYDVIAQAQSGTGK (SEQ ID NO: 39) of the EIF4A1 protein having the UniProtKB accession number P60842. In some embodiments, also disclosed herein is a small molecule ligand which binds to the EIF4A1 protein, wherein the small molecule ligand binds a ligand binding site defined by: MFVLDEADEMLSR (SEQ ID NO: 38) or GYDVIAQAQSGTGK (SEQ ID NO: 39) of the EIF4A1 protein having the UniProtKB accession number P60842. In some cases, the small molecule ligand is probe 9, 13 or 14.

In some embodiments, disclosed herein is a small molecule ligand which binds to the EIF4A2 protein, wherein the small molecule ligand binds to one or more of the following residues: GYDVIAQAQSGTGK (SEQ ID NO: 40) of the EIF4A2 protein having the UniProtKB accession number Q14240. In some embodiments, also disclosed herein is a small molecule ligand which binds to the EIF4A2 protein, wherein the small molecule ligand binds a ligand binding site defined by the following residues: GYDVIAQAQSGTGK (SEQ ID NO: 40) of the EIF4A2 protein having the UniProtKB accession number Q14240. In some instances, the small molecule ligand is probe 13.

In some embodiments, disclosed herein is a small molecule ligand which binds to the ETFB protein, wherein the small molecule ligand binds to one or more of the following residues: HSMNPFCEIAVEEAVR (SEQ ID NO: 41) of the ETFB protein having the UniProtKB accession number P38117. In some embodiments, also disclosed herein is a small molecule ligand which binds to the ETFB protein, wherein the small molecule ligand binds a ligand binding site defined by the following residues: HSMNPFCEIAVEEAVR (SEQ ID NO: 41) of the ETFB protein having the UniProtKB accession number P38117. In some cases, the small molecule ligand is probe 3.

In some embodiments, disclosed herein is a small molecule ligand which binds to the FECH protein, wherein the small molecule ligand binds to one or more of the following residues: SEVVILFSAHSLPMSVVNR (SEQ ID NO: 42) of the FECH protein having the UniProtKB accession number P22830. In some embodiments, also disclosed herein is a small molecule ligand which binds to the FECH protein, wherein the small molecule ligand binds a ligand binding site defined by the following residues: SEVVILFSAHSLPMSVVNR (SEQ ID NO: 42) of the FECH protein having the UniProtKB accession number P22830. In some cases, the small molecule ligand is probe 4.

In some embodiments, disclosed herein is a small molecule ligand which binds to the GLA protein, wherein the small molecule ligand binds to one or more residues of a ligand binding site selected from: SILDWTSFNQER (SEQ ID NO: 43), FMCNLDCQEEPDSCISEK (SEQ ID NO: 44) and LFMEMAELMVSEGWK (SEQ ID NO: 45) of the GLA protein having the UniProtKB accession number P06280. In some embodiments, also disclosed herein is a small molecule ligand which binds to the GLA protein, wherein the small molecule ligand binds a ligand binding site defined by: SILDWTSFNQER (SEQ ID NO: 43), FMCNLDCQEEPDSCISEK (SEQ ID NO: 44) or LFMEMAELMVSEGWK (SEQ ID NO: 45) of the GLA protein having the UniProtKB accession number P06280. In some cases, the small molecule ligand is probe 4 or 9.

In some embodiments, disclosed herein is a small molecule ligand which binds to the GLB1 protein, wherein the small molecule ligand binds to one or more of the following residues: TEAVASSLYDILAR (SEQ ID NO: 46) of the GLB1 protein having the UniProtKB accession number P16278. In some embodiments, also disclosed herein is a small molecule ligand which binds to the GLB1 protein, wherein the small molecule ligand binds a ligand binding site defined by the following residues: TEAVASSLYDILAR (SEQ ID NO: 46) of the GLB1 protein having the UniProtKB accession number P16278. In some instances, the small molecule ligand is probe 9.

In some embodiments, disclosed herein is a small molecule ligand which binds to the GLO1 protein, wherein the small molecule ligand binds to one or more of the following residues: GLAFIQDPDGYWIEILNPNK (SEQ ID NO: 47) of the GLO1 protein having the UniProtKB accession number Q04760. In some embodiments, also disclosed herein is a small molecule ligand which binds to the GLO1 protein, wherein the small molecule ligand binds a ligand binding site defined by the following residues: GLAFIQDPDGYWIEILNPNK (SEQ ID NO: 47) of the GLO1 protein having the UniProtKB accession number Q04760. In some instances, the small molecule ligand is probe 3 or 14.

In some embodiments, disclosed herein is a small molecule ligand which binds to the GLUD1 protein, wherein the small molecule ligand binds to one or more residues of a ligand binding site selected from: YSTDVSVDEVK (SEQ ID NO: 48) and HGGTIPIVPTAEFQDR (SEQ ID NO: 49) of the GLUD1 protein having the UniProtKB accession number P00367. In some embodiments, also disclosed herein is a small molecule ligand which binds to the GLUD1 protein, wherein the small molecule ligand binds a ligand binding site defined by: YSTDVSVDEVK (SEQ ID NO: 48) or HGGTIPIVPTAEFQDR (SEQ ID NO: 49) of the GLUD1 protein having the UniProtKB accession number P00367. In some instances, the small molecule ligand is probe 6.

In some embodiments, disclosed herein is a small molecule ligand which binds to the GOLPH3 protein, wherein the small molecule ligand binds to one or more of the following residues: EGYTSFWNDCISSGLR (SEQ ID NO: 50) of the GOLPH3 protein having the UniProtKB accession number Q9H4A6. In some embodiments, also disclosed herein is a small molecule ligand which binds to the GOLPH3 protein, wherein the small molecule ligand binds a ligand binding site defined by the following residues: EGYTSFWNDCISSGLR (SEQ ID NO: 50) of the GOLPH3 protein having the UniProtKB accession number Q9H4A6. In some instances, the small molecule ligand is probe 14.

In some embodiments, disclosed herein is a small molecule ligand which binds to the GSTP1 protein, wherein the small molecule ligand binds to one or more of the following residues: FQDGDLTLYQSNTILR (SEQ ID NO: 51) of the GSTP1 protein having the UniProtKB accession number P09211. In some embodiments, also disclosed herein is a small molecule ligand which binds to the GSTP1 protein, wherein the small molecule ligand binds a ligand binding site defined by the following residues: FQDGDLTLYQSNTILR (SEQ ID NO: 51) of the GSTP1 protein having the UniProtKB accession number P09211. In some instances, the small molecule ligand is probe 2.

In some embodiments, disclosed herein is a small molecule ligand which binds to the HBA2 protein, wherein the small molecule ligand binds to one or more residues of a ligand binding site selected from: VGAHAGEYGAEALER (SEQ ID NO: 52) and VDPVNFK (SEQ ID NO: 53) of the HBA2 protein having the UniProtKB accession number P69905. In some embodiments, also disclosed herein is a small molecule ligand which binds to the HBA2 protein, wherein the small molecule ligand binds a ligand binding site defined by: VGAHAGEYGAEALER (SEQ ID NO: 52) or VDPVNFK (SEQ ID NO: 53) of the HBA2 protein having the UniProtKB accession number P69905. In some instances, the small molecule ligand is probe 4.

In some embodiments, disclosed herein is a small molecule ligand which binds to the HEXA protein, wherein the small molecule ligand binds to one or more of the following residues: LTSDLTFAYER (SEQ ID NO: 54) of the HEXA protein having the UniProtKB accession number P06865. In some embodiments, also disclosed herein is a small molecule ligand which binds to the HEXA protein, wherein the small molecule ligand binds a ligand binding site defined by the following residues: LTSDLTFAYER (SEQ ID NO: 54) of the HEXA protein having the UniProtKB accession number P06865. In some instances, the small molecule ligand is probe 9.

In some embodiments, disclosed herein is a small molecule ligand which binds to the HMOX2 protein, wherein the small molecule ligand binds to one or more of the following residues: AENTQFVK (SEQ ID NO: 55) and LATTALYFTYSALEEEMER (SEQ ID NO: 56) of the HMOX2 protein having the UniProtKB accession number P30519. In some embodiments, also disclosed herein is a small molecule ligand which binds to the HMOX2 protein, wherein the small molecule ligand binds a ligand binding site defined by the following residues: AENTQFVK (SEQ ID NO: 55) or LATTALYFTYSALEEEMER (SEQ ID NO: 56) of the HMOX2 protein having the UniProtKB accession number P30519. In some instances, the small molecule ligand is probe 2, 3, 4, 6, 8, 14 or 15.

In some embodiments, disclosed herein is a small molecule ligand which binds to the HSD17B4 protein, wherein the small molecule ligand binds to one or more of the following residues: LGLLGLANSLAIEGR (SEQ ID NO: 57) of the HSD17B4 protein having the UniProtKB accession number P51659. In some embodiments, also disclosed herein is a small molecule ligand which binds to the HSD17B4 protein, wherein the small molecule ligand binds a ligand binding site defined by the following residues: LGLLGLANSLAIEGR (SEQ ID NO: 57) of the HSD17B4 protein having the UniProtKB accession number P51659. In some instances, the small molecule ligand is probe 3.

In some embodiments, disclosed herein is a small molecule ligand which binds to the HSP90AB1 protein, wherein the small molecule ligand binds to one or more residues of a ligand binding site selected from: VFIMDSCDELIPEYLNFIR (SEQ ID NO: 58) and GFEVVYMTEPIDEYCVQQLK (SEQ ID NO: 59) of the HSP90AB1 protein having the UniProtKB accession number P08238. In some embodiments, also disclosed herein is a small molecule ligand which binds to the HSP90AB1 protein, wherein the small molecule ligand binds a ligand binding site defined by: VFIMDSCDELIPEYLNFIR (SEQ ID NO: 58) or GFEVVYMTEPIDEYCVQQLK (SEQ ID NO: 59) of the HSP90AB1 protein having the UniProtKB accession number P08238. In some instances, the small molecule ligand is probe 13 or 14.

In some embodiments, disclosed herein is a small molecule ligand which binds to the HSP90B1 protein, wherein the small molecule ligand binds to one or more residues of a ligand binding site selected from: LISLTDENALSGNEELTVK (SEQ ID NO: 60) and YSQFINFPIYVWSSK (SEQ ID NO: 61) of the HSP90B1 protein having the UniProtKB accession number P14625. In some embodiments, also disclosed herein is a small molecule ligand which binds to the HSP90B1 protein, wherein the small molecule ligand binds a ligand binding site defined by: LISLTDENALSGNEELTVK (SEQ ID NO: 60) or YSQFINFPIYVWSSK (SEQ ID NO: 61) of the HSP90B1 protein having the UniProtKB accession number P14625. In some instances, the small molecule ligand is probe 6 or 9.

In some embodiments, disclosed herein is a small molecule ligand which binds to the HSPA8 protein, wherein the small molecule ligand binds to one or more of the following residues: SFYPEEVSSMVLTK (SEQ ID NO: 62) of the HSPA8 protein having the UniProtKB accession number P11142. In some embodiments, also disclosed herein is a small molecule ligand which binds to the HSPA8 protein, wherein the small molecule ligand binds a ligand binding site defined by the following residues: SFYPEEVSSMVLTK (SEQ ID NO: 62) of the HSPA8 protein having the UniProtKB accession number P11142. In some instances, the small molecule ligand is probe 13 or 14.

In some embodiments, disclosed herein is a small molecule ligand which binds to the IMPDH2 protein, wherein the small molecule ligand binds to one or more of the following residues: YEQGFITDPVVLSPK (SEQ ID NO: 63) of the IMPDH2 protein having the UniProtKB accession number P12268. In some embodiments, also disclosed herein is a small molecule ligand which binds to the IMPDH2 protein, wherein the small molecule ligand binds a ligand binding site defined by the following residues: YEQGFITDPVVLSPK (SEQ ID NO: 63) of the IMPDH2 protein having the UniProtKB accession number P12268. In some instances, the small molecule ligand is probe 13.

In some embodiments, disclosed herein is a small molecule ligand which binds to the LDHA protein, wherein the small molecule ligand binds to one or more of the following residues: DLADELALVDVIEDK (SEQ ID NO: 64) of the LDHA protein having the UniProtKB accession number P00338. In some embodiments, also disclosed herein is a small molecule ligand which binds to the LDHA protein, wherein the small molecule ligand binds a ligand binding site defined by the following residues: DLADELALVDVIEDK (SEQ ID NO: 64) of the LDHA protein having the UniProtKB accession number P00338. In some instances, the small molecule ligand is probe 9.

In some embodiments, disclosed herein is a small molecule ligand which binds to the LDHB protein, wherein the small molecule ligand binds to one or more of the following residues: MVVESAYEVIK (SEQ ID NO: 65) of the LDHB protein having the UniProtKB accession number P07195. In some embodiments, also disclosed herein is a small molecule ligand which binds to the LDHB protein, wherein the small molecule ligand binds a ligand binding site defined by the following residues: MVVESAYEVIK (SEQ ID NO: 65) of the LDHB protein having the UniProtKB accession number P07195. In some instances, the small molecule ligand is probe 4.

In some embodiments, disclosed herein is a small molecule ligand which binds to the LGMN protein, wherein the small molecule ligand binds to one or more of the following residues: DYTGEDVTPQNFLAVLR (SEQ ID NO: 66) of the LGMN protein having the UniProtKB accession number Q99538. In some embodiments, also disclosed herein is a small molecule ligand which binds to the LGMN protein, wherein the small molecule ligand binds a ligand binding site defined by the following residues: DYTGEDVTPQNFLAVLR (SEQ ID NO: 66) of the LGMN protein having the UniProtKB accession number Q99538. In some instances, the small molecule ligand is probe 9.

In some embodiments, disclosed herein is a small molecule ligand which binds to the LTA4H protein, wherein the small molecule ligand binds to one or more of the following residues: LVVDLTDIDPDVAYSSVPYEK (SEQ ID NO: 67) of the LTA4H protein having the UniProtKB accession number P09960. In some embodiments, also disclosed herein is a small molecule ligand which binds to the LTA4H protein, wherein the small molecule ligand binds a ligand binding site defined by the following residues: LVVDLTDIDPDVAYSSVPYEK (SEQ ID NO: 67) of the LTA4H protein having the UniProtKB accession number P09960. In some cases, the small molecule ligand is probe 4, 8 or 13.

In some embodiments, disclosed herein is a small molecule ligand which binds to the NAMPT protein, wherein the small molecule ligand binds to one or more of the following residues: YLLETSGNLDGLEYK (SEQ ID NO: 68) of the NAMPT protein having the UniProtKB accession number P43490. In some embodiments, also disclosed herein is a small molecule ligand which binds to the NAMPT protein, wherein the small molecule ligand binds a ligand binding site defined by the following residues: YLLETSGNLDGLEYK (SEQ ID NO: 68) of the NAMPT protein having the UniProtKB accession number P43490. In some cases, the small molecule ligand is probe 3, 6, 8, 13, 14 or 15.

In some embodiments, disclosed herein is a small molecule ligand which binds to the NPM1 protein, wherein the small molecule ligand binds to one or more residues of a ligand binding site selected from: DELHIVEAEAMNYEGSPIK (SEQ ID NO: 69) and MSVQPTVSLGGFEITPPVVLR (SEQ ID NO: 70) of the NPM1 protein having the UniProtKB accession number P06748. In some embodiments, also disclosed herein is a small molecule ligand which binds to the NPM1 protein, wherein the small molecule ligand binds a ligand binding site defined by: DELHIVEAEAMNYEGSPIK (SEQ ID NO: 69) or MSVQPTVSLGGFEITPPVVLR (SEQ ID NO: 70) of the NPM1 protein having the UniProtKB accession number P06748. In some cases, the small molecule ligand is probe 13.

In some embodiments, disclosed herein is a small molecule ligand which binds to the PCMT1 protein, wherein the small molecule ligand binds to one or more of the following residues: LILPVGPAGGNQMLEQYDK (SEQ ID NO: 71) of the PCMT1 protein having the UniProtKB accession number P22061. In some embodiments, also disclosed herein is a small molecule ligand which binds to the PCMT1 protein, wherein the small molecule ligand binds a ligand binding site defined by the following residues: LILPVGPAGGNQMLEQYDK (SEQ ID NO: 71) of the PCMT1 protein having the UniProtKB accession number P22061. In some instances, the small molecule ligand is probe 2, 3 or 14.

In some embodiments, disclosed herein is a small molecule ligand which binds to the PDHB protein, wherein the small molecule ligand binds to one or more of the following residues: VFLLGEEVAQYDGAYK (SEQ ID NO: 72) of the PDHB protein having the UniProtKB accession number P11177. In some embodiments, also disclosed herein is a small molecule ligand which binds to the PDHB protein, wherein the small molecule ligand binds a ligand binding site defined by the following residues: VFLLGEEVAQYDGAYK (SEQ ID NO: 72) of the PDHB protein having the UniProtKB accession number P11177. In some instances, the small molecule ligand is probe 2, 3, 13 or 14.

In some embodiments, disclosed herein is a small molecule ligand which binds to the PGK1 protein, wherein the small molecule ligand binds to one or more of the following residues: QIVWNGPVGVFEWEAFAR (SEQ ID NO: 73) of the PGK1 protein having the UniProtKB accession number P00558. In some embodiments, also disclosed herein is a small molecule ligand which binds to the PGK1 protein, wherein the small molecule ligand binds a ligand binding site defined by the following residues: QIVWNGPVGVFEWEAFAR (SEQ ID NO: 73) of the PGK1 protein having the UniProtKB accession number P00558. In some instances, the small molecule ligand is probe 3.

In some embodiments, disclosed herein is a small molecule ligand which binds to the PKM protein, wherein the small molecule ligand binds to one or more of the following residues: IYVDDGLISLQVK (SEQ ID NO: 74) and LAPITSDPTEATAVGAVEASFK (SEQ ID NO: 75) of the PKM protein having the UniProtKB accession number P14618. In some embodiments, also disclosed herein is a small molecule ligand which binds to the PKM protein, wherein the small molecule ligand binds a ligand binding site defined by the following residues: IYVDDGLISLQVK (SEQ ID NO: 74) or LAPITSDPTEATAVGAVEASFK (SEQ ID NO: 75) of the PKM protein having the UniProtKB accession number P14618. In some instances, the small molecule ligand is probe 2 or 9.

In some embodiments, disclosed herein is a small molecule ligand which binds to the POR protein, wherein the small molecule ligand binds to one or more of the following residues: TALTYYLDITNPPR (SEQ ID NO: 76) of the POR protein having the UniProtKB accession number P16435. In some embodiments, also disclosed herein is a small molecule ligand which binds to the POR protein, wherein the small molecule ligand binds a ligand binding site defined by the following residues: TALTYYLDITNPPR (SEQ ID NO: 76) of the POR protein having the UniProtKB accession number P16435. In some instances, the small molecule ligand is probe 13 or 14.

In some embodiments, disclosed herein is a small molecule ligand which binds to a protein selected from PPP1CA and PPP1CC, wherein the small molecule ligand binds to one or more of the following residues: IYGFYDECK (SEQ ID NO: 77), which corresponds to IYGFYDECK (SEQ ID NO: 78) of the PPP1CC protein having the UniProtKB accession number P36873. In some embodiments, also disclosed herein is a small molecule ligand which binds to a protein selected from PPP1CA and PPP1CC, wherein the small molecule ligand binds a ligand binding site defined by the following residues: IYGFYDECK (SEQ ID NO: 77), which corresponds to IYGFYDECK (SEQ ID NO: 78) of the PPP1CC protein having the UniProtKB accession number P36873. In some instances, the small molecule ligand is probe 2.

In some embodiments, disclosed herein is a small molecule ligand which binds to the PPP1CC protein, wherein the small molecule ligand binds to one or more of the following residues: EIFLSQPILLELEAPLK (SEQ ID NO: 79) of the PPP1CC protein having the UniProtKB accession number P36873. In some embodiments, also disclosed herein is a small molecule ligand which binds to the PPP1CC protein, wherein the small molecule ligand binds a ligand binding site defined by the following residues: EIFLSQPILLELEAPLK (SEQ ID NO: 79) of the PPP1CC protein having the UniProtKB accession number P36873. In some instances, the small molecule ligand is probe 14.

In some embodiments, disclosed herein is a small molecule ligand which binds to the PPT1 protein, wherein the small molecule ligand binds to one or more of the following residues: TLMEDVENSFFLNVNSQVTTVCQALAK (SEQ ID NO: 80) of the PPT1 protein having the UniProtKB accession number P50897. In some embodiments, also disclosed herein is a small molecule ligand which binds to the PPT1 protein, wherein the small molecule ligand binds a ligand binding site defined by the following residues: TLMEDVENSFFLNVNSQVTTVCQALAK (SEQ ID NO:

80) of the PPT1 protein having the UniProtKB accession number P50897. In some cases, the small molecule ligand is probe 2, 4, 8, 9, 13, 14 or 15.

In some embodiments, disclosed herein is a small molecule ligand which binds to the PRDX2 protein, wherein the small molecule ligand binds to one or more of the following residues: TDEGIAYR (SEQ ID NO: 81) of the PRDX2 protein having the UniProtKB accession number P32119. In some embodiments, also disclosed herein is a small molecule ligand which binds to the PRDX2 protein, wherein the small molecule ligand binds a ligand binding site defined by the following residues: TDEGIAYR (SEQ ID NO: 81) of the PRDX2 protein having the UniProtKB accession number P32119. In some cases, the small molecule ligand is probe 13.

In some embodiments, disclosed herein is a small molecule ligand which binds to the PSMB4 protein, wherein the small molecule ligand binds to one or more of the following residues: FEGGVVIAADMLGSYGSLAR (SEQ ID NO: 82) of the PSMB4 protein having the UniProtKB accession number P28070. In some embodiments, also disclosed herein is a small molecule ligand which binds to the PSMB4 protein, wherein the small molecule ligand binds a ligand binding site defined by the following residues: FEGGVVIAADMLGSYGSLAR (SEQ ID NO: 82) of the PSMB4 protein having the UniProtKB accession number P28070. In some cases, the small molecule ligand is probe 6.

In some embodiments, disclosed herein is a small molecule ligand which binds to the PSMB5 protein, wherein the small molecule ligand binds to one or more residues of a ligand binding site selected from: LLANMVYQYK (SEQ ID NO: 83) and DAYSGGAVNLYHVR (SEQ ID NO: 84) of the PSMB5 protein having the UniProtKB accession number P28074. In some embodiments, also disclosed herein is a small molecule ligand which binds to the PSMB5 protein, wherein the small molecule ligand binds a ligand binding site defined by: LLANMVYQYK (SEQ ID NO: 83) or DAYSGGAVNLYHVR (SEQ ID NO: 84) of the PSMB5 protein having the UniProtKB accession number P28074. In some instances, the small molecule ligand is probe 3, 4 or 6.

In some embodiments, disclosed herein is a small molecule ligand which binds to the PSMB6 protein, wherein the small molecule ligand binds to one or more of the following residues: SGSAADTQAVADAVTYQLGFHSIELNEPPLVHTAASLFK (SEQ ID NO: 85) of the PSMB6 protein having the UniProtKB accession number P28072. In some embodiments, also disclosed herein is a small molecule ligand which binds to the PSMB6 protein, wherein the small molecule ligand binds a ligand binding site defined by the following residues: SGSAADTQAVADAVTYQLGFHSIELNEPPLVHTAASLFK (SEQ ID NO: 85) of the PSMB6 protein having the UniProtKB accession number P28072. In some instances, the small molecule ligand is probe 3, 6 or 14.

In some embodiments, disclosed herein is a small molecule ligand which binds to the RAB7A protein, wherein the small molecule ligand binds to one or more of the following residues: DEFLIQASPR (SEQ ID NO: 86) of the RAB7A protein having the UniProtKB accession number P51149. In some embodiments, also disclosed herein is a small molecule ligand which binds to the RAB7A protein, wherein the small molecule ligand binds a ligand binding site defined by the following residues: DEFLIQASPR (SEQ ID NO: 86) of the RAB7A protein having the UniProtKB accession number P51149. In some instances, the small molecule ligand is probe 14.

In some embodiments, disclosed herein is a small molecule ligand which binds to the RUVBL2 protein, wherein the small molecule ligand binds to one or more of the following residues: ALESDMAPVLIMATNR (SEQ ID NO: 87) of the RUVBL2 protein having the UniProtKB accession number Q9Y230. In some embodiments, also disclosed herein is a small molecule ligand which binds to the RUVBL2 protein, wherein the small molecule ligand binds a ligand binding site defined by the following residues: ALESDMAPVLIMATNR (SEQ ID NO: 87) of the RUVBL2 protein having the UniProtKB accession number Q9Y230. In some instances, the small molecule ligand is probe 14.

In some embodiments, disclosed herein is a small molecule ligand which binds to the SMYD3 protein, wherein the small molecule ligand binds to one or more of the following residues: DQYCFECDCFR (SEQ ID NO: 88) of the SMYD3 protein having the UniProtKB accession number Q9H7B4. In some embodiments, also disclosed herein is a small molecule ligand which binds to the SMYD3 protein, wherein the small molecule ligand binds a ligand binding site defined by the following residues: DQYCFECDCFR (SEQ ID NO: 88) of the SMYD3 protein having the UniProtKB accession number Q9H7B4. In some cases, the small molecule ligand is probe 9.

In some embodiments, disclosed herein is a small molecule ligand which binds to the TPP1 protein, wherein the small molecule ligand binds to one or more of the following residues: GCHESCLDEEVEGQGFCSGPGWDPVTGWGTPNFPALLK (SEQ ID NO: 89) of the TPP1 protein having the UniProtKB accession number O14773. In some embodiments, also disclosed herein is a small molecule ligand which binds to the TPP1 protein, wherein the small molecule ligand binds a ligand binding site defined by the following residues: GCHESCLDEEVEGQGFCSGPGWDPVTGWGTPNFPALLK (SEQ ID NO: 89) of the TPP1 protein having the UniProtKB accession number O14773. In some instances, the small molecule ligand is probe 4, 9, 13, 14 or 15.

In some embodiments, disclosed herein is a small molecule ligand which binds to the TXNDC17 protein, wherein the small molecule ligand binds to one or more of the following residues: YEEVSVSGFEEFHR (SEQ ID NO: 90) of the TXNDC17 protein having the UniProtKB accession number Q9BRA2. In some embodiments, also disclosed herein is a small molecule ligand which binds to the TXNDC17 protein, wherein the small molecule ligand binds a ligand binding site defined by the following residues: YEEVSVSGFEEFHR (SEQ ID NO: 90) of the TXNDC17 protein having the UniProtKB accession number Q9BRA2. In some instances, the small molecule ligand is probe 14.

In some embodiments, disclosed herein is a small molecule ligand which binds to the YWHAE protein, wherein the small molecule ligand binds to one or more residues of a ligand binding site selected from: EAAENSLVAYK (SEQ ID NO: 91) and AAFDDAIAELDTLSEESYK (SEQ ID NO: 92) of the YWHAE protein having the UniProtKB accession number P62258. In some embodiments, also disclosed herein is a small molecule ligand which binds to the YWHAE protein, wherein the small molecule ligand binds a ligand binding site defined by: EAAENSLVAYK (SEQ ID NO: 91) or AAFDDAIAELDTLSEESYK (SEQ ID NO: 92) of the YWHAE protein having the UniProtKB accession number P62258. In some cases, the small molecule ligand is probe 13.

In some embodiments, disclosed herein is a small molecule ligand which binds to the YWHAQ protein, wherein the small molecule ligand binds to one or more of the following residues: TAFDEAIAELDTLNEDSYK (SEQ ID NO: 93) of the YWHAQ protein having the UniProtKB accession number P27348. In some embodiments, also disclosed herein is a small molecule ligand which binds to the YWHAQ protein, wherein the small molecule ligand binds a ligand binding site defined by the following residues: TAFDEAIAELDTLNEDSYK (SEQ ID NO: 93) of the YWHAQ protein having the UniProtKB accession number P27348. In some cases, the small molecule ligand is probe 14.

In some embodiments, disclosed herein is a small molecule ligand which binds to the YWHAZ protein, wherein the small molecule ligand binds to one or more of the following residues: TAFDEAIAELDTLSEESYK (SEQ ID NO: 94) of the YWHAZ protein having the UniProtKB accession number P63104. In some embodiments, also disclosed herein is a small molecule ligand which binds to the YWHAZ protein, wherein the small molecule ligand binds a ligand binding site defined by the following residues: TAFDEAIAELDTLSEESYK (SEQ ID NO: 94) of the YWHAZ protein having the UniProtKB accession number P63104. In some instances, the small molecule ligand is probe 13 or 14.

In some embodiments, disclosed herein is a small molecule ligand which binds to the EXO1 protein, wherein the small molecule ligand binds to one or more of the following residues: SQGVDCLVAPYEADAQLAYLNK (SEQ ID NO: 95) of the EXO1 protein having the UniProtKB accession number Q9UQ84. In some embodiments, also disclosed herein is a small molecule ligand which binds to the EXO1 protein, wherein the small molecule ligand binds a ligand binding site defined by the following residues: SQGVDCLVAPYEADAQLAYLNK (SEQ ID NO: 95) of the EXO1 protein having the UniProtKB accession number Q9UQ84. In some instances, the small molecule ligand is probe 2, 6, 8, 9 or 13.

In some embodiments, disclosed herein is a small molecule ligand which binds to the LMNA protein, wherein the small molecule ligand binds to one or more of the following residues: MQQQLDEYQELLDIK (SEQ ID NO: 96) of the LMNA protein having the UniProtKB accession number P02545. In some embodiments, also disclosed herein is a small molecule ligand which binds to the LMNA protein, wherein the small molecule ligand binds a ligand binding site defined by the following residues: MQQQLDEYQELLDIK (SEQ ID NO: 96) of the LMNA protein having the UniProtKB accession number P02545. In some instances, the small molecule ligand is probe 6 or 13.

In some cases, the small molecule ligand which binds to a protein has a structure represented by Formula (Ia):

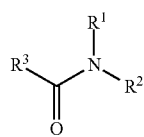

(Ia)

wherein $R^1$ is hydrogen and $R^2$ is selected from substituted alkyl, optionally substituted aryl, optionally substituted heteroaryl, optionally substituted cycloalkyl, optionally substituted heterocyclyl, optionally substituted heteroaryl, optionally substituted aralkyl, optionally substituted heteroarylalkyl, or optionally substituted heterocyclylalkyl; or $R^1$ and $R^2$ together with the nitrogen to which they are attached form an optionally substituted heterocyclyl ring wherein $R^1$ is hydrogen and $R^2$ is selected from substituted alkyl, optionally substituted aryl, optionally substituted heteroaryl, optionally substituted cycloalkyl, optionally substituted heterocyclyl, optionally substituted heteroaryl, optionally substituted aralkyl, optionally substituted heteroarylalkyl, or optionally substituted heterocyclylalkyl; or $R^1$ and $R^2$ together with the nitrogen to which they are attached form an optionally substituted heterocyclyl ring; and $R^3$ is an optionally substituted C2-C6 alkyl.

In some cases, the small molecule ligand which binds to a protein has a structure represented by Formula (IIa):

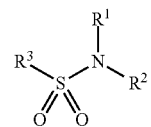

(IIa)

wherein $R^1$ is hydrogen and $R^2$ is selected from substituted alkyl, optionally substituted aryl, optionally substituted heteroaryl, optionally substituted cycloalkyl, optionally substituted heterocyclyl, optionally substituted heteroaryl, optionally substituted aralkyl, optionally substituted heteroarylalkyl, or optionally substituted heterocyclylalkyl; or $R^1$ and $R^2$ together with the nitrogen to which they are attached form an optionally substituted heterocyclyl ring; and $R^3$ is an optionally substituted C2-C6 alkyl.

In some cases, the small molecule ligand which binds to a protein has a structure represented by Formula (IIIa):

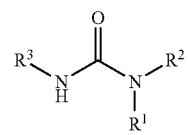

(IIIa)

wherein $R^1$ is hydrogen and $R^2$ is selected from substituted alkyl, optionally substituted aryl, optionally substituted heteroaryl, optionally substituted cycloalkyl, optionally substituted heterocyclyl, optionally substituted heteroaryl, optionally substituted aralkyl, optionally substituted heteroarylalkyl, or optionally substituted heterocyclylalkyl; or $R^1$ and $R^2$ together with the nitrogen to which they are attached form an optionally substituted heterocyclyl ring; and $R^3$ is an optionally substituted C2-C6 alkyl.

In some cases, the small molecule ligand which binds to a protein has a structure represented by Formula (IVa):

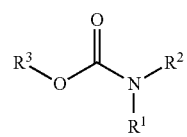

(IVa)

wherein $R^1$ is hydrogen and $R^2$ is selected from substituted alkyl, optionally substituted aryl, optionally substituted heteroaryl, optionally substituted cycloalkyl, optionally substituted heterocyclyl, optionally substituted heteroaryl, optionally substituted aralkyl, optionally substituted heteroarylalkyl, or optionally substituted heterocyclylalkyl; or R¹ and R² together with the nitrogen to which they are attached form an optionally substituted heterocyclyl ring; and R³ is an optionally substituted C2-C6 alkyl.

In some cases, the small molecule ligand which binds to a protein has a structure represented by Formula (Va):

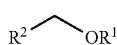

(Va)

wherein R¹ is selected from substituted alkyl, optionally substituted aryl, optionally substituted heteroaryl, optionally substituted cycloalkyl, optionally substituted heterocyclyl, optionally substituted heteroaryl, optionally substituted aralkyl, optionally substituted heteroarylalkyl, or optionally substituted heterocyclylalkyl; and R² is an optionally substituted C2-C6 alkyl.

In some cases, the small molecule ligand which binds to a protein has a structure represented by Formula (VIa):

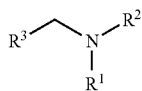

(VIa)

wherein R¹ is hydrogen and R² is selected from substituted alkyl, optionally substituted aryl, optionally substituted heteroaryl, optionally substituted cycloalkyl, optionally substituted heterocyclyl, optionally substituted heteroaryl, optionally substituted aralkyl, optionally substituted heteroarylalkyl, or optionally substituted heterocyclylalkyl; or R¹ and R² together with the nitrogen to which they are attached form an optionally substituted heterocyclyl ring; and R³ is an optionally substituted C2-C6 alkyl.

Cells, Analytical Techniques, and Instrumentation

In certain embodiments, one or more of the methods disclosed herein comprise a cell sample. In some embodiments, the cell sample for use with the methods described herein is obtained from cells of an animal. In some instances, the animal cell includes a cell from a marine invertebrate, fish, insects, amphibian, reptile, or mammal. In some instances, the mammalian cell is a primate, ape, equine, bovine, porcine, canine, feline, or rodent. In some instances, the mammal is a primate, ape, dog, cat, rabbit, ferret, or the like. In some cases, the rodent is a mouse, rat, hamster, gerbil, hamster, chinchilla, or guinea pig. In some embodiments, the bird cell is from a canary, parakeet or parrots. In some embodiments, the reptile cell is from a turtles, lizard or snake. In some cases, the fish cell is from a tropical fish. In some cases, the fish cell is from a zebrafish (e.g. Danino rerio). In some cases, the worm cell is from a nematode (e.g. C. elegans). In some cases, the amphibian cell is from a frog. In some embodiments, the arthropod cell is from a tarantula or hermit crab.

In some embodiments, the cell sample for use with the methods described herein is obtained from a mammalian cell. In some instances, the mammalian cell is an epithelial cell, connective tissue cell, hormone secreting cell, a nerve cell, a skeletal muscle cell, a blood cell, or an immune system cell.

Exemplary mammalian cells include, but are not limited to, 293A cell line, 293FT cell line, 293F cells, 293 H cells, HEK 293 cells, CHO DG44 cells, CHO-S cells, CHO-KI cells, Expi293F™ cells, Flp-In™ T-REx™ 293 cell line, Flp-In™-293 cell line, Flp-In™-3T3 cell line, Flp-In™-BHK cell line, Flp-In™-CHO cell line, Flp-In™-CV-1 cell line, Flp-In™-Jurkat cell line, FreeStyle™ 293-F cells, FreeStyle™ CHO-S cells, GripTite™ 293 MSR cell line, GS-CHO cell line, HepaRG™ cells, T-REx™ Jurkat cell line, Per.C6 cells, T-REx™-293 cell line, T-REx™-CHO cell line, T-REx™-HeLa cell line, NC-HIMT cell line, and PC12 cell line.

In some instances, the cell sample for use with the methods described herein is obtained from cells of a tumor cell line. In some instances, the sample is obtained from cells of a solid tumor cell line. In some instances, the solid tumor cell line is a sarcoma cell line. In some instances, the solid tumor cell line is a carcinoma cell line. In some embodiments, the sarcoma cell line is obtained from a cell line of alveolar rhabdomyosarcoma, alveolar soft part sarcoma, ameloblastoma, angiosarcoma, chondrosarcoma, chordoma, clear cell sarcoma of soft tissue, dedifferentiated liposarcoma, desmoid, desmoplastic small round cell tumor, embryonal rhabdomyosarcoma, epithelioid fibrosarcoma, epithelioid hemangioendothelioma, epithelioid sarcoma, esthesioneuroblastoma, Ewing sarcoma, extrarenal rhabdoid tumor, extraskeletal myxoid chondrosarcoma, extraskeletal osteosarcoma, fibrosarcoma, giant cell tumor, hemangiopericytoma, infantile fibrosarcoma, inflammatory myofibroblastic tumor, Kaposi sarcoma, leiomyosarcoma of bone, liposarcoma, liposarcoma of bone, malignant fibrous histiocytoma (MFH), malignant fibrous histiocytoma (MFH) of bone, malignant mesenchymoma, malignant peripheral nerve sheath tumor, mesenchymal chondrosarcoma, myxofibrosarcoma, myxoid liposarcoma, myxoinflammatory fibroblastic sarcoma, neoplasms with perivascular epitheioid cell differentiation, osteosarcoma, parosteal osteosarcoma, neoplasm with perivascular epitheioid cell differentiation, periosteal osteosarcoma, pleomorphic liposarcoma, pleomorphic rhabdomyosarcoma, PNET/extraskeletal Ewing tumor, rhabdomyosarcoma, round cell liposarcoma, small cell osteosarcoma, solitary fibrous tumor, synovial sarcoma, telangiectatic osteosarcoma.

In some embodiments, the carcinoma cell line is obtained from a cell line of adenocarcinoma, squamous cell carcinoma, adenosquamous carcinoma, anaplastic carcinoma, large cell carcinoma, small cell carcinoma, anal cancer, appendix cancer, bile duct cancer (i.e., cholangiocarcinoma), bladder cancer, brain tumor, breast cancer, cervical cancer, colon cancer, cancer of Unknown Primary (CUP), esophageal cancer, eye cancer, fallopian tube cancer, gastroenterological cancer, kidney cancer, liver cancer, lung cancer, medulloblastoma, melanoma, oral cancer, ovarian cancer, pancreatic cancer, parathyroid disease, penile cancer, pituitary tumor, prostate cancer, rectal cancer, skin cancer, stomach cancer, testicular cancer, throat cancer, thyroid cancer, uterine cancer, vaginal cancer, or vulvar cancer.

In some instances, the cell sample is obtained from cells of a hematologic malignant cell line. In some instances, the hematologic malignant cell line is a T-cell cell line. In some instances, B-cell cell line. In some instances, the hematologic malignant cell line is obtained from a T-cell cell line of: peripheral T-cell lymphoma not otherwise specified (PTCL-NOS), anaplastic large cell lymphoma, angioimmunoblastic lymphoma, cutaneous T-cell lymphoma, adult T-cell leukemia/lymphoma (ATLL), blastic NK-cell lymphoma, enteropathy-type T-cell lymphoma, hematosplenic gamma-delta T-cell lymphoma, lymphoblastic lymphoma, nasal NK/T-cell lymphomas, or treatment-related T-cell lymphomas.

In some instances, the hematologic malignant cell line is obtained from a B-cell cell line of: acute lymphoblastic leukemia (ALL), acute myelogenous leukemia (AML), chronic myelogenous leukemia (CML), acute monocytic leukemia (AMoL), chronic lymphocytic leukemia (CLL), high-risk chronic lymphocytic leukemia (CLL), small lymphocytic lymphoma (SLL), high-risk small lymphocytic lymphoma (SLL), follicular lymphoma (FL), mantle cell lymphoma (MCL), Waldenstrom's macroglobulinemia, multiple myeloma, extranodal marginal zone B cell lymphoma, nodal marginal zone B cell lymphoma, Burkitt's lymphoma, non-Burkitt high grade B cell lymphoma, primary mediastinal B-cell lymphoma (PMBL), immunoblastic large cell lymphoma, precursor B-lymphoblastic lymphoma, B cell prolymphocytic leukemia, lymphoplasmacytic lymphoma, splenic marginal zone lymphoma, plasma cell myeloma, plasmacytoma, mediastinal (thymic) large B cell lymphoma, intravascular large B cell lymphoma, primary effusion lymphoma, or lymphomatoid granulomatosis.

In some embodiments, the cell sample for use with the methods described herein is obtained from a tumor cell line. Exemplary tumor cell line includes, but is not limited to, 600MPE, AU565, BT-20, BT-474, BT-483, BT-549, Evsa-T, Hs578T, MCF-7, MDA-MB-231, SkBr3, T-47D, HeLa, DU145, PC3, LNCaP, A549, H1299, NCI-H460, A2780, SKOV-3/Luc, Neuro2a, RKO, RKO-AS45-1, HT-29, SW1417, SW948, DLD-1, SW480, Capan-1, MC/9, B72.3, B25.2, B6.2, B38.1, DMS 153, SU.86.86, SNU-182, SNU-423, SNU-449, SNU-475, SNU-387, Hs817.T, LMH, LMH/2A, SNU-398, PLHC-1, HepG2/SF, OCI-Ly1, OCI-Ly2, OCI-Ly3, OCI-Ly4, OCI-Ly6, OCI-Ly7, OCI-Ly10, OCI-Ly18, OCI-Ly19, U2932, DB, HBL-1, RIVA, SUDHL2, TMD8, MEC1, MEC2, 8E5, CCRF-CEM, MOLT-3, TALL-104, AML-193, THP-1, BDCM, HL-60, Jurkat, RPMI 8226, MOLT-4, RS4, K-562, KASUMI-1, Daudi, GA-10, Raji, JeKo-1, NK-92, and Mino.

In some embodiments, the cell sample for use in the methods is from any tissue or fluid from an individual. Samples include, but are not limited to, tissue (e.g. connective tissue, muscle tissue, nervous tissue, or epithelial tissue), whole blood, dissociated bone marrow, bone marrow aspirate, pleural fluid, peritoneal fluid, central spinal fluid, abdominal fluid, pancreatic fluid, cerebrospinal fluid, brain fluid, ascites, pericardial fluid, urine, saliva, bronchial lavage, sweat, tears, ear flow, sputum, hydrocele fluid, semen, vaginal flow, milk, amniotic fluid, and secretions of respiratory, intestinal or genitourinary tract. In some embodiments, the sample is a tissue sample, such as a sample obtained from a biopsy or a tumor tissue sample. In some embodiments, the sample is a blood serum sample. In some embodiments, the sample is a blood cell sample containing one or more peripheral blood mononuclear cells (PBMCs). In some embodiments, the sample contains one or more circulating tumor cells (CTCs). In some embodiments, the sample contains one or more disseminated tumor cells (DTC, e.g., in a bone marrow aspirate sample).

In some embodiments, the cell samples are obtained from the individual by any suitable means of obtaining the sample using well-known and routine clinical methods. Procedures for obtaining tissue samples from an individual are well known. For example, procedures for drawing and processing tissue sample such as from a needle aspiration biopsy is well-known and is employed to obtain a sample for use in the methods provided. Typically, for collection of such a tissue sample, a thin hollow needle is inserted into a mass such as a tumor mass for sampling of cells that, after being stained, will be examined under a microscope.

Sample Preparation and Analysis

In some embodiments, the sample is a sample solution. In some instances, the sample solution comprises a solution such as a buffer (e.g. phosphate buffered saline) or a media. In some embodiments, the media is an isotopically labeled media. In some instances, the sample solution is a cell solution.

In some embodiments, the sample (e.g., cells or a cell solution) is incubated with one or more probes for analysis of protein-probe interactions. In some instances, the sample (e.g., cells or a cell solution) is further incubated in the presence of an additional probe prior to addition of the one or more probes. In other instances, the sample (e.g., cells or a cell solution) is further incubated with a non-probe small molecule ligand, in which the non-probe small molecule ligand does not contain a photoreactive moiety and/or an alkyne group. In such instances, the sample is incubated with a probe and non-probe small molecule ligand for competitive protein profiling analysis.

In some cases, the sample is compared with a control. In some cases, a difference is observed between a set of probe protein interactions between the sample and the control. In some instances, the difference correlates to the interaction between the small molecule fragment and the proteins.

In some embodiments, one or more methods are utilized for labeling a sample (e.g. cells or a cell solution) for analysis of probe protein interactions. In some instances, a method comprises labeling the sample (e.g. cells or a cell solution) with an enriched media. In some cases, the sample (e.g. cells or a cell solution) is labeled with isotope-labeled amino acids, such as $^{13}C$ or $^{15}N$-labeled amino acids. In some cases, the labeled sample is further compared with a non-labeled sample to detect differences in probe protein interactions between the two samples. In some instances, this difference is a difference of a target protein and its interaction with a small molecule ligand in the labeled sample versus the non-labeled sample. In some instances, the difference is an increase, decrease or a lack of protein-probe interaction in the two samples. In some instances, the isotope-labeled method is termed SILAC, stable isotope labeling using amino acids in cell culture.

In some instances, the sample is divided into a first cell solution and a second cell solution. In some cases, the first cell solution is incubated with a first probe for an extended period of time to generate a first group of probe-protein complexes. In some instances, the extended period of time is about 5, 10, 15, 20, 30, 60, 90, 120 minutes or longer. In some instances, the second cell solution comprises a second probe to generate a second group of probe-protein complexes. In some instances, the first probe and the second probe are different. In some embodiments, cells from the second cell solution are treated with a buffer, such as a control buffer, in which the buffer does not contain a small molecule fragment probe. In some embodiments, the control buffer comprises dimethyl sulfoxide (DMSO).

In some embodiments, a method comprises incubating a sample (e.g. cells or a cell solution) or a processed sample (e.g., a cell lysate) with a labeling group (e.g., an isotopically labeled labeling group) to tag one or more proteins of interest for further analysis. In such cases, the labeling group comprises a biotin, a streptavidin, bead, resin, a solid support, or a combination thereof, and further comprises a linker that is optionally isotopically labeled. As described above, the linker can be about 5, 6, 7, 8, 9, 10, 11, 12, 13, 14, 15 or more residues in length and can further comprise a cleavage site, such as a protease cleavage site (e.g., TEV cleavage site). In some cases, the labeling group is a biotin-linker moiety, which is optionally isotopically labeled with $^{13}C$ and $^{15}N$ atoms at one or more amino acid residue positions within the linker. In some cases, the biotin-linker moiety is a isotopically-labeled TEV-tag as described in Weerapana, et al., "Quantitative reactivity profiling predicts functional cysteines in proteomes," Nature 468(7325): 790-795.

In some embodiments, an isotopic reductive dimethylation (ReDi) method is utilized for processing a sample. In some cases, the ReDi labeling method involves reacting peptides with formaldehyde to form a Schiff base, which is then reduced by cyanoborohydride. This reaction dimethylates free amino groups on N-termini and lysine side chains and monomethylates N-terminal prolines. In some cases, the ReDi labeling method comprises methylating peptides from a first processed sample with a "light" label using reagents with hydrogen atoms in their natural isotopic distribution and peptides from a second processed sample with a "heavy" label using deuterated formaldehyde and cyanoborohydride. Subsequent proteomic analysis (e.g., mass spectrometry analysis) based on a relative peptide abundance between the heavy and light peptide version can be used for analysis of probe-protein interactions.

In some embodiments, isobaric tags for relative and absolute quantitation (iTRAQ) method is utilized for processing a sample. In some cases, the iTRAQ method is based on the covalent labeling of the N-terminus and side chain amines of peptides from a processed sample. In some cases, reagent such as 4-plex or 8-plex is used for labeling the peptides.

In some embodiments, the probe-protein complex is further conjugated to a chromophore, such as a fluorophore. In some instances, the probe-protein complex is separated and visualized utilizing an electrophoresis system, such as through a gel electrophoresis, or a capillary electrophoresis. Exemplary gel electrophoresis includes agarose based gels, polyacrylamide based gels, or starch based gels. In some instances, the probe-protein is subjected to a native electrophoresis condition. In some instances, the probe-protein is subjected to a denaturing electrophoresis condition.

In some instances, the probe-protein after harvesting is further fragmentized to generate protein fragments. In some instances, fragmentation is generated through mechanical stress, pressure, or chemical means. In some instances, the protein from the probe-protein complexes is fragmented by a chemical means. In some embodiments, the chemical means is a protease. Exemplary proteases include, but are not limited to, serine proteases such as chymotrypsin A, penicillin G acylase precursor, dipeptidase E, DmpA aminopeptidase, subtilisin, prolyl oligopeptidase, D-Ala-D-Ala peptidase C, signal peptidase I, cytomegalovirus assemblin, Lon-A peptidase, peptidase Clp, *Escherichia coli* phage KlF endosialidase CIMCD self-cleaving protein, nucleoporin 145, lactoferrin, murein tetrapeptidase LD-carboxypeptidase, or rhomboid-1; threonine proteases such as ornithine acetyltransferase; cysteine proteases such as TEV protease, amidophosphoribosyltransferase precursor, gamma-glutamyl hydrolase (*Rattus norvegicus*), hedgehog protein, DmpA aminopeptidase, papain, bromelain, cathepsin K, calpain, caspase-1, separase, adenain, pyroglutamyl-peptidase I, sortase A, hepatitis C virus peptidase 2, sindbis virus-type nsP2 peptidase, dipeptidyl-peptidase VI, or DeSI-1 peptidase; aspartate proteases such as beta-secretase 1 (BACE1), beta-secretase 2 (BACE2), cathepsin D, cathepsin E, chymosin, napsin-A, nepenthesin, pepsin, plasmepsin, presenilin, or renin; glutamic acid proteases such as AfuGprA; and metalloproteases such as peptidase_M48.

In some instances, the fragmentation is a random fragmentation. In some instances, the fragmentation generates specific lengths of protein fragments, or the shearing occurs at particular sequence of amino acid regions.

In some instances, the protein fragments are further analyzed by a proteomic method such as by liquid chromatography (LC) (e.g. high performance liquid chromatography), liquid chromatography-mass spectrometry (LC-MS), matrix-assisted laser desorption/ionization (MALDI-TOF), gas chromatography-mass spectrometry (GC-MS), capillary electrophoresis-mass spectrometry (CE-MS), or nuclear magnetic resonance imaging (NMR).

In some embodiments, the LC method is any suitable LC methods well known in the art, for separation of a sample into its individual parts. This separation occurs based on the interaction of the sample with the mobile and stationary phases. Since there are many stationary/mobile phase combinations that are employed when separating a mixture, there are several different types of chromatography that are classified based on the physical states of those phases. In some embodiments, the LC is further classified as normal-phase chromatography, reverse-phase chromatography, size-exclusion chromatography, ion-exchange chromatography, affinity chromatography, displacement chromatography, partition chromatography, flash chromatography, chiral chromatography, and aqueous normal-phase chromatography.

In some embodiments, the LC method is a high performance liquid chromatography (HPLC) method. In some embodiments, the HPLC method is further categorized as normal-phase chromatography, reverse-phase chromatography, size-exclusion chromatography, ion-exchange chromatography, affinity chromatography, displacement chromatography, partition chromatography, chiral chromatography, and aqueous normal-phase chromatography.

In some embodiments, the HPLC method of the present disclosure is performed by any standard techniques well known in the art. Exemplary HPLC methods include hydrophilic interaction liquid chromatography (HILIC), electrostatic repulsion-hydrophilic interaction liquid chromatography (ERLIC) and reverse phase liquid chromatography (RPLC).

In some embodiments, the LC is coupled to a mass spectroscopy as a LC-MS method. In some embodiments, the LC-MS method includes ultra-performance liquid chromatography-electrospray ionization quadrupole time-of-flight mass spectrometry (UPLC-ESI-QTOF-MS), ultra-performance liquid chromatography-electrospray ionization tandem mass spectrometry (UPLC-ESI-MS/MS), reverse phase liquid chromatography-mass spectrometry (RPLC-MS), hydrophilic interaction liquid chromatography-mass spectrometry (HILIC-MS), hydrophilic interaction liquid chromatography-triple quadrupole tandem mass spectrometry (HILIC-QQQ), electrostatic repulsion-hydrophilic interaction liquid chromatography-mass spectrometry (ERLIC-MS), liquid chromatography time-of-flight mass spectrometry (LC-QTOF-MS), liquid chromatography-tandem mass spectrometry (LC-MS/MS), multidimensional liquid chromatography coupled with tandem mass spectrometry (LC/LC-MS/MS). In some instances, the LC-MS method is LC/LC-MS/MS. In some embodiments, the LC-MS methods of the present disclosure are performed by standard techniques well known in the art.

In some embodiments, the GC is coupled to a mass spectroscopy as a GC-MS method. In some embodiments, the GC-MS method includes two-dimensional gas chromatography time-of-flight mass spectrometry (GC*GC-TOFMS), gas chromatography time-of-flight mass spectrometry (GC-QTOF-MS) and gas chromatography-tandem mass spectrometry (GC-MS/MS).

In some embodiments, CE is coupled to a mass spectroscopy as a CE-MS method. In some embodiments, the CE-MS method includes capillary electrophoresis-negative electrospray ionization-mass spectrometry (CE-ESI-MS), capillary electrophoresis-negative electrospray ionization-quadrupole time of flight-mass spectrometry (CE-ESI-QTOF-MS) and capillary electrophoresis-quadrupole time of flight-mass spectrometry (CE-QTOF-MS).

In some embodiments, the nuclear magnetic resonance (NMR) method is any suitable method well known in the art for the detection of one or more cysteine binding proteins or protein fragments disclosed herein. In some embodiments, the NMR method includes one dimensional (1D) NMR methods, two dimensional (2D) NMR methods, solid state NMR methods and NMR chromatography. Exemplary 1D NMR methods include $^1$Hydrogen, $^{13}$Carbon, $^{15}$Nitrogen, $^{17}$Oxygen, $^{19}$Fluorine, $^{31}$Phosphorus, $^{39}$Potassium, $^2$Sodium, $^{33}$Sulfur, $^{87}$Strontium, $^{27}$Aluminium, $^{43}$Calcium, $^{35}$Chlorine, $^{37}$Chlorine, $^{63}$Copper, $^{65}$Copper, $^{57}$Iron, $^{25}$Magnesium, $^{199}$Mercury or $^{67}$Zinc NMR method, distortionless enhancement by polarization transfer (DEPT) method, attached proton test (APT) method and 1D-incredible natural abundance double quantum transition experiment (INADEQUATE) method. Exemplary 2D NMR methods include correlation spectroscopy (COSY), total correlation spectroscopy (TOCSY), 2D-INADEQUATE, 2D-adequate double quantum transfer experiment (ADEQUATE), nuclear overhauser effect spectroscopy (NOSEY), rotating-frame NOE spectroscopy (ROESY), heteronuclear multiple-quantum correlation spectroscopy (HMQC), heteronuclear single quantum coherence spectroscopy (HSQC), short range coupling and long range coupling methods. Exemplary solid state NMR method include solid state $^{13}$Carbon NMR, high resolution magic angle spinning (HR-MAS) and cross polarization magic angle spinning (CP-MAS) NMR methods. Exemplary NMR techniques include diffusion ordered spectroscopy (DOSY), DOSY-TOCSY and DOSY-HSQC.

In some embodiments, the protein fragments are analyzed by method as described in Weerapana et al., "Quantitative reactivity profiling predicts functional cysteines in proteomes," *Nature,* 468:790-795 (2010).

In some embodiments, the results from the mass spectroscopy method are analyzed by an algorithm for protein identification. In some embodiments, the algorithm combines the results from the mass spectroscopy method with a protein sequence database for protein identification. In some embodiments, the algorithm comprises ProLuCID algorithm, Probity, Scaffold, SEQUEST, or Mascot.

In some embodiments, a value is assigned to each of the protein from the probe-protein complex. In some embodiments, the value assigned to each of the protein from the probe-protein complex is obtained from the mass spectroscopy analysis. In some instances, the value is the area-under-the curve from a plot of signal intensity as a function of mass-to-charge ratio. In some embodiments, a first value is assigned to the protein obtained from the first cell solution and a second value is assigned to the same protein obtained from the second cell solution. In some instances, a ratio is calculated between the two values. In some instances, a ratio of greater than 2 indicates that the protein is a candidate for interacting with a drug. In some instances, the ratio is greater than 2.5, 3, 3.5, 4, 4.5, 5, 6, 7, 8, 9, 10, 11, 12, 13, 14, 15, 16, 17, 18, 19, or 20. In some cases, the ratio is at most 20.

In some instances, the ratio is calculated based on averaged values. In some instances, the averaged value is an average of at least two, three, or four values of the protein from each cell solution, or that the protein is observed at least two, three, or four times in each cell solution and a value is assigned to each observed time. In some instances, the ratio further has a standard deviation of less than 12, 10, or 8.

In some instances, a value is not an averaged value. In some instances, the ratio is calculated based on value of a protein observed only once in a cell population. In some instances, the ratio is assigned with a value of 20.

Kits/Article of Manufacture

Disclosed herein, in certain embodiments, are kits and articles of manufacture for use with one or more methods described herein. In some embodiments, described herein is a kit for generating a protein comprising a photoreactive ligand. In some embodiments, such kit includes photoreactive small molecule ligands described herein, small molecule fragments or libraries and/or controls, and reagents suitable for carrying out one or more of the methods described herein. In some instances, the kit further comprises samples, such as a cell sample, and suitable solutions such as buffers or media. In some embodiments, the kit further comprises recombinant proteins for use in one or more of the methods described herein. In some embodiments, additional components of the kit comprises a carrier, package, or container that is compartmentalized to receive one or more containers such as vials, tubes, and the like, each of the container(s) comprising one of the separate elements to be used in a method described herein. Suitable containers include, for example, bottles, vials, plates, syringes, and test tubes. In one embodiment, the containers are formed from a variety of materials such as glass or plastic.

The articles of manufacture provided herein contain packaging materials. Examples of pharmaceutical packaging materials include, but are not limited to, bottles, tubes, bags, containers, and any packaging material suitable for a selected formulation and intended mode of use.

For example, the container(s) include probes, test compounds, and one or more reagents for use in a method disclosed herein. Such kits optionally include an identifying description or label or instructions relating to its use in the methods described herein.

A kit typically includes labels listing contents and/or instructions for use, and package inserts with instructions for use. A set of instructions will also typically be included.

In one embodiment, a label is on or associated with the container. In one embodiment, a label is on a container when letters, numbers or other characters forming the label are attached, molded or etched into the container itself; a label is associated with a container when it is present within a receptacle or carrier that also holds the container, e.g., as a package insert. In one embodiment, a label is used to indicate that the contents are to be used for a specific therapeutic application. The label also indicates directions for use of the contents, such as in the methods described herein.

Certain Terminology

Unless defined otherwise, all technical and scientific terms used herein have the same meaning as is commonly understood by one of skill in the art to which the claimed subject matter belongs. It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

As used herein, ranges and amounts can be expressed as "about" a particular value or range. About also includes the exact amount. Hence "about 5 µL" means "about 5 µL" and also "5 µL." Generally, the term "about" includes an amount that would be expected to be within experimental error.

The section headings used herein are for organizational purposes only and are not to be construed as limiting the subject matter described.

The term "protein", as used herein, refers to any polymeric chain of amino acids. The term "protein" encompasses native or modified protein, protein fragments, or polypeptide analogs comprising non-native amino acid residues. In some instances, a protein is monomeric. In other instances, a protein is polymeric. In some instances, a protein described herein is also referred to as an "isolated polypeptide", or a polypeptide that by virtue of its origin or source of derivation is not associated with naturally associated components that accompany it in its native state; is substantially free of other proteins from the same species; is expressed by a cell from a different species; or does not occur in nature.

In some embodiments, the term "bind(s)" or "binding" encompass a covalent interaction between a small molecule ligand and a protein binding site described herein. In other embodiments, the term "bind(s)" or "binding" encompass a non-covalent interaction between a small molecule ligand and a protein binding site described herein. In additional embodiments, the term "bind(s)" or "binding" encompass an interaction between a small molecule ligand and a region of a protein of interest in which the region on the protein is about 1 Å, 2 Å, 3 Å, 4 Å, 5 Å, 6 Å, 7 Å, 8 Å, 9 Å or 10 Å away from a binding site on the protein of interest. In some cases, the binding site is a functional or active site on the protein. In some cases, the binding site on the protein is not a functional or active site. In additional cases, the binding site on the protein is distal from a functional or active site. In the context of a competition interaction with two or more different small molecule ligands, the term "bind(s)" or "binding" can encompass blocking or displacement of small molecule ligands from interacting with a region or binding site on a protein of interest.

As used herein, the term "functional site" or "active site" are used interchangeably and refer to a region of a protein that has a specific biological activity. For example, the functional site can be a site that binds a substrate or other binding partner and optionally contributes the amino acid residues that directly participate in the making and breaking of chemical bonds. In some instances, a functional site or active site encompass, e.g., catalytic sites of enzymes, ligand binding domains of receptors, binding domains of regulators, or receptor binding domains of secreted proteins. In some cases, the functional or active site also encompass transactivation, protein-protein interaction, or DNA binding domains of transcription factors and regulators.

EXAMPLES

These examples are provided for illustrative purposes only and not to limit the scope of the claims provided herein.

Example 1—Cell Lines

HEK293T cells were maintained in high-glucose DMEM (Gibco) supplemented with 10% (v/v) fetal bovine serum (FBS), penicillin (100 U/mL), streptomycin (100 µg/mL) and L-glutamine (2 mM). K562 and HSC-5 cells were maintained in high-glucose IMDM (Gibco) supplemented with 10% (v/v) fetal bovine serum (FBS), penicillin (100 U/mL) and streptomycin (100 µg/mL). All cell lines were grown at 37° C. in a humidified 5% CO2 atmosphere. For SILAC experiments, each cell line was passaged at least six times in either SILAC DMEM or SILAC IMDM, (Thermo), which lack L-lysine and L-arginine, and supplemented with 10% (v/v) dialyzed FBS (Gemini), PSQ (as above), and either [$^{13}C_6$, $^{15}N_2$]-L-lysine and [$^{13}C_6$, $^{15}N_4$]-L-arginine (100 µg/mL each) or L-lysine.HCl and L-arginine.HCl (100 µg/mL each). Heavy and light cells were maintained in parallel and cell aliquots were frozen after six passages in SILAC media and stored in liquid $N_2$ until needed. Whenever thawed, cells were passaged at least three times before being used in experiments.

3T3-L1 preadipocytes were maintained in DMEM supplemented with 10% bovine calf serum. 10T1/2 cells were maintained in DMEM with 10% fetal bovine serum (FBS). To induce differentiation, confluent cells were cultured in DMEM with 10% FBS and exposed to dexamethasone (1 µM), 3-isobutyl-1-methylxanthine (IBMX; 0.5 mM), and insulin (1 µg/ml) for 2 days, followed by culture with insulin alone (1 µg/ml).

Example 2—In Situ Labeling of Live Cells with "Fully Functionalized" Fragment (FFF) Probes For gel-based experiments, cells were grown in 6-well plates to ~90% confluence at the time of treatment. Cells were carefully washed with Dulbecco's phosphate buffered saline (DPBS) and replenished with fresh serum-free media containing indicated FFF probe, and, if applicable, competitors or DMSO vehicle (1 mL). Following incubation at 37° C. for 30 min, cells were directly exposed to 365 nm light for 10 min. For no UV experiments, cells were incubated at 4° C. for 10 min under ambient light. For MS-based experiments, cell labeling was performed in a similar manner as described above. Modifications to this protocol included using isotopically 'light' and 'heavy' SILAC cells that were grown to near complete confluence prior to treatment in 10 cm plates. In probe-versus-control probe and probe-versus-probe experiments, isotopically light cells were treated with indicated fragment probe, while the heavy cells were treated with control probe (1), or additional FFF probe to be compared, at indicated concentrations. In competition type experiments, heavy and light cells were co-treated with the indicated FFF probe and competitor or DMSO, respectively. Following treatments and photocrosslinking, cells were harvested in cold DPBS by scraping, centrifuged (1,400 g, 3 min, 4° C.), and pellets washed with cold DPBS (2×) and then aspirated. Pellets were either directly processed or kept frozen at −80° C. until use.

Example 3—Preparation of Probe-Labeled Proteome for Gel- and MS-Based Protein Analyses Cells pellets were lysed in cold DPBS (100-500 µL) using a Branson Sonifier probe sonicator (10 pulses, 30% duty cycle, output setting=4). For experiments requiring cell fractionation into membrane and soluble proteomes, cell lysates were then centrifuged (100,000×g, 45 min) to provide soluble (supernatant) and membrane (pellet) fractions. Membrane pellets were resuspended in cold DPBS after separation by sonication. Protein concentration was determined using the DC Protein Assay (Bio-Rad) and absorbance read using a Tecan, Infinite F500 plate reader following manufacturer's instructions. For SILAC experiments, isotopically heavy and light whole cell lysates were adjusted to 1.5 mg/mL, and were then mixed in equal proportions (500 µL each) in cold DPBS.

Example 4—Gel-Based Analysis of Crosslinked Proteins in Cells

Proteomes from treated cells were diluted to 1 mg/mL. To each sample (50 µL), 6 µL of a freshly prepared "click" reagent mixture containing 0.1 mM tris(benzyltriazolylmethyl)amine (TBTA) (3 µL/sample, 1.7 mM in 1:4 DMSO:t-ButOH), 1 mM $CuSO_4$ (1 µL/sample, 50 mM in $H_2O$), 25 µM tetramethylrhodamine (TAMRA) azide (1 µL/sample, 1.25 mM in DMSO), and freshly prepared 1 mM tris(2-carboxyethyl)phosphine HCl (TCEP) (1 µL/sample, 50 mM in PBS or $H_2O$) was added to conjugate the fluorophore to probe-labeled proteins. Upon addition of the click mixture, each reaction was immediately mixed by vortexing and then allowed to react at ambient temperature for 1 hr before quenching the reactions with SDS loading buffer (4× stock, 17 µL). Proteins (25 µg total protein loaded per gel lane) were resolved using SDS-PAGE (10% acrylamide) and visualized by in-gel fluorescence on a Hitachi FMBIO-II or a Bio-Rad ChemiDoc™ MP flatbed fluorescence scanner.

Example 5—Preparation of Labeled Proteome for MS-Based Analysis

Profiling experiments were adapted methods previously reported. To the combined mixture of heavy and light soluble proteomes (1.5 mg) in 1 mL DPBS, a mixture of TBTA (60 µL/sample, 1.7 mM in 1:4 DMSO:t-BuOH), $CuSO_4$ (20 µL/sample, 50 mM in $H_2O$), TCEP (20 µL/sample, 50 mM in DPBS) and Biotin-N3 (10 µL/sample, 10 mM in DMSO) was added and each sample was rotated at room temperature. After 1 hr, the mixture was transferred to a 15 mL falcon tube and a cold 4:1 mixture (2.5 mL) of methanol (MeOH)/chloroform ($CHCl_3$) was added followed by cold PBS (1 mL) on ice. The resulting cloudy mixture was centrifuged (5,000×g, 10 min, 4° C.) to fractionate the protein interphase from the organic and aqueous solvent layers. After washing the protein disc carefully with cold 1:1 MeOH:$CHCl_3$ (3×1 mL) followed by sonication in cold 4:1 MeOH:$CHCl_3$ (3 mL) to ensure click reagents were efficiently removed, the remaining precipitate was pelleted by centrifugation (5,000×g, 10 min, 4° C.). The pellet was aspirated and resuspended in a freshly-prepared solution of proteomics-grade urea (500 µL, 6 M in DPBS) containing 10 µL of 10% SDS and then dissolved by sonication. Disulfides were reduced by adding 50 µL of a 1:1 mixture containing TCEP (200 mM in DPBS) pre-neutralized with potassium carbonate (600 mM DPBS) for 30 min at 37° C. Reduced thiols were then alkylated by addition of iodoacetamide (70 µL of 400 mM in DPBS) for 30 min at ambient temperature protected from light. To each solution, 130 µL of 10% SDS (in DPBS) was added and then diluted to ~0.2% SDS with DPBS (5.5 mL) and incubated with pre-equilibrated streptavidin agarose resin (100 µL 1:1 slurry, Pierce) for 1.5 hr at ambient temperature on a rotator. The streptavidin beads were collected by centrifugation (1,400 g, 1-2 min) and sequentially washed with 0.2% SDS in DPBS (1×5 mL), detergent-free DPBS (2×5 mL), and $H_2O$ (2×5 mL) to remove unbound protein, excess detergent, and small molecules. The resin was transferred to a Protein LoBind tube (Eppendorf) and bound proteins were digested on-bead overnight at 37° C. in ~200 µL total volume containing sequencing grade porcine trypsin (2 µg, Promega) in the presence of urea (2 M in DPBS) and $CaCl_2$ (1 mM). The proteolyzed supernatant was transferred to a fresh Protein LoBind tube, acidified with formic acid (5% final) and stored at −20° C. until analyzed.

Example 6—Multidimensional Liquid Chromatography-Tandem Mass Spectrometry (LC/LC-MS/MS) Analysis of Tryptic Digests Peptides from tryptic digests were pressure loaded onto a 250 µm (inner diameter) fused silica capillary column packed with C18 resin (4 cm, Aqua 5 µm, Phenomenex). Samples were analyzed using an LTQ-Orbitrap Velos mass spectrometer (Thermo Scientific) coupled to an Agilent 1200 series quaternary pump. Peptides were eluted by two-dimensional separation on a column with a 5 µm tip [100 µm fused silica, packed with C18 (10 cm) and strong cation exchange (SCX) resin (4 cm, Phenomenex)] using a five-step 'MudPIT' protocol that involves 0%, 25%, 50%, 80% and 100% salt bumps of ammonium acetate ($NH_4OAc$; 500 mM) to elute peptides stepwise from the SCX to the C18 resin followed by an increasing gradient of acetonitrile in each step (5%-100% buffer B in buffer A; buffer A: 95% $H_2O$, 5% acetonitrile, 0.1% formic acid; buffer B: 5% $H_2O$, 95% acetonitrile, 0.1% formic acid). The flow rate through the column was 0.25 µl/min and the voltage applied to the nano-LC electrospray ionization source was 2.5 kV. Spectra were collected in a data-dependent acquisition mode such that each scan cycle involved a single high-resolution full MS spectrum of parent ions (MS1 scan from 400-1800 m/z) collected in the orbitrap coupled to 30 CID-induced fragmentation (MS2) scans in the ion trap of the 30 most abundant parent ions from the MS1 scan. Dynamic exclusion (repeat count of 1, exclusion duration of 20 s). Parent ions with unassigned or +1 charge states by the instrument were excluded for fragmentation. All other parameters were left at default values.

Example 7—Peptide and Protein Identification and Quantification

From each of the five .raw files (one for each salt 'bump') generated by the instrument (Xcalibur software), the MS2 spectra for all fragmented parent ions (.ms2 file) were extracted using RAW Xtract (version 1.9.9.2; 2004 release). Each .ms2 file was searched using the ProLuCID algorithm against a reverse-concatenated, nonredundant (gene-centric) database of the human proteome (Uniprot release—Nov. 5, 2012) or mouse proteome (Nov. 5, 2012) and filtered using DTASelect 2.0 within the Integrated Proteomics Pipeline (IP2) software. All cysteine residues were specified with a static modification for carbamidomethylation (+57.0215 Da) and one oxidized methionine residue per peptide (if found) was allowed as a variable oxidation (+15.9949 Da). In addition, peptides were required to have at least one tryptic terminus. Each dataset was simultaneously searched for both light and heavy isotopologues of the same peptide by specifying the mass shift of heavy residues as static modifications on lysine (+8.0142 Da) and arginine (+10.0082 Da) in a coupled 'heavy' search. The precursor ion mass tolerance for a minimum envelope of three isotopic peaks was set to 50 ppm, the minimum peptide length was six residues, the false-positive rate was set at 1% or lower and at least 2 peptides of a protein must be detected in order to be advanced to the next step of analysis.

Heavy and light parent ion chromatograms associated with successfully identified peptides were extracted and compared using in-house software (CIMAGE). Briefly, extracted MS1 ion chromatograms (+10 ppm error tolerance of predicted m/z) from both 'light' and 'heavy' target peptide masses (m/z) were generated using a retention time window (+10 min) centered on the time when the peptide ion was selected for MS/MS fragmentation (minimum 3 MS1's per peak), and subsequently identified. Next, the ratio of the peak areas under the light and heavy signals (signal-to-noise ratio>2.5) was calculated. Computational filters used to ensure that the correct peak-pair was used for quantification include a co-elution correlation score filter (R2≥0.8), removing target peptides with bad co-elution profile, and an 'envelope correlation score' filter (R2>0.8) that eliminates target peptides whose predicted pattern of the isotopic envelope distribution does not match the experimentally observed high-resolution MS1 spectrum. In addition, peptides detected as 'singletons,' where only the heavy ion of a peptide pair was identified, but that cleared all other filtering parameters, are given a default assigned ratio of '20,' which is defined as any measured ratio that is ≥20 and is the maximum ratio reported here.

Example 8—Proteomic Analysis of Probe-Labeled Proteins by Mass Spectrometry

Median SILAC ratios were filtered to ensure that each protein ratio was resultant from three or more unique and quantified peptides and that the combined peptide ratios possessed a standard deviation of less than 60% of the median; if greater, the combined ratio was assigned the lowest quantified peptide value. SILAC ratios meeting these criteria were then combined with replicate data sets from the same probe, cell line and experimental conditions. Identification of probe targets enriched in fragment probe versus control probe experiments in HEK293T cells represent averaged data from at least two biological replicate experiments and K562 data in single replicate experiments. Identification of probe targets from comparison of probe versus probe experiments and from fragment probe competition experiments represent averaged values of at least two biological replicate experiments.

In order to be classified as a probe target, proteins must (1) comply with the above criteria and (2) be enriched greater than 5-fold over control probe 1 (SILAC>5) in at least two different probe data sets (200 µM). If protein is enriched 5-fold or more by only one probe, then it had to be quantified in three or more independent experiments. In order to be included in probe-versus-probe comparisons, protein must abide by the above criteria and also be a target for at least one of the two probes, as designated above. For competition experiments, proteins (1) must be designated probe targets for the probe being used, as described above, (2) competed greater than 3-fold (competition SILAC ratio>3) unless otherwise noted, and (3) must have SILAC ratios derived from three or more quantified peptides.

Example 9—Fragment Probe Target Meta-Analysis

Custom python scripts were used to compile functional annotations of final probe targets available in the UniProtKB/Swiss-Prot Protein Knowledge database. Probe targets were queried against the DrugBank database (Version 4.2) and fractionated into DrugBank and non-DrugBank proteins. Functional keywords assigned at the protein level were collected from the Uniprot database and the two DrugBank and non-DrugBank categories were further classified into protein functional classes. Membrane proteins were defined as proteins possessing known or predicted transmembrane domains (UniProt analysis), and the remaining targets were considered soluble. Heatmaps were generated using RStudio software.

Example 10—Cell Treatments and Preparation for MS-Based Analyses of Probe-Modified Peptides Preparation and analysis was adapted from methods previously reported. In brief, for global mapping of fragment probe-modified peptides, separate 10 cm dishes of cells were treated with probes (200-250 µM) in 3.0 mL of DMEM (serum-free) and (if applicable) competitor ligands, proteomes harvested and subjected to click chemistry conditions with either light or heavy isotopically labeled biotin-TEV-azide (10 µL of 5 mM stocks in DMSO, final concentration=100 µM), TCEP, ligand and $CuSO_4$ as detailed above. The samples were allowed to react for 1 h at which point the samples were centrifuged (16,000 g, 5 min, 4° C.). The resulting pellets were sonicated in ice-cold methanol (500 µL) and the resuspended light- and heavy-labeled samples were then combined and centrifuged (16, 000 g, 5 min, 4° C.). The pellets were then solubilized in PBS containing 1.2% SDS (1 mL) with sonication and heating (5 min, 95° C.). Samples were transferred to falcon tubes containing DPBS (5 mL), to which a 100 µL of streptavidin-agarose beads slurry was added. After incubation, the beads (3 hr) were pelleted by centrifugation (1,400 g, 3 min) and were washed (2×10 mL PBS and 2×10 mL water). The beads were transferred to eppendorf tubes with 1 mL DPBS, centrifuged (1,400 g, 3 min), and resuspended in PBS containing 6 M urea. To this was added 10 mM DTT (25 µL of a 200 mM stock in water) and the beads were incubated at 65° C. for 15 mins. 20 mM iodoacetamide (25 µL of a 400 mM stock in water) was then added and allowed to react at 37° C. for 30 mins with shaking. The bead mixture was diluted with 900 µL PBS, pelleted by centrifugation (1,400 g, 3 min), and resuspended in 200 µL 2M urea (DPBS) containing trypsin and $CaCl_2$ as described above. The beads were separated from the digest by centrifugation (1,000 g, 1 min), washed (2×1 mL PBS and 2×1 mL water) and then transferred to fresh eppendorfs with 1 mL water. The washed beads were washed once further in 150 µL TEV buffer (50 mM Tris, pH 8, 0.5 mM EDTA, 1 mM DTT) by centrifugation (1,400 g, 3 min) and the resuspended in 150 µL TEV buffer. 5 µL TEV protease (80 µM) was added and the reactions were rotated overnight at 29° C. The TEV digest was separated from the beads by centrifugation (1,400 g, 3 min) and the beads were washed once with water (100 µL). The samples were then acidified to a final concentration of 5% (v/v) formic acid and stored at −80° C. prior to analysis.

The resulting probe-modified peptides were collected for MS analysis, which was performed as described above with differences in the salt bumps applied in the chromatographic gradients which in this case were 0%, 30%, 60%, 90% and 100% $NH_4OAc$ (500 µM). The protein identification searches of the MS data were performed with the following changes applied to identify the peptides modified with the corresponding fragment probe and the cleaved TEV tag. All amino acids were considered as possible residues for modification. To facilitate the computational searches, sets of up to 3 amino acids were searched using ProLuCID and filtered with DTASelect as described above. The mass of the modification used to search for probe-modified peptides was +665.4013 m/z for 8, +667.3264 m/z for 4, +665.3285 m/z for 3, +678.3602 m/z for 6, +680.4122 m/z for 9, +679.4179 m/z for 13, +755.3867 m/z for 2, +655.4170 m/z for 14, and +669.3598 m/z for 15, which are the masses for the corresponding probe plus the light TEV-tag and an additional +6.0138 m/z for the heavy counterpart. The isoTOP ratios for probe labeled peptides were quantified using the in-house software CIMAGE.

Example 11—Analysis of Probe Labeled Peptides

For protein mapping experiments, fragment probe-modified peptides were expected to show a ratio of heavy and light signals of ~1.0 (0.5<ratio<2.0) and were required to have been designated an enriched target by the corresponding probe in whole-protein capture experiments. For each protein in the site-of-labeling dataset, the UniProtKB accession number was used to map and collect relevant structures from the RCSB Protein Data Bank (PDB) fulfilling the following criteria: structures determined by X-ray crystallography, wild-type protein, Homo sapiens as the sole source organism. For proteins with multiple available structures, custom R scripts were used to further filter the PDB files, privileging higher sequence coverage for isoTOP peptides (see Tables 1-3 for selected PDB accessions). Fpocket 2.0 was used to detect potential binding pockets for the resultant structures with all parameters set at recommended default. Pockets with volume less than 500 Å$^3$ were removed from output prior to further analysis. Residues surrounding fpocket predicted binding pockets for each protein were collected to determine the number of residues overlapping with isoTOP peptides. For structures with multiple chains, the average number of overlapping residues for all chains possessing isoTOP peptide was used. Custom Python scripts were used to compile functional site annotations using the UniProtKB/Swiss-Prot Protein Knowledge database (release-2016_06). Relevant UniProt entries were searched for available functional residues, specifically for annotations regarding enzyme catalytic residues (active sites), substrate binding sites, and metal-binding sites. At the isoTOP peptide level, the distances between all possible atom pairs, consisting of one atom from isoTOP peptide and the other atom from a functional site, were calculated and the minimum distance was designated as the spatial distance between isoTOP peptide and functional sites. Annotated FFF-labeled peptides and corresponding analyses shown in Table 1-3.

Example 12—PPARγ Luciferase Reporter Assay

HEK293T cells were transiently co-transfected using Polyethylenimine (Sigma) with a UAS-Luciferase reporter and a vector expressing the heterologous GAL4 DNA binding domain (DBD) or a GAL4 DNA binding domain:: PPARγ ligand binding domain (LBD) chimeric protein, and full-length PTGR2. 24 hr after transfection, cells were treated either with vehicle (DMSO), 15k-PGE$_2$ (20 µM), or fragment compounds. Rosiglitazone (2 µM), a synthetic PPARγ ligand, was used as control. 16 hr after incubation, cells were lysed in Cell Culture Lysis Reagent (Promega) and luciferase activity measured using the Luciferase Assay System (Promega).

Example 13—Oxygen Consumption Rate Measurements

Palmitate-BSA oxidation measurements were performed using the Seahorse XFe96 Extracellular Flux Analyzer. Briefly, HSC5 cells were plated at 4.0×10$^4$ cells/well and incubated for 24 hr in a 37° C., 5% CO$_2$ incubator. One hour prior to the XF assay, media was changed to 1× Krebs-Henseleit buffer (111 mM NaCl, 4.7 mM KCl, 2 mM MgSO$_4$, 1.2 mM Na$_2$HPO$_4$, pH 7.4) with 2.5 mM glucose, 0.5 mM carnitine, and 5 mM HEPES. 20 min after media exchange, cells were treated with either vehicle (DMSO), 24 (100 µM) or 21 (100, 50, 20 and 5 µM respectively). After 40 min, cells were given palmitate:BSA (667 µM and 167 µM respectively) or BSA alone and the XF assay was started. Perturbation compounds (oligomycin 4 µM, FCCP 4 µM, RAA 2 µM) were prepared in 1× KH buffer and injected from the reagent ports automatically onto wells.

Example 14—Adipocyte Phenotypic Screen

3T3-L1 preadipocytes were induced to differentiate in the presence of 50 µM of each fragment probe. Rosiglitazone (2 µM) was used as a positive control. Media was replaced every two days and compounds refreshed. On day 8 of differentiation, cells were fixed with 4% PFA and stained with the fluorescent lipid stain Nile red (AdipoRed) and Hoechst for nuclei counterstain. Cells were imaged using a Celigo S Cell Imaging Cytometer (Nexcelom Bioscience) and compounds promoting increased lipid accumulation (i.e. fluorescence) identified. Hits were validated at two concentrations (10 µM and 50 µM) in 12-well plate format. To prepare primary brown preadipocytes, interscapular fat depots of neonatal mice were digested for 40 min at 37° C. with 1.5 mg/mL collagenase type I in 61.5 mM NaCl, 2.5 mM KCl, 0.65 mM CaCl$_2$, 2.5 mM glucose, 50 mM Hepes, 50 µg/mL penicillin-streptomycin and 2% (wt/vol) BSA. Cells were next filtered through a 100 µm cell strainer, plated in DMEM supplemented with 20 mM Hepes, 20% FBS, and penicillin/streptomycin, and grown to confluency. Cells were induced to differentiate in DMEM with 10% FBS, dexamethasone (1 µM), IBMX (0.5 mM), insulin (1 µg/ml), triiodothyronine (1 nM), and either DMSO (0.1%), 25 (10 µM), or rosiglitazone (2 µM). Two days later, media was switched and differentiating cells were maintained in DMEM, 10% FBS, insulin, triiodothyronine, and experimental compounds. Media was refreshed every 2 days. Human mesenchymal stem cells were maintained in DMEM supplemented with 10% FBS and grown to confluence. Two days after confluence, cells were induced to differentiate in media containing DMEM supplemented with 10% FBS, dexamethasone (1 µM), IBMX (0.5 mM), insulin (1 µg/ml), indomethacin (125 µM), and either DMSO (0.1%), 25 (10 µM), or rosiglitazone (2 µM) for 2 days. Media and compounds were refreshed every 2 days, alternating complete differentiation media with maintenance media (DMEM 10% FBS supplemented only with insulin) for 18 days.

Example 15—RNAseq Analysis

For RNA-seq, 0.6-1×10$^6$ cells were collected in Trizol (Invitrogen) and total RNA was extracted using Direct-Zol RNA extraction kit (Zymo Research). PolyA+ RNA was fragmented and prepared into strand-specific libraries using the Illumina True-seq stranded RNA kit (Illumina) and analyzed on an Illumina HiSeq 2500 sequencer. Libraries were sequenced using single-end 50 bp reads at a depth of 10-15 million reads per library. Single-end sequencing reads were mapped to the mouse reference genome (mm9, NCBI37) using STAR (version 2.3.0.c, default parameters). Only reads that aligned uniquely to a single genomic location were used for downstream analysis (MAPQ>10). Gene expression values were calculated for read counts on exons of annotated RefSeq genes using HOMER. Differentially expressed genes between GFP- and PGRMC2-overexpressing cells were calculated from three replicates per condition using EdgeR and a threshold of adjusted p-value<0.05 was used to call differentially expressed genes. Gene expression values are shown as read counts normalized to 107 mapped reads. Differentially expressed genes were used for pathway analysis. Gene ontology functional enrichment analysis was performed using Ingenuity Pathway Analysis (Qiagen). Heatmaps were generated using RStudio software (package 'gplots'). RNA-seq data have been deposited in the GEO repository under accession number GSE90731.

Example 16—Cell Viability Assay

Cells were seeded in white-opaque 96-well plates in full growth media at a density of 6,000 cells/well (100 µL) and were allowed to grow for 14 hrs at 37° C. in a humidified 5% $CO_2$ atmosphere. The cells were then treated with compounds or DMSO (1% DMSO final for all wells) in triplicate and incubated at 37° C. in a humidified 5% $CO_2$ atmosphere for 45 min. Note, all photoaffinity probe incubations for MS- and gel-based experiments were performed for 30 min. Cell viability was determined using the luciferase-based CellTiter-Glo Luminescent Cell Viability Assay (Promega).

Example 17—Cloning and Transient Overexpression of Proteins in HEK293T Cells

Full-length genes encoding proteins of interest were PCR amplified from a cDNA library derived from low-passage HEK293T cells. Gene products were cloned into the pRK5 vector with a C-terminal FLAG tag using SalI (N-terminal) and NotI (C-terminal) restriction sites. All clone sequences were verified. To recombinantly overexpress proteins used in in situ treatments, HEK293T cells were grown to 40-60% confluency under standard growth conditions in 6-well (for gel-based experiments) or 10 cm tissue culture plates (for MS-based experiments) and transiently transfected with 1-3 µg of desired construct (6-well plates) or 5 µg (10 cm plates) using polyethyleneimine 'MAX' (MW 40,000, PEI; Polysciences, Inc.). 'Mock' transfected cells were transfected with a vector containing METAP2 for 48 hr. Human SLC25A20 in a pCMV6-Entry vector with a C-terminal DDK tag was purchased from Origene. Empty pCMV-Entry vector was used as 'mock' control for experiments with SLC25A20. The pRK5 vector was a gift from David Sabatini (MIT).

Example 18—Lentiviral Infection

3T3-L1 preadipocytes were infected overnight at 70% confluency in 10 cm Petri dishes with lentiviruses expressing a non-targeting scramble shRNA or two different shRNAs against mouse PGRMC2. Two days after infection, cells were re-plated into 12-well plates and grown to confluence. Two days after confluence, cells were induced to differentiate in presence of dexamethasone (1 µM), IBMX (0.5 mM), insulin (1 µg/ml) and either DMSO (0.1%), test compound (10 µM), or Rosiglitazone (2 µM). Cells were stained at day 7 of differentiation with Nile Red and Hoechst, imaged and harvested for RNA and protein extraction. For rescue experiments, scramble and PGRMC2 knockdown cells were co-infected with lentiviruses overexpressing human V5-tagged PGRMC2. 3T3-L1 preadipocytes stably overexpressing GFP or hPGRMC2 were selected with blasticidin (20 µg/ml) for 10 days and maintained in culture in 10% BCS.

Example 19—Confocal Imaging of PGRMC2

For immunostaining, cells were grown on gelatin-coated cover glasses, fixed in 4% PFA, permeabilized in 0.5% Triton-PBS and blocked with 5% FBS-PBS solution. Rabbit anti-PGRMC2 (Bethyl Labs) and mouse KDEL monoclonal antibody (SEQ ID NO: 925) (clone 10C3, Enzo Life Sciences) were diluted at 0.4 µg/ml and 1 µg/ml using blocking buffer and samples were incubated overnight at 4° C. in a humidified chamber. Alexafluor-488 anti-rabbit and alexafluor-568 anti-mouse secondary antibodies were diluted to 1:500 dilution in blocking buffer and samples incubated for 1 hour at RT. Nuclei and actin filaments were stained by Hoechst and Acti-stain 670 phalloidin dyes, respectively. Cells were washed 3 times with PBS for 10 minutes after each incubation. Images were acquired with a Zeiss LSM 710 laser scanning confocal microscope and analyzed with IMARIS (Bitplane Inc.) and Adobe Photoshop CS3 (Adobe Systems Incorporated) software.

Example 20—Western Blot Analysis

After scanning for fluorescence, proteins were transferred to a nitrocellulose membrane in Towbin buffer, the membrane was blocked for ~1 hr at ambient temperature with 5% nonfat dry milk (w/v) or 5% BSA in Tris-buffered saline with Tween 20 (TBST) and incubated with primary antibodies in the same solution overnight at 4° C. The blots were washed (3×5 min, TBST), incubated with secondary antibodies (IRDye 800CW or HRP-conjugated anti-mouse and anti-rabbit) in milk or BSA for 1 hr at ambient temperature, washed (3×5 min, TBST), rinsed in water and visualized on a LICOR Odyssey Scanner or resolved by film exposure.

Example 21—Gene Expression Analysis

Total RNA was isolated from cells using Direct-zol™ RNA MiniPrep Plus (Zymo Research). Taqman-based quantitative real-time PCR was performed using the SuperScript III Platinum One-Step qRT-PCR reagent (Thermo Fisher Scientific). Samples were run in triplicate as multiplexed reactions and normalized to an internal control (36B4; acidic ribosomal phosphoprotein P0 mRNA).

Example 22—In Vitro LCMS-Based Activity Assay for PTGR2

Aliquots (1 µL) of test compounds dissolved in DMSO were transferred to 1.5 mL eppendorf tubes followed by addition of recombinant human PTGR2 (44 µL, 200 nM final concentration) in freshly prepared reaction buffer (Tris Buffer, 1 mM EDTA, 50 µM TCEP, 300 µM NADPH). The resulting mixture was vortexed and then incubated at 37° C. for 20 min. Next, a 5 µL solution of 15-keto-$PGE_2$ substrate (20 µM final concentration) in reaction buffer was added and the reaction was allowed to proceed for 30 min at 37° C. Reactions were quenched by the addition of 0.5% AcOH in ethyl acetate (800 µL), water (300 µL) and 100 µL of internal standard $PGE_2$-$d_4$ (30 pmol/sample) dissolved in 1:1 methanol/water. Phases were separated by centrifugation and the organic layer was collected and dried under a stream of $N_2$, then stored at −80° C. until analysis. Directly prior to analysis, samples were reconstituted in 100 µL of MeCN:

$H_2O$ (1:1, v/v) and analyzed by LC/MS/MS. All conditions were performed in triplicate and repeated at least three independent times.

| LCMS Conditions for prostaglandin measurements | |
|---|---|
| Instrument | Agilent 6460 Triple Quadrupole LC/MS system |
| Column | Kinetex 5 μm C18 100 A, 50 × 4.6 mm column |
| Injection | 15 μL |
| Gas temperature | 350° C. |
| Gas flow | 9 L/min |
| nebulizer | 35 psi |
| capillary | 4000 V positive/4000 V negative |
| MRM scan type | 300 delta EMV (+) |
| Mobile Phase A | 70:30:0.1 $H_2O$/Acetonitrile/Formic acid |
| Mobile Phase B | 50:50:0.1 Isopropyl Alcohol/Acetonitrile/Formic Acid |

The following MS parameters were used to measure the indicated metabolites by MRM (precursor ion, product ion, collision energy, polarity): $PGE_2$-$d_4$ (355, 275, 18), 13,14-dihydro-15-keto-$PGE_2$ (351, 333, 18) and 15-keto-$PGE_2$ (349, 161, 20). 15-keto-$PGE_2$ and 13,14-dihydro-15-keto-$PGE_2$ levels were quantified by determining peak areas in relation to internal standard $PGE_2$-$d_4$. Non-deuterated 15-keto-$PGE_2$ and 13,14-dihydro-15-keto-$PGE_2$ standards were used to confirm retention time and fragmentation.

Chromatography Method

| Time (min) | B (%) | Flow rate (mL/min) |
|---|---|---|
| 0.0 | 0 | 0.6 |
| 1.0 | 0 | 0.6 |
| 2.0 | 20 | 0.6 |
| 4.0 | 20 | 0.6 |
| 7.0 | 75 | 0.6 |
| 7.2 | 100 | 0.6 |
| 11.0 | 100 | 0.6 |
| 11.1 | 0 | 0.6 |
| 13.0 | 0 | 0.6 |

To minimize carryover, LC solvents were cycled between 100% Mobile Phase A and 100% Mobile Phase B over 5 min after each run.

Example 23—LCMS Analysis of Acylcarnitines in HSC-5 Cells

HSC-5 cells were seeded in 10 cm plates and grown to ~90% confluency. Media was aspirated, cells were washed carefully with DPBS (3 mL) and resuspended in freshly-prepared serum-free IMDM media containing test compound(s) or vehicle. After incubation at 37° C. for 3 hr, the media was removed and cells were washed with cold DPBS (2×3 mL). Cells were scraped in 4 mL cold DPBS, transferred to a falcon tube and centrifuged at 2000 rpm for 8 min, and resuspended in 1 mL cold DPBS. Cells were lysed using a probe sonicator, and 1 mL of lysates normalized to 1.5 mg/mL were transferred to 2-dram glass vials. MeCN (3 mL) containing acyl carnitine internal standard mix (Cambridge Isotope Laboratories) was added to lysates and vigorously vortexed. Internal standards include $^2H_9$-carnitine (2.28 nmol); $^2H_3$-acetyl carnitine (C2, 570 pmol); $^2H_3$ propionyl carnitine (C3, 120 pmol); $^2H_3$ butyryl carnitine (C4, 120 pmol); $^2H_9$ isovaleryl carnitine (C5, 120 pmol); $^2H_3$ octanoyl carnitine (C8, 120 pmol); $^2H_9$ myristoyl carnitine (C14, 120 pmol); $^2H_3$ palmitoyl carnitine (C16, 240 pmol). Samples were centrifuged at 1000 rpm for 5 min to pellet insoluble precipitate, and the remaining eluent carefully transferred to fresh 2-dram vials to avoid disturbing the precipitate. The eluent was concentrated under a stream of $N_2$, and samples were stored at −80° C. until analysis. Directly prior to analysis, samples were reconstituted in 500 uL of $MeCN$:$H_2O$ (1:1, v/v) and analyzed by LC/MS/MS. The indicated acyl carnitines were quantified by measuring the area under the peak relative to an internal standard ($2H_3$ palmitoyl carnitine for C16, C18 and C18:1; $^2H_9$ myristoyl carnitine for C12 and C14; $^2H_3$ octanoyl carnitine for C5DC/C10-OH and C4DC; $^2H_9$ isovaleryl carnitine for C5 and C7).

| LCMS Conditions for acyl carnitine measurements | |
|---|---|
| Instrument | Agilent 6460 Triple Quadrupole LC/MS system |
| Column | Kinetex 5 μm C18 100 A, 50 × 4.6 mm column |
| Injection | 15 μL |
| Gas temperature | 350° C. |
| Gas flow | 9 L/min |
| nebulizer | 35 psi |
| capillary | 4000 V positive/4000 V negative |
| MRM scan type | 300 delta EMV (+) |
| Mobile Phase A | 95:5:0.1 $H_2O$/Methanol/Formic Acid |
| Mobile Phase B | 60:35:5:0.1 Isopropyl Alcohol/Methanol/$H_2O$/Formic Acid |

Chromatography Method:

| Time (min) | % B | Flow (mL/min) |
|---|---|---|
| 0 | 0 | 0.1 |
| 5 | 0 | 0.1 |
| 5.01 | 0 | 0.4 |
| 7 | 0 | 0.4 |
| 30 | 100 | 0.4 |
| 30.01 | 100 | 0.5 |
| 38 | 100 | 0.5 |
| 38.01 | 0 | 0.5 |
| 42 | 0 | 0.5 |
| 46 | 100 | 0.5 |
| 50 | 100 | 0.5 |
| 54 | 0 | 0.5 |
| 57 | 0 | 0.5 |
| 57.01 | 0 | 0.4 |
| 59 | 0 | 0.1 |

To minimize carryover, LC solvents were cycled between 100% Mobile Phase A and 100% Mobile Phase B over 5 min after each run.

Transition Table:

| Acyl Carnitine | Precursor → product ion |
|---|---|
| C12 | 344.2 → 85.1 |
| C14 | 372.3 → 85.1 |
| C16 | 400.3 → 85.1 |
| C18:1 | 426.3 → 85.1 |
| C18 | 428.3 → 85.1 |
| C4DC | 318.2 → 85.1 |
| C5 | 246.1 → 85.1 |
| C10-OH | 332.2 → 85.1 |
| C7 | 274.1 → 85.1 |
| D3 acetyl | 207.1 → 85.1 |
| D3 butyryl | 235.1 → 85.1 |
| D3 octanoyl | 291.2 → 85.1 |
| D3 palmitoyl | 403.3 → 85.1 |
| D3 propionyl | 221.1 → 85.1 |
| D9 isovaleryl | 255.1 → 85.1 |
| D9 myristoyl | 381.3 → 85.1 |

Example 24—Quantification and Statistical Analysis

All data fitting and statistical analysis performed using GraphPad Prism version 6.00 for Windows, GraphPad Software, La Jolla Calif. USA, www.graphpad.com. Statistical values including the exact n and statistical significance are also reported. Probe binding blockade and PTGR2 inhibition curves are plotted as mean±SD (n=3 or 4 per group) for a representative biological replicate using a variable slope (four parameter) non-linear fit. Gene expression data are presented as mean±SD (n=3 per group). HSC5 metabolite data are shown as mean±SD (n=3 per group). Statistical significance was defined as P<0.05 and determined by 2-tailed Student t tests, or two-way ANOVA with Bonferroni's post-tests.

Example 25—Data and Software Availability

Data Resources: The RNA-seq data reported has been deposited in the NCBI under the ID code GEO: GSE90731.
Software: All custom scripts used have been deposited to GitHub (https://github.com/Chymichead/FBDDinCell).

Figure 1C:
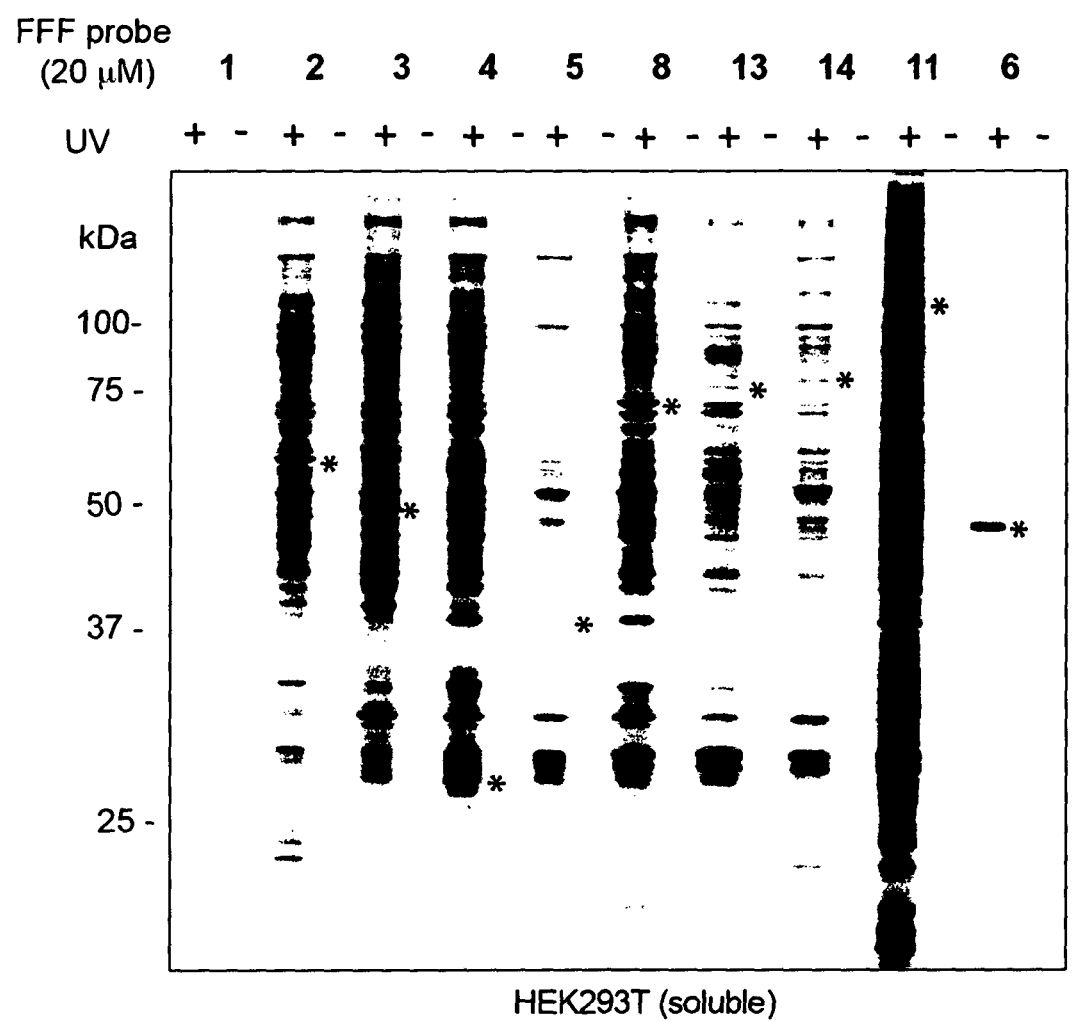
Figure 1D:
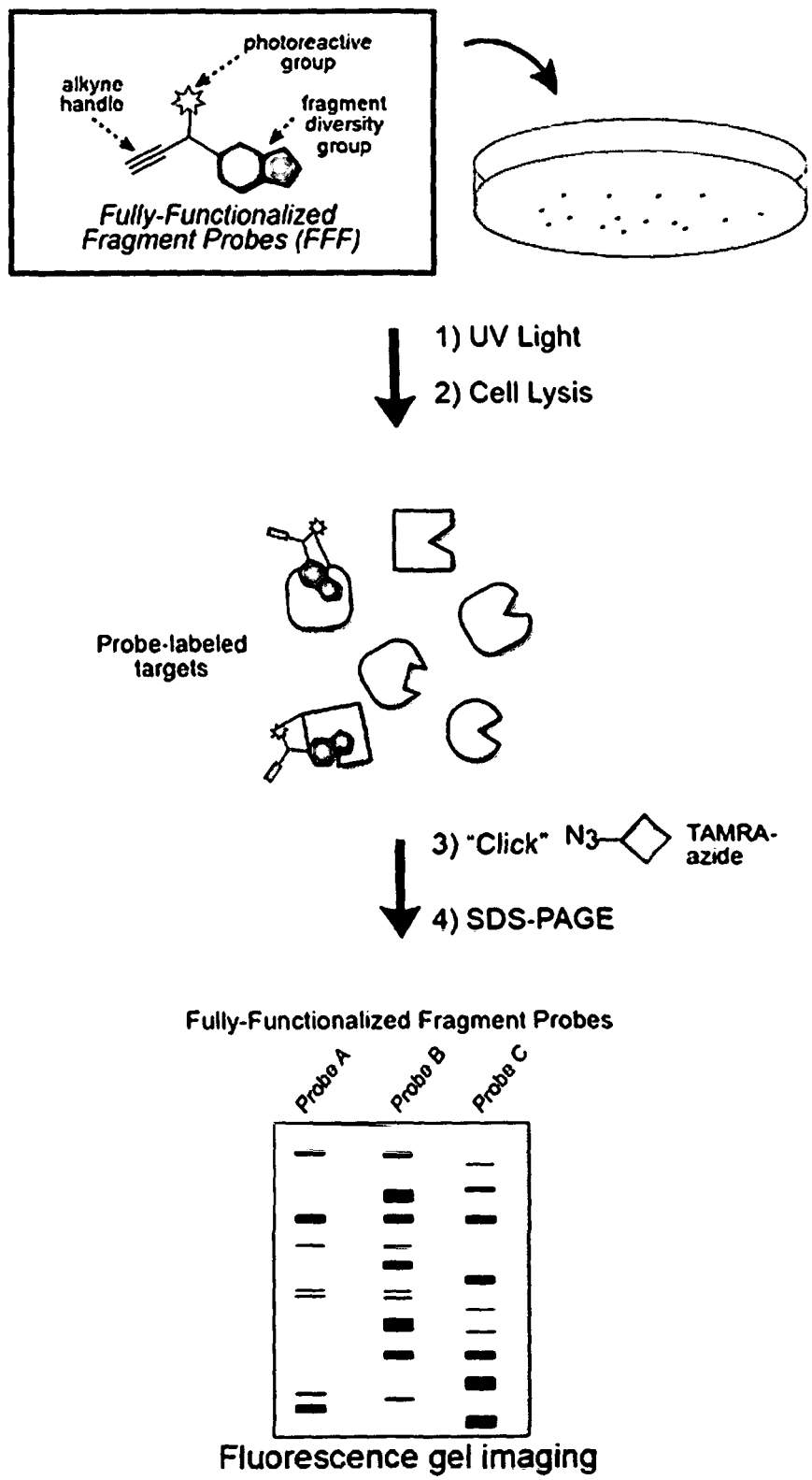
Figure 1E:
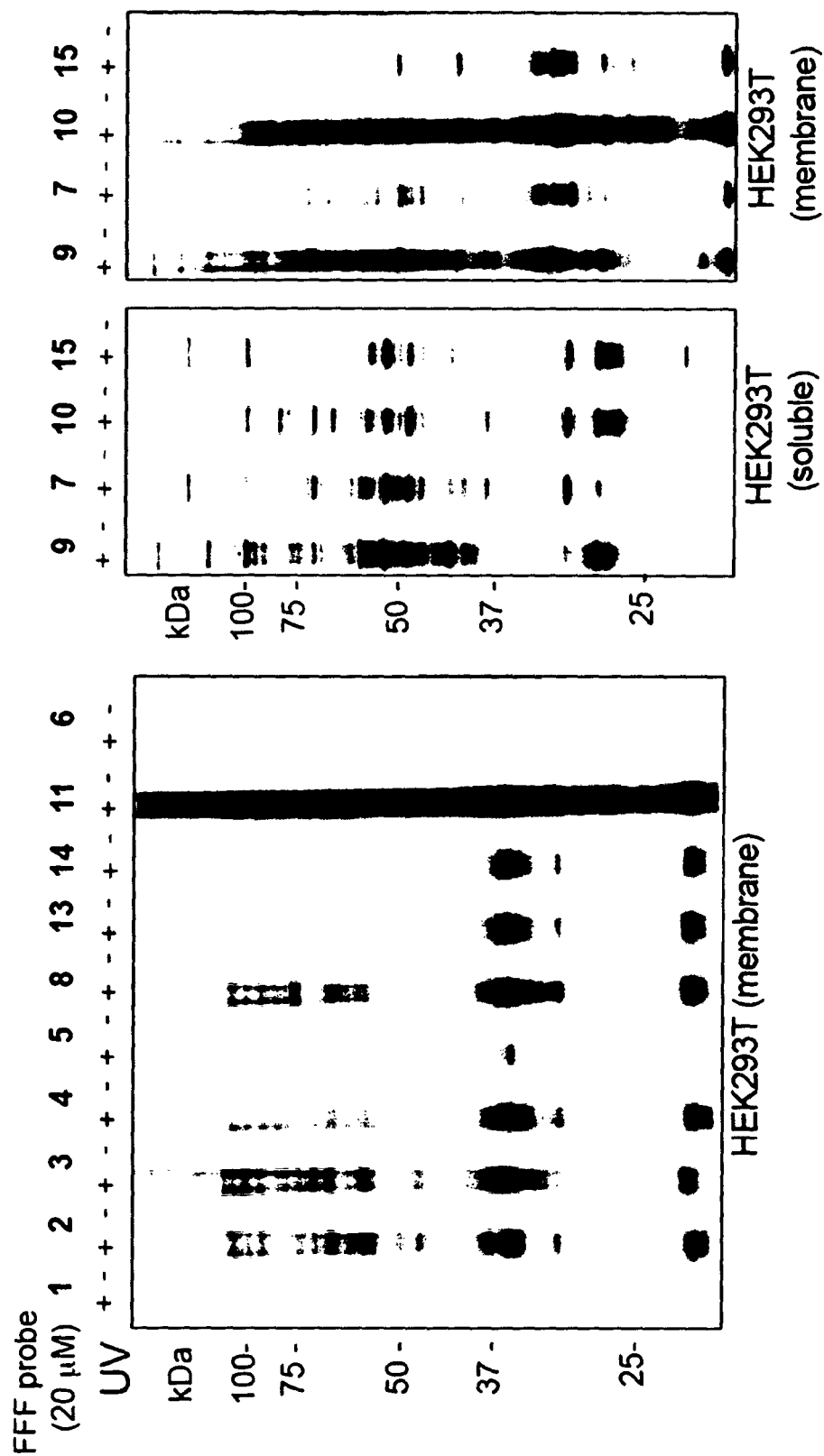
Figure 1F:
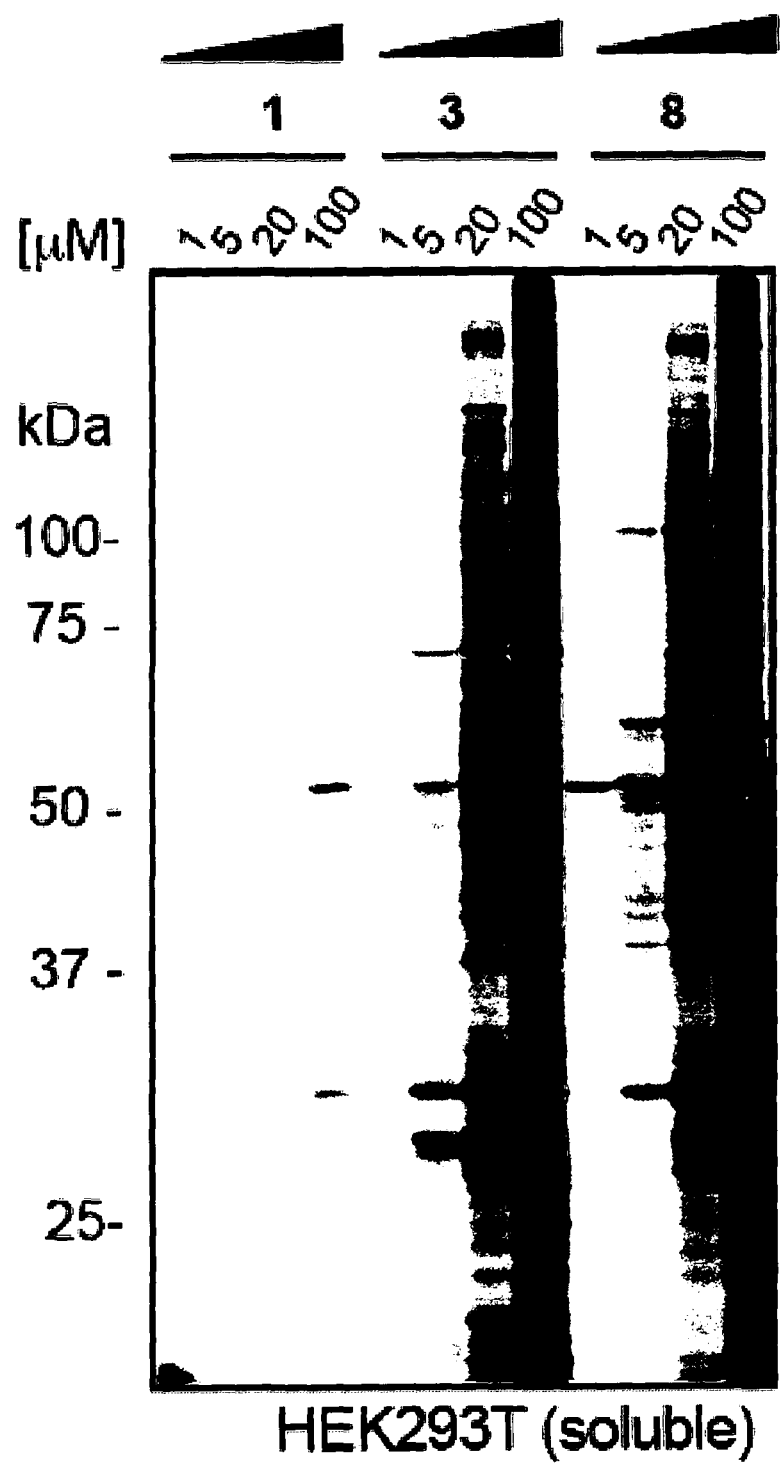
Figure 1G:
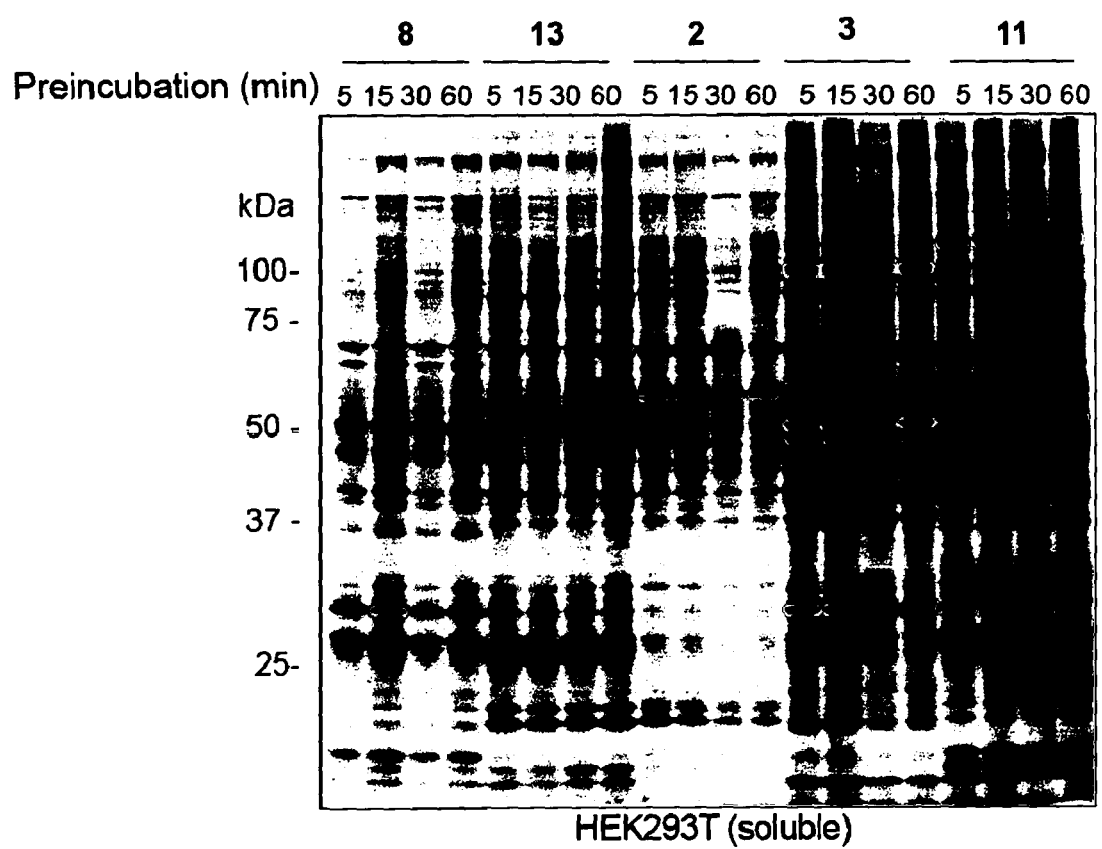
Figure 1H:
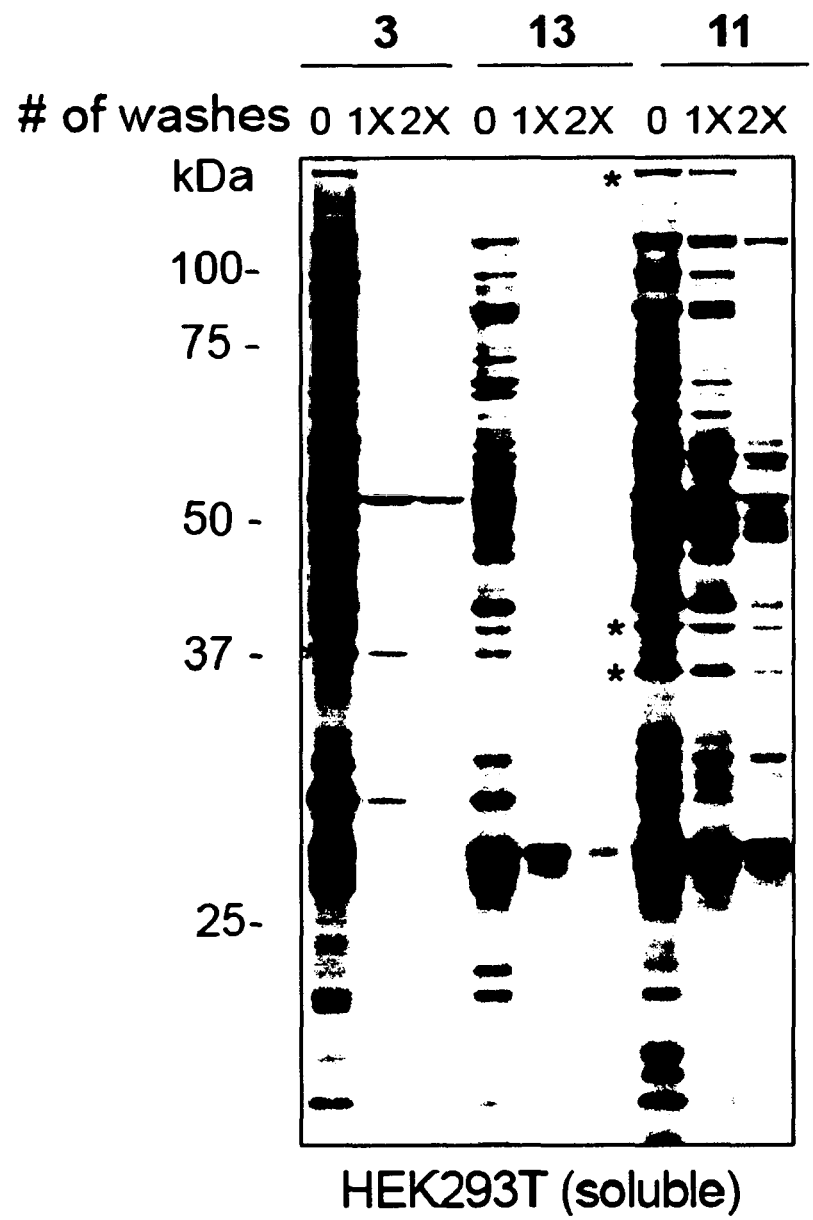

Example 26—Profiling Small-Molecule Fragment-Protein Interactions in Human Cells A small library of 14 "fully functionalized" fragment (FFF) probes were synthesized as described in Example 30 with each member possessing a variable small-molecule fragment conjugated to a constant tag bearing an alkyne and photoactivatable diazirine group (FIG. 1A). The variable fragment groups had an average molecular weight of 176 Da and were selected because they represent structural motifs found in many biologically active natural products and clinically approved drugs (FIG. 1B). The FFF probes were initially assessed using gel-based profiling (FIG. 1D) by treating HEK293T cells with each fragment probe (20 μM, 30 min), followed by exposure to UV light (10 min, 4° C.), cell lysis, coupling to a rhodamine (Rh)-azide tag using copper-catalyzed azide alkyne cycloaddition (CuAAC) chemistry, and separation and visualization of fragment-modified proteins by SDS-PAGE coupled with in-gel fluorescence scanning. Despite the structural simplicity and small size of the variable fragment groups, each probe produced marked and differential concentration-dependent protein labeling in HEK293T cells (FIG. 1C, FIG. 1E, and FIG. 1F). Negligible protein labeling was observed in the absence of UV light (FIG. 1C and FIG. 1E), exemplifying that the fragment-protein interactions correspond to reversible binding events that were converted to covalent adducts by photoreactivity. Exposure of cells to UV light from 5-60 min produced equivalent protein labeling (FIG. 1G), while washing cells prior to UV exposure substantially decrease FFF probe labeling for most, but not all proteins (FIG. 1H). Finally, a "fragment-less" probe bearing a methyl group (1) produced much less protein labeling, exemplifying that the variable group of FFF probes is critical for protein binding and further that 1 serves as a useful control probe for the chemical proteomic mapping of fragment-protein interactions in cells.

Example 27—a Global Analysis of Fragment-Protein Interactions in Cells

Fragment-binding proteins in human cells were globally mapped by quantitative chemical proteomics following the general protocol shown in FIG. 1A. Each FFF probe was initially compared to control probe 1 in pairwise experiments using isotopically light and heavy amino acid-labeled HEK293T cells, where proteins strongly enriched by the test FFF probe over 1 (light:heavy ratios>5) were designated as test probe targets. Adhering to the general principles of FBLD, where a relatively small number of fragments are screened at high concentrations against proteins, 11 FFF probes (2-4, 6, 8-9, 11-15) were analyzed at 200 μM each (30 min incubation; n=2-3 per probe) in HEK293T cells, with a subset of probes also being evaluated in K562 cells. Under these conditions, FFF probes displayed little to no cytotoxicity (FIG. 2K) and interacted with an extensive array of proteins. To minimize false-positives, proteins were only designated as fragment targets if they were detected with at least three unique, quantifiable peptides and enriched (>five-fold over 1, FIG. 2L) by more than one FFF probe, or, if enriched by only one probe, then required to be quantified in at least three independent experiments. Control experiments were also conducted with representative probes to confirm that targets were enriched in a UV-dependent manner and showed SILAC ratios of ~1.0 in experiments where heavy and light cells were treated with equal concentrations of the same FFF probe (FIG. 2M, FIG. 2N).

Figure 2A:
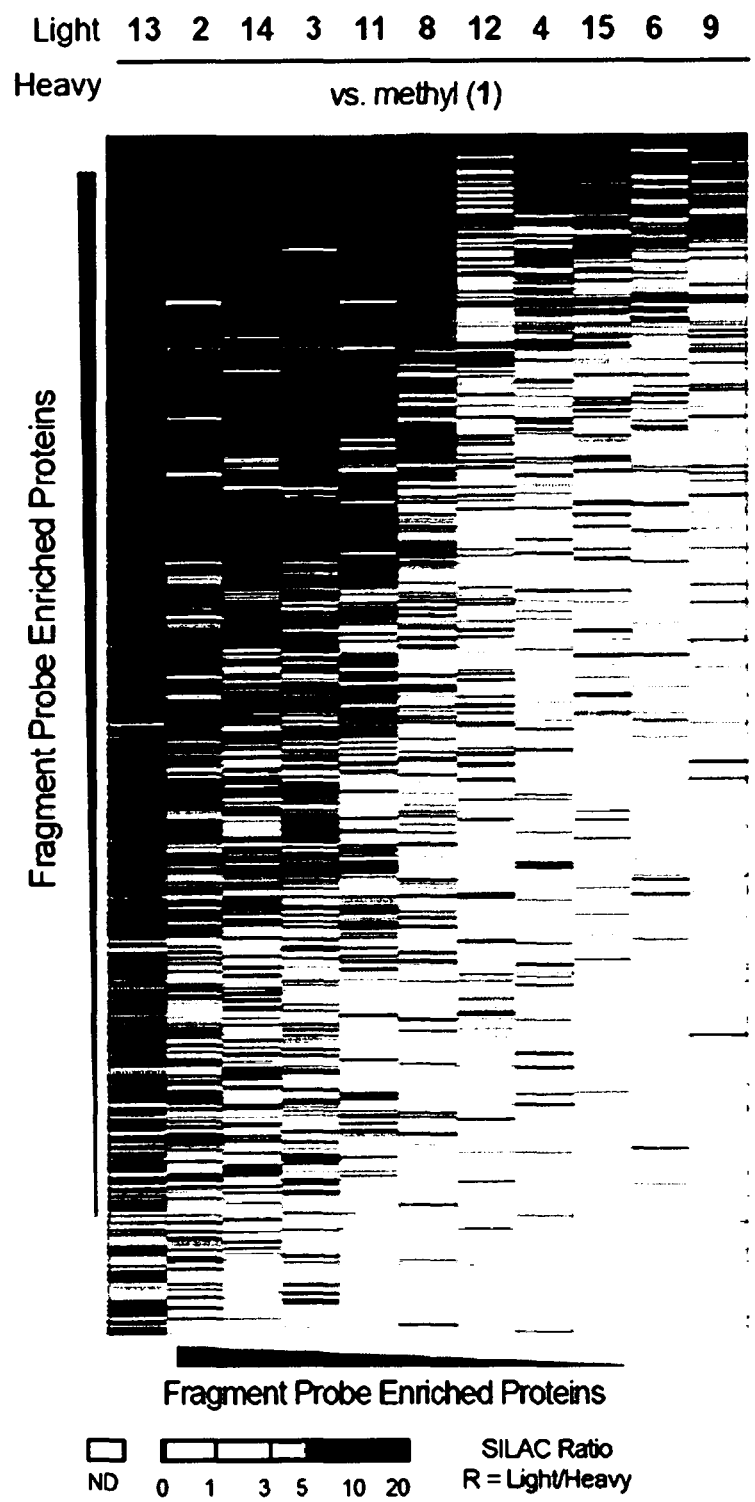
FIG. 2A-FIG. 2T exemplify quantitative MS-based proteomic analysis of fragment-protein interactions in cells.
Figure 2B:
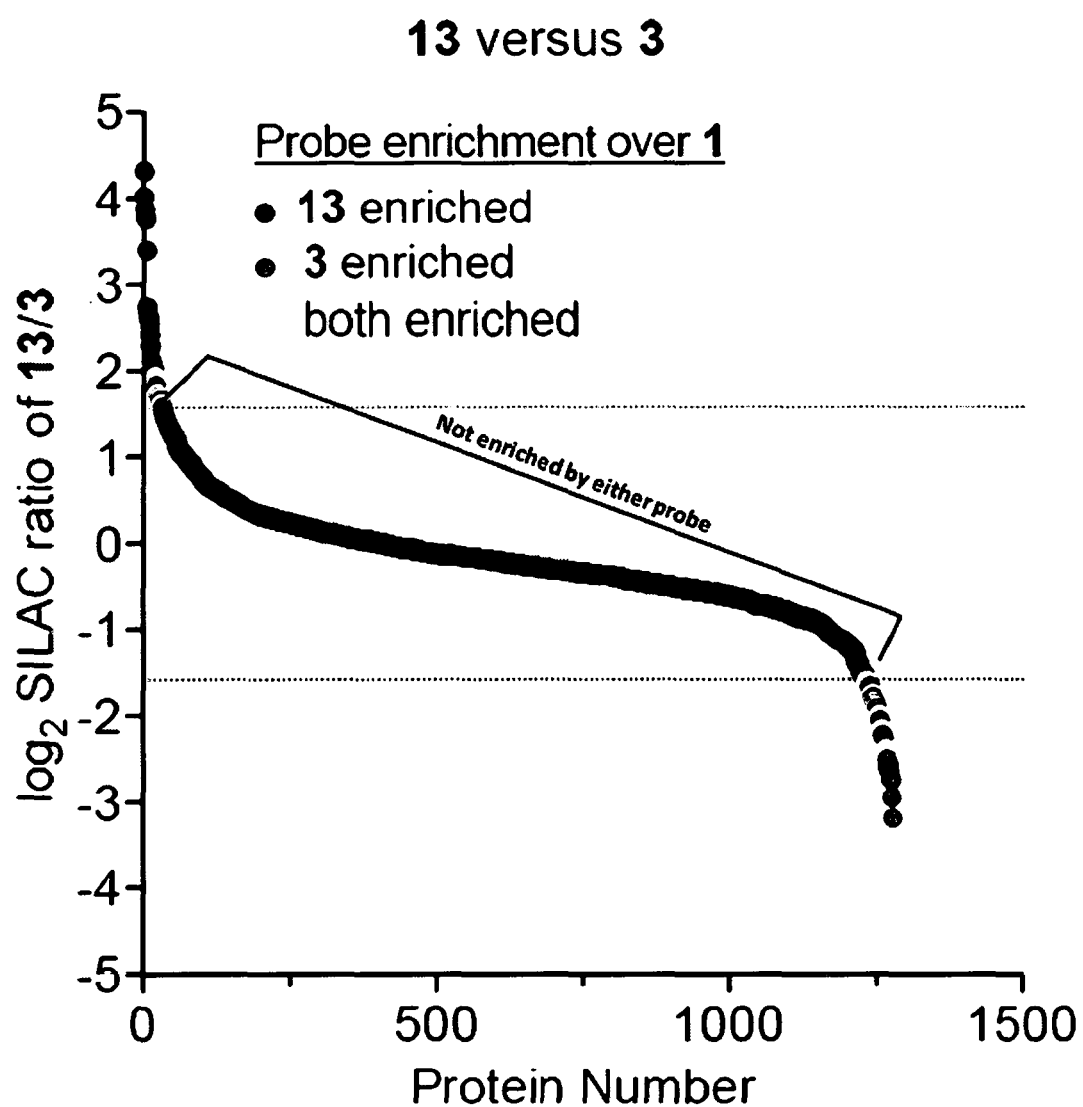
FIG. 2B is a representative SILAC ratio plot of proteins differentially enriched in probe-vs-probe (13 versus 3) experiments in HEK293T cells. Proteins preferentially enriched (>3-fold by either probe, depicted with dashed lines) in 13-vs-3 experiments that were also preferentially enriched (>2-fold) by 13 or 3 in probe-vs-control 1 experiments are depicted.
Figure 2E:
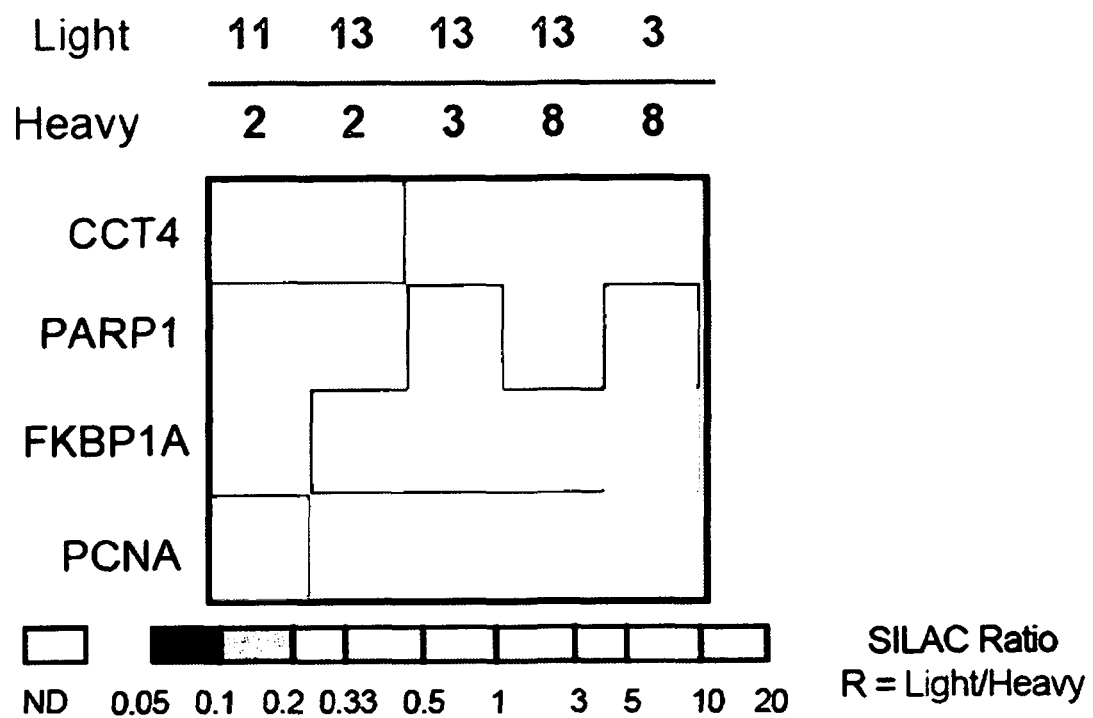
Figure 2F:
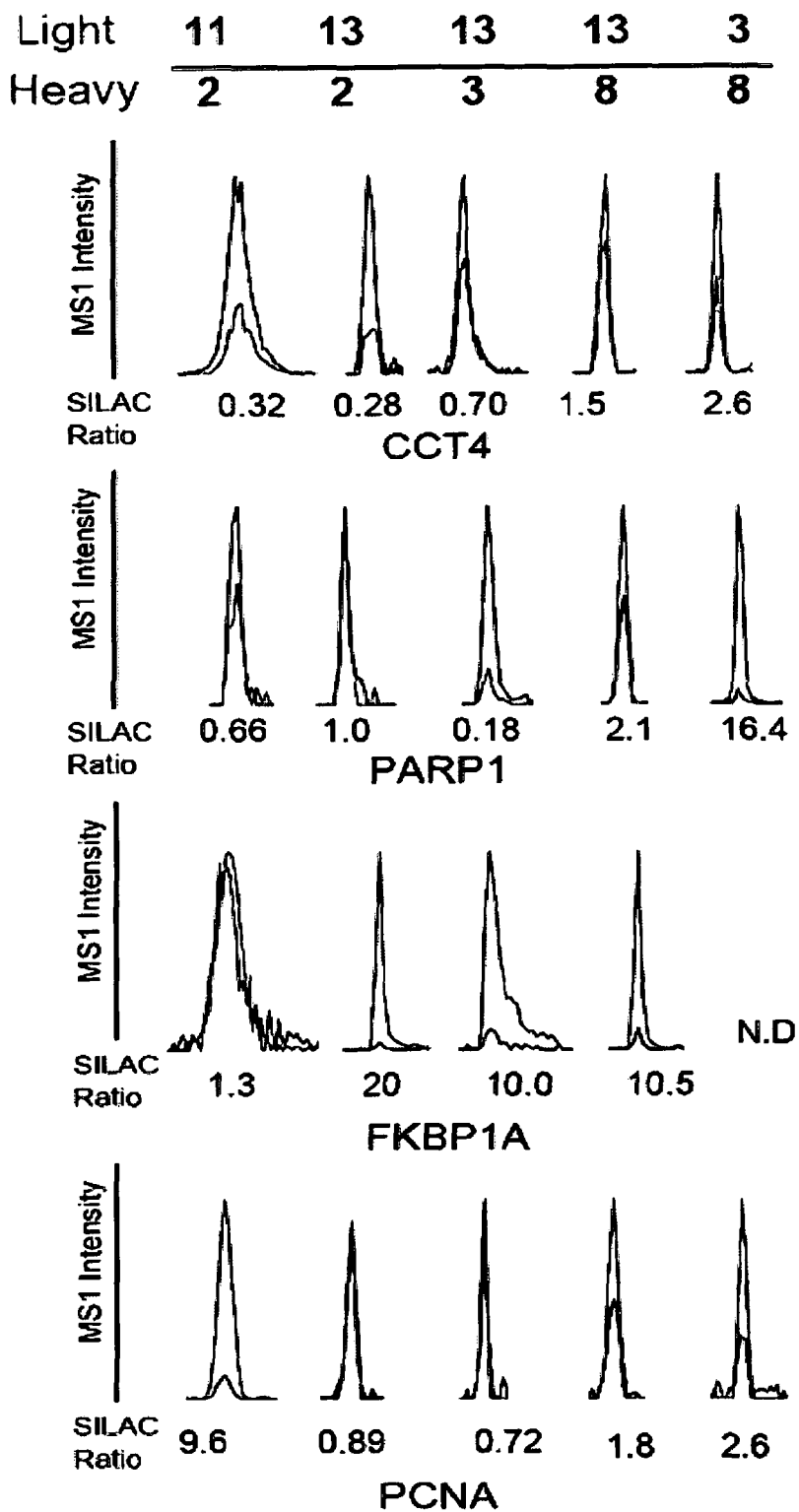
Figure 2G:
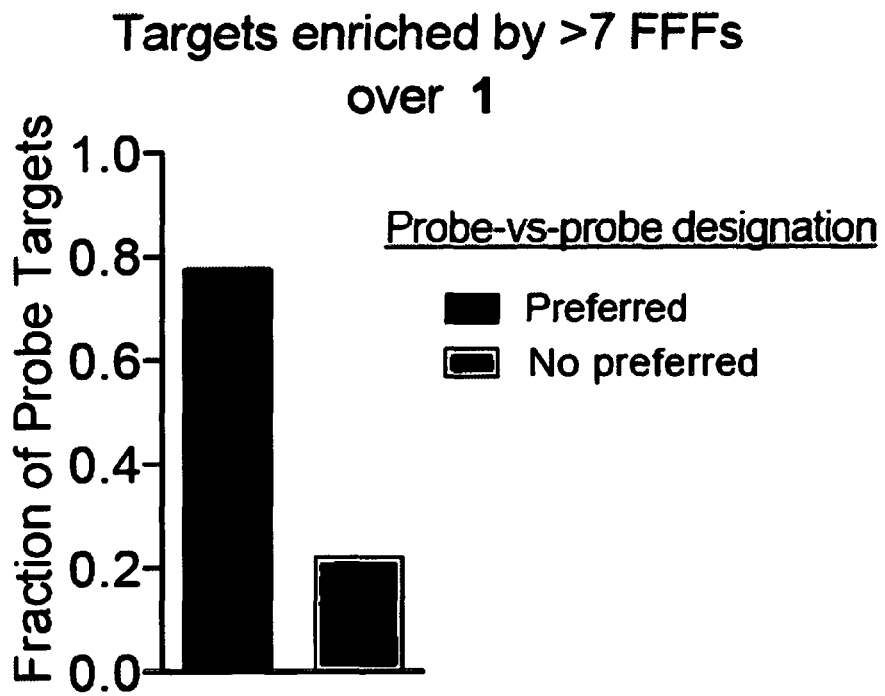
FIG. 2G exemplifies that the majority of proteins that are strongly enriched (SILAC ratio>10) by most FFF probes (≥8 of 11) in probe-vs-control 1 experiments show preferential enrichment by one FFF probe in probe-vs-probe experiments.
Figure 2H:
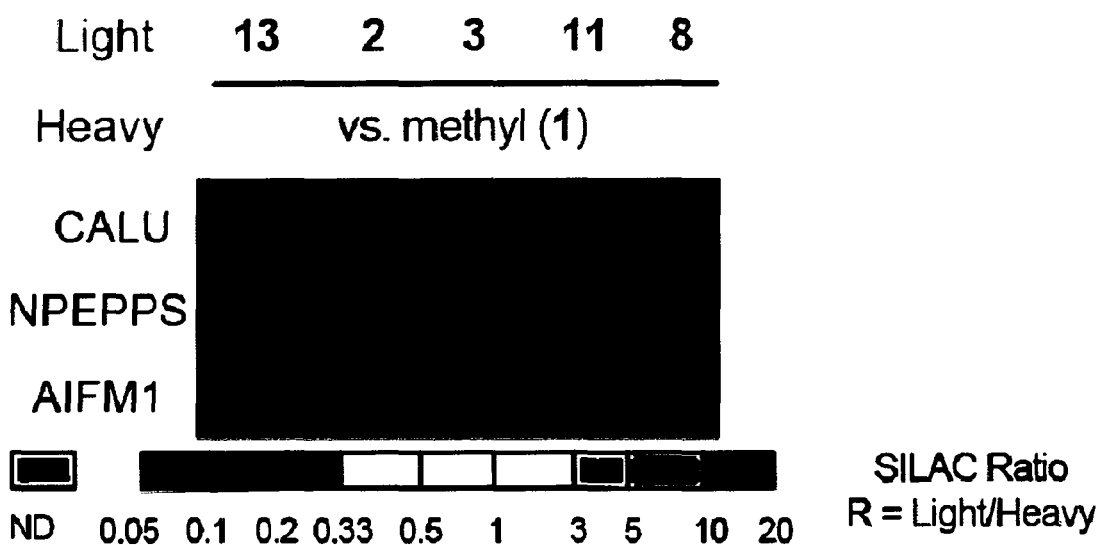
(FIG. 2H-FIG. 2J) Heatmaps (FIG. 2H, FIG. 2I) and extracted MS1 chromatograms of representative tryptic peptides (FIG. 2J) for three example proteins showing enrichment by the majority of FFF probes over control 1 (FIG. 2H) and preferential enrichment by FFF probe 3 in probe-vs-probe experiments (FIG. 2I).
Figure 2I:
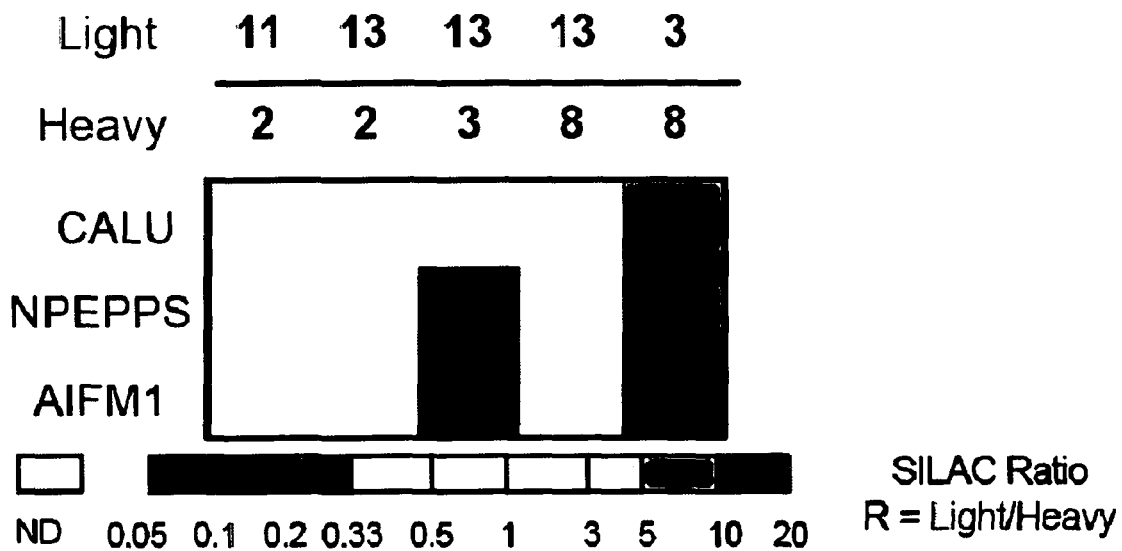
Figure 2J:
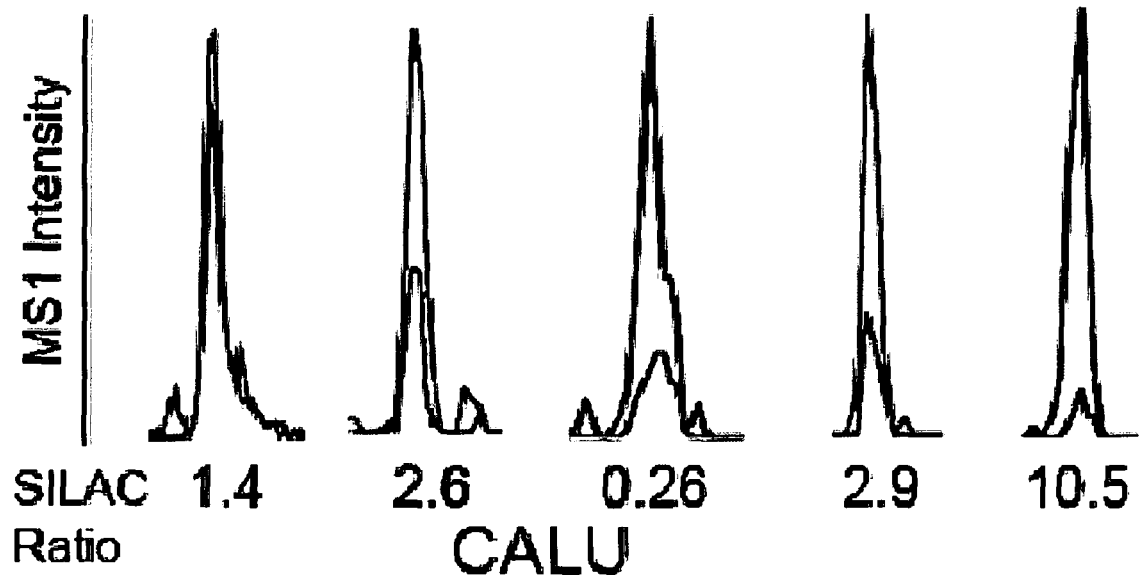
Figure 2L:
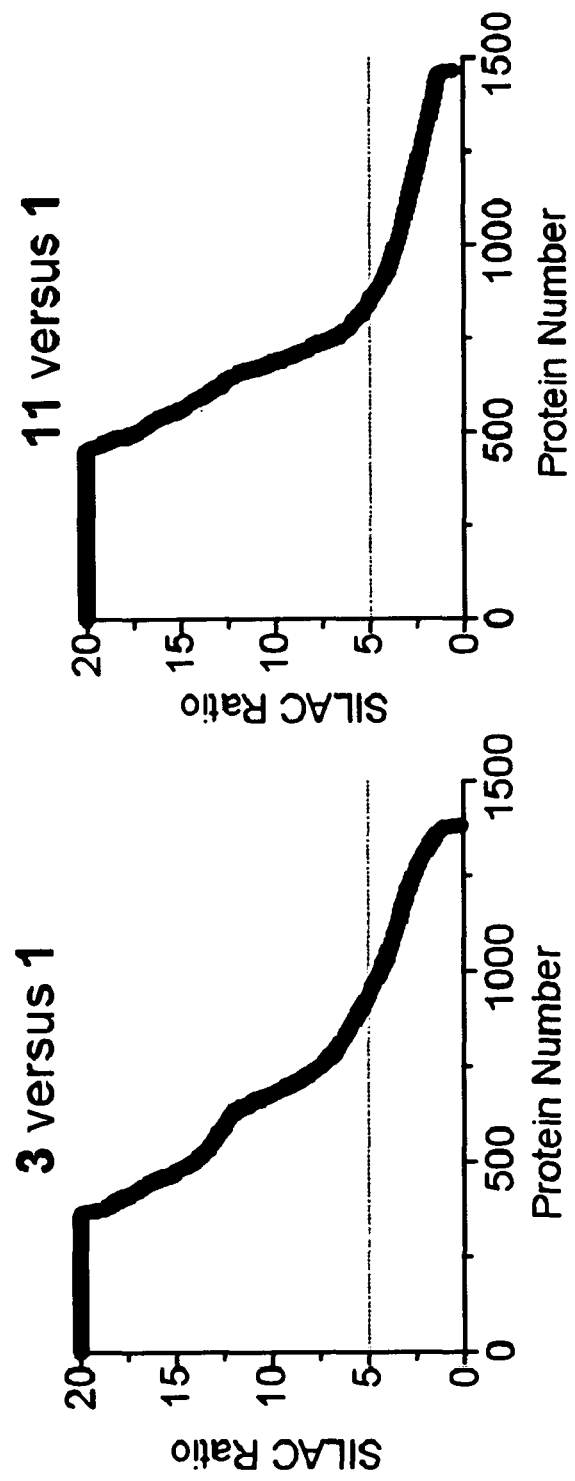
FIG. 2L exemplifies SILAC ratio plots for representative FFF probes in which isotopically heavy and light amino acid-labeled HEK293T cells were treated with control 1 or the indicated FFF probe (200 µM each). Dashed line indicates required threshold enrichment ratio (>5-fold) for designation of FFF targets.
Figure 2M:
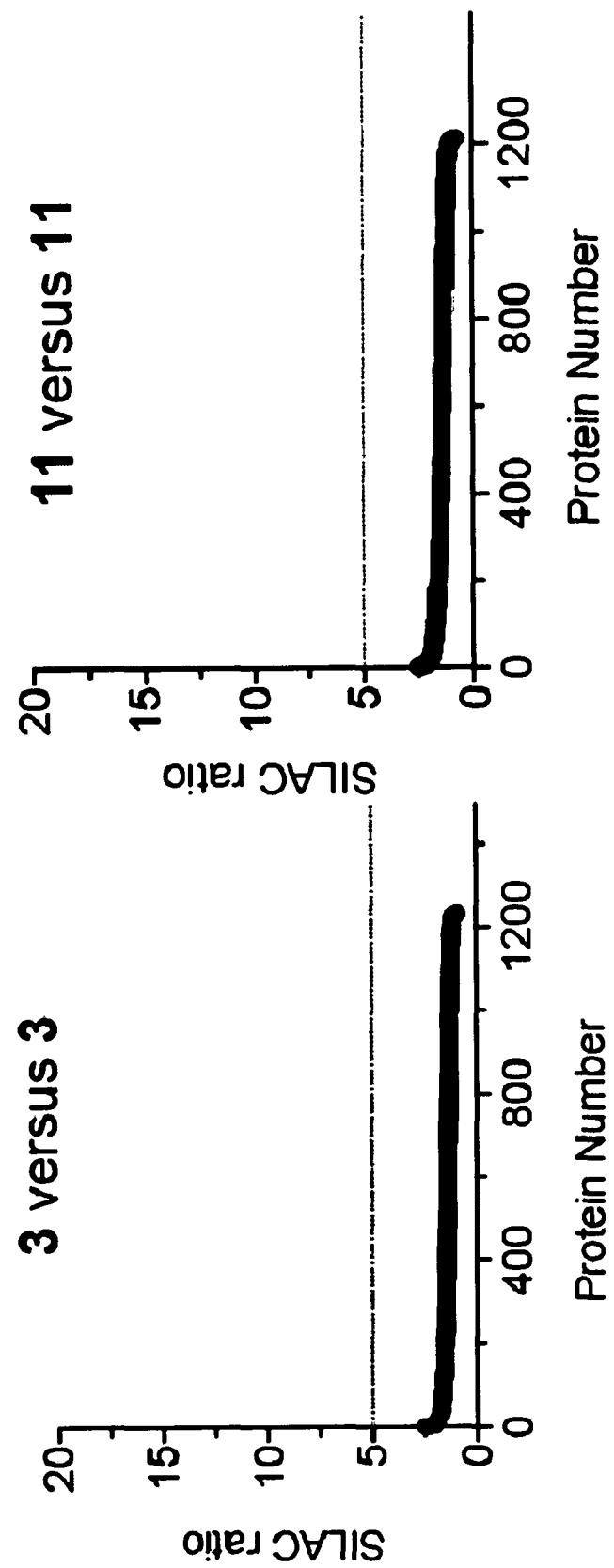
FIG. 2M exemplifies representative SILAC ratio plots for control experiments in which isotopically heavy and light amino acid-labeled HEK293T cells were treated with the same FFF probe (200 µM).
Figure 2N:
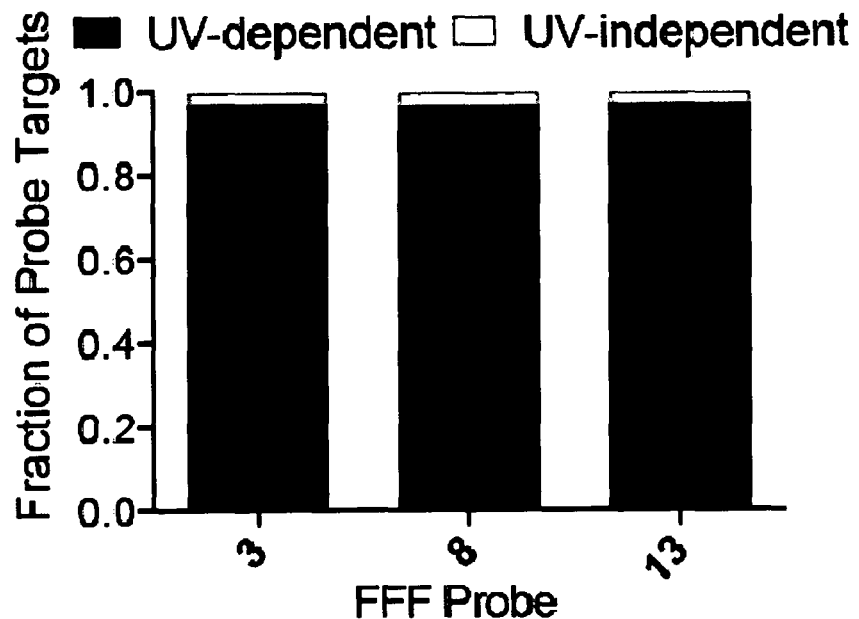
FIG. 2N exemplifies that fraction of targets for representative FFF probes that exhibit UV-dependent enrichment. Briefly, 'light' cells were treated with 200 µM of the corresponding probe and UV-irradiated while 'heavy' cells were treated with the same probe and not exposed to UV light. Proteins were considered to be labeled in a UV-dependent fashion if >3-fold enrichment in light cells was observed. For each probe, >97% of protein targets exhibited UV-dependent enrichment.
Figure 2O:
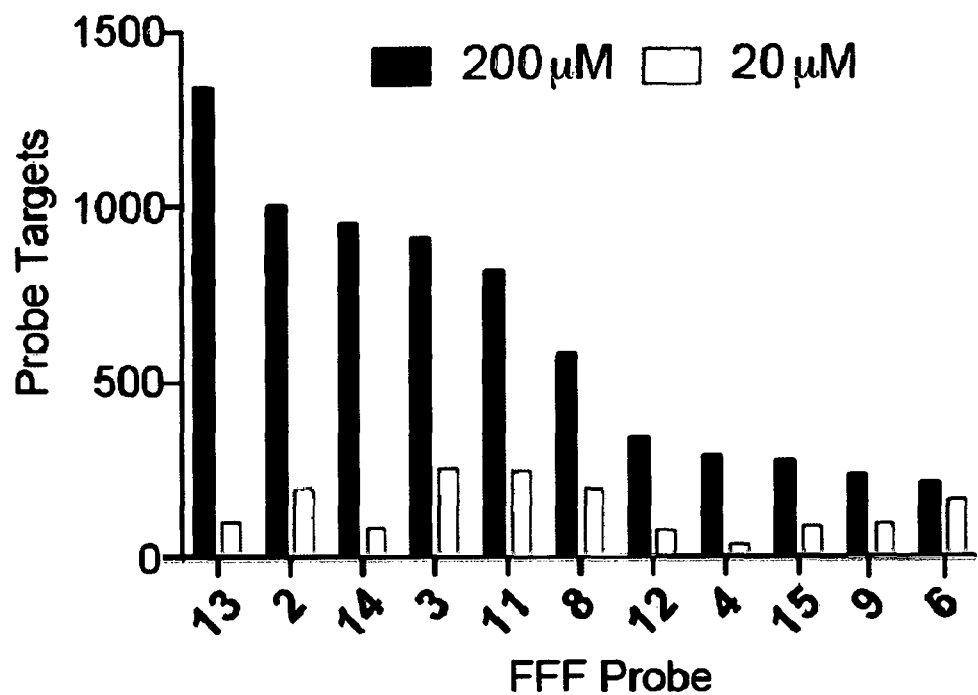
FIG. 2O exemplifies the number of protein targets enriched by corresponding FFF probes tested at 20 and 200 µM.
Figure 2P:
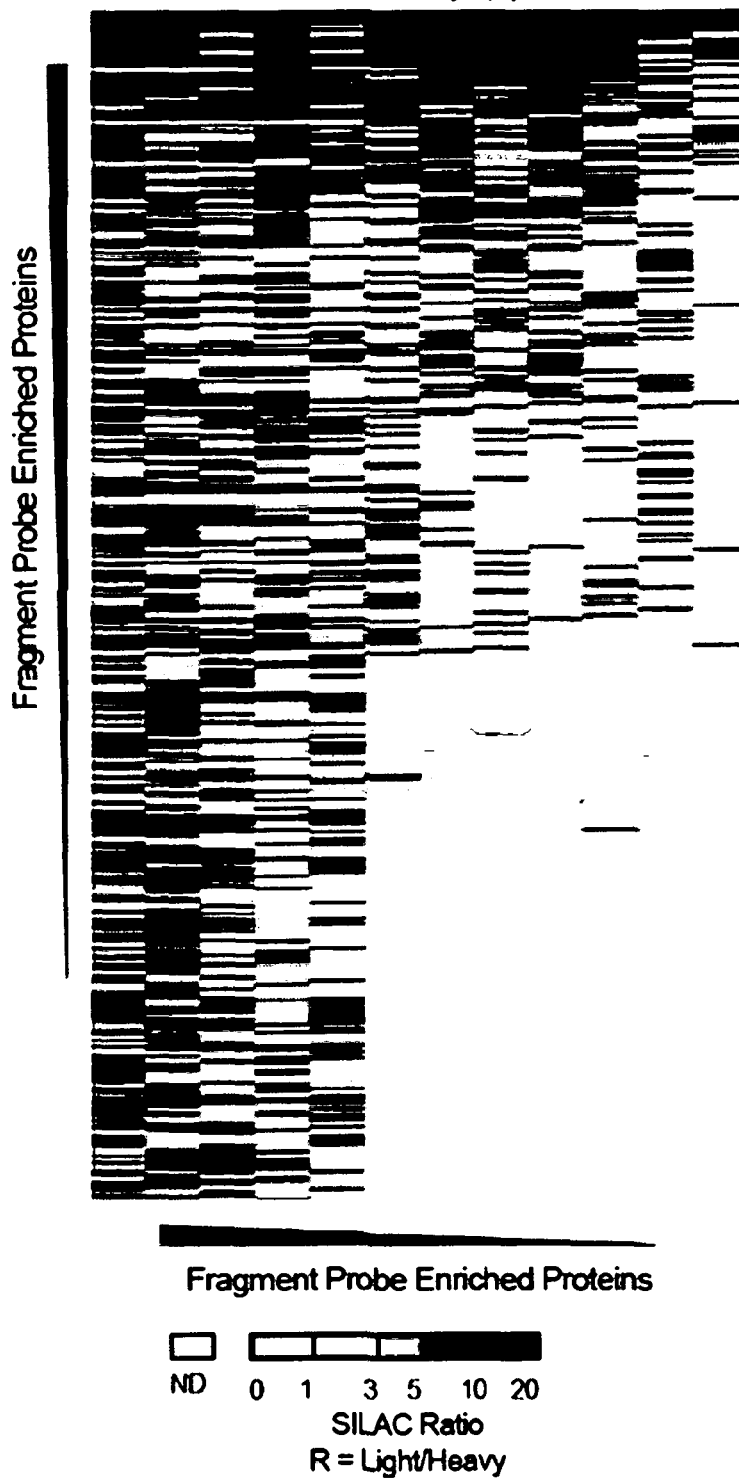
(FIG. 2P) Heatmap of enriched proteins in FFF probe-versus-control 1 experiments using 20 µM FFF probe in HEK293T cells.
Figure 2Q:
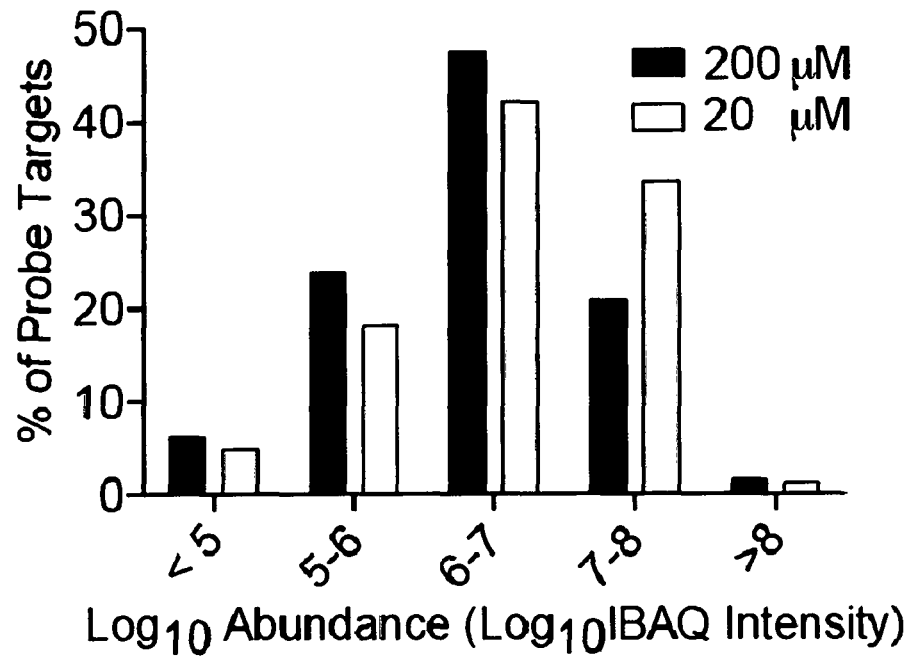
FIG. 2Q exemplifies histogram of HEK293T cell-derived iBAQ values as estimates of the abundance distribution for protein targets of FFF probes.
Figure 2R:
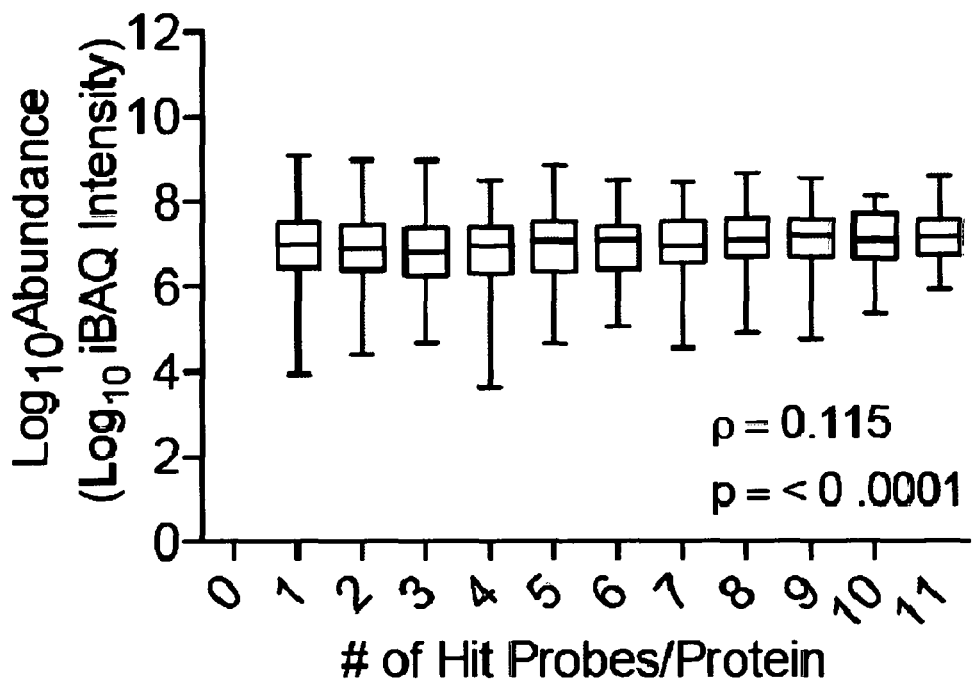
FIG. 2R exemplifies box-and-whisker plot of iBAQ values for FFF protein targets plotted versus the number of FFF probes that enriched each protein (□=Spearman's correlation coefficient).
Figure 2S:
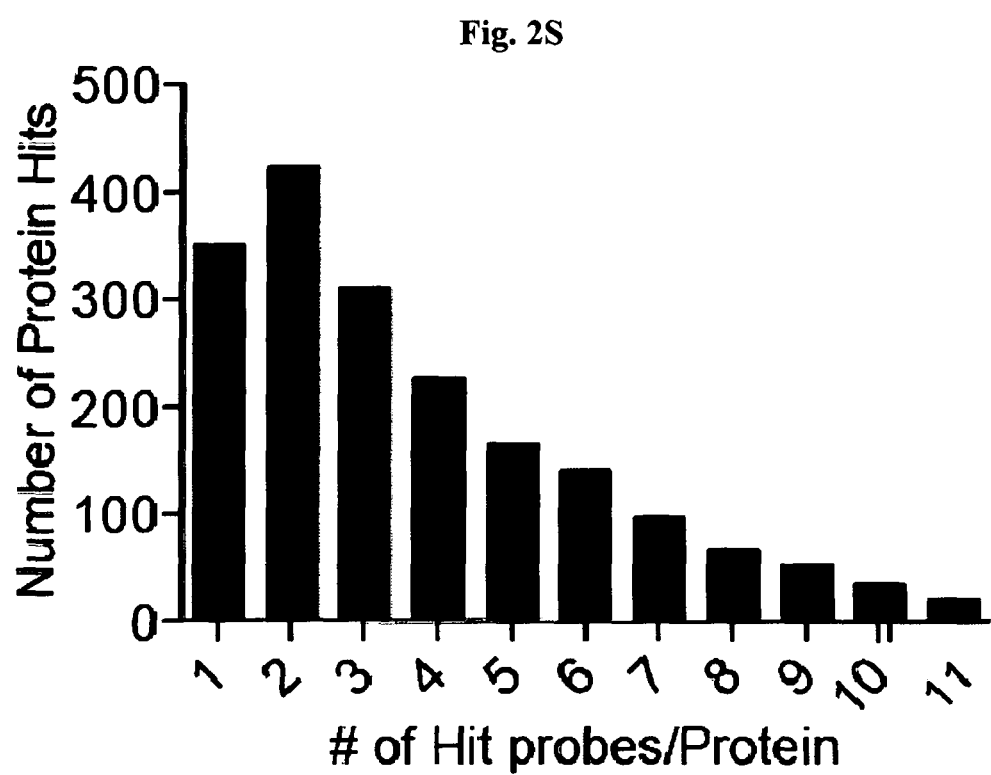
FIG. 2S exemplifies histogram showing the number of FFF probe hits per protein target; a median value of three probes were found per protein.

In aggregate, more than 2000 protein targets were identified for the FFF probes, which individually displayed a broad range of protein enrichments (FIG. 2A, FIG. 2O). When tested at lower concentrations (20 μM), FFF probes enriched fewer protein targets (FIG. 2O, FIG. 2P), confirming that the extent of proteome engagement depends on probe concentration. A review of expression-based proteomics data generated in HEK293T cells revealed that the protein targets of FFF probes spanned more than five orders of magnitude in abundance and this range bracketed the median protein abundance value in HEK293T cells (FIG. 2Q), exemplifying, along with other analyses (FIG. 2R, FIG. 2S), that FFF probes enriched proteins across a broad range of expression.

To more quantitatively assess the structure-activity relationships (SARs) emerging from the initial FFF probe experiments, additional studies were performed comparing the relative protein interaction profiles of FFF probes, wherein isotopically light and heavy cells were treated with two different probes (probe-vs-probe comparisons) and processed as shown in FIG. 1A. These experiments exemplified that proteins preferentially enriched by one FFF probe relative to another in probe-vs-probe comparisons were also often preferentially enriched by the same probe in original comparisons to control 1 (FIG. 2B-FIG. 2F). The probe-vs-probe comparisons also revealed that most of the proteins showing broad interaction potential across the fragment library in probe-vs-control 1 experiments (light gray sub-bars, FIG. 2C) still exhibited preferential interactions with one or a subset of FFF probes (FIG. 2G-FIG. 2J).

Figure 2T:
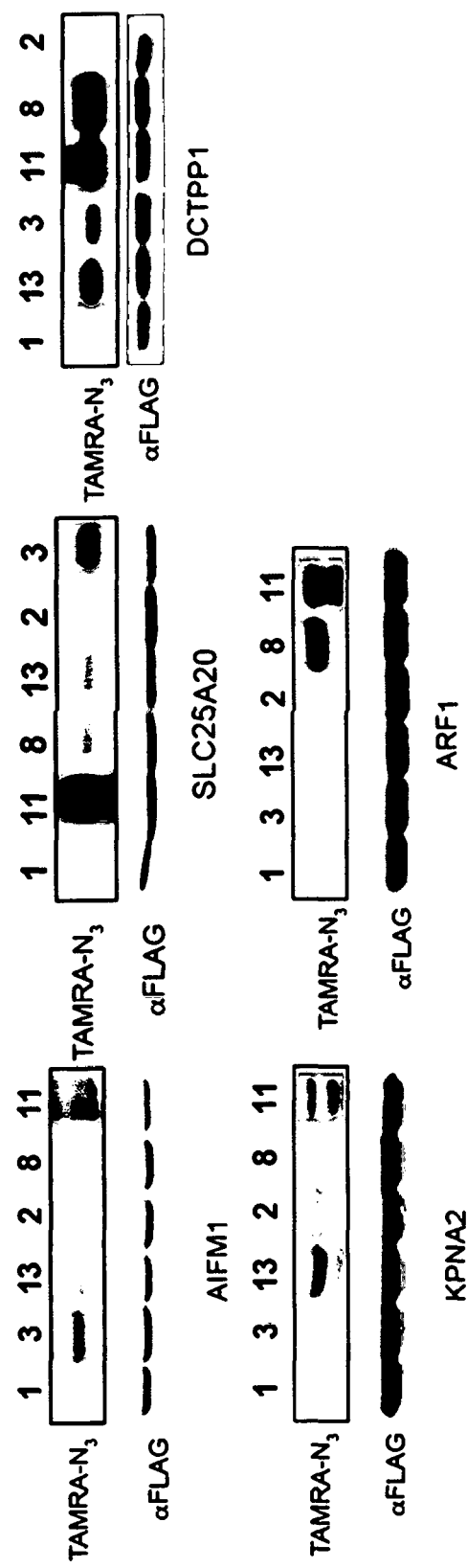
Figure 2U:
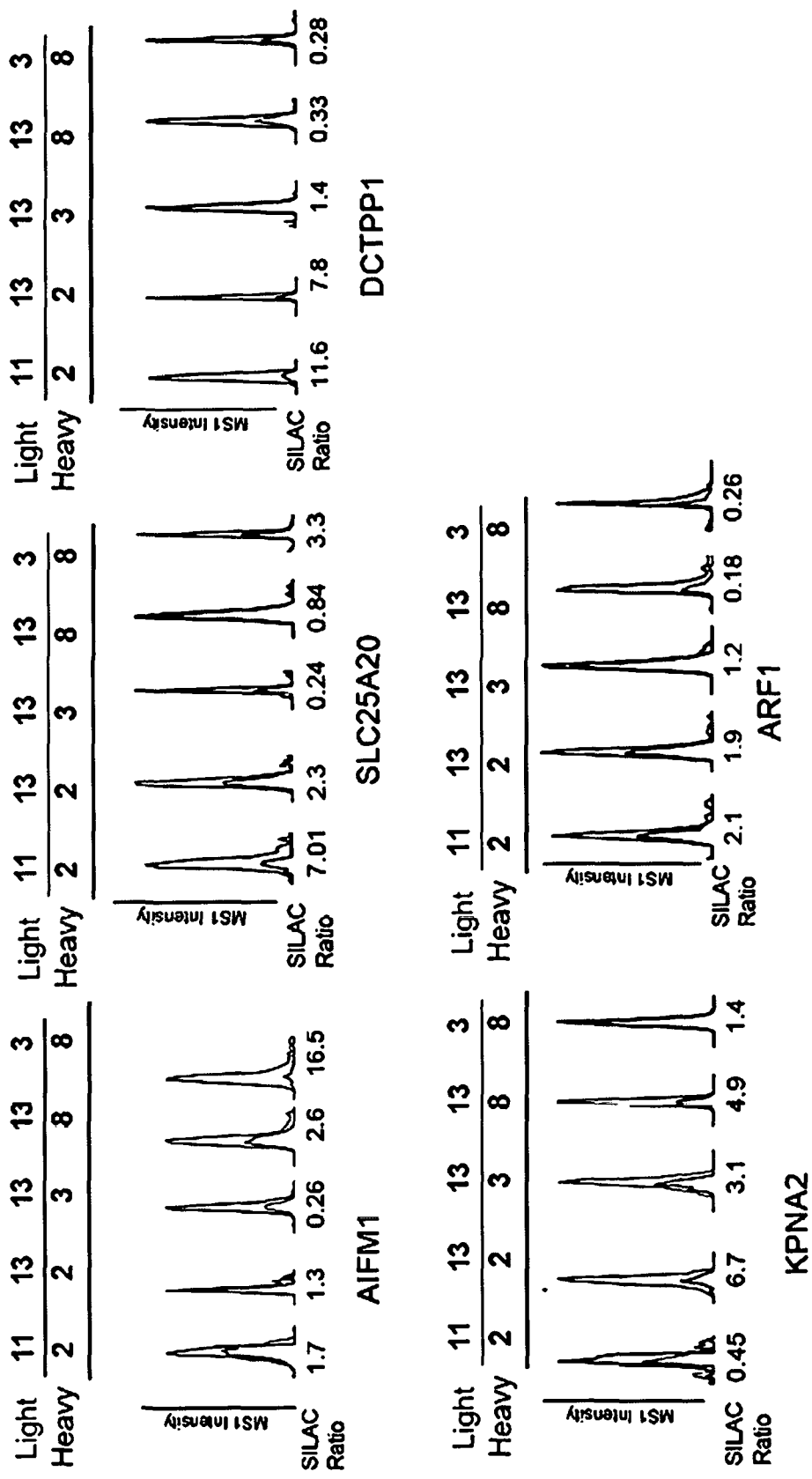
FIG. 2U exemplifies that for proteins shown in FIG. 2T, extracted MS1 chromatograms and corresponding SILAC ratios of representative tryptic peptides quantified in the indicated probe-versus-probe experiments.

The fragment interactions profiles were verified for representative proteins by recombinant expression in HEK293T cells. It was found that the fragment interaction profile for each recombinant protein, as measured by gel-based profiling (FIG. 1D), matched that of its endogenous form as determined by quantitative MS-based proteomics, with each target showing a strong preference for a distinct fragment probe (FIG. 2T, FIG. 2U).

Example 28—Types of Proteins and Protein Sites Targeted by Fragments

Figure 3A:
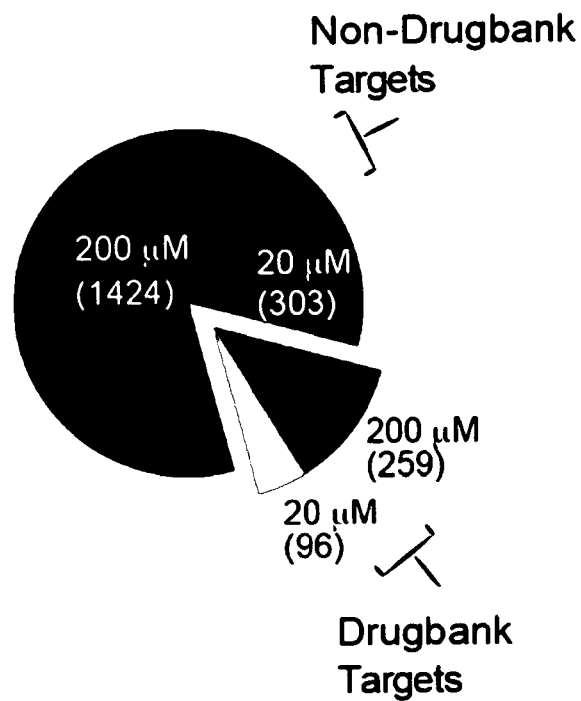
Figure 3B:
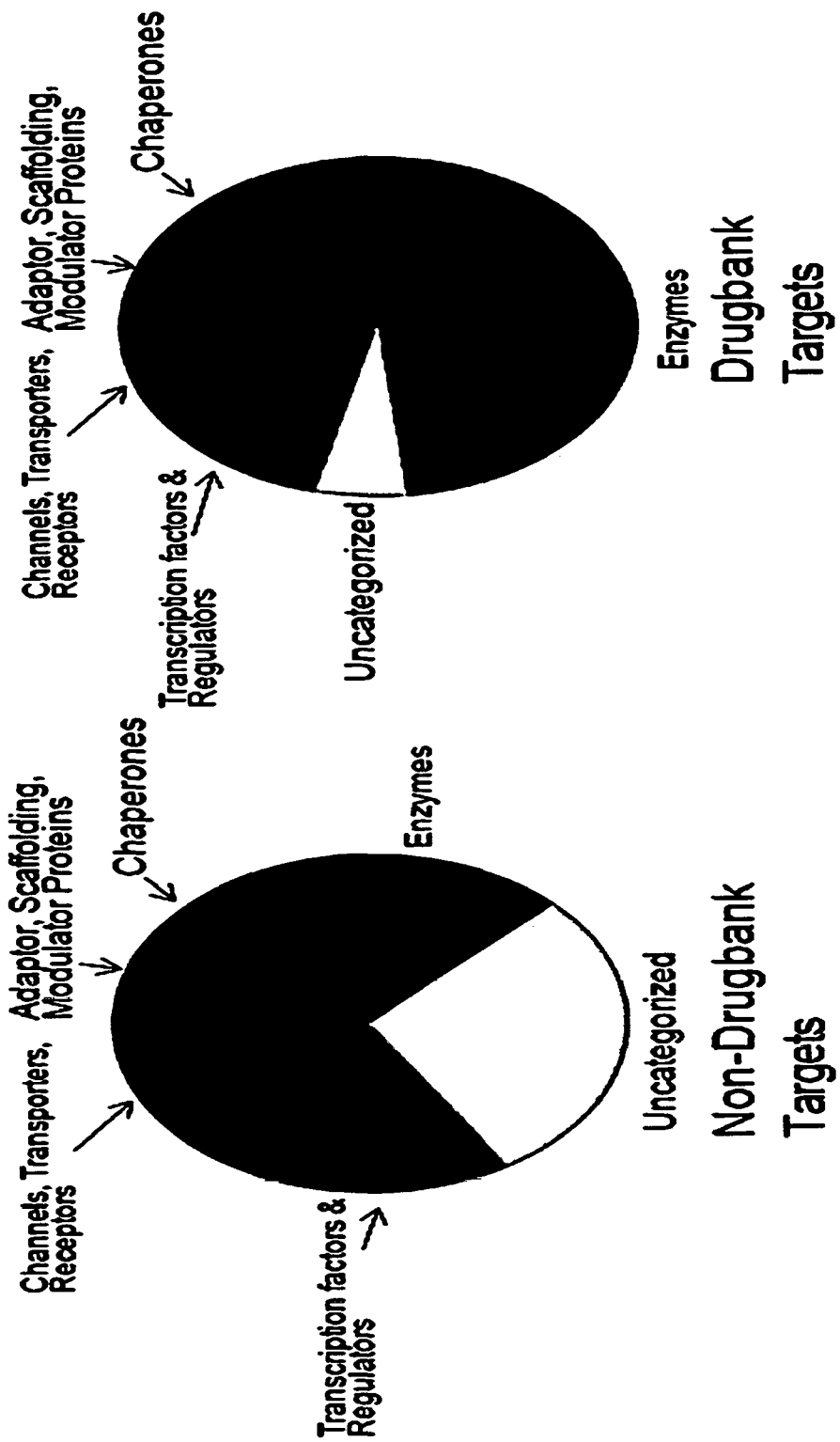

The fragment probes targeted both membrane and soluble proteins (FIG. 3H), and only a small fraction (17%) of these proteins had known ligands as estimated by their presence in the DrugBank database (FIG. 3A). This subset of previously liganded proteins was mainly enzymes (FIG. 3B). In contrast, the much larger subset of fragment probe targets (83%) not represented in DrugBank showed a broader functional distribution, with a reduced fractional representation of enzymes counterbalanced by expanded coverage of channels/transporters/receptors, transcription factors/regulators, and uncategorized proteins (FIG. 3B). A greater percentage of targets enriched by low (20 µM, 24%) versus high (200 µM, 12%) concentrations of fragments were found in DrugBank (FIG. 3A), exemplifying that the capacity to screen higher concentrations of fragment probes expanded the scope of newly discovered ligandable proteins in human cells.

Figure 3C:
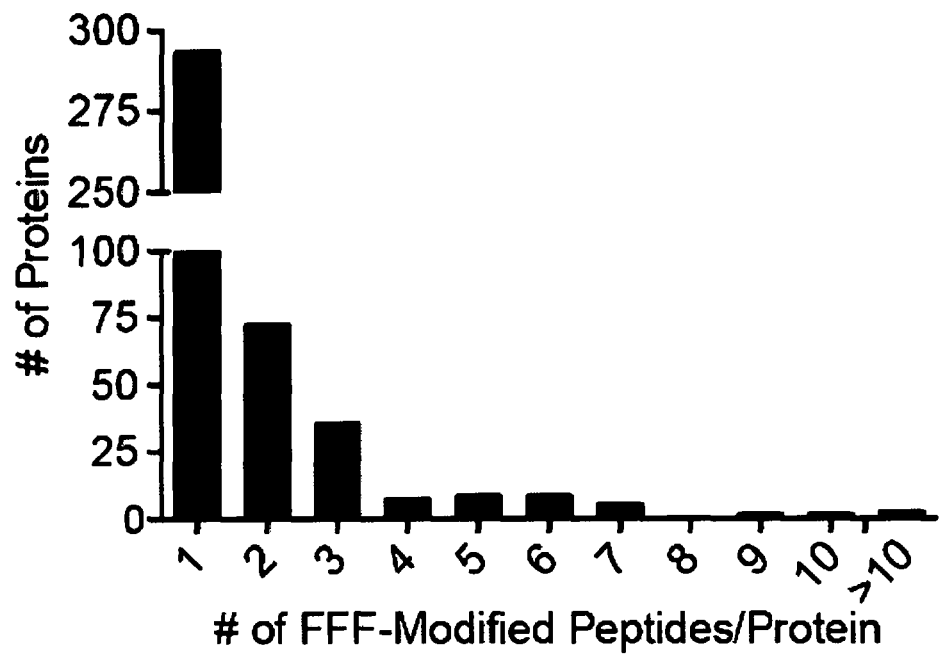
FIG. 3C exemplifies the number of FFF probe-modified peptides per protein target.

Considering that the chemical proteomic results provided the first evidence of ligandability for many protein targets, the fragment binding sites on these proteins were aimed to be identified next. Determining the sites of photoreactive probe binding to proteins is technically challenging, but the simple structures of FFF probes, along with the implementation of advanced chemical proteomic methods for isotopically labeling small-molecule probe-modified peptides is advantageous. Using these methods, over 800 unique peptides modified by one or more FFF probes were identified that collectively derived from 443 proteins (FIG. 3I and Tables 1-3) in HEK293T cells. Fragment-modified peptides were found in both membrane and soluble proteins (FIG. 3I), and, while many proteins were targeted by multiple FFF probes at the same site (FIG. 3J), in the substantial majority of cases, only a single fragment-modified peptide was identified per protein (FIG. 3C).

Figure 3D:
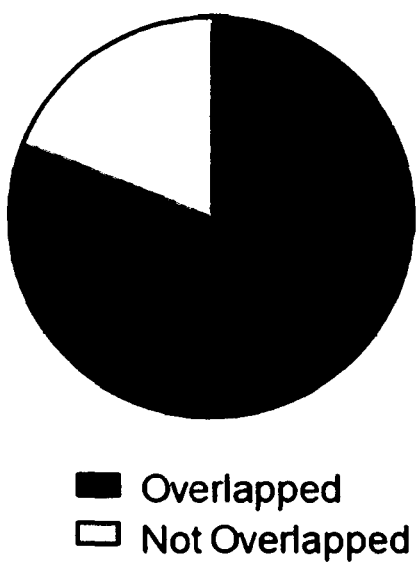
FIG. 3D represents the distribution of probe-modified peptides that overlap (or do not overlap) with residues in predicted binding pockets of proteins with structures available in the PDB (as determined by fpocket analysis).
Figure 3E:
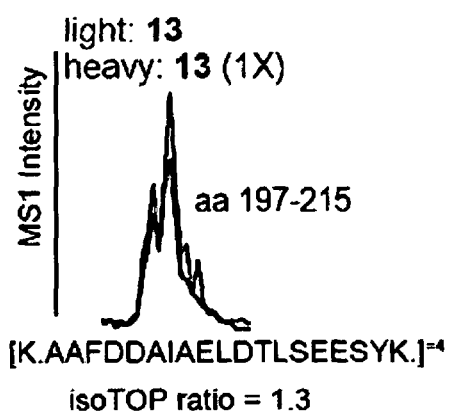
(FIG. 3E-FIG. 3G) Examples of probe labeling sites mapped onto protein structures. Tryptic peptides containing probe-labeled sites are shown in green, and residues that overlap with predicted binding pockets are shown in beige.
Figure 3E:
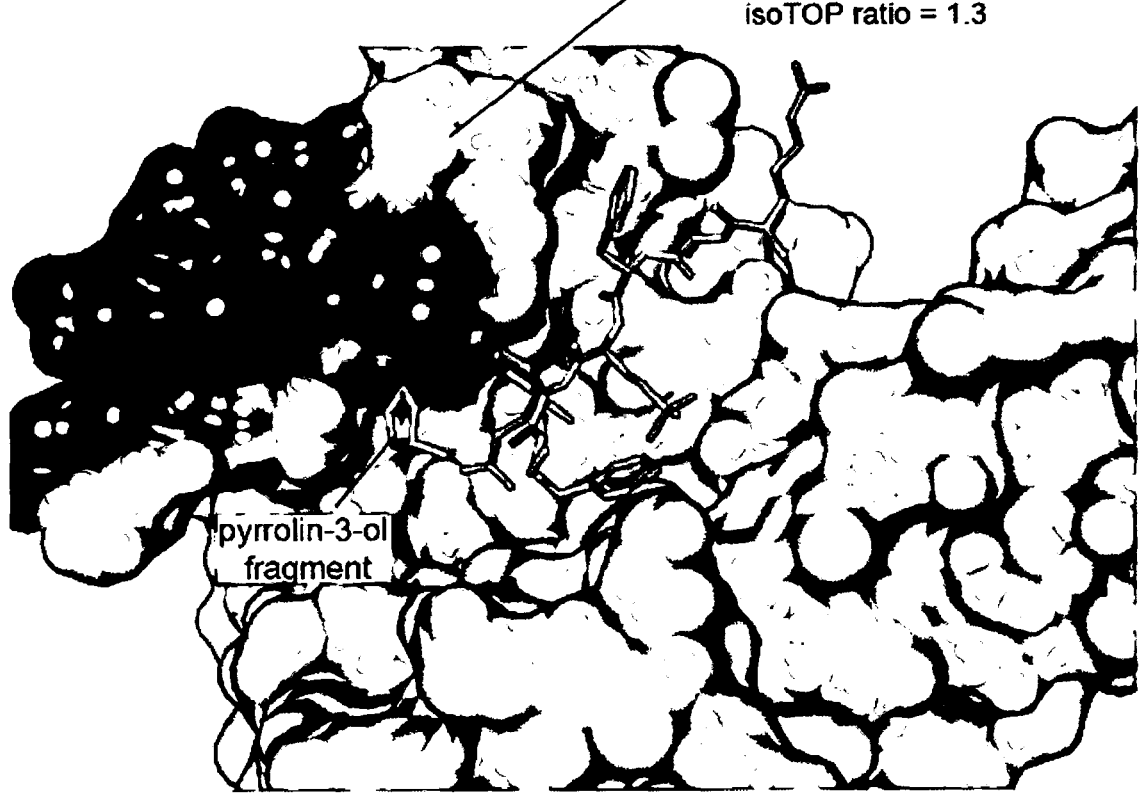
Figure 3F:
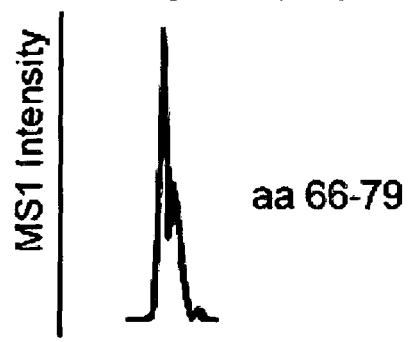
Figure 3F:
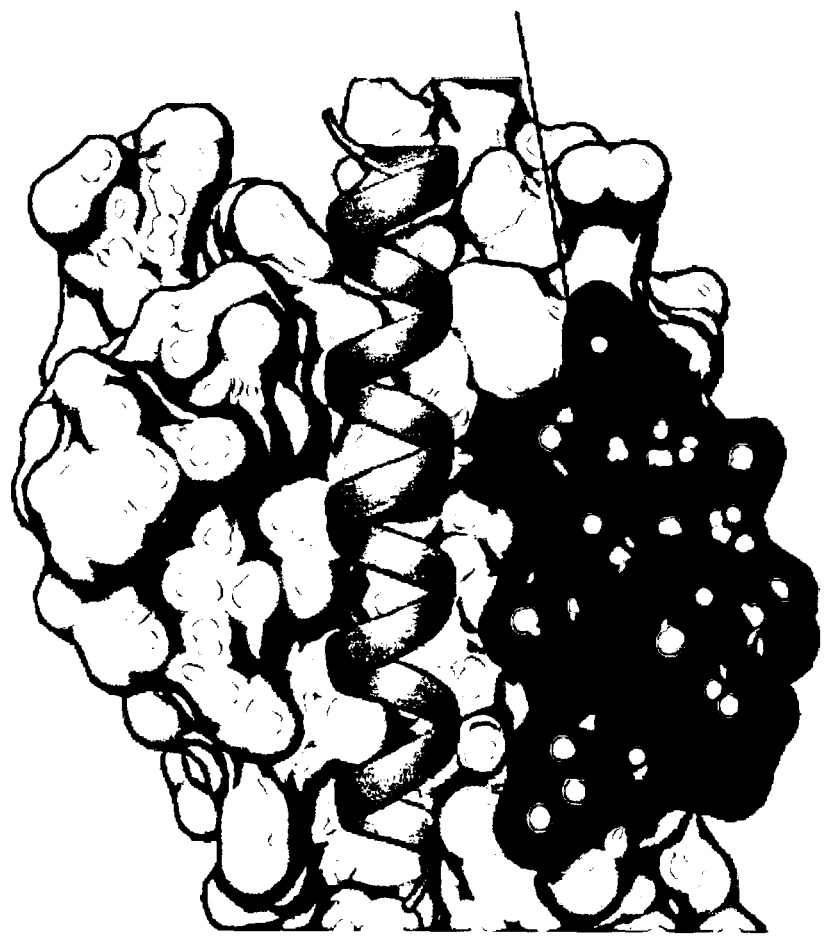
Figure 3G:
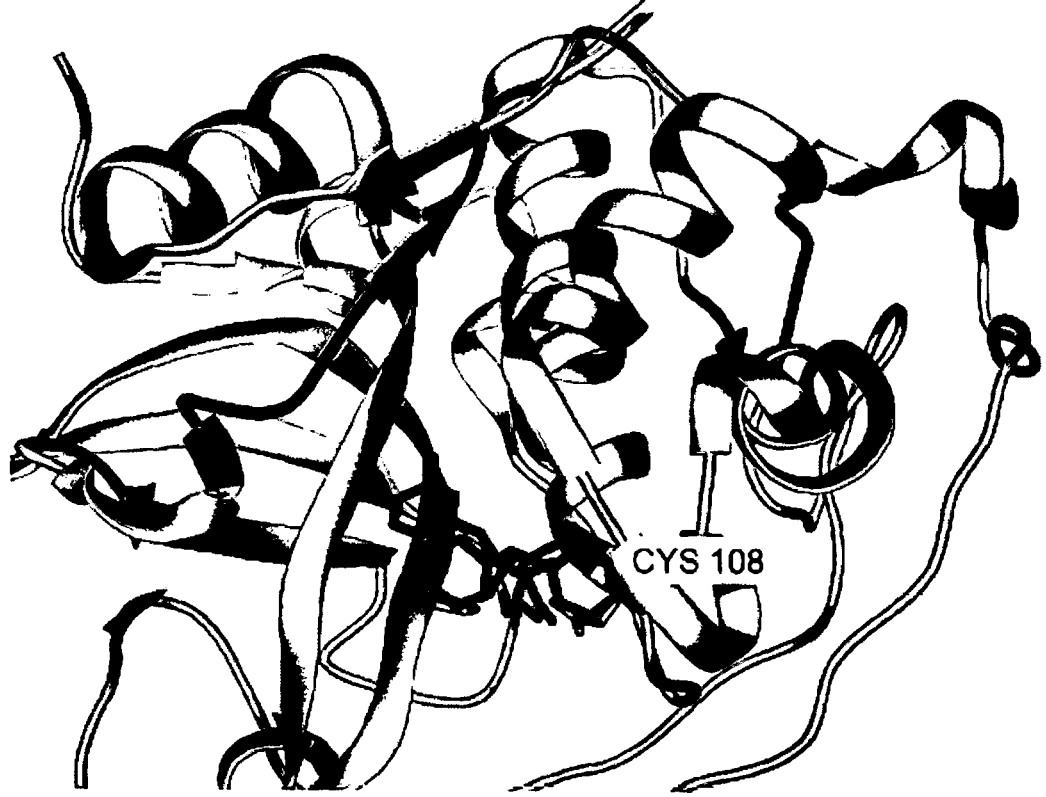
Figure 3H:
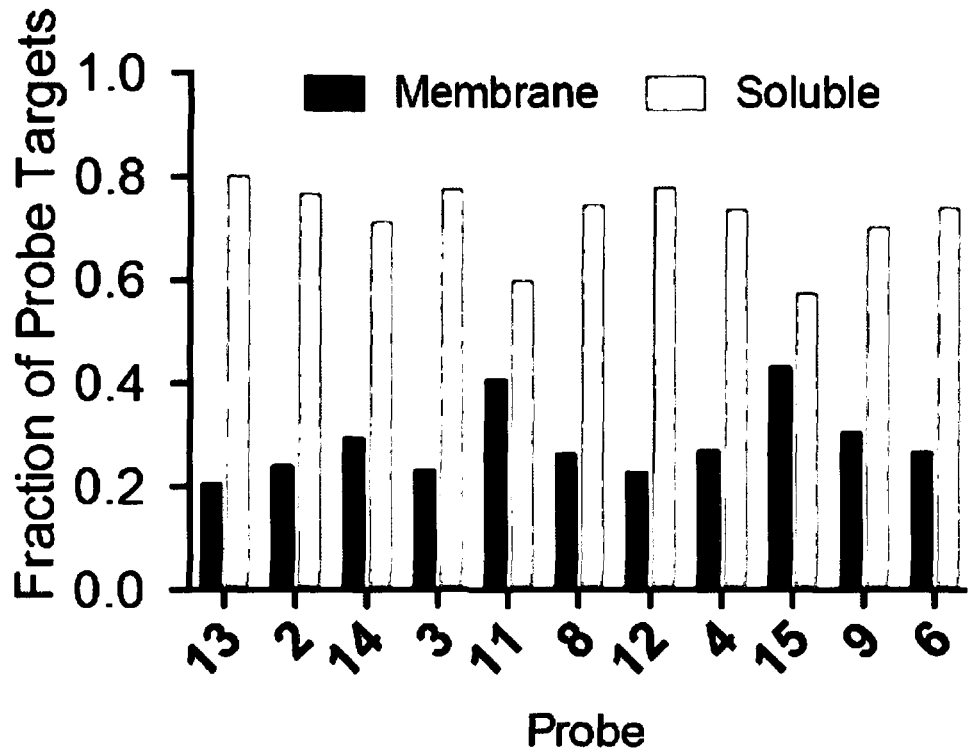
FIG. 3H exemples that fraction of FFF probe targets with (membrane) or without (soluble) known/predicted transmembrane domains.
Figure 3I:
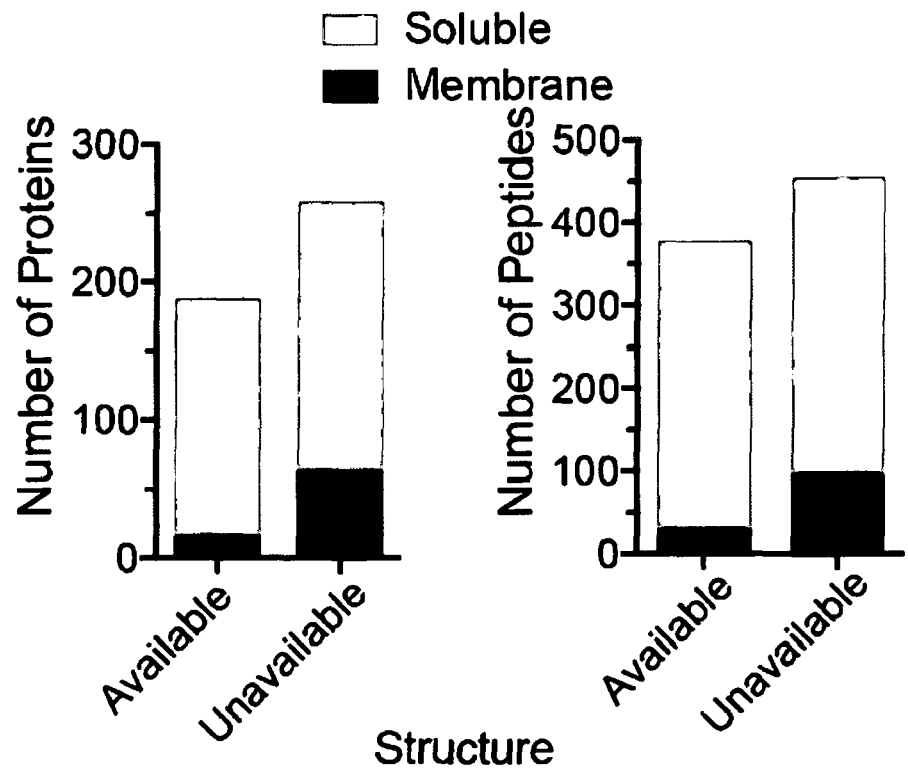
FIG. 3I exemplifies the breakdown of soluble and membrane proteins, and corresponding probe-modified peptides from these proteins, with available crystal structures.
Figure 3J:
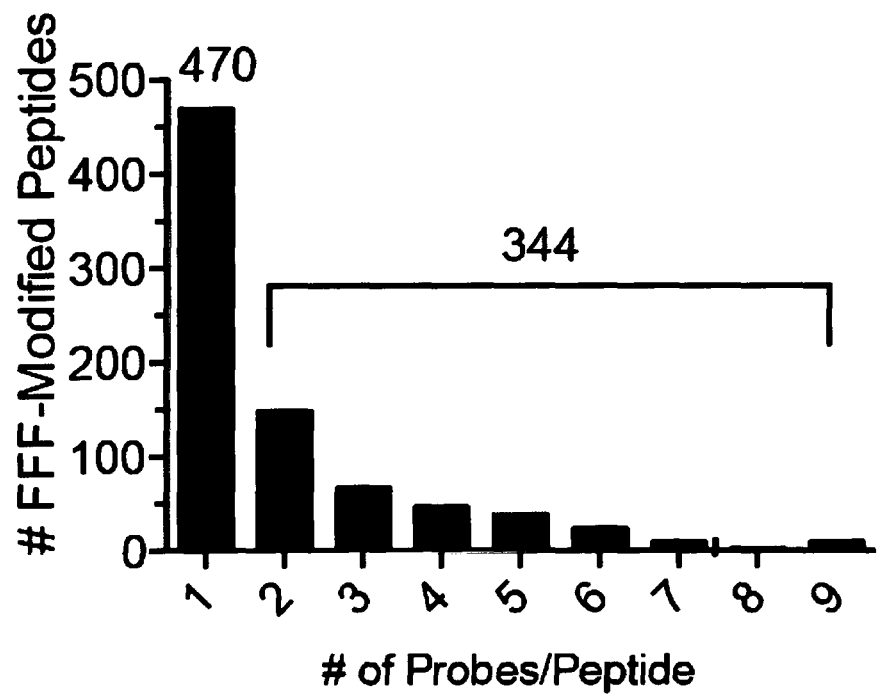
FIG. 3J exemplifies the distribution of peptides labeled by one or more FFF probes.
Figure 3K:
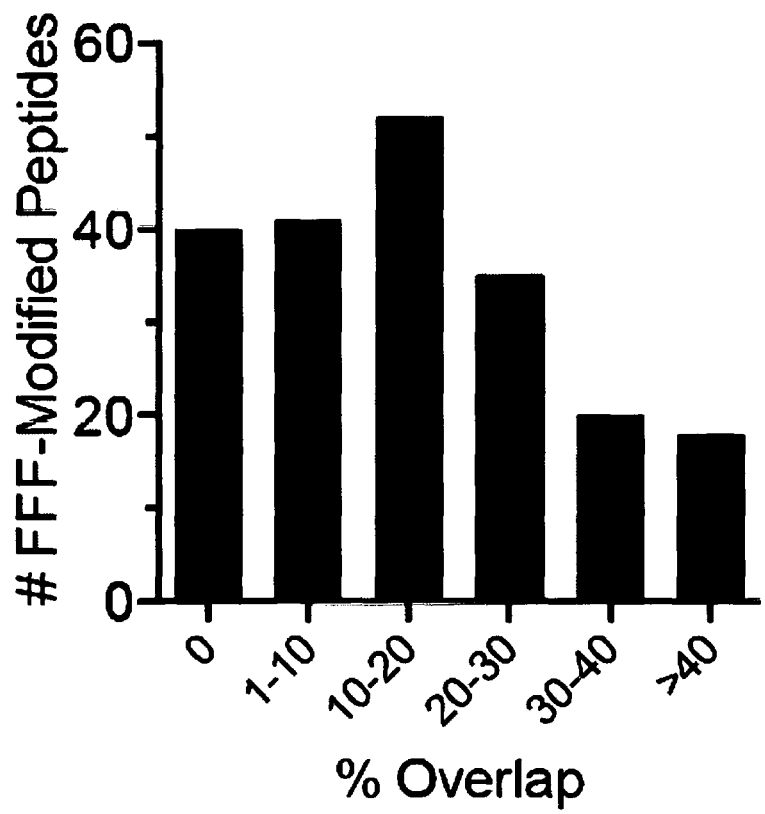
FIG. 3K exemplifies the distribution of probe-modified peptides based on overlap of their amino acid sequence with predicted binding pocket residues determined by fpocket analysis.
Figure 3L:
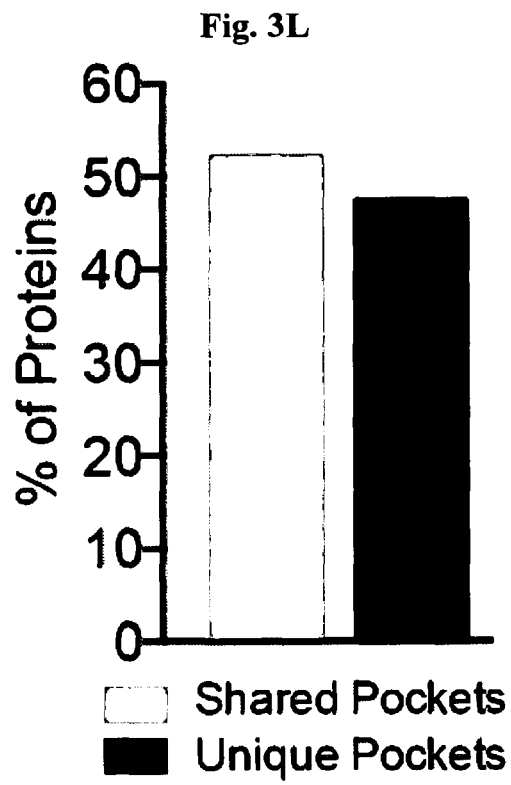
FIG. 3L exemplifies the fraction of proteins with multiple probe-modified peptides that correspond to shared or distinct binding pockets.
Figure 3M:
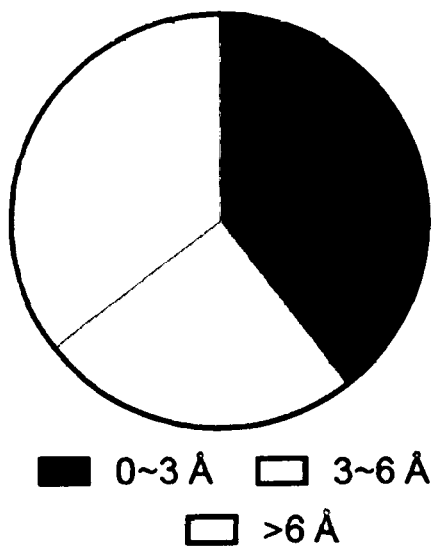
FIG. 3M exemplifies for proteins with annotated functional sites, distances of functional sites from probe-modified peptides. Functional sites include annotated enzyme catalytic residues (active sites), substrate binding sites, and metal-binding sites.

Using the pocket-detection algorithm fpocket, for the 186 proteins harboring fragment-modified peptides for which crystal structures were also available (FIG. 3I), it was found that the vast majority of fragment-modified peptides (~80%) overlapped directly and substantially with predicted ligand-binding pocket residues (FIG. 3D and FIG. 3K and Tables 1-3). For proteins possessing multiple distinct fragment-modified peptides, it was found that these peptides often mapped to a shared predicted pocket (FIG. 3L). For proteins with annotated functional residues (e.g., active site residues; 77 total proteins), approximately 60% of the probe-modified peptides were within 6 angstroms of a functional residue (FIG. 3M).

Figure 3N:
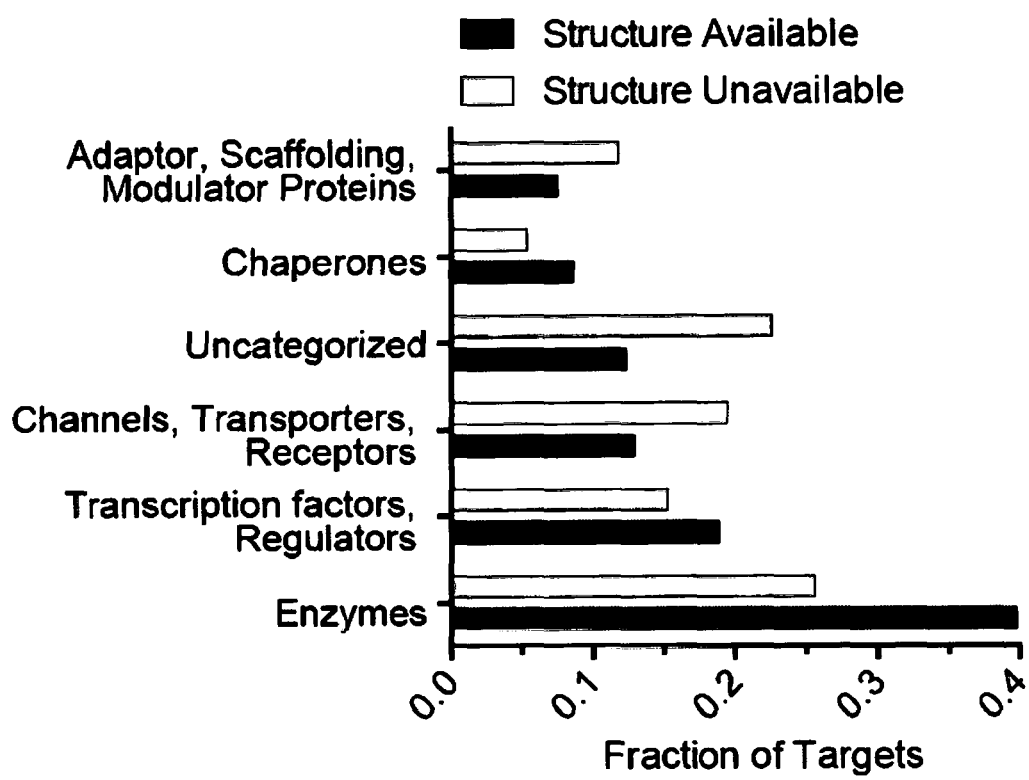
FIG. 3N exemplifies the functional class distribution for proteins with FFF-modified peptides and subdivided based on availability of crystal structures for these proteins.
Figure 3O:
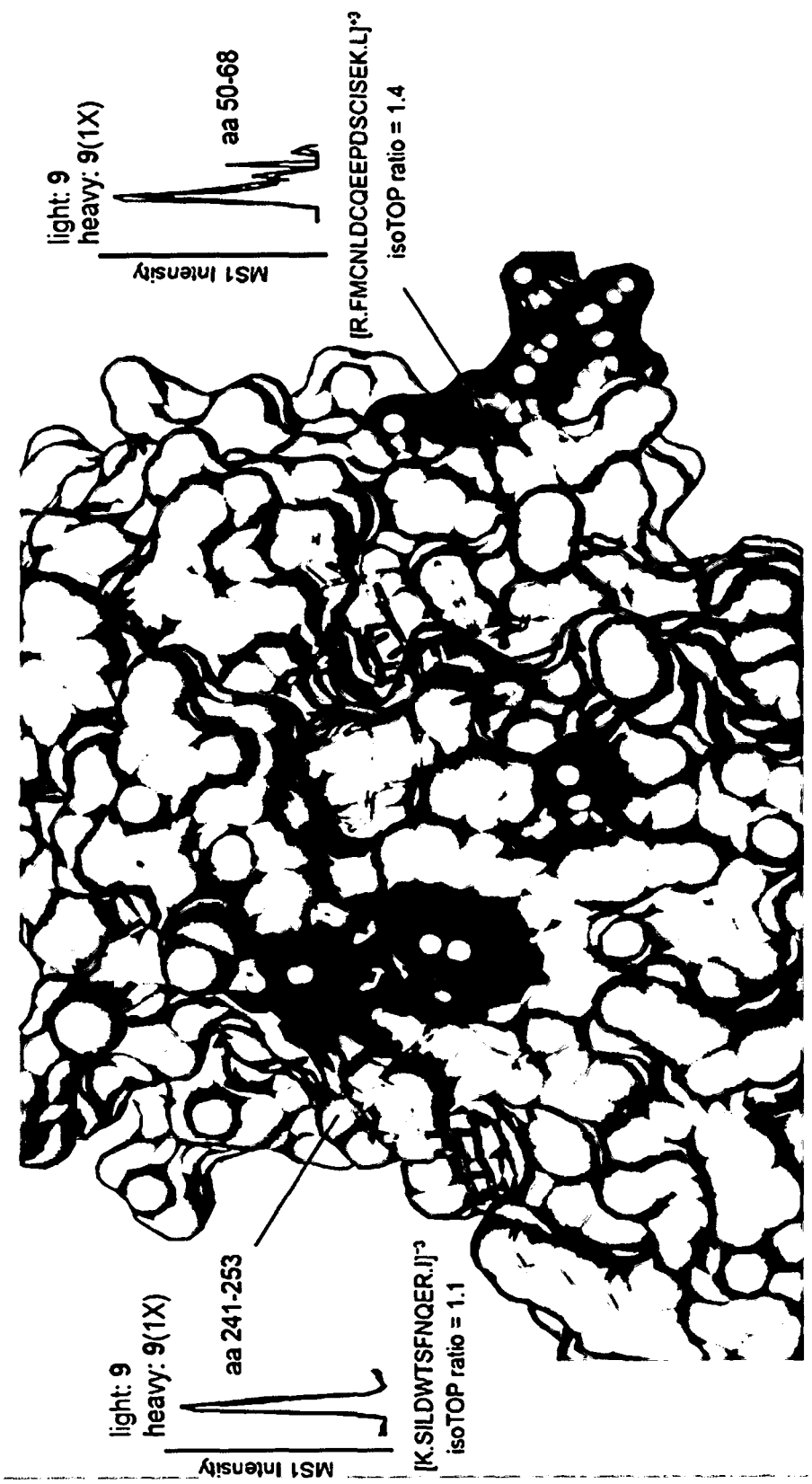
FIG. 3O exemplifies FFF 9-modified peptides (green/tan, where tan further designates residues that overlap with those predicted to be part of binding pockets as determined by fpocket) in the structure of human GLA (gray, PDB 3S5Z). Peptides aa 50-68 and aa 241-253 are found near the active site (purple, with substrate alpha D-galactose depicted in yellow) and a secondary ligand binding site (with the beta D-galactose ligand depicted in yellow), respectively.

Many of the proteins with mapped fragment-binding sites and crystal structures corresponded to enzymes (FIG. 3N), but non-enzymes of note included: i) the 14-3-3 adapter protein YWHAE, which was modified by probe 13 on a peptide (aa 197-215) that lines the primary interaction cleft for binding the oncoprotein myeloid leukaemia factor 1 (MLF1) (FIG. 3E); and ii) the proapoptotic effector protein BAX, which was also modified by probe 13 on a peptide (aa 66-79) within a groove that binds the BH3-domain containing activators Bim and Bid (FIG. 3F). Among the enzymes with mapped fragment-binding sites, the cysteine protease cathepsin B (CTSB) was targeted by probe 9 at an active-site proximal peptide (aa 315-332), and this interaction was blocked by the CTSB inhibitor Z-FA-FMK (FIG. 3G). Fragment-modified peptides at allosteric or secondary ligand-binding sites were also identified, including, for instance, a pocket on α-galactosidase (GLA) proposed to constitute a site for pharmacological chaperoning (FIG. 3O). Lastly, little overlap (<15%) was found between FFF targets and proteins liganded by cysteine-reactive electrophilic fragments (FIG. 3P). Even if this analysis was restricted to proteins that contained IA-reactive, the overlap between FFF targets and electrophilic fragments targets remained modest (~28%) (FIG. 3P). These results exemplify that reversible and irreversible fragments interact with largely distinct subsets of the human proteome.

Example 29—Functional Characterization of Fragment-Protein Interactions

Figure 4A:
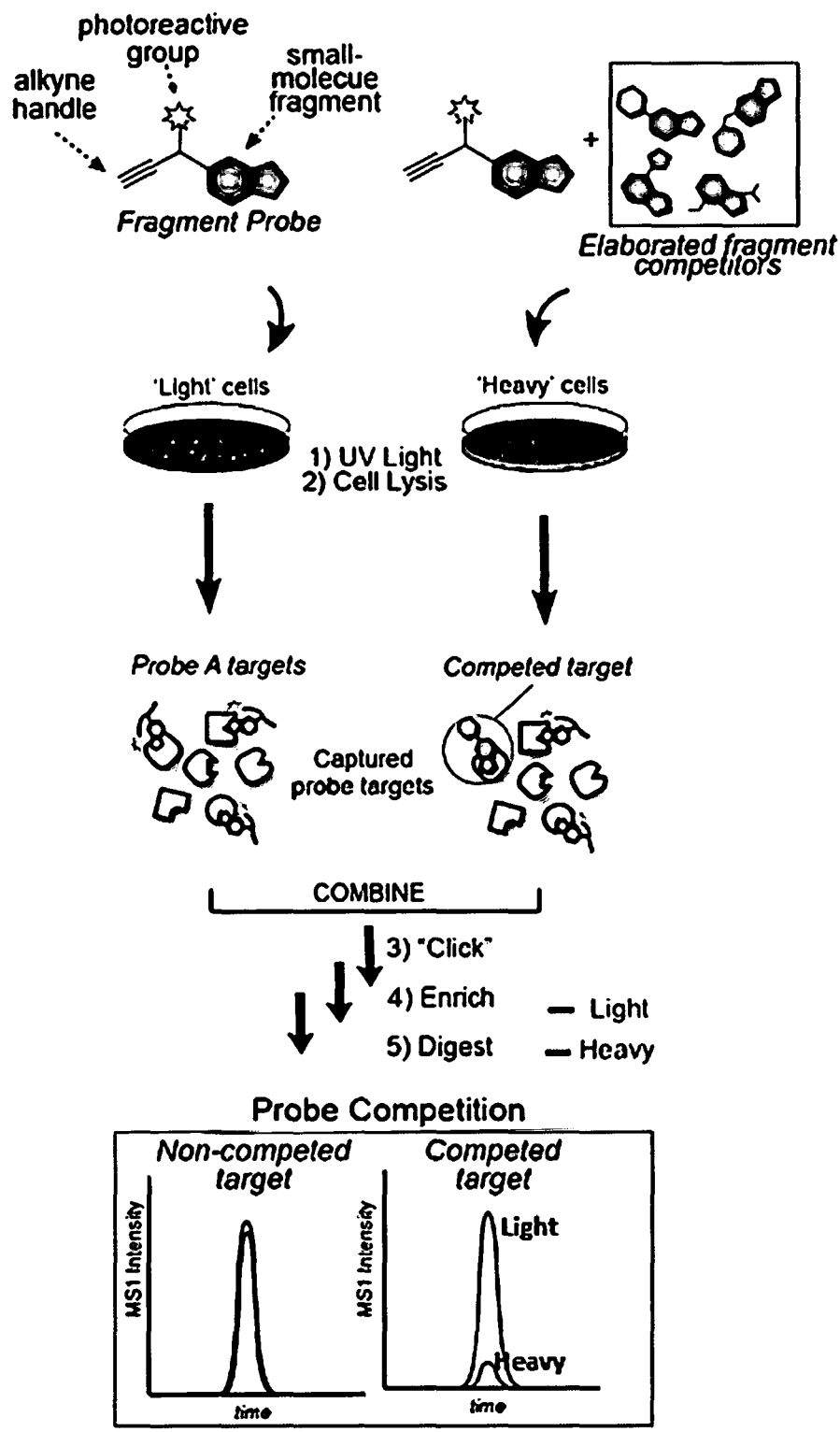
Figure 4B:
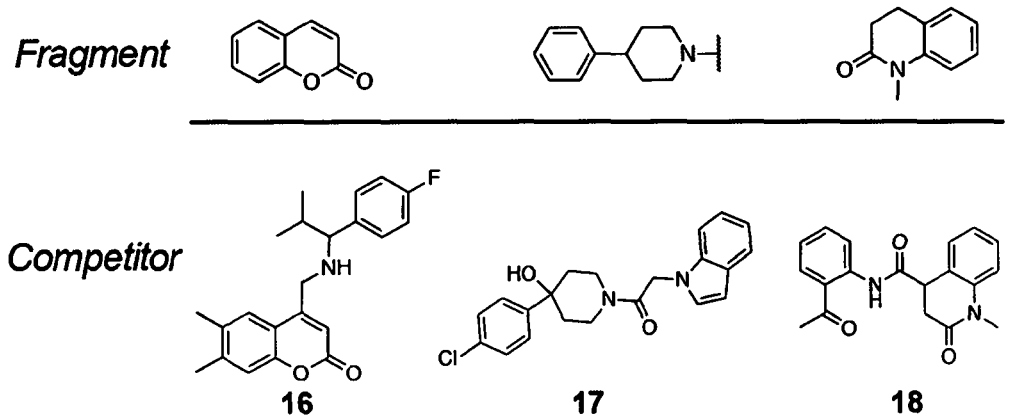
Figure 4C:
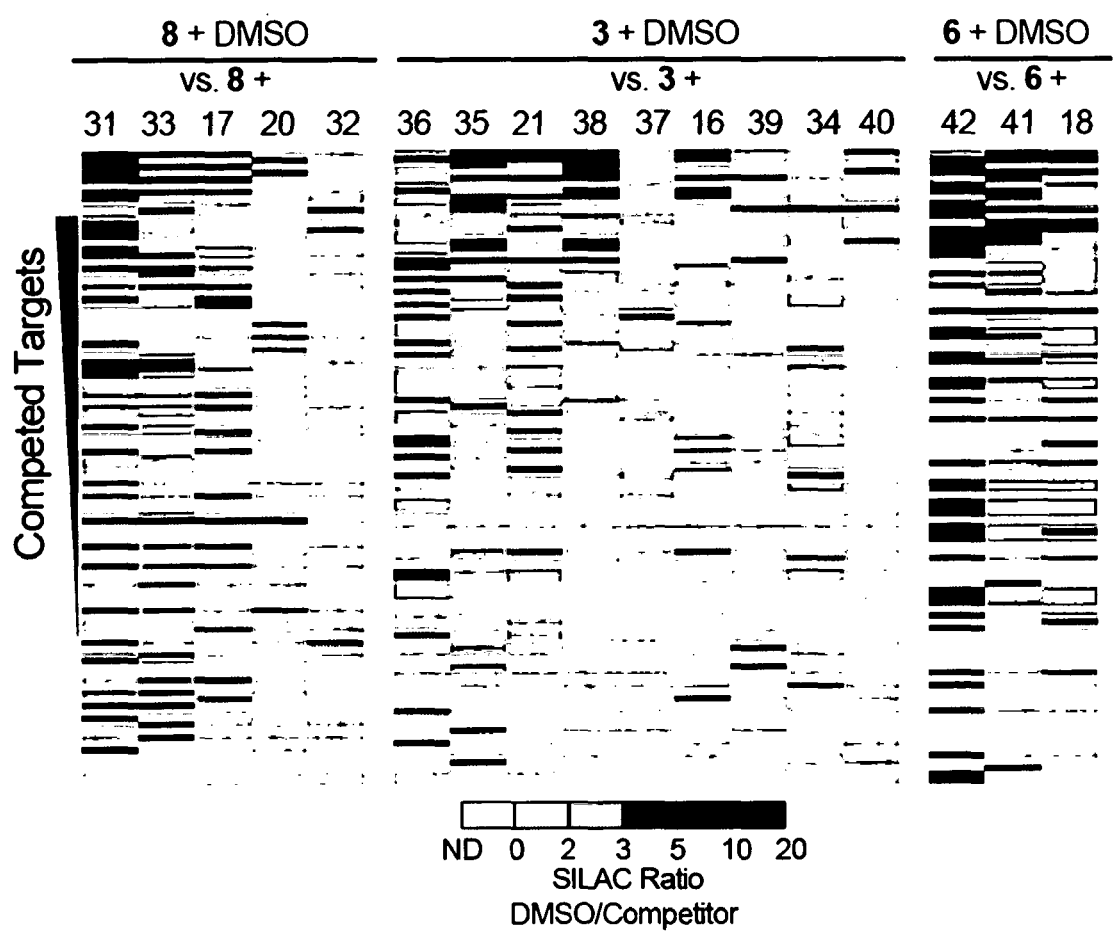
Figure 4D:
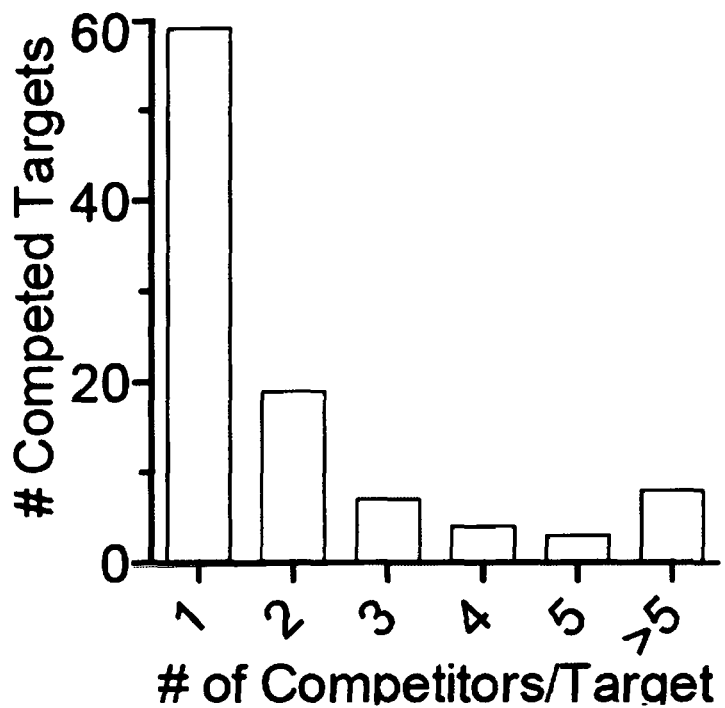

FBLD typically identifies low-affinity (high µM to mM) hit compounds that often require substantial, structure-guided medicinal chemistry optimization to improve potency and selectivity. As an alternative and complementary approach to structure-based ligand development, the proteome-wide, cell-based fragment screens are adapted to identify higher potency ligand-protein interactions. This goal is accomplished by screening focused libraries of small molecules containing representative fragment cores elaborated with additional "binding" substituents for competitive blockade of FFF probe-protein interactions in cells (FIG. 4A). Elaborated competitor molecules were purchased or synthesized for three FFF probes—3, 6, and 8 (FIG. 4B and FIG. 4I-FIG. 4K)—and treated cells with these competitors (17 total, each screened versus DMSO as a control) in eight-fold excess over the corresponding FFF probe (160 µM competitor, 20 µM FFF probe), after which FFF-modified proteins enriched and identified as shown in FIG. 4A. A total of 100 competed targets—defined as proteins that displayed substantial reductions (>3-fold) in signal in small-molecule competitor (heavy) versus DMSO (light) treated cells—were identified (FIG. 4C-FIG. 4F, FIG. 4L). Competed proteins showed widely varied SARs that ranged from broad interactions with several (>5) competitors to preferential binding to a single competitor (FIG. 4D).

Figure 4E:
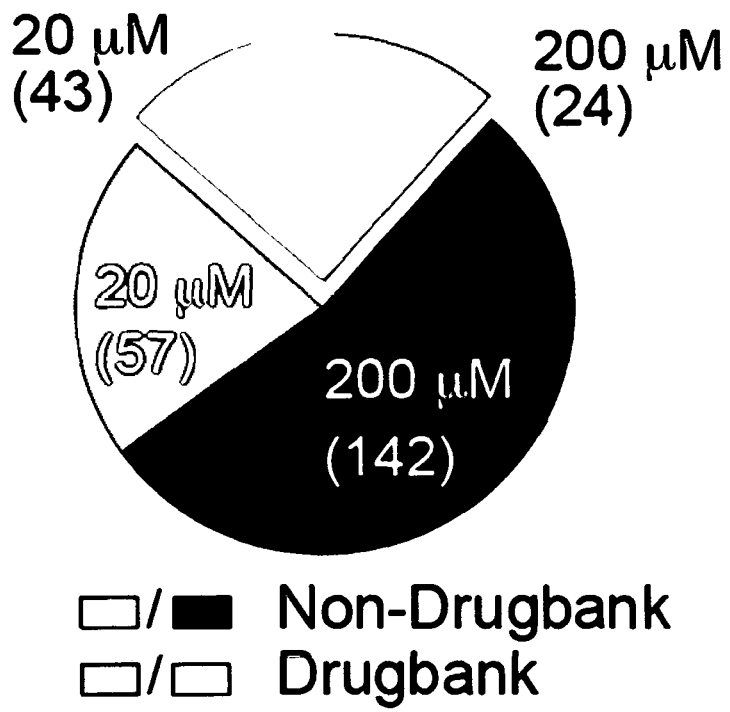
Figure 4F:
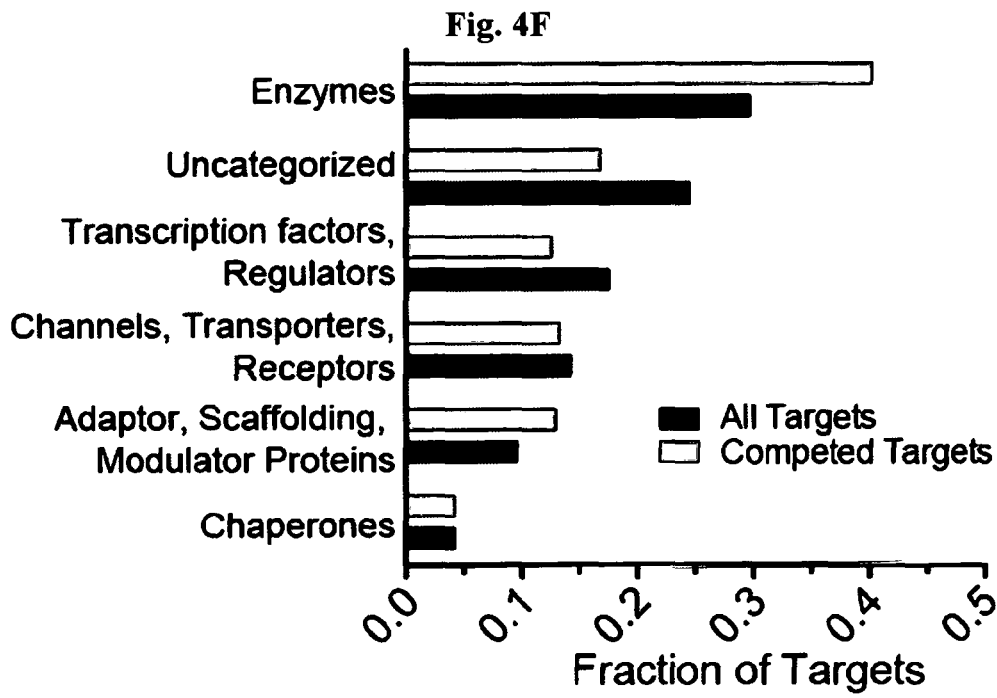
Figure 4G:
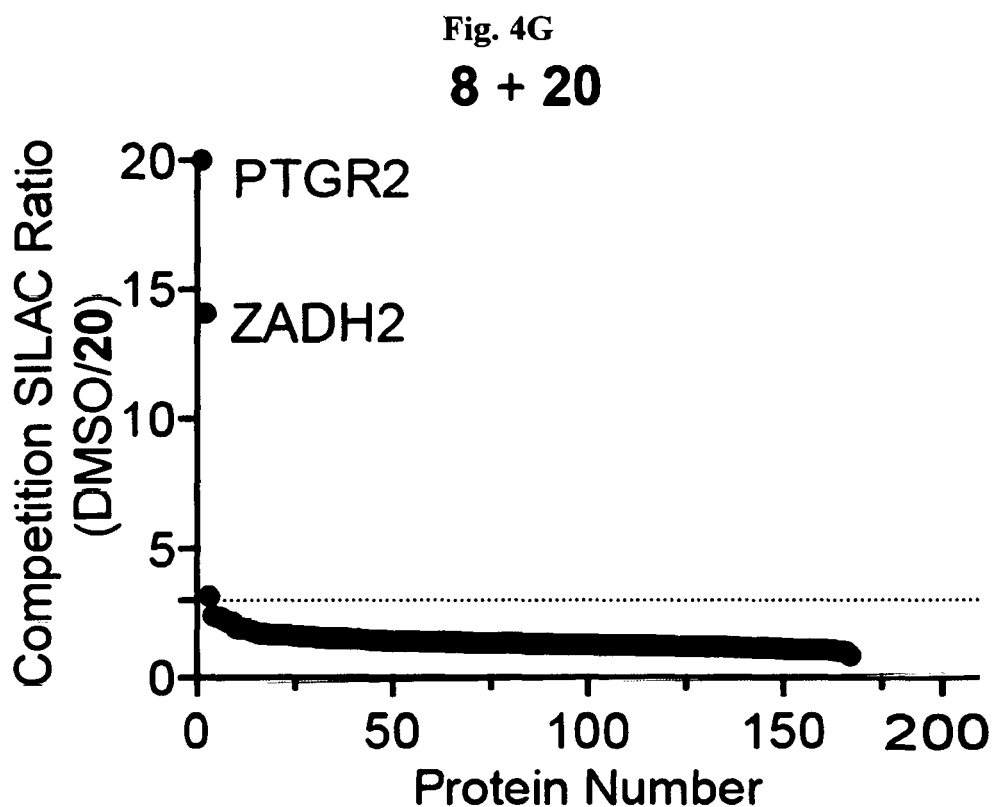
Figure 4I:
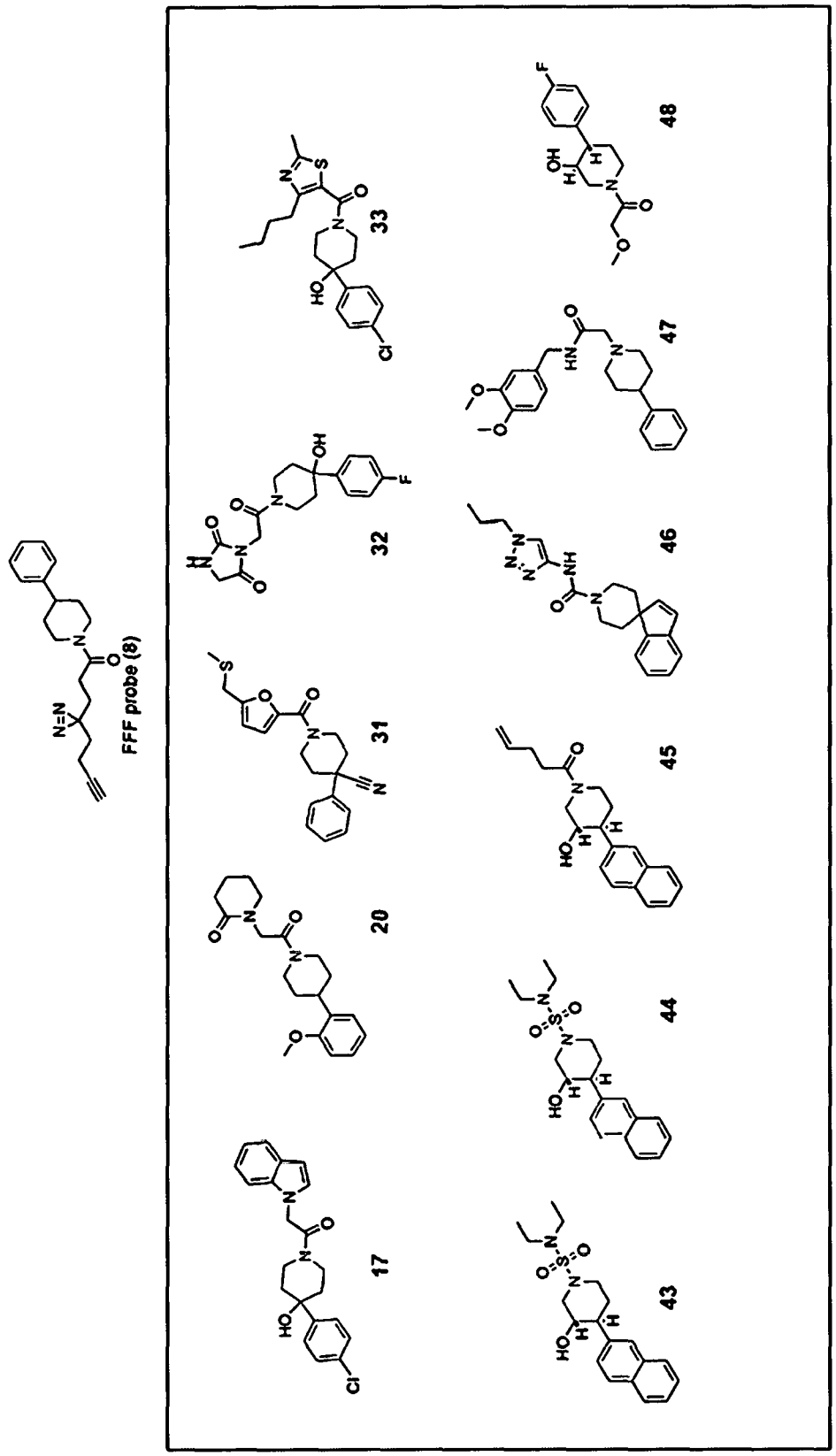
Figure 4J:
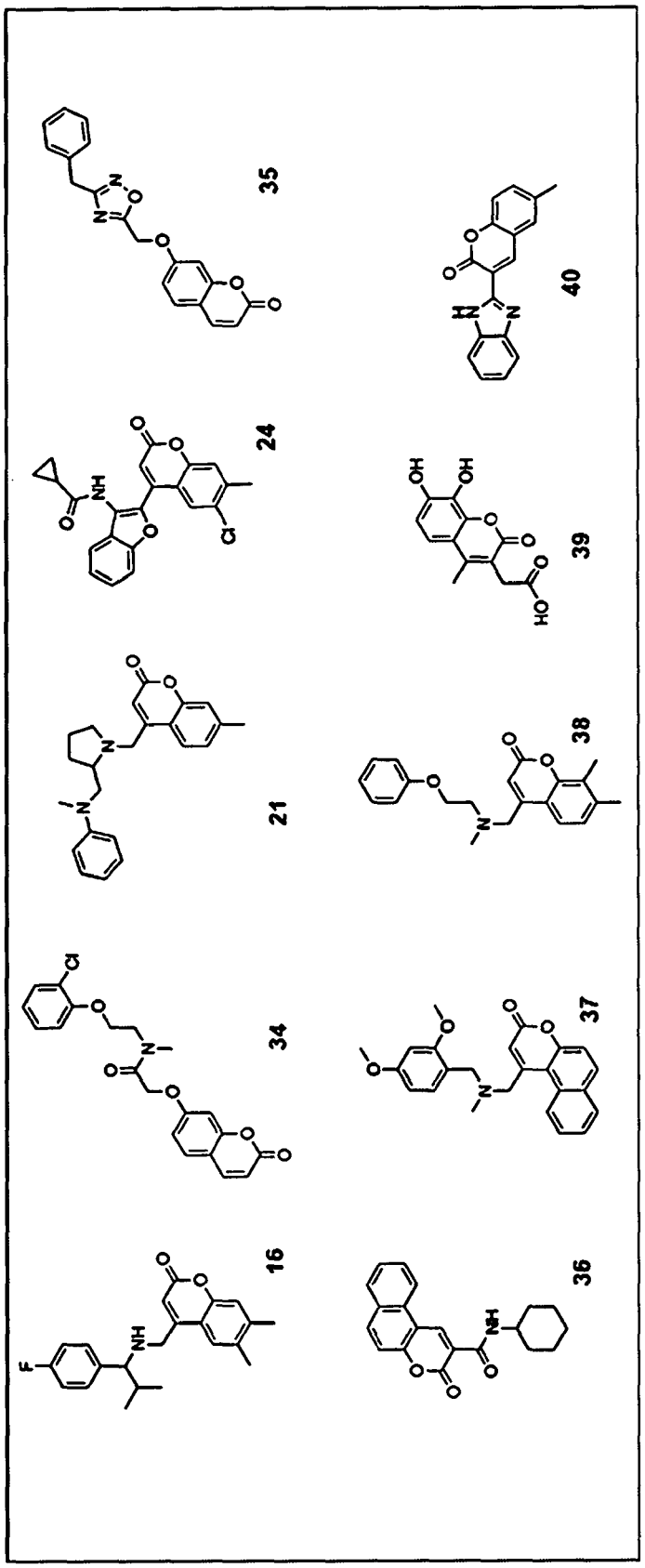
Figure 4K:
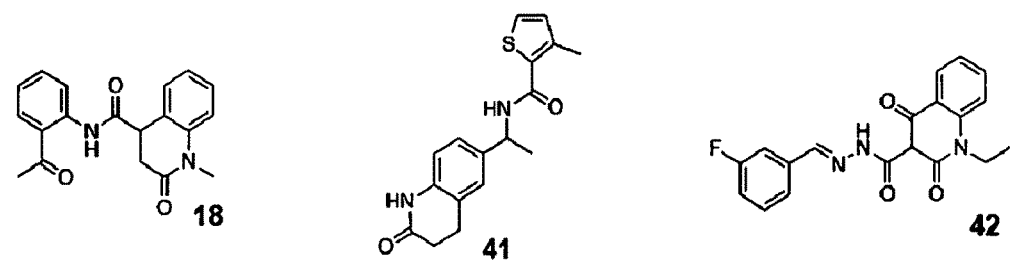
Figure 4L:
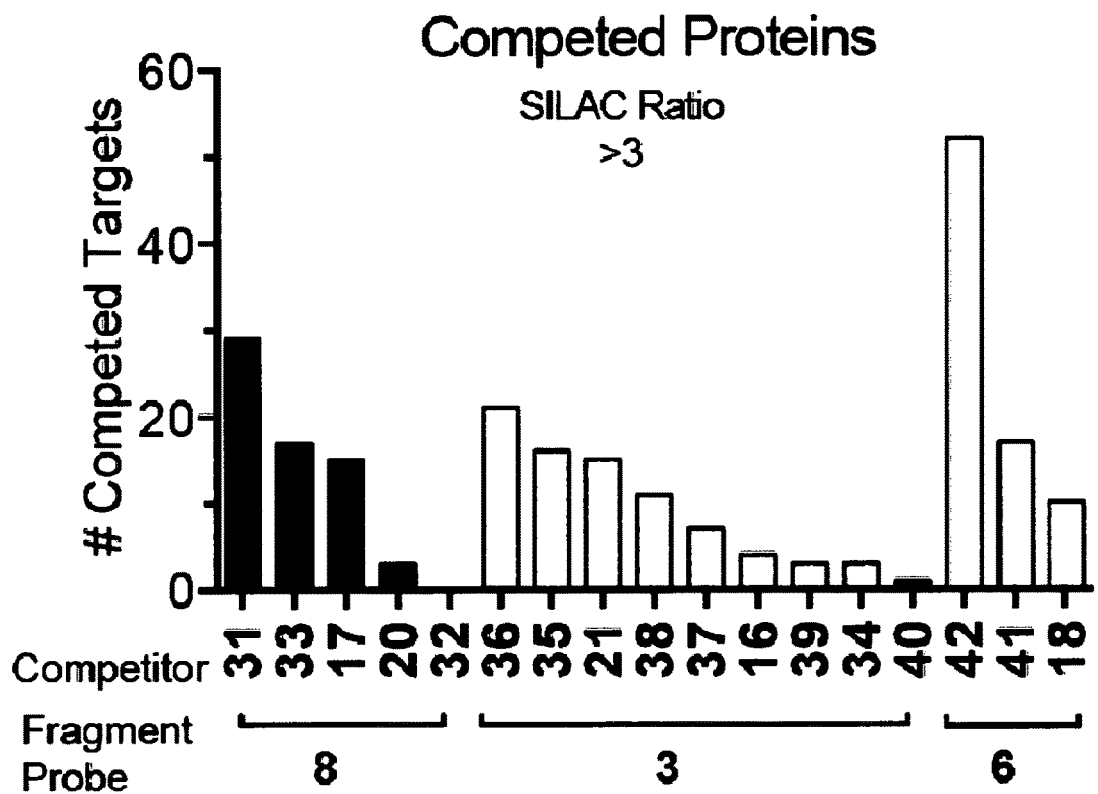
Figure 4M:
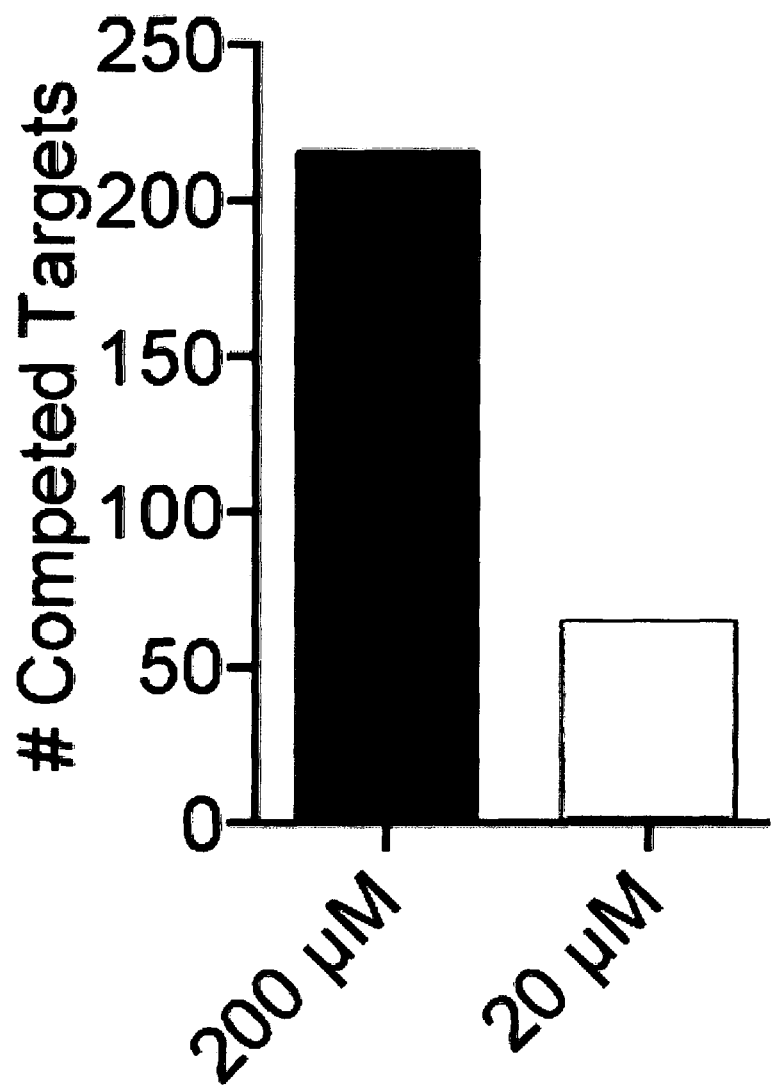

Another 215 competed targets were mapped in experiments where a subset of the competitors (five total) was tested against higher concentrations of the corresponding FFF probes (200 µM) (FIG. 4M). A greater representation of DrugBank proteins was noted for competed targets identified with low (20 µM) versus high (200 µM) concentrations of FFF probes (43% and 20%, respectively) (FIG. 4E). These results exemplify that performing small-molecule competition studies with higher concentrations of FFF probes, where a much greater proportion of probe targets are enriched and quantified (FIG. 2O), increases not only the total number of identified competed protein targets, but also the fraction of these targets that represent heretofore unliganded proteins. Finally, the competed protein targets exemplified a broad functional class distribution generally matching that found for the greater collection of FFF targets (FIG. 4F), exemplifying that high-occupancy small-molecule interactions were not biased toward a specific category of protein in human cells.

Figure 5A:
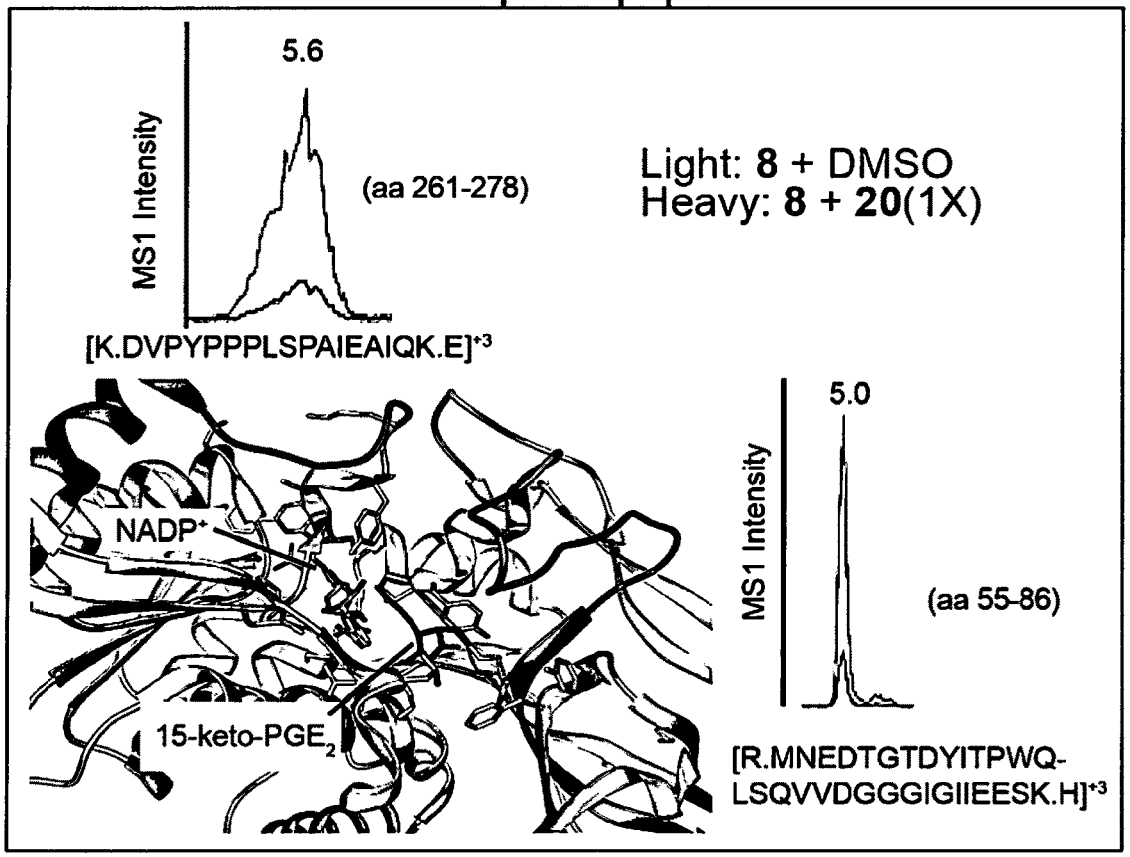
FIG. 5A-FIG. 5S exemplify fragment-derived ligands disrupt function of PTGR2 and SLC25A20 in human cells.
Figure 5B:
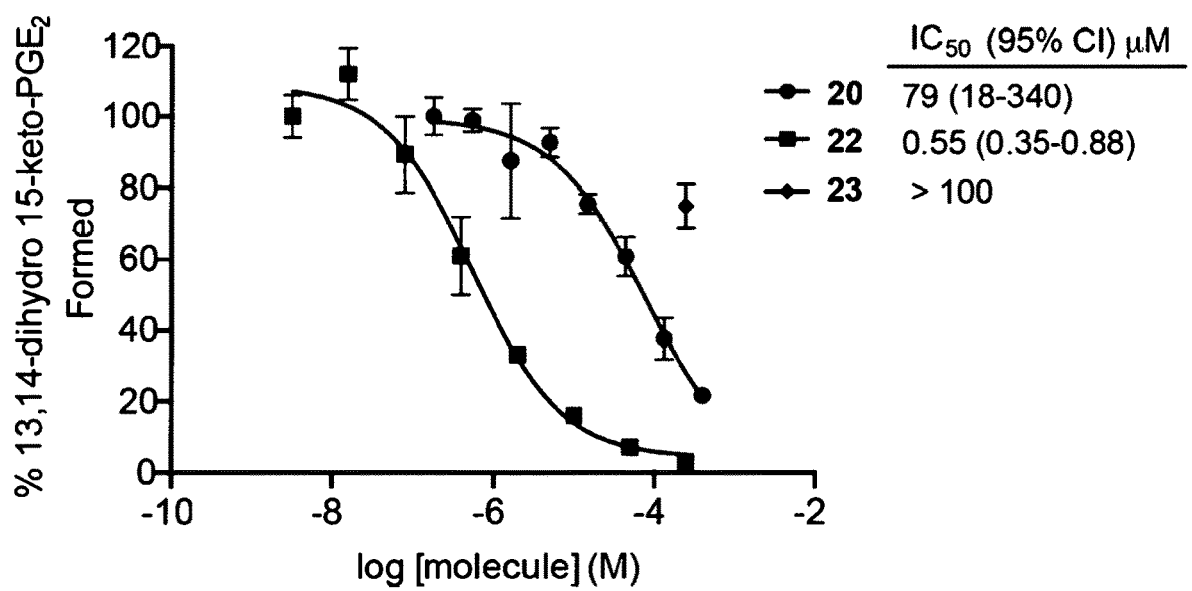
FIG. 5B exemplifies PTGR2 ligands 22 and 20 but not inactive control 23, inhibited 15-keto prostaglandin E2 (15-keto-PGE2) reductase activity of recombinant PTGR2. Data represent average values±SD; n=3 per group.
Figure 5C:
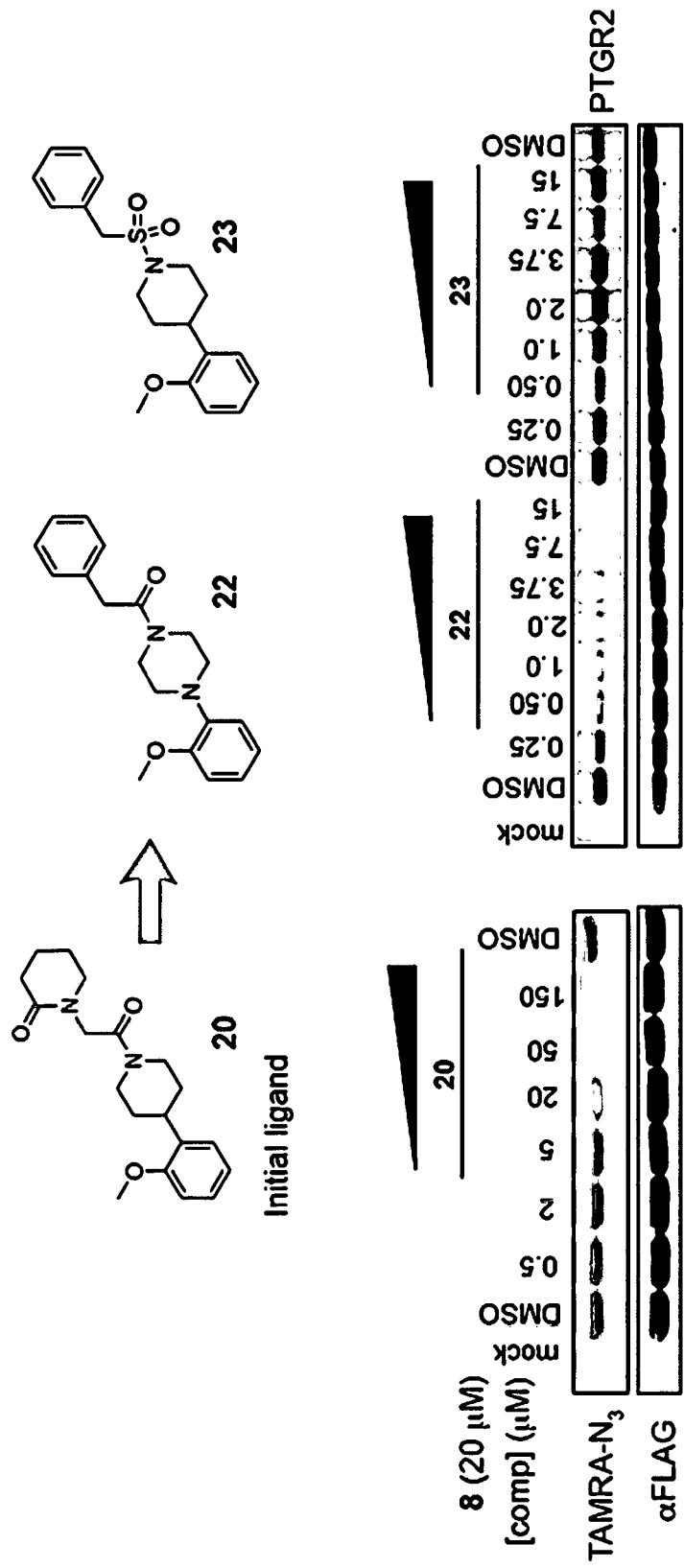
FIG. 5C exemplifies structures (top) and activities (bottom gels) of initial PTGR2 ligand 20, optimized ligand 22, and inactive analog 23. Gels show concentration-dependent competitor blockade of FFF 8 labeling of recombinantly expressed FLAG-tagged PTGR2 in HEK29T cells.
Figure 5D:
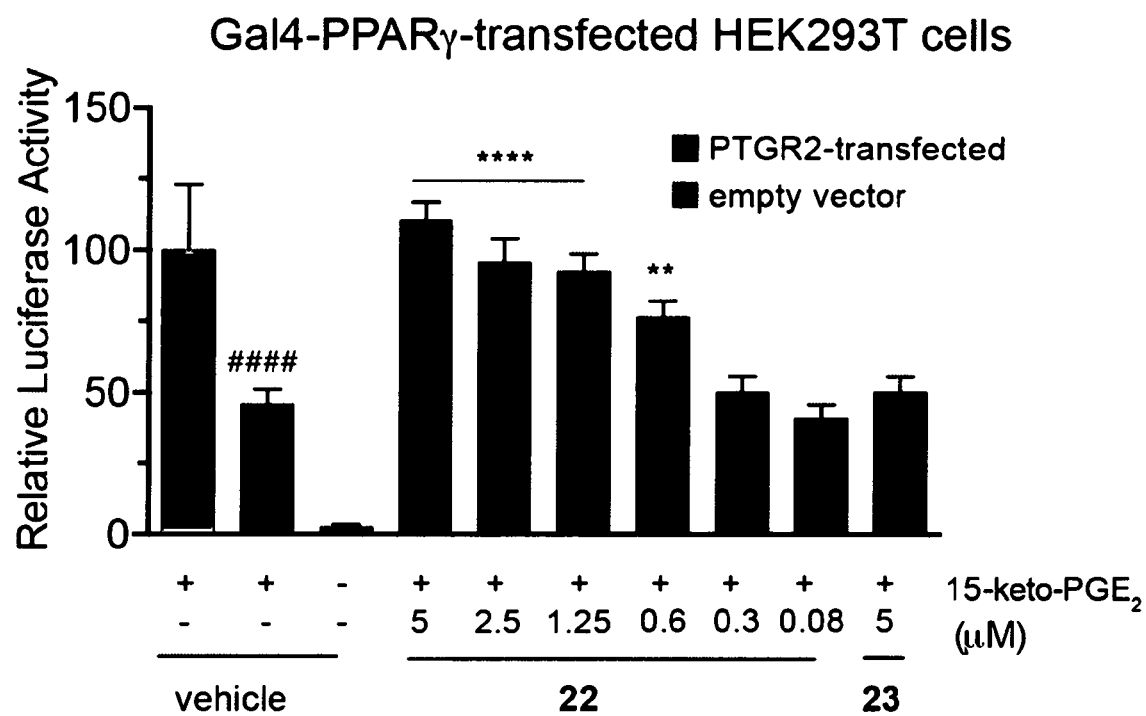
FIG. 5D exemplifies compound 22, but not inactive control 23, increased 15-keto-PGE2-dependent PPARγ transcriptional activity in PTGR2-transfected HEK293T cells. Data represent average values±SD; ####p<0.0001 for 15k-PGE2-treated PTGR2-transfected cells versus empty vector group, **p<0.0001 for compound- versus DMSO-treated groups; n=3 per group.
Figure 5E:
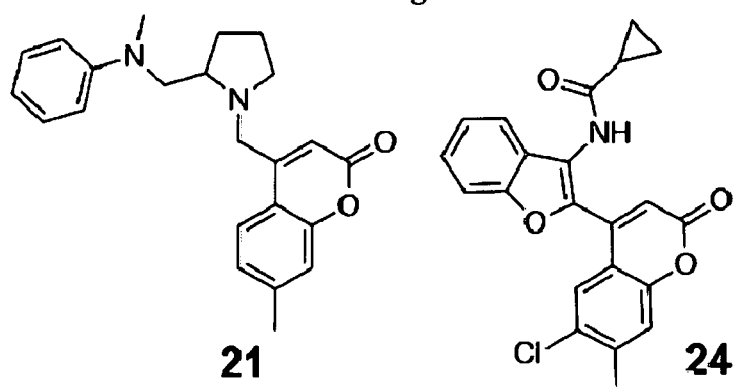
FIG. 5E exemplifies structures (top) and activities (bottom gels) of SLC25A20 ligand 21 and inactive analog 24. Gel shows concentration-dependent competitor blockade of FFF 3 labeling (20 μM) of recombinantly expressed FLAG-tagged SLC25A20 in HEK29T cells.
Figure 5E:
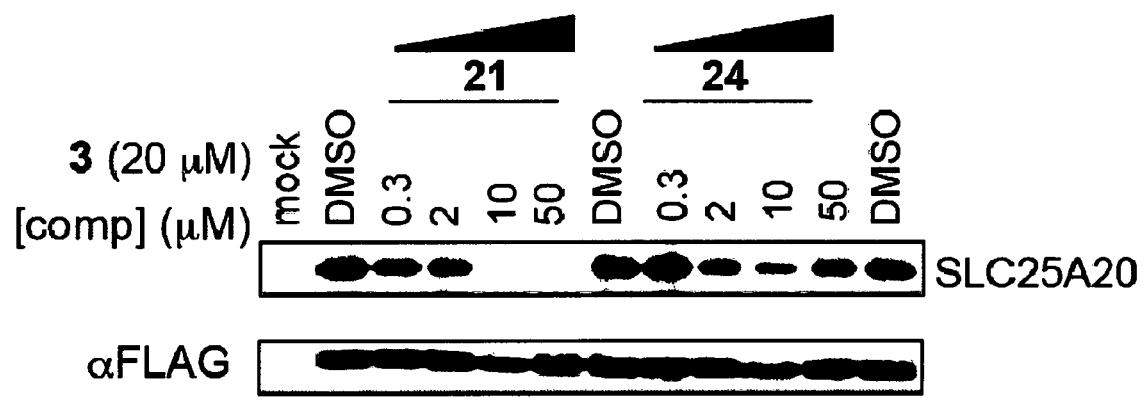
Figure 5F:
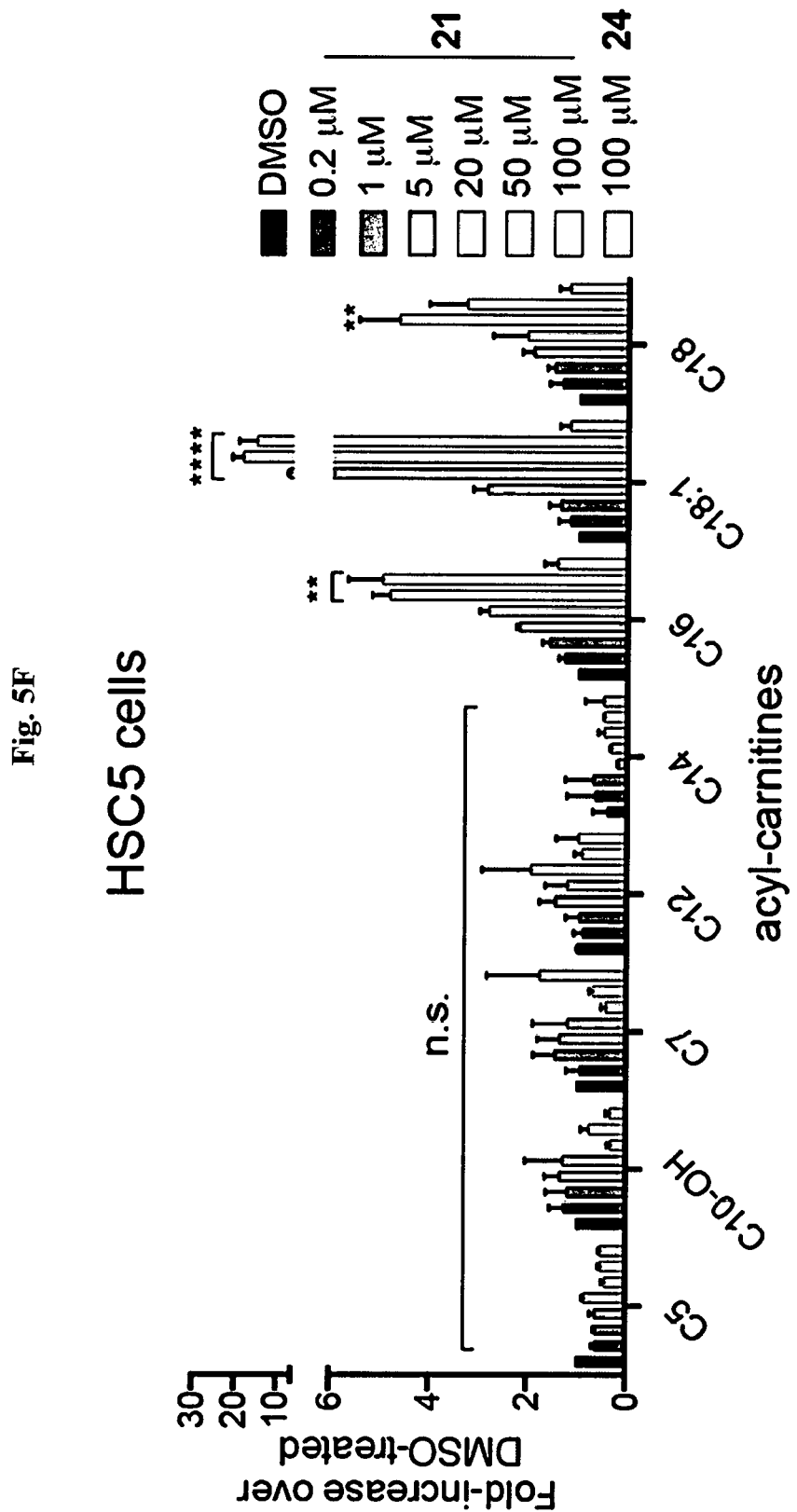
(FIG. 5F, FIG. 5G) Compound 21, but not 24, increases long-chain (>C14) acylcarnitine content (FIG. 5F) and reduces maximal exogenous fatty acid oxidation (FIG. 5G) of HSC-5 cells. Data represent average values±SD; p<0.01 and ****p<0.0001 for compound- versus DMSO-treated groups; n=3-5 per group.
Figure 5G:
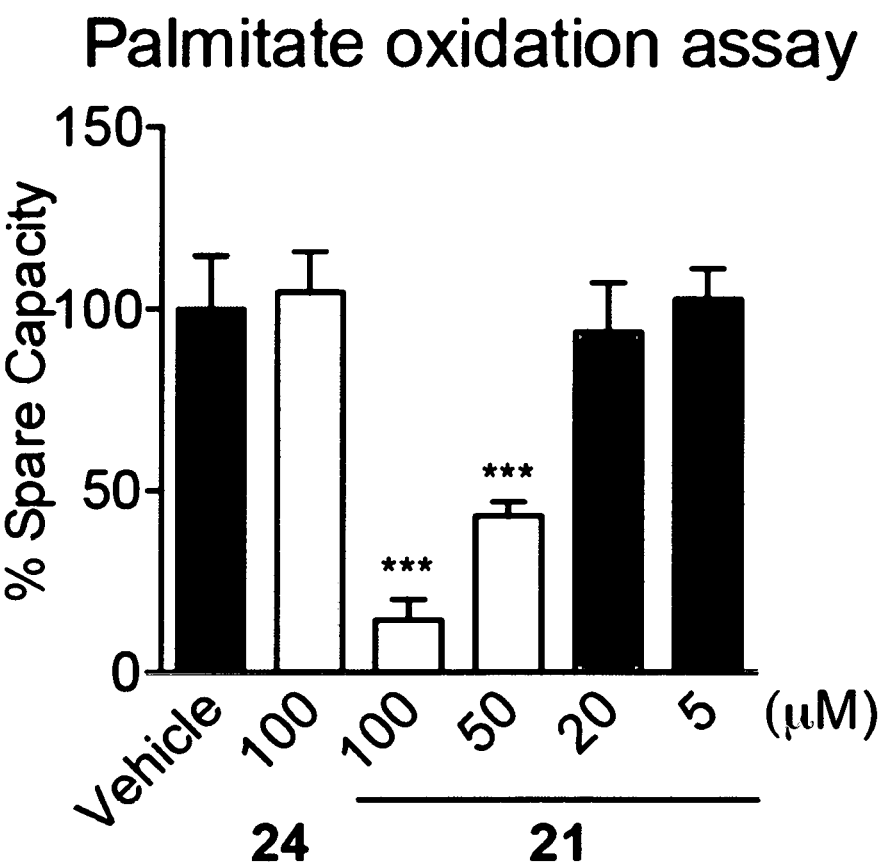
Figure 5H:
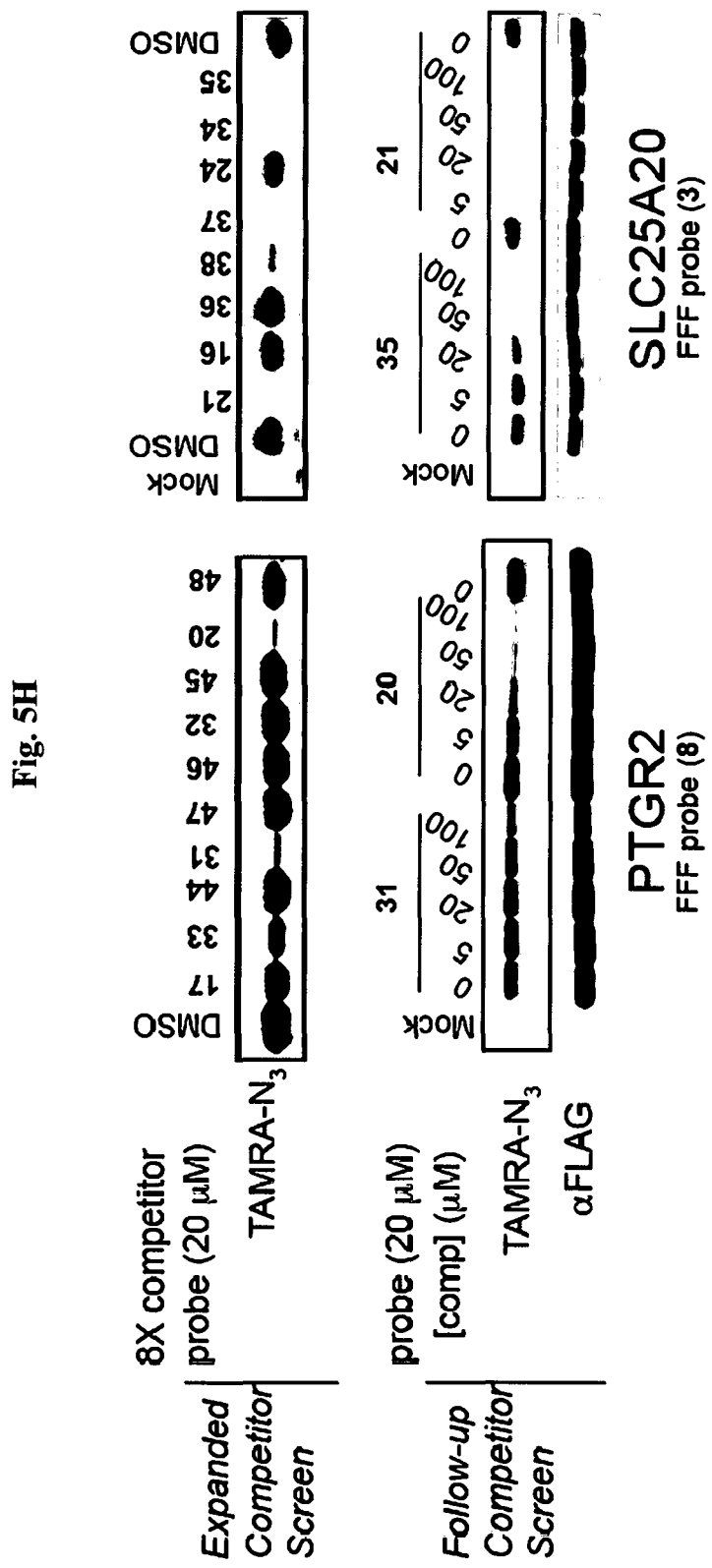
FIG. 5H exemplifies expanded screen of competitor compounds by monitoring reductions in FFF probe labeling of recombinantly expressed, FLAG-tagged human PTGR2 and SLC25A20 in HEK293T cells.
Figure 5I:
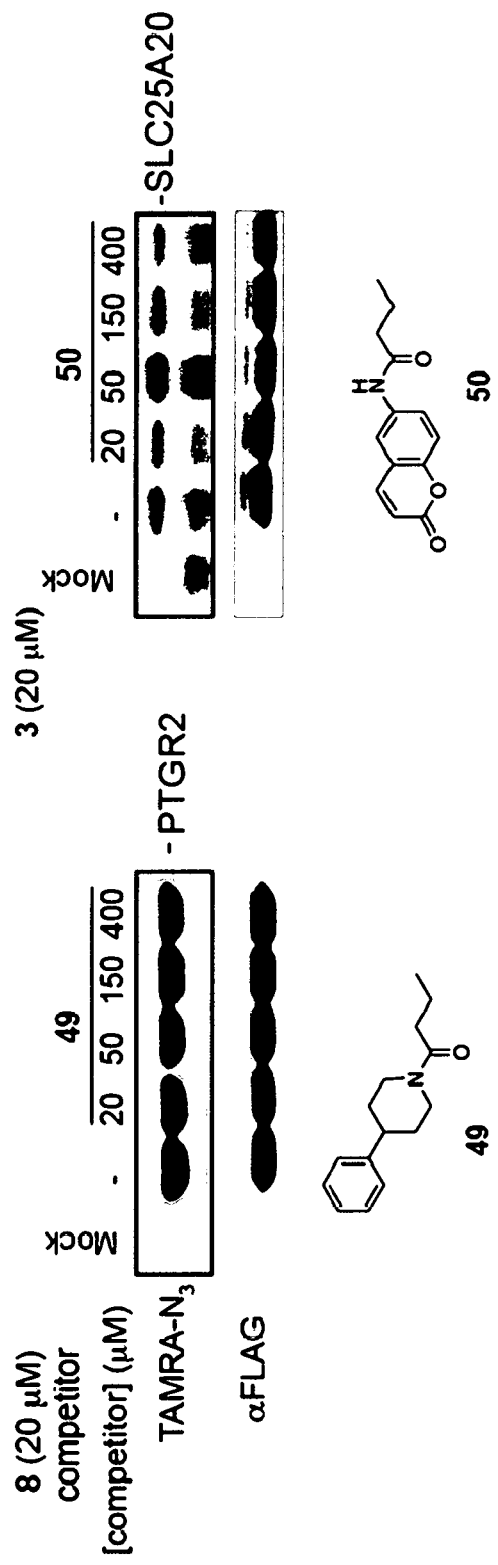
FIG. 5I exemplifies competition gel profiles for competitor compounds corresponding to fragment elements from FFF probes 8 (competitor 49 for PTGR2) and 3 (competitor 50 for SLC25A20).

For determining if the discovered small-molecule ligands affected protein functions, one enzyme (PTGR2) and one transporter (SLC25A20) were selected for which distinct high-occupancy ligands were identified in competitor profiling experiments (FIG. 4G, FIG. 4H). These proteins also have important roles in human metabolism, but lack selective, cell-active inhibitors. Gel-based competitor profiling of recombinant PTGR2 and SLC25A20 (FIG. 5H) exemplified the preferential binding of ligands determined by MS-based proteomics (20 for PTGR2 and 21 for SLC25A20; FIG. 4G, FIG. 4H). Competitor molecules containing only the fragment head groups of FFF probes did not appreciably block probe labeling of PTGR2 and SLC25A20 (FIG. 5I). These results exemplify that chemical proteomics discover weak fragment-protein interactions in cells and, through competitive profiling of structurally elaborated fragment analogues, efficiently identify compounds that display superior protein binding.

Figure 5J:
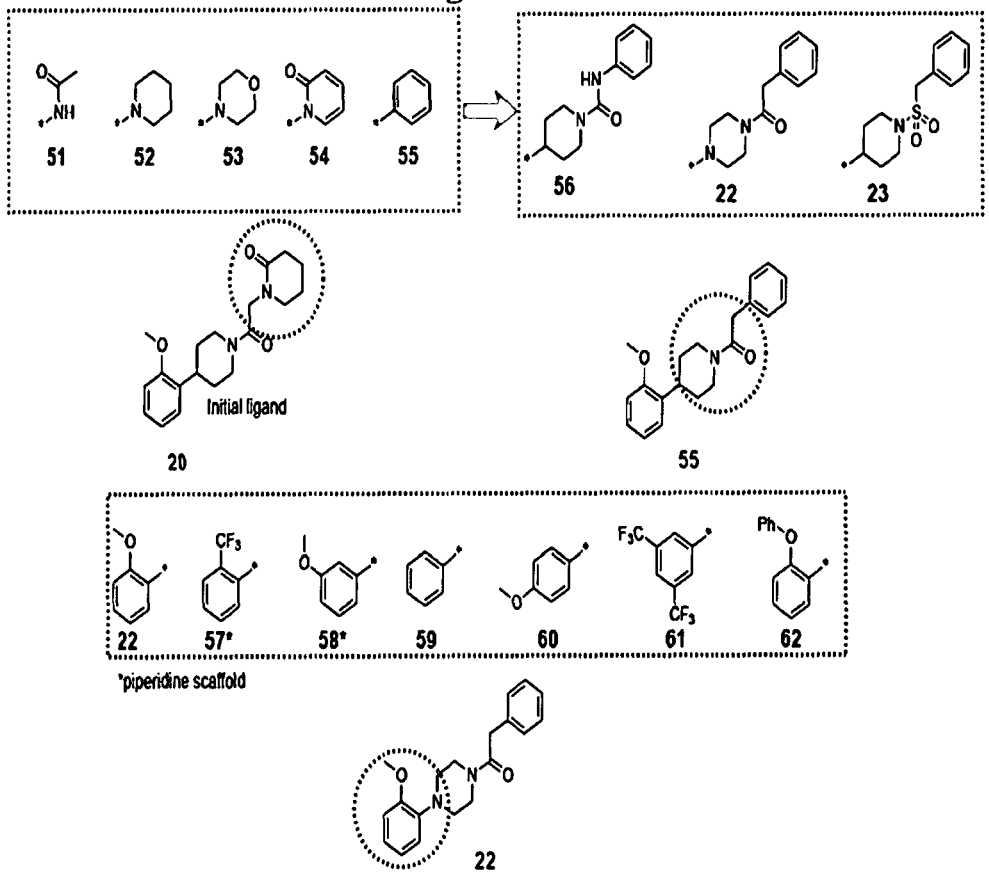
FIG. 5J exemplifies optimization of PTGR2 inhibitors. Upper images show structures of analogs of lead inhibitor 20 that were synthesized and tested. Lower image shows competition gel profiles for these analogs with human PTGR2 expressed in HEK293T cells.
Figure 5J:
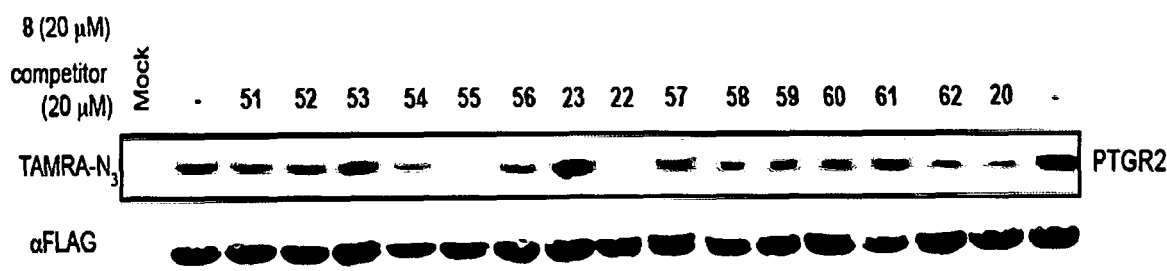

PTGR2, or prostaglandin reductase 2, catalyzes the NADPH-dependent reduction of 15-keto-PGE2 to 13,14-dihydro-15-keto-PGE2 and regulates adipogenesis through restricting 15-keto-PGE2 activity as a natural ligand for the nuclear receptor PPARγ. The only reported inhibitor of PTGR2 is the NSAID drug indomethacin, which exhibits a very weak in vitro IC50 value of ~200 µM. Probe 8 modified two active site-proximal peptides in PTGR2, and these reactions were sensitive to competition by 20 (FIG. 5A), which also inhibited PTGR2-mediated reduction of 15-keto-PGE2 with an IC50 value of 79 µM (FIG. 5B). A screen of structural analogues of 20 exemplified that substitution of the lactam ring with a phenyl group and conversion of the piperidine core to a piperazine furnished 22 (FIG. 5C and FIG. 5J), which showed substantially increased potency (>20-fold) in assays measuring either competition of 8-labeling (FIG. 5C) or 15-keto-PGE2 reductase activity (IC50=0.6 µM; FIG. 5B) of recombinant PTGR2. An inactive analogue 23 was also identified, which did not affect labeling of PTGR2 by 8 (FIG. 5C and FIG. 5J) or PTGR2 catalytic activity (FIG. 5B).

Figure 5M:
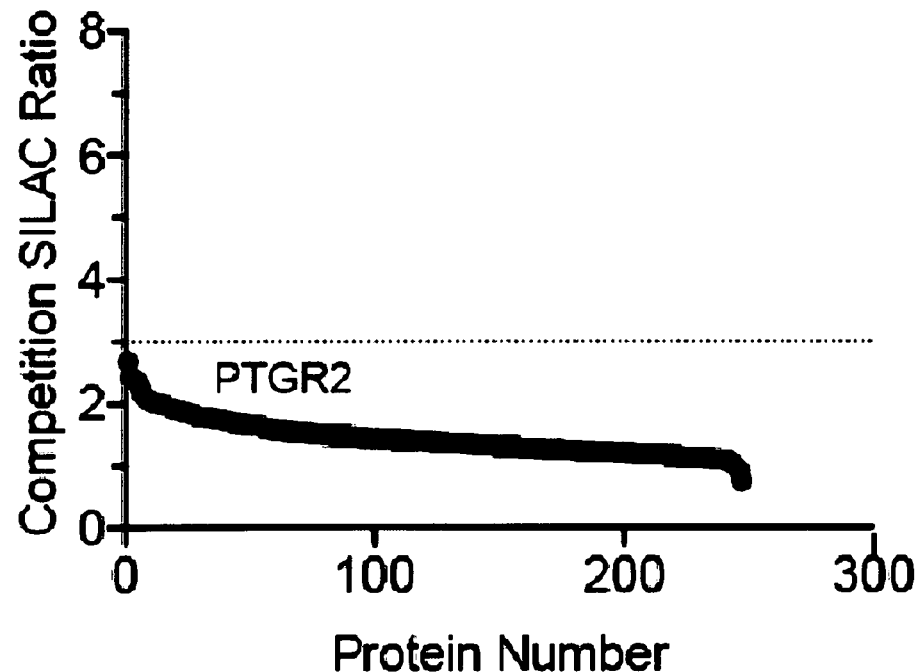
Figure 5N:
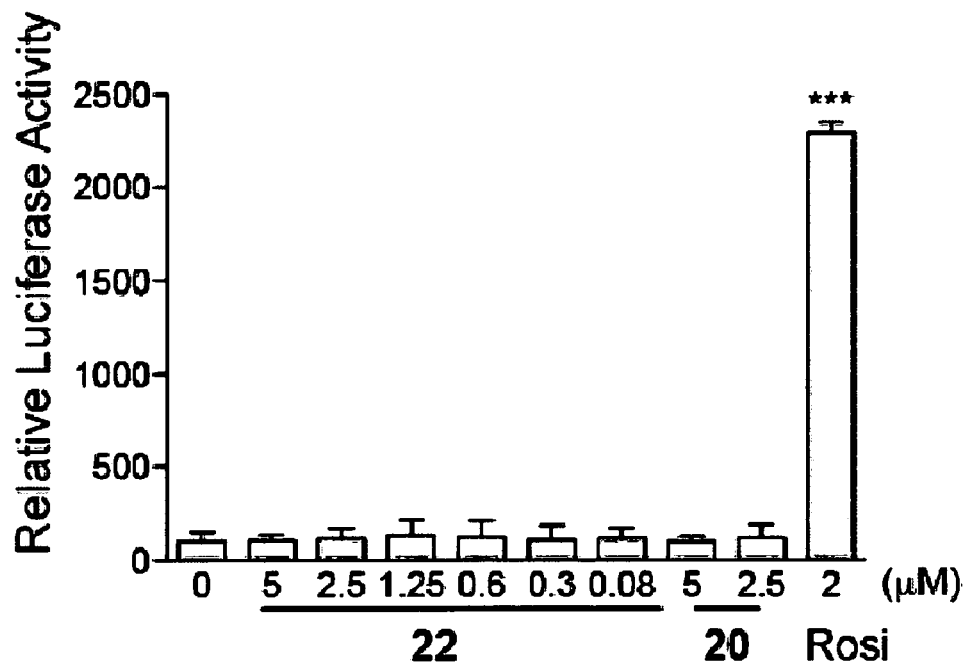
FIG. 5N exemplifies PTGR2 ligands 20 and 22 do not directly induce PPARγ transcriptional activity in HEK293T cells co-transfected with a GAL4-PPARγ luciferase reporter and an empty control vector.
Figure 5O:
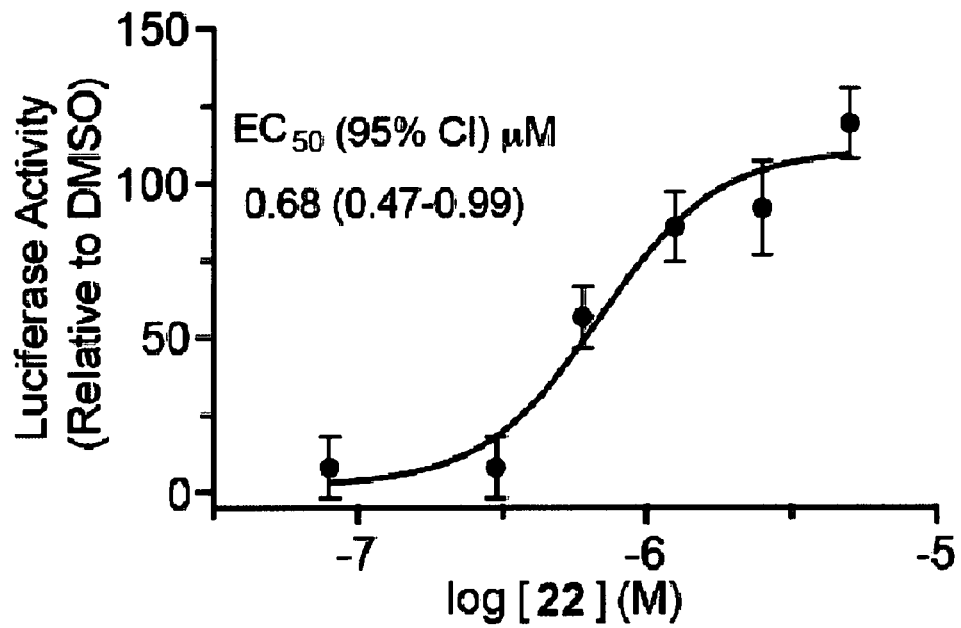
FIG. 5O exemplifies fitted full dose-response of data exemplified in FIG. 5D.

Compound 22, but not 23, blocked FFF 8 labeling of endogenous PTGR2 in HEK293T cells with good potency (complete inhibition at 5 µM and ~80% inhibition at 500 nM) and excellent selectivity (FIG. 5K-FIG. 5M). 22 did not cross-react with ZADH2 (FIG. 5L), a sequence-related homologue of PTGR2 that was a principal off-target of 20 (FIG. 4G). Addition of 22 also produced a concentration-dependent rescue of 15-keto-PGE2-dependent PPARγ transcriptional activity in cells recombinantly expressing PTGR2 (FIG. 5D); in contrast, the inactive control compound 23 showed no effect (FIG. 5D). Neither 22 nor 23 directly modulated PPARγ (FIG. 5N). The $IC_{50}$ value displayed by 22 for inhibition of PTGR2 in cells was ~0.7 µM (FIG. 5O), which meets the criterion for in situ activity of chemical probes put forth by the Structural Genomics Consortium.

Figure 5P:
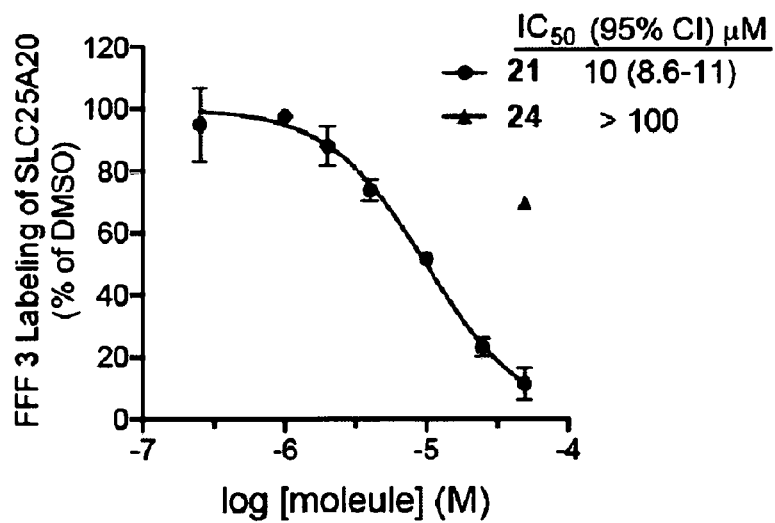
FIG. 5P exemplify fitted $IC_{50}$ curve for the concentration-dependent blockade of 3 (20 μM) labeling of SLC25A20 expressed in HEK293T cells by 21 with representative competition gel shown below. Data represent average values±SD; n=3 per group.
Figure 5Q:
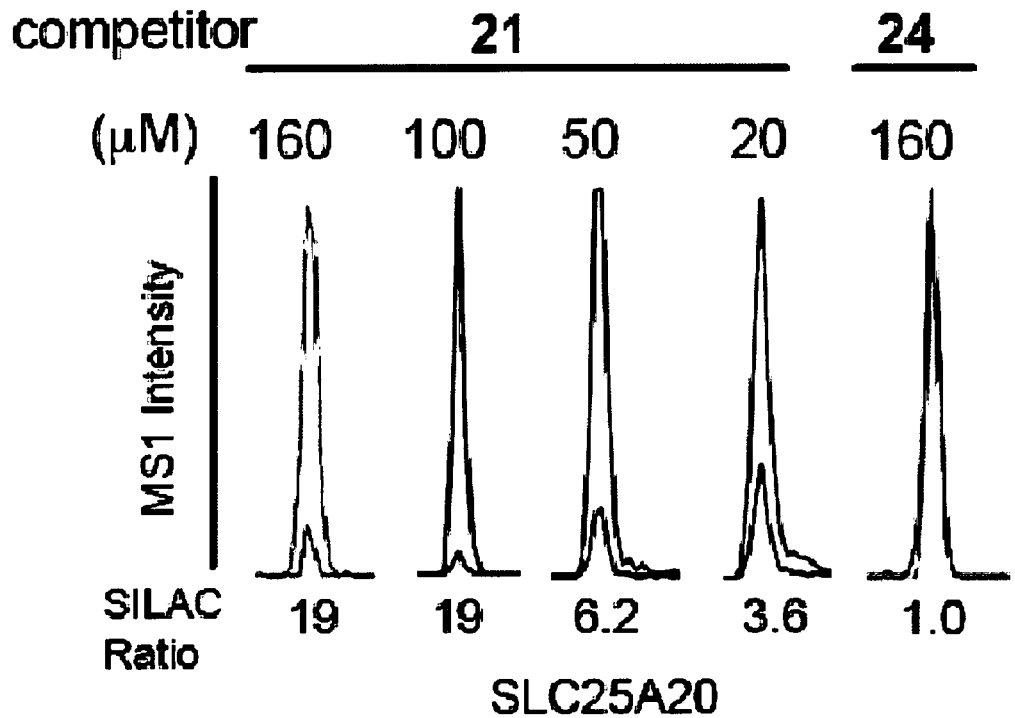
FIG. 5Q exemplify extracted MS1 chromatograms and corresponding SILAC ratios for representative tryptic peptides of SLC25A20 from competition experiments with the indicated compounds at the indicated concentrations.

SLC25A20 is a multi-pass transmembrane protein that transports long-chain acylcarnitines into the mitochondrial matrix, where these lipids provide fatty acid substrates for β-oxidation. There are no selective small-molecule probes to study SLC25A20 function in human cells. The quantitative MS experiments exemplified SLC25A20 as a primary target of the elaborated coumarin-based competitor 21 (FIG. 4H), and this interaction was confirmed for recombinant SLC25A20 in HEK293T cells, where 21 blocked FFF probe 3 labeling of SLC25A20 with an $IC_{50}$ of ~10 µM (FIG. 5E). The coumarin-based compound 24 was identified as an inactive control (FIG. 5E, FIG. 5P, and FIG. 5Q).

Figure 5R:
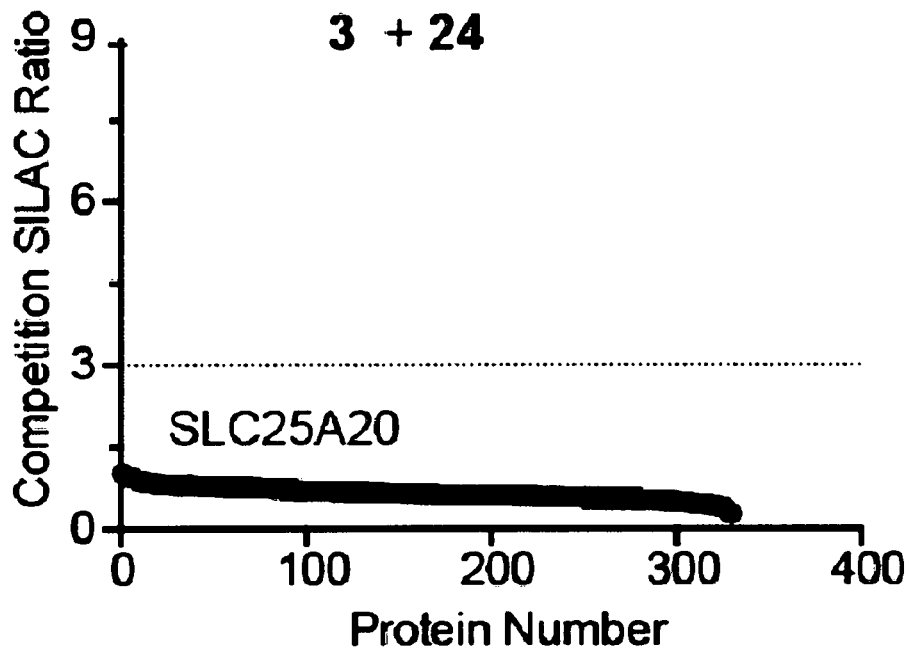
FIG. 5R exemplify competition SILAC plots for inactive control 24 (160 μM) tested with FFF probe 3 (20 μM).
Figure 5S:
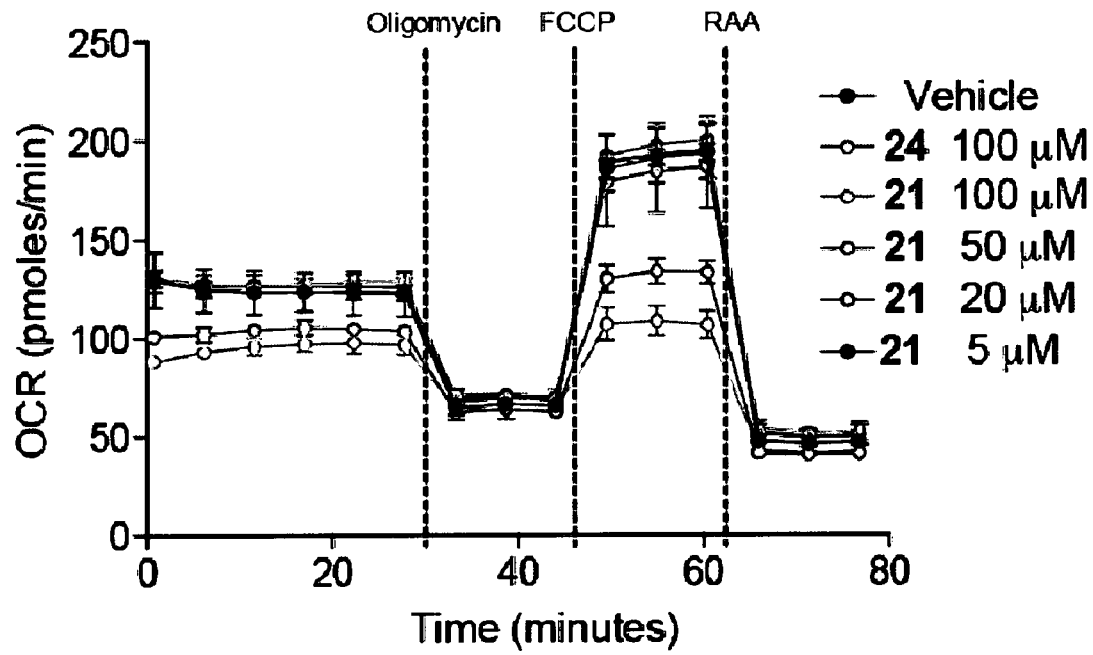
Figure 6A:
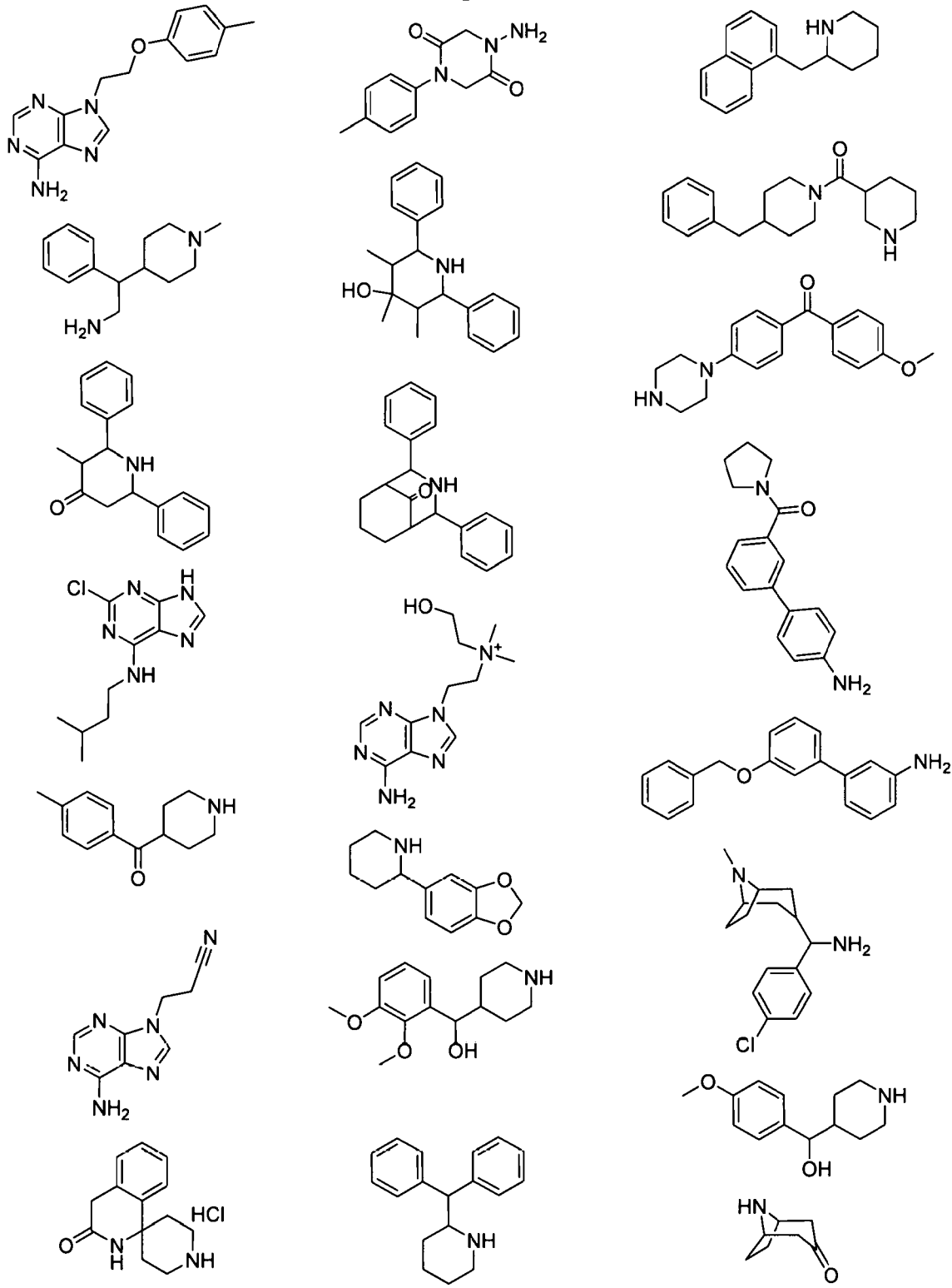
FIG. 6A-J illustrates additional small molecule ligands substituents disclosed herein.
Figure 6B:
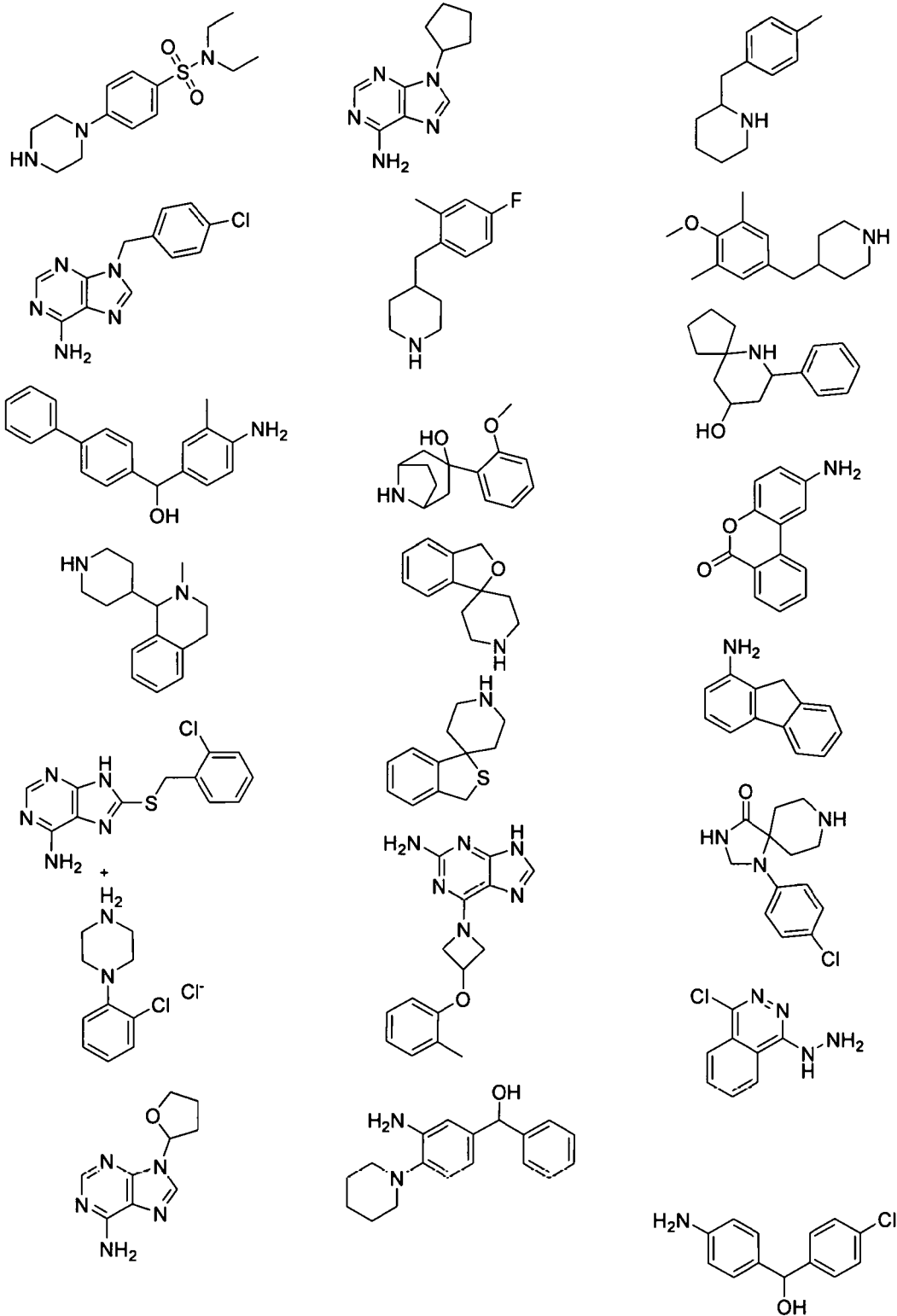
Figure 6C:
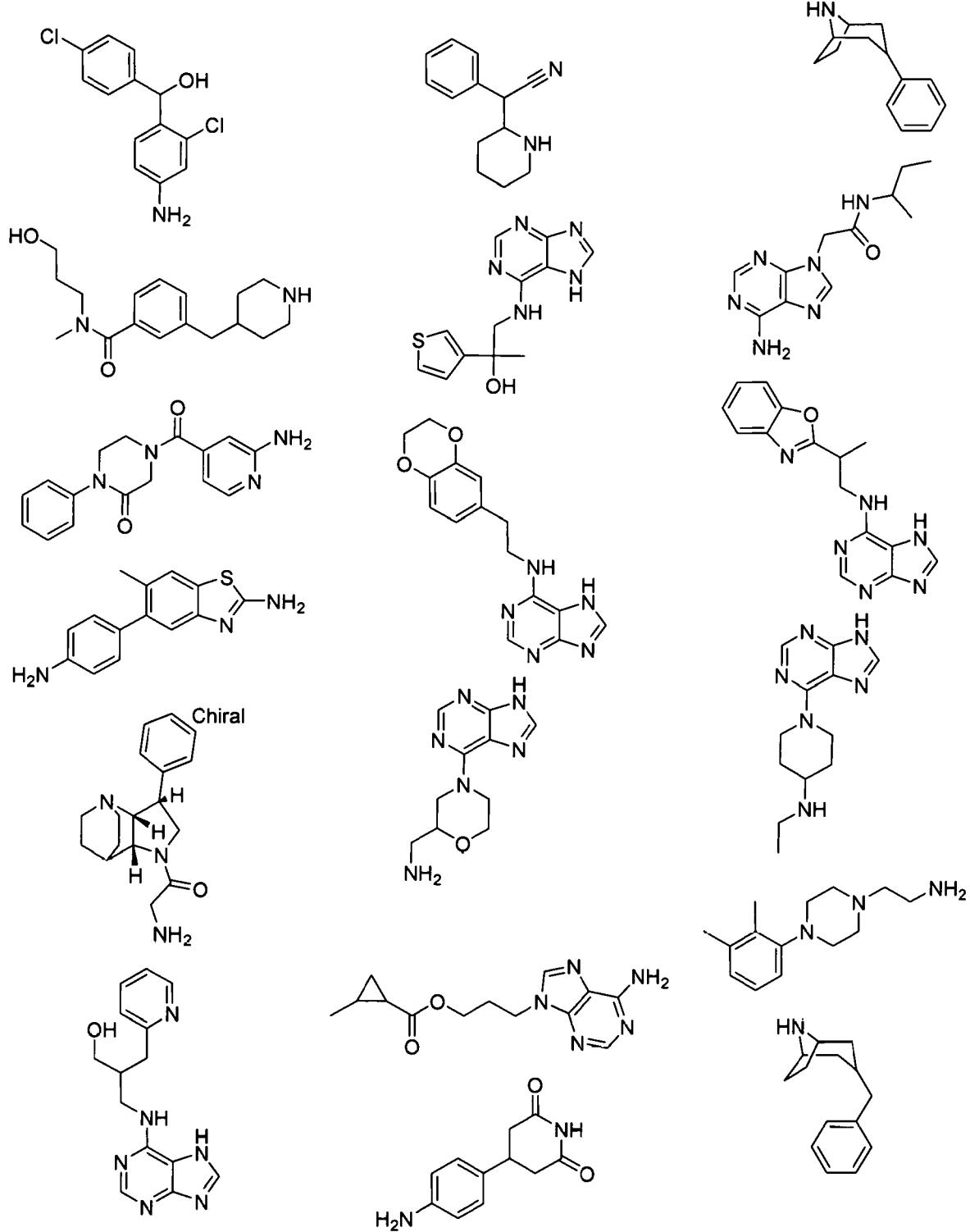
Figure 6D:
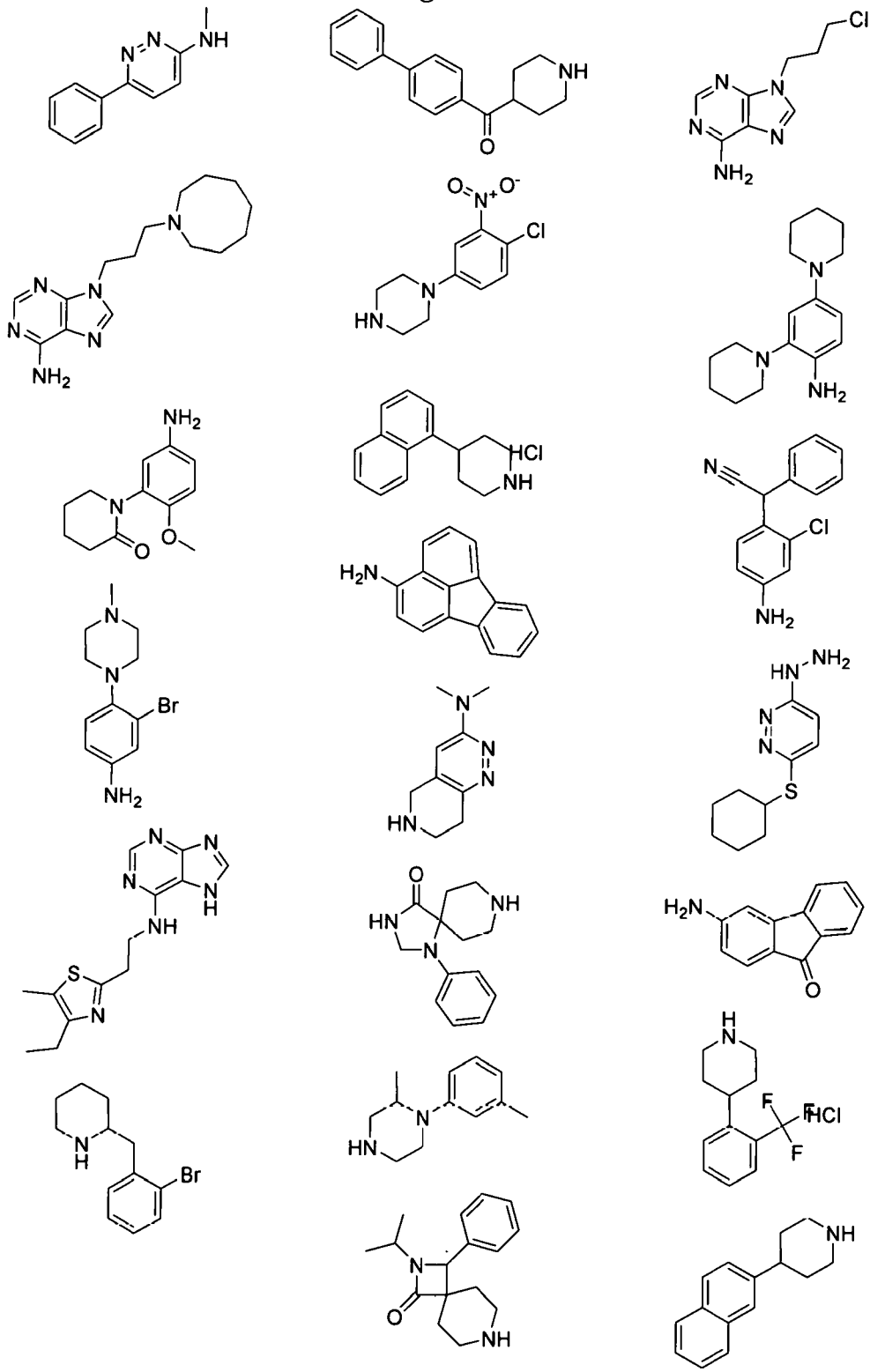
Figure 6E:
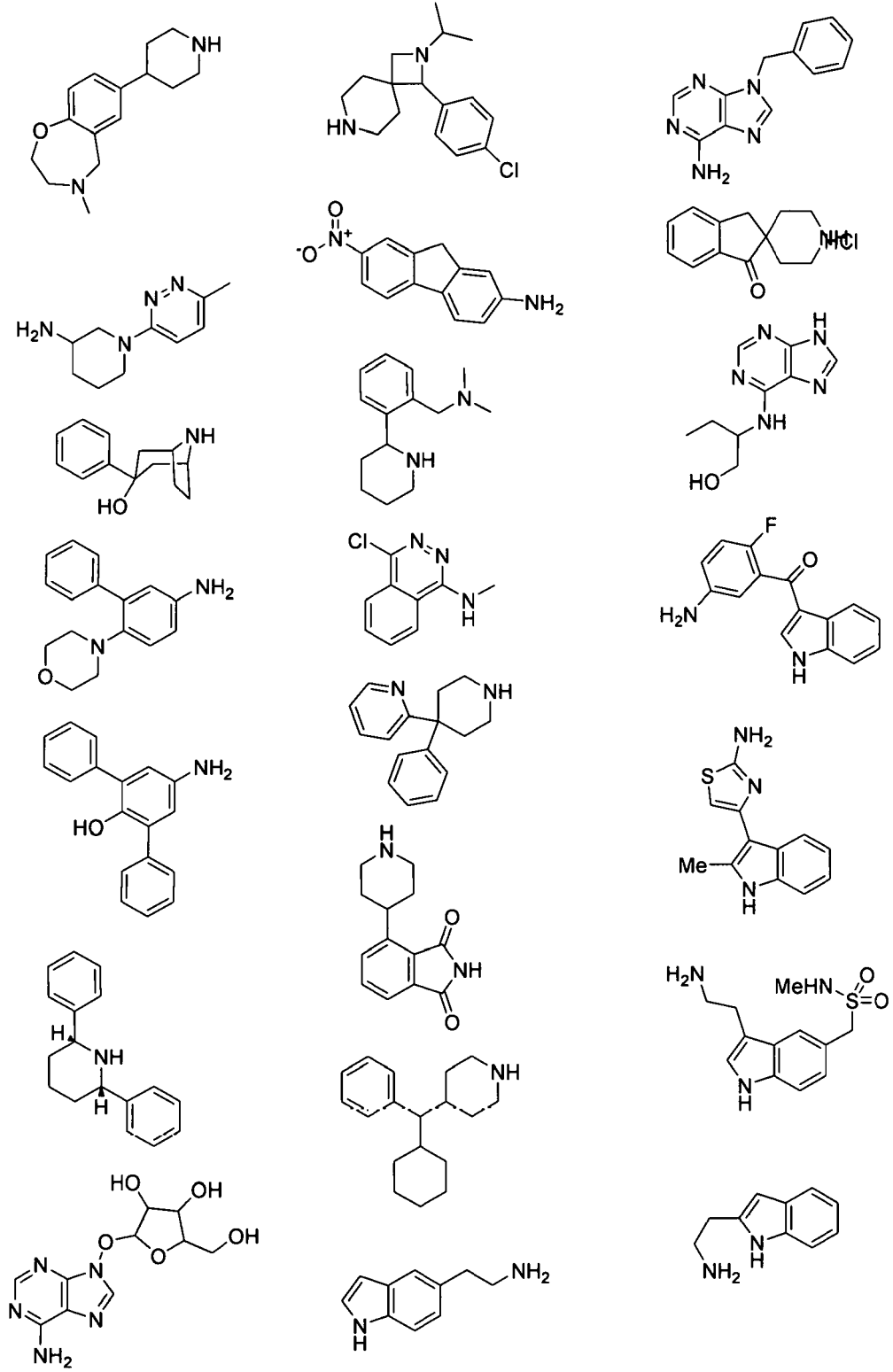
Figure 6F:
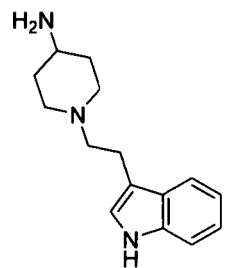
Figure 6F:
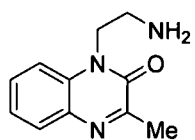
Figure 6F:
Figure 6F:
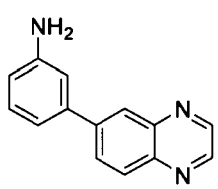
Figure 6F:
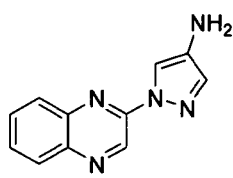
Figure 6F:
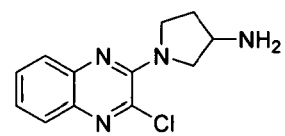
Figure 6F:
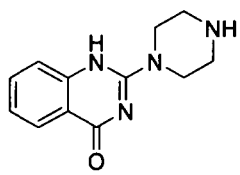
Figure 6F:
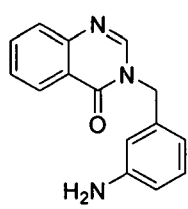
Figure 6F:
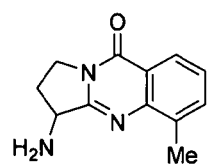
Figure 6F:
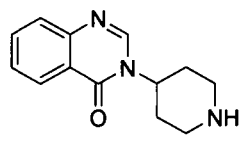
Figure 6F:
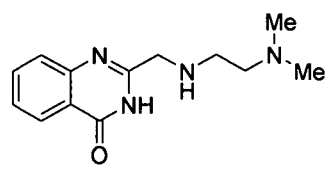
Figure 6F:
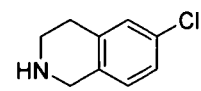
Figure 6F:
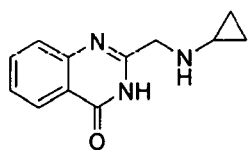
Figure 6F:
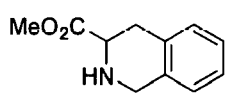
Figure 6F:
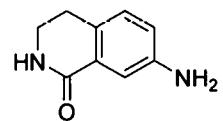
Figure 6F:
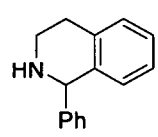
Figure 6F:
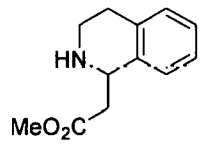
Figure 6F:
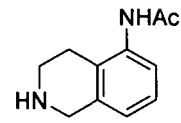
Figure 6F:
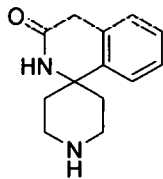
Figure 6F:
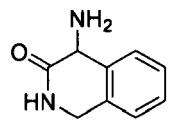
Figure 6F:
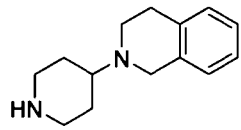
Figure 6G:
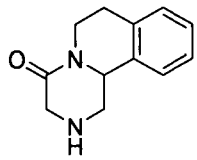
Figure 6G:
Figure 6G:
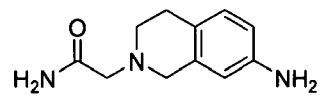
Figure 6G:
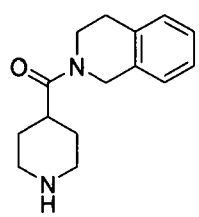
Figure 6G:
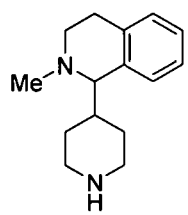
Figure 6G:
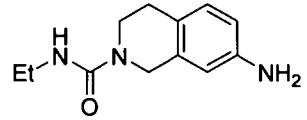
Figure 6G:
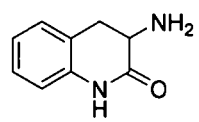
Figure 6G:
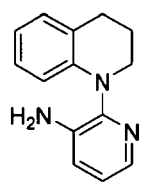
Figure 6G:
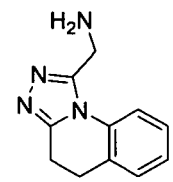
Figure 6G:
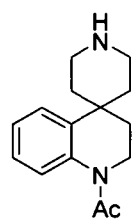
Figure 6G:
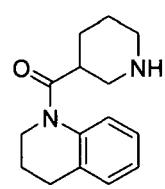
Figure 6G:
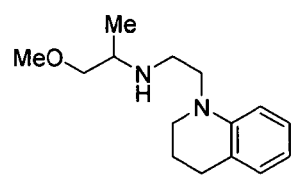
Figure 6G:
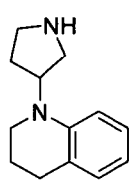
Figure 6G:
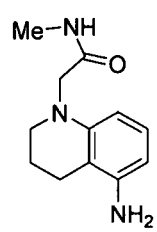
Figure 6G:
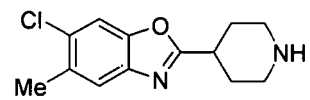
Figure 6G:
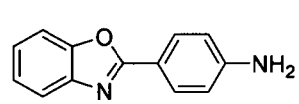
Figure 6G:
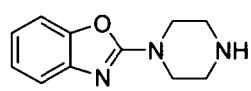
Figure 6G:
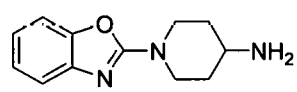
Figure 6G:
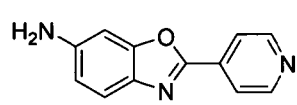
Figure 6G:
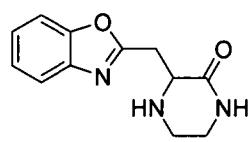
Figure 6G:
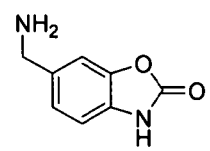
Figure 6H:
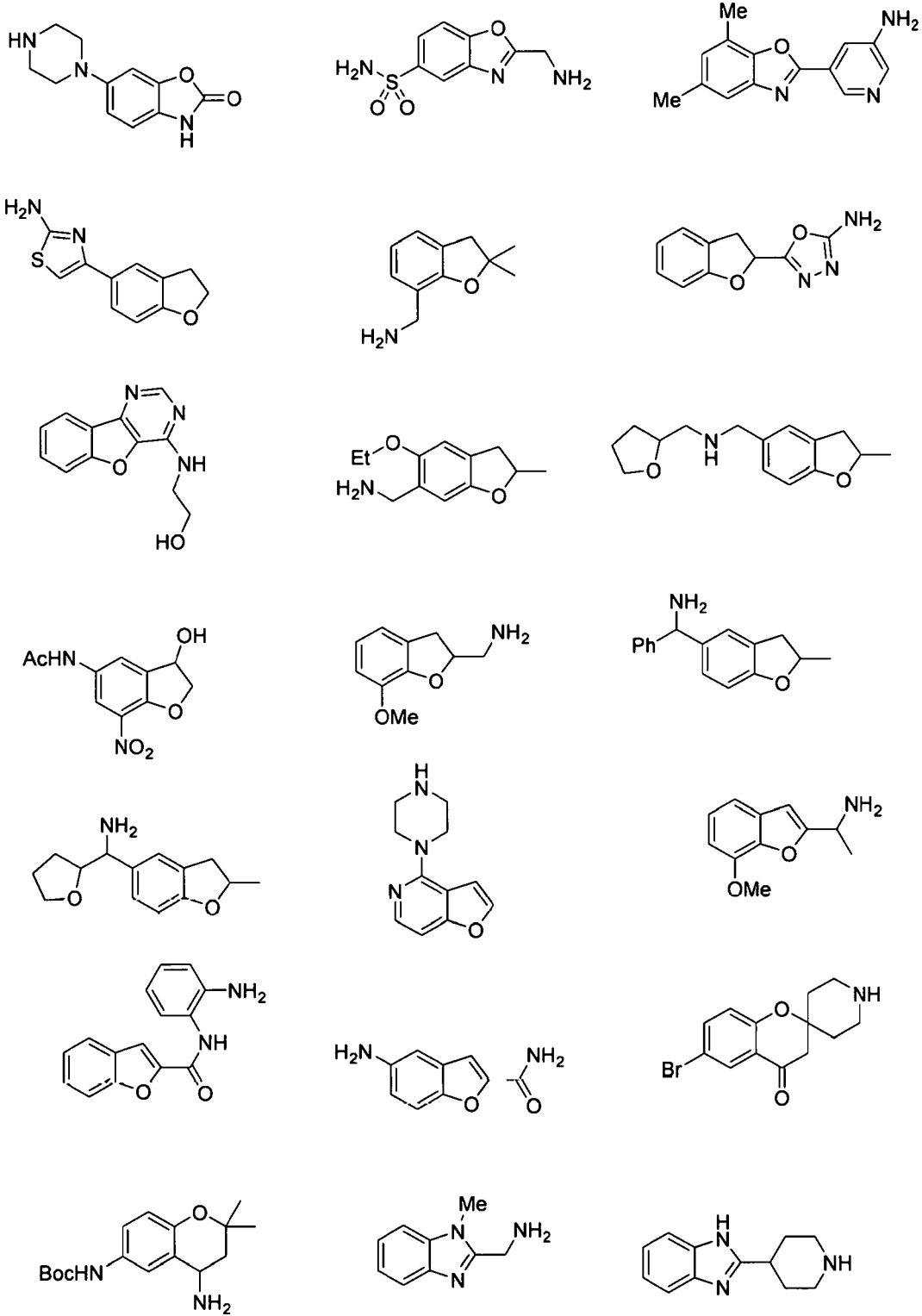
Figure 6I:
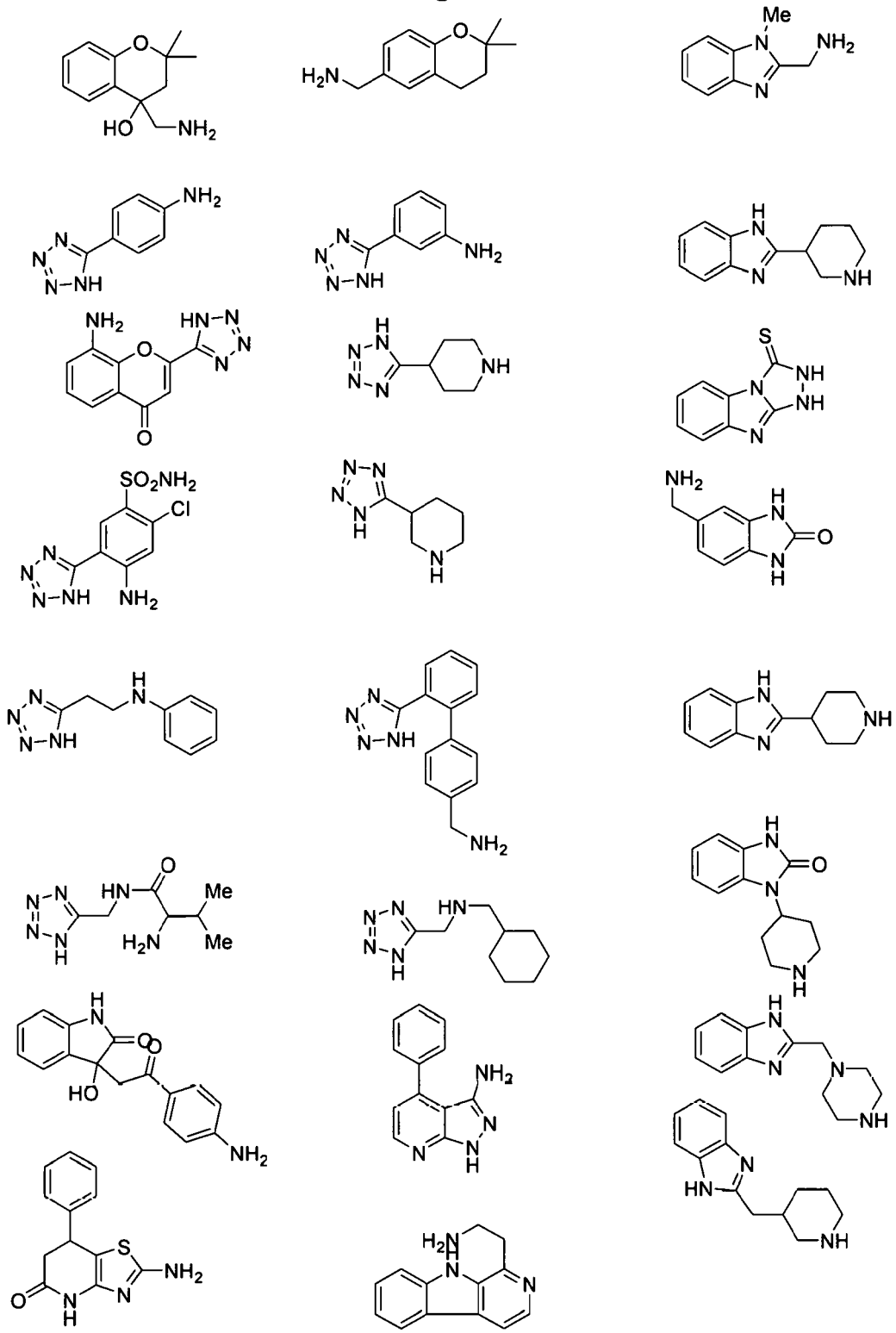
Figure 6J:
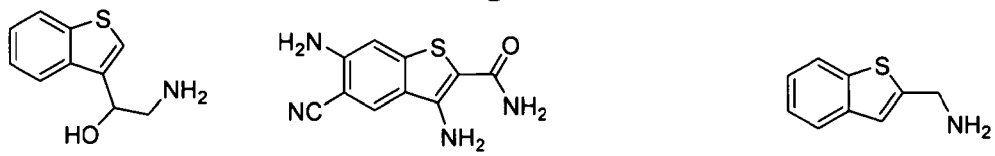
Figure 6J:
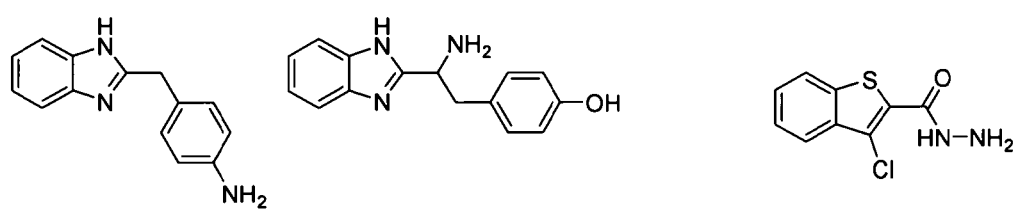
Figure 6J:
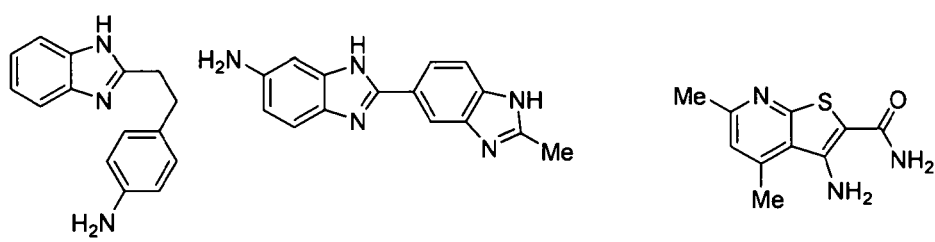
Figure 6J:
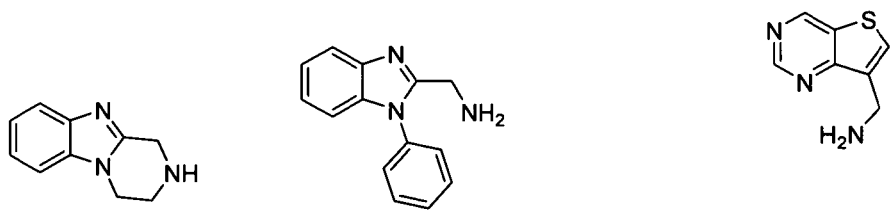
Figure 6J:
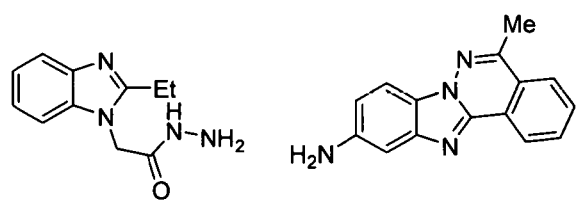
Figure 6J:
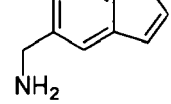
Figure 6J:
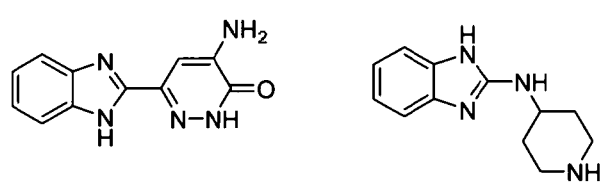
Figure 6J:
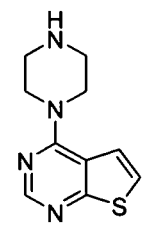

Compound 21 (0.2-100 µM, 3 h), but not the inactive control 24 (100 µM), produced a strong, concentration-dependent increase in long-chain (C16, C18, C18:1) acylcarnitines in human squamous cell carcinoma (HSC5) cells, with significant effects being observed for 21 at concentrations (20-50 µM; FIG. 5F), where 21 also substantially blocked probe 3 labeling of SLC25A20 in cells as measured by quantitative MS-based proteomics (FIG. 5Q, FIG. 5R). No changes were found in short- or medium-chain acylcarnitines (<C16), which are thought to cross the mitochondrial membranes without conversion to acylcarnitine esters. HSC5 cells treated with 21, but not 24 showed impaired capacity to oxidize palmitate (FIG. 5G and FIG. 5S). These results exemplify that 21 acts as a selective, cell-active inhibitor of SLC25A20, leading to disruption of mitochondrial long-chain acylcarnitine transport and FAO.

Example 30—Chemical Synthesis

Materials

Purchased starting materials were used as received unless otherwise noted. All moisture sensitive reactions were performed in an inert, dry atmosphere of nitrogen in flame dried glassware. Reagent grade solvents were used for extractions and flash chromatography. All amines used in probe library synthesis are available from commercial vendors. All fragment-based competitors were synthesized or purchased through Sigma Aldrich Market Select vendors. Reaction progress was checked by analytical thin-layer chromatography (TLC, Merck silica gel 60 F-254 plates). The plates were monitored either with UV illumination, or by charring with anisaldehyde (2.5% p-anisaldehyde, 1% AcOH, 3.5% $H_2SO_4$ (conc.) in 95% EtOH) or ninhydrin (0.3% ninhydrin (w/v), 97:3 EtOH-AcOH) stains. Flash column chromatography was performed using silica gel (F60, 40-63 um, 60 Å). Preparative thin layer chromotography (PTLC) was carried out using glass backed PTLC plates 1000-2000 µm thickness (Analtech). The solvent compositions reported for all chromatographic separations are on a volume/volume (v/v) basis. $^1$H-NMR spectra were recorded at either 400, 500 or 600 MHz and are reported in parts per million (ppm) on the δ scale relative to $CDCl_3$ (δ 7.26) as an internal standard. Data are reported as follows: chemical shift, multiplicity (s=singlet, d=doublet, t=triplet, q=quartet, br=broad, m=multiplet), coupling constants (Hz), and integration. $^{13}$C-NMR spectra were recorded at either 100 or 125 MHz and are reported in parts per million (ppm) on the δ scale relative to $CDCl_3$ (δ 77.00). Mass spectrometry data were collected on a HP1100 single-quadrupole instrument (ESI; low resolution) or an Agilent ESI-TOF instrument (HRMS).

Synthesis of 3-(3-(but-3-yn-1-yl)-3H-diazirin-3-yl) propanoic acid (30-3)

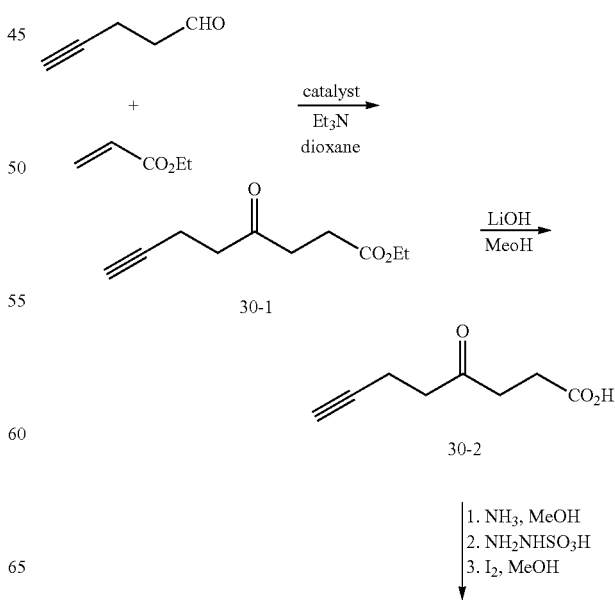

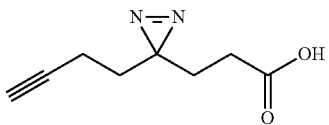

30-3

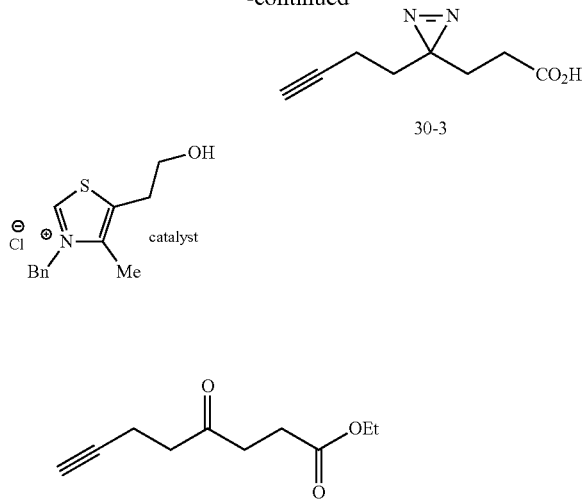

Ethyl 4-oxooct-7-ynoate (30-1) was synthesized following similar procedures previously reported. A solution of crude pent-4-ynal (17.2 g, 210 mmol) and ethyl acrylate (45.5 mL, 420 mmol, 2 equiv) in dioxane (250 mL) was added dropwise over a period of 4 h to a suspension of thiazolium salt catalyst (7.88 g, 29.2 mmol, 0.14 equiv), triethylamine (20.4 mL, 147 mmol, 0.7 equiv) and ethyl acrylate (45.5 mL) in dioxane (300 mL) at 80° C. under an atmosphere of nitrogen. The mixture was stirred and heated at 80° C. for 54 h and then volatiles removed by rotary evaporation. The residue was resuspended in methylene chloride (600 mL) and washed with aqueous 10% $H_2SO_4$ (150 mL), saturated aqueous $NaHCO_3$ (250 mL) and brine (250 mL), then dried over anhydrous $Na_2SO_4$ and volatiles removed by rotary evaporation. Crude 30-1 was purified by flash column chromatography (100% hexanes→5%→10%→15%→20% ethyl acetate in hexanes), resulting in 30-1 as a light brown oil (10.7 g, 28%). $^1$H NMR (400 MHz, $CDCl_3$) δ 4.20 (q, J=7.1, 2H), 2.86-2.76 (m, 4H), 2.68 (t, J=6.5, 2H), 2.54 (td, J=2.6, 7.3, 2H), 2.04 (t, J=2.7, 1H), 1.33 (td, J=2.2, 7.2, 4H). MS (ESI) calc'd for [M+H]+ $C_{10}H_{15}O_3^+$ 183.1, found 183.1.

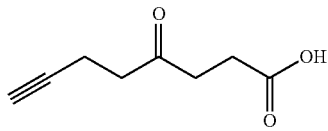

4-Oxooct-7-ynoic acid (30-2). To a solution of 30-1 (9.46 g, 52 mmol) in methanol (400 mL), added LiOH (6.2 g, 260 mmol, 5 equiv) and water (4.8 mL, 267 mmol, 5.1 equiv) and let resulting solution stir at room temperature for 15 h when TLC (3:1 hexanes/ethyl acetate) indicated the complete consumption of starting material. The solution was carefully acidified with aqueous HCl (6 M) until a pH of ~3 was achieved. The resulting solution was then extracted with methylene chloride and the combined organic layers were dried over anhydrous $Na_2SO_4$ and volatiles were removed by rotary evaporation, resulting in 30-2 as a brown solid (7.6 g, 95%), which was used without further purification. $^1$H NMR (400 MHz, $CDCl_3$) δ 2.90-2.57 (m, 6H), 2.48 (td, J=2.5, 7.3, 2H), 1.98 (t, J=2.5, 1H). MS (ESI) calc'd for [M–H]– $C_8H_9O_3^-$ 153.0, found 153.0.

3-(3-(But-3-yn-1-yl)-3H-diazirin-3-yl)propanoic acid (30-3). A dried round bottom flask containing 30-2 (3.1 g, 20 mmol) cooled to 0° C. was charged with 7N $NH_3$ in methanol (195 mL) and resulting solution was stirred at 0° C. under an atmosphere of nitrogen for 3 h. At this time, a solution of hydroxylamine-O-sulfonic acid (3.2 g, 28.2 mmol, 1.4 equiv) in anhydrous methanol (25 mL) was added dropwise via addition funnel at 0° C. The resulting solution was stirred at 0° C. for an additional 1 h and then allowed to warm to room temperature over 14 h. Resulting suspension was evaporated to dryness and resuspended in methanol (30 mL) and solid was filtered and washed several times with methanol. The combined filtrate was evaporated and resuspended in anhydrous methanol (180 mL), then cooled to 0° C. (protected from light). Diisopropylethylamine (7.8 mL) was added, followed by iodine (portion-wise), until a dark brown color persisted for more than 30 min, indicating total oxidation of diaziridine. The solution was then diluted with ethyl acetate (200 mL) and washed with aq. 1N HCl (200 mL), saturated aqueous $Na_2S_2O_3$ (3×200 mL or until organic phase clarified) and brine. Combined aqueous phases were washed once with ethyl acetate and all organic layers were combined, then dried over anhydrous $Na_2SO_4$ and volatiles removed by rotary evaporation. Crude 30-3 was purified by flash column chromatography (100% hexanes→2%→5%→10%→20% ethyl acetate in hexanes), resulting in 30-3 as a colorless oil (889 mg, 27%). $^1$H NMR (400 MHz, $CDCl_3$) δ 2.18 (t, J=7.7, 2H), 2.06-1.98 (m, 3H), 1.81 (t, J=7.7, 2H), 1.66 (t, J=7.4, 2H). $^{13}$C NMR (101 MHz, $CDCl_3$) δ 178.63, 82.56, 69.37, 32.16, 28.21, 27.72, 27.46, 13.21. MS (ESI) calc'd for [M–H]– $C_8H_9N_2O_2^-$ 165.1, found 165.1. Characterization matches that previously reported by Li et al Angew Chem Int Ed. (2013) 52, 8551-6.

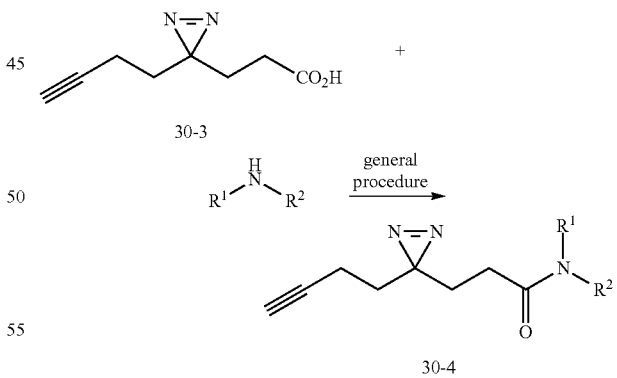

General Procedure 1: Coupling Procedure for the Synthesis of Simple Fragment-Based Probes To a 4 mL vial containing 3-(3-(but-3-yn-1-yl)-3H-diazirin-3-yl)propanoic acid (30-3, 1 eq.) in DCM, commercially available amine (1.1 eq.), DIPEA (3.0 eq.) EDC-HCl (1.5 eq.), and HOBt (1.5 eq.) were added. Reaction mixtures were stirred at room temperature for 4 h to overnight when TLC indicated reaction completed. The crude samples were diluted with DCM and washed first with saturated aqueous NH$_4$Cl (10 mL) and saturated aqueous NaHCO$_3$ (10 mL), then dried over anhydrous Na$_2$SO$_4$ and volatiles removed by rotary evaporation. Crude products were purified by PTLC or flash column chromatography.

General Procedure 2: Coupling Procedure for the Synthesis of Photoaffinity Probe Library Used in Phenotypic Screening A 4 mL vial was charged with 3-(3-(but-3-yn-1-yl)-3H-diazirin-3-yl)propanoic acid (10 mg, 0.060 mmol) or propionic acid (0.060 mmol), commercially available amine (0.060 mmol, 1 eq.), DIPEA (0.032 mL, 0.181 mmol, 3.0 eq.), HATU (34.3 mg, 0.090 mmol, 1.5 eq.) and DMF (1 mL). Reaction mixtures were stirred at room temperature for 4 h. The crude samples were diluted with methanol to a total volume of 1.6 mL then purified by reverse phase HPLC using following conditions:

| LC/MS conditions for Library Characterization | |
|---|---|
| Column | Xbridge Prep C18 19 × 150 mm, 10 µm |
| Flow Rate | 15 ml/min |
| Mobile Phase A | 10 mM ammonium acetate in water |
| Mobile Phase B | Acetonitrile |
| Gradient | 10% B to 100% B over 20 min followed by a 3 min wash at 100% B and 2 min equilibration at 10% B. |

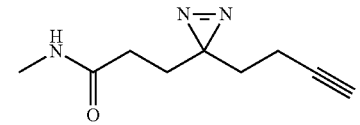

3-(3-(But-3-yn-1-yl)-3H-diazirin-3-yl)-N-methylpropanamide (1) General Procedure 1. Purified by SiO$_2$ flash chromatography (Hexane/EtOAc, 7:3→1:1) to afford 1 as a colorless sticky solid (6 mg, 93%). $^1$H NMR (400 MHz, CDCl$_3$) δ 5.56 (brs, 1H), 2.82 (d, J=2.2 Hz, 2H), 2.08-1.98 (m, 3H), 1.94 (m, 2H), 1.90-1.83 (m, 2H), 1.66 (t, J=7.4 Hz, 2H). $^{13}$C NMR (126 MHz, CDCl$_3$) δ 172.12, 83.09, 69.57, 32.79, 30.58, 28.83, 28.25, 26.80, 13.68. HRMS (ESI-TOF) calcd for C$_9$H$_{14}$N$_3$O 180.1131 (M+H$^+$), found 180.1131.

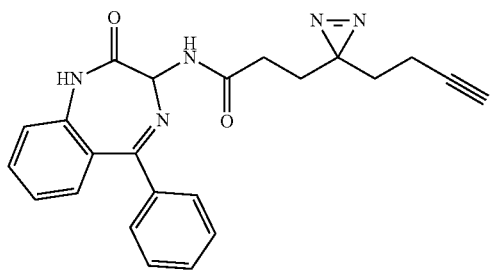 [SMILES: C#CCCC1(CCC(=O)NC2N=C(c3ccccc3)c3ccccc3NC2=O)N=N1]

3-(3-(But-3-yn-1-yl)-3H-diazirin-3-yl)-N-(2-oxo-5-phenyl-2,3-dihydro-1H-benzo[e][1,4]diazepin-3-yl)propanamide (2) General Procedure 1. Purified by SiO$_2$ flash chromatography (Hexane/EtOAc, 3:1) to afford 2 as a white sticky solid (22 mg, 76%). $^1$H NMR (400 MHz, CDCl$_3$) δ 9.18 (s, 1H), 7.56-7.30 (m, 8H), 7.22-7.10 (m, 2H), 5.53 (d, J=7.9 Hz, 1H), 2.29-2.13 (m, 2H), 2.07-1.97 (m, 3H), 1.87 (t, J=7.4 Hz, 2H), 1.68 (t, J=7.4 Hz, 2H). $^{13}$C NMR (101 MHz, CDCl$_3$) δ 171.34, 168.74, 138.54, 137.36, 132.21, 131.45, 130.69, 129.87, 128.25, 127.61, 124.18, 121.46, 82.76, 69.26, 67.13, 32.30, 30.37, 28.30, 27.87, 13.33. HRMS (ESI-TOF) calcd for C$_{23}$H$_{22}$N$_5$O$_2$ 400.1768 (M+H$^+$), found 400.1768.

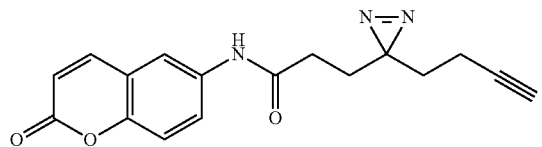 [SMILES: C#CCCC1(CCC(=O)Nc2ccc3oc(=O)ccc3c2)N=N1]

3-(3-(But-3-yn-1-yl)-3H-diazirin-3-yl)-N-(2-oxo-2H-chromen-6-yl)propanamide (3) General Procedure 1. Purified by SiO$_2$ flash chromatography (Hexane/EtOAc, 3:2) to afford 3 as a yellow sticky solid (12.8 mg, 57%). $^1$H NMR (400 MHz, CDCl$_3$) δ 8.01 (d, J=2.2 Hz, 1H), 7.69 (d, J=9.6 Hz, 1H), 7.62 (br s, 1H), 7.42 (dd, J=8.9, 2.5 Hz, 1H), 7.29 (d, 7.7 Hz, 1H), 6.44 (d, J=9.6 Hz, 1H), 2.16 (t, J=7.5 Hz, 2H), 2.04 (td, J=7.4, 2.6 Hz, 2H), 2.01-1.92 (m, 3H), 1.75 δ 1.62 (m, 2H). $^{13}$C NMR (101 MHz, CDCl$_3$) δ 169.69, 160.82, 150.48, 143.49, 134.28, 123.57, 119.04, 118.58, 117.20, 82.67, 69.33, 32.44, 31.16, 28.09, 27.80, 13.29. HRMS (ESI-TOF) calcd for C$_{17}$H$_{16}$N$_3$O$_3$ 310.1186 (M+H$^+$), found 310.1186.

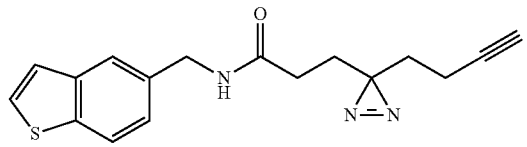 [SMILES: C#CCCC1(CCC(=O)NCc2ccc3sccc3c2)N=N1]

N-(Benzo[b]thiophen-5-ylmethyl)-3-(3-(but-3-yn-1-yl)-3H-diazirin-3-yl)propanamide (4) General Procedure 1. Purified by SiO$_2$ flash chromatography (Hexane/EtOAc, 3:1) to afford 4 as a off-white sticky solid (12.3 mg, 44%). $^1$H NMR (500 MHz, CDCl$_3$) δ 7.84 (d, J=8.3 Hz, 1H), 7.73 (s, 1H), 7.46 (d, J=5.4 Hz, 1H), 7.30 (d, J=5.4 Hz, 1H), 7.26 (d, J=8.0 Hz, 1H), 5.80 (br s, 1H), 4.54 (d, J=5.7 Hz, 2H), 2.03-1.95 (m, 5H), 1.91 δ 1.86 (m, 2H), 1.64 (t, J=7.5 Hz, 2H). $^{13}$C NMR (126 MHz, CDCl$_3$) δ 171.27, 140.32, 139.41, 134.65, 127.61, 124.71, 124.06, 123.22, 83.10, 69.62, 44.23, 32.82, 30.73, 28.75, 13.70. HRMS (ESI-TOF) calcd for C$_{17}$H$_{18}$N$_3$OS 312.1165 (M+H$^+$), found 312.1167

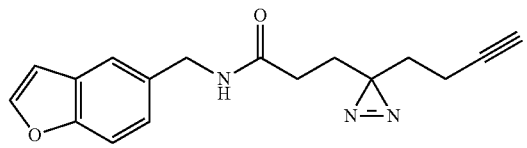 [SMILES: C#CCCC1(CCC(=O)NCc2ccc3occc3c2)N=N1]

N-(Benzofuran-5-ylmethyl)-3-(3-(but-3-yn-1-yl)-3H-diazirin-3-yl)propanamide (5) General Procedure 1. Purified by PTLC (Hexane/EtOAc, 3:1) to afford 5 as a off-white sticky solid (10.8 mg, 76%). $^1$H NMR (400 MHz, CDCl$_3$) δ 7.63 (d, J=2.2 Hz, 1H), 7.54-7.49 (m, 1H), 7.46 (d, J=8.5 Hz, 1H), 7.21 (dd, J=8.5, 1.8 Hz, 1H), 6.74 (dd, J=2.2, 1.0 Hz, 1H), 5.75 (brs, 1H), 4.51 (d, J=5.7 Hz, 2H), 2.06-1.83 (m, 7H), 1.65 (t, J=7.4 Hz, 2H). HRMS (ESI-TOF) calcd for C$_{17}$H$_{18}$N$_3$O$_2$ 296.1393 (M+H$^+$), found 296.1392

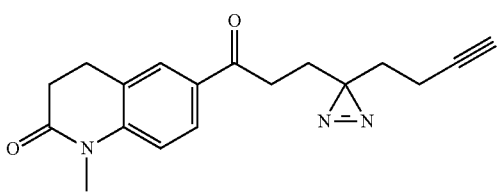 [SMILES: C#CCCC1(CCC(=O)c2ccc3c(c2)CCC(=O)N3C)N=N1]

3-(3-(But-3-yn-1-yl)-3H-diazirin-3-yl)-N-(1-methyl-2-oxo-1,2,3,4-tetrahydroquinolin-7-yl)propanamide (6) General Procedure 1. Purified by SiO$_2$ flash chromatography (Hexane/EtOAc, 3:1) to afford 6 as a light brown sticky solid (33 mg, 56%). $^1$H NMR (500 MHz, CDCl$_3$) δ 7.43 (d, 2.4 Hz, 1H), 7.35 (brs, 1H), 7.29 (dd, J=8.7, 2.5 Hz, 1H), 6.91 (d, J=8.7 Hz, 1H), 3.33 (s, 3H), 2.99-2.89 (m, 2H), 2.76-2.65 (m, 2H), 2.19 (t, J=7.5, 6.7 Hz, 2H), 2.12 (td, J=7.4, 2.6 Hz, 2H), 2.07 (t, J=2.6 Hz, 1H), 2.02 (t, J=7.5 Hz, 2H), 1.76 (t, J=7.5 Hz, 2H). $^{13}$C NMR (126 MHz, CDCl$_3$) δ 170.59, 169.79, 137.62, 133.17, 127.38, 120.28, 119.32, 115.38, 83.09, 69.69, 32.87, 31.99, 31.58, 29.98, 28.61, 28.23, 25.88, 13.71. HRMS (ESI-TOF) calcd for C$_{18}$H$_{21}$N$_4$O$_2$ 325.1659 (M+H$^+$), found 325.1658

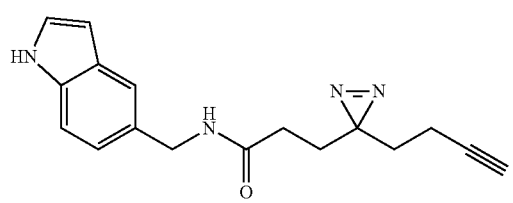 [SMILES: C#CCCC1(CCC(=O)NCc2ccc3[nH]ccc3c2)N=N1]

N-((1H-Indol-5-yl)methyl)-3-(3-(but-3-yn-1-yl)-3H-diazirin-3-yl)propanamide (7) General Procedure 1. Purified by PTLC (Hexane/EtOAc, 3:1) to afford 7 as an off-white sticky solid (12.2 mg, 57%). $^1$H NMR (500 MHz, CDCl$_3$) δ 8.31 (brs, 1H), 7.57-7.50 (m, 1H), 7.36 (d, J=8.3 Hz, 1H), 7.22 (dd, J=3.2, 2.4 Hz, 1H), 7.11 (dd, J=8.3, 1.7 Hz, 1H), 6.53-6.51 (m, 1H), 5.71 (brs, 1H), 4.50 (d, J=5.4 Hz, 2H), 2.00 (td, J=7.4, 2.6 Hz, 2H), 1.98-1.92 (m, 3H), 1.89-1.84 (m, 2H), 1.64 (t, J=7.4 Hz, 2H). $^{13}$C NMR (126 MHz, CDCl$_3$) δ 171.11, 135.68, 129.70, 128.47, 125.34, 122.74, 120.65, 111.79, 102.96, 83.14, 69.61, 44.83, 32.78, 30.79, 28.86, 13.70. HRMS (ESI-TOF) calcd for C$_{17}$H$_{19}$N$_4$O 295.1553 (M+H$^+$), found 295.1555.

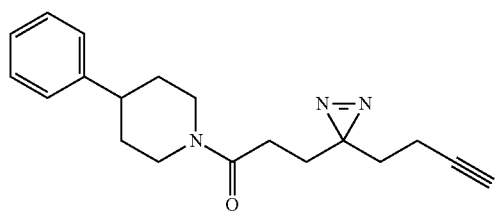 [SMILES: C#CCCC1(CCC(=O)N2CCC(c3ccccc3)CC2)N=N1]

3-(3-(But-3-yn-1-yl)-3H-diazirin-3-yl)-1-(4-phenylpiperidin-1-yl)propan-1-one (8) General Procedure 1. Purified by SiO$_2$ flash chromatography (Hexane/EtOAc, 3:1) to afford 8 as an off-white sticky solid (19.7 mg, 88%). $^1$H NMR (400 MHz, CDCl$_3$) δ 7.31 (t, J=7.5 Hz, 2H), 7.25-7.16 (m, 3H), 4.85-4.69 (m, 1H), 3.92-3.83 (m, 1H), 3.10 (apparent td, J=13.3, 2.7 Hz, 1H), 2.73 (apparent tt, J=12.2, 3.7 Hz, 1H), 3.62 (apparent td, J=13.3, 2.8 Hz, 1H), 2.13-2.08 (m, 2H), 2.05 (td, J=7.5, 2.7 Hz, 2H), 1.98 (t, J=2.6 Hz, 1H), 1.92-1.84 (m, 2H), 1.69 (t, J=7.5 Hz, 2H) (rotomeric isomers present). $^{13}$C NMR (101 MHz, CDCl$_3$) δ 169.33, 145.08, 128.59, 126.70, 126.54, 82.80, 69.12, 46.09, 42.75, 42.55, 33.81, 32.80, 32.57, 28.08, 26.99, 13.34. HRMS (ESI-TOF) calcd for C$_{19}$H$_{23}$N$_3$O 310.1914 (M+H$^+$), found 310.1916.

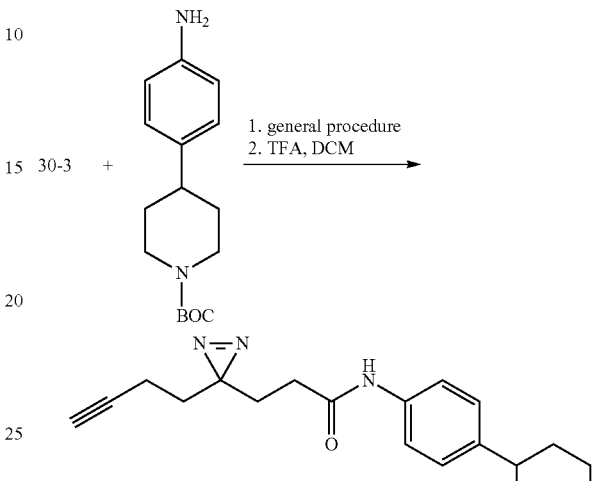

3-(3-(But-3-yn-1-yl)-3H-diazirin-3-yl)-N-(4-(piperidin-4-yl)phenyl)propanamide (9) Followed General Procedure 1 for amide bond coupling. Crude 9 was then re-dissolved in DCM (1 mL) and TFA (0.3 mL) was carefully added. The resulting mixture was evaporated and crude 9 was purified by PTLC (DCM/MeOH, 6:1) yielding 9 as a white solid (22 mg, 67%, 2 steps). $^1$H NMR (500 MHz, CDCl$_3$) δ 7.44 (d, J=8.1 Hz, 2H), 7.18 (d, J=8.2 Hz, 2H), 7.13 (s, 1H), 3.45 (d, J=12.7 Hz, 2H), 3.00-2.89 (m, 2H), 2.76-2.65 (m, 3H), 2.12 (t, J=7.5 Hz, 2H), 2.04 (td, J=7.5, 2.6 Hz, 2H), 2.02-1.91 (m, 3H), 1.68 (t, J=7.4 Hz, 2H). HRMS (ESI-TOF) calcd for C$_{19}$H$_{25}$N$_4$O 325.2023 (M+H$^+$), found 325.2023.

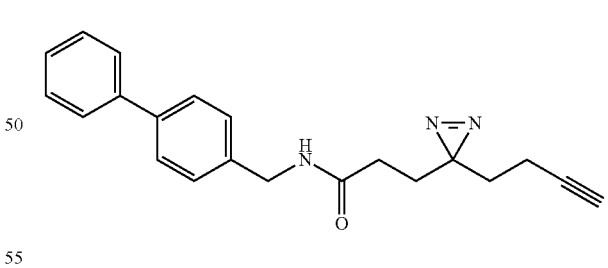

N-([1,1'-Biphenyl]-4-ylmethyl)-3-(3-(but-3-yn-1-yl)-3H-diazirin-3-yl)propanamide (10) General Procedure 1. Purified by PTLC (Hexane/EtOAc, 4:1) to afford 10 as a white sticky solid (18.5 mg, 78%). $^1$H NMR (400 MHz, CDCl$_3$) δ 7.61-7.52 (m, 4H), 7.44 (t, J=7.5 Hz, 2H), 7.38-7.33 (m, 4H), 5.77 (br s, 1H), 4.47 (d, J=5.7 Hz, 2H), 2.09-1.94 (m, 5H), 1.94-1.85 (m, 2H), 1.66 (t, J=7.4 Hz, 2H). $^{13}$C NMR (101 MHz, CDCl$_3$) δ 170.92, 140.63, 137.05, 128.80, 128.32, 127.48, 127.39, 127.06, 82.70, 69.22, 43.47, 32.42, 30.32, 28.34, 27.86, 13.31. HRMS (ESI-TOF) calcd for C$_{21}$H$_{22}$N$_3$O 332.1757 (M+H$^+$), found 332.1755.

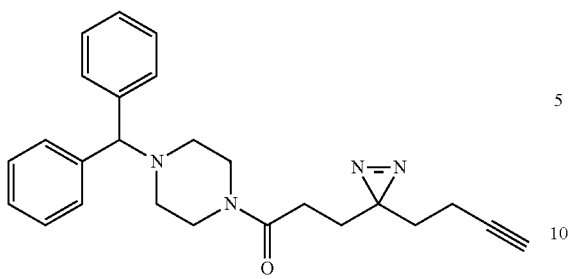

1-(4-Benzhydrylpiperazin-1-yl)-3-(3-(but-3-yn-1-yl)-3H-diazirin-3-yl)propan-1-one (11) General Procedure 1. Purified by PTLC (DCM/MeOH, 20:1) to afford 11 as an off-white sticky residue (12 mg, 75%). $^1$H NMR (500 MHz, CDCl$_3$) δ 7.43-7.38 (m, 4H), 7.31-7.24 (m, 4H), 7.22-7.16 (m, 2H), 4.23 (s, 1H), 3.66-3.54 (m, 2H), 3.48-3.34 (m, 2H), 2.36 (apparent t, J=5.0 Hz, 4H), 2.06-1.98 (m, 4H), 1.96 (t, J=2.7 Hz, 1H), 1.85-1.80 (m, 2H), 1.65 (t, J=7.4 Hz, 2H). $^{13}$C NMR (126 MHz, CDCl$_3$) δ 169.84, 142.47, 129.01, 128.25, 127.58, 69.52, 52.34, 51.93, 45.96, 42.33, 32.93, 28.41, 27.22, 13.71. HRMS (ESI-TOF) calcd for C$_{25}$H$_{29}$N$_4$O 401.2336 (M+H$^+$), found 401.2335.

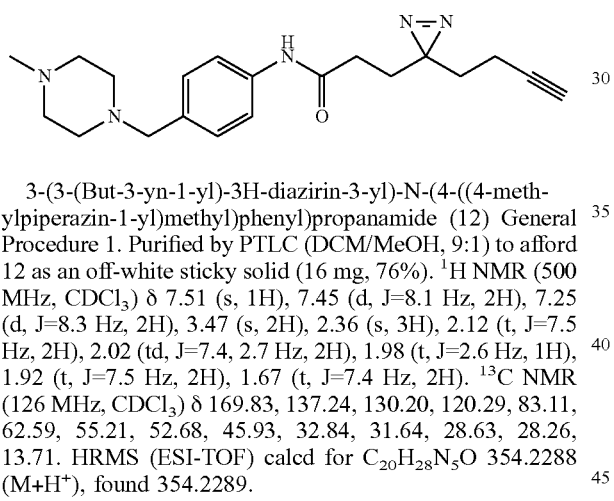

3-(3-(But-3-yn-1-yl)-3H-diazirin-3-yl)-N-(4-((4-methylpiperazin-1-yl)methyl)phenyl)propanamide (12) General Procedure 1. Purified by PTLC (DCM/MeOH, 9:1) to afford 12 as an off-white sticky solid (16 mg, 76%). $^1$H NMR (500 MHz, CDCl$_3$) δ 7.51 (s, 1H), 7.45 (d, J=8.1 Hz, 2H), 7.25 (d, J=8.3 Hz, 2H), 3.47 (s, 2H), 2.36 (s, 3H), 2.12 (t, J=7.5 Hz, 2H), 2.02 (td, J=7.4, 2.7 Hz, 2H), 1.98 (t, J=2.6 Hz, 1H), 1.92 (t, J=7.5 Hz, 2H), 1.67 (t, J=7.4 Hz, 2H). $^{13}$C NMR (126 MHz, CDCl$_3$) δ 169.83, 137.24, 130.20, 120.29, 83.11, 62.59, 55.21, 52.68, 45.93, 32.84, 31.64, 28.63, 28.26, 13.71. HRMS (ESI-TOF) calcd for C$_{20}$H$_{28}$N$_5$O 354.2288 (M+H$^+$), found 354.2289.

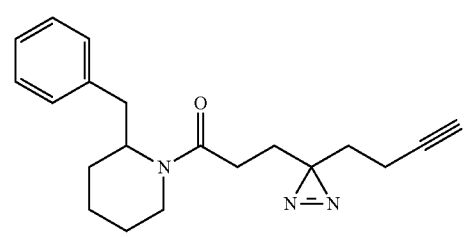 [SMILES: C#CCCC1(CCC(=O)N2CCCCC2Cc2ccccc2)N=N1]

1-(2-Benzylpiperidin-1-yl)-3-(3-(but-3-yn-1-yl)-3H-diazirin-3-yl)propan-1-one (13) $^1$H NMR (500 MHz, CDCl$_3$) General Procedure 1. Purified by PTLC (Hexane/EtOAc, 1:1) to afford 13 as an off-white sticky solid (9 mg, 77%). δ 7.35-7.15 (m, 3H), 7.11 (apparent d, J=7.4 Hz, 2H), 5.14-4.95 (m, 0.5H), 4.68-4.57 (m, 0.5H), 4.13-3.97 (m, 0.5H), 3.63-3.50 (m, 0.5H), 3.21-3.02 (m, 1H), 2.89-2.69 (m, 2H), 2.09-1.87 (m, 4H), 1.83-1.24 (m, 11H). $^{13}$C NMR (126 MHz, CDCl$_3$) δ 169.99, 139.08, 139.01, 129.61, 129.46, 129.19, 128.73, 127.17, 126.63, 83.19, 69.49, 69.42, 55.55, 50.01, 41.70, 37.16, 37.04, 36.10, 32.88, 32.70, 29.92, 28.49, 28.46, 28.18, 27.78, 26.86, 26.47, 26.45, 25.89, 19.67, 19.27, 13.72, 13.70. Note: rotomeric isomers observed. HRMS (ESI-TOF) calcd for C$_{20}$H$_{26}$N$_3$O 324.2070 (M+H$^+$), found 324.2068.

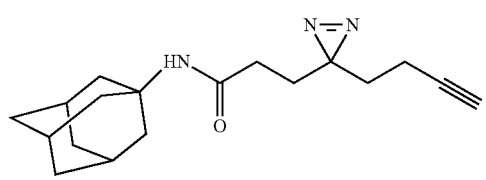 [SMILES: C#CCCC1(CCC(=O)NC23CC4CC(CC(C4)C2)C3)N=N1]

N-((3s,5s,7s)-Adamantan-1-yl)-3-(3-(but-3-yn-1-yl)-3H-diazirin-3-yl)propanamide (14) General Procedure 1. Purified by SiO$_2$ flash chromatography (Hexane/EtOAc, 10:1→6:1→3:1) to afford 14 as a colorless sticky solid (14.7 mg, 68%). $^1$H NMR (500 MHz, CDCl$_3$) δ 5.08 (brs, 1H), 2.15 (m, 3H), 2.04-1.95 (m, 9H), 1.88-1.75 (m, 4H), 1.72-1.59 (m, 8H). $^{13}$C NMR (126 MHz, CDCl$_3$) δ 170.46, 83.17, 69.52, 52.41, 42.02, 36.74, 32.89, 31.69, 29.86, 29.84, 28.73, 13.71. HRMS (ESI-TOF) calcd for C$_{28}$H$_{26}$N$_3$O 300.2070 (M+H$^+$), found 300.2067.

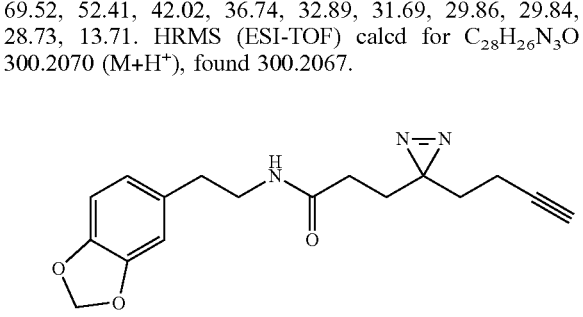

N-(2-(Benzo[d][1,3]dioxol-5-yl)ethyl)-3-(3-(but-3-yn-1-yl)-3H-diazirin-3-yl)propanamide (15) General Procedure 1. Purified by SiO$_2$ flash chromatography (Hexane/EtOAc, 3:1) to afford 15 as a white solid (20.2 mg, 71%). $^1$H NMR (500 MHz, CDCl$_3$) δ 6.74 (d, J=7.9 Hz, 1H), 6.67 (d, J=1.7 Hz, 1H), 6.62 (dd, J=7.9, 1.7 Hz, 1H), 5.93 (s, 2H), 5.43 (d, J=7.4 Hz, 1H), 3.45 (td, J=6.9, 5.8 Hz, 2H), 2.72 (t, J=6.9 Hz, 2H), 2.01 (td, J=7.4, 2.7 Hz, 2H), 1.96 (t, J=2.6 Hz, 1H), 1.90 δ 1.78 (m, 4H), 1.62 (t, J=7.4 Hz, 2H). $^{13}$C NMR (126 MHz, CDCl$_3$) δ 171.37, 148.27, 146.65, 132.85, 122.01, 109.43, 108.79, 101.34, 83.10, 69.59, 41.21, 35.71, 32.81, 30.74, 28.72, 13.69. HRMS (ESI-TOF) calcd for C$_{17}$H$_{20}$N$_3$O$_3$ 314.1499 (M+H$^+$), found 314.1500.

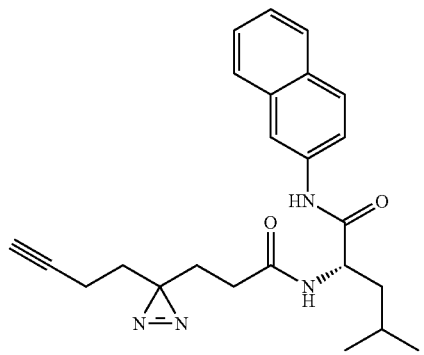 [SMILES: C#CCCC1(CCC(=O)N[C@@H](CC(C)C)C(=O)Nc2ccc3ccccc3c2)N=N1]

(S)-2-(3-(3-(but-3-yn-1-yl)-3H-diazirin-3-yl)propanamido)-4-methyl-N-(naphthalen-2-yl)pentanamide (25) General Procedure 1. Purified by SiO$_2$ flash chromatography (Hexane/EtOAc, 3:1) to afford 25 as a white solid (27 mg, 53%). $^1$H NMR (500 MHz, CDCl$_3$) δ 9.39 (s, 1H), 8.20 (d, J=2.2 Hz, 1H), 7.70-7.63 (m, 1H), 7.63-7.54 (m, 2H), 7.41 (dd, J=8.8, 2.1 Hz, 1H), 7.37-7.30 (m, 2H), 6.94 (d, J=7.9 Hz, 1H), 4.80 (td, J=8.3, 5.6 Hz, 1H), 2.09-1.94 (m, 2H), 1.93 (t, J=2.6 Hz, 1H), 1.91-1.70 (m, 7H), 1.51 (t, J=7.4 Hz, 2H), 1.00 (dd, J=12.9, 6.1 Hz, 6H). $^{13}$C NMR (125 MHz, CDCl$_3$) δ 172.64, 171.84, 135.71, 134.08, 131.04, 129.03, 128.02, 126.74, 125.37, 120.43, 117.39, 83.02, 69.65, 53.48, 41.31, 32.56, 30.42, 28.65, 28.13, 25.35, 23.40, 22.59, 13.59. HRMS (ESI-TOF) calcd for C$_{24}$H$_{29}$N$_4$O$_2$ 405.2285 (M+H$^+$), found 405.2285

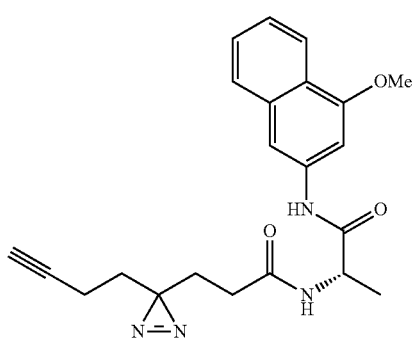 [SMILES: C#CCCC1(CCC(=O)N[C@@H](C)C(=O)Nc2cc(OC)c3ccccc3c2)N=N1]

(S)-3-(3-(but-3-yn-1-yl)-3H-diazirin-3-yl)-N-(1-((4-methoxynaphthalen-2-yl)amino)-1-oxopropan-2-yl)propanamide (26) General Procedure 1. Purified by SiO$_2$ flash chromatography (Hexane/EtOAc, 9:1→4:1→2:1) to afford 26 as a white solid (147 mg, 73%). $^1$H NMR (500 MHz, CDCl$_3$) δ 8.86 (s, 1H), 8.29-8.14 (m, 1H), 7.79-7.63 (m, 2H), 7.50 (ddd, J=8.2, 6.7, 1.4 Hz, 1H), 7.44 (ddd, J=8.2, 6.8, 1.3 Hz, 1H), 7.17 (d, J=1.8 Hz, 1H), 6.39 (d, J=7.5 Hz, 1H), 4.83 (p, J=7.1 Hz, 1H), 4.02 (s, 3H), 2.21-2.03 (m, 5H), 2.02-1.93 (m, 2H), 1.71 (t, J=7.2 Hz, 2H), 1.61 (d, J=7.0 Hz, 3H). $^{13}$C NMR (125 MHz, CDCl$_3$) δ 172.31, 171.22, 156.39, 136.00, 134.77, 127.54, 124.74, 123.51, 122.22, 109.59, 99.18, 82.97, 69.77, 55.92, 50.34, 32.66, 30.70, 28.76, 28.18, 18.39, 13.62. HRMS (ESI-TOF) calcd for C$_{22}$H$_{25}$N$_4$O$_3$ 393.1921 (M+H$^+$), found 393.1923

General Procedure 3:

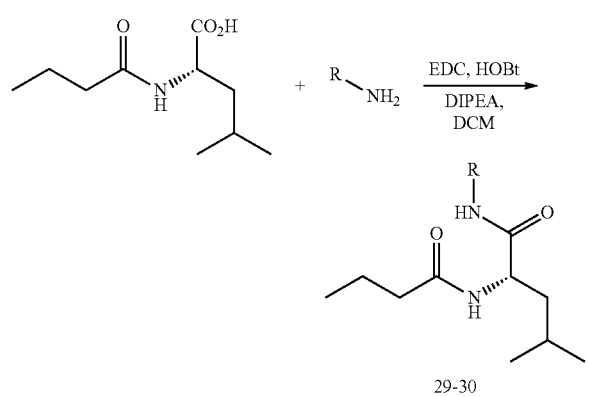

To a solution of N-butanoyl-L-leucine (Effenberger et al., 2015) (1 equiv) in DCM (0.06M relative to acid), added commercially available amine (1.1 equiv), DIPEA (2.2 equiv) EDC-HCl (1.2 equiv) and HOBt (1.2 equiv) were added. Reaction mixtures were stirred at room temperature for 4 h to overnight when TLC indicated reaction completed. The crude samples were diluted with DCM and washed first with saturated aqueous NH$_4$Cl and saturated aqueous NaHCO$_3$, then dried over anhydrous Na$_2$SO$_4$ and volatiles removed by rotary evaporation. Crude products were purified by PTLC or flash column chromatography.

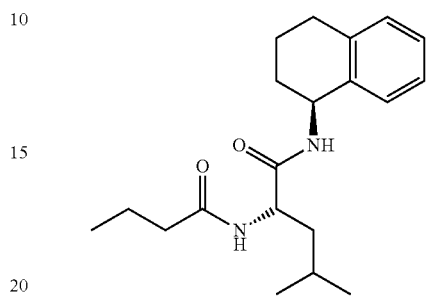

(S)-2-butyramido-4-methyl-N—((S)-1,2,3,4-tetrahydronaphthalen-1-yl)pentanamide (29) General Procedure 3. Purified by PTLC (Hexane/EtOAc, 1:1) to afford 29 as an off-white solid (24 mg, 73%). $^1$H NMR (400 MHz, CDCl$_3$) δ 7.23-7.04 (m, 4H), 6.39 (d, J=8.8 Hz, 1H), 5.99 (d, J=8.3 Hz, 1H), 5.16-5.08 (m, 1H), 4.44 (td, J=8.4, 5.4 Hz, 1H), 2.77 (qd, J=16.9, 8.7 Hz, 2H), 2.16 (td, J=7.3, 1.4 Hz, 2H), 2.08-1.93 (m, 1H), 1.91-1.39 (m, 8H), 1.03-0.81 (m, 9H). $^{13}$C NMR (125 MHz, CDCl$_3$) δ 173.37, 171.79, 137.83, 136.59, 129.52, 128.83, 127.71, 126.68, 52.03, 48.02, 41.91, 38.87, 30.49, 29.59, 25.28, 23.27, 22.76, 20.46, 19.48, 14.09. HRMS (ESI-TOF) calcd for C$_{20}$H$_{31}$N$_2$O$_2$ 331.2380 (M+H$^+$), found 331.2383

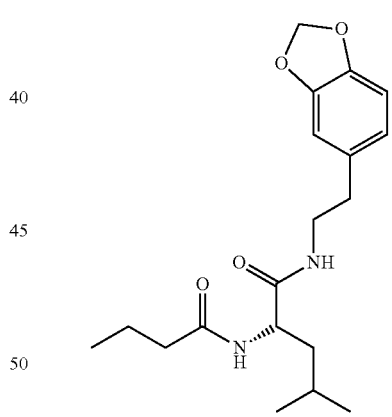

(S)—N-(2-(benzo[d][1,3]dioxol-5-yl)ethyl)-2-butyramido-4-methylpentanamide (30) General Procedure 3. Purified by SiO$_2$ flash chromatography (Hexane/EtOAc, 3:2) to afford 30 as a white solid (181 mg, 75%). $^1$H NMR (500 MHz, CDCl$_3$) δ 6.73 (d, J=7.9 Hz, 1H), 6.69-6.64 (m, 1H), 6.62 (dd, J=7.9, 1.7 Hz, 1H), 6.45-6.34 (m, 1H), 6.06 (t, J=7.9 Hz, 1H), 5.92 (s, 2H), 4.39 (td, J=8.3, 6.1 Hz, 1H), 3.49 (dq, J=13.5, 6.9 Hz, 1H), 3.38 (dq, J=13.3, 6.8 Hz, 1H), 2.71 (t, J=7.1 Hz, 2H), 2.15 (t, J=7.5 Hz, 2H), 1.70-1.41 (m, 5H), 0.97-0.85 (m, 9H). $^{13}$C NMR (125 MHz, CDCl$_3$) δ 173.43, 172.46, 148.18, 146.60, 132.80, 122.02, 109.46, 108.72, 101.29, 51.89, 41.55, 41.20, 38.82, 35.70, 25.18, 23.17, 22.69, 19.44, 14.08. HRMS (ESI-TOF) calcd for C$_{19}$H$_{29}$N$_2$O$_4$ 349.2122 (M+H$^+$), found 349.2124

General Procedure 4:

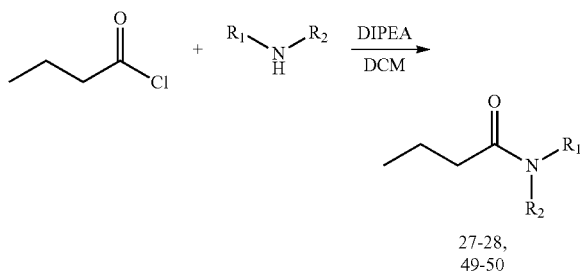

To commercially available amine (1.0 equiv) in DCM (0.1 M), added DIPEA (1.1 equiv) followed by the slow addition of butanoyl chloride (1.0 equiv). Resulting mixture was allowed to stir at room temperature until amine was fully consumed, as indicated by TLC. The crude mixture was diluted with DCM, washed first with saturated aqueous NH$_4$Cl and saturated aqueous NaHCO$_3$, then dried over anhydrous Na$_2$SO$_4$ and volatiles removed by rotary evaporation. Crude products were purified by PTLC.

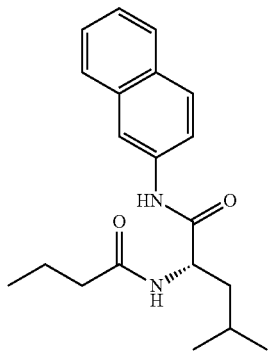 [SMILES: CCCC(=O)N[C@@H](CC(C)C)C(=O)Nc1ccc2ccccc2c1]

(S)-2-butyramido-4-methyl-N-(naphthalen-2-yl)pentanamide (27) General Procedure 4. Purified by PTLC (DCM/MeOH, 20:1) to afford 27 as a white solid (15 mg, 58%). $^1$H NMR (400 MHz, CDCl$_3$) δ 9.41 (s, 1H), 8.26-8.09 (m, 1H), 7.69-7.54 (m, 3H), 7.42 (dd, J=8.8, 2.1 Hz, 1H), 7.38-7.29 (m, J=7.1, 3.5 Hz, 2H), 6.62 (d, J=8.0 Hz, 1H), 4.83 (td, J=8.3, 5.9 Hz, 1H), 2.22 (apparent td, J=7.3, 2.9 Hz, 2H), 1.92-1.57 (m, 5H), 0.99 (dd, J=12.4, 6.1 Hz, 6H), 0.90 (t, J=7.4 Hz, 3H). $^{13}$C NMR (125 MHz, CDCl$_3$) δ 174.40, 171.36, 135.78, 134.13, 131.00, 128.96, 128.00, 127.85, 126.69, 125.26, 120.40, 117.15, 53.08, 40.96, 38.78, 25.33, 23.34, 22.67, 19.53, 14.04. HRMS (ESI-TOF) calcd for C$_{20}$H$_{26}$N$_2$O$_2$ 327.2067 (M+H$^+$), found 327.2069

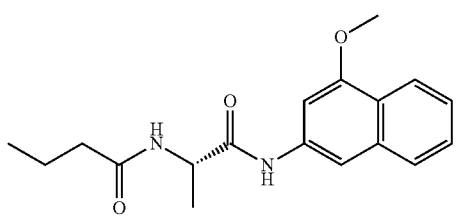 [SMILES: CCCC(=O)N[C@@H](C)C(=O)Nc1cc(OC)c2ccccc2c1]

(S)—N-(1-((4-methoxynaphthalen-2-yl)amino)-1-oxopropan-2-yl)butyramide (28) General Procedure 4. Purified by PTLC (DCM/MeOH, 9:1) to afford 28 as a colorless solid (22.7 mg, 68%). $^1$H NMR (500 MHz, CDCl$_3$) δ 9.36 (s, 1H), 8.12 (dd, J=8.2, 1.4 Hz, 1H), 7.69-7.64 (m, 1H), 7.62 (d, J=8.1 Hz, 1H), 7.40 (ddd, J=8.2, 6.7, 1.4 Hz, 1H), 7.34 (ddd, J=8.2, 6.8, 1.3 Hz, 1H), 7.10 (d, J=1.8 Hz, 1H), 6.56 (d, J=7.5 Hz, 1H), 4.91 (p, J=7.1 Hz, 1H), 3.91 (s, 3H), 2.27 (apparent td, J=7.4, 3.1 Hz, 2H), 1.78-1.68 (m, 2H), 1.55 (d, J=6.9 Hz, 3H), 0.96 (t, J=7.4 Hz, 3H). $^{13}$C NMR (125 MHz, CDCl$_3$) δ 173.23, 170.49, 155.47, 135.40, 133.97, 126.67, 123.75, 122.56, 121.34, 108.54, 98.25, 55.04, 49.29, 38.06, 18.74, 17.78, 13.23. HRMS (ESI-TOF) calcd for C$_{18}$H$_{23}$N$_2$O$_3$ 315.1703 (M+H$^+$), found 315.1703

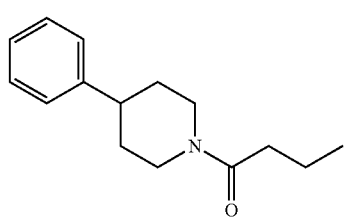 [SMILES: CCCC(=O)N1CCC(c2ccccc2)CC1]

1-(4-phenylpiperidin-1-yl)butan-1-one (49) General Procedure 4. Purified by SiO$_2$ flash chromatography (Hexanes/EtOAc, 10:1→3:1) to afford 49 as a white solid (110 mg, 77%). $^1$H NMR (500 MHz, CDCl$_3$) δ 7.31 (t, J=7.6 Hz, 2H), 7.24-7.16 (m, 3H), 4.81 (ddd, J=13.5, 4.2, 2.2 Hz, 1H), 3.99 (ddt, J=13.8, 4.2, 2.2 Hz, 1H), 3.12 (td, J=13.1, 2.6 Hz, 1H), 2.73 (tt, J=12.2, 3.7 Hz, 1H), 2.68-2.56 (m, 1H), 2.44-2.25 (m, 2H), 2.00-1.83 (m, 2H), 1.75-1.52 (m, 4H), 0.99 (t, J=7.4 Hz, 3H). HRMS (ESI-TOF) calcd for C$_{13}$H$_{14}$NO$_3$ 232.0968 [M+H$^+$], found 232.0967

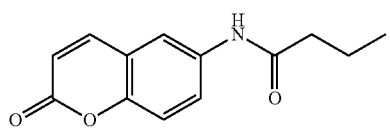 [SMILES: CCCC(=O)Nc1ccc2oc(=O)ccc2c1]

N-(2-oxo-2H-chromen-6-yl)butyramide (50) General Procedure 4. Purified by SiO$_2$ flash chromatography (Hexanes/EtOAc, 10:1→3:1) to afford 50 as a light yellow solid (116 mg, 81%). $^1$H NMR (400 MHz, CDCl$_3$) δ 8.07 (d, J=2.5 Hz, 1H), 7.69 (d, J=9.5 Hz, 1H), 7.52 (brs, 1H), 7.42 (dd, J=8.9, 2.6 Hz, 1H), 7.28 (d, J=2.4 Hz, 1H), 6.44 (d, J=9.6 Hz, 1H), 2.39 (t, J=7.4 Hz, 2H), 1.79 (h, J=7.4 Hz, 2H), 1.03 (t, J=7.4 Hz, 3H). HRMS (ESI-TOF) calcd for C$_{15}$H$_{22}$NO 232.1696 [M+H$^+$], found 232.1696

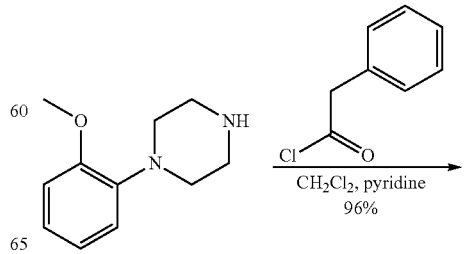

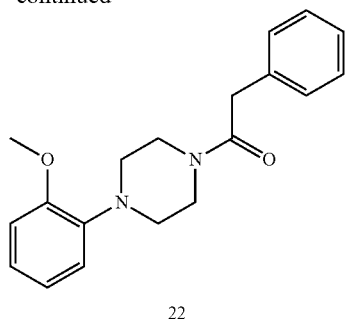

22

1-(4-(2-Methoxyphenyl)piperazin-1-yl)-2-phenylethan-1-one (22). To a mixture of 1-(2-methoxyphenyl)piperazine (30 mg, 0.156 mmol) in anhydrous $CH_2Cl_2$ (1.5 mL) and pyridine (0.5 mL) was added phenylacetylchloride (23 mg, 0.172 mmol, 1.1 equiv). The reaction mixture was stirred at room temperature for 12 h before removing the solvent under reduced pressure. The remaining residue was purified by PTLC (Hexanes/EtOAc, 2/1) providing the title compound 22 as a colorless oil (46 mg, 96%). $^1$H NMR (600 MHz, $CDCl_3$) δ 7.33 (t, J=7.5 Hz, 2H), 7.29-7.22 (m, 3H), 7.02 (td, J=7.7, 1.5 Hz, 1H), 6.93-6.81 (m, 3H), 3.85-3.83 (m, 5H), 3.79 (s, 2H), 3.64-3.59 (m, 2H), 3.00 (t, J=5.1 Hz, 2H), 2.85 (t, J=5.0 Hz, 2H). $^{13}$C NMR (151 MHz, $CDCl_3$) δ 40.66, 41.58, 46.00, 50.02, 50.37, 54.99, 110.86, 117.95, 120.58, 123.08, 126.39, 128.16, 128.33, 134.67, 140.20, 151.78, 169.08. HRMS (ESI-TOF) calcd for $C_{19}H_{23}N_2O_2$ 311.1754 [M+H$^+$], found 311.1753

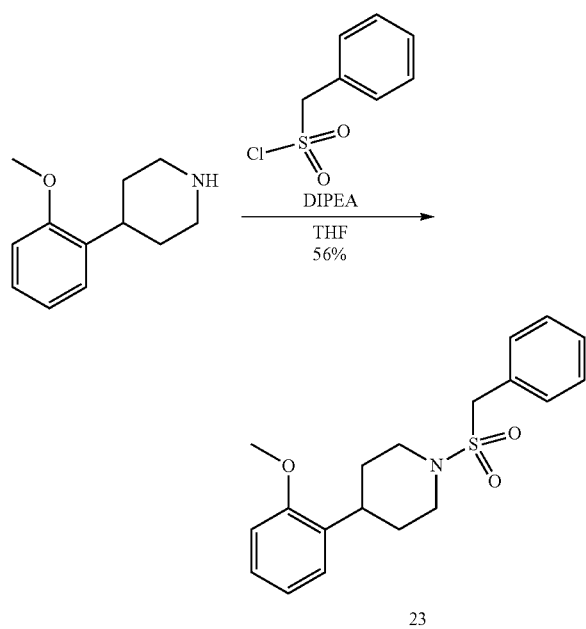

23

1-(Benzylsulfonyl)-4-(2-methoxyphenyl)piperidine (23). To a mixture of 4-(2-methoxyphenyl)piperidine (50 mg, 0.26 mmol) and N,N-diisopropylethylamine (DIPEA, 0.100 mL, 0.58 mmol) in anhydrous THF (3.0 mL) was added benzylsulfonyl chloride (55 mg, 0.28 mmol, 1.1 equiv.) under $N_2$. The reaction mixture was stirred at 50° C. for 12 h. The reaction mixture was poured into a separatory funnel with brine (10 mL) and extracted with EtOAc (2×10 mL). The combined organic layers were then dried over anhydrous $Na_2SO_4$ and concentrated under reduced pressure. The remaining residue was purified by $SiO_2$ flash chromatography (Hexanes/EtOAc, 5/1) providing the title compound 23 as a slightly beige powder (50 mg, 56%). $^1$H NMR (600 MHz, $CDCl_3$) δ 7.46-7.35 (m, 5H), 7.19 (ddd, J=8.3, 7.4, 1.7 Hz, 1H), 7.10 (dd, J=7.6, 1.7 Hz, 1H), 6.93 (td, J=7.5, 1.1 Hz, 1H), 6.85 (dd, J=8.2, 1.1 Hz, 1H), 4.24 (s, 2H), 3.83-3.75 (m, 5H), 2.96 (tt, J=12.1, 3.5 Hz, 1H), 2.72 (td, J=12.4, 2.5 Hz, 2H), 1.80-1.73 (m, 2H), 1.64 (qd, J=12.6, 4.2 Hz, 2H). $^{13}$C NMR (151 MHz, $CDCl_3$) δ 169.48, 152.18, 140.60, 135.07, 128.73, 128.56, 126.79, 123.48, 120.98, 118.35, 111.26, 55.39, 50.77, 50.42, 46.40, 41.98, 41.06. HRMS (ESI-TOF) calcd for $C_{19}H_{24}NO_3S$ 346.1471 (M+H$^+$), found 346.1472.

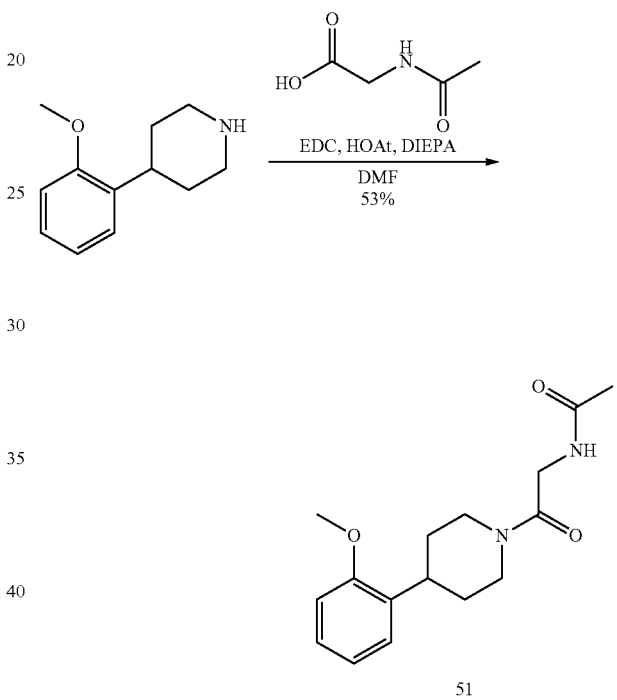

N-(2-(4-(2-methoxyphenyl)piperidin-1-yl)-2-oxoethyl)acetamide (51). 4-(2-methoxyphenyl)piperidine (50 mg, 0.26 mmol), acetylglycine (46 mg, 0.39 mmol, 1.5 equiv.) and N,N-diisopropylethylamine (DIPEA, 0.137 mL, 0.58 mmol, 3.0 equiv.) in anhydrous DMF (1.0 mL) were added EDC (75 mg, 0.39 mmol, 1.5 equiv.) and HOAt (53 mg, 0.39 mmol, 1.5 equiv.). The reaction mixture was stirred at room temperature for ~12 h before removing the solvent under reduced pressure. The remaining residue was purified by PTLC ($CH_2Cl_2$/MeOH, 9/1) providing the title compound 51 as a colorless oil (40 mg, 53%). $^1$H NMR (600 MHz, $CDCl_3$) δ 7.21 (ddd, J=8.2, 7.4, 1.7 Hz, 1H), 7.10 (dd, J=7.6, 1.8 Hz, 1H), 6.93 (td, J=7.5, 1.1 Hz, 1H), 6.87 (dd, J=8.2, 1.1 Hz, 1H), 6.67 (brs, 1H), 4.77-4.71 (m, 1H), 4.16-4.09 (m, 1H), 4.05 (dd, J=17.3, 3.8 Hz, 1H), 3.83-3.81 (m, 4H), 3.24-3.12 (m, 2H), 2.75 (td, J=12.9, 2.8 Hz, 1H), 2.05 (s, 3H), 1.94-1.85 (m, 2H), 1.68-1.52 (m, 2H). $^{13}$C NMR (151 MHz, $CDCl_3$) δ 23.07, 31.26, 32.12, 35.43, 41.40, 43.13, 45.30, 55.28, 110.42, 120.70, 126.38, 127.40, 132.74, 156.66, 166.03, 170.09. HRMS (ESI-TOF) calcd for $C_{16}H_{23}N_2O_3$ 291.1703 (M+H$^+$), found 291.1704.

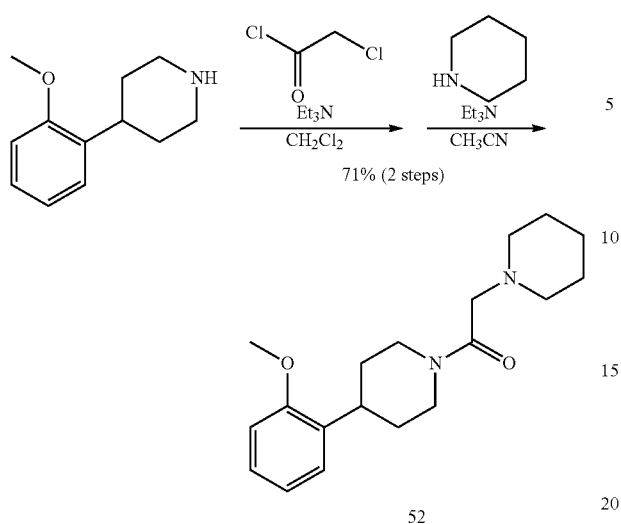

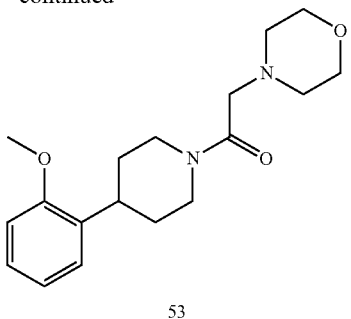

1-(4-(2-Methoxyphenyl)piperidin-1-yl)-2-(piperidin-1-yl)ethan-1-one (52).

To a mixture of 4-(2-methoxyphenyl)piperidine (350 mg, 1.83 mmol) and triethylamine (0.643 mL, 4.57 mmol, 2.5 equiv.) in anhydrous $CH_2Cl_2$ (3.5 mL) was slowly added chloroacetyl chloride (0.175 mL, 2.20 mmol, 1.2 equiv.) under $N_2$ at 0° C. The reaction mixture was stirred at room temperature for 1 h and diluted with EtOAc (10 mL). The mixture was washed with 1N aqueous HCl (1×10 mL) and brine. The organic layer was then dried over anhydrous $Na_2SO_4$ and concentrated under reduced pressure to afford a crude compound as a dark brown oil which was used to next reaction without further purification.

To a mixture of the oil (100 mg, 0.37 mmol) and triethylamine (0.156 mL, 1.12 mmol, 3.0 equiv.) in $CH_3CN$ (1 mL) was added piperidine (0.110 mL, 1.12 mmol, 3.0 equiv.) under $N_2$. The reaction mixture was stirred at room temperature for 1 h and then quenched with $H_2O$ (1 mL). The product was extracted with EtOAc (2×10 mL). The combined organic layers were then dried over anhydrous $Na_2SO_4$ and concentrated under reduced pressure. The remaining residue was purified by $SiO_2$ flash chromatography (Hexanes/EtOAc, 3/1, 3% $Et_3N$) providing the title compound 52 as a pale yellow oil (84 mg, 71% in 2 steps). $^1H$ NMR (600 MHz, $CDCl_3$) δ 7.20 (ddd, J=8.2, 7.4, 1.7 Hz, 1H), 7.12 (dd, J=7.6, 1.7 Hz, 1H), 6.93 (td, J=7.5, 1.2 Hz, 1H), 6.87 (dd, J=8.2, 1.1 Hz, 1H), 4.77-4.70 (m, 1H), 4.32-4.25 (m, 1H), 3.83 (s, 3H), 3.25 (d, J=13.3 Hz, 1H), 3.22-3.14 (m, 1H), 3.12-3.04 (m, 3H), 2.65 (td, J=12.9, 2.7 Hz, 1H), 2.47-2.41 (m, 4H), 1.87-1.83 (m, 1H), 1.66 (qd, J=12.6, 4.1 Hz, 1H), 1.61-1.53 (m, 5H), 1.45-1.41 (m, 2H). $^{13}C$ NMR (151 MHz, $CDCl_3$) δ 24.01, 24.04, 26.03, 31.72, 32.59, 35.61, 42.84, 46.71, 54.32, 54.42, 55.26, 62.61, 109.95, 110.38, 120.66, 126.47, 126.49, 127.15, 133.53, 156.74, 168.41. HRMS (ESI-TOF) calcd for $C_{19}H_{29}N_2O_2$ 317.2223 (M+H$^+$), found 317.2226.

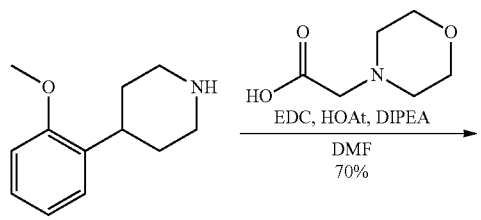

1-(4-(2-Methoxyphenyl)piperidin-1-yl)-2-morpholinoethan-1-one (53).

4-(2-methoxyphenyl)piperidine (30 mg, 0.16 mmol), morpholin-4-ylacetic acid (27 mg, 0.19 mmol, 1.2 equiv.) and DIPEA (0.084 mL, 0.48 mmol, 3.0 equiv.) in anhydrous DMF (1.0 mL) were added EDC (45 mg, 0.23 mmol, 1.5 equiv.) and HOAt (32 mg, 0.23 mmol, 1.5 equiv.). The reaction mixture was stirred at room temperature for 2 days. $H_2O$ (1 mL) was added to the reaction mixture and product was extracted with EtOAc (2×1 mL). The combined organic layers were concentrated under reduced pressure. The remaining residue was purified by PTLC (EtOAc/MeOH, 5/1) providing the title compound 53 as a colorless oil (35 mg, 70%). $^1H$ NMR (400 MHz, $CDCl_3$) δ 7.21 (td, J=7.8, 1.7 Hz, 1H), 7.11 (dd, J=7.6, 1.7 Hz, 1H), 6.98-6.84 (m, 2H), 4.74 (d, J=12.9 Hz, 1H), 4.18 (d, J=13.4 Hz, 1H), 3.83 (s, 3H), 3.74 (t, J=4.7 Hz, 4H), 3.28 (d, J=13.5 Hz, 1H), 3.24-3.07 (m, 3H), 2.72-2.61 (m, 1H), 2.60-2.47 (m, 4H), 1.88 (t, J=14.4 Hz, 2H), 1.69-1.59 (m, 2H). HRMS (ESI-TOF) calcd for $C_{18}H_{27}N_2O_3$ 319.2016 (M+H$^+$), found 319.2017.

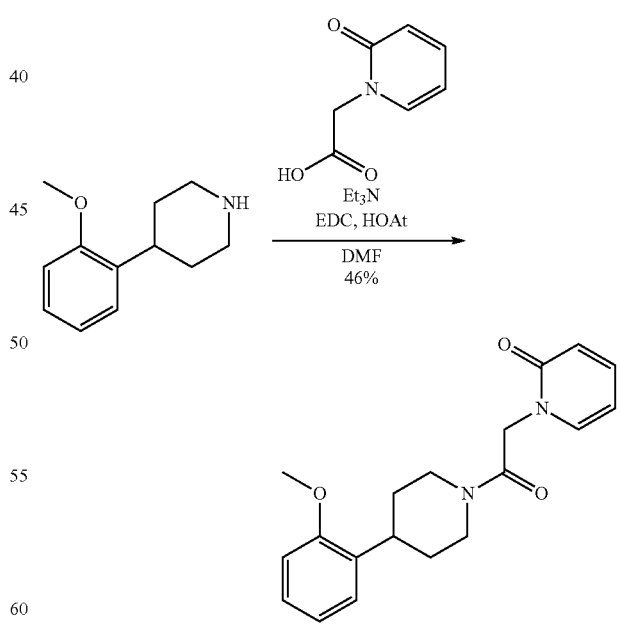

1-(2-(4-(2-Methoxyphenyl)piperidin-1-yl)-2-oxoethyl)pyridin-2(1H)-one (54).

4-(2-methoxyphenyl)piperidine (50 mg, 0.26 mmol), (2-oxo-2H-pyridin-1-yl)-acetic acid (48 mg, 0.31 mmol, 1.2 equiv.) and triethylamine (0.054 mL, 0.39 mmol, 1.5 equiv.) in anhydrous DMF (1.0 mL) were added EDC (76 mg, 0.39 mmol, 1.5 equiv.) and HOAt (53 mg, 0.39 mmol, 1.5 equiv.). The reaction mixture was stirred at room temperature for ~12 h before removing the solvent under reduced pressure. The remaining residue was purified by PTLC (EtOAc/MeOH, 6/1) providing the title compound 54 as a colorless oil (39 mg, 46%). $^1$H NMR (600 MHz, CDCl$_3$) δ 7.39-7.30 (m, 2H), 7.20 (ddd, J=8.2, 7.4, 1.7 Hz, 1H), 7.12 (dd, J=7.5, 1.7 Hz, 1H), 6.93 (td, J=7.5, 1.1 Hz, 1H), 6.87 (dd, J=8.2, 1.1 Hz, 1H), 6.58 (ddd, J=9.2, 1.4, 0.7 Hz, 1H), 6.21 (td, J=6.7, 1.4 Hz, 1H), 4.86 (d, J=15.2 Hz, 1H), 4.80-4.69 (m, 2H), 4.15-4.04 (m, 1H), 3.83 (s, 3H), 3.31-3.16 (m, 2H), 2.75 (td, J=13.0, 2.9 Hz, 1H), 1.97-1.90 (m, 1H), 1.90-1.83 (m, 1H), 1.72-1.58 (m, 2H). $^{13}$C NMR (151 MHz, CDCl$_3$) δ 30.90, 31.84, 34.98, 42.98, 45.82, 48.40, 54.87, 105.52, 109.56, 109.96, 120.22, 120.29, 126.06, 126.91, 132.51, 138.06, 139.59, 156.27, 161.96, 164.46. HRMS (ESI-TOF) calcd for C$_{19}$H$_{23}$N$_2$O$_3$ 327.1703 (M+H$^+$), found 327.1705.

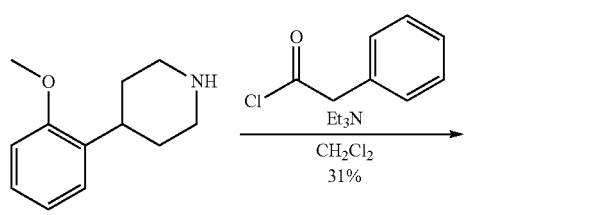

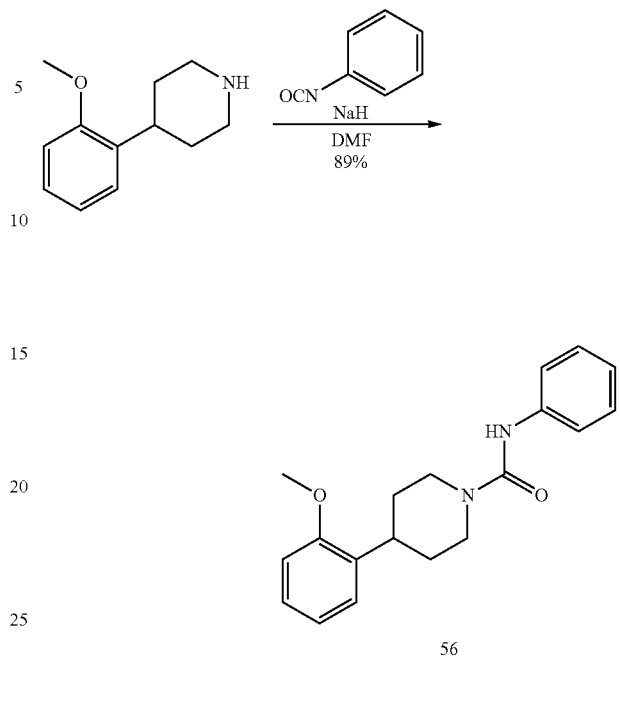

56

4-(2-Methoxyphenyl)-N-phenylpiperidine-1-carboxamide (56). To a solution of 4-(2-methoxyphenyl)piperidine (50 mg, 0.26 mmol) in anhydrous DMF (1.0 mL) was added sodium hydride (in 60% oil, 12.5 mg, 0.31 mmol, 1.2 equiv.) under N$_2$ at 0° C. The mixture was stirred at 0° C. for 15 min. Phenylisocyanate (37 mg, 0.31 mmol, 1.2 equiv.) in anhydrous DMF (0.5 mL) was added to the mixture. The reaction was then allowed to warm to room temperature. After stirring at room temperature for 1 h, the reaction was quenched with saturated aqueous NH$_4$Cl and the product was extracted with EtOAc (2×10 mL). The combined organic layers were then dried over anhydrous Na$_2$SO$_4$ and concentrated under reduced pressure. The remaining residue was purified by PTLC (Hexanes/EtOAc, 1/1) providing the title compound 56 as an off-white powder (71 mg, 89%). $^1$H NMR (600 MHz, CDCl$_3$) δ 7.41-7.36 (m, 2H), 7.36-7.25 (m, 2H), 7.24-7.13 (m, 2H), 7.03 (tt, J=7.4, 1.2 Hz, 1H), 6.94 (td, J=7.5, 1.1 Hz, 1H), 6.88 (dd, J=8.1, 1.1 Hz, 1H), 6.39 (brs, 1H), 4.24-4.18 (m, 2H), 3.84 (s, 3H), 3.17 (tt, J=12.1, 3.5 Hz, 1H), 3.03 (td, J=13.0, 2.6 Hz, 2H), 1.92-1.86 (m, 2H), 1.76-1.66 (m, 2H). $^{13}$C NMR (151 MHz, CDCl$_3$) δ 31.26, 34.92, 44.81, 54.85, 76.31, 76.81, 76.91, 76.99, 109.94, 119.33, 119.36, 120.24, 120.25, 122.45, 122.49, 126.06, 126.79, 128.40, 128.43, 154.45, 156.27. HRMS (ESI-TOF) calcd for C$_{19}$H$_{23}$N$_2$O$_2$ 311.1754 (M+H$^+$), found 311.1753.

55

1-(4-(2-Methoxyphenyl)piperidin-1-yl)-2-phenylethan-1-on (55). To a mixture of 4-(2-methoxyphenyl)piperidine (30 mg, 0.16 mmol) and triethylamine (0.073 mL, 0.24 mmol, 1.5 equiv.) in anhydrous CH$_2$Cl$_2$ (1.0 mL) was added phenylacetyl chloride (26 mg, 0.17 mmol, 1.1 equiv.) under N$_2$ at 0° C. The reaction mixture was stirred at room temperature for 1 h before removing the solvent under reduced pressure. The remaining residue was purified by PTLC (Hexanes/EtOAc, 2/1) providing the title compound 55 as a white solid (15 mg, 31%). $^1$H NMR (500 MHz, CDCl$_3$) δ 7.36-7.27 (m, 3H), 7.27-7.14 (m, 3H), 7.03 (dd, J=7.5, 1.7 Hz, 1H), 6.94-6.82 (m, 2H), 4.81 (d, J=13.1 Hz, 1H), 3.97 (d, J=13.4 Hz, 1H), 3.80 (s, 3H), 3.78 (s, 2H), 3.17-3.04 (m, 2H), 2.67 (td, J=12.9, 2.8 Hz, 1H), 1.83 (d, J=13.5 Hz, 1H), 1.73 (d, J=13.3 Hz, 1H), 1.59 (td, J=12.7, 4.3 Hz, 1H), 1.31 (qd, J=12.6, 4.1 Hz, 1H). HRMS (ESI-TOF) calcd for C$_{20}$H$_{24}$NO$_2$ 310.1801 (M+H$^+$), found 310.1801.

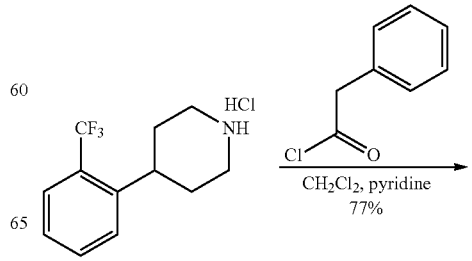

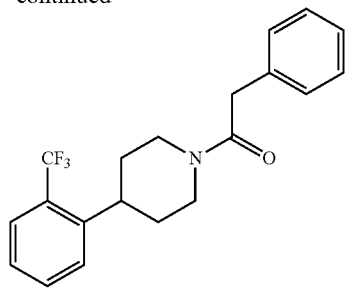

57

2-Phenyl-1-(4-(2-(trifluoromethyl)phenyl)piperidin-1-yl)ethan-1-one (57). To a mixture of 4-(2-(trifluoromethyl)phenyl)piperidine hydrochloride (40 mg, 0.15 mmol) in anhydrous $CH_2Cl_2$ (1.5 mL) and pyridine (0.5 mL) was added phenylacetylchloride (26 mg, 0.17 mmol, 1.1 equiv.) under $N_2$ at 0° C. The reaction mixture was stirred at room temperature for 12 h before removing the solvent under reduced pressure. The remaining residue was purified by PTLC (Hexanes/EtOAc, 2/1) providing the title compound 57 as a colorless oil (40 mg, 77%). $^1$H NMR (600 MHz, $CDCl_3$) δ 7.61 (dd, J=7.9, 1.2 Hz, 1H), 7.51-7.45 (m, 1H), 7.38-7.22 (m, 7H), 4.88-4.81 (m, 1H), 4.02-3.96 (m, 1H), 3.84-3.75 (m, 2H), 3.15-3.04 (m, 2H), 2.65 (td, J=13.0, 2.8 Hz, 1H), 1.82 (d, J=13.3 Hz, 1H), 1.69 (d, J=13.2 Hz, 1H), 1.63 (qd, J=12.6, 4.2 Hz, 1H), 1.31 (qd, J=12.6, 4.1 Hz, 1H). $^{13}$C NMR (151 MHz, $CDCl_3$) δ 32.46, 33.25, 37.85, 40.91, 42.24, 46.50, 125.05, 125.42, 125.46, 125.91, 126.40, 127.37, 127.55, 128.21, 128.34, 131.65, 134.85, 143.64, 168.99. HRMS (ESI-TOF) calcd for $C_{20}H_{21}F_3NO$ 348.1570 (M+H$^+$), found 348.1572.

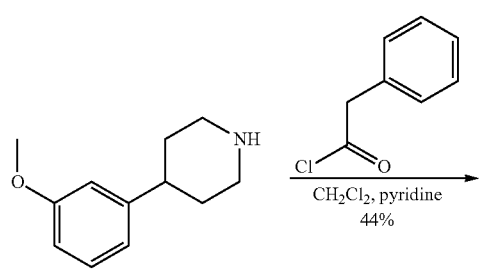

58

1-(4-(3-Methoxyphenyl)piperidin-1-yl)-2-phenylethan-1-one (58). To a mixture of 4-(2-(trifluoromethyl)phenyl)piperidine hydrochloride (40 mg, 0.15 mmol) in anhydrous $CH_2Cl_2$ (1.5 mL) and pyridine (0.5 mL) was added phenylacetylchloride (26 mg, 0.17 mmol, 1.1 equiv.) under $N_2$ at 0° C. The reaction mixture was stirred at room temperature for 12 h before removing the solvent under reduced pressure. The remaining residue was purified by PTLC (Hexanes/EtOAc, 2/1) providing the title compound 58 as a colorless oil (40 mg, 44%). $^1$H NMR (500 MHz, $CDCl_3$) δ 7.37-7.28 (m, 3H), 7.28-7.17 (m, 3H), 6.78-6.69 (m, 2H), 6.67-6.65 (m, 1H), 4.81 (d, J=13.3 Hz, 1H), 3.98 (d, J=13.7 Hz, 1H), 3.83-3.73 (m, 4H), 3.10-3.01 (m, 1H), 2.70-2.59 (m, 2H), 1.87 (d, J=13.5 Hz, 1H), 1.74 (d, J=14.7 Hz, 1H), 1.65-1.56 (m, 1H), 1.38-1.23 (m, 2H). HRMS (ESI-TOF) calcd for $C_{20}H_{24}NO_2$ 310.1801 (M+H$^+$), found 310.1801.

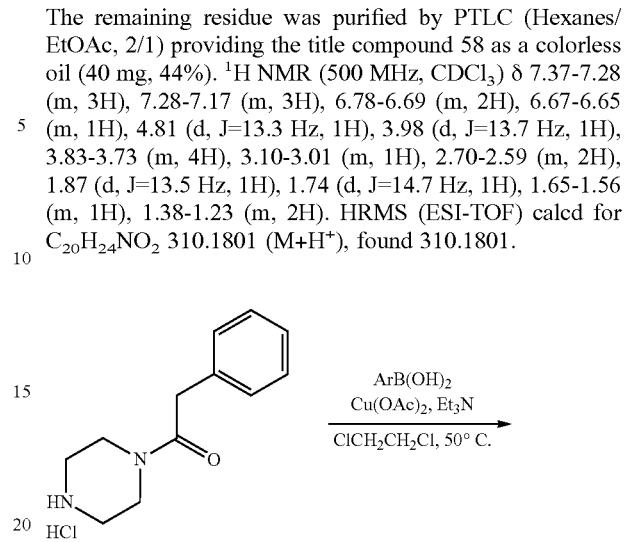

59-62

General Procedure 5:

To a mixture of 1-phenylacetyl-piperazin hydrochloride (30 mg, 0.13 mmol), phenylboronic acid (2.0 equiv.) and triethylamine (0.092 mL, 0.66 mmol, 5.0 equiv.) in $ClCH_2CH_2Cl$ (1.0 mL) was added $Cu(OAc)_2$ (48 mg, 0.17 mmol, 2.0 equiv.). The reaction mixture was stirred at 50° C. for 12 h before removing the solvent under reduced pressure. The remaining residue was purified by PTLC (Hexanes/EtOAc, 1/1) providing the title compound.

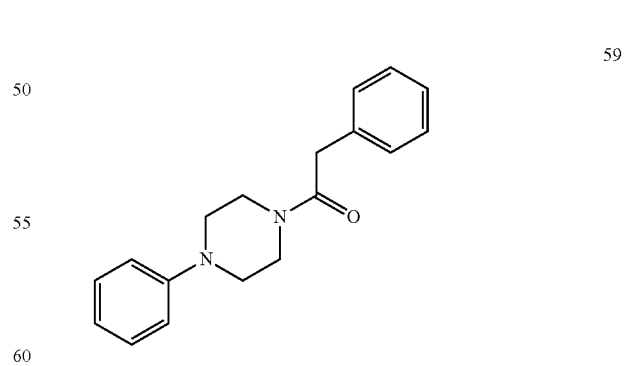

59

2-phenyl-1-(4-phenylpiperazin-1-yl)ethan-1-one (59). (10 mg, colorless oil, 27%): $^1$H NMR (500 MHz, $CDCl_3$) δ 7.36-7.30 (m, 3H), 7.30-7.21 (m, 4H), 6.92-6.85 (m, 3H), 3.84-3.77 (m, 4H), 3.63-3.57 (m, 2H), 3.17-3.11 (m, 2H), 2.99-2.95 (m, 2H). HRMS (ESI-TOF) calcd for $C_{18}H_{21}N_2O$ 281.1648 (M+H$^+$), found 281.1649.

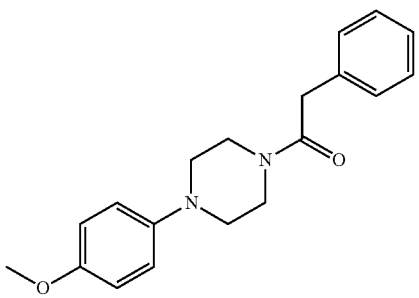

60

1-(4-(4-methoxyphenyl)piperazin-1-yl)-2-phenylethan-1-one (60). (7.2 mg, colorless oil, 18%): $^1$H NMR (500 MHz, CDCl$_3$) δ 7.36-7.29 (m, 3H), 7.29-7.25 (m, 4H), 6.88-6.79 (m, 2H), 3.83-3.74 (m, 7H), 3.62-3.56 (m, 2H), 3.01 (t, J=5.2 Hz, 2H), 2.87-2.83 (m, 2H). HRMS (ESI-TOF) calcd for C$_{19}$H$_{23}$N$_2$O$_2$ 311.1754 (M+H$^+$), found 311.1755.

61

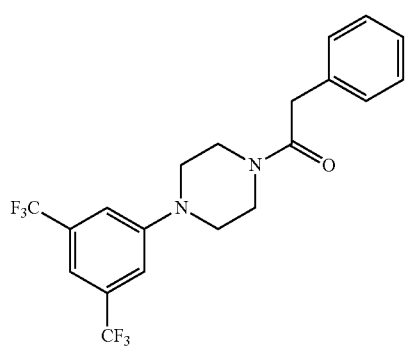

1-(4-(4-methoxyphenyl)piperazin-1-yl)-2-phenylethan-1-one (61). (1.6 mg, white solid, 3.0%): $^1$H NMR (500 MHz, CDCl$_3$) δ 7.38-7.24 (m, 6H), 7.21-7.17 (m, 2H), 3.86-3.78 (m, 4H), 3.63 (t, J=5.2 Hz, 2H), 3.26 (t, J=5.3 Hz, 2H), 3.08 (t, J=5.1 Hz, 2H). HRMS (ESI-TOF) calcd for C$_{20}$H$_{19}$F$_6$N$_2$O 417.1396 (M+H$^+$), found 417.1397

62

1-(4-(2-phenoxyphenyl)piperazin-1-yl)-2-phenylethan-1-one (62). (3.3 mg, colorless oil, 6.8%): $^1$H NMR (500 MHz, CDCl$_3$) δ 7.34-7.20 (m, 6H), 7.13-6.85 (m, 8H), 3.72 (s, 2H), 3.60 (t, J=5.1 Hz, 2H), 3.40-3.34 (m, 2H) 3.02 (t, J=5.1 Hz, 2H), 2.87 (t, J=5.0 Hz, 2H). HRMS (ESI) calcd for C$_{24}$H$_{25}$N$_2$O$_2$ 373.191 (M+H$^+$), found 373.1909.

Tables 1-3 illustrate proteins and binding sites described herein.

TABLE 1

| Accession # | Protein Name | Labeled Peptide | Peptide Sequence | Probes | Family |
|---|---|---|---|---|---|
| Q9NUJ1 | ABHD10 Abhydrolase domain-containing protein 10, mitochondrial | 285-300 | ADIQLLVYTIDDLIDK (SEQ ID NO: 97) | 3 | Enzymes |
| Q9NUJ1 | ABHD10 Abhydrolase domain-containing protein 10, mitochondrial | 209-223 | YSEEGVYNVQYSFIK (SEQ ID NO: 98) | 13 14 15 3 4 8 | Enzymes |
| Q99798 | ACO2 Aconitate hydratase, mitochondrial | 32-50 | VAMSHFETNEYIHYDLLEK (SEQ ID NO: 99) | 6 | Enzymes |
| P24666 | ACP1 Low molecular weight phosphotyrosine protein phosphatase | 42-59 | VDSAATSGYEIGNPPDYR (SEQ ID NO: 1) | 13 | Enzymes |
| P68133 | ACTA1 Actin, alpha skeletal muscle | 241-256 | SYELPDGQVITIGNER (SEQ ID NO: 100) | 13 3 9 | Adapter, Scaffolding, Modulator Proteins |
| P68133 | ACTA1 Actin, alpha skeletal muscle | 71-86 | YPIEHGIITNWDDMEK (SEQ ID NO: 101) | 13 | Adapter, Scaffolding, Modulator Proteins |

TABLE 1-continued

| Accession # | Protein Name | Labeled Peptide | Peptide Sequence | Probes | Family |
|---|---|---|---|---|---|
| P62736 | ACTA2 Actin, aortic smooth muscle | 241-256 | SYELPDGQVITIGNER (SEQ ID NO: 102) | 13 9 | Adapter, Scaffolding, Modulator Proteins |
| P62736 | ACTA2 Actin, aortic smooth muscle | 71-86 | YPIEHGIITNWDDMEK (SEQ ID NO: 103) | 13 | Adapter, Scaffolding, Modulator Proteins |
| P60709 | ACTB Actin, cytoplasmic 1 | 148-177 | TTGIVMDSGDGVTHTVPIYEGYALPHAILR (SEQ ID NO: 104) | 14 13 | Adapter, Scaffolding, Modulator Proteins |
| P60709 | ACTB Actin, cytoplasmic 1 | 197-206 | GYSFTTTAER (SEQ ID NO: 105) | 3 | Adapter, Scaffolding, Modulator Proteins |
| P60709 | ACTB Actin, cytoplasmic 1 | 216-238 | LCYVALDFEQEMATAASSSSLEK (SEQ ID NO: 106) | 13 14 3 9 8 | Adapter, Scaffolding, Modulator Proteins |
| P60709 | ACTB Actin, cytoplasmic 1 | 239-254 | SYELPDGQVITIGNER (SEQ ID NO: 107) | 13 14 3 9 8 | Adapter, Scaffolding, Modulator Proteins |
| P60709 | ACTB Actin, cytoplasmic 1 | 96-113 | VAPEEHPVLLTEAPLNPK (SEQ ID NO: 108) | 14 3 13 | Adapter, Scaffolding, Modulator Proteins |
| Q562R1 | ACTBL2 Beta-actin-like protein 2 | 240-255 | SYELPDGQVITIGNER (SEQ ID NO: 109) | 13 | Adapter, Scaffolding, Modulator Proteins |
| Q562R1 | ACTBL2 Beta-actin-like protein 2 | 97-114 | VAPDEHPILLTEAPLNPK (SEQ ID NO: 110) | 13 | Adapter, Scaffolding, Modulator Proteins |
| O96019 | ACTL6A Actin-like protein 6A | 25-34 | AGYAGEDCPK (SEQ ID NO: 111) | 3 | Transcription factors, Regulators |
| P12814 | ACTN1 Alpha-actinin-1 | 237-254 | AIMTYVSSFYHAFSGAQK (SEQ ID NO: 112) | 13 | Adapter, Scaffolding, Modulator Proteins |
| P12814 | ACTN1 Alpha-actinin-1 | 377-387 | GYEEWLLNEIR (SEQ ID NO: 113) | 13 | Adapter, Scaffolding, Modulator Proteins |
| O43707 | ACTN4 Alpha-actinin-4 | 256-273 | AIMTYVSSFYHAFSGAQK (SEQ ID NO: 114) | 13 | Channels, Transporters, Receptors |
| O43707 | ACTN4 Alpha-actinin-4 | 396-406 | GYEEWLLNEIR (SEQ ID NO: 115) | 13 | Channels, Transporters, Receptors |
| O43707 | ACTN4 Alpha-actinin-4 | 470-494 | VEQIAAIAQELNELDYYDSHNVNTR (SEQ ID NO: 116) | 14 | Channels, Transporters, Receptors |
| O43707 | ACTN4 Alpha-actinin-4 | 792-805 | ACLISLGYDVENDR (SEQ ID: 117) | 14 | Channels, Transporters, Receptors |
| Q8NI60 | ADCK3 Chaperone activity of bc1 complex-like, mitochondrial | 277-295 | LGQMLSIQDDAFINPHLAK (SEQ ID NO: 2) | 14 14 | Enzymes |
| P55263 | ADK Adenosine kinase | 209-224 | IFTLNLSAPFISQFYK (SEQ ID NO: 3) | 2 | Enzymes |
| P30520 | ADSS Adenylosuccinate synthetase isozyme 2 | 431-441 | FIEDELQIPVK (SEQ ID NO: 4) | 14 | Enzymes |
| Q53H12 | AGK Acylglycerol kinase, mitochondrial AGPS | 283-304 | LASYWAQPQDALSQEVSPEVWK (SEQ ID NO: 118) | 14 | Enzymes |

TABLE 1-continued

| Accession # | Protein Name | Labeled Peptide | Peptide Sequence | Probes | Family |
|---|---|---|---|---|---|
| O00116 | Alkyldihydroxyacetonephosphate synthase, peroxisomal | 587-603 | GISDPLTVFEQTEAAAR (SEQ ID NO: 119) | 13 14 | Enzymes |
| O43865 | AHCYL1 Putative adenosylhomocysteinase 2 | 250-261 | GIVEESVTGVHR (SEQ ID NO: 120) | 6 | Transcription factors, Regulators |
| Q96HN2 | AHCYL2 Putative adenosylhomocysteinase 3 | 331-342 | GIVEESVTGVHR (SEQ ID NO: 121) | 6 | Enzymes |
| O95433 | AHSA1 Activator of 90 kDa heat shock protein ATPase homolog 1 | 225-246 | VFTTQELVQAFTHAPATLEADR (SEQ ID NO: 122) | 4 | Chaperones |
| O95433 | AHSA1 Activator of 90 kDa heat shock protein ATPase homolog 1 | 322-328 | YYFEGIK (SEQ ID NO: 123) | 4 | Chaperones |
| O95831 | AIFM1 Apoptosis-inducing factor 1, mitochondrial | 475-510 | PYWHQSMIEWSDLGPDVGYEAIGLVDSSLPTVGVFAK (SEQ ID NO: 5) | 3 2 4 6 | Enzymes |
| P54886 | ALDH18A1 Delta-1-pyrroline-5-carboxylate synthase | 650-662 | FASYLTFSPSEVK (SEQ ID NO: (12) | 14 | Enzymes |
| Q3SY69 | ALDH1L2 Mitochondrial 10-formyltetraydrofolate dehydrogen | 152-172 | AGFSVFWADDGLDTGPILLQR (SEQ ID NO: 125) | 6 | Enzymes |
| P49419 | ALDH7A1 Alpha-aminoadipic semialdehyde dehydrogenase | 139-162 | ILVEGVGEVQEYVDICDYAVGLSR (SEQ ID NO: 6) | 13 8 | Enzymes |
| Q9UJX3 | ANAPC7 Anaphase-promoting complex subunit 7 | 407-424 | LDCYEGLIECYLASNSIR (SEQ ID NO: 126) | 3 | Uncategorized |
| Q10567 | ANP32A Acidic leucine-rich nuclear phosphoprotein 32 family member A | 117-132 | SLDLFNCEVTNLNDYR (SEQ ID NO: 127) | 13 | Transcription factors, Regulators |
| Q92688 | ANP32B Acidic leucine-rich nuclear phosphoprotein 32 family member B | 117-132 | SLDLFNCEVTNLNDYR (SEQ ID NO: 128) | 13 | Chaperones |
| Q10567 | AP1B1 AP-1 complex subunit beta-1 | 902-913 | LTNGIWVLAELR (SEQ ID NO: 129) | 13 | Channels, Transporters, Receptors |
| Q9BZZ5 | API5 Apoptosis inhibitor 5 | 182-196 | VLEDVTFEEFVLFMK (SEQ ID NO: 130) | 4 | Uncategorized |
| Q9BZZ5 | API5 Apoptosis inhibitor 5 | 131-148 | GTLGGLFSQILQGEDIVR (SEQ ID NO: 131) | 4 | Uncategorized |
| Q9BZZ5 | API5 Apoptosis inhibitor 5 | 211-237 | QQLVELVAEQADLEQTFNPSDPDCVDR (SEQ ID NO: 132) | 4 | Uncategorized |
| Q9BUR5 | APOO Apolipoprotein O | 173-182 | GYIVIEDLWK (SEQ ID NO: 133) | 14 4 2 | Channels, Transporters, Receptors |
| P84077 | ARF1 ADP-ribosylation factor 1 | 39-59 | LGEIVTTIPTIGFNVETVEYK (SEQ ID NO: 7) | 13 3 2 8 | Channels, Transporters, Receptors |
| P61204 | ARF3 ADP-ribosylation factor 3 | 39-59 | LGEIVTTIPTIGFNVETVEYK (SEQ ID NO: 7) | 13 3 2 8 | Channels, Transporters, Receptors |

TABLE 1-continued

| Accession # | Protein Name | Labeled Peptide | Peptide Sequence | Probes | Family |
|---|---|---|---|---|---|
| P18085 | ARF4 ADP-ribosylation factor 4 | 39-59 | LGEIVTTIPTIGFNVETVEYK (SEQ ID NO: 7) | 13 3 2 8 | Channels, Transporters, Receptors |
| P84085 | ARF5 ADP-ribosylation factor 5 | 39-59 | LGEIVTTIPTIGFNVETVEYK (SEQ ID NO: 7) | 13 3 2 8 | Channels, Transporters, Receptors |
| P40616 | ARL1 ADP-ribosylation factor-like protein 1 | 163-178 | GTGLDEAMEQLVETLK (SEQ ID NO: 9) | 14 13 | Transcription factors Regulators |
| P40616 | ARL1 ADP-ribosylation factor-like protein 1 | 37-59 | LQVGEVVTTIPTIGFNVETVTY (SEQ ID NO: 10) | 13 | Transcription factors Regulators |
| O43681 | ASNA1 ATPase ASNA1 | 131-153 | MMQEAMSAFPGIDEAMSYAEVMR (SEQ ID NO: 134) | 14 | Enzymes |
| Q9NV17 | ATAD3A ATPase family AAA domain-containing protein 3A | 287-294 | AFVTDWDK (SEQ ID NO: 135) | 4 6 | Enzymes |
| P31939 | ATIC Bifunctional purine biosynthesis protein PURH | 178-194 | AFTHTAQYDEAISDYFR (SEQ ID NO: 11) | 13 | Enzymes |
| P05023 | ATP1A1 Sodium/potassium-transporting ATPase subunit apha | 360-377 | NLEAVETLGSTSTICSDK (SEQ ID NO: 136) | 13 14 | Channels, Transporters, Receptors |
| P05023 | ATP1A1 Sodium/potassium-transporting ATPase subunit apha | 894-911 | WINDVEDSYGQQWTYEQR (SEQ ID NO: 137) | 9 | Channels, Transporters, Receptors |
| P16615 | ATP2A2 Sarcoplasic/endoplasmic reticulum calcium ATPase | 335-352 | SLPSVETLGCTSVICSD (SEQ ID NO: 138) | 14 | Channels, Transporters, Receptors |
| P20020 | ATP2B1 Plasma membrane calcium-transporting ATPase 1 | 824-840 | EASDIILTDDNFTSIVK (SEQ ID NO: 139) | 14 | Channels, Transporters, Receptors |
| P23634 | ATP2B4 Plasma membrane calcium-transporting ATPase 4 | 812-828 | EASDILTDDFTSIV (SEQ ID NO: 140) | 14 | Channels, Transporters, Receptors |
| P25705 | ATP5A1 ATP synthase subunit alpha, mitochondrial | 104-123 | GMSLNLEPDNVGVVVFGNDK (SEQ ID NO: 141) | 14 3 13 | Channels, Transporters, Receptors |
| P25705 | ATP5A1 ATP synthase subunit alpha, mitochondrial | 442-463 | EVAAFAQFGSDLDAATQQLLSR (SEQ ID NO: 142) | 13 14 3 2 9 8 | Channels, Transporters, Receptors |
| P06576 | ATP5B ATP synthase subunit beta, mitochondrial | 144-155 | IMNVGEPIDER (SEQ ID NO: 143) | 2 6 | Channels, Transporters, Receptors |
| P06576 | ATP5B ATP synthase subunit beta, mitochondrial | 226-239 | AHGGYSVFAGCGER (SEQ ID NO: 144) | 6 | Channels, Transporters, Receptors |
| P06576 | ATP5B ATP synthase subunit beta, mitochondrial | 242-259 | EGNDLYHEMIESGVINLK (SEQ ID NO: 145) | 9 6 | Channels, Transporters, Receptors |
| P06576 | ATP5B ATP synthase subunit beta, mitochondrial | 295-310 | DQEGQDVLLFIDNIFR (SEQ ID NO: 146) | 6 | Channels, Transporters, Receptors |
| P06576 | ATP5B ATP synthase subunit | 352-387 | GSITSVQAIYVPADDLTDPAPATTFAHLDATTVLSR (SEQ ID | 14 9 6 | Channels, Transporters, |

TABLE 1-continued

| Accession # | Protein Name | Labeled Peptide | Peptide Sequence | Probes | Family |
|---|---|---|---|---|---|
| | beta, mitochondrial | | 147) | | Receptors |
| P06576 | ATP5B ATP synthase subunit beta, mitochondrial | 388-406 | AIAELGIYPAVDPLDSTSR (SEQ ID NO: 148) | 13 14 3 2 6 8 | Channels, Transporters, Receptors |
| P06576 | ATP5B ATP synthase subunit beta, mitochondrial | 407-422 | IMDPNIVGSEHYDVAR (SEQ ID NO: 149) | 14 | Channels, Transporters, Receptors |
| P06576 | ATP5B ATP synthase subunit beta, mitochondrial | 433-451 | SLQDIIAILGMDELSEEDK (SEQ ID NO: 150) | 14 6 | Channels, Transporters, Receptors |
| P06576 | ATP5B ATP synthase subunit beta, mitochondrial | 463-480 | FLSQPFQVAEVFTGHMGK (SEQ ID NO: 151) | 6 | Channels, Transporters, Receptors |
| P06576 | ATP5B ATP synthase subunit beta, mitochondrial | 95-109 | LVLEVAQHLGESTVR (SEQ ID NO: 152 | 13 6 | Channels, Transporters, Receptors |
| P36542 | ATP5C1 ATP synthase subunit gamma, mitochondrial | 116-126 | SEVATLTAAGK (SEQ ID NO: 153) | 6 | Channels, Transporters, Receptors |
| P24539 | ATP5F1 ATP synthase subunit b, mitochondrial | 116-126 | YGPFVADFADK (SEQ ID NO: 154) | 14 | Channels, Transporters, Receptors |
| P24539 | ATP5F1 ATP synthase subunit b, mitochondrial | 56-70 | YGLIPEEFFQFLYPK (SEQ ID NO: 155) | 14 4 2 13 | Channels, Transporters, Receptors |
| P24539 | ATP5F1 ATP synthase subunit b, mitochondrial | 71-90 | TGVTGPYVLGTGLILYALSK (SEQ ID NO: 156) | 13 | Channels, Transporters, Receptors |
| P21281 | ATP5F1 ATP ATP6V1B2 V-type proton ATPase subunit B, brain isoform | 437-457 | AVVGEEALTSDDLLYLEFLQK (SEQ ID NO: 157) | 14 | Channels, Transporters, Receptors |
| P21281 | ATP6V1B2 V-type proton ATPase subunit B, brain isoform | 83-93 | SGQVLEVSGSK (SEQ ID NO: 158) | 13 | Channels, Transporters, Receptors |
| P36543 | ATP6V1BE1 V-type proton ATPase subunit E 1 | 200-212 | LDLIAQQMMPEVR (SEQ ID NO: 159) | 13 | Channels, Transporters, Receptors |
| P46379 | BAG6 Large proline-rich protein BAG6 | 332-344 | LLGNTFVALSDLR (SEQ ID NO: 160) | 8 | Chaperones |
| Q07812 | BAX Apoptosis regulator BAX | 66-78 | IGDELDSNMELQR (SEQ ID NO: 161) | 13 | Uncategorized |
| O75934 | BCAS2 Pre-mRNA-splicing factor SPF27 | 137-151 | VYNENLVHMIEHAQK (SEQ ID NO: 162) | 4 | Uncategorized |
| Q13867 | BLMH Bleomycin hydrolase | 203-218 | GEISATQDVMMEEIFR (SEQ ID NO: 13) | 13 | Enzymes |
| Q13867 | BLMH Bleomycin hydrolase | 111-124 | CYFFLSAFVDTAQR (SEQ ID NO: 12) | 14 | Enzymes |
| P35613 | BSG Basigin | 283-300 | SELHIENLNMEADPGQYR (SEQ ID NO: 163) | 13 14 4 | Uncategorized |
| P35613 | BSG Basigin | 228-243 | SSEHINEGETAMLVCK (SEQ ID NO: 164) | 2 | Uncategorized |
| Q4ZIN3 | C19orf6 Membralin | 254-271 | LLLDEFLGYDDILMSSVK (SEQ ID NO: 165) | 9 | Uncategorized |
| Q07021 | C1QBP Complement component 1 Q subcomponent-binding protein | 247-276 | GVDNTFADELVELSTALEHQEYIT FLEDLK (SEQ ID N: 166) | 13 14 3 9 | Transcription factors, Regulators |
| Q07021 | C1QBP Complement component 1 Q | 155-174 | VEEQEPELTSTPNFVVEVIK (SEQ ID NO: 167) | 13 14 3 9 | Transcription factors, Regulators |

TABLE 1-continued

| Accession # | Protein Name | Labeled Peptide | Peptide Sequence | Probes | Family |
|---|---|---|---|---|---|
| Q07021 | C1QBP Complement component 1 Q subcomponent-binding protein | 105-119 | MSGGWELELNGTEAK (SEQ ID NO: 168) | 9 | Transcription factors, Regulators |
| Q07021 | C1QBP Complement component 1 Q subcomponent-binding protein | 181-207 | ALVLDCHYPEDEVGQEDEAESDIFSIR (SEQ ID NO: 169) | 13 9 | Transcription factors, Regulators |
| Q07021 | C1QBP Complement component 1 Q subcomponent-binding protein | 81-91 | AFVDFLSDEIK (SEQ ID NO: 170) | 9 | Transcription factors, Regulators |
| Q07021 | C1QBP Complement component 1 Q subcomponent-binding protein | 129-154 | ITVTFNINNSIPPTFDGEEEPSQGQK (SEQ ID NO: 171) | 9 | Transcription factors, Regulators |
| Q07021 | C1QBP Complement component 1 Q subcomponent-binding protein | 208-220 | EVSFQSTGESEWK (SEQ ID NO: 172) | 3 9 | Transcription factors, Regulators |
| P62158 | CALM3 Calmodulin | 128-149 | EADIDGDGQVNYEEFVQMMTAK (SEQ ID NO: 173) | 13 | Adapter, Scaffolding, Modulator Proteins |
| P62158 | CALM3 Calmodulin | 39-75 | SLGQNPTEAELQDMINEVDADGNGTIDFPEFLTMMAR (SEQ ID NO: 174) | 14 | Adapter, Scaffolding, Modulator Proteins |
| P27797 | CALR Calreticulin | 323-351 | SGTIFDNFLITNDEAYAEEFGNETWGVTK (SEQ ID NO: 14) | 13 9 6 | Chaperones |
| P27797 | CALR Calreticulin | 99-111 | HEQNIDCGGGYVK (SEQ ID NO: 15) | 6 | Chaperones |
| P27824 | CANX Calnexin | 235-274 | THLYTLILNPDNSFEILVDQSVVNSGNLLNDMTPPVNPSR (SEQ ID NO: 175) | 6 | Chaperones |
| P07384 | CAPN1 Calpain-1 catalytic subunit | 175-193 | LVFVHSAEGNEFWSALLEK (SEQ ID NO: 16) | 14 | Enzymes |
| Q96A33 | CCDCC47 Coiled-coil domain-containing protein 47 | 197-212 | LNQENEHIYNLWCSGR (SEQ ID NO: 177) | 4 2 | Uncategorized |
| Q96A33 | CCDCC47 Coiled-coil domain-containing protein 47 | 375-392 | DMEALLPLMNMVIYSIDK (SEQ ID NO: 178) | 6 | Uncategorized |
| Q96ER9 | CCDCC51 Coiled-coil domain-containing protein 51 | 86-96 | YEEFVGLNEVR (SEQ ID NO: 179) | 14 | Uncategorized |
| P78371 | CCT2 T-complex protein 1 subunit beta | 294-322 | QLIYNYPEQLFGAAGVMAIEHADFAGVER (SEQ ID NO: 180) | 14 | Chaperones |
| P78371 | CCT2 T-complex protein 1 subunit beta | 502-516 | QVLLSAAEAAEVILR (SEQ ID NO: 181) | 14 3 | Chaperones |
| P78371 | CCT2 T-complex protein 1 subunit beta | 90-111 | VQDDEVGDGTTSVTVLAAELLR (SEQ ID NO: 182) | 14 | Chaperones |
| P49368 | CCT3 T-complex protein 1 subunit gamma | 439-449 | AVAQALEVIPR (SEQ ID NO: 183) | 14 | Chaperones |

TABLE 1-continued

| Accession # | Protein Name | Labeled Peptide | Peptide Sequence | Probes | Family |
|---|---|---|---|---|---|
| P49368 | CCT3 T-complex protein 1 subunit gamma | 86-127 | TQDEEVGDGTTSVIILAGEMLSVA EHFLEQQMHPTVVISAYR (SEQ ID NO: 184) | 14 | Chaperones |
| P50991 | CCT4 T-complex protein 1 subunit delta | 175-193 | VVSQYSSLLSPMSVNAVMK (SEQ ID NO: 185) | 2 | Chaperones |
| P50991 | CCT4 T-complex protein 1 subunit delta | 453-481 | AFADAMEVIPSTLAENAGLNPIST VTELR (SEQ ID NO: 186) | 14 4 2 | Chaperones |
| P48643 | CCT5 T-complex protein 1 subunit epsilon | 294-323 | ETGANLAICQWGFDDEANHLLLQ NLPAVR (SEQ ID NO: 187) | 6 | Chaperones |
| P48643 | CCT5 T-complex protein 1 subunit epsilon | 324-340 | WVGGPEIELIAIATGGR (SEQ ID NO: 188) | 14 3 13 6 | Chaperones |
| P48643 | CCT5 T-complex protein 1 subunit epsilon | 450-478 | AFADALEVIPMALSENSGMNPIQT MTEVR (SEQ ID NO: 189) | 14 6 | Chaperones |
| P48643 | CCT5 T-complex protein 1 subunit epsilon | 97-126 | SQDDEIGDGTTGVVVLAGALLE AEQLLDR (SEQID NO: 190) | 13 14 6 9 | Chaperones |
| P40227 | CCT6A T-complex protein 1 subunit zeta | 400-424 | NAIDDGCVVPGAGAVEVAMAEA LIK (SEQ ID NO: 191) | 9 | Chaperones |
| Q99832 | CCT7 T-complex protein 1 subunit eta | 85-106 | SQDAEVGDGTTSVTLLAAEFLK (SEQ ID NO: 192) | 13 | Chaperones |
| P50990 | CCT8 T-complex protein 1 subunit theta | 441-450 | FAEAFEAIPR (SEQ ID NO: 193) | 8 | Chaperones |
| Q16543 | CDC37 Hsp90 co-chaperone Cdc37 | 287-307 | LGPGGLDPVEVYESLPEELQK (SEQ ID NO: 194) | 8 | Chaperones |
| Q96JB5 | CDK5RAP3 CDK5 regulatory subuni-associated protein 3 | 351-367 | NQFLDELMELEIFLAQR (SEQ ID NO: 195) | 3 | Adapter, Scaffolding, Modulator Proteins |
| Q07065 | CKAP4 Cytoskeleton-associated protein 4 | 312-326 | STLQTMESDIYTEVR (SEQ ID NO: 196) | 13 14 9 8 | Adapter, Scaffolding, Modulator Proteins |
| P12277 | CKB Creatine kinase B-type | 224-236 | TFLVWVNEEDHLR (SEQ ID NO: 19) | 3 | Enzymes |
| P12277 | CKB Creatine kinase B-type | 342-358 | LGFSEVELVQMVVDGVK (SEQ ID NO: 21) | 3 13 | Enzymes |
| P12277 | CKB Creatine kinase B-type | 367-381 | LEQGQAIDDLMPAQK (SEQ ID NO: 22) | 13 | Enzymes |
| P12277 | CKB Creatine kinase B-type | 14-32 | FPAEDEFPDLSAHNNHMAK (SEQ ID NO: 17) | 3 | Enzymes |
| P12277 | CKB Creatine kinase B-type | 157-172 | LAVEALSSLDGDLAGR (SEQ ID NO: 18) | 13 | Enzymes |
| P12277 | CKB Creatine kinase B-type | 253-265 | FCTGLTQIETLFK (SEQ ID NO: 20) | 13 | Enzymes |
| P12532 | CKMT1B Creatine kinase U-type, motochondrial | 257-269 | SFLIWVNEEDHTR (SEQ ID NO: 23) | 3 | Enzymes |
| O75503 | CLN5 Ceroid-lipofuscinosis neuronal protein 5 | 74-96 | YTFCPTGSPIPVMEGDDDIEVFR (SEQ ID NO: 197) | 9 | Uncategorized |
| Q9H078 | CLPB Caseinolytic peptidase B protein homolog | 630-650 | VVNQLAAAYEQDLLPGGCTLR (SEQ ID NO: 198) | 14 | Enzymes |
| Q16740 | CLPP Putative ATP-dependent Clp protease proteolytic subunit | 215-226 | QSLQVIESAMER (SEQ ID NO: 24) | 6 | Enzymes |
| O96005 | CLPTM1 Cleft lip and palate transmembrane protein 1 | 325-346 | SPWNFLGDELYEQSDEEQDSVK (SEQ ID NO: 199) | 13 14 2 6 | Uncategorized |

TABLE 1-continued

| Accession # | Protein Name | Labeled Peptide | Peptide Sequence | Probes | Family |
|---|---|---|---|---|---|
| O96005 | CLPTM1 Cleft lip and palate transmembrane protein 1 | 548-562 | ALNTFIDDLFAFVIK (SEQ ID NO: 200) | 2 | Uncategorized |
| P53618 | COPB1 Coatomer subunit beta | 262-279 | YEAAGTLVTLSSAPTAIK (SEQ ID NO: 201) | 13 | Channels, Transporters, Receptors |
| Q9BT78 | COPS4 COP9 signalosome complex subunit 4 | 154-170 | LYLEDDDPVQAEAYINR (SEQ ID NO: 202) | 13 15 | Uncategorized |
| Q5HYK3 | COQ5 2-methoxy-6-polyprenyl-1,4-benzoquinol methylase, | 258-279 | LYDLYSFQVIPVLGEVIAGDWK (SEQ ID NO: 203) | 14 2 | Enzymes |
| Q7KZN9 | COX15 Cytochrome coxidase assembly protein COX15 homolo | 296-313 | MGESWIPEDLFTFSPILR (SEQ ID NO: 204) | 14 | Uncategorized |
| P20674 | COX5A Cytochrome coxidase subunit 5A, mitochondrial | 73-87 | GINTLVTYDMVPEPK (SEQ ID NO: 205) | 13 14 3 2 9 | Adapter, Scaffolding, Modulator Proteins |
| P23786 | CPT2 Carnitine O-palmitoyltransferase 2, mitochondrial | 363-382 | DGSTAVHFEHSWGDGVAVLR (SEQ ID NO: 206) | 15 13 | Enzymes |
| P23786 | CPT2 Carnitine O-palmitoyltransferase 2, mitochondrial | 478-495 | QYGQTVATYESCSTAAFK (SEQ ID NO: 207) | 4 | Enzymes |
| Q9H3G5 | CPVL Probable serine carboxypeptidase CPVL | 281-292 | QNWFEAFEILDK (SEQ ID NO: 208) | 4 9 | Enzymes |
| Q9H3G5 | CPVL Probable serine carboxypeptidase CPVL | 320-331 | CTEPEDQLYYVK (SEQ ID NO: 209) | 13 9 | Enzymes |
| Q9H3G5 | CPVL Probable serine carboxypeptidase CPVL | 195-208 | NNDFYVTGESYAGK (SEQ ID NO: 210) | 9 | Enzymes |
| P55060 | CSE1L Exportin-2 | 32-52 | FLESVEGNQNYPLLLLTLLEK (SEQ ID NO: 211) | 14 3 | Channels, Transporters, Receptors |
| P55060 | CSE1L Exportin-2 | 396-418 | FFEGPVTGIFSGYVNSMLQEYAK (SEQ ID NO: 212) | 14 | Channels, Transporters, Receptors |
| P48729 | CSNK1A1 Casein kinase I isoform alpha | 84-106 | DYNVLVMDLLGPSLEDLFNFCSR (SEQ ID NO: 25) | 14 | Enzymes |
| P67870 | CSNK2B Casein kinase II subunit beta | 112-134 | VYCENQPMLPIGLSDIPGEAMVK (SEQ ID NO: 26) | 14 | Uncategorized |
| Q12996 | CSTF3 Cleavage stimulation factor subunit 3 | 440-464 | YGDIPEYVLAYIDYLSHLNEDNNTR (SEQ ID NO: 213) | 13 | Uncategorized |
| Q12996 | CSTF3 Cleavage stimulation factor subunit 3 | 319-330 | LFSDEAANIYER (SEQ ID NO: 214) | 13 14 | Uncategorized |
| P35222 | CTNNB1 Catenin beta-1 | 648-661 | NEGVATYAAAVLFR (SEQ ID NO: 215) | 14 13 | Adapter Scaffolding, Modulator Proteins |
| P07858 | CTSB Cathepsin B | 315-331 | GQDHCGIESEVVAGIPR (SEQ ID NO: 27) | 13 4 2 9 | Enzymes |
| P07339 | CTSD Cathepsin D | 236-253 | DPDAQPGGELMLGGTDSK (SEQ ID NO: 28) | 9 | Enzymes |

TABLE 1-continued

| Accession # | Protein Name | Labeled Peptide | Peptide Sequence | Probes | Family |
|---|---|---|---|---|---|
| P07339 | CTSD Cathespin D | 288-309 | EGCEAIVDTGTSLMVGPVDEVR (SEQ ID NO: 29) | 13 14 15 4 6 9 8 | Enzymes |
| P07339 | CTSD Cathespin D | 314-331 | AIGAVPLIQGEYMIPCEK (SEQ ID NO 30) | 14 15 3 2 4 13 6 9 8 | Enzymes |
| O43169 | CYB5B Cytochrome b5 type B | 138-144 | YYTSESK (SEQ ID NO: 216) | 4 2 | Adapter Scaffolding, Modulator Proteins |
| P00387 | CYB5R3 NADH-cytochrome b5 reductase 3 | 235-241 | LWYTLDR (SEQ ID NO: 31) | 3 | Enzymes |
| Q6UW02 | CYP20A1 Cytochrome P450 20A1 | 397-413 | TFSSLGFSGTQCPELR (SEQ ID NO: 217) | 14 4 3 | Enzymes |
| P61962 | DCAF7 DDB1- and CUL4-associated factor 7 | 82-96 | GVYPDLLATSGDYLR (SEQ ID NO: 218) | 14 | Uncategorized |
| Q13561 | DCTN2 Dynactin subunit 2 | 380-395 | ENLATVEGNFASIDER (SEQ ID NO: 219) | 13 6 | Adapter Scaffolding, Modulator Proteins |
| Q9H773 | DCTPP1 dCTP pyrophosphatase 1 | 90-109 | AALQEELSDVLIYLVALAAR (SEQ ID NO: 220) | 14 4 | Enzymes |
| Q92841 | DDX17 Propable ATP-dependent RNA helicase DDX17 | 406-417 | LIQLMEEIMAEK (SEQ ID NO: 221) | 13 14 2 9 | Transcription factors, Regulators |
| Q92841 | DDX17 Propable ATP-dependent RNA helicase DDX17 | 536-547 | VLEEANQAINPK (SEQ ID NO: 222) | 3 | Transcription factors, Regulators |
| Q16698 | DECR1 2,4-dienoyl-CoA reductase, mitochondrial | 299-315 | FDGGEEVLISGEFNDLR (SEQ ID NO: 32) | 6 | Enzymes |
| Q15392 | DHCR24 Delta(24)-sterol reductase | 334-352 | SIFWELQDIIPFGNNPIFR (SEQ ID NO: 223) | 3 15 2 | Enzymes |
| Q15392 | DHCR24 Delta(24)-sterol reductase | 428-444 | GNEAELYIDIGAYGEPR (SEQ ID NO: 224) | 13 14 8 | Enzymes |
| Q9H2U1 | DHX36 Probable ATP-dependent RNA helicase A | 754-770 | SDHLTVVNAFEGWEEAR (SEQ ID NO: 225) | 6 | Transcription factors, Regulators |
| Q08211 | DHX9 ATP-dependent RNA helicase A | 448-456 | ISAVSVAER (SEQ ID NO: 33) | 3 | Transcription factors, Regulators |
| Q08211 | DHX9 ATP-dependent RNA helicase A | 121-141 | AENNSEVGASGYGVPGPTWDR (SEQ ID NO: 226) | 8 | Transcription factors, Regulators |
| Q9NR28 | DIABLO Diablo homolog, mitochondrial | 124-140 | MNSEEEDEVWQVIIGAR (SEQ ID NO: 227) | 13 | Uncategorized |
| P09622 | DLD Dihydrolipoyl dehydrogenase, mitochondrial | 450-482 | VLGAHILGPGAGEMVEAALALE YGASCEDIAR (SEQ ID NO: 34) | 14 4 13 | Enzymes |
| Q9NVH1 | DNAJC11 DnaJ homolog subfamily C member 11 | 207-226 | GWGELEFGAGDLQGPLFGLK (SEQ ID NO: 228) | 14 6 | Chaperones |
| O00115 | DNASE2 Deoxyribonuclease-2-alpha | 173-202 | QLTYTYPWVYNYQLEGIFAQEFP DLENVVK (SEQ ID NO: 229) | 9 | Enzymes |
| P42892 | ECE1 Endothelin-converting enzyme 1 | 434-453 | FCVSDTENNLGFALGPMFVK (SEQ ID NO: 230) | 14 13 | Enzymes |
| Q13011 | ECH1 Delta(3,5)-Delta(2,4)- | 197-211 | EVDVGLAADVGTLQR (SEQ ID NO: 37) | 13 14 15 3 4 6 8 | Enzymes |

TABLE 1-continued

| Accession # | Protein Name | Labeled Peptide | Peptide Sequence | Probes | Family |
|---|---|---|---|---|---|
| Q13011 | dienoyl-CoA isomerase, mitochondrial ECH1 Delta(3,5)-Delta(2,4)-dienoyl-CoA isomerase, mitochondrial | 149-158 | YQETFNVIER (SEQ ID NO: 36) | 6 | Enzymes |
| Q13011 | ECH1 Delta(3,5)-Delta(2,4)-dienoyl-CoA isomerase, mitochondrial | 113-131 | MFTAGIDLMDMASDILQPK (SEQ ID NO: 35) | 6 | Enzymes |
| Q9NTX5 | ECHDC1 Ethylmalonyl-CoA decarboxylase | 272-283 | ELYLEEALQNER (SEQ ID NO: 231) | 9 | Enzymes |
| P68104 | EEF1A1 Elongation factor 1-alpha 1 | 135-146 | EHALLAYTLGVK (SEQ ID NO: 232) | 13 | Transcription factors, Regulators |
| P26641 | EEF1G Elongation factor 1-gamma | 379-400 | GQELAFPLSPDWQVDYESYTWR (SEQ ID NO: 233) | 13 | Uncategorized |
| P26641 | EEF1G Elongation factor 1-gamma | 58-85 | VPAFEGDDGFCVFESNAIAYYVSNEELR (SEQ ID NO: 234) | 3 | Uncategorized |
| P13639 | EEF2 Elongation factor 2 | 457-481 | YVEPIEDVPCGNIVGLVGVDQFLVK (SEQ ID NO: 235) | 3 | Transcription factors, Regulators |
| P13639 | EEF2 Elongation factor 2 | 740-765 | LMEPIYLVEIQCPEQVVGGIYGVLNR (SEQ ID NO: 236) | 3 | Transcription factors, Regulators |
| P13639 | EEF2 Elongation factor 2 | 768-785 | HVFEESQVAGTPMFVVK (SEQ ID NO: 237) | 3 | Transcription factors, Regulators |
| P60228 | EIF3E Eukaryotic translation initiation factor 3 submit | 173-191 | LASEILMQNWDAAMEDLTR (SEQ ID NO: 238) | 2 | Uncategorized |
| O00303 | EIF3F Eukaryotic translation initiation factor 3 submit | 193-210 | EAPNPIHLTVDTSLQNGR (SEQ ID NO: 239) | 3 6 | Enzymes |
| O00303 | EIF3F Eukaryotic translation initiation factor 3 submit | 279-297 | IQDALSTVLQYAEDVLSGK (SEQ ID NO: 240) | 3 9 | Enzymes |
| O15372 | EIF3H Eukaryotic translation initiation factor 3 submit | 207-220 | NSHLINVLMWELEK (SEQ ID NO: 241) | 2 | Uncategorized |
| Q9Y262 | EIF3L Eukaryotic translation initiation factor 3 submit | 404-419 | GDPQVYEELFSYSCPK (SEQ ID NO: 242) | 13 | Uncategorized |
| Q9Y262 | EIF3L Eukaryotic translation initiation factor 3 submit | 243-262 | QLEVYTSGGDPESVAGEYGR (SEQ ID NO: 243) | 13 14 | Uncategorized |
| P60842 | EIF4A1 Eukaryotic initiation factor 4A-I | 69-82 | GYDVIAQAQSGTGK (SEQ ID NO: 39) | 14 13 9 | Transcription factors, Regulators Transcription factors, Regulators |
| P60842 | EIF4A1 Eukaryotic initiation factor 4A-I | 178-190 | MFVLDEADEMLSR (SEQ ID NO: 38) | 13 | Transcription factors, Regulators |
| Q14240 | EIF4A2 Eukaryotic | 70-83 | GYDVIAQAQSGTGK (SEQ ID NO: 40) | 13 | Transcription |

TABLE 1-continued

| Accession # | Protein Name | Labeled Peptide | Peptide Sequence | Probes | Family |
|---|---|---|---|---|---|
| | initiation factor 4A-II | | | | factors, Regulators |
| Q15056 | EIF4H Eukaryotic translation initiation factor 4H | 97-109 | EALTYDGALLGDR (SEQ ID NO: 244) | 9 | Transcription factors, Regulators |
| P55010 | EIF5 Eukaryotic translation initiation factor 5 | 274-288 | AMGPLVLTEVLFNEK (SEQ ID NO: 245) | 14 3 2 4 13 6 | Transcription factors, Regulators |
| Q15717 | ELAVL1 ELAV-like protein 1 | 20-37 | TNLIVNYLPQNMTQDELR (SEQ ID NO: 246) | 13 4 2 | Transcription factors, Regulators |
| Q9NXB9 | ELOVL2 Elongation of very long chain fatty acids protein | 42543 | AFDDEINAFLDNMFGPR (SEQ ID NO: 247) | 14 9 | Enzymes |
| P50402 | EMD Emerin | 212-221 | APGAGLGQDR (SEQ ID NO: 248) | 4 | Adapter, Scaffolding, Modulator Proteins |
| P50402 | EMD Emerin | 89-103 | GYNDDYYEESYFTTR (SEQ ID NO: 249) | 6 8 | Adapter, Scaffolding, Modulator Proteins |
| P07099 | EPHX1 Epoxide hydolase 1 | 329-338 | FSTWTNTEFR (SEQ ID NO: 250) | 3 6 | Enzymes |
| P84090 | ERH Enhancer of rudimentary homolog | 18-34 | TYADYESVNECMEGVCK (SEQ ID NO: 251) | 13 | Uncategorized |
| P38117 | ETFB Electron transfer flavoprotein subunit beta | 36-51 | HSMNPFCEIAVEEAVR (SEQ ID NO: 41) | 3 | Channels, Transporters, Receptors |
| Q01844 | EQSR1 RNA-binding protein EWS | 269-292 | QDHPSSMGVYGQESGGFSGPGENR (SEQ ID NO: 252) | 2 | Transcription factors, Regulators |
| Q9UQ84 | EXO1 Exonuclease 1 | 139-160 | SQGVDCLVAPYEADAQLAYLNK (SEQ ID NO: 95) | 13 2 6 9 8 | Enzymes |
| Q96CS3 | FAF2 FAS-associated factor 2 | 249-277 | LEGLIQPDDLINQLTFIMDANQTYLVSER (SEQ ID NO: 253) | 6 | Uncategorized |
| P16930 | FAH Fumarylacetoacetase | 242-253 | WEYVPLGPFLGK (SEQ ID NO: 254) | 14 | Enzymes |
| Q9NRY5 | FAM114A2 Protein FAM114A2 | 184-196 | TMDVIAEGDPGFK (SEQ ID NO: 255) | 14 | Uncategorized |
| Q9NSD9 | FARSB Phenylalanini--tRNA ligase beta subunit | 72-82 | YDLLCLEGLVR (SEQ ID NO: 256) | 9 | Enzymes |
| Q9NSD9 | FARSB Phenylalanini--tRNA ligase beta subunit | 518-530 | IMQLLDVPPGEDK (SEQ ID NO: 257) | 2 | Enzymes |
| P49327 | FASN Fatty acid synthase | 1350-1383 | GHPLGDIVAFLTSTEPQYGQGILSQDAWESLFSR (SEQ ID NO: 258) | 14 13 | Enzymes |
| P37268 | FDFT1 Squalene synthase | 78-92 | ALDTLEDDMTISVEK (SEQ ID NO: 259) | 15 | Enzymes |
| P22830 | FECH Ferrochelatase, mitochondrial | 254-272 | SEVVILFSAHSLPMSVVNR (SEQ ID NOW: 42) | 4 | Enzymes |
| O95684 | FGFR1OP FGFR1 oncogene partner | 39-50 | AAVFLALEEQEK (SEQ ID NO: 260) | 14 13 8 | Adapter, Scaffolding, Modulator Proteins |
| Q96AY3 | FKBP10 Peptidyl-prolyl cis-trans isomerase FKBP10 | 198-212 | GGTYDTYVGSGWLIK (SEQ ID NO: 261) | 13 | Enzymes |
| Q02790 | FKBP4 Peptidyl-prolyl | 190-206 | FEIGEGENLDLPYGLER (SEQ ID NO: 262) | 13 | Chaperones |

TABLE 1-continued

| Accession # | Protein Name | Labeled Peptide | Peptide Sequence | Probes | Family |
|---|---|---|---|---|---|
| | cis-trans isomerase FKBP4 | | | | |
| Q96AE4 | FUBP1 Far upstream element-binding protein 1 | 593-620 | MGQAVPAPTGAPPGGQPDYSAA WAEYYR (SEQ ID NO: 263) | 14 | Transcription factors, Regulators |
| Q96AE4 | FUBP1 Far upstream element-binding protein 1 | 272-284 | IGGNEGIDVPIPR (SEQ ID NO: 264) | 6 | Transcription factors, Regulators |
| P35637 | FUS RNA-binding protein FUS | 335-348 | GEATVSFDDPPSAK (SEQ ID NO: 265) | 2 | Transcription factors, Regulators |
| P10253 | GAA Lysosomal alpha-glucosidase | 855-870 | GELFWDDGESLEVLER (SEQ ID NO: 266) | 9 | Enzymes |
| P50395 | GDI2 Rab GDP dissociation inhibitor beta | 119-137 | VPSTEAEALASSLMGLFEK (SEQ ID NO: 267) | 13 14 | Uncategorized |
| P50395 | GDI2 Rab GDP dissociation inhibitor beta | 222-240 | SPYLYPLYGLGELPQGFAR (SEQ IN NO: 268) | 3 13 | Uncategorized |
| Q9H3K2 | GHITM Growth hormone-inducible transmembrane protein | 218-240 | AAWYTAGIVGGLSTVAMCAPSEK (SEQ ID NO: 269) | 14 | Uncategorized |
| P06280 | GLA Alpha-galactosidase A | 241-252 | SILDWTSFNQER (SEQ ID NO: 43) | 9 | Enzymes |
| P06280 | GLA Alpha-galactosidase A | 68-82 | LFMEMAELMVSEGWK (SEQ ID NO: 45) | 4 | Enzymes |
| P06280 | GLA Alpha-galactosidase A | 50-67 | FMCNLDCQEEPDSCISEK (SEQ ID NO: 44) | 9 | Enzymes |
| P16278 | GLB1 Beta-galactosidase | 286-299 | TEAVASSLYDILAR (SEQ ID NO: 46) | 9 | Enzymes |
| Q04760 | GLO1 Lactoylglutathione lyase | 160-179 | GLAFIQDPDGYWIEILNPNK (SEQ ID NO: 47) | 14 3 | Enzymes |
| Q9HC38 | GLOD4 Glyoxalase domain-containing protein 4 | 71-96 | TMVGFGPEDDHFVAELTYNYGV GDYK (SEQ ID NO: 270) | 4 13 | Uncategorized |
| P00367 | GLUD1 Glutamate dehydrogenase 1, mitochondrial | 481-496 | HGGTIPIVPTAEFQDR (SEQ ID NO: 49) | 6 | Enzymes |
| P00367 | GLUD1 Glutamate dehydrogenase 1, mitochondrial | 152-162 | YSTDVSVDEVK (SEQ ID NO: 48) | 6 | Enzymes |
| P49448 | GLUD2 Glutamate dehydrogenase 2, mitochondrial | 152-162 | YSTDVSVDEVK (SEQ ID NO: 48) | 6 | Enzymes |
| Q9H4A6 | GOLPH3 Golgi phophoprotein 3 | 75-90 | EGYTSFWNDCISSGLR (SEQ ID NO: 50) | 14 | Adapter, Scaffolding, Modulator Proteins |
| Q9BQ67 | GRWD1 Glutamate-rich WD repeat-containing protein 1 | 183-198 | LLQVVEEPQALAAFLR (SEQ ID NO: 271) | 3 | Uncategorized |
| Q9BQ67 | GRWD1 Glutamate-rich WD repeat-containing protein 1 | 263-287 | SVEDLQWSPTENTVFASCSADASI R (SEQ ID NO: 272) | 13 | Uncategorized |
| P09211 | GSTP1 Glutathione S-transferase P | 56-71 | FQDGDLTLYQSNTILR (SEQ ID NO: 51) | 2 | Enzymes |
| P0C0S5 | H2AFZ Histone H2A.Z | 47-75 | VGATAAVYSAAILEYLTAEVLEL AGNASK (SEQ ID NO: 273) | 3 | Transcription factors, Regulators |

TABLE 1-continued

| Accession # | Protein Name | Labeled Peptide | Peptide Sequence | Probes | Family |
|---|---|---|---|---|---|
| Q16836 | HADH Hydroxyacyl-coenzyme A dehydrogenase, mitochondrial | 250-271 | LGAGYPMGPFELLDYVGLDTTK (SEQ ID NO: 274) | 13 2 | Enzymes |
| P40939 | HADHA Trifunctional enzyme subunit alpha, mitochondrial | 112-125 | TLQEVTQLSQEAQR (SEQ ID NO: 275) | 4 8 | Enzymes |
| P12081 | HARS Histidine--tRNA ligase, cytoplasmic | 170-193 | EFYQCDFDIAGNFDPMIPDAECLK (SEQ ID NO: 276) | 15 14 4 | Enzymes |
| Q96CS2 | HAUS1 HAUS augmin-like complex subunit 1 | 94-108 | YLNALVDSAVALETK (SEQ ID NO: 277) | 14 | Adapter, Scaffolding, Modulator Proteins |
| Q9NVX0 | HAUS2 HAUS augmin-like complex subunit 2 | 173-189 | MDILVTETEELAENILK (SEQ ID NO: 278) | 14 | Adapter, Scaffolding, Modulator Proteins |
| P69905 | HBA2 Hemoglobin subunit alpha | 18-32 | VGAHAGEYGAEALER (SEQ ID NO: 52) | 4 | Adapter, Scaffolding, Modulator Proteins |
| P69905 | HBA2 Hemoglobin subunit alpha | 94-100 | VDPVNFK (SEQ ID NO: 53) | 4 | Adapter, Scaffolding, Modulator Proteins |
| P53701 | HCCS Cytochrome c-type heme lyase | 200-210 | SWMGYELPFDE (SEQ ID NO: 279) | 4 | Enzymes |
| Q7Z4Q2 | HEATR3 HEAT repeat-containing protein 3 | 224-250 | SFSATALNMLESALLSPVSSMESLLLK (SEQ ID NO: 280) | 4 2 | Uncategorized |
| P06865 | HEXA Beta-hexosaminidase subuit alpha | 489-499 | LTSDLTFAYER (SEQ ID NO: 54) | 9 | Enzymes |
| Q6NVY1 | HIBACH 3-hydroxyisobutyryl-CoA hydrolase, mitochondrial | 238-252 | ENIASVLENYHTESK (SEQ ID NO: 281) | 6 | Enzymes |
| P16403 | HIST1H1C Histone H1.2 | 65-75 | ALAAAGYDVEK (SEQ ID NO: 282) | 8 | Transcription factors, Regulators |
| P01892 | HLA-A HLAC class I histocompatibility antigen, A-2 alpha | 46-59 | FIAVGYVDDTQFVR (SEQ ID NO: 283) | 14 | Uncategorized |
| Q8TCT9 | HM13 Minor histocompatibility antigen H13 | 62-73 | NASDMPETITSR (SEQID NO: 284) | 13 14 2 4 8 | Enzymes |
| P30519 | HMOX2 Heme oxygenase 2 | 48-55 | AENTQFVK (SEQ ID NO: 55) | 15 14 3 4 2 6 8 | Enzymes |
| P03519 | HMOX2 Heme oxygenase 2 | 69-87 | LATTALYFTYSALEEEMER (SEQ ID NO: 56) | 14 | Enzymes |
| P09651 | HNRNPA1 Heterogeneous nuclear ribonucleoprotein A1 | 353-370 | NQGGYGGSSSSSSYGSGR (SEQ ID NO: 285) | 13 14 3 2 9 | Channels, Transporters, Receptors |
| P09651 | HNRNPA1 Heterogeneous nuclear ribonucleoprotein A1 | 337-350 | SSGPYGGGGQYGAK (SEQ ID NO: 286) | 3 2 | Channels, Transporters, Receptors |
| P09651 | HNRNPA1 Heterogeneous nuclear ribonucleoprotein A1 | 56-75 | GFGFVTYATVEEVDAAMNAR (SEQ ID NO: 287) | 3 | Channels, Transporters, Receptors |

TABLE 1-continued

| Accession # | Protein Name | Labeled Peptide | Peptide Sequence | Probes | Family |
|---|---|---|---|---|---|
| P09651 | HNRNPA1 Heterogeneous nuclear ribonucleoprotein A1 | 233-265 | GGGGYGGSGDGYNGFGNDGGYG GGGPGYSGGSR (SEQ ID NO: 288) | 8 | Channels, Transporters, Receptors |
| P09651 | HNRNPA1 Heterogeneous nuclear ribonucleoprotein A1 | 16-31 | LFIGGLSFETTDESLR (SEQ ID NO: 289) | 14 3 2 | Channels, Transporters, Receptors |
| P09651 | HNRNPA1 Heterogeneous nuclear ribonucleoprotein A1 | 131-140 | IEVIEIMTDR (SEQ ID NO: 290) | 3 9 8 | Channels, Transporters, Receptors |
| Q32P51 | HNRNPA1L2 Heterogeneous nuclear ribonucleoprotein A1-like 2 | 285-298 | SSGPYGGGGQYFAK (SEQ ID NO: 291) | 3 2 4 | Channels, Transporters, Receptors |
| Q32P51 | HNRNPA1L2 Heterogeneous nuclear ribonucleoprotein A1-like 2 | 131-140 | IEVIEIMTDR (SEQ ID NO: 292) | 3 4 9 | Channels, Transporters, Receptors |
| Q32P51 | HNRNPA1L2 Heterogeneous nuclear ribonucleoprotein A1-like 2 | 16-31 | LFIGGLSFETTDESLR (SEQ ID NO: 293) | 14 3 4 2 | Channels, Transporters, Receptors |
| P22626 | HNRNPA2L1 Heterogeneous nuclear ribonucleoproteins A2/B1 | 130-137 | DYFEEYGK (SEQ ID NO: 294) | 6 | Channels, Transporters, Receptors |
| P22626 | HNRNPA2L1 Heterogeneous nuclear ribonucleoproteins A2/B1 | 138-147 | IDTIEIITDR (SEQ ID NO: 295) | 13 | Channels, Transporters, Receptors |
| P22626 | HNRNPA2L1 Heterogeneous nuclear ribonucleoproteins A2/B1 | 191-200 | QEMQEVQSSR (SEQ ID NO: 296) | 6 | Channels, Transporters, Receptors |
| P22626 | HNRNPA2L1 Heterogeneous nuclear ribonucleoproteins A2/B1 | 229-238 | GGSDGYGSGR (SEQ ID NO: 297) | 3 6 | Channels, Transporters, Receptors |
| P22626 | HNRNPA2L1 Heterogeneous nuclear ribonucleoproteins A2/B1 | 239-266 | GFGDGYNGYGGGPGGGNFGGSP GYGGGR (SEQ ID NO: 298) | 13 14 3 2 6 8 | Channels, Transporters, Receptors |
| P22626 | HNRNPA2L1 Heterogeneous nuclear ribonucleoproteins A2/B1 | 23-38 | LFIGGLSFETTEESLR (SEQ ID NO: 299) | 13 3 2 6 9 | Channels, Transporters, Receptors |
| P22626 | HNRNPA2L1 Heterogeneous nuclear ribonucleoproteins A2/B1 | 267-317 | GGYGGGPGYGNQGGGYGGGY DNYGGGNYGSGNYNDFGNYNQQ PSNYPGMK (SEQ ID NO: 300) | 13 2 9 6 | Channels, Transporters, Receptors |
| P22626 | HNRNPA2L1 Heterogeneous nuclear ribonucleoproteins A2/B1 | 326-350 | NMGGPYGGGNYGPGGSGGSGGY GGR (SEQ ID NO: 301) | 14 3 2 13 8 6 | Channels, Transporters, Receptors |
| P22626 | HNRNPA2L1 Heterogeneous nuclear ribonucleoproteins A2/B1 | 42472 | TLETVPLER (SEQ ID NO: 302) | 6 | Channels, Transporters, Receptors |
| P51991 | HNRNPA3 Heterogeneous | 152-161 | IETIEVMEDR (SEQ ID NO: 303) | 9 6 | Transcription factors, |

TABLE 1-continued

| Accession # | Protein Name | Labeled Peptide | Peptide Sequence | Probes | Family |
|---|---|---|---|---|---|
| P51991 | nuclear ribonucleoprotein A3 HNRNPA3 | 355-376 | SSGSPYGGGYGSGGGSGGYGSR (SEQ ID NO: 304) | 13 14 3 2 4 6 | Transcription factors, Regulators |
| P51991 | Heterogeneous nuclear ribonucleoprotein A3 HNRNPA3 | 37-52 | LFIGGLSFETTDDSLR (SEQ ID NO: 305) | 4 | Transcription factors, Regulators |
| P07910 | Heterogeneous nuclear ribonucleoprotein A3 HNRNP C | 100-130 | SAAEMYGSVTEHPSPSPLLSSSFD LDYDFQR (SEQ ID NO: 306) | 13 4 | Transcription factors, Regulators |
| P07910 | Heterogeneous nuclear ribonucleoproteins C1/C2 HNRNPC | 136-142 | MYSYPAR (SEQ ID NO: 307) | 4 3 | Transcription factors, Regulators |
| P07910 | Heterogeneous nuclear ribonucleoproteins C1/C2 HNRNP C | 51-61 | GFAFVQVYVNER (SEQ ID NO: 308) | 2 13 | Transcription factors, Regulators |
| P07910 | Heterogeneous nuclear ribonucleoproteins C1/C2 HNRNPC | 65-73 | AAVAGEDGR (SEQ ID NO: 309) | 4 | Transcription factors, Regulators |
| P07910 | Heterogeneous nuclear ribonucleoproteins C1/C2 HNRNP C | 74-89 | MIAGQVLDINLAAEPK (SEQ ID NO: 310) | 4 3 2 13 | Transcription factors, Regulators |
| Q14103 | Heterogeneous nuclear ribonucleoproteins C1/C2 HNRNP D | 184-197 | IFVGGLSPDTPEEK (SEQ ID NO: 311) | 13 6 | Transcription factors, Regulators |
| P52597 | Heterogeneous nuclear ribonucleoprotein D0 HNRNPF | 151-167 | ITGEAFVQFASQELAEK (SEQ ID NO: 312) | 4 2 13 9 | Transcription factors, Regulators |
| P52597 | Heterogeneous nuclear ribonucleoprotein F HNRNPF | 53-68 | QSGEAFVELGSEDDVK (SEQ ID NO: 313) | 6 | Transcription factors, Regulators |
| P52597 | Heterogeneous nuclear ribonucleoprotein F HNRNP F | 99-114 | HSGPNSADSANDGFVR (SEQ ID NO: 314) | 6 | Transcription factors, Regulators |
| P52597 | Heterogeneous nuclear ribonucleoprotein F HNRNPF | 125-150 | EEIVQFFSGLEIVPNGITLPVDPEG K (SEQ ID NO: 315) | 3 6 | Transcription factors, Regulators |
| P52597 | Heterogeneous nuclear ribonucleoprotein F HNRNP F | 300-316 | ATENDIYNFFSPLNPVR (SEQ ID NO: 316) | 13 3 2 4 6 | Transcription factors, Regulators |
| P52597 | Heterogeneous nuclear ribonucleoprotein F HNRNPF | 317-326 | VHIEIGPDGR (SEQ ID NO: 317) | 6 | Transcription factors, Regulators |
| | Heterogeneous nuclear ribonucleoprotein F | | | | |

TABLE 1-continued

| Accession # | Protein Name | Labeled Peptide | Peptide Sequence | Probes | Family |
|---|---|---|---|---|---|
| P31943 | HNRNPH1 Heterogeneous nuclear ribonucleoprotein H | 125-150 | EEIVQFFSGLEIVPNGITLPVDFQGR (SEQ ID NO: 318) | 2 6 | Transcription factors, Regulators |
| P31943 | HNRNPH1 Heterogeneous nuclear ribonucleoprotein H | 151-167 | STGEAFVQFASQEIAEK (SEQ ID NO: 319) | 13 14 3 6 8 | Transcription factors, Regulators |
| P31943 | HNRNPH1 Heterogeneous nuclear ribonucleoprotein H | 234-259 | GAYGGGYGGYDDYNGYNDGYGFGSDR (SEQ ID NO: 320) | 3 2 13 6 8 | Transcription factors, Regulators |
| P31943 | HNRNPH1 Heterogeneous nuclear ribonucleoprotein H | 263-275 | DLNYCFSGMSDHR (SEQ ID NO: 321) | 6 | Transcription factors, Regulators |
| P31943 | HNRNPH1 Heterogeneous nuclear ribonucleoprotein H | 276-294 | YGDGGSTFQSTTGHCVHMR (SEQ ID NO: 322) | 6 | Transcription factors, Regulators |
| P31943 | HNRNPH1 Heterogeneous nuclear ribonucleoprotein H | 300-316 | ATENDIYNFFSPLNPVR (SEQ ID NO: 323) | 13 14 3 2 6 | Transcription factors, Regulators |
| P31943 | HNRNPH1 Heterogeneous nuclear ribonucleoprotein H | 317-326 | VHIEIGPDGR (SEQ ID NO: 324) | 3 6 | Transcription factors, Regulators |
| P31943 | HNRNPH1 Heterogeneous nuclear ribonucleoprotein H | 356-375 | YVELFLNSTAGASGGAYEHR (SEQ ID NO: 325) | 3 6 | Transcription factors, Regulators |
| P31943 | HNRNPH1 Heterogeneous nuclear ribonucleoprotein H | 99-114 | HTGPNSPDTANDGFVR (SEQ ID NO: 326) | 6 | Transcription factors, Regulators |
| P55795 | HNRNPH2 Heterogeneous nuclear ribonucleoprotein H2 | 151-167 | STGEAFVQFASQEIAEK (SEQ ID NO: 327) | 13 14 3 8 6 | Transcription factors, Regulators |
| P55795 | HNRNPH2 Heterogeneous nuclear ribonucleoprotein H2 | 234-259 | GAYGGGYGGYDDYGGYNDGYGFGSDR (SEQ ID NO: 328) | 8 6 | Transcription factors, Regulators |
| P55795 | HNRNPH2 Heterogeneous nuclear ribonucleoprotein H2 | 263-275 | DLNYCFSGMSDHR (SEQ ID NO: 329) | 6 | Transcription factors, Regulators |
| P55795 | HNRNPH2 Heterogeneous nuclear ribonucleoprotein H2 | 300-316 | ATENDIYNFFSPLNPMR (SEQ ID NO: 330) | 6 | Transcription factors, Regulators |
| P55795 | HNRNPH2 Heterogeneous nuclear ribonucleoprotein H2 | 317-326 | VHIEIGPDGR (SEQ ID NO: 331) | 6 | Transcription factors, Regulators |
| P55795 | HNRNPH2 Heterogeneous nuclear ribonucleoprotein H2 | 99-114 | HTGPNSPDTANDGFVR (SEQ ID NO: 332) | 6 | Transcription factors, Regulators |
| P31942 | HNRNPH3 Heterogeneous | 139-169 | GGDGYDGGYGGFDDYGGYNNYGYGNDGFDDR (SEQ ID NO: 333) | 6 | Transcription factors, |

TABLE 1-continued

| Accession # | Protein Name | Labeled Peptide | Peptide Sequence | Probes | Family |
|---|---|---|---|---|---|
| | nuclear ribonucleoprotein H3 | | | | Regulators |
| P31942 | HNRNPH3 Heterogeneous nuclear ribonucleoprotein H3 | 206-222 | ATENDIANFFSPLNPIR (SEQ ID NO: 334) | 2 4 6 | Transcription factors, Regulators |
| P31942 | HNRNPH3 Heterogeneous nuclear ribonucleoprotein H3 | 262-287 | YIELFLNSTPGGGSGMGGSGMGG YGR (SEQ ID NO: 335) | 14 4 2 6 | Transcription factors, Regulators |
| P31942 | HNRNPH3 Heterogeneous nuclear ribonucleoprotein H3 | 288-301 | DGMDNQGGYGSVGR (SEQ ID NO: 336) | 8 6 | Transcription factors, Regulators |
| P31942 | HNRNPH3 Heterogeneous nuclear ribonucleoprotein H3 | 324-343 | GGGGSGGYYGQGGMSGGGWR (SEQ ID NO: 337) | 2 | Transcription factors, Regulators |
| P31942 | HNRNPH3 Heterogeneous nuclear ribonucleoprotein H3 | 56-67 | STGEAFVQFASK (SEQ ID NO: 338) | 6 | Transcription factors, Regulators |
| P61978 | HNRNP K Heterogeneous nuclear ribonucleoprotein K | 423-433 | IDEPLEGSEDR (SEQ ID NO: 339) | 4 | Transcription factors, Regulators |
| P61978 | HNRNPK Heterogeneous nuclear ribonucleoprotein K | 397-405 | DLAGSIIGK (SEQ ID NO: 340) | 4 3 | Transcription factors, Regulators |
| P61978 | HNRNPK Heterogeneous nuclear ribonucleoprotein K | 415-422 | HESGASIK (SEQ ID NO: 341) | 4 3 13 | Transcription factors, Regulators |
| P61978 | HNRNP K Heterogeneous nuclear ribonucleoprotein K | 434-456 | IITITGTQDQIQNAQYLLQNSVK (SEQ ID NO: 342) | 13 14 3 2 4 9 8 | Transcription factors, Regulators |
| P61978 | HNRNPK Heterogeneous nuclear ribonucleoprotein K | 70-86 | TDYNASVSVPDSSGPER (SEQ ID NO: 343) | 8 4 | Transcription factors, Regulators |
| P61978 | HNRNP K Heterogeneous nuclear ribonucleoprotein K | 87-102 | ILSISADIETIGEILK (SEQ ID NO: 344) | 4 | Transcription factors, Regulators |
| P61978 | HNRNPK Heterogeneous nuclear ribonucleoprotein K | 104-139 | IIPTLEEGLQLPSPTATSQLPLESDA VECLNYQHYK (SEQ ID NO: 345) | 13 14 3 4 2 | Transcription factors, Regulators |
| P61978 | HNRNP K Heterogeneous nuclear ribonucleoprotein K | 180-191 | LFQECCPHSTDR (SEQ ID NO: 346) | 13 | Transcription factors, Regulators |
| P61978 | HNRNPK Heterogeneous nuclear ribonucleoprotein K | 208-219 | IILDLISESPIK (SEQ ID NO: 347) | 14 4 2 13 9 | Transcription factors, Regulators |
| P61978 | HNRNP K Heterogeneous | 222-246 | AQPYDPNFYDETYDYGGFTMMF DDR (SEQ ID NO: 348) | 4 | Transcription factors, |

TABLE 1-continued

| Accession # | Protein Name | Labeled Peptide | Peptide Sequence | Probes | Family |
|---|---|---|---|---|---|
| | nuclear ribonucleoprotein K | | | | Regulators |
| P61978 | HNRNPK Heterogeneous nuclear ribonucleoprotein K | 279-286 | DYDDMSPR (SEQ ID NO: 349) | 4 | Transcription factors, Regulators |
| P61978 | HNRNP K Heterogeneous nuclear ribonucleoprotein K | 317-325 | GGDLMAYDR (SEQ ID NO: 350) | 2 | Transcription factors, Regulators |
| P61978 | HNRNPK Heterogeneous nuclear ribonucleoprotein K | 378-396 | GSYGDLGGPIITTQVTIPK (SEQ ID NO: 351) | 14 3 2 4 13 9 8 | Transcription factors, Regulators |
| P14866 | HNRNP L Heterogeneous nuclear ribonucleoprotein L | 108-136 | GLIDGVVEADLVEALQEFGPISYVVVMPK (SEQ ID NO: 352) | 14 3 9 | Transcription factors, Regulators |
| P14866 | HNRNPL Heterogeneous nuclear ribonucleoprotein L | 399-411 | VFNVFCLYGNVEK (SEQ ID NO: 353) | 2 | Transcription factors, Regulators |
| P14866 | HNRNPL Heterogeneous nuclear ribonucleoprotein L | 47-56 | YYGGGSEGGR (SEQ ID NO: 354) | 3 | Transcription factors, Regulators |
| P52272 | HNRNPM Heterogeneous nuclear ribonucleoprotein M | 346-362 | MGGMEGPFGGGMENMGR (SEQ ID NO: 355) | 14 2 6 | Transcription factors, Regulators |
| P52272 | HNRNPM Heterogeneous nuclear ribonucleoprotein M | 532-543 | MVPAGMGAGLER (SEQ ID NO: 356) | 6 | Transcription factors, Regulators |
| P52272 | HNRNPM Heterogeneous nuclear ribonucleoprotein M | 202-214 | LGSTVFVANLDYK (SEQ ID NO: 357) | 6 | Transcription factors, Regulators |
| P52272 | HNRNPM Heterogeneous nuclear ribonucleoprotein M | 323-345 | GIGMGNIGPAGMGMEGIGFGINK (SEQ ID NO: 358) | 3 2 6 | Transcription factors, Regulators |
| P52272 | HNRNPM Heterogeneous nuclear ribonucleoprotein M | 437-443 | MGLVMDR (SEQ ID NO: 359) | 6 | Transcription factors, Regulators |
| P52272 | HNRNPM Heterogeneous nuclear ribonucleoprotein M | 457-471 | MGPLGLDHMASSIER (SEQ ID NO: 360) | 3 6 | Transcription factors, Regulators |
| P52272 | HNRNPM Heterogeneous nuclear ribonucleoprotein M | 544-550 | MGPVMDR (SEQ ID NO: 361) | 6 | Transcription factors, Regulators |
| P52272 | HNRNPM Heterogeneous nuclear ribonucleoprotein M | 551-557 | MATGLER (SEQ ID NO: 362) | 6 | Transcription factors, Regulators |
| P52272 | HNRNPM Heterogeneous | 571-578 | MGANSLER (SEQ ID NO: 363) | 6 | Transcription factors, |

TABLE 1-continued

| Accession # | Protein Name | Labeled Peptide | Peptide Sequence | Probes | Family |
|---|---|---|---|---|---|
| | nuclear ribonucleoprotein M | | | | Regulators |
| P52272 | HNRNPM Heterogeneous nuclear ribonucleoprotein M | 592-606 | MGPAMGPALGAGIER (SEQ ID NO: 364) | 2 6 | Transcription factors, Regulators |
| P52272 | HNRNPM Heterogeneous nuclear ribonucleoprotein M | 699-707 | FESPEVAER (SEQ ID NO: 365) | 6 | Transcription factors, Regulators |
| P52272 | HNRNPM Heterogeneous nuclear ribonucleoprotein M | 95-110 | VGEVTYVELLMDAEGK (SEQ ID NO: 366) | 13 14 3 2 6 9 | Transcription factors, Regulators |
| P52272 | HNRNPM Heterogeneous nuclear ribonucleoprotein M | 113-120 | GCAVVEFK (SEQ ID NO: 367) | 6 | Transcription factors, Regulators |
| P52272 | HNRNPM Heterogeneous nuclear | 486-496 | MGAGMGFGLER (SEQ ID NO: 368) | 6 | Transcription factors, Regulators |
| O43390 | HNRNPR Heterogeneous nuclear ribonucleoprotein R | 147-171 | YGGPPPDSVYSGVQPGIGTEVFVGK (SEQ ID NO: 369) | 6 | Transcription factors, Regulators |
| O43390 | HNRNPR Heterogeneous nuclear ribonucleoprotein R | 316-339 | VWGNVVTVEWADPVEEPDPEVMAK (SEQ ID NO: 370) | 6 | Transcription factors, Regulators |
| O43390 | HNRNPR Heterogeneous nuclear ribonucleoprotein R | 347-359 | NLATTVTEEILKE (SEQ ID NO: 371) | 6 | Transcription factors, Regulators |
| O43390 | HNRNPR Heterogeneous nuclear ribonucleoprotein R | 428-441 | STAYEDYYYHPPPR (SEQ ID NO: 372) | 2 6 | Transcription factors, Regulators |
| Q99714 | HSD17B10 3-hydroxyacyl-CoA dehydrogenase type-2 | 42672 | GLVAVITGGASGLGLATAER (SEQ ID NO: 373) | 3 2 | Enzymes |
| Q53GQ0 | HSD17B12 Estradio 17-beta-dehydrogenase 12 | 182-206 | GAILNISSGSGMLPVPLLTIYSATK (SEQ ID NO: 374) | 14 2 | Enzymes |
| Q53GQ0 | HSD17B12 Estradio 17-beta-dehydrogenase 12 | 36-64 | VWGVGNEAGVGPGLGEQAVVTGSTDGIGK (SEQ ID NO: 375) | 14 4 2 | Enzymes |
| P51659 | HSD17B4 Peroxisomal multifunctional enzyme type 2 | 169-183 | LGLLGLANSLAIEGR (SEQ ID NO: 57) | 3 | Enzymes |
| P51659 | HSD17B4 Peroxisomal multifunctional enzyme type 2 | 385-403 | SMMGGGLAEIPGLSINFAK (SEQ ID NO: 376) | 14 | Enzymes |
| P51659 | HSD17B4 Peroxisomal multifunctional enzyme type 2 | 622-633 | LQSTFVFEEIGR (SEQ ID NO: 377) | 14 | Enzymes |
| P07900 | HSP90AA1 Heat shock protein HSP 90-alpha | 368-386 | VFIMDNCEELIPEYLNFIR (SEQ ID NO: 378) | 13 | Chaperones |

TABLE 1-continued

| Accession # | Protein Name | Labeled Peptide | Peptide Sequence | Probes | Family |
|---|---|---|---|---|---|
| P07900 | HSP90AA1 Heat shock protein HSP 90-alpha | 300-314 | NPDDITNEEYGEFYK (SEQ ID NO: 379) | 13 | Chaperones |
| P07900 | HSP90AA1 Heat shock protein HSP 90-alpha | 514-534 | HGLEVIYMIERPIDEYCVQQLK (SEQ ID NO: 380) | 13 | Chaperones |
| P08238 | HSP90AB1 Heat shock protein HSP 90-beta | 360-378 | VFIMDSCDELIPEYLNFIR (SEQ ID NO: 58) | 14 13 | Chaperones |
| P08238 | HSP90AB1 Heat shock protein HSP 90-beta | 507-526 | GFEVVYMTEPIDEYCVQQLK (SEQ ID NO: 59) | 13 14 | Chaperones |
| P08238 | HSP90AB1 Heat shock protein HSP 90-beta | 686-719 | LGLGIDEDEVAAEEPNAAVPDEIP PLEGDEDASR (SEQ ID NO: 381) | 13 14 | Chaperones |
| P14625 | HSP90B1 Endoplasmin | 664-671 | AQAYQTGK (SEQ ID NO: 382) | 13 8 | Chaperones |
| P14625 | HSP90B1 Endoplasmin | 117-135 | LISLTDENALSGNEELTVK (SEQ ID NO: 60) | 9 | Chaperones |
| P14625 | HSP90B1 Endoplasmin | 271-285 | YSQFINFPIYVWSSK (SEQ ID NO: 61) | 6 | Chaperones |
| P14625 | HSP90B1 Endoplasmin | 495-503 | LGVIEDHSNR (SEQ ID NO: 383) | 6 | Chaperones |
| P14625 | HSP90B1 Endoplasmin | 52-67 | EEEAIQLDGLNASQIR (SEQ ID NO: 384) | 6 | Chaperones |
| P08107 | HSPA1B Heat shock 70 kDa protein 1A/1B | 113-126 | AFYPEEISSMVLTK (SEQ ID NO: 385) | 13 | Chaperones |
| P08107 | HSPA1B Heat shock 70 kDa protein 1A/1B | 176-187 | IINEPTAAAIAYGLDR (SEQ ID NO: 386) | 13 | Chaperones |
| P08107 | HSPA1B Heat shock 70 kDa protein 1A/1B | 362-384 | SINPDEAVAYGAAVQAAILMGDK (SEQ ID NO: 387) | 13 | Chaperones |
| P08107 | HSPA1B Heat shock 70 kDa protein 1A/1B | 424-447 | QTQIFTTYSDNQPGVLIQVYEGER (SEQ ID NO: 388) | 13 3 | Chaperones |
| P08107 | HSPA1B Heat shock 70 kDa protein 1A/1B | 598-628 | ELEQVCNPIISGLYQGAGGPGPGG FGAQGPK (SEQ ID NO: 389) | 13 | Chaperones |
| P11021 | HSPA5 78 kDa glucose-regulated protein | 602-617 | IEWLESHQDADIEDFK (SEQ ID NO: 390) | 6 | Chaperones |
| P11021 | HSPA5 78 kDa glucose-regulated protein | 82-96 | NQLTSNPENTVFDAK (SEQ ID NO: 391) | 9 6 | Chaperones |
| P11021 | HSPA5 78 kDa glucose-regulated protein | 475-492 | DNHLLGTFDLTGIPPAPR (SEQ ID NO: 392) | 6 | Chaperones |
| P11021 | HSPA5 78 kDa glucose-regulated protein | 61-74 | ITPSYVAFTPEGER (SEQ ID NO: 393) | 6 | Chaperones |
| P11142 | HSPA8 Heat shock cognate 71 kDa protein | 424-447 | QTQTFTTYSDNQPGVLIQVYEGER (SEQ ID NO: 394) | 13 14 | Chaperones |
| P11142 | HSPA8 Heat shock cognate 71 kDa protein | 113-126 | SFYPEEVSSMVLTK (SEQ ID NO: 62) | 13 14 | Chaperones |
| P38646 | HSPA9 Stress-70 protein, mitochondrial | 266-284 | STNGDTFLGGEDFDQALLR (SEQ ID NO: 395) | 13 8 | Chaperones |
| P10809 | HSPD1 60 kDA heat shock protein, mitochondrial | 345-352 | VGEVIVTK (SEQ ID NO: 396) | 3 | Chaperones |
| P10809 | HSPD1 60 kDA heat shock protein, mitochondrial | 206-218 | TLNDELEIIEGMK (SEQ ID NO: 397) | 13 3 | Chaperones |
| P10809 | HSPD1 60 kDA heat shock | 222-233 | GYISPYGINTSK (SEQ ID NO: 398) | 13 | Chaperones |

TABLE 1-continued

| Accession # | Protein Name | Labeled Peptide | Peptide Sequence | Probes | Family |
|---|---|---|---|---|---|
| P10809 | HSPD1 60 kDA heat shock protein, mitochondrial | 251-268 | ISSIQSIVPALEIANAHR (SEQ ID NO: 399) | 3 13 | Chaperones |
| P10809 | HSPD1 60 kDA heat shock protein, mitochondrial | 371-387 | IQEIIEQLDVTTSEYEK (SEQ ID NO: 400) | 13 | Chaperones |
| P10809 | HSPD1 60 kDA heat shock protein, mitochondrial | 494-516 | IMQSSSEGYDAMAGDFVNMVEK (SEZ ID NO: 401) | 13 8 | Chaperones |
| P10809 | HSPD1 60 kDA heat shock protein, mitochondrial | 97-121 | LVQDVANNTNEEAGDGTTTATVLAR (SEQ ID NO: 402) | 13 8 | Chaperones |
| Q9NSE4 | HSPD1 60 kDA IARS2 Isoleucine--tRNA ligase, mitochondrial | 818-832 | SCQTALVEILDVIVR (SEQ ID NO: 403) | 14 3 2 13 6 | Enzymes |
| Q9NSE4 | IARS2 Isoleucine--tRNA ligase, mitochondrial | 793-803 | ELSNFYFSIIK (SEQ ID NO: 404) | 2 6 | Enzymes |
| P14735 | IDE Insulin-degrading enzyme | 312-324 | NLYVTFPIPDLQK (SEQ ID NO: 405) | 4 | Enzymes |
| P48735 | IDH2 Isocitrate dehydrogenase | 244-251 | WPLYMSTK (SEQ ID NO: 406) | 3 6 | Enzymes |
| P13284 | IFI30 Gamma-interferon-inducible lysosomal thiol reductase | 129-157 | VEACVLDELDMELAFLTIVCMEEFEDMER (SEQ ID NO: 407) | 9 | Enzymes |
| Q9NZI8 | IGF2BP1 Insulin-like growth factor 2 mRNA-binding protein | 509-525 | TVNELQNLTAAEVVVPR (SEQ ID NO: 408) | 3 13 | Channels, Transporters, Receptors |
| Q12905 | ILF2 Interleukin enhancer-binding factor 2 | 329-356 | ILGQEGDASYLASEISTWDGVIVTPSE (SEQ ID NO: 409) | 4 | Transcription factors, Regulators |
| Q12905 | ILF2 Interleukin enhancer-binding factor 2 | 81-103 | INNVIDNLIVAPGTFEVQIEEVR (SEQ ID NO: 410) | 13 4 | Transcription factors, Regulators |
| A1L0T0 | ILVBL Acetolactate synthase-like protein | 557-577 | EQVPSLGSNVACGLAYTDYHK (SEQ ID NO: 411) | 13 | Enzymes |
| Q16891 | IMMT Mitochondrial inner membrane protein | 345-353 | VQAAQSEAK (SEQ ID NO: 412) | 4 3 6 | Uncategorized |
| Q16891 | IMMT Mitochondrial inner membrane protein | 527-545 | LSQEQVDNFTLDINTAYAR (SEQ ID NO: 413) | 13 14 6 8 | Uncategorized |
| Q16891 | IMMT Mitochondrial inner membrane protein | 548-564 | GIEQAVAQSHAVAEEEAR (SEQ ID NO: 414) | 13 4 6 | Uncategorized |
| P12268 | IMPDH2 Inosine-5-monophosphate dehydrogenase 2 | 110-124 | YEQGFITDPVVLSPK (SEQ ID NO: 63) | 13 | Enzymes |
| Q8TEX9 | IPO4 Importin-4 | 163-182 | LLNETLGEVGSPGLLFYSLR (SEQ ID NO: 415) | 4 | Channels, Transporters, Receptors |
| O00410 | IPO5 Importin-5 | 721-735 | VAAAESMPLLLECAR (SEQ ID NO: 416) | 14 2 13 8 | Channels, Transporters, Receptors |
| O95373 | IPO7 Importin-7 | 441-427 | TMGFCYQILTEPNADRP (SEQ ID NO: 417) | 13 | Channels, Transporters, Receptors |

TABLE 1-continued

| Accession # | Protein Name | Labeled Peptide | Peptide Sequence | Probes | Family |
|---|---|---|---|---|---|
| Q96P70 | IPO9 Importin-9 | 49-74 | VLEVTEEFGVHLAELTVDPQGALAIR (SEQ ID NO: 418) | 14 | Channels, Transporters, Receptors |
| O14654 | IRS4 Insulin receptor substrate 4 | 256-267 | LCLTDEEVVFVR (SEQ ID NO: 419) | 14 | Uncategorized |
| Q92945 | KHSRP Far upstream element-binding dehydrogenase 2 | 629-646 | IGQQPQQPGAPPQQDYTK (SEQ ID NO: 420) | 2 6 | Transcription factors, Regulators |
| P52732 | KIF11 Kinesin-like protein KIF11 | 158-181 | VSLLEIYNEELFDLLNPSSDVSER (SEQ ID NO: 421) | 6 | Adapter, Scaffolding, Modulator Proteins |
| P52292 | KPNA2 Importin subunit alpha-2 | 203-227 | YGAVDPLLALLAVPDMSSLACGYLR (SEQ ID NO: 422) | 14 13 | Channels, Transporters, Receptors |
| P52292 | KPNA2 Importin subunit alpha-2 | 301-315 | LLGASELPIVTPALR (SEQ ID NO: 423) | 13 | Channels, Transporters, Receptors |
| Q14974 | KPNB1 Importin subunit beta-1 | 317-332 | GALQYLVPILTQTLTK (SEQ ID NO: 424) | 14 13 | Channels, Transporters, Receptors |
| Q14974 | KPNB1 Importin subunit beta-1 | 28-42 | AAVENLPTFLVELSR (SEQ ID NO: 425) | 14 13 | Channels, Transporters, Receptors |
| Q14974 | KPNB1 Importin subunit beta-1 | 526-537 | SSAYESLMEIVK (SEQ ID NO: 426) | 13 14 | Channels, Transporters, Receptors |
| P13473 | LAMP2 Lysosome-associated membrane glycoprotein 2 | 133-144 | GILTVDELLAIR (SEQ ID NO: 427) | 14 9 | Uncategorized |
| Q9P2J5 | LARS Leucine--tRNA ligase, cytoplasmic | 1007-1017 | ILDLQLEFDEK (SEQ ID NO: 428) | 13 | Enzymes |
| P00338 | LDHA L-lactate dehydrogenase A chain | 43-57 | DLADELALVDVIEDK (SEQ ID NO: 64) | 9 | Enzymes |
| P07195 | LDHB L-lactate dehydrogenase B chain | 234-244 | MVVESAYEVIK (SEQ ID NO: 65) | 4 | Enzymes |
| O95202 | LETM1 LETM1 and EF-hand domain-containing protein 1, mit | 452-463 | VAEVEGEQVDNK (SEQ ID NO: 429) | 13 14 4 3 8 | Uncategorized |
| Q08380 | LGALS3BP Galectin-3-binding protein | 522-541 | ALMLCEGLFVADVTDFEGWK (SEQ ID NO: 430) | 9 | Uncategorized |
| Q99538 | LGMN Legumain | 102-118 | DYTGEDVTPQNFLAVLR (SEQ ID NO: 66) | 9 | Enzymes |
| P38571 | LIPA Lysosomal acid lipase/cholestery 1 ester hydrolase | 255-270 | ELCGNLCFLLCGFNER (SEQ ID NO: 431) | 14 | Enzymes |
| P02545 | LMNA Prelamin-A/C | 63-72 | ITESEEVVSR (SEQ ID NO: 432) | 6 | Uncategorized |
| P02545 | LMNA Prelamin-A/C | 172-180 | LEAALGEAK (SEQ ID NO: 433) | 3 | Uncategorized |
| P02545 | LMNA Prelamin-A/C | 209-216 | NIYSEELR (SEQ ID NO: 434) | 6 | Uncategorized |
| P02545 | LMNA Prelamin-A/C | 281-296 | NSNLVGAAHEELQQSR (SEQ ID NO: 435) | 6 | Uncategorized |
| P02545 | LMNA Prelamin-A/C | 352-366 | MQQQLDEYQELLDIK (SEQ ID NO: 96) | 13 6 | Uncategorized |
| P20700 | LMNB1 Lamin-B1 | 321-330 | IQELEDLLAK (SEQ ID NO: 436) | 6 | Uncategorized |
| P20700 | LMNB1 Lamin-B1 | 80-90 | ALYETELADAR (SEQ ID NO: 437) | 13 | Uncategorized |
| P20700 | LMNB1 Lamin-B1 | 351-367 | DQMQQQLNDYEQLLDVK (SEQ ID NO: 438) | 14 8 | Uncategorized |
| P20700 | LMNB1 Lamin-B1 | 210-220 | SMYEEEINETR (SEQ ID NO: 439) | 13 | Uncategorized |
| P20700 | LMNB1 Lamin-B1 | 52-67 | SLETENSALQLQVTER (SEQ ID NO: 440) | 13 14 6 8 | Uncategorized |

TABLE 1-continued

| Accession # | Protein Name | Labeled Peptide | Peptide Sequence | Probes | Family |
|---|---|---|---|---|---|
| Q03252 | LMNB2 Lamin-B2 | 106-113 | AELDEVNK (SEQ ID NO: 441) | 6 | Uncategorized |
| Q03252 | LMNB2 Lamin-B2 | 74-84 | ALYESELADAR (SEQ ID NO: 442) | 13 | Uncategorized |
| Q03252 | LMNB2 Lamin-B2 | 139-150 | SEVELAAALSDK (SEQ ID NO: 443) | 13 | Uncategorized |
| P36776 | LONP1 Lon protease homolog, mitochondrial | 598-632 | GYQGDPSSALLELLDPEQNANFLDHYLDVPVDLSK (SEQ ID NO: 444) | 13 6 | Channels, Transporters, Receptors |
| Q96AG4 | LRRC59 Leucine-rich repeat-containing protein 59 | 268-292 | VTELQQQPLCTSVNTIYDNAVQGLR (SEQ ID NO: 445) | 13 14 2 8 | Uncategorized |
| P09960 | LTA4H Leukotriene A-4 hydrolase | 366-386 | LVVDLTDIDPDVAYSSVPYEK (SEQ ID NO: 67) | 13 4 8 | Enzymes |
| O00754 | MAN2B1 Lysosomal alpha-mannosidase | 291-305 | ELVDYFLNVATAQGR (SEQ ID NO: 446) | 14 | Enzymes |
| O00754 | MAN2B1 Lysosomal alpha-mannosidase | 614-638 | ATFDPDTGLLMEIMNMNQQLLLPVR (SEQ ID NO: 447) | 9 | Enzymes |
| Q9Y2E5 | MAN2B2 Epididymis specific alpha-mannosidase | 642-664 | AAVPAWEAVEMEIVAGQLVTEIR (SEQ ID NO: 448) | 9 | Enzymes |
| Q15691 | MAPRE1 Microtubule-associated protein RP/EB family member | 223-241 | NIELICQENEGENDPVLQR (SEQ ID NO: 449) | 13 | Adapter, Scaffolding, Modulator Proteins |
| Q8NI22 | MCFD2 Multiple coagulation factor deficiency protein 2 | 103-126 | EEGSEQAPLMSEDELINIIDGVLR (SEQ ID NO: 450) | 14 | Channels, Transporters, Receptors |
| P49736 | MCM2 DNA replication licensing factor MCM2 | 797-807 | VMLESFIDTQK (SEQ ID NO: 451) | 13 | Transcription factors, Regulators |
| P33991 | MCM4 DNA replication licensing factor MCM4 | 502-516 | AEINILLCGDPGTSK (SEQ ID NO: 452) | 15 | Transcription factors, Regulators |
| P33991 | MCM4 DNA replication licensing factor MCM4 | 517-529 | SQLLQYVYNLVPR (SEQ ID NO: 453) | 6 | Transcription factors, Regulators |
| Q14566 | MCM6 DNA replication licensing factor MCM6 | 59-85 | NTLVVSFVDLEQFNQQLSTTIQEEFYR (SEQ ID NO: 454) | 14 15 3 6 | Transcription factors, Regulators |
| Q14696 | MESDC2 LDLR chaperone MESD | 113-127 | TLMMFVTVSGSPTEK (SEQ ID NO: 455) | 2 | Chaperones |
| Q9H8H3 | METTL7A Methyltransferase-like protein 7A | 94-105 | VTCIDPNPNFEK (SEQ ID NO: 456) | 13 | Enzymes |
| P46013 | MKI67 Anitgen KI-67 | 648-659 | SGASEANLIVAK (SEQ ID NO: 457) | 8 | Transcription factors, Regulators |
| Q7Z7F7 | MRPL55 39S ribosomal protein L55, mitochondrial | 59-67 | QDGSTIHIR (SEQ ID NO: 458) | 6 | Uncategorized |
| P43246 | MSH2 DNA mismathc repair protein Msh2 | 848-871 | ALELEEFQYIGESQGYDIMEPAAK (SEQ ID NO: 459) | 14 | Transcription factors, Regulators |
| P00403 | MT-CO2 Cytochrome c oxidase subunit 2 | 142-151 | VVLPIEAPIR (SEQ ID NO: 460) | 6 | Channels, Transporters, Receptors |

TABLE 1-continued

| Accession # | Protein Name | Labeled Peptide | Peptide Sequence | Probes | Family |
|---|---|---|---|---|---|
| P03891 | MT-ND2 NADH-ubiquinone oxidoreductase chain 2 | 264-272 | WAIIEEFTK (SEQ ID NO: 461) | 14 | Enzymes |
| Q9NZJ7 | MTCH1 Mitochondrial carrier homolog 1 | 65-103 | MDGGSGGLGSGDNAPTTEALFVALGAGVTALSHPLLYVK (SEQ ID NO: 462) | 14 2 | Channels, Transporters, Receptors |
| Q86UE4 | MTDH Protein LYRIC | 42510 | SWQDELAQQAEEGSAR (SEQ ID NO: 463) | 14 4 2 13 8 | Uncategorized |
| Q86UE4 | MTDH Protein LYRIC | 34-45 | TELGLDGLEPK (SEQ ID NO: 464) | 13 14 4 2 9 8 | Uncategorized |
| Q9UDX5 | MTFP1 Mitochondrial fission process protein 1 | 21-33 | YLGYANEVGEAFR (SEQ ID NO: 465) | 13 14 2 9 | Uncategorized |
| Q9UDX5 | MTFP1 Mitochondrial fission process protein 1 | 103-116 | VCAASLYVLGTATR (SEQ ID NO: 466) | 14 | Uncategorized |
| Q6UB35 | MTHFD1L Monofunctional C1-tetrahydrofolate synthase, mitochondrial | 307-326 | IHFGGLIEEDDVILLAAALR (SEQ ID NO: 467) | 6 | Enzymes |
| Q13505 | MTX1 Metaxin-1 | 238-252 | QGADTLAFMSLLEEK (SEQ ID NO: 468) | 14 3 4 2 6 8 | Channels, Transporters, Receptors |
| P35580 | MYH10 Myosin-10 | 1546-1562 | TQLEELEDEDELQATEDAK (SEQ ID NO: 469) | 13 6 9 | Adapter, Scaffolding, Modulator Proteins |
| P35580 | MYH10 Myosin-10 | 1684-1701 | SLEAEILQLQEELASSER (SEQ ID NO: 470) | 14 13 6 | Adapter, Scaffolding, Modulator Proteins |
| P35580 | MYH10 Myosin-10 | 1738-1758 | IAQLEEELEEEQSNMELLNDR (SEQ ID NO: 471) | 6 | Adapter, Scaffolding, Modulator Proteins |
| P35580 | MYH10 Myosin-10 | 1814-1822 | ATISALEAK (SEQ ID NO: 472) | 6 | Adapter, Scaffolding, Modulator Proteins |
| P35580 | MYH10 Myosin-10 | 248-268 | INFDVTGYIVGANIETYLLEK (SEQ ID NO: 473) | 6 9 | Adapter, Scaffolding, Modulator Proteins |
| P35580 | MYH10 Myosin-10 | 890-910 | NILAEQLQAETELFAEAEEMR (SEQ ID NO: 474) | 13 14 6 9 | Adapter, Scaffolding, Modulator Proteins |
| P35579 | MYH9 Myosin-9 | 1539-1555 | TQLEELEDEDELQATEDAK (SEQ ID NO: 475) | 13 | Adapter, Scaffolding, Modulator Proteins |
| P35579 | MYH9 Myosin-9 | 1677-1694 | SMEAEMIQLQEELAAAER (SEQ ID NO: 476) | 13 | Adapter, Scaffolding, Modulator Proteins |
| Q9BXJ9 | NAA15 N-alpha-acetyltransferase 15, NatA auxiliary subunit | 798-818 | NLQTCMEVLEALYDGSLGDCK (SEQ ID NO: 477) | 14 4 2 | Transcription factors, Regulators |
| P54802 | NAGLU Alpha-N-acetylglucosaminidase | 566-580 | QAVQELVSLYYEEAR (SEQ ID NO: 478) | 9 | Enzymes |
| P54802 | NAGLU Alpha-N-acetylglucosaminidase | 594-615 | AGGVLAYELLPALDEVLASDSR (SEQ ID NO: 479) | 13 15 | Enzymes |

TABLE 1-continued

| Accession # | Protein Name | Labeled Peptide | Peptide Sequence | Probes | Family |
|---|---|---|---|---|---|
| P43490 | NAMPT Nicotinamide phosphoribosyltransferase | 175-189 | YLLETSGNLDGLEYK (SEQ ID NO: 68) | 13 14 15 3 6 8 | Enzymes |
| P55209 | NAP1L1 Nucleosome assembly protein 1-like 1 | 95-104 | FYEEVHDLER (SEQ ID NO: 480) | 3 4 13 6 9 8 | Uncategorized |
| P55209 | NAP1L1 Nucleosome assembly protein 1-like 1 | 177-194 | NVDLLSDMVQEHDEPILK (SEQ ID NO: 481) | 6 | Uncategorized |
| P55209 | NAP1L1 Nucleosome assembly protein 1-like 1 | 56-72 | LDGLVETPTGYIESLPR (SEQ ID NO: 482) | 14 4 2 9 | Uncategorized |
| Q99733 | NAP1L14 Nucleosome assembly protein 1-like 4 | 84-93 | FYEEVHDLER (SEQ ID NO: 483) | 3 4 13 6 9 8 | Uncategorized |
| P49321 | NASP Nuclear autoantigenic sperm protein | 503-526 | SLQENEEEIGNLELAWDMLDLAK (SEQ ID NO: 484) | 13 14 8 | Channels, Transporters, Receptors |
| P49321 | NASP Nuclear autoantigenic sperm protein | 77-93 | YGETANECGEAFFFYGK (SEQ ID MO: 485) | 13 | Channels, Transporters, Receptors |
| Q9H0A0 | NAT10 N-acetyltransferase 10 | 600-625 | ASGDLIPWTVSEQFQDPDFGGLSGGR (SEQ ID NO: 486) | 13 3 | Enzymes |
| Q08161 | NCBP1 Nuclear cap-binding protein subunit 1 | 42-65 | SACSLESNLEGLAGVLEADLPNYK (SEQ ID NO: 487) | 13 14 3 2 | Channels, Transporters, Receptors |
| P28331 | NDUFS1 NADH-ubiquinone oxidoreductase 75 kDa subunit, mit | 312-325 | GLLTYTSWEDALSR (SEQ ID NO: 488) | 14 | Enzymes |
| Q9UMX5 | NENF Neudesin | 85-94 | GAPYNALTGK (SEQ ID NO: 489) | 6 | Adapter, Scaffolding, Modulator Proteins |
| P55769 | NHP2L1 NHP2-like protein 1 | 114-125 | QQIQSIQQSIER (SEQ ID NO: 490) | 3 2 6 | Transcription factors, Regulators |
| Q9BPW8 | NIPSNAP1 Protein NipSnap homolog 1 | 255-268 | GWDENVYYTVPLVR (SEQ ID NO: 491) | 4 6 | Uncategorized |
| Q9Y3T9 | NOC2L Nucleolar complex protein 2 homolog | 591-606 | VSFGVSEQQAVEAWEK (SEQ ID NO: 492) | 2 | Transcription factors, Regulators |
| Q15233 | NONO Non-POU domain-containing octamer-binding protein | 127-135 | VELDNMPLR (SEQ ID NO: 493) | 3 | Transcription factors, Regulators |
| Q15233 | NONO Non-POU domain-containing octamer-binding protein | 257-270 | FAQPGSFEYEYAMR (SEQ ID NO: 494) | 6 | Transcription factors, Regulators |
| Q15233 | NONO Non-POU domain-containing octamer-binding protein | 296-304 | LEMEMEAAR (SEQ ID NO: 495) | 6 | Transcription factors, Regulators |
| Q15233 | NONO Non-POU domain-containing octamer-binding protein | 154-176 | NLPQYVSNELLEEAFSVFGQVER (SEQ ID NO: 496) | 13 14 3 2 6 9 | Transcription factors, Regulators |
| Q15233 | NONO Non-POU domain-containing octamer-binding protein | 177-184 | AVVIVDDR (SEQ ID NO: 497) | 6 | Transcription factors, Regulators |

TABLE 1-continued

| Accession # | Protein Name | Labeled Peptide | Peptide Sequence | Probes | Family |
|---|---|---|---|---|---|
| Q15233 | NONO Non-POU domain-containing octamer-binding protein | 326-336 | MEELHNQEVQK (SEQ ID NO: 498) | 13 | Transcription factors, Regulators |
| Q15233 | NONO Non-POU domain-containing octamer-binding protein | 435-456 | FGQAATMEGIGAIGGTPPAFNR (SEQ ID NO: 499) | 6 | Transcription factors, Regulators |
| P06748 | NPM1 Nucleophosmin | 278-291 | MTDQEAIQDLWQWR (SEQ ID NO: 500) | 13 | Chaperones |
| P06748 | NPM1 Nucleophosmin | 33-45 | VDNDENEHQLSLR (SEQ ID NO: 501) | 13 | Chaperones |
| P06748 | NPM1 Nucleophosmin | 55-73 | DELHIVEAEAMNYEGSPIK (SEQ ID NO: 69) | 13 | Chaperones |
| P06748 | NPM1 Nucleophosmin | 81-101 | MSVQPTVSLGGFEITPPVVLR (SEQ ID NO: 70) | 13 | Chaperones |
| Q08J23 | NSUN2 tRNA (cytosine(34)-C(5))-methyltransferase | 603-618 | LAQEGIYTLYPFINSR (SEQ ID NO: 502) | 3 6 | Transcription factors, Regulators |
| Q9BV86 | NTMT1 N-terminal Xaa-Pro-Lys N-methyltransferase 1 | 167-185 | DNMAQEGVILDDVDSSVCR (SEQ ID NO: 503) | 13 | Enzymes |
| Q02818 | NUCB1 Nucleobindin-1 | 54-69 | YLQEVIDVLETDGHFR (SEQ ID NO: 504) | 13 14 2 4 3 6 | Transcription factors, Regulators |
| P80303 | NUCB2 Nucleobindin-1 | 60-69 | QVIDVLETDK (SEQ ID NO: 505) | 4 13 6 | Transcription factors, Regulators |
| Q9BQG2 | NUDT12 Peroxisomal NADH pyrophosphatase NUDT12 | 143-166 | ESHPATVFILFSDLNPLVTLGGNK (SEQ ID NO: 506) | 15 | Enzymes |
| A8MXV4 | NUDT19 Nucleoside diphosphate-linked moiety X motif 19, mitochondrial | 223-252 | EPPPVYPDLAEVVGYQWSSPSEATESFLSK (SEQ ID NO: 507) | 6 | Enzymes |
| O75694 | NUP155 Nuclear pore complex protein Nup155 | 952-968 | HGEPEEDIVGLQAFQER (SEQ ID NO: 508) | 13 | Channels, Transporters, Receptors |
| Q12769 | NUP160 Nuclear pore complex protein Nup160 | 638-661 | AAEQILEDMITIDVENVMEDICSK (SEQ ID NO: 509) | 14 | Channels, Transporters, Receptors |
| Q92621 | NUP205 Nuclear pore complex protein Nup205 | 1235-1252 | VLVAEVNALQGMAAIGQR (SEQ ID NO: 510) | 14 | Channels, Transporters, Receptors |
| P35658 | NUP214 Nuclear pore complex protein Nup214 | 770-783 | TTLLEGFAGVEEAR (SEQ ID NO: 511) | 14 | Channels, Transporters, Receptors |
| Q8NFH4 | NUP37 Nucleoporin Nup37 | 136-150 | EGQEIASVSDDHTCR (SEQ ID NO: 512) | 13 9 | Channels, Transporters, Receptors |
| Q8N1F7 | NUP93 Nuclear pore complex protein Nup93 | 539-545 | FESTDPR (SEQ ID NO: 513) | 4 | Channels, Transporters, Receptors |
| P61970 | NUTF2 Nuclear transport factor 2 | 91-106 | ADEDPIMGFHQMFLLK (SEQ ID NO: 514) | 14 | Channels, Transporters, Receptors |
| Q6DKJ4 | NXN Nucleoredoxin | 384-403 | DYTNLPEAAPLLTILDMSAR (SEQ ID NO: 515) | 14 | Enzymes |
| P04181 | OAT Ornithine aminotransferase, mitochondrial | 33-46 | TVQGPPTSDDIFER (SEQ ID NO: 516) | 14 13 | Enzymes |
| P04181 | OAT Ornithine aminotransferase, mitochondrial | 332-351 | VAIAALEVLEEENLAENADK (SEQ ID NO: 517) | 14 13 | Enzymes |

TABLE 1-continued

| Accession # | Protein Name | Labeled Peptide | Peptide Sequence | Probes | Family |
|---|---|---|---|---|---|
| Q9NX40 | OCIAD1 OCIA domain-containing protein 1 | 34-46 | VFAECNDESFWFR (SEQ ID NO: 518) | 13 2 | Uncategorized |
| O60313 | OPA1 Dynamin-like 120 kDa protein, mitochondrial | 801-818 | CNEEHPAYLASDEITTVR (SEQ ID NO: 519 | 13 | Enzymes |
| P07237 | P4HB Protein disulfide-isomerase | 133-162 | TGPAATTLPDGAAAESLVESSEVAVIGFFK (SEQ ID NO: 520) | 14 3 9 | Chaperones |
| P07237 | P4HB Protein disulfide-isomerase | 171-195 | QFLQAAEAIDDIPFGITSNSDVFSK (SEQ ID NO: 521) | 9 | Chaperones |
| P07237 | P4HB Protein disulfide-isomerase | 231-247 | HNQLPLVIEFTEQTAPK (SEQ ID NO: 522) | 14 2 13 | Chaperones |
| P11940 | PABPC1 Polyadenylate-binding protein 1 | 114-129 | ALYDTFSAFGNILSCK (SEQ ID NO: 523) | 14 | Transcription factors, Regulators |
| P11940 | PABPC1 Polyadenylate-binding protein 1 | 51-67 | SLGYAYVNFQQPADAER (SEQ ID NO: 524) | 14 3 | Transcription factors, Regulators |
| P11940 | PABPC1 Polyadenylate-binding protein 1 | 581-604 | ITGMLLEIDNSELLHMLESPESLR (SEQ ID NO: 525) | 14 | Transcription factors, Regulators |
| Q11310 | PABPC4 Polyadenylate-binding protein 4 | 51-67 | SLGYAYVNFQQPADAER (SEQ ID NO: 526) | 14 3 | Transcription factors, Regulators |
| Q13310 | PABPC4 Polyadenylate-binding protein 4 | 590-613 | ITGMLLEIDNSELLHMLESPESLR (SEQ ID NO: 527) | 14 | Transcription factors, Regulators |
| Q13310 | PABPC4 Polyadenylate-binding protein 4 | 114-129 | ALYDTFSAFGNILSCK (SEQ ID NO: 528) | 14 | Transcription factors, Regulators |
| P09874 | PARP1 Poly | 762-779 | VEMLDNLLDIEVAYSLLR (SEQ ID NO: 529) | 3 6 | Transcription factors, Regulators |
| P09874 | PARP1 Poly | 954-1000 | TTPDPSANISLDGVDVPLGTGISSGVNDTSLLYNEYIVYDIAQVNLK (SEQ ID NO: 530) | 3 | Transcription factors, Regulators |
| Q16822 | PCK2 Phosphoenolypruvate carboxykinase | 245-261 | EIISFGSGYGGNSLLGK (SEQ ID NO: 531) | 14 15 13 | Enzymes |
| P22061 | PCMT1 Protein-L-isoaspartate(D-aspartate) O-methyltransferase | 179-197 | LILPVGPAGGNQMLEQYDK (SEQ ID NO: 71) | 14 3 2 | Enzymes |
| P12004 | PCNA Proliferating cell nuclear antigen | 118-138 | LMDLDVEQLGIPEQEYSCVVK (SEQ ID NO: 532) | 14 | Transcription factors, Regulators |
| Q9UHG3 | PCYOX1 Prenylcysteine oxidase 1 | 267-280 | SNLISGSVMYIEEK (SEQ ID NO: 533) | 14 9 | Enzymes |
| Q9UHG3 | PCYOX1 Prenylcysteine oxidase 1 | 292-304 | MYEVVYQIGTETR (SEQ ID NO: 534) | 9 | Enzymes |
| Q9UHG3 | PCYOX1 Prenylcysteine oxidase 1 | 152-162 | MHMWVEDVLDK (SEQ ID NO: 535) | 4 13 | Enzymes |
| Q9UHG3 | PCYOX1 Prenylcysteine oxidase 1 | 37-54 | IAIIGAGIGGTSAAYYLR (SEQ ID NO: 536) | 14 | Enzymes |
| Q53EL6 | PDCD4 Programmed cell death protein 4 | 246-256 | DLPELALDTPR (SEQ ID NO: 537) | 13 | Transcription factors, Regulators |
| P11177 | PDHB Pyruvate dehydrogenase | 53-68 | VFLLGEEVAQYDGAYK (SEQ ID NO: 72) | 13 14 3 2 | Enzymes |

TABLE 1-continued

| Accession # | Protein Name | Labeled Peptide | Peptide Sequence | Probes | Family |
|---|---|---|---|---|---|
| | E1 component subunit beta, | | | | |
| P13667 | PDIA4 Protein disulfide-isomerase A4 | 486-499 | FAMEPEEFDSDTLR (SEQ ID NO: 538) | 9 | Enzymes |
| Q29RF7 | PDS5A Sister chromatid cohesion protein PDS5 homolog A | 638-657 | SIEGTADDEEEGVSPDTAIR (SEQ ID NO: 539) | 13 | Uncategorized |
| Q99471 | PFDN5 Prefoldin subunit 5 | 20-37 | NQLDQEVEFLSTSIAQLK (SEQ ID NO: 540) | 2 | Chaperones |
| P07737 | PFN1 Profilin-1 | 39-54 | TFVNITPAEVGVLVGK (SEQ ID NO: 541) | 13 | Adapter, Scaffolding, Modulator Proteins |
| P07737 | PFN1 Profilin-1 | 76-89 | DSLLQDGEFSMDLR (SEQ ID NO: 542) | 13 8 | Adapter, Scaffolding, Modulator Proteins |
| P00558 | PGK1 Phosphoglycerate kinase 1 | 333-350 | QIVWNGPVGVFEWEAFAR (SEQ ID NO: 73) | 3 | Enzymes |
| O00264 | PGRMC1 Membrane-associated progesterone receptor component | 106-119 | FYGPEGPYGVFAGR (SEQ ID NO: 543) | 14 2 4 3 13 | Channels, Transporters, Receptors |
| O00264 | PGRMC1 Membrane-associated progesterone receptor component | 48-67 | GDQPAASGDSDDDEPPPLR (SEQ ID NO: 544) | 13 14 2 4 8 | Channels, Transporters, Receptors |
| O15173 | PGRMC2 Membrane-associated progesterone receptor component | 136-149 | FYGPAGPYGIFAGR (SEQ ID NO: 545) | 4 | Channels, Transporters, Receptors |
| P35232 | PHB Prohibitin | 220-239 | AAELIANSLATAGDGLIELR (SEQ ID NO: 546) | 9 | Uncategorized |
| P35232 | PHB Prohibitin | 241-253 | LEAAEDIAYQLSR (SEQ ID NO: 547) | 14 | Uncategorized |
| P35232 | PHB Prohibitin | 42501 | VFESIGK (SEQ ID NO: 548) | 13 | Uncategorized |
| Q99623 | PHB2 Prohibitin-2 | 38-48 | ESVFTVEGGHR (SEQ ID NO: 549) | 2 6 | Channels, Transporters, Receptors |
| Q99623 | PHB2 Prohibitin-2 | 55-71 | IGGVQQDTILAEGLHFR (SEQ ID NO: 550) | 3 4 2 6 | Channels, Transporters, Receptors |
| Q99623 | PHB2 Prohibitin-2 | 225-236 | IVQAEGEAEAAK (SEQ ID NO: 551) | 6 | Channels, Transporters, Receptors |
| O43175 | PHGDH D-3-phosphoglycerate dehydrogenase | 295-308 | CGEEIAVQFVDMVK (SEQ ID NO: 552) | 13 | Enzymes |
| P48739 | PITPNB Phosphatidylinositol transfer protein beta isoform | 32-44 | NETGGGEGIEVLK (SEQ ID NO: 553) | 14 3 | Adapter, Scaffolding, Modulator Proteins |
| Q5JRX3 | PITRM1 Presequence protease, mitochondrial | 364-385 | ALIESGLGTDFSPDVGYNGYTRTQNGR (SEQ ID NO: 554) | 14 2 13 8 6 | Enzymes |
| P14618 | PKM Pyruvate kinase isozymes M1/M2 | 174-186 | IYVDDGLISLQVK (SEQ ID NO: 74) | 2 9 | Enzymes |
| P14618 | PKM Pyruvate kinase isozymes M1/M2 | 401-422 | LAPITSDPTEATAVGAVEASFK (SEQ ID NO: 75) | 2 9 | Enzymes |
| Q8IV08 | PLD3 Phospholipase D3 | 425-453 | ATYIGTSNWSGNYFTETAGTSLLVTQNGR (SEQ ID NO: 555) | 3 6 9 | Enzymes |

TABLE 1-continued

| Accession # | Protein Name | Labeled Peptide | Peptide Sequence | Probes | Family |
|---|---|---|---|---|---|
| P13797 | PLS3 Plastin-3 | 72-85 | ISFDEFVYIFQEVK (SEQ ID NO: 556) | 14 | Uncategorized |
| Q10713 | PMPCA Mitochondrial-processing peptidase subunit alpha | 443-451 | PVIFEDVGR (SEQ ID NO: 557) | 14 8 6 | Enzymes |
| O75439 | PMPCB Mitochondrial-processing peptidase subunit beta | 406-424 | TNMLLQLDGSTPICEDIGR (SEQ ID NO: 558) | 13 | Enzymes |
| Q9Y2S7 | POLDIP2 Polymerase delta-interacting protein 2 | 166-199 | ALYAIPGLDYVSHEDILPYTSTDQ VPIQHELFER (SEQ ID NO: 559) | 6 | Uncategorized |
| O00411 | POLRMT DNA-directed RNA polymerase, mitochondrial | 482-502 | MLLQVLQALPAQGESFTTLAR (SEQ ID NO: 560) | 14 3 2 6 | Enzymes |
| P16435 | POR NADPH--cytochrome P450 reductase | 369-382 | TALTYYLDITNPPR (SEQ ID NO: 76) | 13 14 | Enzymes |
| P62136 | PPP1CA Serine/threonine-protein phosphate PP1-alpha cat | 133-141 | IYGFYDECK (SEQ ID NO: 77) | 2 | Enzymes |
| P62140 | PPP1CB Serine/threonine-protein phosphate PP1-alpha cat | 132-140 | IYGFYDECK (SEQ ID NO: 78) | 2 | Enzymes |
| P62140 | PPP1CB Serine/threonine-protein phosphate PP1-alpha cat | 43-59 | IEFLSQPILLELEAPLK (SEQ ID NO: 79) | 14 | Enzymes |
| P36873 | PPP1CC Serine/threonine-protein phosphate PP1-gamma cat | 44-60 | EIFLSQPILLELEAPLK (SEQ ID NO: 79) | 14 | Enzymes |
| P36873 | PPP1CC Serine/threonine-protein phosphate PP1-gamma cat | 133-141 | IYGFYDECK (SEQ ID NO: 78) | 2 | Enzymes |
| P50897 | PPT1 Palmitoyl-protein thioesterase 1 | 75-101 | TLMEDVENSFFLNVNSQVTTVCQ ALKA (SEQ ID NO: 80) | 13 14 15 4 2 9 8 | Enzymes |
| P32119 | PRDX2 Peroxiredoxin-2 | 120-127 | TDEGIAYR (SEQ ID NO: 81) | 13 | Enzymes |
| P78527 | PRKDC DNA-dependent protein kinase catalytic subunit | 3030-3046 | IWSEPFYQETLPYMIR (SEQ ID NO: 561) | 14 | Enzymes |
| P78527 | PRKDC DNA-dependent protein kinase catalytic subunit | 758-782 | LGLSYTPLAEVGLNALEEWSIYID R (SEQ ID NO: 562) | 14 | Enzymes |
| Q99873 | PRMT1 Protein argine N-methyltransferase 1 | 380-391 | DVDFMYVELIQR (SEQ ID NO: 563) | 13 | Enzymes |
| Q9UMS4 | PRPF19 Pre-mRNA-processing factor 19 | 186-196 | ATLYVTAIEDR (SEQ ID NO: 564) | 14 | Enzymes |
| P07602 | PSAP Proactivator polypeptide | 77-93 | ALQDEWDAVMLHSFTLR (SEQ ID NO: 565) | 4 | Adapter, Scaffolding, Modulator Proteins |
| P07602 | PSAP Proactivator polypeptide | 108-122 | EIVDSYLPVILDIIK (SEQ ID NO: 566) | 13 14 3 2 4 15 6 9 8 | Adapter, Scaffolding, Modulator Proteins |

TABLE 1-continued

| Accession # | Protein Name | Labeled Peptide | Peptide Sequence | Probes | Family |
|---|---|---|---|---|---|
| P07602 | PSAP Proactivator polypeptide | 263-275 | EICALVGFCDEVK (SEQ ID NO: 567) | 14 | Adapter, Scaffolding, Modulator Proteins |
| P07602 | PSAP Proactivator polypeptide | 311-323 | SDVYCEVCEFLVK (SEQ ID NO: 568) | 13 4 9 8 | Adapter, Scaffolding, Modulator Proteins |
| P07602 | PSAP Proactivator polypeptide | 430-438 | QEILAALEK (SEQ ID NO: 569) | 2 6 | Adapter, Scaffolding, Modulator Proteins |
| P07602 | PSAP Proactivator polypeptide | 439-449 | GCSFLPDPYQK (SEQ ID NO: 570) | 14 9 | Adapter, Scaffolding, Modulator Proteins |
| P07602 | PSAP Proactivator polypeptide | 450-478 | QCDQFVAEYEPVLIEILVEVMDPS FVCLK (SEQ ID NO: 571) | 14 4 9 | Adapter, Scaffolding, Modulator Proteins |
| P07602 | PSAP Proactivator polypeptide | 68-78 | DVVTAAGDMLK (SEQ ID NO: 572) | 14 4 9 | Adapter, Scaffolding, Modulator Proteins |
| P25787 | PSMA2 Proteasome subunit alpha type-2 | 144-159 | PYLFQSDPSGAYFAWK (SEQ ID NO: 573) | 2 | Enzymes |
| P25787 | PSMA2 Proteasome subunit alpha type-2 | 19-39 | LVQIEYALAAVAGGAPSVGIK (SEQ ID NO: 574) | 3 | Enzymes |
| P25789 | PSMA4 Proteasome subunit alpha type-4 | 68-91 | LNEDMACSVAGITSDANVLTNEL R (SEQ ID NO: 575) | 13 14 3 6 8 | Enzymes |
| P20618 | PSMB1 Proteasome subunit beta type-1 | 129-146 | FFPYYVYNIIGGLDEEGK (SEQ ID NO: 576) | 13 14 2 15 | Enzymes |
| P49721 | PSMB2 Proteasome subunit beta type-2 | 96-126 | TPYHVNLLLAGYDEHEGPALYY MDYLAALAK (SEQ ID NO: 577) | 2 6 | Enzymes |
| P49721 | PSMB2 Proteasome subunit beta type-2 | 42-62 | ILLLCVGEAGDTVQFAEYIQ (SEQ ID NO: 578) | 6 | Enzymes |
| P49720 | PSMB3 Proteasome subunit beta type-3 | 100-115 | FGPYYTEPVIAGLDPK (SEQ ID NO: 579) | 13 14 15 3 6 | Enzymes |
| P28070 | PSMB4 Proteasome subunit beta type-4 | 61-80 | FEGGVVIAADMLGSYGSLAR (SEQ ID NO: 82) | 6 | Enzymes |
| P28074 | PSMB5 Proteasome subunit beta type-5 | 141-150 | LLANMVYQYK (SEQ ID NO: 83) | 4 3 6 | Enzymes |
| P28074 | PSMA5 Proteasome subunit beta type-5 | 226-239 | DAYSGGAVNLYHVR (SEQ ID NO: 84) | 6 | Enzymes |
| P28072 | PSMB6 Proteasome subunit beta type-6 | 80-118 | SGSAADTQAVADAVTYQLGFHSI ELNEPPLVHTAASLFK (SEQ ID NO: 85) | 14 3 6 | Enzymes |
| O00231 | PSMD11 26S proteasome non-ATPase regulatory subunit 11 | 164-175 | ALLVEVQLLESK (SEQ ID NO: 580) | 2 | Uncategorized |
| O00231 | PSMD11 26S proteasome non- | 227-246 | TAYSFYEAFEGYDSIDSPK (SEQ ID NO: 581) | 2 4 | Uncategorized |

TABLE 1-continued

| Accession # | Protein Name | Labeled Peptide | Peptide Sequence | Probes | Family |
|---|---|---|---|---|---|
| O00231 | PSMD11 26S proteasome non-ATPase regulatory subunit 11 | 298-304 | SLADFEX (SEQ ID NO: 582) | 4 | Uncategorized |
| O43242 | PSMD3 26S proteasome non-ATPase regulatory subunit 3 | 242-256 | HDADGQATLLNLLLR (SEQ ID NO: 583) | 14 4 | Uncategorized |
| O43242 | PSMD3 26S proteasome non-ATPase regulatory subunit 3 | 426-440 | LQLDSPEDAEFIVAK (SEQ ID NO: 584) | 14 | Uncategorized |
| Q9UL46 | PSME2 Proteasome activator complex subunit 2 | 132-145 | IEDGNDFGVAIQEK (SEQ ID NO: 585) | 6 | Uncategorized |
| P61289 | PSME3 Proteasome activator complex subunit 3 | 147-166 | IEDGNNFGVSIQEETVAELR (SEQ ID NO: 586) | 14 4<br>13 8 | Uncategorized |
| P61289 | PSME3 Proteasome activator complex subunit 3 | 167-181 | TVESEAASYLDQISR (SEQ ID NO: 587) | 13 4 8 | Uncategorized |
| P61289 | PSME3 Proteasome activator complex subunit 3 | 22-36 | ITSEAEDLVANFFPK (SEQ ID NO: 588) | 4 | Uncategorized |
| Q8WXF1 | PSPC1 Paraspeckle component 1 | 229-247 | PVIVEPMEQFDDEDGLPEK (SEQ ID NO: 589) | 14 6 | Transcription factors, Regulators |
| P26599 | PTBP1 Polypyrimidine tract-binding protein 1 | 219-238 | NNQFQALLQYADPVSAQHA (SEQ ID NO: 590) | 14 | Transcription factors, Regulators |
| Q96EY7 | PTCD3 Pentatricopeptide repeat-containing protein 3, mit | 119-126 | FIINSYPK (SEQ ID NO: 591) | 2 | Transcription factors, Regulators |
| Q8N8N7 | PTGR2 Prostaglandin reductase 2 | 93-106 | GDFVTSFYWPWQTK (SEQ ID NO: 592) | 14 | Enzymes |
| Q8N8N7 | PTGR2 Prostaglandin reductase 2 | 262-278 | DVPYPPPLSPAIEAIQK (SEQ ID NO: 593) | 14 3 2 | Enzymes |
| Q9P035 | PTPLAD1 3-hydroxyacyl-CoA dehydratase 3 | 133-146 | LESEGSPETLTNLR (SEQ ID NO: 594) | 13 | Enzymes |
| Q9UHX1 | PUF60 Poly(U)-binding-splicing factor PUF60 | 474-489 | DIDDDLEGEVTEECGK (SEQ ID NO: 595) | 13 15<br>14 4 8 | Transcription factors, Regulators |
| Q5XLP0 | QIL1 Protein QIL1 | 15-36 | GSVAGGAVYLVYDQELLGPSDK (SEQ ID NO: 596) | 14 | Uncategorized |
| Q96PU8 | QKI Protein quaking | 192-205 | MQLMELAILNGTYR (SEQ ID NO: 597) | 2 | Channels, Transporters, Receptors |
| P51149 | RAB7A Ras-related protein Rab-7a | 104-113 | DEFLIQASPR (SEQ ID NO: 86) | 14 | Adapter, Scaffolding, Modulator Proteins |
| Q7Z6M1 | RABEPK Rab9 effector protein with kelch motifs | 87-100 | YEHASFIPSCTPDR (SEQ ID NO: 598) | 14 | Uncategorized |

TABLE 1-continued

| Accession # | Protein Name | Labeled Peptide | Peptide Sequence | Probes | Family |
|---|---|---|---|---|---|
| P11233 | RALA Ras-related protein Ral-A | 28-47 | SALTLQFMYDEFVEDYEPTK (SEQ ID NO: 599) | 9 | Transcription factors, Regulators |
| P54136 | RARS Arginine--tRNA ligase, cytoplasmic | 528-540 | GNTAAYLLYAFTR (SEQ ID NO: 600) | 14 | Enzymes |
| Q96PK6 | RBM14 RNA-binding protein 14 | 224-238 | ASYVAPTAQPATYR (SEQ ID NO: 601) | 6 | Transcription factors, Regulators |
| Q96PK6 | RBM14 RNA-binding protein 14 | 65-72 | ALVVEMSR (SEQ ID NO: 602) | 6 | Transcription factors, Regulators |
| P98179 | RMB3 Putative RNA-binding protein 3 | 8-39 | LFVGGLNFNTDEQALEDHFSSFGP ISEVVVVK (SEQ ID NO: 603) | 13 3 2 9 | Transcription factors, Regulators |
| P38159 | RMBX RNA-binding motif protein, X chromosome | 126-144 | GGHMDDGGYSMNFNMSSSR (SEQ ID NO: 604) | 6 | Transcription factors, Regulators |
| P38159 | RMBX RNA-binding motif protein, X chromosome | 23-30 | ALEAVFGK (SEQ ID NO: 605) | 3 13 6 | Transcription factors, Regulators |
| P38159 | RMBX RNA-binding motif protein, X chromosome | 245-252 | DYGHSSSR (SEQ ID NO: 606) | 3 | Transcription factors, Regulators |
| P38159 | RMBX RNA-binding motif protein, X chromosome | 283-292 | DSYESYGNSR (SEQ ID NO: 607) | 6 | Transcription factors, Regulators |
| P38159 | RMBX RNA-binding motif protein, X chromosome | 299-309 | GPPPSYGGSSR (SEQ ID NO: 608) | 6 | Transcription factors, Regulators |
| P38159 | RMBX RNA-binding motif protein, X chromosome | 332-339 | SDLYSSGR (SEQ ID NO: 609) | 6 | Transcription factors, Regulators |
| P38159 | RMBX RNA-binding motif protein, X chromosome | 50-63 | GFAFVTFESPADAK (SEQ ID NO: 610) | 6 | Transcription factors, Regulators |
| Q96E39 | RBMXL1 RNA binding motif protein, X-linked-like-1 | 299-309 | GPPPSYGGSSR (SEQ ID NO: 611) | 6 | Transcription factors, Regulators |
| Q96E39 | RBMXL1 RNA binding motif protein, X-linked-like-1 | 50-63 | GFAFVTFESPADAK (SEQ ID NO: 612) | 6 | Transcription factors, Regulators |
| Q96E39 | RBMXL1 RNA binding motif protein, X-linked-like-1 | 245-252 | DYGHSSSR (SEQ ID NO: 613) | 3 | Transcription factors, Regulators |
| Q96E39 | RBMXL1 RNA binding motif protein, X-linked-like-1 | 283-292 | DSYESYGNSR (SEQ ID NO: 614) | 6 | Transcription factors, Regulators |
| Q96E39 | RBMXL1 RNA binding motif protein, X-linked-like-1 | 126-144 | GGHMDDGGYSMNFNMSSSR (SEQ ID NO: 615) | 6 | Transcription factors, Regulators |
| Q15293 | RCN1 Reticulocalbin-1 | 91-105 | IDNDGDGFVTTEELK (SEQ ID NO: 616) | 13 | Uncategorized |
| Q14257 | RCN2 Reticulocalbin-2 | 283-305 | LSEEEILENPDLFLTSEATDYGR (SEQ ID NO: 617) | 14 3 15 6 9 8 | Uncategorized |
| Q14257 | RCN2 Reticulocalbin-2 | 130-148 | VIDFDENTALDDAEEESFR (SEQ ID NO: 618) | 13 9 6 | Uncategorized |
| Q14257 | RCN2 Reticulocalbin-2 | 217-232 | WDPTANEDPEWILVE (SEQ ID NO: 619) | 14 4 6 | Uncategorized |
| Q14257 | RCN2 Reticulocalbin-2 | 96-103 | HYAMQEAK (SEQ ID NO: 620) | 6 | Uncategorized |
| Q14257 | RCN2 Reticulocalbin-2 | 161-200 | ANQDSGPGLSLEEFIAFEHPEEVD YMTEFVIQEALEEHDK (SEQ ID NO: 621) | 9 | Uncategorized |

TABLE 1-continued

| Accession # | Protein Name | Labeled Peptide | Peptide Sequence | Probes | Family |
|---|---|---|---|---|---|
| P35250 | RBC2 Replication factor C subunit 2 | 211-230 | VPYTDDGLEAIIFTAQGDMR (SEQ ID NO: 622) | 13 | Transcription factors, Regulators |
| P62888 | RPL30 60S ribosomal protein L30 | 58-68 | SEIEYYAMLAK (SEQ ID NO: 623) | 13 | Uncategorized |
| P62917 | RPL8 60S ribosomal protein L8 | 129-144 | ASGNYATVISHNPETK (SEQ ID NO: 624) | 2 | Transcription factors, Regulators |
| P05387 | RPLP2 60S acidic ribosomal protein P2 | 50-61 | NIEDVIAQGIGK (SEQ ID NO: 625) | 14 | Uncategorized |
| P04843 | RPN1 Dolichyl-diphosphooligosaccharide--protein glycosyltransferase subunit 1 | 152-169 | QFVVFEGNHYFYSPYPTK (SEQ ID NO: 626) | 6 | Enzymes |
| P04843 | RPN1 Dolichyl-diphosphooligosaccharide--protein glycosyltransferase subunit 1 | 328-352 | THYIVGYNLPSYEYLYNLGDQYALK (SEQ ID NO: 627) | 6 | Enzymes |
| P04843 | RPN1 Dolichyl-diphosphooligosaccharide--protein glycosyltransferase subunit 1 | 525-536 | ALTSEIALLQSR (SEQ ID NO: 628) | 13 6 | Enzymes |
| P04844 | RPN2 Dolichyl-diphosphooligosaccharide--protein glycosyltransferase subunit 2 | 155-178 | EETVLATVQALQTASHLSQQADL (SEQ ID NO: 629) | 6 | Enzymes |
| P04844 | RPN2 Dolichyl-diphosphooligosaccharide--protein glycosyltransferase subunit 2 | 179-190 | SIVEEIEDLVAR (SEQ ID NO: 630) | 14 3 13 6 9 | Enzymes |
| P04844 | RPN2 Dolichyl-diphosphooligosaccharide--protein glycosyltransferase subunit 2 | 443-456 | TGQEVVFVAEPDNK (SEQ ID NO: 631) | 9 | Enzymes |
| P46783 | RPS10 40S ribosomal protein S10 | 81-95 | DYLHLPPEIVPATR (SEQ ID NO: 632) | 3 13 | Uncategorized |
| P23396 | RPS3 40S ribosomal protein S3 | 152-173 | FVDGLMIHSGDPVNYYVDTAVR (SEQ ID NO: 633) | 6 | Transcription factors, Regulators |
| P23396 | RPS3 40S ribosomal protein S3 | 28-40 | ELAEDGYSGVEVR (SEQ ID NO: 634) | 13 6 | Transcription factors, Regulators |
| P23396 | RPS3 40S ribosomal protein S3 | 46-54 | TEIIILATR (SEQ ID NO: 635) | 6 | Transcription factors, Regulators |
| P23396 | RPS3 40S ribosomal protein S3 | 77-90 | FGFPEGSVELYAEK (SEQ ID NO: 636) | 2 6 | Transcription factors, Regulators |
| P62241 | RPS8 40S ribosomal protein S8 | 158-170 | ISSLLEEQFQGK (SEQ ID NO: 637) | 13 | Uncategorized |
| Q9NQC3 | RTN4 Reticulon-4 | 1075-1090 | AYLESEVAISEELVQK (SEQ ID NO: 638) | 13 14 | Uncategorized |
| Q9Y265 | RUVBL1 RuvB-like 1 | 318-333 | ALESSIAPIVIFASNR (SEQ ID NO: 639) | 2 | Enzymes |
| Q9Y265 | RUVBL1 RuvB-like 1 | 91-107 | VPFCPMVGSEVYSTEIK (SEQ ID NO: 640) | 2 | Enzymes |
| Q9Y230 | RUVBL2 RuvB-like 2 | 315-330 | ALESDMAPVLIMATNR (SEQ ID NO: 87) | 14 | Transcription factors, Regulators |

TABLE 1-continued

| Accession # | Protein Name | Labeled Peptide | Peptide Sequence | Probes | Family |
|---|---|---|---|---|---|
| Q9Y512 | SAMM50 Sorting and assembly machinery component 50 homolo | 128-148 | LTGSYNTMVGNNEGSMVLGLK (SEQ ID NO: 641) | 14 4 | Uncategorized |
| Q8NBX0 | SCCPDH Saccharopine dehydrogenase-like oxidoreductase | 145-167 | GVYIIGSSGFDSIPADLGVIYTR (SEQ ID NO: 642) | 14 | Enzymes |
| Q9HB40 | SCPEP1 Retinoid-inducible serine carboxypeptidase | 256-275 | AEMIIEQNTDGVNFYNILTK (SEQ ID NO: 643) | 13 14 15 3 2 4 6 9 8 | Enzymes |
| Q01105 | SET Protein SET | 91-122 | IPNFWVTTFVNHPQVSALLGEEDEEALHYLTR (SEQ ID NO: 644) | 3 | Chaperones |
| P23246 | SFPQ Splicing factor, proline- and glutamine-rich | 377-399 | NLSPYVSNELLEEAFSQFGPIER (SEQ ID NO: 645) | 13 14 3 2 4 9 | Transcription factors, Regulators |
| P23246 | SFPQ Splicing factor, proline- and glutamine-rich | 444-462 | PVIVEPLEQLDDEDGLPEK (SEQ ID NO: 646) | 14 4 2 | Transcription factors, Regulators |
| Q9H9B4 | SFXN1 Sideroflexin-1 | 36-48 | NILLTNEQLESAR (SEQ ID NO: 647) | 14 | Channels Transporters, Receptors |
| Q9H9B4 | SFXN1 Sideroflexin-1 | 137-170 | SGDAPLTVNELGTAYVSATTGAVATALGLNALTK (SEQ ID NO: 648) | 14 | Channels Transporters, Receptors |
| Q9H9B4 | SFXN1 Sideroflexin-1 | 56-70 | QGIVPPGLTENELWR (SEQ ID NO: 649) | 14 | Channels Transporters, Receptors |
| Q9H9B4 | SFXN1 Sideroflexin-1 | 93-112 | MSAQVPMNMTITGCMMTFYR (SEQ ID NO: 650) | 6 | Channels Transporters, Receptors |
| Q9H9B4 | SFXN1 Sideroflexin-1 | 234-253 | ILMAAPGMAIPPFIMNTLEK (SEQ ID NO: 651) | 6 | Channels Transporters, Receptors |
| Q6P4A7 | SFXN4 Sideroflexin-4 | 43-66 | FLQWTELLDPTNVFISVESIENSR (SEQ ID NO: 652) | 14 2 | Channels Transporters, Receptors |
| O95470 | SGPL1 Sphingosine-1-phophate lyase 1 | 42699 | AFEPYLEILEVYSTK (SEQ ID NO: 653) | 14 | Enzymes |
| Q9Y371 | SH3GLB1 Endophilin-B1 | 22-29 | AVQFTEEK (SEQ ID NO: 654) | 4 8 | Adapter, Scaffolding, Modulator Proteins |
| P34897 | SHMT2 Serine hydroxymethyltransferase, mitochondrial | 105-121 | YYGGAEVVDEIELLCQR (SEQ ID NO: 655) | 13 14 15 3 2 8 | Enzymes |
| Q9UBX3 | SLC25A10 Mitochondrial dicarboxylate carrier | 171-186 | GALVTVGQLSCYDQAK (SEQ ID NO: 656) | 14 | Channels Transporters, Receptors |
| O75746 | SCLC25A12 Calcium-binding mitochondrial carrier protein Ara1 | 260-283 | YGQVTPLEIDILYQLADLYNASGR (SEQ ID NO: 657) | 14 4 | Channels Transporters, Receptors |
| O75746 | SCLC25A12 Calcium-binding mitochondrial carrier protein Ara1 | 641-652 | LATATFAGIENK (SEQ ID NO: 658) | 14 4 | Channels Transporters, Receptors |
| Q9UJS0 | SCLC25A13 Calcium-binding mitochondrial carrier protein Ara1 | 293-310 | IAPLEEGTLPFNLAEAQR (SEQ ID NO: 659) | 4 6 | Channels Transporters, Receptors |
| Q9UJS0 | SCLC25A13 Calcium-binding mitochondrial | 261-282 | FGQVTPMEVDILFQLADLYEPR (SEQ ID NO: 660) | 14 15 3 4 2 6 | Channels Transporters, Receptors |

TABLE 1-continued

| Accession # | Protein Name | Labeled Peptide | Peptide Sequence | Probes | Family |
|---|---|---|---|---|---|
| Q9UJS0 | carrier protein Ara1 SCLC25A13 Calcium-binding mitochondrial carrier protein Ara1 | 642-653 | LAVATFAGIENK (SEQ ID NO: 661) | 14 4 3<br>15 6 8 | Channels Transporters, Receptors |
| Q6NUK1 | SCLC25A24 Calcium-binding mitochondrial carrier protein SCaM | 454-469 | VLPAVGISYVVYENMK (SEQ ID NO: 662) | 2 | Channels Transporters, Receptors |
| Q00325 | SLC25A3 Phophate carrier protein, mitochondrial | 146-161 | VLYSNMLGEENTYLWR (SEQ ID NO: 663) | 4 | Channels Transporters, Receptors |
| Q00325 | SLC25A3 Phophate carrier protein, mitochondrial | 162-187 | TSLYLAASASAEFFADIALAPMEA AK (SEQ ID NO: 664) | 4 | Channels Transporters, Receptors |
| Q9H2D1 | SLC25A32 Mitochondrial folate transporter/carrier | 118-145 | LEATEYLVSAAEAGAMTLCITNPL WVTK (SEQ ID NO: 665) | 14 | Channels Transporters, Receptors |
| P12235 | SLC25A4 ADP/ATP translocase 1 | 189-199 | AAYFGVYDTAK (SEQ ID NO: 666) | 14 2 8<br>4 | Channels Transporters, Receptors |
| Q8TBP6 | SLC25A40 Solute carrier family 25 member 40 | 136-152 | LGENETCIPIVAGIVAR (SEQ ID NO: 667) | 14 | Channels Transporters, Receptors |
| P05141 | SLC25A5 ADP/ATP translocase 2 | 42697 | DFLAGGVAAAISK (SEQ ID NO: 668) | 14 2 4 | Channels Transporters, Receptors |
| P05141 | SLC25A5 ADP/ATP translocase 2 | 189-199 | AAYFGIYDTAK (SEQ ID NO: 669) | 14 2 4<br>3 9 8 | Channels Transporters, Receptors |
| P12236 | SLC25A6 ADP/ATP translocase 3 | 42697 | DFLAGGIAAAISK (SEQ ID NO: 670) | 14 4 2<br>13 | Channels Transporters, Receptors |
| P12236 | SLC25A6 ADP/ATP translocase 3 | 189-199 | AAYFGVYDTAK (SEQ ID NO: 671) | 14 2 8<br>4 | Channels Transporters, Receptors |
| Q8IXU6 | SLC35F2 Solute carrier family 35 member F2 | 188-221 | EDNSGSDVLIGDILVLLGASLYAIS NVCEEYIVK (SEQ ID NO: 672) | 9 | Channels Transporters, Receptors |
| Q9H2G2 | SLK STE20-like serine/threonine-protein kinase | 27-47 | DLNPEDFWEIIGELGDGAFGK (SEQ ID NO: 673) | 6 | Enzymes |
| Q92922 | SMARCC1 SWI/SNF complex subunit SMARCC1 | 894-905 | SLVALLVETQMK (SEQ ID NO: 674) | 13 | Transcription factors, Regulators |
| Q14683 | SMC1A Structureal maintenance of chromosomes protein 1A | 1070-1086 | FNACFESVATNIDEIYK (SEQ ID NO: 675) | 8 | Adapter, Scaffolding, Modulator Proteins |
| Q9H7B4 | SMYD3 SET and MYND domain-containing protein 3 | 255-265 | DQYCFECDCFR (SEQ ID NO: 88) | 9 | Enzymes |
| Q96DI7 | SNRNP40 U5 small nuclear ribonucleoprotein 40 kDa protein | 233-260 | GHADSVTGLSLSSEGSYLLSNAM DNTVR (SEQ ID NO: 676) | 13 | Uncategorized |
| P62314 | SNRNP40 U5 small nuclear ribonucleoprotein Sm D1 | 67-86 | YFILPDSLPLDTLLVDVEPK (SEQ ID NO: 677) | 13 | Uncategorized |
| Q13813 | SPTAN1 Spectrin alpha chain, non-erythrocytic 1 | 2354-2382 | SLGYDLPMVEEGEPDPEFEAILDT VDPNR (SEQ ID NO: 678) | 13 14 | Adapter, Scaffolding, Modulator Proteins |
| Q01082 | SPTAN1 Spectrin beta | 1706-1717 | EVDDLEQWIAER (SEQ ID NO: 679) | 13 | Adapter, Scaffolding, |

TABLE 1-continued

| Accession # | Protein Name | Labeled Peptide | Peptide Sequence | Probes | Family |
|---|---|---|---|---|---|
| | chain, non-erythrocytic 1 | | | | Modulator Proteins |
| Q9UHB9 | SRP68 Signal recognition particle 68 kDa protein | 312-333 | IFLLGLADNEAAIVQAESEETK (SEQ ID NO: 680) | 14 13 | Transcription factors, Regulators |
| Q04837 | SSBP1 Single-stranded DNA-binding protein, mitochondrial | 67-81 | SGDSEVYQLGDVSQK (SEQ ID NO: 681) | 13 8 | Transcription factors, Regulators |
| Q8N3U4 | STAG2 Cohesin subunit SA-2 | 273-290 | ELQENQDEIENMMNAIFK (SEQ ID NO: 682) | 13 | Uncategorized |
| P31948 | STIP1 Stress-induced-phosphoprotein 1 | 416-429 | DCEECIQLEPTFIK (SEQ ID NO: 683) | 14 | Uncategorized |
| Q9UJZ1 | STOML2 Stomatin-like protein 2 | 58-72 | ILEPGLNILIPVLDR (SEQ ID NO: 684) | 6 | Adapter, Scaffolding, Modulator Proteins |
| Q9UJZ1 | STOML2 Stomatin-like protein 2 | 35-51 | NTVVLFVPQQEAWVVER (SEQ ID NO: 685) | 6 | Adapter, Scaffolding, Modulator Proteins |
| Q9UJZ1 | STOML2 Stomatin-like protein 2 | 115-135 | ASYGVEDPEYAVTQLAQTTMR (SEQ ID NO: 686) | 13 8 | Adapter, Scaffolding, Modulator Proteins |
| P46977 | STT3A Dolichyl-diphosphooligosaccharide--protein glycosy | 330-340 | FYSLLDPSYAK (SEQ ID NO: 687) | 14 | Enzymes |
| P46977 | STT3A Dolichyl-diphosphooligosaccharide--protein glycosy | 59-67 | FLAEEGFYK (SEQ ID NO: 688) | 6 | Enzymes |
| P46977 | STT3A Dolichyl-diphosphooligosaccharide--protein glycosy | 672-690 | DFELDVLEEAYTTEHWLVR (SEQ ID NO: 689) | 6 | Enzymes |
| P46977 | STT3A Dolichyl-diphosphooligosaccharide--protein glycosy | 572-595 | ELDVSYVLVIFGGLTGYSSDDINK (SEQ ID NO: 690) | 9 | Enzymes |
| Q8TCJ2 | STT3B Dolichyl-diphosphooligosaccharide--protein glycosy | 692-703 | ESDYFTPQGEFR (SEQ ID NO: 691) | 14 | Enzymes |
| Q8TCJ2 | STT3B Dolichyl-diphosphooligosaccharide--protein glycosy | 651-674 | TLDVDYVLVIFGGVIGYSGDDINK (SEQ ID NO: 692) | 9 | Enzymes |
| Q96I99 | SUCLG2 Succinyl-CoA ligase | 151-160 | ETYLAILMDR (SEQ ID NO: 693) | 3 | Enzymes |
| O15260 | SURF4 Surfeit locus protein 4 | 31-43 | LCLISTFLEDGIR (SEQ ID NO: 694) | 13 14 | Uncategorized |
| O60506 | SYNCRIP Heterogeneous nuclear ribonucleoprotein Q | 334-356 | NLANTVTEEILEK (SEQ ID NO: 695) | 9 6 | Transcription factors, Regulators |
| Q92804 | TAF15 TATA-binding protein-associated factor 2N | 284-297 | GEATVSFDDPPSAK (SEQ ID NO: 696) | 2 | Transcription factors, Regulators |
| Q92804 | TAF15 TATA-binding protein-associated factor 2N | 423-431 | SGGGYGGDR (SEQ ID NO: 697) | 6 | Transcription factors, Regulators |

TABLE 1-continued

| Accession # | Protein Name | Labeled Peptide | Peptide Sequence | Probes | Family |
|---|---|---|---|---|---|
| Q12788 | TBL3 Transducin beta-like protein 3 | 755-766 | AALEALLPYTER (SEQ ID NO: 698) | 13 8 | Uncategorized |
| P52888 | THOP1 Thimet oligopeptidase | 67-79 | ALADVEVTYTVQR (SEQ ID NO: 699) | 14 8 | Enzymes |
| P52888 | THOP1 Thimet oligopeptidase | 105-115 | LSEFDVEMSMR (SEQ ID NO: 700) | 14 | Enzymes |
| P52888 | THOP1 Thimet oligopeptidase | 499-520 | DFVEAPSQMLENWVWEQEPLLR (SEQ ID NO: 701) | 14 | Enzymes |
| P62072 | TIMM10 Mitochondrial import inner membrane translocase su | 42545 | AQQLAAELEVEMMADMYNR (SEQ ID NO: 702) | 13 14 9 8 | Chaperones |
| Q99595 | TIMM17A Mitochondrial import inner membrane translocase su | 13-35 | IVDDCGGAFTMGTIGGGIFQAIK (SEQ ID NO: 703) | 14 15 2 4 8 | Channels Transporters, Receptors |
| O60830 | TIMM17B Mitochondrial import inner membrane translocase su | 13-35 | IVDDCGGAFTMGVIGGGVFQAIK (SEQ ID NO: 704) | 14 15 2 4 3 13 6 9 | Channels Transporters, Receptors |
| O43615 | TIMM44 Mitochondrial import inner membrane translocase su | 428-439 | DQDELNPYAAWR (SEQ ID NO: 705) | 13 | Channels Transporters, Receptors |
| P49755 | TMED10 Transmembrane emp24 domain-containg protein 10 | 154-169 | LEDLSESIVNDFAYMK (SEQ ID NO: 706) | 14 3 9 | Channels Transporters, Receptors |
| Q9BVK6 | TMED9 Transmembrane emp24 domain-containg protein 9 | 49-65 | CFIEEIPDETMVIGNYR (SEQ ID NO: 707) | 9 | Channels Transporters, Receptors |
| Q9H061 | TMEM126A Transmembrane protein 126A | 85-105 | CFVSFPLNTGDLDCETCRITR (SEQ ID NO: 708) | 14 | Uncategorized |
| P42166 | TMPO Lamina-associated polypeptide 2, isoform alpha | 621-637 | TYDAASYICEAAFDEVK (SEQ ID NO: 709) | 4 | Transcription factors, Regulators |
| Q92973 | TNPO1 Transportin-1 | 273-298 | TQDQDENVALEACEFWLTLAEQPICK (SEQ ID NO: 710) | 9 | Channels Transporters, Receptors |
| Q92973 | TNPO1 Transportin-1 | 45-64 | LEQLNQYPDFNNYLIFVLTK (SEQ ID NO: 711) | 13 14 2 | Channels Transporters, Receptors |
| Q9NS69 | TOMM22 Mitochondrial import receptor subunit TOM22 homolog | 106-117 | LQMEQQQQLQQR (SEQ ID NO: 712) | 14 | Channels Transporters, Receptors |
| Q9NS69 | TOMM22 Mitochondrial import receptor subunit TOM22 homolog | 61-76 | SAAGATFDLSLFVAQK (SEQ ID NO: 713) | 14 4 2 13 | Channels Transporters, Receptors |
| O96008 | TOMM40 Mitochondrial import receptor subunit TOM40 homolog | 278-293 | ASDQLQVGVEFEASTR (SEQ ID NO: 714) | 14 | Channels Transporters, Receptors |
| O94826 | TOMM70A Mitochondrial import receptor subunit TOM70 | 475-494 | CAEGYALYAQALTDQQQFGK (SEQ ID NO: 715) | 14 | Uncategorized |
| P67936 | TPM4 Tropomyosin alpha-4-chain | 170-177 | SLEAASEK (SEQ ID NO: 716) | 13 3 | Adapter, Scaffolding, Modulator Proteins |

TABLE 1-continued

| Accession # | Protein Name | Labeled Peptide | Peptide Sequence | Probes | Family |
|---|---|---|---|---|---|
| O14773 | TPP1 Tripeptidyl-peptidase 1 | 521-558 | GCHESCLDEEVEGQGFCSGPGWD PVTGWGTPNFPALLK (SEQ ID NO: 89) | 13 14 15 4 9 | Enzymes |
| Q9H4I3 | TRABD TraB domain-containing protein | 235-253 | DLLEQMMAEMIGEFPDLHR (SEQ ID NO: 717) | 14 | Uncategorized |
| Q12931 | TRAP1 Heat shock protein 75 kDa, mitochondrial | 603-619 | LDTHPAMVTVLEMGAAR (SEQ ID NO: 718) | 13 | Chaperones |
| Q15631 | TSN Translin | 205-215 | VEEVVYDLSIR (SEQ ID NO: 719) | 2 | Transcription factors, Regulators |
| Q6DKK2 | TTC19 Tetratricopeptide repeat protein 19, mitochondrial | 134-149 | AITYTYDLMANLAFIR (SEQ ID NO: 720) | 6 | Adapter, Scaffolding, Modulator Proteins |
| Q14166 | TTLL12 Tubulin--tyrosine ligase-like protein 12 | 254-287 | CMLLPWAPTDMLDLSSCTPEPPA EHYQAILEENK (SEQ ID NO: 721) | 4 | Enzymes |
| Q71U36 | TUBA1A Tubulin alpha-1A chain | 353-370 | VGINYQPPTVVPGGDLAK (SEQ ID NO: 722) | 4 | Adapter, Scaffolding, Modulator Proteins |
| Q71U36 | TUBA1A Tubulin alpha-1A chain | 244-264 | FDGALNVDLTEFQTNLVPYPR (SEQ ID NO: 723) | 13 3 2 4 | Adapter, Scaffolding, Modulator Proteins |
| Q71U36 | TUBA1A Tubulin alpha-1A chain | 281-304 | AYHEQLSVAEITNACFEPANQMV K (SEQ ID NO: 724) | 4 3 13 | Adapter, Scaffolding, Modulator Proteins |
| Q71U36 | TUBA1A Tubulin alpha-1A chain | 374-390 | AVCMLSNTTAIAEAWAR (SEQ ID NO: 725) | 4 | Adapter, Scaffolding, Modulator Proteins |
| Q71U36 | TUBA1A Tubulin alpha-1A chain | 65-79 | AVFVDLEPTVIDEVR (SEQ ID NO: 726) | 13 4 3 2 | Adapter, Scaffolding, Modulator Proteins |
| Q71U36 | TUBA1A Tubulin alpha-1A chain | 403-422 | AFVHWYVGEGMEEGEFSEAR (SEQ ID NO: 727) | 4 | Adapter, Scaffolding, Modulator Proteins |
| Q71U36 | TUBA1A Tubulin alpha-1A chain | 41-60 | TIGGGDDSFNTFFSETGAGK (SEQ ID NO: 728) | 13 | Adapter, Scaffolding, Modulator Proteins |
| Q13748 | TUBA3D Tubulin alpha-3C/D chain | 244-264 | FDGALNVDLTEFQTNLVPYPR (SEQ ID NO: 729) | 14 13 9 4 | Adapter, Scaffolding, Modulator Proteins |
| Q13748 | TUBA3D Tubulin alpha-3C/D chain | 281-304 | AYHEQLSVAEITNACFEPANQMV K (SEQ ID NO: 730) | 14 13 4 | Adapter, Scaffolding, Modulator Proteins |
| Q13748 | TUBA3D Tubulin alpha-3C/D chain | 41-60 | TIGGGDDSFNTFFSETGAGK (SEQ ID NO: 731) | 13 9 | Adapter, Scaffolding, Modulator Proteins |
| P68366 | TUBA4A Tubulin alpha-4A chain | 244-264 | FDGALNVDLTEFQTNLVPYPR (SEQ ID NO: 732) | 3 2 13 9 4 | Adapter, Scaffolding, Modulator Proteins |
| P68366 | TUBA4A Tubulin alpha-4A chain | 281-304 | AYHEQLSVAEITNACFEPANQMV K (SEQ ID NO: 733) | 3 13 4 | Adapter, Scaffolding, Modulator Proteins |
| P68366 | TUBA4A Tubulin alpha-4A chain | 340-352 | SIQFVDWCPTGFK (SEQ ID NO: 734) | 13 | Adapter, Scaffolding, Modulator Proteins |
| Q9NY65 | TUBA8 Tubulin alpha-8 chain | 244-264 | FDGALNVDLTEFQTNLVPYPR (SEQ ID NO: 735) | 3 2 13 9 4 | Adapter, Scaffolding, |

TABLE 1-continued

| Accession # | Protein Name | Labeled Peptide | Peptide Sequence | Probes | Family |
|---|---|---|---|---|---|
| P07437 | TUBB Tubulin beta chain | 104-121 | GHYTEGAELVDSVLDVVR (SEQ ID NO: 736) | 13 9 6 | Adapter, Scaffolding, Modulator Proteins |
| P07437 | TUBB Tubulin beta chain | 175-213 | VSDTVVEPYNATLSVHQLVENTD ETYCIDNEALYDICFR (SEQ ID NO: 737) | 6 | Adapter, Scaffolding, Modulator Proteins |
| P07437 | TUBB Tubulin beta chain | 20-46 | FWEVISDEHGIDPTGTYHGDSDLQ LDR (SEQ ID NO: 738) | 6 | Adapter, Scaffolding, Modulator Proteins |
| P07437 | TUBB Tubulin beta chain | 217-241 | LTTPTYGDLNHLVSATMSGVTTC LR (SEQ ID NO: 739) | 3 13 6 | Adapter, Scaffolding, Modulator Proteins |
| P07437 | TUBB Tubulin beta chain | 283-297 | ALTVPELTQQVFDAK (SEQ ID NO: 740) | 6 | Adapter, Scaffolding, Modulator Proteins |
| P07437 | TUBB Tubulin beta chain | 310-318 | YLTVAAVFR (SEQ ID NO: 741) | 6 | Adapter, Scaffolding, Modulator Proteins |
| P07437 | TUBB Tubulin beta chain | 337-350 | NSSYFVEWIPNNVK (SEQ ID NO: 742) | 13 3 9 8 6 | Adapter, Scaffolding, Modulator Proteins |
| P07437 | TUBB Tubulin beta chain | 381-390 | ISEQFTAMFR (SEQ ID NO: 743) | 6 | Adapter, Scaffolding, Modulator Proteins |
| P07437 | TUBB Tubulin beta chain | 47-58 | ISVYYNEATGGK (SEQ ID NO: 744) | 13 6 | Adapter, Scaffolding, Modulator Proteins |
| P07437 | TUBB Tubulin beta chain | 63-77 | AILVDLEPGTMDSVR (SEQ ID NO: 745) | 6 | Adapter, Scaffolding, Modulator Proteins |
| Q9BVA1 | TUBB2B Tubulin beta-2B chain | 381-390 | ISEQFTAMFR (SEQ ID NO: 746) | 6 | Adapter, Scaffolding, Modulator Proteins |
| Q9BVA1 | TUBB2B Tubulin beta-2B chain | 63-77 | AILVDLEPGTMDSVR (SEQ ID NO: 747) | 6 | Adapter, Scaffolding, Modulator Proteins |
| Q9BVA1 | TUBB2B Tubulin beta-2B chain | 175-213 | VSDTVVEPYNATLSVHQLVENTD ETYCIDNEALYDICFR (SEQ ID NO: 748) | 6 | Adapter, Scaffolding, Modulator Proteins |
| Q9BVA1 | TUBB2B Tubulin beta-2B chain | 337-350 | NSSYFVEWIPNNVK (SEQ ID NO: 749) | 3 13 9 8 6 | Adapter, Scaffolding, Modulator Proteins |
| Q9BVA1 | TUBB2B Tubulin beta-2B chain | 104-121 | GHYTEGAELVDSVLDVVR (SEQ ID NO: 750) | 9 6 | Adapter, Scaffolding, Modulator Proteins |
| Q9BVA1 | TUBB2B Tubulin beta-2B chain | 217-241 | LTTPTYGDLNHLVSATMSGCTTC LR (SEQ ID NO: 751) | 3 13 | Adapter, Scaffolding, Modulator Proteins |
| Q13509 | TUBB3 Tubulin beta-3 chain | 104-121 | GHYTEGAELVDSVLDVVR (SEQ ID NO: 752) | 9 4 6 | Adapter, Scaffolding, Modulator Proteins |
| Q13509 | TUBB3 Tubulin beta-3 chain | 337-350 | NSSYFVEWIPNNVK (SEQ ID NO: 753) | 4 6 | Adapter, Scaffolding, Modulator Proteins |
| Q13509 | TUBB3 Tubulin beta-3 chain | 63-77 | AILVDLEPGTMDSVR (SEQ ID NO: 754) | 4 | Adapter, Scaffolding, |

TABLE 1-continued

| Accession # | Protein Name | Labeled Peptide | Peptide Sequence | Probes | Family |
|---|---|---|---|---|---|
| P68371 | TUBB4B Tubulin beta-4B chain | 104-121 | GHYTEGAELVDSVLDVVR (SEQ ID NO: 755) | 9 6 | Adapter, Scaffolding, Modulator Proteins |
| P68371 | TUBB4B Tubulin beta-4B chain | 175-213 | VSDTVVEPYNATLSVHQLVENTD ETYCIDNEALYDICFR (SEQ ID NO: 756) | 6 | Adapter, Scaffolding, Modulator Proteins |
| P68371 | TUBB4B Tubulin beta-4B chain | 217-241 | LTTPTYGDLNHLVSATMSGVTTC LR (SEQ ID NO: 757) | 3 13 6 | Adapter, Scaffolding, Modulator Proteins |
| P68371 | TUBB4B Tubulin beta-4B chain | 310-318 | YLTVAAVFR (SEQ ID NO: 758) | 6 | Adapter, Scaffolding, Modulator Proteins |
| P68371 | TUBB4B Tubulin beta-4B chain | 337-350 | NSSYFVEWIPNNVK (SEQ ID NO: 759) | 3 13 9 8 6 | Adapter, Scaffolding, Modulator Proteins |
| P68371 | TUBB4B Tubulin beta-4B chain | 381-390 | ISEQFTAMFR (SEQ ID NO: 760) | 6 | Adapter, Scaffolding, Modulator Proteins |
| Q9BUF5 | TUBB6 Tubulin beta-6 chain | 217-241 | LTTPTYGDLNHLVSATMSGVTTS LR (SEQ ID NO: 761) | 4 | Adapter, Scaffolding, Modulator Proteins |
| Q9BUF5 | TUBB6 Tubulin beta-6 chain | 175-213 | VSDTVVEPYNATLSVHQLVENTD ETYCIDNEALYDICFR (SEQ ID NO: 762) | 6 | Adapter, Scaffolding, Modulator Proteins |
| Q9BUF5 | TUBB6 Tubulin beta-6 chain | 337-350 | NSSYFVEWIPNNVK (SEQ ID NO: 763) | 4 2 13 6 | Adapter, Scaffolding, Modulator Proteins |
| P49411 | TUFM Elongation factor Tu, mitochondrial | 183-200 | ADAVQDSEMVELVELEIR (SEQ ID NO: 764) | 13 4 3 2 8 6 | Transcription factors, Regulators |
| P49411 | TUFM Elongation factor Tu, mitochondrial | 239-252 | LLDAVDTYIPVPAR (SEQ ID NO: 765) | 6 | Transcription factors, Regulators |
| P49411 | TUFM Elongation factor Tu, mitochondrial | 272-281 | GTVVTGTLER (SEQ ID NO: 766) | 3 4 15 6 8 | Transcription factors, Regulators |
| Q9BRA2 | TXNDC17 Thioredoxin domain-containing protein 17 | 42477 | YEEVSVSGFEEFHR (SEQ ID NO: 90) | 14 | Uncategorized |
| Q14157 | UBAP2L Ubiquitin-associated protein 2-like | 239-257 | TATEEWGTEDWNEDLSETK (SEQ ID NO: 767) | 8 | Uncategorized |
| P31930 | UQCRC1 Cytochrome b-c1 complex subunit 1, mitochondrial | 397-415 | NALVSHLDGTTPVCEDIGR (SEQ ID NO: 768) | 13 4 3 2 8 | Channels, Transporters, Receptors |
| P21796 | VDAC1 Voltage-dependent anion-slective channel protein | 140-161 | GALVLGYEGWLAGYQMNFETAK (SEQ ID NO: 769) | 14 2 13 4 6 | Channels, Transporters, Receptors |
| P21796 | VDAC1 Voltage-dependent anion-slective channel protein | 121-139 | EHINLGCDMDFDIAGPSIR (SEQ ID NO: 770) | 13 14 2 4 8 | Channels, Transporters, Receptors |
| P21796 | VDAC1 Voltage-dependent | 75-93 | WNTDNTLGTEITVEDQLAR (SEQ ID NO: 771) | 13 14 15 3 2 4 6 9 | Channels, Transporters, Receptors |

TABLE 1-continued

| Accession # | Protein Name | Labeled Peptide | Peptide Sequence | Probes | Family |
|---|---|---|---|---|---|
| | anion-slective channel protein | | | 8 | |
| P21796 | VDAC1 Voltage-dependent anion-slective channel protein | 164-174 | VTQSNFAVGYK (SEQ ID NO: 772) | 14 4 8 6 | Channels, Transporters, Receptors |
| P21796 | VDAC1 Voltage-dependent anion-slective channel protein | 64-74 | WTEYGLTFTEK (SEQ ID NO: 773) | 13 14 15 3 2 4 6 9 8 | Channels, Transporters, Receptors |
| P21796 | VDAC1 Voltage-dependent anion-slective channel protein | 35-53 | SENGLEFTSSGSANTETTK (SEQ ID NO: 774) | 4 8 9 | Channels, Transporters, Receptors |
| P21796 | VDAC1 Voltage-dependent anion-slective channel protein | 175-197 | TDEFQLHTNVNDGTEFGGSIYQK (SEQ ID NO: 775) | 14 4 8 | Channels, Transporters, Receptors |
| P21796 | VDAC1 Voltage-dependent anion-slective channel protein | 225-236 | YQIDPDACFSAK (SEQ ID NO: 776) | 4 8 | Channels, Transporters, Receptors |
| P45880 | VDAC2 Voltage-dependent anion-slective channel protein | 86-107 | WNTDNTLGTEIAIEDQICQGLK (SEQ ID NO: 777) | 13 14 15 3 2 4 6 9 8 | Channels, Transporters, Receptors |
| P45880 | VDAC2 Voltage-dependent anion-slective channel protein | 178-185 | NNFAVGYR (SEQ ID NO: 778) | 14 2 13 8 4 6 | Channels, Transporters, Receptors |
| P45880 | VDAC2 Voltage-dependent anion-slective channel protein | 186-208 | TGDFQLHTNVNDGTEFGGSIYQK (SEQ ID NO: 779) | 14 4 2 | Channels, Transporters, Receptors |
| P45880 | VDAC2 Voltage-dependent anion-slective channel protein | 209-229 | VCEDLDTSVNLAWTSGTNCTR (SEQ ID NO: 780) | 13 14 15 2 9 8 4 | Channels, Transporters, Receptors |
| P45880 | VDAC2 Voltage-dependent anion-slective channel protein | 236-247 | TQLDPTASISAK (SEQ ID NO: 781) | 13 14 4 | Channels, Transporters, Receptors |
| P45880 | VDAC2 Voltage-dependent anion-slective channel protein | 75-85 | WCEYGLTFTEK (SEQ ID NO: 782) | 13 14 15 3 2 4 6 9 | Channels, Transporters, Receptors |
| Q9Y277 | VDAC3 Voltage-dependent anion-slective channel protein | 164-174 | LSQNNFALGYK (SEQ ID NO: 783) | 14 | Channels, Transporters, Receptors |
| P08670 | VIM Vimentin | 283-292 | NLQEAEEWK (SEQ ID NO: 784) | 13 14 3 2 4 15 6 9 8 | Uncategorized |
| P08670 | VIM Vimentin | 322-334 | QVQSLTCEVDALK (SEQ ID NO: 785) | 4 9 6 | Uncategorized |
| P08670 | VIM Vimentin | 176-184 | DNAEDIMR (SEQ ID NO: 786) | 6 | Uncategorized |
| P08670 | VIM Vimentin | 197-207 | EEAENTLQSFR (SEQ ID NO: 787) | 13 14 3 2 15 9 6 | Uncategorized |
| P08670 | VIM Vimentin | 130-139 | ILLAELEQLK (SEQ ID NO: 788) | 14 3 2 4 69 | Uncategorized |
| P08670 | VIM Vimentin | 29-36 | SYVTTSTR (SEQ ID NO: 789) | 14 6 | Uncategorized |
| P08670 | VIM Vimentin | 146-155 | LGDLYEEEMR (SEQ ID NO: 790) | 6 | Uncategorized |
| P08670 | VIM Vimentin | 42502 | SVSSSSYR (SEQ ID NO: 791) | 6 | Uncategorized |

TABLE 1-continued

| Accession # | Protein Name | Labeled Peptide | Peptide Sequence | Probes | Family |
|---|---|---|---|---|---|
| P08670 | VIM Vimentin | 189-196 | LQEEMLQR (SEQ ID NO: 792) | 3 6 | Uncategorized |
| P08670 | VIM Vimentin | 105-113 | VELQELNDR (SEQ ID NO: 793) | 4 6 | Uncategorized |
| P08670 | VIM Vimentin | 79-97 | LLQDSVDFSLADAINTEFK (SEQ ID NO: 794) | 13 14 15 4 3 2 6 9 8 | Uncategorized |
| P08670 | VIM Vimentin | 295-304 | FADLSEAANR (SEQ ID NO: 795) | 6 | Uncategorized |
| P08670 | VIM Vimentin | 346-364 | EMEENFAVEAANYQDTIGR (SEQ ID NO: 796) | 13 14 15 3 2 4 6 9 8 | Uncategorized |
| P08670 | VIM Vimentin | 335-342 | GTNESLER (SEQ ID NO: 797) | 6 | Uncategorized |
| P08670 | VIM Vimentin | 114-120 | GANYIDK (SEQ ID NO: 798) | 4 3 8 6 | Uncategorized |
| P08670 | VIM Vimentin | 365-373 | LQDEIQNMK (SEQ ID NO: 799) | 4 3 2 6 | Uncategorized |
| P08670 | VIM Vimentin | 382-390 | EYQDLLNVK (SEQ ID NO: 800) | 3 | Uncategorized |
| P08670 | VIM Vimentin | 51-64 | SLYASSPGGVYATR (SEQ ID NO: 801) | 14 2 4 3 13 8 6 | Uncategorized |
| P08670 | VIM Vimentin | 224-235 | VESLQEEIAFLK (SEQ ID NO: 802) | 14 4 6 | Uncategorized |
| Q96GC9 | VMP1 Vacuole membrane protein 1 | 214-243 | LSGAEPDDEEYQEFEEMLEHAESAQDFASR (SEQ ID NO: 803) | 14 | Uncategorized |
| Q96AX1 | VPS33A Vacuolar protein sorting-associated protein 33A | 233-262 | NVDLLTPLATQLTYEGLIDEIYGIQNSYVK (SEQ ID NO: 804) | 14 | Channels, Transporters, Receptors |
| Q9UID3 | VPS51 Vacuolar protein sorting-associated protein 51 hom | 742-763 | FVADEELVHLLLDEVVASAALR (SEQ ID NO: 805) | 14 | Channels, Transporters, Receptors |
| O43592 | XPOT Exportin-T | 825-843 | VLVTVIQGAVEYPDPIAQK (SEQ ID NO: 806) | 132 | Channels, Transporters, Receptors |
| P12956 | XRCC6 X-ray repair cross-complementing protein 6 | 475-488 | SDSFENPVLQQHFR (SEQ ID NO: 807) | 3 4 2 13 8 | Transcription factors, Regulators |
| P12956 | XRCC6 X-ray repair cross-complementing protein 6 | 489-510 | NLEALALDLMEPQAVDLTLPK (SEQ ID NO: 808) | 13 3 2 4 8 | Transcription factors, Regulators |
| P67809 | YBX1 Nuclease-sensitive element-binding protein 1 | 102-118 | SVGDGETVEFDVVEGEK (SEQ ID NO: 809) | 6 | Transcription factors, Regulators |
| P62258 | YWHAE 14-3-3 protein epsilon | 197-215 | AAFDDAIAELDTLSEESYK (SEQ ID NO: 92) | 13 | Uncategorized |
| P62258 | YWHAE 14-3-3 protein epsilon | 143-153 | EAAENSLVAYK (SEQ ID NO: 91) | 13 | Uncategorized |
| P27348 | YWHAQ 14-3-3 protein theta | 194-212 | TAFDEAIAELDTLNEDSYK (SEQ ID NO: 93) | 14 | Uncategorized |
| P63104 | YWHAZ 14-3-3 protein zelta/delta | 194-212 | TAFDEAIAELDTLSEESY (SEQ ID NO: 94) | 14 13 | Uncategorized |

TABLE 2

| Protein Name | Labeled Peptide | Peptide Sequence | Probes | PDB | Predicted pocket residue overlap | Overlapping pockets (fpocket designation) |
|---|---|---|---|---|---|---|
| ACP1 Low molecular weight phosphotyrosine protein phosp | 42-59 | VDSAATSGYEIGNPPDYR (SEQ ID NO: 1) | 13 | 3N8I | 47.A,50.A | 1 |
| ADCK3 Chaperone activity of bc1 | 277-295 | LGQMLSIQDDAFINPHLAK | 14 | 4PED | 278.A,283.A | 1 |

TABLE 2-continued

| Protein Name | Labeled Peptide | Peptide Sequence | Probes | PDB | Predicted pocket residue overlap | Overlapping pockets (fpocket designation) |
|---|---|---|---|---|---|---|
| complex-like, mitochondr | | (SEQ ID NO: 2) | | | | |
| ADK Adenosine kinase | 209-224 | IFTLNLSAPFISQFYK (SEQ ID NO: 3) | 2 | 4O1L | 200.A,205.A, 207.A,200.B, 201.B,206.B, 207.B | 1, 5, 10, 12, 20, 21 |
| ADSS Adenylosuccinate synthetase isozyme 2 | 431-441 | FIEDELQIPVK (SEQ ID NO: 4) | 14 | 2V40 | 435.A | 8 |
| AHCYL2 Putative adenosylhomocysteinase 3 | 331-342 | GIVEESVTGVHR (SEQ ID NO: 810) | 6 | 3GVP | 335.A,336.A, 337.A,338.A, 341.A,342.A, 335.B, 336.B,337.B, 338.B,332.C. 334.C, 335.C,337.C, 339.C,342.C, 332.D,334.D, 335.D,336.D, 337.D, 339.D,342.D | 5, 6, 16, 17, 18, 22, 27, 38, 51 |
| AIFM1 Apoptosis-inducing factor 1, mitochondrial | 475-510 | PYWHQSMFWSDLGP DVGYEAIGLVDSSLPT VGVFAK (SEQ ID NO: 5) | 2 3 4 6 | 4LII | 480.A,482.A, 492.A | 1 |
| ALDH7A1 Alpha-aminoadipic semialdehyde dehydrogenase | 139-162 | ILVEGVGEVQEYVDIC DYAVGLSR (SEQ ID NO: 6) | 8 13 | 4ZUL | 117.A,118.A, 1220.A,123.A, 127.A,128.A, 130.A, 131.A,132.A, 133.A,134.A, 111.B,112.B, 113.B, 114.B,117.B, 120.B,123.B, 127.B,128.B, 130.B, 132.B,133.B, 134.B,120.C, 123.C,127.C, 128.C, 120.D,123.D, 127.D,128.D, 130.D,132.D, 133.D, 134.D,116.E, 120.E,124.E, 128.E,120.F, 127.F,128.F, 130.F, 131.F,132.F, 133.F,134.F, 128.G,130.G, 132.G,133.G, 134.G,120.H, 124.H, 128.H,130.H, 133.H,134.H | 3, 6, 26, 37, 47, 48, 52, 69, 71, 84, 86, 93, 95, 102, 115 |
| ANP32A Acidic leucine-rich nuclear phosphoprotein 32 fami | 117-132 | SLDLFNCEVTNLNDY R (SEQ ID NO: 811) | 13 | 4XOS | No Overlap | — |
| API5 Apoptosis inhibitor 5 | 182-196 | VLEDVTGEEFVLFMK (SEQ ID NO: 812) | 4 | 3U0R | 187.A,193.A | 3 |
| API5 Apoptosis inhibitors | 131-148 | GTLGGLFSQILQGEDI VR (SEQ ID NO: 813) | 4 | 3U0R | 145.A | 3 |
| API5 Apoptosis inhibitor 5 | 211-237 | QQLVELVAEQADLEQ TFNPSDPDCVDR (SEQ ID NO: 814) | 4 | 3U0R | No Overlap | — |
| ARF1 ADP-ribosylation factor 1 | 39-59 | LGEIVTTIPTIGFNVET VEYK (SEQ ID NO: 7) | 2 3 8 13 | 3O47 | 175.A,176.A, 177.A,178.A, 179.A,181.A, 183.A, | 1, 2, 9, 11, 15 |

TABLE 2-continued

| Protein Name | Labeled Peptide | Peptide Sequence | Probes | PDB | Predicted pocket residue overlap | Overlapping pockets (fpocket designation) |
|---|---|---|---|---|---|---|
| | | | | | 185.A,172.B, 173.B,174.B, 185.B,187.B, 189.B | |
| ARF4 ADP-ribosylation factor 4 | 39-59 | LGEIVTTIPTIGFNVET VEYK (SEQ ID NO: 7) | 2 3 8 13 | 1Z6X | 48.A,49.A,50.A, 51.A,52.A, 54.A,49.B, 52.B,54.B | 1, 5, 6 |
| ARF5 ADP-ribosylation factor 5 | 39-59 | LGEIVTTIPTIGFNVET VEYK (SEQ ID NO: 7) | 2 3 4 8 13 | 2B6H | 44.A,52.A,53.A, 54.A,57.A, 59.A | 1, 2 |
| ARL1 ADP-ribosylation factor-like protein 1 | 163-178 | GTGLDEAMEWLVET LK (SEQ ID NO: 9) | 13 14 | 4DCN | No Overlap | — |
| ARL1 ADP-ribosylation factor-like protein 1 | 37-59 | LQVGEVVTTIPTIGFN VETVTYK (SEQ ID NO: 10) | 13 | 4DCN | 38.A,44.A,4.6A, 47.A,51.A, 52.A,53.A, 54.A,38.B, 43.B,44.B, 46.B,47.B, 48.B,52.B, 54.B | 1, 2, 3, 4 |
| ATIC Bifunctional purine biosynthesis protein PURH | 178-194 | AFTHTAQYDEAISDY FR (SEQ ID NO: 11) | 13 | 1PKX | 183.A,184.A, 187.A,191.A, 194.A,183.B, 187.B, 188.B,190.B, 191.B,194.B, 180.C,181.C, 183.C, 184.C,185.C, 187.C,188.C, 191.C, 194.C,181.D, 183.D,184.D, 185.D,187.D, 188.D,190.D, 194.D | 5, 12, 17, 18, 49, 51, 54 |
| BAX Apoptosis regulator BAX | 66-78 | IGDELDSNMELQR (SEQ ID NO: 815) | 13 | 4ZIG | No Overlap | — |
| BLMH Bleomycin hydrolase | 203-218 | GEISATQDVMMEEIFR (SEQ ID NO: 13) | 13 | 1CB5 | 210.A,213.A, 217.A,218.A, 210.B, 213.B,217.B, 210.C,213.C, 217.C | 29, 30, 31, 78 |
| | | | " | ′ | | |
| BLMH Bleomycin hydrolase | 111-124 | CYFFLSAFVDTAQR (SEQ ID NO: 12) | 14 | 1CB5 | 112.A,122.A, 123.A,112.B, 113.B, 122.B,123.B, 112.C,122.C, 123.C | 4, 29, 30, 31 67, 76, 77 |
| C1QBP Complement component 1 Q subcomponent-binding prot | 247-276 | GVDNTFADELVELST ALEHQEYITFLEDLK (SEQ ID NO: 816) | 3 9 13 14 | 3RPX | 264.A,265.A, 268.A,274.A, 260.C,261.C, 264.C, 265.C,268.C | 1, 2, 6, 8 |
| C1QBP Complement component 1 Q subcomponent-binding prot | 105-119 | MSGGWELELNGTEA K (SEQ ID NO: 817) | 9 | 3RPX | 108.A,110. A,111.A | 7 |
| CALM3 Calmodulin | 39-75 | SLGQNPTEAELQDMI NEVDADGNGTIDFPE FLTMMAR NO: 818) | 14 | 4UPU | No Overlap | — |
| CALR Calreticulin | 323-351 | SGTIFDNFLITNDEAY AEEFGNETWGVTK (SEQ ID NO: 14) | 6 9 13 | 3POW | 329.A,345.A, 346.A,349.A | 4 |
| CALR Calreticulin | 99-111 | HEQNIDCGGGYVK (SEQ ID NO: 15) | 6 | 3POW | No Overlap | — |
| CAPN1 Calpain-1 catalytic subunit | 175-193 | LVFVHSAEGNEFWSA LLEK (SEQ ID NO: 16) | 14 | 2ARY | 175.A,179.A, 180.A,181.A, 182.A,183.A, 186.A, | 1, 14 |

TABLE 2-continued

| Protein Name | Labeled Peptide | Peptide Sequence | Probes | PDB | Predicted pocket residue overlap | Overlapping pockets (fpocket designation) |
|---|---|---|---|---|---|---|
| CKB Creatine kinase B-type | 224-236 | TFLVWVNEEDHLR (SEQ ID NO: 19) | 3 | 3B6R | 175.B,176.B, 179.B,180.B, 181.B,186.B 228.A,232.A 233.A,228.B, 232.B | 1, 2, 4 |
| CKB Creatine kinase B-type | 342-358 | LGFSEVELVQMVVDGVK (SEQ ID NO: 21) | 3 13 | 3B6R | 342.A | 21 |
| CKB Creatine kinase B-type | 367-381 | LEQGQAIDDLMPAQK (SEQ ID NO: 22) | 13 | 3B6R | No Overlap | — |
| CKB Creatine kinase B-type | 14-32 | FPAEDEFPDLSAHNNHMAK (SEQ ID NO: 17) | 3 | 3B6R | 29.B | 5 |
| CKB Creatine kinase B-type | 157-172 | LAVEALSSLDGDLAGR (SEQ ID NO: 18) | 13 | 3B6R | 159.B,160.B, 163.B,164.B, 168.B,169.B, 170.B, 171.B,172.B | 3, 10, 15 |
| CKB Creatine kinase B-type | 253-265 | FCTGLTQIETLFK (SEQ ID NO: 20) | 13 | 3B6R | 261.A,265.A, 261.B,265.B | 7, 17 |
| CKMT1B Creatine kinase U-type, mitochondria' | 257-269 | SFLIWVNEEDHTR (SEQ ID NO: 23) | 3 | 1QK1 | 223.B,227.B, 223.C,221.D, 223.D,226.D, 221.H, 223.H,226.H | 4, 6, 38, 78, 80, 82 |
| CLPP Putative ATP-dependent Clp protease proteolyticsu | 215-226 | QSLQVIESAMER (SEQ ID NO: 24) | 6 | 1TG6 | 166.A,167.A, 168.A,169.A, 170.A,169.B, 170.B, 159.C,167.C, 168.C,169.C, 170.C,159.E, 159.G, 161.G,163.G, 165.G,167.G, 168.G,169.G, 170.G | 20, 41, 49, 53, 56, 58, 60, 62, 65 |
| COPS4 COP9 signalosome complex subunit 4 | 154-170 | LYLEDDDPVQAEAYINR (SEQ ID NO: 819) | 13 15 | 4D18 | 157.D,158.D | 178 |
| CSNK1A1 Casein kinase I isoform alpha | 84-106 | DYNVLVMDLLGPSLEDLFNFCSR (SEQ ID NO: 25) | 14 | 5FQD | 95.C,100.C, 88.F,90.F, 91.F,93.F,94.F, 95.F,99.F | 14, 15, 69, 88 |
| CSNK2B Casein kinase II subunit beta | 112-134 | VYCENQPMLPIGLSDIPGEAMVK (SEQ ID NO: 26) | 14 | 4NH1 | 126.C,126.D | 1, 4 |
| CTNNB1 Catenin beta-1 | 648-661 | NEGVATYAAAVLFR (SEQ ID NO: 820) | 13 14 | 3TX7 | 660.A,661.A | 28 |
| CTSB Cathepsin B | 315-331 | GQDHCGIESEVVAGIPR (SEQ ID NO: 27) | 2 49 13 | 3K9M | 237.A,238.A, 240.A,241.A, 251.A,252.A, 251.B,252.B | 4, 10, 13, 19 |
| CTSD Cathepsin D | 236-253 | DPDAQPGGELMLGGTDSK (SEQ ID NO: 28) | 9 | 4OD9 | 173.B | 10 |
| CTSD Cathepsin D | 288-309 | EGCEAIVDTGTSLMVGPVDEVR (SEQ ID NO: 29) | 4 6 8 9 13 14 15 | 4OD9 | 231.B,233.B, 234.B,238.B, 241.B,242.B, 245.B, 231.D,233.D, 234.D,235.D, 236.D,238.D | 1, 2, 7 |
| CTSD Cathepsin D | 314-331 | AIGAVPLIQGEYMIPCEK (SEQ ID NO: 30) | 2 3 4 6 8 9 13 14 15 | 4OD9 | 258.B,260.B, 258.D,260.D | 1, 2 |
| CYB5R3 NADH-cytochrome b5 reductase 3 | 235-241 | LWYTLDR (SEQ ID NO: 31) | 3 | 1UMK | 237.A,238.A, 239.A | 1 |
| DECR1 2,4-dienoyl-CoA reductase, mitochondrial | 299-315 | FDGGEEVLISGEFNDLR (SEQ ID NO: 32) | 6 | 1W6U | 306.A,307.A, 308.A,309.A, 311.A,312.A, 313.A, 314.A,315.A, 304.B,305.B, | 1, 2, 9, 10, 14, 23, 25, 27, 35, 42, 47 |

TABLE 2-continued

| Protein Name | Labeled Peptide | Peptide Sequence | Probes | PDB | Predicted pocket residue overlap | Overlapping pockets (fpocket designation) |
|---|---|---|---|---|---|---|
| | | | | | 308.B,310.B, 311.B, 313.B,314.B, 315.B,303.C, 304.C,305.C, 306 C, 308.C,310.C, 311.C,312.C, 315.C,305.D, 306.D, 307.D,308.D, 309.D,310.D, 311.D,312.D, 313.D, 314.D,315.D | |
| DHX9 ATP-dependent RNA helicase A | 448-456 | ISAVSVAER (SEQ ID NO: 33) | 3 | 3LLM | 449.B,453.B, 456.B | 6 |
| DIABLO Diablo homolog, mitochondrial | 124-140 | MNSEEEDEVWQVIIG AR (SEQ ID NO: 821) | 13 | 4TX5 | 78.A,82.A,85.A, 71.B,74.B, 75.B,78.B, 84.B | 5, 11, 12 |
| DLD Dihydrolipoyl dehydrogenase, mitochondrial | 450-482 | VLGAHILGPGAGEMV NEAALALEYGASCED IAR (SEQ ID NO: 34) | 4 13 14 | 3RNM | 416.A,417.A, 418.A,423.A, 424.A,443.A, 444.A, 445.A,446.A, 447.A,415.B, 416.B,423.B, 424 B, 428.B,433.B, 436.B,437.B, 446.B,421.C, 423.C, 424.C,427.C, 436.C,437.C, 443.C,447.C, 421.D, 423.D,424.D, 446.D | 2, 3, 8, 9, 10, 11, 12, 17, 37, 44, 50, 54, 67 |
| ECH1 Delta(3,5)-Delta(2,4)-dienoyl-CoA isomerase, mitoc | 197-211 | EVDVGLAADVGTLQ R (SEQ ID NO: 37) | 3 4 6 8 13 14 15 | 2VRE | 171.A,174.A, 171.B,176.B, 179.B,180.B, 171.C,174.C | 1, 3, 4, 24 |
| ECH1 Delta(3,5)-Delta(2,4)-dienoyl-CoA isomerase, mitoc | 149-158 | YQETFNVIER (SEQ ID NO: 36) | 6 | 2VRE | 123.A,124.A, 128.A,131.A, 123.B,125.B, 126.B, 128.B,131.B, 123.C,124.C, 125.C,128.C, 131.C | 1, 2, 3, 4, 5, 8, 9, 12 |
| ECH1 Delta(3,5)-Delta(2,4)-dienoyl-CoA isomerase, mitoc | 113-131 | MFTAG1DLMDMASDI LQPK (SEQ ID NO: 35) | 6 | 2VRE | 98.A,100.A, 101.A,102.A, 92.B,97.B, 98.B,100.B, 90.C,92.0, 93.C,94.C, 95.C,97.C, 98.C,100.C, 101.C,104.C | 1, 3, 4, 12, 23, 24 |
| EIF4A1 Eukaryotic initiation factor 4A-I | 69-82 | GYDVIAQAQSGTGK (SEQ ID NO: 39) | 9 13 14 | 2ZU6 | 75.A,76.A, 78.A,82.A, 75.C,78.C, 79.C,80.C,82.C | 1, 5, 10, 53, 84 |
| EIF4A1 Eukaryotic initiation factor 4A-I | 178-190 | MFVLDEADEML SR (SEQ ID NO: 38) | 13 | 2ZU6 | 178.C,190.C,1 85.D,186.D, 188.D,189.D, 190.D | 2, 4, 5 |
| EIF4A2 Eukaryotic initiation factor 4A-II | 70-83 | EukaryoticGYDVIAQAQSGTGK (SEQ ID NO: 40) | 13 | 3BOR | 76.A,82.A, 83.A | 1 |
| ELAVL1 ELAV-like protein 1 | 20-37 | TNLIVNYLPQNMTQD ELR (SEQ ID NO: 822) | 2 4 13 | 4FXV | 33.A,26.B, 28.B,30.B, 32.B,34.B, | 1, 2, 4, 5, 6 |

TABLE 2-continued

| Protein Name | Labeled Peptide | Peptide Sequence | Probes | PDB | Predicted pocket residue overlap | Overlapping pockets (fpocket designation) |
|---|---|---|---|---|---|---|
| | | | | | 35.B,37.B,20.C, 21.C,32.D, 34.D,35.D,37.D | |
| ERH Enhancer of rudimentary homolog | 18-34 | TYADYESVNECMEG VCK (SEQ ID NO: 823) | 13 | 2NML | 18.A | 2 |
| ETFB Electron transfer flavoprotein subunit beta | 36-51 | HSMNPFCEIAVEEAV R (SEQ ID NO: 41) | 3 | 2A1T | 36.S,37.S, 39.S,40.S, 41.S,43.S,44.S | 1, 4 |
| EXO1 Exonuclease 1 | 139-160 | SQGVDCLVAPYEADA QLAYLNK (SEQ ID NO: 95) | 2 6 8 9 13 | 3QEB | 143.Z,144.Z, 145.Z,149.Z, 150.Z | 1, 9, 11 |
| FARSB Phenylalanine--tRNA ligase beta subunit | 72-82 | YDLLCLEGLVR (SEQ ID NO: 824) | 9 | 3L4G | 72.B,72.D, 76.D,72.F, 76.F,72.H,72.J, 74.J,76.J, 75.L, 76.N,78.N, 72.P,75.P, 76.P | 1, 5, 8, 9, 43, 44, 45, 53, 57, 99, 113, 124, 273, 279 |
| FARSB Phenylalanine--tRNA ligase beta subunit | 518-530 | IMQLLDVPPGEDK (SEQ ID NO: 825) | 2 | 3L4G | 519.B,520.B, 524.B,526.B, 528.B,530.B, 520.D, 521.D,523.D, 524.D,525.D, 530.D,519.F, 520.F, 523.F,524.F, 525.F,520.H, 521.H,523.H, 524.H,526.H, 530.H, 519.J,520.J, 523.J,524.J, 525.J,526.J, 529.J,530.J, 523.N,520.P, 523.P | 2, 7, 35, 54, 97, 106, 107, 134, 136, 181, 215, 218, 224, 267, 288, 295, 308 |
| FDFT1 Squalene synthase | 78-92 | ALDTLEDDMTISVEK (SEQ ID NO: 826) | 15 | 3VJ9 | 80.A,83.A | 1 |
| FECH Ferrochelatase, mitochondrial | 254-272 | SEVVILFSAHSLPMSV VNR (SEQ ID NO: 42) | 4 | 3HCN | 255.A,263.A, 270.A,271.A, 754.B,755.B, 763.B, 764.B,766.B, 768.B,770.B, 771.B | 1, 2, 3, 8, 12, 17, 21, 27 |
| FKBP4 Peptidyl-prolyl cis-trans isomerase FKBP4 | 190-206 | FEIGEGENLDLPYGLE R (SEQ ID NO: 827) | 13 | 4LAY | No Overlap | — |
| GLA Alpha-galactosidase A | 241-252 | SILDWTSFNQER (SEQ ID NO: 43) | 9 | 3S5Z | 244.A,247.A, 250.B,251.B, 252.B | 11, 20 |
| GLA Alpha-galactosidase A | 68-82 | LFMEMAELMVSEGW K (SEQ ID NO: 45) | 4 | 3S5Z | 70.A,68.B, 71.B | 13, 16 |
| GLA Alpha-galactosidase A | 50-67 | FMCNLDCQEEPDSCIS EK (SEQ ID NO: 44) | 9 | 3S5Z | 50.A,51.A, 52.A,53.A, 59.A,60.A, 61.A,62.A, 66.A,50.B, 51.B,52.B,53.B, 55.B,59.B, 60.B,61.B, 62.B,63.B, 65.B,67.B | 1, 3, 13, 16 |
| GLB1 Beta-galactosidase | 286-299 | TEAVASSLYDILAR (SEQ ID NO: 46) | 9 | 3THC | No Overlap | — |
| GLO1 Lactoylglutathione lyase | 160-179 | GLAFIQDPDGYWIEIL NPNK (SEQ ID NO: 47) | 3 14 | 3W0T | 159.A,164.A, 165.A,166.A, 175.A,178.A, 160.B, 162.B,170.B, | 1, 2, 4, 8, 12, 19 |

TABLE 2-continued

| Protein Name | Labeled Peptide | Peptide Sequence | Probes | PDB | Predicted pocket residue overlap | Overlapping pockets (fpocket designation) |
|---|---|---|---|---|---|---|
| | | | | | 172.B,160.C, 162.C,170.C, 172.C, 162.D,164.D, 166.D,167.D, 168.D,170.D, 172.D | |
| GLUD1 Glutamate dehydrogenase 1, mitochondria | 481-496 | HGGTIPIVPTAEFQDR (SEQ ID NO: 49) | 6 | 1L1F | 443.A,440.B, 443.B,439.F, 443.F | 35, 39, 66 |
| GLUD1 Glutamate dehydrogenase 1, mitochondrial | 152-162 | YSTDVSVDEVK (SEQ ID NO: 48) | 6 | 1L1F | 99.A,100.A, 101.A,102.A, 99.B,100.B, 101.B,107.B, 99.C,101.C, 102.C,99.D, 100.D,101.D, 102.D, 109.D,99.E, 100.E,101.E, 102.E,99.F, 100.F,101.F, 102.F,109.F | 4, 17, 44, 55, 57, 60, 61, 65 |
| GOLPH3 Golgi phosphoprotein 3 | 75-90 | EGYTSFWNDCISSGLR (SEQ ID NO: 50) | 14 | 3KN1 | 76.A,79.A, 80.A,81.A,83.A, 84.A,85.A, 87.A,90.A | 1, 5, 9 |
| GSTP1 Glutathione S-transferase P | 56-71 | FQDGDLTLYQSNTILR (SEQ ID NO: 51) | 2 | 2A2R | 61.B,63.B, 64.B | 1, 14 |
| H2AFZ Histone H2A.Z | 47-75 | VGATAAVYSAAILEY LTAEVLELAGNASK (SEQ ID NO: 828) | 3 | 5FUG | 48.A,49.A, 52.A,53.A, 71.A,72.A,73.A, 74.A,49.D, 67.D,70.D, 71.D,46.G, 54.G,57.G, 59.G,60.G, 63.G,71.G, 72.G,73.G, 74.G,48.J, 49.J,52.J | 1, 2, 3, 4, 5, 7, 8, 10, 11, 18, 27 |
| HADH Hydroxyacyl-coenzyme A dehydrogenase, mitochondria | 250-271 | LGAGYPMGPFELLDY VGLDTTK (SEQ ID NO: 829) | 2 13 | 3HAD | 238.A,239.A, 240.A,242.A, 243.A,252.A, 256.A, 257.A,239.B, 240.B,242.B, 243.B,245.B, 252.B, 253.B,256.B, 257.B | 1, 2, 3 |
| HARS Histidine--tRNA ligase, cytoplasmic | 170-193 | EFYQCDFDIAGNFDP MIPDAECLK(SEQ ID NO: 830) | 4 14 15 | 4PHC | 171.A,173.A, 171.B,172.B, 173.B,171.C, 172.C, 173.C,177.C, 180.C,181.C, 182.C,184.C, 185.C, 188.C,170.D, 171.D,172.D | 1, 2, 4, 5, 32, 43 |
| HBA2 Hemoglobin subunit alpha | 18-32 | VGAHAGEYGAEALE R (SEQ ID NO: 52) | 4 | 4X0L | 27.A,31.A | 6 |
| HBA2 Hemoglobin subunit alpha | 94-100 | VDPVNFK (SEQ ID NO: 53) | 4 | 4X0L | 96.A | 2 |
| HEXA Beta-hexosaminidase subunit alpha | 489-499 | LTSDLTFAYER (SEQ ID NO: 54) | 9 | 2GJX | 497.E,497.H, 498.H | 47, 70 |
| HLA-A HLA class I histocompatibility antigen, A-2 alpha | 46-59 | FIAVGYVDDTQFVR (SEQ ID NO: 831) | 14 | 5EU3 | 23.A,30.A, 31.A,32.A | 1, 5 |
| HMOX2 Heme oxygenase 2 | 48-55 | AENTQFVK (SEQ ID NO: 55) | 2 3 4 6 8 14 15 | 4WMH | 52.A,54.A | 1 |
| HMOX2 Heme | 69-87 | LATTALYFTYSALEE E | 14 | 4WMH | 73.A,74.A, | 1, 5 |

TABLE 2-continued

| Protein Name | Labeled Peptide | Peptide Sequence | Probes | PDB | Predicted pocket residue overlap | Overlapping pockets (fpocket designation) |
|---|---|---|---|---|---|---|
| oxygenase 2 | | MER (SEQ ID NO: 56) | | | 76.A,77.A, 79.A,80.A | |
| HNRNPA1 Heterogeneous nuclear ribonucleoprotein A1 | 56-75 | GFGFVTYATVEEVDA AMNAR (SEQ ID NO: 832) | 3 | 2UP1 | No Overlap | - |
| HNRNPA1 Heterogeneous nuclear ribonucleoprotein A1 | 16-31 | LFIGGLSFETTDESLR (SEQ ID NO: 833) | 23 14 | 2UP1 | 27.A | 2 |
| HNRNPA1 Heterogeneous nuclear ribonucleoprotein A1 | 131-140 | IEVIEIMTDR (SEQ ID NO: 834) | 3 8 9 | 2UP1 | No Overlap | - |
| HNRNPK Heterogeneous nuclear ribonucleoprotein K | 423-433 | IDEPLEGSEDR (SEQ ID NO: 835) | 4 | 1ZZK | No Overlap | - |
| HNRNPK Heterogeneous nuclear ribonucleoprotein K | 397-405 | DLAGSIIGK (SEQ ID NO: 836) | 3 4 | 1ZZK | No Overlap | - |
| HNRNPK Heterogeneous nuclear ribonucleoprotein K | 415-422 | HESGASIK (SEQ ID NO: 837) | 3 4 13 | 1ZZK | 42.A | 2 |
| HNRNPK Heterogeneous nuclear ribonucleoprotein K | 434-456 | IITITGTQDQIQNAQYL LQNSVK (SEQ ID NO: 838) | 2 3 4 8 9 13 14 | 1ZZK | 75.A,76.A, 78.A,79.A, 80.A | 1, 2 |
| HNRNPL Heterogeneous nuclear ribonucleoprotein L | 399-411 | VFNVFCLYGNVEK (SEQ ID NO: 839) | 2 | 3TO8 | 405.A,406.A | 2 |
| HSD17B10 3-hydroxyacyl-CoA dehydrogenase type-2 | 10-29 | GLVAVITGGASGLGL ATAER (SEQ ID NO: 840) | 2 3 | 2O23 | 20.A,29.A, 20.B,29.B | 1, 2, 16 |
| HSD17B4 Peroxisomal multifunctional enzyme type 2 | 169-183 | LGLLGLANSLAIEGR (SEQ ID NO: 57) | 3 | 1ZBQ | 175.A,176.A, 179.A,180.A, 183.A,169.B, 175.B, 176.B,169.C, 172.C,176.C, 179.C,180.C, 169.D, 172.D,179.D, 180.D,183.D, 179.F,180.F | 10, 12, 15, 22, 44 |
| HSP90AB1 Heat shock protein HSP 90-beta | 360-378 | VFIMDSCDELIPEYLN FIR (SEQ ID NO: 58) | 13 14 | 3PRY | 361.A,362.A, 363.A,364.A, 365.A,366.A, 367.A, 368.A,370.A, 371.A,375.A, 365.B,366.B, 367.B, 362.C,365.C, 366.C,367.C, 370.C,371.C, 372.C, 373.C,375.C | 1,2, 3, 4, 5, 7, 12, 30 |
| HSP90AB1 Heat shock protein HSP 90-beta | 507-526 | GFEVVYMTEPIDEYC VQQLK (SEQ ID NO: 59) | 13 14 | 3PRY | 508.A,512.A, 513.A,514.A, 515.A,516.A, 517.A, 518.A,519.A, 520.A,523.A, 525.A, 514.B,516.B, 518.B,525.B, 508.C,512.C, | 1, 3, 4, 5, 6, 7, 11, 13, 18, 20, 21, 25, 28, 33 |

TABLE 2-continued

| Protein Name | Labeled Peptide | Peptide Sequence | Probes | PDB | Predicted pocket residue overlap | Overlapping pockets (fpocket designation) |
|---|---|---|---|---|---|---|
| | | | | | 513.C,514.C, 515.C, 516.C,517.C, 518.C,519.C, 520.C,524.C | |
| HSP90B1 Endoplasmin | 117-135 | LISLTDENALSGNEEL TVK (SEQ ID NO: 60) | 9 | 4NH9 | No Overlap | - |
| HSP90B1 Endoplasmin | 271-285 | YSQFINFPIYVWSSK (SEQ ID NO: 61) | 6 | 4NH9 | No Overlap | - |
| HSPA1B Heat shock 70 kDa protein 1A/1B | 424-447 | QTQIFTTYSDNQPGVL IQVYEGER (SEQ ID NO: 841) | 3 | 13 4WV5 | 429.A,431.A, 432.A,433.A, 434.A,435.A, 436.A, 439.A,444.A, 436.B,439.B, 445.B,446.B, 447.B | 1, 3, 7, 10, 11 |
| HSPA5 78 kDa glucose-regulated protein | 602-617 | IEWLESHQDADIEDFK (SEQ ID NO: 842) | 6 | 5E85 | 602.A,605.A, 606.A,609.A | 6 |
| HSPA5 78 kDa glucose-regulated protein | 475-492 | DNHLLGTFDLTGIPPA PR (SEQ ID NO: 843) | 6 | 5E85 | 490.A,491.A, 492.A | 6, 7 |
| HSPA8 Heat shock cognate 71 kDa protein | 113-126 | SFYPEEVSSMVLIK (SEQ ID NO: 62) | 13 | 14 3LDQ | 115.A,116.A, 117.A | 15 |
| HSPA9 Stress-70 protein, mitochondrial | 266-284 | STNGDTFLGGEDFDQ ALLR (SEQ ID NO: 844) | 8 | 13 4KBO | 268.A,269.A, 270.A,271.A, 279.A,283.A | 1, 3 |
| HSPD1 60 Da heat shock protein, mitochondrial | 206-218 | TLNDELEIIEGMK (SEQ ID NO: 845) | 3 | 13 4PJ1 | 183.A,184.A, 188.A,190.A, 194.A,183.B, 193.B, 183.C,186.C, 188.C,190.C, 194.C,183.D, 184.D, 188.D,190.D, 191.D,193.D, 183.E,184.E, 190.E, 192.E,193.E, 183.F,184.F, 188.F,190.F, 191.F,192.F, 193.F,183.G, 184.G, 189.G,191.G, 193.G,183.H, 184.H,190.H, 194.H, 183.I,191.I, 193.I,183.J, 192.J,193.J, 183.K,184.K, 192.K,193.K, 182.L,183.L, 184.L, 185.L,186.L, 187.L,188.L, 190.L,193.L, 194.L,183.M, 184.M, 190.M,193.M, 183.N,184.N, 188.N,189.N, 190.N, 191.N,192.N, 193.N,194.N | 1, 2, 3, 4, 7, 14, 17, 21, 27, 29, 34, 36, 37, 44, 46, 47, 48, 49, 53, 54, 55, 57, 58, 60, 63, 64, 67, 72, 73, 82, 84, 95, 100, 103, 117, 118, 119, 129, 131, 135, 154, 160, 204, 244, 269, 277, 281, 310, 369, 371, 381, 382, 385, 472 |
| HSPD1 60 kDa heat shock protein, mitochondrial | 222-233 | GYISPYFINTSK (SEQ ID NO: 846) | 13 | 4PJ1 | 199.A,200. A,201.A,202.A, 203.A,205.A, 208.A, 200.B,201.B, | 18, 19, 22, 25, 28, 30, |

TABLE 2-continued

| Protein Name | Labeled Peptide | Peptide Sequence | Probes | PDB | Predicted pocket residue overlap | Overlapping pockets (fpocket designation) |
|---|---|---|---|---|---|---|
| | | | | | 202.B,203.B, 204.B,205.B, 206.B, 207.B,208.B, 209.B,200.D, 201.D,202.D, 203.D, 208.D,199.E, 202.E,203.E, 205.E,206.E, 208.E,209.E, 199.F, 200.F,201.F, 202.F,203.F, 206.F,198.G, 199.G,200.G, 201.G,202.G, 205.G, 206.G,200.H, 201.H,202.H, 203.H,206.H, 207.H, 199.I,201.I, 202.I,203.I, 205.I,199.J, 200.I,201.J, 202.J,203.J, 200.K,201.K, 202.K,203.K, 206.K,207K, 198.L, 199.L,200.L, 202.L,203.L, 205.L,199.M, 200.M,201.M, 202.M, 203.M,205.M, 208.M | 38, 39, 43, 61, 98, 102, 123, 124, 152, 179, 184, 188, 201, 202, 209, 222, 229, 282, 283, 314, 332, 340, 388, 409, 429, 460, 468, 471, 482 |
| HSPD1 60 kDa heat shock protein, mitochondrial | 251-268 | ISSIQSIVPALEIANAHR (SEQ ID NO: 847) | 3 | 4PJ1 | 230.B,231.B, 234.B,235.B, 238.B,243.B, 229.C, 230.C,231.C, 234.C,235.C, 238.C,243.C, 244.C, 237.E,240.E, 241.E,244.E, 231.F,234.F, 235.F,238.F, 244.F,228.G, 238.G, 240.G,241.G, 242.G,244.G, 237.H,240.H, 241.H, 244.H,237.K, 238.K,241.K, 231.M, 240.M,241.M, 244.M,238.N, 239.N,242.N, 244.N | 18, 66, 83, 96, 147, 176, 179, 183, 216, 217, 305, 362, 374, 377, 380, 391, 439, 473, 482 |
| HSPD1 60 kDa heat shock protein, mitochondrial | 371-387 | IQEIIEQLDVTTSEYEK (SEQ ID NO: 848) | 13 | 4PJ1 | 349.A,350.A, 353.A,361.A, 363.A,352.B, 353.B, 355.B,356.B, 357.B,358.B, 359.B,361.B, 362.B, 363.B,348.C, 350.C,351.C, 352.C,353.C, 354.C, | 1, 2, 3, 4, 7, 14, 17, 24, 25, 30, 37, 43, 46, 49, 52, 53, 54, 55, 57, 63, 73, 85, 95, 98, 100, 102, 111, 118, 128, 134, 150, 154, 173, 181, |

TABLE 2-continued

| Protein Name | Labeled Peptide | Peptide Sequence | Probes | PDB | Predicted pocket residue overlap | Overlapping pockets (fpocket designation) |
|---|---|---|---|---|---|---|
| | | | | | 355.C,361.C, 363.C,348.D, 349.D,350.D, 352.D, 353.D,358.D, 361.D,362.D, 363.D,350.E, 352.E, 353.E,354.E, 355.E,356.E, 357.E,358.E, 359.E,361.E, 362.E,363.E, 348.F, 351.F,354.F, 355.F,358.F, 361.F,363.F, 348.G,361.G, 362.G,348.H, 349.H, 350.H,353.H, 355.H,361.H, 363.H,348.I, 349.I,352.I, 353.I,361.I, 349.J,350.J, 351.J,353.J, 354.J,355.J, 361.J,362.J, 363.J,348.K, 349.K, 353.K,354.K, 355.K,361.K, 348.L,349.L, 351.L, 355.L,356.L, 358.L,361.L, 362.L,348.M, 349.M,350.M, 353.M, 354.M,355.M, 361.M,362.M, 363.M | 184, 197, 198, 201, 202, 206, 222, 229, 237, 240, 242, 278, 280, 282, 283, 297, 330, 332, 353, 371, 389, 449 |
| HSPD1 60 kDa heat shock protein, mitochondrial | 494-516 | IMQSSSEVGYDAMAG DFVNMVEK (SEQ ID NO: 849) | 8 | 13 4PJ1 | 479.A,480.A, 482.A,483.A, 479.B,481.B, 482.B, 484.B,479.C, 484.C,486.C, 479.E,480.E, 481.E, 482.E,491.E, 492.E,479.F, 479.G,483.G, 479.H,482.H, 483.H,484.H, 491.H, 492.I,484.J, 471.K,472.K, 475.K,484.K, 479.L,481.L, 482.L, 483.L,489.L, 471.M,479.M, 479.N,481.N | 5, 6, 8, 9, 10, 11, 12, 15, 16, 33, 106, 133, 213, 252, 279, 334, 390, 469, 477 |
| HSPD1 60 kDa heat shock protein, mitochondrial | 97-121 | LVQDVANNTNEEAG DGTTTATVLAR (SEQ ID NO: 850) | 8 | 13 4PJ1 | 80.A,84.A,94.A, 79.B,84.B, 91.B,97.B, 80.C,84.C, 87.C,90.C, 94.C,97.C,80.D, 82.D,84.D, 88.D,91.D, 75.E,76.E, 80.E,83.E,94.E, | 6, 8, 9, 10, 11, 12, 14, 15, 16 ,17 20' 21' 31' 37' 41' 46' 48, 49, 53, 55, 56, 57, 60, 63, 67, 71, 73, 84, 121, 142, |

TABLE 2-continued

| Protein Name | Labeled Peptide | Peptide Sequence | Probes | PDB | Predicted pocket residue overlap | Overlapping pockets (fpocket designation) |
|---|---|---|---|---|---|---|
| | | | | | 80.F,84.F, 87.F,88.F, 90.F,80.G,82.G, 84.G,87.G, 90.G,94.G, 97.G,80.H, 82.H,83.H, 85.H,86.H, 89.H,80.I, 83.I,91.I,80.J, 83.J,84.J,86.J, 94.J,79.K, 83.K,84.K, 85.K,86.K, 94.K,97.K, 80.L,84.L, 85.L,86.L,87.L, 94.L,97.L, 80.M,82.M, 83.M,88.M, 90.M,94.M, 97.M,80.N, 82.N,84.N, 87.N,90.N | 145, 178, 181, 214, 237, 240, 250, 253, 255, 275, 280, 319, 371 |
| IDE Insulin-degrading enzyme | 312-324 | NLYVTFPIPDLQK (SEQ ID NO: 851) | 4 | 4RAL | 316.A,319.A, 320.A,321.A, 322.A,323.A, 324.A, 316.B,319.B, 320.B | 3, 4, 7, 39, 41, 67, 93 |
| IGF2BP1 Insulin-like growth factor 2 mRNA-binding protein | 509-525 | TVNELQNLTAAEVVV PR (SEQ ID NO: 852) | 3 13 | 3KRM | 525.A,515.B, 518.B,524.B, 525.B,524.C, 525.C | 1, 2, 12, 13, 17 |
| IMPDH2 Inosine-5-monophosphate dehydrogenase 2 | 110-124 | YEQGFITDPVVLSPK (SEQ ID NO: 63) | 13 | 1NF7 | 110.A,111.A, 112.A,113.A, 114.A,116.A, 120.A, 122.A,110.B, 111.B,112.B, 119.B,121.B | 3, 9, 16, 21, 30, 33 |
| KPNA2 Importin subunit alpha-2 | 203-227 | YGAVDPLLALLAVPD MSSLACGYLR (SEQ ID NO: 853) | 13 14 | 4WV6 | No Overlap | — |
| KPNA2 Importin subunit alpha-2 | 301-315 | LLGASELPIVTPALR (SEQ ID NO: 854) | 13 | 4WV6 | No Overlap | — |
| KPNB1 Importin subunit beta-1 | 317-332 | GALQYLVPILTQTLTK (SEQ ID NO: 855) | 13 14 | 3W5K | 318.A,330.A | 1,23 |
| KPNB1 Importin subunit beta-1 | 28-42 | AAVENLPTFLVELSR (SEQ ID NO: 856) | 13 14 | 3W5K | 29.A,30.A,34.A, 3 5.A,36.A, 38.A,39.A, 40.A,42.A | 28, 33, 39 |
| KPNB1 Importin subunit beta-1 | 526-537 | SSAYESLMEIVK (SEQ ID NO: 857) | 13 14 | 3W5K | 537.A | 3 |
| LDHA L-lactate dehydrogenase A chain | 43-57 | DLADELALVDVIEDK (SEQ ID NO: 64) | 9 | 4JNK | 42.A,43.A,44.A, 45.A,46.A, 5 1.A,42.B, 45.B,46.B, 51.B,53.B, 56.B,42.C, 45.C,50.C,51.C, 42.D,43.D, 44.D,45.D, 46.D,51.D, 52.D | 1, 2, 3, 4, 6, 7, 10, 12, 14, 16, 27, 29 |
| LDHB L-lactate dehydrogenase B chain | 234-244 | MVVESAYEVIK (SEQ ID NO: 65) | 4 | 1I0Z | 233.A,238.A, 242.A,238.B, 239.B | 1, 2, 4, 5 |
| LGMN Legumain | 102-118 | DYTGEDVTPQNFLAV LR (SEQ ID NO: 66) | 9 | 4N6O | No Overlap | — |
| LMNA Prelamin-A/C | 352-366 | MQQQLDEYQELLDIK (SEQ ID NO: 96) | 6 13 | 3V5B | No Overlap | — |
| LTA4H Leukotriene A-4 | 366-386 | LVVDLTDIDPDVAYS SVPYEK | 4 8 13 | 3U9W | 1367.A,1369.A, 1377.A, | 1 |

TABLE 2-continued

| Protein Name | Labeled Peptide | Peptide Sequence | Probes | PDB | Predicted pocket residue overlap | Overlapping pockets (fpocket designation) |
|---|---|---|---|---|---|---|
| hydrolase | | (SEQ ID NO: 67) | | | 1380.A,1383.A | |
| NAGLU Alpha-N-acetylglucosaminidase | 566-580 | QAVQELVSLYYEEAR (SEQ ID NO: 858) | 9 | 4XWH | No Overlap | — |
| NAGLU Alpha-N-acetylglucosaminidase | 594-615 | AGGVLAYELLPALDE VLASDSR (SEQ ID NO: 859) | 13 15 | 4XWH | No Overlap | — |
| NAMPT Nicotinamide phosphoribosyltransferase | 175-189 | YLLETSGNLDGLEYK (SEQ ID NO: 68) | 3 6 8 13 14 15 | 4LVF | 185.A,187.A, 188.A,189.A, 184.B,185.B, 189.B | 2, 5, 6 |
| NCBP1 Nuclear cap-binding protein subunit 1 | 42-65 | SACSLESNLEGLAGV LEADLPNYK (SEQ ID NO: 860) | 2 3 13 14 | 3FEY | No Overlap | — |
| NHP2L1 NHP2-like protein 1 | 114-125 | QQIQSIQQSIER (SEQ ID NO: 861) | 236 | 3S1V | 118.A,119.A, 118.J,119J, 120.J,121.J, 125.J | 4, 36, 61 |
| NONO Non-POU domain-containing octamer-binding protein | 127-135 | VELDNMPLR (SEQ ID NO: 862) | 3 | 3SDE | 127.B,131.B | 1 |
| NONO Non-POU domain-containing octamer-binding protein | 257-270 | FAQPGSFEYEYAMR (SEQ ID NO: 863) | 6 | 3SDE | 257.B,258.B, 259.B,260.B, 265.B,267.B | 6, 13 |
| NONO Non-POU domain-containing octamer-binding protein | 296-304 | LEMEMEAAR (SEQ ID NO: 864) | 6 | 3SDE | No Overlap | — |
| NONO Non-POU domain-containing octamer-binding protein | 154-176 | NLPQYVSNELLEEAFS VFGQVER (SEQ ID NO: 865) | 2 3 6 9 13 14 | 3SDE | 154.B,173.B, 174.B,175.B | 2, 5 |
| NONO Non-POU domain-containing octamer-binding protein | 177-184 | AVVIVDDR (SEQ ID NO: 866) | 6 | 3SDE | 181.B,183.B, 184.B | 3 |
| NPM1 Nucleophosmin | 55-73 | DELHIVEAEAMNYEG SPIK (SEQ ID NO: 69) | 13 | 2P1B | 55.A,56.A,57.A, 55.B,56.B, 66.B,67.B, 68.B,72.B, 55.C,56.C, 57.C,64.C,65.C, 67.C,68.C, 55.D,56.D, 57.D,61.D, 73.D,55.E, 56.E,57.E, 61.E,72.E,73.E, 55.F,56.F, 57.F,64.F, 65.F,67.F,68.F, 55.G,56.G, 57.G,61.G, 63 .G,64.G, 65.G,73.G, 55.H,56.H, 57.H,63.H, 64.H,65.H, 55.I,56.I, 57.I,55.J,56.J, 57.J | 1, 4, 5, 7, 12, 13, 19, 23, 25, 27, 32, 38 |
| NPM1 Nucleophosmin | 81-101 | MSVQPTVSLGGFEITP PVVLR (SEQ ID NO: 70) | 13 | 2P1B | 81.A,82.A,83.A, 84.A,86.A, 87.A,88.A, 89.A,90.A, 95.A,81.B, 82.B,83.B, 84.B,86.B, 87.B,88.B,89.B, 90.B,81.C, 82.C,83.C, 84.C,86.0, 87.C,88.C, 89.C,90.0, | 1, 9, 12, 13, 14, 15, 16 17, 25, 29, 30, 31, 32, 33, 36, 37, 38 |

TABLE 2-continued

| Protein Name | Labeled Peptide | Peptide Sequence | Probes | PDB | Predicted pocket residue overlap | Overlapping pockets (fpocket designation) |
|---|---|---|---|---|---|---|
| | | | | | 92 C 93.C,94.C, 95.C,96.C, 81.D,82.D, 83.D,84.D, 88.D,89.D, 90.D,81.E, 82.E,83.E, 84.E,88.E,89.E, 90.E,93.E, 81.F,82.F, 83.F,84.F,86.F, 87.F,88.F, 89.F,90.F, 94.F,95.F,97.F, 99.F,81.G, 82.G,83.G, 84.G,85.G, 86.G,88.G, 89.G,90.G, 94.G,95.G, 96.G,97.G, 99.G,101.G, 81.H,82.H, 83.H,84.H, 86.H,87.H, 88.H,89.H, 90.H,94.H, 95.H,96.H, 98.H,81.I, 82.I,83.I,84.I, 86.I,87.I,88.I, 89.I,90.I, 95.I,96.I,81.J, 82.J,83.J,84.J, 86.J,87.J, 88.J,89.J,90.J, 95.J,96.J | |
| NTMT1 N-terminal Xaa-Pro-Lys N-methyltransferase 1 | 167-185 | DNMAQEGVILDDVDS SVCR (SEQ ID NO: 867) | 13 | 5E2B | 168.A,180.A, 182.A,183.A, 184.A,185.A, 167.B, 168.B,169.B, 170.B,171.B, 178.B,179.B, 182.B, 183.B,184.B, 185.B | 1, 4, 7, 18 |
| OAT Ornithine aminotransferase, mitochondrial | 332-351 | VAIAALEVLEEENLAE NADK (SEQ ID NO: 868) | 13 14 | 2OAT | 340.A,341.A, 344.A,346.A, 334.B,338.B, 344.B, 347.B,350.B, 340.C,341.C, 344.C,350.C | 6, 21, 24, 43 |
| P4HB Protein disulfide-isomerase | 171-195 | QFLQAAEAIDDIPFGIT SNSDVFSK (SEQ ID NO: 869) | 9 | 4JU5 | 178.A,179.A, 181.A,181.B | 4, 13 |
| P4HB Protein disulfide-isomerase | 231-247 | HNQLPLVIEFTEQTAP K (SEQ ID NO: 870) | 2 13 14 | 4JU5 | 231.A,232.A, 233.A,234.A, 235.A,236.A, 242.A, 244.A,245.A, 246.A,231.B, 233.B,234.B, 235.B, 238.B,239.B, 240.B,241.B, 244.B,245.B, 247.B | 2, 3, 4, 5, 7, 11, 13, 15 |
| PABPC1 Polyadenylate-binding protein 1 | 114-129 | ALYDTFSAFGNILSCK (SEQ ID NO: 871) | 14 | 1CVJ | 116.A,127.A, 128.A,116.B, 126.B,127.B, 128.B, 129.B,116.C, 125.C,126.C, | 1, 2, 9, 12, 13, 16, 27 |

TABLE 2-continued

| Protein Name | Labeled Peptide | Peptide Sequence | Probes | PDB | Predicted pocket residue overlap | Overlapping pockets (fpocket designation) |
|---|---|---|---|---|---|---|
| | | | | | 127.C,128.C, 116.D, 116.E,117.E, 125.E,127.E, 128.E,116.G, 126.G,128.G | |
| PABPC1 Polyadenylate-binding protein 1 | 51-67 | SLGYAYVNFQQPADA ER (SEQ ID NO: 872) | 3 1 4 | 1CVJ | 51.A,52.A,58.A, 60.A,58.B, 61.C,64.C, 67.C,51.E, 52.E,56.E,64.E, 66.E,67.E, 52.F,60.F, 60.G,67.G,51.H, 56.H,60.H | 2, 3, 4, 5, 7, 11, 14, 22, 30, 32, 33, 43, 51, 52, 53 |
| PARP1 Poly | 762-779 | VEMLDNLLDIEVAYS LLR (SEQ ID NO: 873) | 3 6 | 4ZZZ | 762.A,763.A, 766.A,767.A, 769.A,773.A, 763.B, 766.B,769.B | 1 2 29 |
| PARP1 Poly | 954-1000 | TTPDPSANISLDGVDV PLGTGISSGVNDTSLL YNEYIVYDIAQVNLK (SEQ ID NO: 874) | 3 | 4ZZZ | 962.A,964.A, 965.A,967.A, 980.A,981.A, 983.A, 985.A,988.A, 992.A,993.A, 996.A,1000.A, 955B, 961.B,968.B, 970.B,981.B, 982.B, 983.B,985.B, 986.B,988.B, 989.B,992.B, 993.B, 996.B | 3, 4, 6, 8, 9, 13, 16, 22, 24, 25, 26 |
| PCMT1 Protein-L-isoaspartate(D-aspartate) O-methyltransf | 179-197 | LILPVGPAGGNQMLE QYDK (SEQ ID NO: 71) | 2 3 14 | 1I1N | 183.A,185.A | 5 |
| PCNA Proliferating cell nuclear antigen | 118-138 | LMDLDVEQLGIPEQE YSCVVK (SEQ ID NO: 875) | 14 | 5E0V | 121.A,122.A, 123.A,122.B, 123.B,124.B, 125.B, 126.B | 1, 2, 11 |
| PDCD4 Programmed cell death protein 4 | 246-256 | DLPELALDTPR (SEQ ID NO: 876) | 13 | 3EIJ | 256.A | 1 |
| PDHB Pyruvate dehydrogenase E1 component subunit beta, | 53-68 | VFLLGEEVAQYDGAY K (SEQ ID NO: 72) | 2 3 13 14 | 3EXE | 31.B,32.B,37.B, 23.D,28.D, 33.D,36.D, 37.D,28.F, 31.F,32.F,33.F, 36.F,37.F, 24.H,28.H, 31.H,32.H, 36.H,37.H | 1,2, 3, 12, 13, 14, 18, 19, 21, 29 |
| PGK1 Phosphoglycerate kinase 1 | 333-350 | QIVWNGPVGVFEWE AFAR (SEQ ID NO: 73) | 3 | 2WZB | No Overlap | — |
| PGRMC1 Membrane-associated progesterone receptor componen | 106-119 | FYGPEGPYGVFAGR (SEQ ID NO: 877) | 2 34 13 14 | 4X8Y | 108.A,109.A, 110.A | 12 |
| PKM Pyruvate kinase isozymes M1/M2 | 174-186 | IYVDDGLISLQVK (SEQ ID NO: 74) | 2 9 | 4FXF | 177.D,180.D, 175.C,177.C, 178.C,179.C, 180.C, 182.C,175.B, 177.B,180.B, 182.B | 1, 2 4, 16, 47, 62 |
| PKM Pyruvate kinase isozymes M1/M2 | 401-422 | LAPITSDPTEATAVGA VEASFK (SEQ ID NO: 75) | 2 9 | 4FXF | 401.A,403.A, 418.A,420.A, 421.A,422.A, | 3, 9, 37, 39, 41, 53, 68, 75, 78 |

TABLE 2-continued

| Protein Name | Labeled Peptide | Peptide Sequence | Probes | PDB | Predicted pocket residue overlap | Overlapping pockets (fpocket designation) |
|---|---|---|---|---|---|---|
| | | | | | 401.D, 408.D,409.D, 420.D,421.D, 404.C,407.C, 408.C, 409.C,410.C, 402.B,403.B, 404.B,414.B | |
| POR NADPH--cytochrome P450 reductase | 369-382 | TALTYYLDITNPPR (SEQ ID NO: 76) | 13 14 | 3QFS | 375.A,376.A | 2, 5 |
| PPP1CA Serine/threonine-protein phosphatase PP1-alpha cat | 133-141 | IYGFYDECK (SEQ ID NO: 77) | 2 | 4XPN | 134.C,139.C | 3, 4 |
| PPP1CC Serine/threonine-protein phosphatase PP1-gamma cat | 44-60 | EIFLSQPILLELEAPLK (SEQ ID NO: 79) | 14 | 4UT2 | 55.A,56.A,47.B, 48.B,49.B, 50.B,51.B | 13, 14 |
| PPP1CC Serine/threonine-protein phosphatase PP1-gamma cat | 133-141 | IYGFYDECK (SEQ ID NO: 78) | 2 | 4UT2 | No | Overlap - |
| PPT1 Palmitoyl-protein thioesterase 1 | 75-101 | TLMEDVENSFFLNVN SQVTTVCQALAK (SEQ ID NO: 80) | 2 4 8 9 13 14 15 | 3GRO | 75.A,76.A,78.A, 75.B,76.B, 80.B,81.B, 85.B,86.B, 87.B,90.B | 1,2, 5, 10 |
| PRDX2 Peroxiredoxin-2 | 120-127 | TDEGIAYR (SEQ ID NO: 81) | 13 | 1QMV | 121.A,122. A,121.B,122.B, 124.B,121.C, 122.C, 124.C,127.C, 120.D,121.D, 122.D,124.D, 126.D, 127.D,121.E, 122.E,124.E, 127.E,121.F, 122.F,124.F, 127.F, 121.G,122.G, 124.G,120.H, 121.H,122.H, 124.H, 126.H,127.H, 120.I,121.I, 122.I,124.I, 126.I,127.I, 120.J,121.J, 122.J,124.J, 126.J,127.J | 3, 5, 6, 7, 8, 14, 15, 18, 20, 26, 27, 29, 30, 32, 36, 42, 43, 54, 72, 111 |
| PSMA2 Proteasome subunit alpha type-2 | 144-159 | PYLFQSDPSGAYFAW K (SEQ ID NO: 878) | 2 | 4R3O | 144.B,152.B, 154.B,155.B, 156.B,147.P, 149.P, 154.P,155.P, 157.P | 1 28, 63 69, 93 |
| PSMA2 Proteasome subunit alpha type-2 | 19-39 | LVQIEYALAAVAGGA PSVGIK (SEQ ID NO: 879) | 3 | 4R3O | 25.P,28.P | 28 |
| PSMA4 Proteasome subunit alpha type-4 | 68-91 | LNEDMACSVAGITSD ANVLTNELR (SEQID NO: 880) | 3 6 8 13 14 | 4R3O | 71.C,80.C,81.C, 84.C,85.C, 88.C,70.Q, 81.Q,85.Q, 87.Q,88.Q, 89.Q,91.Q | 1, 69, 93, 145, 147 |
| PSMB1 Proteasome subunit beta type-1 | 129-146 | FFPYYVYNIIGGLDEE GK (SEQID NO: 881) | 2 13 14 15 | 4R3O | 107.M,108.M, 109.M,118.M, 107.1,109.1 | 4, 11, 57 |
| PSMB2 Proteasome subunit beta type-2 | 96-126 | TPYHVNLLLAGYDEH EGPALYYMDYLAAL AK (SEQ ID NO: 882) | 2 6 | 4R3O | 96.K,97.K,98.K, 99.K,101.K, 108.K,110K 111K, 119.K,101.Y, | 97, 145, 180, 181, 191 |

| Protein Name | Labeled Peptide | Peptide Sequence | Probes | PDB | Predicted pocket residue overlap | Overlapping pockets (fpocket designation) |
|---|---|---|---|---|---|---|
| | | | | | 116.Y,119.Y, 124.Y,125.Y, 126.Y | |
| PSMB2 Proteasome subunit beta type-2 | 42-62 | ILLLCVGEAGDTVQF AEYIQK (SEQ ID NO: 883) | 6 | 4R3O | 49.K,52.K,48.Y, 54.Y,58.Y, 61.Y | 97, 149, 163 |
| PSMB3 Proteasome subunit beta type-3 | 100-115 | FGPYYTEPVIAGLDPK (SEQ ID NO: 884) | 3 6 13 14 15 | 4R3O | 100.J,106.X, 113.X,114.X | 1, 3, 198 |
| PSMB4 Proteasome subunit beta type-4 | 61-80 | FEGGVVIAADMLGSY GSLAR (SEQ ID NO: 82) | 6 | 4R3O | 30.2,35.2 | 67 |
| PSMB5 Proteasome subunit beta type-5 | 141-150 | LLANMVYQYK (SEQ ID NO: 83) | 3 4 6 | 4R3O | 88.L,91.L | 97 |
| PSMB5 Proteasome subunit beta type-5 | 226-239 | DAYSGGAVNLYHVR (SEQ ID NO: 84) | 6 | 4R3O | No Overlap | — |
| PSMB6 Proteasome subunit beta type-6 | 80-118 | SGSAADTQAVADAVT YQLGFHSIELNEPPLV HTAASLFK (SEQ ID NO: 85) | 3614 | 4R3O | 48.H,50.H,51.H, 60.H,61.H,6 4.H,65.H, 67.H,68.H, 69.H,70.H, 71.H,75.H, 77.H,78.H, 84.H,46.V, 48.V,50.V, 51.V,53.V, 62.V,65.V, 70.V,72.V, 75.V,77.V, 78.V,82.V, 84.V | 10, 23, 50, 67, 152, 155, 160, 169, 187, 200, 204, 206, 212 |
| PSPC1 Paraspeckle component 1 | 229-247 | PVIVEPMEQFDDEDG LPEK (SEQ ID NO: 885) | 6 14 | 3SDE | 229.A,231.A, 232.A,233.A, 235.A,237.A, 239.A, 240.A,241.A | 1, 2, 3, 4, 6 |
| PTGR2 Prostaglandin reductase 2 | 93-106 | GDFVTSFYWPWQTK (SEQ ID NO: 886) | 14 | 2ZB4 | 97.A | 2 |
| PTGR2 Prostaglandin reductase 2 | 262-278 | DVPYPPPLSPAIEAIQK (SEQ ID NO: 887) | 2 3 14 | 2ZB4 | 263.A,265.A, 267.A,277.A, 278.A | 1, 4 |
| RAB7A Ras-related protein Rab-7a | 104-113 | DEFLIQASPR (SEQ ID NO: 86) | 14 | 1YHN | NoOverlap | — |
| RARS Arginine--tRNA ligase, cytoplasmic | 528-540 | GNTAAYLLYAFTR (SEQ ID NO: 888) | 14 | 4ZAJ | 464.A,467.A, 468.A | 1 |
| RPL30 60S ribosomal protein L30 | 58-68 | SEIEYYAMLAK (SEQ ID NO: 889) | 13 | 3VI6 | No verlap | — |
| RUVBL1 RuvB-like 1 | 318-333 | ALESSIAPIVIFASNR (SEQ ID NO: 890) | 2 | 2XSZ | 229.A,231.A, 232.A,233.A, 234.A,235.A, 236.A, 237.A,243.A, 229.B,231.B, 232.B,233.B, 236.B, 229.C,230.C, 231.C,232.C, 233.C,234.C, 235.C, 236.C,237.C, 238.C,243.C, 244.0 | 2, 3, 4, 5, 12, 20, 37, 39, 45, 47, 48, 52, 53, 55, 58, 69 |
| RUVBL1 RuvB-like 1 | 91-107 | VPFCPMVGSEVYSTEI K (SEQ ID NO: 891) | 2 | 2XSZ | 105.A,106.A, 107.A,108.A, 115.A,116.A, 117.A, 118.A,119.A, 120.A,121.A, 105.B,106.B, 107.B, 108.B,120.B, 105.C,106.C, | 1, 2, 3, 7, 8, 13, 33 |

TABLE 2-continued

| Protein Name | Labeled Peptide | Peptide Sequence | Probes | PDB | Predicted pocket residue overlap | Overlapping pockets (fpocket designation) |
|---|---|---|---|---|---|---|
| RUVBL2 RuvB-like 2 | 315-330 | ALESDMAPVLIMATNR (SEQ ID NO: 87) | 14 | 3UK6 | 107.C,113.C, 120.0 316.A,317.A, 318.A,319.A, 320.A,322.A, 323.A, 329.A,315.B, 317.B,318.B, 319.B,320.B, 321.B, 322.B,323.B, 329.B,315.C, 316.C,318.C, 322.C, 315.D,316.D, 317.D,318.D, 319.D,321.D, 322.D, 323.D,329.D, 318.E,319.E, 322.E,323.E, 329.E, 315.F,316.F, 317.F,318.F, 319.F,320.F, 322.F,323.F, 329.F,315.G, 320.G, 329.G,330.G, 315.H,318.H, 320.H,322.H, 323.H, 324.H,327.H, 329.H,315.I, 317.I,318.I, 319.I,320.I, 322.I,329.I, 315.J,318.J, 320.J,322.J, 323.J,327.J, 329.J,318.K, 319.K,322.K, 323.K, 325.K,328.K, 318.L,319.L, 320.L,322.L, 323.L, 325.L,329.L | 1, 3, 4, 5, 6, 7, 8, 9, 10, 11, 12, 13, 15, 18, 19, 20, 22, 23, 24, 25, 30, 31, 33, 37, 48, 54, 64, 65, 72, 75, 80, 83, 98, 100, 117, 121, 147, 154, 155 |
| SFPQ Splicing factor, proline- and glutamine-rich | 377-399 | NL SPYVSNELLEEAFS QFGPIER (SEQ ID NO: 892) | 2 3 4 9 13 14 | 4WIK | 377.A,380.A, 381.A,399.A, 377.B | 1, 3, 6, 12 |
| SFPQ Splicing factor, proline- and glutamine-rich | 444-462 | PVIVEPLEQLDDEDGL PEK (SEQ ID NO: 893) | 2 4 14 | 4WIK | 450.A,452.A, 455.A,446.B, 447.B,448.B, 449.B, 455.B | 5, 8, 12 |
| SLC25A12 Calcium-binding mitochondrial carrier protein Aral | 260-283 | YGQVTPLEIDILYQLA DLYNASGR (SEQ ID NO: 894) | 4 14 | 4P5X | No Overlap | — |
| SLC25A13 Calcium-binding mitochondrial carrier protein Aral | 261-282 | FGQVTPMEVDILFQL ADLYEPR (SEQ ID NO: 895) | 2 3 4 6 14 15 | 4P5W | 262.A,263.A, 264.A,265.A, 267.A,273.A, 274.A, 276.A,277.A, 280.A,282.A, 261.B,262.B, 263.B, 264.B,265.B, 267.B,268.B, 270.B,273.B, 274.B, 276.B,280.B | 1, 4, 10, 11 |
| SLC25A13 Calcium-binding | 642-653 | LAVATFAGIENK (SEQ ID NO: 896) | 3 4 6 8 14 15 | 4P5W | 647.A,649.A, 650.A,651.A, | 1, 2, 3, 4, 8 |

TABLE 2-continued

| Protein Name | Labeled Peptide | Peptide Sequence | Probes | PDB | Predicted pocket residue overlap | Overlapping pockets (fpocket designation) |
|---|---|---|---|---|---|---|
| mitochondrial carrier protein Aral | | | | | 653.A,647.B, 648.B, 649.B,650.B, 651.B | |
| SMYD3 SET and MYND domain-containing protein 3 | 255-265 | DQYCFECDCFR (SEQ ID NO: 88) | 9 | 5HQ8 | 255.A,256.A, 258.A,259.A, 260.A,264.A, 255.B, 256.B,258.B, 259.B | 1, 2, 5, 6, 8, 23 |
| SPTBN1 Spectrin beta chain, non-erythrocytic 1 | 1706-1717 | EVDDLEQWIAER (SEQ ID NO: 897) | 13 | 3EDV | No Overlap | — |
| STAG2 Cohesin subunit SA-2 | 273-290 | ELQENQDEIENMMNA JFK (SEQ ID NO: 898) | 13 | 4PK7 | No Overlap | — |
| TIMM10 Mitochondrial import inner membrane translocase su | 6-24 | AQQLAAELEVEMMA DMYNR (SEQ ID NO: 899) | 8 9 13 14 | 2BSK | 15.D,19.D,20.D, 22.D,23.D, 24.D | 3, 11 |
| TIMM44 Mitochondrial import inner membrane translocase su | 428-439 | DQDELNPYAAWR (SEQ ID NO: 900) | 13 | 2CW9 | 434.A,435.A, 438.A | 1 |
| TNPO1 Transportin-1 | 273-298 | TQDQDENVALEACEF WLTLAEQPICK (SEQ ID NO: 901) | 9 | 4OO6 | 265.A,266.A, 267.A | 3 |
| TNPO1 Transportin-1 | 45-64 | LEQLNQYPDFNNYLIF VLTK (SEQ ID NO: 902) | 2 13 14 | 4OO6 | 37.A,38.A,40.A, 43.A,45.A, 46.A | 11, 16, 18 |
| TPP1 Tripeptidyl-peptidase 1 | 521-558 | GCHESCLDEEVEGQG FCSGPGWDPVTGWG TPNFPALLK (SEQ ID NO: 89) | 4 9 13 14 15 | 3EDY | 522.A,524. A,531.A,53 2.A,534.A,5 35.A,537.A, 540.A,541.A, 543.A,548.A | 4, 8, 13 |
| TSN Translin | 205-215 | VEEVVYDLSIR (SEQ ID NO: 903) | 2 | 3PJA | 206.A,207.A, 209.A,210.A, 211.A,215.A, 207.B, 211.B,213.B, 215.B,207.C, 209.C,213.C, 214.C, 215.C,206.D, 207.D,209.D, 210.D,211.D, 213.D, 214.D,215.D, 207.E,211.E, 214.E,215.E, 207.F, 208.F,211.F, 215.F,207.G, 210.G,211.G, 214.G,215.G, 207.H, 211.H,215.H, 207.I,209.I, 211.I,213.I, 214.I,215.I | 1, 2, 3, 4, 6, 11, 15, 49, 54, 65, 68, 94, 101, 116 |
| TXNDC17 Thioredoxin domain-containing protein 17 | 4-17 | YEEVSVSGFEEFHR (SEQ ID NO: 90) | 14 | 1WOU | No Overlap | — |
| VDAC1 Voltage-dependent anion-selective channel protein | 140-161 | GALVLGYEGWLAGY QMNEETAK (SEQ ID NO: 904) | 2 4 6 13 14 | 2JK4 | 144.A,146.A, 149.A,152.A, 153.A,155.A, 157.A | 1 2 6 |
| VDAC1 Voltage-dependent anion-selective channel protein | 121-139 | EHINLGCDMDFDIAG PSIR (SEQ ID NO: 905) | 2 4 8 13 14 | 2JK4 | 126.A,127.A, 131.A,142.A | 1, 6 |
| VDAC1 Voltage-dependent anion- | 75-93 | WNTDNTLGTEITVED QLAR (SEQ ID | 2 3 4 6 8 13 | 2JK4 | 84.A,85.A,86.A, 87.A | 5 |

TABLE 2-continued

| Protein Name | Labeled Peptide | Peptide Sequence | Probes | PDB | Predicted pocket residue overlap | Overlapping pockets (fpocket designation) |
|---|---|---|---|---|---|---|
| selective channel protein | | NO: 906) | 14 15 | | | |
| VDAC1 Voltage-dependent anion-selective channel protein | 164-174 | VTQSNFAVGYK (SEQ ID NO: 907) | 4 6 8 14 | 2JK4 | 173.A,174.A, 175.A,176.A, 177.A | 1, 2 |
| VDAC1 Voltage-dependent anion-selective channel protein | 64-74 | WTEYGLTFTEK (SEQ ID NO: 908) | 2 3 4 6 8 9 13 14 15 | 2JK4 | No Overlap | — |
| VDAC1 Voltage-dependent anion-selective channel protein | 35-53 | SENGLEFTSSGSANTE TTK (SEQ ID NO: 909) | 4 8 9 | 2JK4 | 45.A,47.A | 7 |
| VDAC1 Voltage-dependent anion-selective channel protein | 175-197 | TDEFQLHTNVNDGTE FGGSIYQK(SEQ ID NO: 910) | 4 8 14 | 2JK4 | 180.A,181.A, 184.A,185.A, 186.A,196.A, 198.A | 1, 2, 4 |
| VDAC1 Voltage-dependent anion-selective channel protein | 225-236 | YQIDPDACFSAK (SEQ ID NO: 911) | 4 8 | 2JK4 | 229.A | 4 |
| VIM Vimentin | 176-184 | DNLAEDIMR (SEQ ID NO: 912) | 6 | 4YPC | No Overlap | — |
| VIM Vimentin | 197-207 | EEAENTLQSFR (SEQ ID NO: 913) | 2 3 6 9 13 14 15 | 4YPC | No Overlap | — |
| VIM Vimentin | 189-196 | LQEEMLQR (SEQ ID NO: 914) | 3 6 | 4YPC | No Overlap | — |
| VIM Vimentin | 224-235 | VESLQEEIAFLK (SEQ ID NO: 915) | 4 6 14 | 4YPC | No Overlap | — |
| VPS33A Vacuolar protein sorting-associated protein 33A | 233-262 | NVDLLTPLATQLTYE GLIDEIYGIQNSYVK (SEQ ID NO: 916) | 14 | 4BX9 | No Overlap | — |
| XRCC6 X-ray repair cross-complementing protein 6 | 475-488 | SDSFENPVLQQHFR (SEQ ID NO: 917) | 2 3 4 8 13 | 1JEY | 476.A,486.A, 488.A | 1, 25 |
| XRCC6 X-ray repair cross-complementing protein 6 | 489-510 | NLEALALDLMEPEQA VDLTLPK (SEQ ID NO: 176) | 2 3 4 8 13 | 1JEY | 491.A,497. A,508.A,50 9.A | 14, 25 |
| YWHAE 14-3-3 protein epsilon | 197-215 | AAFDDAIAELDTLSEE SYK (SEQ ID NO: 92) | 13 | 3UBW | 212.A | 1 |
| YWHAE 14-3-3 protein epsilon | 143-153 | EAAENSLVAYK (SEQ ID NO: 91) | 13 | 3UBW | No Overlap | — |
| YWHAQ 14-3-3 protein theta | 194-212 | TAFDEAIAELDTLNED SYK (SEQ ID NO: 93) | 14 | 5IQP | 196.A,197. A,196.B,197.B, 209.B,210.B | 2, 6, 10 |
| YWHAZ 14-3-3 protein zeta/delta | 194-212 | TAFDEAIAELDTLSEE SYK (SEQ ID NO: 94) | 13 14 | 5D2D | 196.A,197.A, 200.A,203.A, 211.A,194.B, 198.B, 211.B,212.B | 1,6, 13, 19 |

TABLE 3

| Accession # | Protein Name | Labeled Peptide | Peptide Sequence | Probes | PDB | Annotated Functional Site | Estimated Distance from Site | SEQ ID NO: |
|---|---|---|---|---|---|---|---|---|
| P24666 | ACP1 Low molecular weight phosphotyrosine protein phosp | 42-59 | VDSAATSGYEIG NPPDYR | 13 | 3N81 | ACT_SITE 13 13, ACT_SITE 19 19, ACT_SITE 130 130 | 2.995 | 1 |
| Q8NI60 | ADCK3 Chaperone | 277-295 | LGQMLSIQDDAFI NPHLAK | 14 | 4PED | NP_BIND 336 344, | 2.639 | 2 |

TABLE 3-continued

| Accession # | Protein Name | Labeled Peptide | Peptide Sequence | Probes | PDB | Annotated Functional Site | Estimated Distance from Site | SEQ ID NO: |
|---|---|---|---|---|---|---|---|---|
| | activity of bc1 complex-like, mitochondr | | | | | ACT_SITE 488 488, BINDING 358 358 | | |
| P55263 | ADK Adenosine kinase | 209-224 | IFTLNLSAPFISQFYK | 2 | 4O1L | ACT_SITE 317 317, METAL 49 49, METAL 147 147, METAL 148 148 | 5.239 | 3 |
| P30520 | ADSS Adenylosuccinate synthetase isozyme 2 | 431-441 | FIEDELQIPVK | 14 | 2V40 | NP_BIND 39 45, NP_BIND 67 69, NP_BIND 362 364, NP_BIND 444 447, ACT_SITE 40 40, ACT_SITE 68 68, METAL 40 40, METAL 67 67, BINDING 40 40, BINDING 162 162, BINDING 176 176, BINDING 255 255, BINDING 270 270, BINDING 334 334, BINDING 336 336 | 6.392 | 4 |
| O95831 | AIFM1 Apoptosis-inducing factor 1, mitochondrial | 475-510 | PYWHQSMFWSDLGPDVGYEAIGLVDSSLPTVGVFAK | 3 2 4 6 | 4LII | NP_BIND 138 142, NP_BIND 164 165, NP_BIND 454 455, BINDING 172 172, BINDING 177 177, BINDING 233 233, BINDING 285 285, BINDING 438 438, BINDING 483 483 | 0 | 5 |
| P49419 | ALDH7A1 Alpha-aminoadipic semialdehyde dehydrogenase | 139-162 | ILVEGVGEVQEYVDICDYAVGLSR | 13 8 | 4ZUL | NP_BIND 274 279, ACT_SITE 296 296, ACT_SITE 330 330, SITE 195 195 | 4.14 | 6 |
| P18085 | ARF4 ADP-ribosylation factor 4 | 39-59 | LGEIVTTIPTIGFN | 13 3 | 1Z6X | NP_BIND 24 31, NP_BIND 67 71, | 2.742 | 7 |
| | | | VETVEYK | 2 8 | | | | |

TABLE 3-continued

| Accession # | Protein Name | Labeled Peptide | Peptide Sequence | Probes | PDB | Annotated Functional Site | Estimated Distance from Site | SEQ ID NO: |
|---|---|---|---|---|---|---|---|---|
| | | | | | | NP_BIND 126 129 | | |
| P84085 | ARF5 ADP-ribosylation factor 5 | 39-59 | LGEIVTTIPTIGFNVETVEYK | 13 3 4 2 8 | 2B6H | NP_BIND 24 31, NP_BIND 67 71, NP_BIND 126 129 | 2.639 | 8 |
| P40616 | ARL1 ADP-ribosylation factor-like protein 1 | 163-178 | GTGLDEAMEWLVETLK | 14 13 | 4DCN | NP_BIND 24 31, NP_BIND 45 48, NP_BIND 67 71, NP_BIND 126 129, NP_BIND 160 161, METAL 31 31, METAL 48 48, BINDING 70 70 | 3.491 | 9 |
| P40616 | ARL1 ADP-ribosylation factor-like protein 1 | 37-59 | LQVGEVVTTIPTIGFNVETVTYK | 13 | 4DCN | NP_BIND 24 31, NP_BIND 45 48, NP_BIND 67 71, NP_BIND 126 129, NP_BIND 160 161, METAL 31 31, METAL 48 48, BINDING 70 70 | 0 | 10 |
| P31939 | ATIC Bifunctional purine biosynthesis protein PURH | 178-194 | AFTHTAQYDEAISDYFR | 13 | 1PKX | NP_BIND 12 14, NP_BIND 34 34, NP_BIND 64 67, NP_BIND 101 104, NP_BIND 125 127, ACT_SITE 137 137, ACT_SITE 267 267, BINDING 316 316, BINDING 339 339, BINDING 431 431, BINDING 451 451, BINDING 541 541, BINDING 588 588, SITE 266 266 | 2.81 | 11 |
| Q13867 | BLMH Bleomycin hydrolase | 111-124 | CYFFLSAFVDTAQR | 14 | 1CB5 | ACT_SITE 73 73, ACT_SITE 372 372, ACT_SITE 396 396 | 15.919 | 12 |

TABLE 3-continued

| Accession # | Protein Name | Labeled Peptide | Peptide Sequence | Probes | PDB | Annotated Functional Site | Estimated Distance from Site | SEQ ID NO: |
|---|---|---|---|---|---|---|---|---|
| Q13867 | BLMH Bleomycin hydrolase | 203-218 | GEISATQDVMME EIFR | 13 | 1CB5 | ACT_SITE 73 73, ACT_SITE 372 372, ACT_SITE 396 396 | 19.295 | 13 |
| P27797 | CALR Calreticulin | 323-351 | SGTIFDNFLITND EAYAEEFGNETW GVTK | 13 9 6 | 3POW | METAL 26 26, METAL 62 62, METAL 64 64, METAL 328 328, BINDING 109 109, BINDING 111 111, BINDING 128 128, BINDING 135 135, BINDING 317 317 | 0 | 14 |
| P27797 | CALR Calreticulin | 99-111 | HEQNEDCGGGYV K | 6 | 3POW | METAL 26 26, METAL 62 62, METAL 64 64, METAL 328 328, BINDING 109 109, BINDING 111 111, BINDING 128 128, BINDING 135 135, BINDING 317 317 | 0 | 15 |
| P07384 | CAPN1 Calpain-1 catalytic subunit | 175-193 | LVFVHSAEGNEF WSALLEK | 14 | 2ARY | ACT_SITE 115 115, ACT_SITE 272 272, ACT_SITE 296 296, SITE 15 16, SITE 27 28 | 7.409 | 16 |
| P12277 | CKB Creatine kinase B-type | 14-32 | FPAEDEFPDLSAH NNHMAK | 3 | 3B6R | NP_BIND 128 132, NP_BIND 320 325, BINDING 72 72, BINDING 130 130, BINDING 132 132, BINDING 191 191, BINDING 232 232, BINDING 236 236, BINDING 285 285, BINDING 292 292, BINDING 320 320, BINDING 335 335 | 2.797 | 17 |

TABLE 3-continued

| Accession # | Protein Name | Labeled Peptide | Peptide Sequence | Probes | PDB | Annotated Functional Site | Estimated Distance from Site | SEQ ID NO: |
|---|---|---|---|---|---|---|---|---|
| P12277 | CKB Creatine kinase B-type | 157-172 | LAVEALSSLDGDLAGR | 13 | 3B6R | NP_BIND 128 132, NP_BIND 320 325, BINDING 72 72, BINDING 130 130, BINDING 132 132, BINDING 191 191, BINDING 232 232, BINDING 236 236, BINDING 285 285, BINDING 292 292, BINDING 320 320, BINDING 335 335 | 7.719 | 18 |
| P12277 | CKB Creatine kinase B-type | 224-236 | TFLVWVNEEDHLR | 3 | 3B6R | NP_BIND 128 132, NP_BIND 320 325, BINDING 72 72, BINDING 130 130, BINDING 132 132, BINDING 191 191, BINDING 232 232, BINDING 236 236, BINDING 285 285, BINDING 292 292, BINDING 320 320, BINDING 335 335 | 0 | 19 |
| P12277 | CKB Creatine kinase B-type | 253-265 | FCTGLTQIETLFK | 13 | 3B6R | NP_BIND 128 132, NP_BIND 320 325, BINDING 72 72, BINDING 130 130, BINDING 132 132, BINDING 191 191, BINDING 232 232, BINDING 236 236, BINDING 285 285, BINDING 292 292, BINDING 320 320, BINDING 335 335 | 3.569 | 20 |

TABLE 3-continued

| Accession # | Protein Name | Labeled Peptide | Peptide Sequence | Probes | PDB | Annotated Functional Site | Estimated Distance from Site | SEQ ID NO: |
|---|---|---|---|---|---|---|---|---|
| P12277 | CKB Creatine kinase B-type | 342-358 | LGFSEVELVQMVVDGVK | 3 | 3B6R | NP_BIND 128 132, NP_BIND 320 325, BINDING 72 72, BINDING 130 130, BINDING 132 132, BINDING 191 191, BINDING 232 232, BINDING 236 236, BINDING 285 285, BINDING 292 292, BINDING 320 320, BINDING 335 335 | 4.632 | 21 |
| P12277 | CKB Creatine kinase B-type | 367-381 | LEQGQAIDDLMPAQK | 13 | 3B6R | NP_BIND 128 132, NP_BIND 320 325, BINDING 72 72, BINDING 130 130, BINDING 132 132, BINDING 191 191, BINDING 232 232, BINDING 236 236, BINDING 285 285, BINDING 292 292, BINDING 320 320, BINDING 335 335 | 15.156 | 22 |
| P12532 | CKMT1B Creatine kinase U-type, mitochondrial | 257-269 | SFLIWVNEEDHTR | 3 | 1QK1 | NP_BIND 161 165, NP_BIND 353 358, BINDING 224 224, BINDING 269 269, BINDING 325 325, BINDING 368 368 | 0 | 2 |
| Q16740 | CLPP Putative ATP-dependent Clp protease proteolytic su | 215-226 | QSLQVIESAMER | 6 | 1TG6 | ACT_SITE 153 153, ACT_SITE 178 178 | 3.045 | 24 |
| P48729 | CSNK1A1 Casein kinase I isoform alpha | 84-106 | DYNVLVMDLLGPSLEDLFNFCSR | 14 | 5FQD | NP_BIND 23 31, ACT_SITE 136 136, BINDING 46 46 | 2.833 | 25 |

TABLE 3-continued

| Accession # | Protein Name | Labeled Peptide | Peptide Sequence | Probes | PDB | Annotated Functional Site | Estimated Distance from Site | SEQ ID NO: |
|---|---|---|---|---|---|---|---|---|
| P67870 | CSNK2B Casein kinase II subunit beta | 112-134 | VYCENQPMLPIG LSDIPGEAMVK | 14 | 4NH1 | METAL 109 109, METAL 114 114, METAL 137 137, METAL 140 140 | 0 | 26 |
| P07858 | CTSB Cathepsin B | 315-331 | GQDHCGIESEVV AGIPR | 13 4 2 9 | 3K9M | ACT_SITE 108 108, ACT_SITE 278 278, ACT_SITE 298 298 | 6.662 | 27 |
| P07339 | CTSD Cathepsin D | 236-253 | DPDAQPGGELML GGTDSK | 9 | 4OD9 | ACT_SITE 97 97, ACT_SITE 295 295 | 11.321 | 28 |
| P07339 | CTSD Cathepsin D | 288-309 | EGCEAIVDTGTSL MVGPVDEVR | 13 14 15 4 6 9 8 | 4OD9 | ACT_SITE 97 97, ACT_SITE 295 295 | 0 | 29 |
| P07339 | CTSD Cathepsin D | 314-331 | AIGAVPLIQGEY MIPCEK | 14 15 3 2 4 13 6 9 8 | 4OD9 | ACT_SITE 97 97, ACT_SITE 295 295 | 13.281 | 30 |
| P00387 | CYB5R3 NADH-cytochrome b5 reductase 3 | 235-241 | LWYTLDR | 3 | 1UMK | NP_BIND 132 147, NP_BIND 171 206 | 2.96 | 31 |
| Q16698 | DECR1 2,4-dienoyl-CoA reductase, mitochondrial | 299-315 | FDGGEEVLISGEF NDLR | 6 | 1W6U | NP_BIND 66 71, NP_BIND 240 243, ACT_SITE 199 199, BINDING 91 91, BINDING 91 91, BINDING 117 117, BINDING 119 119, BINDING 149 149, BINDING 157 157, BINDING 214 214, BINDING 251 251 | 2.779 | 32 |
| Q08211 | DHX9 ATP-dependent RNA helicase A | 448-456 | ISAVSVAER | 3 | 3LLM | NP_BIND 411 419 | 3.525 | 33 |
| P09622 | DLD Dihydrolipoyl dehydrogenase, mitochondrial | 450-482 | VLGAHILGPGAG EMVNEAALALEY GASCEDIAR | 14 4 13 | 3RNM | NP_BIND 71 80, NP_BIND 183 185, NP_BIND 220 227, NP_BIND 361 364, ACT_SITE 487 487, BINDING 89 89, BINDING 154 154, | 6.842 | 34 |

TABLE 3-continued

| Accession # | Protein Name | Labeled Peptide | Peptide Sequence | Probes | PDB | Annotated Functional Site | Estimated Distance from Site | SEQ ID NO: |
|---|---|---|---|---|---|---|---|---|
| | | | | | | BINDING 243 243, BINDING 278 278, BINDING 314 314, BINDING 355 355 | | |
| Q13011 | ECH1 Delta(3,5)-Delta(2,4)-dienoyl-CoA isomerase, mitoc | 113-131 | MFTAGIDLMDM ASDILQPK | 6 | 2VRE | BINDING 174 174, SITE 197 197, SITE 205 205 | 3.9 | 35 |
| Q13011 | ECH1 Delta(3,5)-Delta(2,4)-dienoyl-CoA isomerase, mitoc | 149-158 | YQETFNVIER | 6 | 2VRE | BINDING 174 174, SITE 197 197, SITE 205 205 | 2.823 | 36 |
| Q13011 | ECH1 Delta(3,5)-Delta(2,4)-dienoyl-CoA isomerase, mitoc | 197-211 | EVDVGLAADVG TLQR | 13 14 15 3 4 6 8 | 2VRE | BINDING 174 174, SITE 197 197, SITE 205 205 | 0 | 37 |
| P60842 | EIF4A1 Eukaryotic initiation factor 4A-I | 178-190 | MFVLDEADEMLS R | 13 | 2ZU6 | NP_BIND 76 83 | 2.797 | 38 |
| P60842 | EIF4A1 Eukaryotic initiation factor 4A-I | 69-82 | GYDVIAQAQSGT GK | 14 13 9 6 | 2ZU | NP_BIND 76 83 | 0 | 39 |
| Q14240 | EIF4A2 Eukaryotic initiation factor 4A-II | 70-83 | GYDVIAQAQSGT GK | 13 | 3B0R | NP_BIND 77 84 | 0 | 40 |
| P38117 | ETFB Electron transfer flavoprotein subunit beta | 36-51 | HSMNPFCEIAVEE AVR | 3 | 2A1T | BINDING 16 16 | 5.189 | 41 |
| P22830 | FECH Fen-ochelatase, mitochondrial | 254-272 | SEVVILFSAHSLP MSVVNR | 4 | 3HCN | ACT_SITE 230 230, ACT_SITE 383 383, METAL 196 196, METAL 403 403, METAL 406 406, METAL 411 411 | 3.373 | 42 |
| P06280 | GLA Alpha-galactosidase A | 241-252 | SILDWTSFNQER | 9 | 3S5Z | ACT_SITE 170 170, AC_SITE 231 231 | 5.4 | 43 |
| P06280 | GLA Alpha-galactosidase A | 50-67 | FMCNLDCQEEPD SCISEK | 9 | 3S5Z | ACT_SITE 170 170, ACT_SITE 231 231 | 8.622 | 44 |
| P06280 | GLA Alpha-galactosidase | 68-82 | LFMEMAELMVSE GWK | 4 | 3S5Z | ACT_SITE 170 170, | 14.579 | 45 |

| Accession # | Protein Name | Labeled Peptide | Peptide Sequence | Probes | PDB | Annotated Functional Site | Estimated Distance from Site | SEQ ID NO: |
|---|---|---|---|---|---|---|---|---|
| | A | | | | | ACT_SITE 231 231 | | |
| P16278 | GLB1 Beta-galactosidase | 286-299 | TEAVASSLYDILAR | 9 | 3THC | ACT_SITE 188 188, ACT_SITE 268 268 | 7.48 | 46 |
| Q04760 | GLO1 Lactoyl-glutathione-lyase | 160-179 | GLAFIQDPDGYWIEILNPNK | 14 | 3W0T | ACT_SITE 173 173, METAL 34 34, METAL 100 100, METAL 127 127, METAL 173 173, BINDING 34 34, BINDING 38 38, BINDING 104 104, BINDING 123 123, BINDING 127 127 | 0 | 47 |
| P00367 | GLUD1 Glutamate dehydrogenase 1, mitochondrial | 152-162 | YSTDVSVDEVK | 6 | 1L1F | NP_BIND 141 143, ACT_SITE 183 183, BINDING 147 147, BINDING 171 171, BINDING 176 176, BINDING 252 252, BINDING 266 266, BINDING 270 270, BINDING 319 319, BINDING 322 322, BINDING 438 438, BINDING 444 444, BINDING 450 450, BINDING 516 516 | 3.908 | 48 |
| P00367 | GLUD1 Glutamate dehydrogenase 1, mitochondrial | 481-496 | HGGTIPIVPTAEFQDR | 6 | 1L1F | NP_BIND 141 143, ACT_SITE 183 183, BINDING 147 147, BINDING 171 171, BINDING 176 176, BINDING 252 252, BINDING 266 266, BINDING 270 270, BINDING 319 319, BINDING 322 322, | 10.438 | 49 |

TABLE 3-continued

| Accession # | Protein Name | Labeled Peptide | Peptide Sequence | Probes | PDB | Annotated Functional Site | Estimated Distance from Site | SEQ ID NO: |
|---|---|---|---|---|---|---|---|---|
| | | | | | | BINDING 438 438, BINDING 444 444, BINDING 450 450, BINDING 516 516 | | |
| Q9H4A6 | GOLPH3 Golgi phosphoprotein 3 | 75-90 | EGYTSFWNDCISSGLR | 14 | 3KN1 | BINDING 81 81, BINDING 90 90, BINDING 171 171, BINDING 174 174 | 0 | 50 |
| P09211 | GSTP1 Glutathione S-transferase P | 56-71 | FQDGDLTLYQSNTILR | 2 | 2A2R | BINDING 8 8, BINDING 14 14, BINDING 39 39, BINDING 45 45 | 3.198 | 51 |
| P69905 | HBA2 Hemoglobin subunit alpha | 18-32 | VGAHAGEYGAEALER | 4 | 4X0L | METAL 59 59, METAL 88 88, SITE 12 12, SITE 57 57, SITE 61 61, SITE 91 91, SITE 100 100 | 3.717 | 52 |
| P69905 | HBA2 Hemoglobin subunit alpha | 94-100 | VDPVNFK | 4 | 4X0L | METAL 59 59, METAL 88 88, SITE 12 12, SITE 57 57, SITE 61 61, SITE 91 91, SITE 100 100 | 0 | 53 |
| P06865 | HEXA Beta-hexosaminidase subunit alpha | 489-499 | LTSDLTFAYER | 9 | 2GJX | ACT_SITE 323 323 | 28.463 | 54 |
| P30519 | HMOX2 Heme oxygenase 2 | 48-55 | AENTQFVK | 15 14 3 4 2 6 8 | 4WMB | METAL 45 45 | 3.21 | 55 |
| P30519 | HMOX2 Heme oxygenase 2 | 69-87 | LATTALYFTYSALEEEMER | 14 | 4WMH | METAL 45 45 | 11.935 | 56 |
| P51659 | HSD17B4 multifunctional enzyme type 2 | 169-183 | LGLLGLANSLAIEGR | 3 | 1ZBQ | NP_BIND 13 37, NP_BIND 75 76, NP_BIND 164 168, NP_BIND 196 199, ACT_SITE 164 164, BINDING 21 21, BINDING 40 40, BINDING 99 99, BINDING 151 151, BINDING 435 435, BINDING | 1.327 | 57 |

TABLE 3-continued

| Accession # | Protein Name | Labeled Peptide | Peptide Sequence | Probes | PDB | Annotated Functional Site | Estimated Distance from Site | SEQ ID NO: |
|---|---|---|---|---|---|---|---|---|
| | | | | | | 533 533, BINDING 563 563, BINDING 706 706, BINDING 724 724 | | |
| P08238 | HSP90AB1 Heat shock protein HSP 90-beta | 360-378 | VFIMDSCDELIPE YLNFIR | 14 | 13 3PRY | BINDING 46 46, BINDING 88 88, BINDING 107 107, BINDING 133 133, BINDING 392 392 | 12.676 | 58 |
| P08238 | HSP90AB1 Heat shock protein HSP 90-beta | 507-526 | GFEVVYMTEPID EYCVQQLK | 13 | 14 3PRY | BINDING 46 46, BINDING 88 88, BINDING 107 107, BINDING 133 133, BINDING 392 392 | 35.151 | 59 |
| P14625 | HSP90B1 Endoplasmin | 117-135 | LISLTDENALSGN EELTVK | 9 | 4NH9 | BINDING 107 107, BINDING 149 149, BINDING 162 162, BINDING 168 168, BINDING 199 199, BINDING 448 448 | 3.486 | 60 |
| P14625 | HSP90B1 Endoplasmin | 271-285 | YSQFINFPIYVWS SK | 6 | 4NH9 | BINDING 107 107, BINDING 149 149, BINDING 162 162, BINDING 168 168, BINDING 199 199, BINDING 448 448 | 7.026 | 61 |
| P11142 | HSPA8 Heat shock cognate 71 kDa protein | 113-126 | SFYPEEVSSMVLT K | 13 | 14 3LDQ | NP_BIND 12 15, NP_BIND 202 204, NP_BIND 268 275, NP_BIND 339 342, BINDING 71 71 | 4.637 | 62 |
| P12268 | IMPDH2 Inosine-5-monophosphate dehydrogenase 2 | 110-124 | YEQGFITDPVVLS PK | 13 | 1NF7 | NP_BIND 274 276, NP_BIND 324 326, ACT_SITE 331 331, ACT_SITE 429 429, METAL 326 | 21.6 | 63 |

TABLE 3-continued

| Accession # | Protein Name | Labeled Peptide | Peptide Sequence | Probes | PDB | Annotated Functional Site | Estimated Distance from Site | SEQ ID NO: |
|---|---|---|---|---|---|---|---|---|
| | | | | | | 326, METAL 328 328, METAL 331 331, METAL 500 500, METAL 501 501, METAL 502 502, BINDING 329 329, BINDING 441 441 | | |
| P00338 | LDHA L-lactate dehydrogenase A chain | 43-57 | DLADELALVDVIEDK | 9 | 4JNK | NP_BIND 29 57, ACT_SITE 193 193, BINDING 99 99, BINDING 106 106, BINDING 138 138, BINDING 169 169, BINDING 248 248 | 0 | 64 |
| P07195 | LDHB L-lactate dehydrogenase B chain | 234-244 | MVVESAYEVEK | 4 | 1I0Z | NP_BIND 31 53, ACT_SITE 194 194, BINDING 100 100, BINDING 107 107, BINDING 139 139, BINDING 170 170, BINDING 249 249 | 3.118 | 65 |
| Q99538 | LGMN Legumain | 102-118 | DYTGEDVTPQNFLAVLR | 9 | 4N6O | ACT_SITE 148 148, ACT_SITE 189 189, SITE 323 324 | 10.316 | 66 |
| P09960 | LTA4H Leukotriene A-4 hydrolase | 366-386 | LVVDLTDIDPDVAYSSVPYEK | 13 48 | 3U9W | ACT_SITE 297 297, ACT_SITE 384 384, METAL 296 296, METAL 300 300, METAL 319 319, SITE 376 376, SITE 379 379 | 0 | 67 |
| P43490 | NAMPT Nicotinamide phosphoribosyl transferase | 175-189 | YLLETSGNLDGLEYK | 13 14 15 3 6 8 | 4LVF | BINDING 196 196, BINDING 219 219, BINDING 247 247, BINDING 311 311, BINDING 384 384, BINDING 392 392 | 9.786 | 68 |

TABLE 3-continued

| Accession # | Protein Name | Labeled Peptide | Peptide Sequence | Probes | PDB | Annotated Functional Site | Estimated Distance from Site | SEQ ID NO: |
|---|---|---|---|---|---|---|---|---|
| P06748 | NPM1 Nucleophosmin | 55-73 | DELHIVEAEAMN YEGSPIK | 13 | 2P1B | SITE 55 55, SITE 80 80, SITE 175 176 | 0 | 69 |
| P06748 | NPM1 Nucleophosmin | 81-101 | MSVQPTVSLGGF EITPPVVLR | 13 | 2P1B | SITE 55 55, SITE 80 80, SITE 175 176 | 1.327 | 70 |
| P22061 | PCMT1 Protein-L-isoaspartate(D-aspartate) O-methyhransf | 179-197 | LILPVGPAGGNQ MLEQYDK | 14 3 2 | 1I1N | ACT_SITE 60 60 | 8.729 | 71 |
| P11177 | PDHB Pyruvate dehydrogenase E1 component subunit beta, | 53-68 | VFLLGEEVAQYD GAYK | 13 14 3 2 | 3EXE | BINDING 89 89 | 2.492 | 72 |
| P00558 | PGK1 Phosphoglycerate kinase 1 | 333-350 | QIVWNGPVGVFE WEAFAR | 3 | 2WZB | NP_BIND 373 376, BINDING 39 39, BINDING 123 123, BINDING 171 171, BINDING 220 220, BINDING 313 313, BINDING 344 344 | 0 | 73 |
| P14618 | PKM Pyruyate kinase isozymes M1/M2 | 174-186 | IYVDDGLISLQVK | 2 9 | 4FXF | NP_BIND 75 78, METAL 75 75, METAL 77 77, METAL 113 113, METAL 114 114, METAL 272 272, METAL 296 296, BINDING 70 70, BINDING 73 73, BINDING 106 106, BINDING 120 120, BINDING 207 207, BINDING 270 270, BINDING 295 295, BINDING 296 296, BINDING 328 328, BINDING 464 464, BINDING 482 482, BINDING 489 489, SITE 270 270, SITE 433 433 | 3.318 | 74 |

TABLE 3-continued

| Accession # | Protein Name | Labeled Peptide | Peptide Sequence | Probes | PDB | Annotated Functional Site | Estimated Distance from Site | SEQ ID NO: |
|---|---|---|---|---|---|---|---|---|
| P14618 | PKM Pyruvate kinase isozymes M1/M2 | 401-422 | LAPITSDPTEATAVGAVEASFK | 2 | 9 4FXF | NP_BIND 75 78, METAL 75 75, METAL 77 77, METAL 113 113, METAL 114 114, METAL 272 272, METAL 296 296, BINDING 70 70, BINDING 73 73, BINDING 106 106, BINDING 120 120, BINDING 207 207, BINDING 270 270, BINDING 295 295, BINDING 296 296, BINDING 328 328, BINDING 464 464, BINDING 482 482, BINDING 489 489, SITE 270 270, SITE 433 433 | 9.657 | 75 |
| P16435 | POR NADPH--cytochrome P450 reductase | 369-382 | TALTYYLDITNPPR | 13 | 14 3QFS | NP_BIND 86 91, NP_BIND 138 141, NP_BIND 173 182, NP_BIND 454 457, NP_BIND 472 474, NP_BIND 488 491, NP_BIND 596 597, NP_BIND 602 606, BINDING 208 208, BINDING 298 298, BINDING 424 424, BINDING 478 478, BINDING 535 535, BINDING 638 638, BINDING 676 676 | 3.068 | 76 |
| P62136 | PPP1CA Serine/threonine-protein phosphatase | 133-141 | IYGFYDECK | 2 | 4XPN | ACT_SITE 125 125, METAL 64 64, METAL 66 66, | 4.098 | 77 |

TABLE 3-continued

| Accession # | Protein Name | Labeled Peptide | Peptide Sequence | Probes | PDB | Annotated Functional Site | Estimated Distance from Site | SEQ ID NO: |
|---|---|---|---|---|---|---|---|---|
| | PP1-alpha cat | | | | | METAL 92 92, METAL 92 92, METAL 92 92, METAL 124 124, METAL 124 124, METAL 173 173, METAL 173 173, METAL 248 248, METAL 248 248 | | |
| P36873 | PPP1CC Serine/ threonine- protein phosphatase PP1-gamma cat | 133-141 | IYGFYDECK | 2 | 4UT2 | ACT_SITE 125 125, METAL 64 64, METAL 66 66, METAL 92 92, METAL 92 92, METAL 124 124, METAL 173 173, METAL 248 248, SITE 273 273 | 4.153 | 78 |
| P36873 | PPP1CC Serine/ threonine- protein phosphatase PP1-gamma cat | 44-60 | EIFLSQPILLELEA PLK | 14 | 4UT2 | ACT_SITE 125 125, METAL 64 64, METAL 66 66, METAL 92 92, METAL 92 92, METAL 124 124, METAL 173 173, METAL 248 248, SITE 273 273 | 10.048 | 79 |
| P50897 | PPT1 Palmitoyl- protein thioesterase 1 | 75-101 | TLMEDVENSFFL NVNSQVTTVCQA LAK | 13 14 15 4 2 9 8 | 3GRO | ACT_SITE 115 115, ACT_SITE 233 233, ACT_SITE 289 289 | 9.259 | 80 |
| P32119 | PRDX2 Peroxiredoxin- 2 | 120-127 | TDEGIAYR | 13 | 1QMV | ACT_SITE 51 51 | 2.624 | 81 |
| P28070 | PSMB4 Proteasome subunit beta type-4 | 61-80 | FEGGVVIAADML GSYGSLAR | 6 | 4R3O | ACT_SITE 46 46 | 11.396 | 82 |
| P28074 | PSMB5 Proteasome subunit beta type-5 | 141-150 | LLANMVYQYK | 4 3 6 | 4R3O | ACT_SITE 60 60, BINDING 108 108 | 10.794 | 83 |
| P28074 | PSMB5 Proteasome subunit beta type-5 | 226-239 | DAYSGGAVNLY HVR | 6 | 4R3O | ACT_SITE 60 60, BINDING 108 108 | 2.795 | 84 |
| P28072 | PSMB6 Proteasome subunit beta type-6 | 80-118 | SGSAADTQAVAD AVTYQLGFHSIEL NEPPLVHTAASLF K | 14 3 6 | 4R3O | ACT_SITE 35 35 | 3.784 | 85 |

TABLE 3-continued

| Accession # | Protein Name | Labeled Peptide | Peptide Sequence | Probes | PDB | Annotated Functional Site | Estimated Distance from Site | SEQ ID NO: |
|---|---|---|---|---|---|---|---|---|
| P51149 | RAB7A Ras-related protein Rab-7a | 104-113 | DEFLIQASPR | 14 | 1YHN | NP_BIND 15 22, NP_BIND 34 40, NP_BIND 63 67, NP_BIND 125 128, NP_BIND 156 157 | 8.675 | 86 |
| Q9Y230 | RUVBL2 RuvB-like 2 | 315-330 | ALESDMAPVLIMATNR | 14 | 3UK6 | NP_BIND 77 84 | 3.038 | 87 |
| Q9H7B4 | SMYD3 SET and MYND domain-containing protein 3 | 255-265 | DQYCLECDCFR | 9 | 5HQ8 | BINDING 124 124, BINDING 132 132, BINDING 181 181, BINDING 239 239, BINDING 259 259 | 0 | 88 |
| O14773 | TPP1 Tripeptidyl-peptidase 1 | 521-558 | GCHESCLDEEVEGQGFCSGPGWDPVTGWGTPNFPALLK | 13 14 15 4 9 | 3EDY | ACT_SITE 272 272, ACT_SITE 276 276, ACT_SITE 475 475, METAL 517 517, METAL 518 518, METAL 539 539, METAL 541 541, METAL 543 543 | 0 | 89 |
| Q9BRA2 | TXNDC17 Thioredoxin domain-containing protein 17 | 42477 | YEEVSVSGFEEFHR | 14 | 1WOU | ACT_SITE 43 43, ACT_SITE 46 46, SITE 44 44, SITE 45 45 | 12.278 | 90 |
| P62258 | YWHAE 14-3-3 protein epsilon | 143-153 | EAAENSLVAYK | 13 | 3UBW | SITE 57 57, SITE 130 130 | 2.851 | 91 |
| P62258 | YWHAE 14-3-3 protein epsilon | 197-215 | AAFDDAIAELDTLSEESYK | 13 | 3UBW | SITE 57 57, SITE 130 130 | 14.177 | 92 |
| P27348 | YWHAQ 14-3-3 protein theta | 194-212 | TAFDEAIAELDTLNEDSYK | 14 | 5IQP | SITE 56 56, SITE 127 127 | 14.319 | 93 |
| P63104 | YWHAZ 14-3-3 protein zeta/delta | 194-212 | TAFDEAIAELDTLSEESYK | 14 13 | 5D2D | SITE 56 56, SITE 127 127 | 14.87 | 94 |
| Q9UQ84 | EXO1 Exonuclease 1 | 139-160 | SQGVDCLVAPYEADAQLAYLNK | 13 2 6 9 8 | 3QEB | METAL 30 30, METAL 78 78, METAL 150 150, METAL 152 152, METAL 171 171, METAL 173 173, METAL 225 225 | 0 | 95 |
| P02545 | LMNA Prelamin-A/C | 352-366 | MQQQLDEYQELLDIK | 13 6 | 3V5B | SITE 266 SITE 330 | 28.999 | 96 |

TABLE 3-continued

| Accension # | Protein Name | Labeled Peptide | Peptide Sequence | Probes | PDB | Annotated Functional Site | Estimated Distance from Site | SEQ ID NO: |
|---|---|---|---|---|---|---|---|---|
| | | | | | | 266, SITE 325 330, SITE 646 | 325, 647 | |

Table 4 illustrates exemplary list of proteins identified by a method described herein.

| Accession # | Protein Name |
|---|---|
| P01023 | A2M Alpha-2-macroglobulin |
| Q9NRG9 | AAAS Aladin |
| Q13685 | AAMP Angio-associated migratory cell protein |
| P49588 | AARS Alanine--tRNA ligase, cytoplasmic |
| Q5JTZ9 | AARS2 Alanine--tRNA ligase, mitochondrial |
| Q9NRN7 | AASDHPPT L-aminoadipate-semialdehyde dehydrogenase-phosphop |
| P08183 | ABCB1 Multidrug resistance protein 1 |
| Q9NRK6 | ABCB10 ATP-binding cassette sub-family B member 10, mitoc |
| O75027 | ABCB7 ATP-binding cassette sub-family B member 7, mitoch |
| Q9NUT2 | ABCB8 ATP-binding cassette sub-family B member 8, mitoch |
| P28288 | ABCD3 ATP-binding cassette sub-family D member 3 |
| P61221 | ABCE1 ATP-binding cassette sub-family E member 1 |
| Q8NE71 | ABCF1 ATP-binding cassette sub-family F member 1 |
| Q9UG63 | ABCF2 ATP-binding cassette sub-family F member 2 |
| Q9NUJ1 | ABHD10 Abhydrolase domain-containing protein 10, mitochon |
| Q8N2K0 | ABHD12 Monoacylglycerol lipase ABHD12 |
| O95870 | ABHD16A Abhydrolase domain-containing protein 16A |
| P09110 | ACAA1 3-ketoacyl-CoA thiolase, peroxisomal |
| Q9H845 | ACAD9 Acyl-CoA dehydrogenase family member 9, mitochondr |
| P11310 | ACADM Medium-chain specific acyl-CoA dehydrogenase, mito |
| P45954 | ACADSB Short/branched chain specific acyl-CoA dehydrogena |
| P49748 | ACADVL Very long-chain specific acyl-CoA dehydrogenase, m |
| P24752 | ACAT1 Acetyl-CoA acetyltransferase, mitochondrial |
| Q9BWD1 | ACAT2 Acetyl-CoA acetyltransferase, cytosolic |
| Q9H3P7 | ACBD3 Golgi resident protein GCP60 |
| Q9UKV3 | ACIN1 Apoptotic chromatin condensation inducer in the nu |
| P53396 | ACLY ATP-citrate synthase |
| Q99798 | ACO2 Aconitate hydratase, mitochondrial |
| P49753 | ACOT2 Acyl-coenzyme A thioesterase 2, mitochondrial |
| O00154 | ACOT7 Cytosolic acyl coenzyme A thioester hydrolase |
| Q9Y305 | ACOT9 Acyl-coenzyme A thioesterase 9, mitochondrial |
| Q15067 | ACOX1 Peroxisomal acyl-coenzyme A oxidase 1 |
| P24666 | ACP1 Low molecular weight phosphotyrosine protein phosp |
| P11117 | ACP2 Lysosomal acid phosphatase |
| Q9NPH0 | ACP6 Lysophosphatidic acid phosphatase type 6 |
| P33121 | ACSL1 Long-chain-fatty-acid--CoA ligase 1 |
| O95573 | ACSL3 Long-chain-fatty-acid--CoA ligase 3 |
| O60488 | ACSL4 Long-chain-fatty-acid--CoA ligase 4 |
| Q53FZ2 | ACSM3 Acyl-coenzyme A synthetase ACSM3, mitochondrial |
| P68133 | ACTA1 Actin, alpha skeletal muscle |
| P62736 | ACTA2 Actin, aortic smooth muscle |
| P60709 | ACTB Actin, cytoplasmic 1 |
| Q562R1 | ACTBL2 Beta-actin-like protein 2 |
| P68032 | ACTC1 Actin, alpha cardiac muscle 1 |
| P63261 | ACTG1 Actin, cytoplasmic 2 |
| O96019 | ACTL6A Actin-like protein 6A |
| P12814 | ACTN1 Alpha-actinin-1 |
| Q08043 | ACTN3 Alpha-actinin-3 |
| O43707 | ACTN4 Alpha-actinin-4 |
| P61163 | ACTR1A Alpha-centractin |
| P61160 | ACTR2 Actin-related protein 2 |
| P61158 | ACTR3 Actin-related protein 3 |
| P55265 | ADAR Double-stranded RNA-specific adenosine deaminase |
| Q8NI60 | ADCK3 Chaperone activity of bc1 complex-like, mitochondr |
| Q96D53 | ADCK4 Uncharacterized aarF domain-containing protein kin |
| P35611 | ADD1 Alpha-adducin |
| P55263 | ADK Adenosine kinase |
| Q9BRR6 | ADPGK ADP-dependent glucokinase |
| P30520 | ADSS Adenylosuccinate synthetase isozyme 2 |
| Q9Y4W6 | AFG3L2 AFG3-like protein 2 |
| Q53H12 | AGK Acylglycerol kinase, mitochondrial |
| P35573 | AGL Glycogen debranching enzyme |
| Q99943 | AGPAT1 1-acyl-sn-glycerol-3-phosphate acyltransferase alp |
| Q9NUQ2 | AGPAT5 1-acyl-sn-glycerol-3-phosphate acyltransferase eps |
| Q86UL3 | AGPAT6 Glycerol-3-phosphate acyltransferase 4 |
| O00116 | AGPS Alkyldihydroxyacetonephosphate synthase, peroxisom |
| P23526 | AHCY Adenosylhomocysteinase |
| O43865 | AHCYL1 Putative adenosylhomocysteinase 2 |
| Q96HN2 | AHCYL2 Putative adenosylhomocysteinase 3 |
| O95433 | AHSA1 Activator of 90 kDa heat shock protein ATPase homo |
| O95831 | AIFM1 Apoptosis-inducing factor 1, mitochondrial |
| Q12904 | AIMP1 Aminoacyl tRNA synthase complex-interacting multif |
| Q13155 | AIMP2 Aminoacyl tRNA synthase complex-interacting multif |
| O00170 | AIP AH receptor-interacting protein |
| P54819 | AK2 Adenylate kinase 2, mitochondrial |
| Q92667 | AKAP1 A-kinase anchor protein 1, mitochondrial |
| Q02952 | AKAP12 A-kinase anchor protein 12 |
| O43823 | AKAP8 A-kinase anchor protein 8 |
| Q9ULX6 | AKAP8L A-kinase anchor protein 8-like |
| Q04828 | AKR1C1 Aldo-keto reductase family 1 member C1 |
| P31751 | AKT2 RAC-beta serine/threonine-protein kinase |

| Accession # | Protein Name |
|---|---|
| P54886 | ALDH18A1 Delta-1-pyrroline-5-carboxylate synthase |
| P00352 | ALDH1A1 Retinal dehydrogenase 1 |
| P30837 | ALDH1B1 Aldehyde dehydrogenase X, mitochondrial |
| Q3SY69 | ALDH1L2 Mitochondrial 10-formyltetrahydrofolate dehydrogen |
| P05091 | ALDH2 Aldehyde dehydrogenase, mitochondrial |
| P51648 | ALDH3A2 Fatty aldehyde dehydrogenase |
| Q02252 | ALDH6A1 Methylmalonate-semialdehyde dehydrogenase [acylati |
| P49419 | ALDH7A1 Alpha-aminoadipic semialdehyde dehydrogenase |
| P49189 | ALDH9A1 4-trimethylaminobutyraldehyde dehydrogenase |
| Q9BT22 | ALG1 Chitobiosyldiphosphodolichol beta-mannosyltransfer |
| Q9BV10 | ALG12 Dol-P-Man:Man(7)GlcNAc(2)-PP-Dol alpha-1,6-mannosy |
| Q9Y673 | ALG5 Dolichyl-phosphate beta-glucosyltransferase |
| Q9Y672 | ALG6 Dolichyl pyrophosphate Man9GlcNAc2 alpha-1,3-gluco |
| Q86V81 | ALYREF THO complex subunit 4 |
| Q9UJX4 | ANAPC5 Anaphase-promoting complex subunit 5 |
| Q9UJX3 | ANAPC7 Anaphase-promoting complex subunit 7 |
| Q86XL3 | ANKLE2 Ankyrin repeat and LEM domain-containing protein 2 |
| Q8IZ07 | ANKRD13A Ankyin repeat domain-containing protein 13A |
| Q9NW15 | ANO10 Anoctamin-10 |
| P39687 | ANP32A Acidic leucine-rich nuclear phosphoprotein 32 fami |
| Q92688 | ANP32B Acidic leucine-rich nuclear phosphoprotein 32 fami |
| Q9BTT0 | ANP32E Acidic leucine-rich nuclear phosphoprotein 32 fami |
| P04083 | ANXA1 Annexin A1 |
| P50995 | ANXA11 Annexin A11 |
| P07355 | ANXA2 Annexin A2 |
| P08758 | ANXA5 Annexin A5 |
| P08133 | ANXA6 Annexin A6 |
| P20073 | ANXA7 Annexin A7 |
| Q10567 | AP1B1 AP-1 complex subunit beta-1 |
| P63010 | AP2B1 AP-2 complex subunit beta |
| Q96CW1 | AP2M1 AP-2 complex subunit mu |
| O00203 | AP3B1 AP-3 complex subunit beta-1 |
| O14617 | AP3D1 AP-3 complex subunit delta-1 |
| Q9Y2T2 | AP3M1 AP-3 complex subunit mu-1 |
| P13798 | APEH Acylamino-acid-releasing enzyme |
| Q9BZZ5 | API5 Apoptosis inhibitor 5 |
| Q06481 | APLP2 Amyloid-like protein 2 |
| Q9HDC9 | APMAP Adipocyte plasma membrane-associated protein |
| Q8NCW5 | APOA1BP NAD(P)H-hydrate epimerase |
| Q9UH17 | APOBEC3B Probable DNA dC-dU-editing enzyme APOBEC-3B |
| P02649 | APOE Apolipoprotein E |
| Q9BQE5 | APOL2 Apolipoprotein L2 |
| Q9BUR5 | APOO Apolipoprotein O |
| Q6UXV4 | APOOL Apolipoprotein O-like |
| P05067 | APP Amyloid beta A4 protein |
| P07741 | APRT Adenine phosphoribosyltransferase |
| P10398 | ARAF Serine/threonine-protein kinase A-Raf |
| P48444 | ARCN1 Coatomer subunit delta |
| P84077 | ARF1 ADP-ribosylation factor 1 |
| P61204 | ARF3 ADP-ribosylation factor 3 |
| P18085 | ARF4 ADP-ribosylation factor 4 |
| P84085 | ARF5 ADP-ribosylation factor 5 |
| E7EV62 | ARFGAP1 ADP-ribosylation factor GTPase-activating protein |
| Q8N6H7 | ARFGAP2 ADP-ribosylation factor GTPase-activating protein |
| P53367 | ARFIP1 Arfaptin-1 |
| Q92888 | ARHGEF1 Rho guanine nucleotide exchange factor 1 |
| Q92974 | ARHGEF2 Rho guanine nucleotide exchange factor 2 |
| O14497 | ARID1A AT-rich interactive domain-containing protein 1A |
| P40616 | ARL1 ADP-ribosylation factor-like protein 1 |
| Q8N6S5 | ARL6IP6 ADP-ribosylation factor-like protein 6-interacting |
| Q9NVJ2 | ARL8B ADP-ribosylation factor-like protein 8B |
| Q9NVT9 | ARMC1 Armadillo repeat-containing protein 1 |
| Q8N2F6 | ARMC10 Armadillo repeat-containing protein 10 |
| Q9UH62 | ARMCX3 Armadillo repeat-containing X-linked protein 3 |
| Q13510 | ASAH1 Acid ceramidase |
| Q9UBL3 | ASH2L Set1/Ash2 histone methyltransferase complex subuni |
| O43681 | ASNA1 ATPase ASNA1 |
| P08243 | ASNS Asparagine synthetase [glutamine-hydrolyzing] |
| Q12797 | ASPH Aspartyl/asparaginyl beta-hydroxylase |
| Q8NBU5 | ATAD1 ATPase family AAA domain-containing protein 1 |
| Q9NVI7 | ATAD3A ATPase family AAA domain-containing protein 3A |
| Q5T9A4 | ATAD3B ATPase family AAA domain-containing protein 3B |
| Q5T2N8 | ATAD3C ATPase family AAA domain-containing protein 3C |
| Q7Z3C6 | ATG9A Autophagy-related protein 9A |
| P31939 | ATIC Bifunctional purine biosynthesis protein PURH |
| Q8NHH9 | ATL2 Atlastin-2 |
| Q6DD88 | ATL3 Atlastin-3 |
| Q9HD20 | ATP13A1 Probable cation-transporting ATPase 13A1 |
| P05023 | ATP1A1 Sodium/potassium-transporting ATPase subunit alpha |
| P13637 | ATP1A3 Sodium/potassium-transporting ATPase subunit alpha |
| P54709 | ATP1B3 Sodium/potassium-transporting ATPase subunit beta- |
| P16615 | ATP2A2 Sarcoplasmic/endoplasmic reticulum calcium ATPase |
| Q93084 | ATP2A3 Sarcoplasmic/endoplasmic reticulum calcium ATPase |
| P20020 | ATP2B1 Plasma membrane calcium-transporting ATPase 1 |
| P23634 | ATP2B4 Plasma membrane calcium-transporting ATPase 4 |
| P25705 | ATP5A1 ATP synthase subunit alpha, mitochondrial |
| P06576 | ATP5B ATP synthase subunit beta, mitochondrial |
| P36542 | ATP5C1 ATP synthase subunit gamma, mitochondrial |
| P24539 | ATP5F1 ATP synthase subunit b, mitochondrial |
| O75947 | ATP5H ATP synthase subunit d, mitochondrial |
| O75964 | ATP5L ATP synthase subunit g, mitochondrial |
| P48047 | ATP5O ATP synthase subunit O, mitochondrial |
| Q93050 | ATP6V0A1 V-type proton ATPase 116 kDa subunit a isoform 1 |
| Q9Y487 | ATP6V0A2 V-type proton ATPase 116 kDa subunit a isoform 2 |
| P61421 | ATP6V0D1 V-type proton ATPase subunit d 1 |
| P38606 | ATP6V1A V-type proton ATPase catalytic subunit A |

| Accession # | Protein Name |
|---|---|
| P21281 | ATP6V1B2 V-type proton ATPase subunit B, brain isoform |
| P36543 | ATP6V1E1 V-type proton ATPase subunit E 1 |
| Q9UBB4 | ATXN10 Ataxin-10 |
| Q99700 | ATXN2 Ataxin-2 |
| Q8WWM7 | ATXN2L Ataxin-2-like protein |
| Q9Y679 | AUP1 Ancient ubiquitous protein 1 |
| O14965 | AURKA Aurora kinase A |
| O43505 | B3GNT1 N-acetyllactosaminide beta-1,3-N-acetylglucosaminy |
| O95817 | BAG3 BAG family molecular chaperone regulator 3 |
| O95429 | BAG4 BAG family molecular chaperone regulator 4 |
| Q9UL15 | BAG5 BAG family molecular chaperone regulator 5 |
| P46379 | BAG6 Large proline-rich protein BAG6 |
| Q9UQB8 | BAIAP2 Brain-specific angiogenesis inhibitor 1-associated |
| B0UX83 | BAT3 HLA-B associated transcript 3 |
| B0UXB6 | BAT5 Abhydrolase domain-containing protein 16A |
| Q07812 | BAX Apoptosis regulator BAX |
| Q9NRL2 | BAZ1A Bromodomain adjacent to zinc finger domain protein |
| Q9UIG0 | BAZ1B Tyrosine-protein kinase BAZ1B |
| P51572 | BCAP31 B-cell receptor-associated protein 31 |
| O75934 | BCAS2 Pre-mRNA-splicing factor SPF27 |
| Q9P287 | BCCIP BRCA2 and CDKN1A-interacting protein |
| P12694 | BCKDHA 2-oxoisovalerate dehydrogenase subunit alpha, mito |
| Q9BXK5 | BCL2L13 Bcl-2-like protein 13 |
| Q9NYF8 | BCLAF1 Bcl-2-associated transcription factor 1 |
| Q9Y276 | BCS1L Mitochondrial chaperone BCS1 |
| P55957 | BID BH3-interacting domain death agonist |
| Q13867 | BLMH Bleomycin hydrolase |
| P53004 | BLVRA Biliverdin reductase A |
| P30043 | BLVRB Flavin reductase (NADPH) |
| Q9NSY1 | BMP2K BMP-2-inducible protein kinase |
| Q14137 | BOP1 Ribosome biogenesis protein BOP1 |
| Q6PJG6 | BRAT1 BRCA1-associated ATM activator 1 |
| P25440 | BRD2 Bromodomain-containing protein 2 |
| Q8WY22 | BRI3BP BRI3-binding protein |
| Q8TDN6 | BRIX1 Ribosome biogenesis protein BRX1 homolog |
| Q5VW32 | BROX BRO1 domain-containing protein BROX |
| Q9NW68 | BSDC1 BSD domain-containing protein 1 |
| P35613 | BSG Basigin |
| Q06187 | BTK Tyrosine-protein kinase BTK |
| O60566 | BUB1B Mitotic checkpoint serine/threonine-protein kinase |
| O43684 | BUB3 Mitotic checkpoint protein BUB3 |
| Q13895 | BYSL Bystin |
| Q7L1Q6 | BZW1 Basic leucine zipper and W2 domain-containing prot |
| Q69YU5 | C12orf73 Uncharacterized protein C12orf73 |
| Q9Y224 | C14orf166 UPF0568 protein C14orf166 |
| Q96GQ5 | C16orf58 UPF0420 protein C16orf58 |
| Q9BSF4 | C19orf52 Uncharacterized protein C19orf52 |
| Q4ZIN3 | C19orf6 Membralin |
| E9PFR7 | C1orf27 Protein C1orf27 |
| Q07021 | C1QBP Complement component 1 Q subcomponent-binding prot |
| Q9BQP7 | C20orf72 Uncharacterized protein C20orf72 |
| P30042 | C21orf33 ES1 protein homolog, mitochondrial |
| Q9H6V9 | C2orf43 UPF0554 protein C2orf43 |
| Q8WWC4 | C2orf47 Uncharacterized protein C2orf47, mitochondrial |
| Q96FZ2 | C3orf37 UPF0361 protein C3orf37 |
| Q9H993 | C6orf211 UPF0364 protein C6orf211 |
| Q9H7E9 | C8orf33 UPF0488 protein C8orf33 |
| Q5T6V5 | C9orf64 UPF0553 protein C9orf64 |
| Q9Y376 | CAB39 Calcium-binding protein 39 |
| Q9HB71 | CACYBP Calcyclin-binding protein |
| P27708 | CAD CAD protein |
| Q9BY67 | CADM1 Cell adhesion molecule 1 |
| P05937 | CALB1 Calbindin |
| P62158 | CALM1 Calmodulin |
| P27797 | CALR Calreticulin |
| O43852 | CALU Calumenin |
| Q14012 | CAMK1 Calcium/calmodulin-dependent protein kinase type 1 |
| Q13557 | CAMK2D Calcium/calmodulin-dependent protein kinase type I |
| Q13555 | CAMK2G Calcium/calmodulin-dependent protein kinase type I |
| P27824 | CANX Calnexin |
| P07384 | CAPN1 Calpain-1 catalytic subunit |
| P17655 | CAPN2 Calpain-2 catalytic subunit |
| P04632 | CAPNS1 Calpain small subunit 1 |
| Q14444 | CAPRIN1 Caprin-1 |
| P47756 | CAPZB F-actin-capping protein subunit beta |
| Q86X55 | CARM1 Histone-arginine methyltransferase CARM1 |
| P49589 | CARS Cysteine--tRNA ligase, cytoplasmic |
| P20810 | CAST Calpastatin |
| P04040 | CAT Catalase |
| P35520 | CBS Cystathionine beta-synthase |
| Q13185 | CBX3 Chromobox protein homolog 3 |
| P45973 | CBX5 Chromobox protein homolog 5 |
| Q96G28 | CCDC104 Coiled-coil domain-containing protein 104 |
| O60826 | CCDC22 Coiled-coil domain-containing protein 22 |
| Q96A33 | CCDC47 Coiled-coil domain-containing protein 47 |
| Q96ER9 | CCDC51 Coiled-coil domain-containing protein 51 |
| Q16204 | CCDC6 Coiled-coil domain-containing protein 6 |
| P78371 | CCT2 T-complex protein 1 subunit beta |
| P49368 | CCT3 T-complex protein 1 subunit gamma |
| P50991 | CCT4 T-complex protein 1 subunit delta |
| P48643 | CCT5 T-complex protein 1 subunit epsilon |
| P40227 | CCT6A T-complex protein 1 subunit zeta |
| Q99832 | CCT7 T-complex protein 1 subunit eta |
| P50990 | CCT8 T-complex protein 1 subunit theta |
| O95400 | CD2BP2 CD2 antigen cytoplasmic tail-binding protein 2 |
| P60033 | CD81 CD81 antigen |
| Q9UJX2 | CDC23 Cell division cycle protein 23 homolog |
| P30260 | CDC27 Cell division cycle protein 27 homolog |
| Q16543 | CDC37 Hsp90 co-chaperone Cdc37 |
| P60953 | CDC42 Cell division control protein 42 homolog |
| Q99459 | CDC5L Cell division cycle 5-like protein |
| P19022 | CDH2 Cadherin-2 |
| O14735 | CDIPT CDP-diacylglycerol--inositol 3-phosphatidyltransfe |
| P06493 | CDK1 Cyclin-dependent kinase 1 |
| P24941 | CDK2 Cyclin-dependent kinase 2 |
| P11802 | CDK4 Cyclin-dependent kinase 4 |
| Q96JB5 | CDK5RAP3 CDK5 regulatory subunit-associated protein 3 |
| Q00534 | CDK6 Cyclin-dependent kinase 6 |
| P50750 | CDK9 Cyclin-dependent kinase 9 |
| Q5VV42 | CDKAL1 Threonylcarbamoyladenosine tRNA methylthiotransfer |
| O95674 | CDS2 Phosphatidate cytidylyltransferase 2 |
| Q03701 | CEBPZ CCAAT/enhancer-binding protein zeta |

| Accession # | Protein Name |
|---|---|
| Q9BXW7 | CECR5 Cat eye syndrome critical region protein 5 |
| Q92879 | CELF1 CUGBP Elav-like family member 1 |
| Q5SW79 | CEP170 Centrosomal protein of 170 kDa |
| Q9C0F1 | CEP44 Centrosomal protein of 44 kDa |
| Q9Y6K0 | CEPT1 Choline/ethanolaminephosphotransferase 1 |
| P27544 | CERS1 Ceramide synthase 1 |
| Q96G23 | CERS2 Ceramide synthase 2 |
| Q6ZMG9 | CERS6 Ceramide synthase 6 |
| Q9NX63 | CHCHD3 Coiled-coil-helix-coiled-coil-helix domain-contain |
| O14646 | CHD1 Chromodomain-helicase-DNA-binding protein 1 |
| Q14839 | CHD4 Chromodomain-helicase-DNA-binding protein 4 |
| O14757 | CHEK1 Serine/threonine-protein kinase Chk1 |
| Q8IWX8 | CHERP Calcium homeostasis endoplasmic reticulum protein |
| Q9NZZ3 | CHMP5 Charged multivesicular body protein 5 |
| Q14011 | CIRBP Cold-inducible RNA-binding protein |
| Q9NZ45 | CISD1 CDGSH iron-sulfur domain-containing protein 1 |
| Q8N5K1 | CISD2 CDGSH iron-sulfur domain-containing protein 2 |
| Q8WWK9 | CKAP2 Cytoskeleton-associated protein 2 |
| Q07065 | CKAP4 Cytoskeleton-associated protein 4 |
| P12277 | CKB Creatine kinase B-type |
| P12532 | CKMT1B Creatine kinase U-type, mitochondrial |
| F5H604 | CLASP2 CLIP-associating protein 2 |
| Q96S66 | CLCC1 Chloride channel CLIC-like protein 1 |
| O14967 | CLGN Calmegin |
| O15247 | CLIC2 Chloride intracellular channel protein 2 |
| Q9Y696 | CLIC4 Chloride intracellular channel protein 4 |
| O75503 | CLN5 Ceroid-lipofuscinosis neuronal protein 5 |
| P54105 | CLNS1A Methylosome subunit pICln |
| Q9H078 | CLPB Caseinolytic peptidase B protein homolog |
| Q16740 | CLPP Putative ATP-dependent Clp protease proteolytic su |
| O96005 | CLPTM1 Cleft lip and palate transmembrane protein 1 |
| Q96KA5 | CLPTM1L Cleft lip and palate transmembrane protein 1-like |
| P30085 | CMPK1 UMP-CMP kinase |
| Q99439 | CNN2 Calponin-2 |
| Q15417 | CNN3 Calponin-3 |
| A5YKK6 | CNOT1 CCR4-NOT transcription complex subunit 1 |
| Q9NZN8 | CNOT2 CCR4-NOT transcription complex subunit 2 |
| P09543 | CNP 2,3-cyclic-nucleotide 3-phosphodiesterase |
| Q9BT09 | CNPY3 Protein canopy homolog 3 |
| Q9Y2R0 | COA3 Cytochrome C oxidase assembly factor 3 homolog, mi |
| Q13057 | COASY Bifunctional coenzyme A synthase |
| P21964 | COMT Catechol O-methyltransferase |
| P53618 | COPB1 Coatomer subunit beta |
| P35606 | COPB2 Coatomer subunit beta |
| O14579 | COPE Coatomer subunit epsilon |
| Q9Y678 | COPG1 Coatomer subunit gamma-1 |
| Q9UBF2 | COPG2 Coatomer subunit gamma-2 |
| P61201 | COPS2 COP9 signalosome complex subunit 2 |
| Q9UNS2 | COPS3 COP9 signalosome complex subunit 3 |
| Q9BT78 | COPS4 COP9 signalosome complex subunit 4 |
| Q92905 | COPS5 COP9 signalosome complex subunit 5 |
| Q7L5N1 | COPS6 COP9 signalosome complex subunit 6 |
| Q5HYK3 | COQ5 2-methoxy-6-polyprenyl-1,4-benzoquinol methylase, |
| Q9ULV4 | CORO1C Coronin-1C |
| I3L416 | CORO7 Coronin |
| Q9Y6N1 | COX11 Cytochrome c oxidase assembly protein COX11, mitoc |
| Q7KZN9 | COX15 Cytochrome c oxidase assembly protein COX15 homolo |
| P13073 | COX4I1 Cytochrome c oxidase subunit 4 isoform 1, mitochon |
| P20674 | COX5A Cytochrome c oxidase subunit 5A, mitochondrial |
| O75976 | CPD Carboxypeptidase D |
| Q99829 | CPNE1 Copine-1 |
| O75131 | CPNE3 Copine-3 |
| P36551 | CPOX Coproporphyrinogen-III oxidase, mitochondrial |
| Q9BRF8 | CPPED1 Calcineurin-like phosphoesterase domain-containing |
| Q9UKF6 | CPSF3 Cleavage and polyadenylation specificity factor su |
| Q16630 | CPSF6 Cleavage and polyadenylation specificity factor su |
| Q8N684 | CPSF7 Cleavage and polyadenylation specificity factor su |
| P50416 | CPT1A Carnitine O-palmitoyltransferase 1, liver isoform |
| P23786 | CPT2 Carnitine O-palmitoyltransferase 2, mitochondrial |
| Q9H3G5 | CPVL Probable serine carboxypeptidase CPVL |
| P46108 | CRK Adapter molecule crk |
| P46109 | CRKL Crk-like protein |
| O75390 | CS Citrate synthase, mitochondrial |
| P16989 | CSDA DNA-binding protein A |
| O75534 | CSDE1 Cold shock domain-containing protein E1 |
| P55060 | CSE1L Exportin-2 |
| P41240 | CSK Tyrosine-protein kinase CSK |
| P48729 | CSNK1A1 Casein kinase I isoform alpha |
| P49674 | CSNK1E Casein kinase I isoform epsilon |
| P68400 | CSNK2A1 Casein kinase II subunit alpha |
| P19784 | CSNK2A2 Casein kinase II subunit alpha |
| P67870 | CSNK2B Casein kinase II subunit beta |
| P04080 | CSTB Cystatin-B |
| Q05048 | CSTF1 Cleavage stimulation factor subunit 1 |
| P33240 | CSTF2 Cleavage stimulation factor subunit 2 |
| Q12996 | CSTF3 Cleavage stimulation factor subunit 3 |
| O15320 | CTAGE5 Cutaneous T-cell lymphoma-associated antigen 5 |
| Q13363 | CTBP1 C-terminal-binding protein 1 |
| P32929 | CTH Cystathionine gamma-lyase |
| P35221 | CTNNA1 Catenin alpha-1 |
| P35222 | CTNNB1 Catenin beta-1 |
| O60716 | CTNND1 Catenin delta-1 |
| P17812 | CTPS1 CTP synthase 1 |
| P10619 | CTSA Lysosomal protective protein |
| P07858 | CTSB Cathepsin B |
| P53634 | CTSC Dipeptidyl peptidase 1 |
| P07339 | CTSD Cathepsin D |
| Q14247 | CTTN Src substrate cortactin |
| Q13620 | CUL4B Cullin-4B |
| O60888 | CUTA Protein CutA |
| Q69YN2 | CWF19L1 CWF19-like protein 1 |
| Q9BVG4 | CXorf26 UPF0368 protein Cxorf26 |
| P00167 | CYB5A Cytochrome b5 |
| O43169 | CYB5B Cytochrome b5 type B |
| Q8WUJ1 | CYB5D2 Neuferricin |
| Q9UHQ9 | CYB5R1 NADH-cytochrome b5 reductase 1 |
| P00387 | CYB5R3 NADH-cytochrome b5 reductase 3 |
| P08574 | CYC1 Cytochrome c1, heme protein, mitochondrial |

| Accession # | Protein Name |
|---|---|
| Q7L576 | CYFIP1 Cytoplasmic FMR1-interacting protein 1 |
| Q6UW02 | CYP20A1 Cytochrome P450 20A1 |
| Q16850 | CYP51A1 Lanosterol 14-alpha demethylase |
| P51398 | DAP3 28S ribosomal protein S29, mitochondrial |
| P14868 | DARS Aspartate--tRNA ligase, cytoplasmic |
| Q6PI48 | DARS2 Aspartate--tRNA ligase, mitochondrial |
| Q96EP5 | DAZAP1 DAZ-associated protein 1 |
| Q16643 | DBN1 Drebrin |
| Q9UJU6 | DBNL Drebrin-like protein |
| P61962 | DCAF7 DDB1- and CUL4-associated factor 7 |
| Q8WVC6 | DCAKD Dephospho-CoA kinase domain-containing protein |
| P81605 | DCD Dermcidin |
| Q14203 | DCTN1 Dynactin subunit 1 |
| Q13561 | DCTN2 Dynactin subunit 2 |
| Q9UJW0 | DCTN4 Dynactin subunit 4 |
| Q9H773 | DCTPP1 dCTP pyrophosphatase 1 |
| Q92564 | DCUN1D4 DCN1-like protein 4 |
| Q7Z4W1 | DCXR L-xylulose reductase |
| Q16531 | DDB1 DNA damage-binding protein 1 |
| P39656 | DDOST Dolichyl-diphosphooligosaccharide--protein glycosy |
| Q96HY6 | DDRGK1 DDRGK domain-containing protein 1 |
| Q13206 | DDX10 Probable ATP-dependent RNA helicase DDX10 |
| Q92841 | DDX17 Probable ATP-dependent RNA helicase DDX17 |
| Q9NVP1 | DDX18 ATP-dependent RNA helicase DDX18 |
| Q9UHI6 | DDX20 Probable ATP-dependent RNA helicase DDX20 |
| Q9NR30 | DDX21 Nucleolar RNA helicase 2 |
| Q9BUQ8 | DDX23 Probable ATP-dependent RNA helicase DDX23 |
| Q9GZR7 | DDX24 ATP-dependent RNA helicase DDX24 |
| O00148 | DDX39A ATP-dependent RNA helicase DDX39A |
| Q13838 | DDX39B Spliceosome RNA helicase DDX39B |
| O00571 | DDX3X ATP-dependent RNA helicase DDX3X |
| Q86XP3 | DDX42 ATP-dependent RNA helicase DDX42 |
| Q7L014 | DDX46 Probable ATP-dependent RNA helicase DDX46 |
| P17844 | DDX5 Probable ATP-dependent RNA helicase DDX5 |
| Q9BQ39 | DDX50 ATP-dependent RNA helicase DDX50 |
| Q8TDD1 | DDX54 ATP-dependent RNA helicase DDX54 |
| P26196 | DDX6 Probable ATP-dependent RNA helicase DDX6 |
| Q16698 | DECR1 2,4-dienoyl-CoA reductase, mitochondrial |
| O15121 | DEGS1 Sphingolipid delta(4)-desaturase DES1 |
| Q9BUN8 | DERL1 Derlin-1 |
| Q9BSY9 | DESI2 Desumoylating isopeptidase 2 |
| O00273 | DFFA DNA fragmentation factor subunit alpha |
| Q96DF8 | DGCR14 Protein DGCR14 |
| Q15392 | DHCR24 Delta(24)-sterol reductase |
| P00374 | DHFR Dihydrofolate reductase |
| P49366 | DHPS Deoxyhypusine synthase |
| Q9Y394 | DHRS7 Dehydrogenase/reductase SDR family member 7 |
| Q6IAN0 | DHRS7B Dehydrogenase/reductase SDR family member 7B |
| O43143 | DHX15 Putative pre-mRNA-splicing factor ATP-dependent RN |
| Q7Z478 | DHX29 ATP-dependent RNA helicase DHX29 |
| Q7L2E3 | DHX30 Putative ATP-dependent RNA helicase DHX30 |
| Q9H2U1 | DHX36 Probable ATP-dependent RNA helicase DHX36 |
| Q14562 | DHX8 ATP-dependent RNA helicase DHX8 |
| Q08211 | DHX9 ATP-dependent RNA helicase A |
| Q9NR28 | DIABLO Diablo homolog, mitochondrial |
| O60610 | DIAPH1 Protein diaphanous homolog 1 |
| Q9Y2L1 | DIS3 Exosome complex exonuclease RRP44 |
| P10515 | DLAT Dihydrolipoyllysine-residue acetyltransferase comp |
| P09622 | DLD Dihydrolipoyl dehydrogenase, mitochondrial |
| Q15398 | DLGAP5 Disks large-associated protein 5 |
| P31689 | DNAJA1 DnaJ homolog subfamily A member 1 |
| O60884 | DNAJA2 DnaJ homolog subfamily A member 2 |
| Q96EY1 | DNAJA3 DnaJ homolog subfamily A member 3, mitochondrial |
| P25685 | DNAJB1 DnaJ homolog subfamily B member 1 |
| Q9NXW2 | DNAJB12 DnaJ homolog subfamily B member 12 |
| Q96KC8 | DNAJC1 DnaJ homolog subfamily C member 1 |
| Q8IXB1 | DNAJC10 DnaJ homolog subfamily C member 10 |
| Q9NVH1 | DNAJC11 DnaJ homolog subfamily C member 11 |
| Q99543 | DNAJC2 DnaJ homolog subfamily C member 2 |
| Q9H3Z4 | DNAJC5 DnaJ homolog subfamily C member 5 |
| Q99615 | DNAJC7 DnaJ homolog subfamily C member 7 |
| O75937 | DNAJC8 DnaJ homolog subfamily C member 8 |
| Q8WXX5 | DNAJC9 DnaJ homolog subfamily C member 9 |
| O00115 | DNASE2 Deoxyribonuclease-2-alpha |
| Q05193 | DNM1 Dynamin-1 |
| O00429 | DNM1L Dynamin-1-like protein |
| P50570 | DNM2 Dynamin-2 |
| Q9UQ16 | DNM3 Dynamin-3 |
| Q9BU89 | DOHH Deoxyhypusine hydroxylase |
| Q9UPQ8 | DOLK Dolichol kinase |
| Q86YN1 | DOLPP1 Dolichyldiphosphatase 1 |
| O60762 | DPM1 Dolichol-phosphate mannosyltransferase |
| Q9NY33 | DPP3 Dipeptidyl peptidase 3 |
| Q9UHL4 | DPP7 Dipeptidyl peptidase 2 |
| Q9Y295 | DRG1 Developmentally-regulated GTP-binding protein 1 |
| Q08554 | DSC1 Desmocollin-1 |
| Q02413 | DSG1 Desmoglein-1 |
| P15924 | DSP Desmoplakin |
| P60981 | DSTN Destrin |
| Q14204 | DYNC1H1 Cytoplasmic dynein 1 heavy chain 1 |
| Q13409 | DYNC1I2 Cytoplasmic dynein 1 intermediate chain 2 |
| Q9Y6G9 | DYNC1LI1 Cytoplasmic dynein 1 light intermediate chain 1 |
| P63167 | DYNLL1 Dynein light chain 1, cytoplasmic |
| Q96FJ2 | DYNLL2 Dynein light chain 2, cytoplasmic |
| Q99848 | EBNA1BP2 Probable rRNA-processing protein EBP2 |
| O95905 | ECD Protein SGT1 |

| Accession # | Protein Name |
|---|---|
| P42892 | ECE1 Endothelin-converting enzyme 1 |
| Q13011 | ECH1 Delta(3,5)-Delta(2,4)-dienoyl-CoA isomerase, mitoc |
| Q9NTX5 | ECHDC1 Ethylmalonyl-CoA decarboxylase |
| P30084 | ECHS1 Enoyl-CoA hydratase, mitochondrial |
| P42126 | ECI1 Enoyl-CoA delta isomerase 1, mitochondrial |
| O75521 | ECI2 Enoyl-CoA delta isomerase 2, mitochondrial |
| Q5VYK3 | ECM29 Proteasome-associated protein ECM29 homolog |
| Q6P2E9 | EDC4 Enhancer of mRNA-decapping protein 4 |
| P68104 | EEF1A1 Elongation factor 1-alpha 1 |
| Q5VTE0 | EEF1A1P5 Putative elongation factor 1-alpha-like 3 |
| P24534 | EEF1B2 Elongation factor 1-beta |
| E9PRY8 | EEF1D Elongation factor 1-delta |
| P26641 | EEF1G Elongation factor 1-gamma |
| P13639 | EEF2 Elongation factor 2 |
| Q8IYU8 | EFHA1 EF-hand domain-containing family member A1 |
| Q15029 | EFTUD2 116 kDa U5 small nuclear ribonucleoprotein compone |
| Q9H4M9 | EHD1 EH domain-containing protein 1 |
| Q9H223 | EHD4 EH domain-containing protein 4 |
| O14681 | EI24 Etoposide-induced protein 2.4 homolog |
| Q9BY44 | EIF2A Eukaryotic translation initiation factor 2A |
| P19525 | EIF2AK2 Interferon-induced, double-stranded RNA-activated |
| Q9NR50 | EIF2B3 Translation initiation factor eIF-2B subunit gamma |
| P05198 | EIF2S1 Eukaryotic translation initiation factor 2 subunit |
| P20042 | EIF2S2 Eukaryotic translation initiation factor 2 subunit |
| P41091 | EIF2S3 Eukaryotic translation initiation factor 2 subunit |
| Q14152 | EIF3A Eukaryotic translation initiation factor 3 subunit |
| P55884 | EIF3B Eukaryotic translation initiation factor 3 subunit |
| B5ME19 | EIF3CL Eukaryotic translation initiation factor 3 subunit |
| O15371 | EIF3D Eukaryotic translation initiation factor 3 subunit |
| P60228 | EIF3E Eukaryotic translation initiation factor 3 subunit |
| B0QY89 | EIF3EIP Eukaryotic translation initiation factor 3 subunit |
| O00303 | EIF3F Eukaryotic translation initiation factor 3 subunit |
| O75821 | EIF3G Eukaryotic translation initiation factor 3 subunit |
| O15372 | EIF3H Eukaryotic translation initiation factor 3 subunit |
| Q13347 | EIF3I Eukaryotic translation initiation factor 3 subunit |
| O75822 | EIF3J Eukaryotic translation initiation factor 3 subunit |
| Q9Y262 | EIF3L Eukaryotic translation initiation factor 3 subunit |
| Q7L2H7 | EIF3M Eukaryotic translation initiation factor 3 subunit |
| P60842 | EIF4A1 Eukaryotic initiation factor 4A-I |
| Q14240 | EIF4A2 Eukaryotic initiation factor 4A-II |
| P38919 | EIF4A3 Eukaryotic initiation factor 4A-III |
| P23588 | EIF4B Eukaryotic translation initiation factor 4B |
| P06730 | EIF4E Eukaryotic translation initiation factor 4E |
| Q04637 | EIF4G1 Eukaryotic translation initiation factor 4 gamma 1 |
| P78344 | EIF4G2 Eukaryotic translation initiation factor 4 gamma 2 |
| Q15056 | EIF4H Eukaryotic translation initiation factor 4H |
| P55010 | EIF5 Eukaryotic translation initiation factor 5 |
| P63241 | EIF5A Eukaryotic translation initiation factor 5A-1 |
| Q9GZV4 | EIF5A2 Eukaryotic translation initiation factor 5A-2 |
| O60841 | EIF5B Eukaryotic translation initiation factor 5B |
| P56537 | EIF6 Eukaryotic translation initiation factor 6 |
| Q9BQ52 | ELAC2 Zinc phosphodiesterase ELAC protein 2 |
| Q15717 | ELAVL1 ELAV-like protein 1 |
| Q8IZ81 | ELMOD2 ELMO domain-containing protein 2 |
| Q9NXB9 | ELOVL2 Elongation of very long chain fatty acids protein |
| Q8N766 | EMC1 ER membrane protein complex subunit 1 |
| Q9NPA0 | EMC7 ER membrane protein complex subunit 7 |
| P50402 | EMD Emerin |
| O94919 | ENDOD1 Endonuclease domain-containing 1 protein |
| Q9UHY7 | ENOPH1 Enolase-phosphatase E1 |
| P11171 | EPB41 Protein 4.1 |
| O43491 | EPB41L2 Band 4.1-like protein 2 |
| Q9UM22 | EPDR1 Mammalian ependymin-related protein 1 |
| P07099 | EPHX1 Epoxide hydrolase 1 |
| P34913 | EPHX2 Bifunctional epoxide hydrolase 2 |
| P07814 | EPRS Bifunctional glutamate/proline--tRNA ligase |
| P42566 | EPS15 Epidermal growth factor receptor substrate 15 |
| Q9UBC2 | EPS15L1 Epidermal growth factor receptor substrate 15-like |
| Q9NZ08 | ERAP1 Endoplasmic reticulum aminopeptidase 1 |
| Q9Y282 | ERGIC3 Endoplasmic reticulum-Golgi intermediate compartme |
| P84090 | ERH Enhancer of rudimentary homolog |
| O75477 | ERLIN1 Erlin-1 |
| O94905 | ERLIN2 Erlin-2 |
| Q96HE7 | ERO1L ERO1-like protein alpha |
| P30040 | ERP29 Endoplasmic reticulum resident protein 29 |
| Q9BS26 | ERP44 Endoplasmic reticulum resident protein 44 |
| Q9BSJ8 | ESYT1 Extended synaptotagmin-1 |
| A0FGR8 | ESYT2 Extended synaptotagmin-2 |
| P62495 | ETF1 Eukaryotic peptide chain release factor subunit 1 |
| P13804 | ETFA Electron transfer flavoprotein subunit alpha, mito |
| P38117 | ETFB Electron transfer flavoprotein subunit beta |
| Q16134 | ETFDH Electron transfer flavoprotein-ubiquinone oxidored |
| Q01844 | EWSR1 RNA-binding protein EWS |
| Q9UQ84 | EXO1 Exonuclease 1 |
| Q96KP1 | EXOC2 Exocyst complex component 2 |
| Q96A65 | EXOC4 Exocyst complex component 4 |
| O00471 | EXOC5 Exocyst complex component 5 |
| Q01780 | EXOSC10 Exosome component 10 |
| Q9NQT5 | EXOSC3 Exosome complex component RRP40 |
| P15311 | EZR Ezrin |
| Q9Y624 | F11R Junctional adhesion molecule A |
| O60427 | FADS1 Fatty acid desaturase 1 |
| O95864 | FADS2 Fatty acid desaturase 2 |
| Q9UNN5 | FAF1 FAS-associated factor 1 |
| Q96CS3 | FAF2 FAS-associated factor 2 |

| Accession # | Protein Name |
|---|---|
| P16930 | FAH Fumarylacetoacetase |
| Q9NRY5 | FAM114A2 Protein FAM114A2 |
| Q96TA1 | FAM129B Niban-like protein 1 |
| Q96A26 | FAM162A Protein FAM162A |
| Q9BTY7 | FAM203A Protein FAM203A |
| P0CB43 | FAM203B Protein FAM203B |
| Q9UK61 | FAM208A Protein FAM208A |
| Q9BRX8 | FAM213A Redox-regulatory protein FAM213A |
| Q92520 | FAM3C Protein FAM3C |
| Q9NUQ9 | FAM49B Protein FAM49B |
| Q9H019 | FAM54B Protein FAM54B |
| Q96TC7 | FAM82A2 Regulator of microtubule dynamics protein 3 |
| Q96DB5 | FAM82B Regulator of microtubule dynamics protein 1 |
| Q9UBU6 | FAM8A1 Protein FAM8A1 |
| Q8NCA5 | FAM98A Protein FAM98A |
| Q52LJ0 | FAM98B Protein FAM98B |
| Q9NVI1 | FANCI Fanconi anemia group I protein |
| Q8WVX9 | FAR1 Fatty acyl-CoA reductase 1 |
| Q9Y285 | FARSA Phenylalanine--tRNA ligase alpha subunit |
| Q9NSD9 | FARSB Phenylalanine--tRNA ligase beta subunit |
| P49327 | FASN Fatty acid synthase |
| P22087 | FBL rRNA 2-O-methyltransferase fibrillarin |
| P37268 | FDFT1 Squalene synthase |
| P22830 | FECH Ferrochelatase, mitochondrial |
| P39748 | FEN1 Flap endonuclease 1 |
| Q86UX7 | FERMT3 Fermitin family homolog 3 |
| O95684 | FGFR1OP FGFR1 oncogene partner |
| P07954 | FH Fumarate hydratase, mitochondrial |
| Q9Y613 | FHOD1 FH1/FH2 domain-containing protein 1 |
| Q6UN15 | FIP1L1 Pre-mRNA 3-end-processing factor FIP1 |
| Q96AY3 | FKBP10 Peptidyl-prolyl cis-trans isomerase FKBP10 |
| Q9NWM8 | FKBP14 Peptidyl-prolyl cis-trans isomerase FKBP14 |
| P62942 | FKBP1A Peptidyl-prolyl cis-trans isomerase FKBP1A |
| Q00688 | FKBP3 Peptidyl-prolyl cis-trans isomerase FKBP3 |
| Q02790 | FKBP4 Peptidyl-prolyl cis-trans isomerase FKBP4 |
| Q13451 | FKBP5 Peptidyl-prolyl cis-trans isomerase FKBP5 |
| Q9Y680 | FKBP7 Peptidyl-prolyl cis-trans isomerase FKBP7 |
| Q14318 | FKBP8 Peptidyl-prolyl cis-trans isomerase FKBP8 |
| Q8NFF5 | FLAD1 FAD synthase |
| Q13045 | FLII Protein flightless-1 homolog |
| Q14315 | FLNC Filamin-C |
| O75955 | FLOT1 Flotillin-1 |
| Q14254 | FLOT2 Flotillin-2 |
| Q06787 | FMR1 Fragile X mental retardation protein 1 |
| Q9H479 | FN3K Fructosamine-3-kinase |
| P49354 | FNTA Protein farnesyltransferase/geranylgeranyltransfer |
| Q96CU9 | FOXRED1 FAD-dependent oxidoreductase domain-containing pro |
| Q16658 | FSCN1 Fascin |
| Q8IY81 | FTSJ3 pre-rRNA processing protein FTSJ3 |
| Q96AE4 | FUBP1 Far upstream element-binding protein 1 |
| Q96I24 | FUBP3 Far upstream element-binding protein 3 |
| P04066 | FUCA1 Tissue alpha-L-fucosidase |
| Q9BTY2 | FUCA2 Plasma alpha-L-fucosidase |
| P35637 | FUS RNA-binding protein FUS |
| P51114 | FXR1 Fragile X mental retardation syndrome-related prot |
| P51116 | FXR2 Fragile X mental retardation syndrome-related prot |
| Q13283 | G3BP1 Ras GTPase-activating protein-binding protein 1 |
| Q9UN86 | G3BP2 Ras GTPase-activating protein-binding protein 2 |
| P11413 | G6PD Glucose-6-phosphate 1-dehydrogenase |
| P10253 | GAA Lysosomal alpha-glucosidase |
| O14976 | GAK Cyclin-G-associated kinase |
| Q10472 | GALNT1 Polypeptide N-acetylgalactosaminyltransferase 1 |
| Q10471 | GALNT2 Polypeptide N-acetylgalactosaminyltransferase 2 |
| Q8N4A0 | GALNT4 Polypeptide N-acetylgalactosaminyltransferase 4 |
| Q14697 | GANAB Neutral alpha-glucosidase AB |
| Q14C86 | GAPVD1 GTPase-activating protein and VPS9 domain-containi |
| P41250 | GARS Glycine--tRNA ligase |
| P22102 | GART Trifunctional purine biosynthetic protein adenosin |
| P04062 | GBA Glucosylceramidase |
| O75323 | GBAS Protein NipSnap homolog 2 |
| Q92538 | GBF1 Golgi-specific brefeldin A-resistance guanine nucl |
| O75600 | GCAT 2-amino-3-ketobutyrate coenzyme A ligase, mitochon |
| Q92616 | GCN1L1 Translational activator GCN1 |
| P31150 | GDI1 Rab GDP dissociation inhibitor alpha |
| P50395 | GDI2 Rab GDP dissociation inhibitor beta |
| Q8N9F7 | GDPD1 Glycerophosphodiester phosphodiesterase domain-con |
| Q7L5D6 | GET4 Golgi to ER traffic protein 4 homolog |
| Q96RP9 | GFM1 Elongation factor G, mitochondrial |
| Q06210 | GFPT1 Glucosamine--fructose-6-phosphate aminotransferase |
| P38435 | GGCX Vitamin K-dependent gamma-carboxylase |
| Q92820 | GGH Gamma-glutamyl hydrolase |
| Q9UJ14 | GGT7 Gamma-glutamyltransferase 7 |
| Q9H3K2 | GHITM Growth hormone-inducible transmembrane protein |
| Q6Y7W6 | GIGYF2 PERQ amino acid-rich with GYF domain-containing pr |
| P32189 | GK Glycerol kinase |
| P06280 | GLA Alpha-galactosidase A |
| P16278 | GLB1 Beta-galactosidase |
| Q92896 | GLG1 Golgi apparatus protein 1 |
| Q04760 | GLO1 Lactoylglutathione lyase |
| Q9HC38 | GLOD4 Glyoxalase domain-containing protein 4 |
| O76003 | GLRX3 Glutaredoxin-3 |
| O94925 | GLS Glutaminase kidney isoform, mitochondrial |
| Q68CQ7 | GLT8D1 Glycosyltransferase 8 domain-containing protein 1 |
| P00367 | GLUD1 Glutamate dehydrogenase 1, mitochondrial |
| P49448 | GLUD2 Glutamate dehydrogenase 2, mitochondrial |
| P17900 | GM2A Ganglioside GM2 activator |
| P49915 | GMPS GMP synthase [glutamine-hydrolyzing] |
| P04899 | GNAI2 Guanine nucleotide-binding protein G(i) subunit al |
| P08754 | GNAI3 Guanine nucleotide-binding protein G(k) subunit al |
| P62873 | GNB1 Guanine nucleotide-binding protein G(I)/G(S)/G(T) |
| P62879 | GNB2 Guanine nucleotide-binding protein G(I)/G(S)/G(T) |
| P63244 | GNB2L1 Guanine nucleotide-binding protein subunit beta-2- |
| Q13823 | GNL2 Nucleolar GTP-binding protein 2 |

| Accession # | Protein Name |
| --- | --- |
| Q9BVP2 | GNL3 Guanine nucleotide-binding protein-like 3 |
| O15228 | GNPAT Dihydroxyacetone phosphate acyltransferase |
| P15586 | GNS N-acetylglucosamine-6-sulfatase |
| Q08378 | GOLGA3 Golgin subfamily A member 3 |
| Q8TBA6 | GOLGA5 Golgin subfamily A member 5 |
| O00461 | GOLIM4 Golgi integral membrane protein 4 |
| Q8NBJ4 | GOLM1 Golgi membrane protein 1 |
| Q9H4A6 | GOLPH3 Golgi phosphoprotein 3 |
| Q9H4A5 | GOLPH3L Golgi phosphoprotein 3-like |
| Q9HD26 | GOPC Golgi-associated PDZ and coiled-coil motif-contain |
| O95249 | GOSR1 Golgi SNAP receptor complex member 1 |
| P00505 | GOT2 Aspartate aminotransferase, mitochondrial |
| O43292 | GPAA1 Glycosylphosphatidylinositol anchor attachment 1 p |
| Q9HCL2 | GPAM Glycerol-3-phosphate acyltransferase 1, mitochondr |
| P43304 | GPD2 Glycerol-3-phosphate dehydrogenase, mitochondrial |
| Q5VW38 | GPR107 Protein GPR107 |
| P0CG08 | GPR89B Golgi pH regulator B |
| P36969 | GPX4 Phospholipid hydroperoxide glutathione peroxidase, |
| Q8TED1 | GPX8 Probable glutathione peroxidase 8 |
| P62993 | GRB2 Growth factor receptor-bound protein 2 |
| Q9UBQ7 | GRHPR Glyoxylate reductase/hydroxypyruvate reductase |
| Q9HAV7 | GRPEL1 GrpE protein homolog 1, mitochondrial |
| Q12849 | GRSF1 G-rich sequence factor 1 |
| Q9BQ67 | GRWD1 Glutamate-rich WD repeat-containing protein 1 |
| P15170 | GSPT1 Eukaryotic peptide chain release factor GTP-bindin |
| Q8IYD1 | GSPT2 Eukaryotic peptide chain release factor GTP-bindin |
| P00390 | GSR Glutathione reductase, mitochondrial |
| P48637 | GSS Glutathione synthetase |
| Q9Y2Q3 | GSTK1 Glutathione S-transferase kappa 1 |
| P21266 | GSTM3 Glutathione S-transferase Mu 3 |
| P78417 | GSTO1 Glutathione S-transferase omega-1 |
| P09211 | GSTP1 Glutathione S-transferase P |
| P78347 | GTF2I General transcription factor II-I |
| Q9Y5Q9 | GTF3C3 General transcription factor 3C polypeptide 3 |
| O00178 | GTPBP1 GTP-binding protein 1 |
| Q9BZE4 | GTPBP4 Nucleolar GTP-binding protein 1 |
| P08236 | GUSB Beta-glucuronidase |
| P13807 | GYS1 Glycogen |
| P16104 | H2AFX Histone H2A.x |
| O75367 | H2AFY Core histone macro-H2A.1 |
| P0C0S5 | H2AFZ Histone H2A.Z |
| Q16836 | HADH Hydroxyacyl-coenzyme A dehydrogenase, mitochondria |
| P40939 | HADHA Trifunctional enzyme subunit alpha, mitochondrial |
| P55084 | HADHB Trifunctional enzyme subunit beta, mitochondrial |
| P12081 | HARS Histidine--tRNA ligase, cytoplasmic |
| O14929 | HAT1 Histone acetyltransferase type B catalytic subunit |
| Q96CS2 | HAUS1 HAUS augmin-like complex subunit 1 |
| Q9NVX0 | HAUS2 HAUS augmin-like complex subunit 2 |
| Q68CZ6 | HAUS3 HAUS augmin-like complex subunit 3 |
| Q9H6D7 | HAUS4 HAUS augmin-like complex subunit 4 |
| O94927 | HAUS5 HAUS augmin-like complex subunit 5 |
| O00165 | HAX1 HCLS1-associated protein X-1 |
| P69905 | HBA2 Hemoglobin subunit alpha |
| P68871 | HBB Hemoglobin subunit beta |
| P02100 | HBE1 Hemoglobin subunit epsilon |
| P69891 | HBG1 Hemoglobin subunit gamma-1 |
| P69892 | HBG2 Hemoglobin subunit gamma-2 |
| Q9Y450 | HBS1L HBS1-like protein |
| P02008 | HBZ Hemoglobin subunit zeta |
| P53701 | HCCS Cytochrome c-type heme lyase |
| Q13547 | HDAC1 Histone deacetylase 1 |
| Q92769 | HDAC2 Histone deacetylase 2 |
| P51858 | HDGF Hepatoma-derived growth factor |
| Q9BSH5 | HDHD3 Haloacid dehalogenase-like hydrolase domain-contai |
| Q00341 | HDLBP Vigilin |
| Q9H583 | HEATR1 HEAT repeat-containing protein 1 |
| Q86Y56 | HEATR2 HEAT repeat-containing protein 2 |
| Q7Z4Q2 | HEATR3 HEAT repeat-containing protein 3 |
| Q9NRZ9 | HELLS Lymphoid-specific helicase |
| Q9BXL5 | HEMGN Hemogen |
| P06865 | HEXA Beta-hexosaminidase subunit alpha |
| P07686 | HEXB Beta-hexosaminidase subunit beta |
| P31937 | HIBADH 3-hydroxyisobutyrate dehydrogenase, mitochondrial |
| Q6NVY1 | HIBCH 3-hydroxyisobutyryl-CoA hydrolase, mitochondrial |
| Q9Y241 | HIGD1A HIG1 domain family member 1A |
| P49773 | HINT1 Histidine triad nucleotide-binding protein 1 |
| Q9NQE9 | HINT3 Histidine triad nucleotide-binding protein 3 |
| P16403 | HIST1H1C Histone H1.2 |
| P16402 | HIST1H1D Histone H1.3 |
| Q16777 | HIST2H2AC Histone H2A type 2-C |
| P19367 | HK1 Hexokinase-1 |
| P52789 | HK2 Hexokinase-2 |
| P30443 | HLA-A HLA class I histocompatibility antigen, A-1 alpha |
| P01892 | HLA-A HLA class I histocompatibility antigen, A-2 alpha |
| P04439 | HLA-A HLA class I histocompatibility antigen, A-3 alpha |
| P01891 | HLA-A HLA class I histocompatibility antigen, A-68 alpha |
| P30462 | HLA-B HLA class I histocompatibility antigen, B-14 alpha |
| P18463 | HLA-B HLA class I histocompatibility antigen, B-37 alpha |
| Q29940 | HLA-B HLA class I histocompatibility antigen, B-59 alpha |
| Q31612 | HLA-B HLA class I histocompatibility antigen, B-73 alpha |
| P30460 | HLA-B HLA class I histocompatibility antigen, B-8 alpha |
| P30499 | HLA-C HLA class I histocompatibility antigen, Cw-1 alpha |
| F8VZB9 | HLA-C HLA class I histocompatibility antigen, Cw-14 alph |
| Q07000 | HLA-C HLA class I histocompatibility antigen, Cw-15 alph |
| Q29963 | HLA-C HLA class I histocompatibility antigen, Cw-6 alpha |
| P10321 | HLA-C HLA class I histocompatibility antigen, Cw-7 alpha |
| Q8TCT9 | HM13 Minor histocompatibility antigen H13 |
| P09429 | HMGB1 High mobility group protein B1 |
| P26583 | HMGB2 High mobility group protein B2 |
| O15347 | HMGB3 High mobility group protein B3 |
| Q01581 | HMGCS1 Hydroxymethylglutaryl-CoA synthase, cytoplasmic |
| P09601 | HMOX1 Heme oxygenase 1 |
| P30519 | HMOX2 Heme oxygenase 2 |
| Q13151 | HNRNPA0 Heterogeneous nuclear ribonucleoprotein A0 |
| P09651 | HNRNPA1 Heterogeneous nuclear ribonucleoprotein A1 |

| Accession # | Protein Name |
|---|---|
| Q32P51 | HNRNPA1L2 Heterogeneous nuclear ribonucleoprotein A1-like 2 |
| P22626 | HNRNPA2B1 Heterogeneous nuclear ribonucleoproteins A2/B1 |
| P51991 | HNRNPA3 Heterogeneous nuclear ribonucleoprotein A3 |
| Q99729 | HNRNPAB Heterogeneous nuclear ribonucleoprotein A/B |
| P07910 | HNRNPC Heterogeneous nuclear ribonucleoproteins C1/C2 |
| O60812 | HNRNPCL1 Heterogeneous nuclear ribonucleoprotein C-like 1 |
| Q14103 | HNRNPD Heterogeneous nuclear ribonucleoprotein D0 |
| P52597 | HNRNPF Heterogeneous nuclear ribonucleoprotein F |
| P31943 | HNRNPH1 Heterogeneous nuclear ribonucleoprotein H |
| P55795 | HNRNPH2 Heterogeneous nuclear ribonucleoprotein H2 |
| P31942 | HNRNPH3 Heterogeneous nuclear ribonucleoprotein H3 |
| P61978 | HNRNPK Heterogeneous nuclear ribonucleoprotein K |
| P14866 | HNRNPL Heterogeneous nuclear ribonucleoprotein L |
| P52272 | HNRNPM Heterogeneous nuclear ribonucleoprotein M |
| O43390 | HNRNPR Heterogeneous nuclear ribonucleoprotein R |
| Q00839 | HNRNPU Heterogeneous nuclear ribonucleoprotein U |
| Q9BUJ2 | HNRNPUL1 Heterogeneous nuclear ribonucleoprotein U-like pro |
| Q1KMD3 | HNRNPUL2 Heterogeneous nuclear ribonucleoprotein U-like pro |
| O14979 | HNRPDL Heterogeneous nuclear ribonucleoprotein D-like |
| Q8WVV9 | HNRPLL Heterogeneous nuclear ribonucleoprotein L-like |
| Q5SSJ5 | HP1BP3 Heterochromatin protein 1-binding protein 3 |
| P37235 | HPCAL1 Hippocalcin-like protein 1 |
| P00492 | HPRT1 Hypoxanthine-guanine phosphoribosyltransferase |
| Q86YZ3 | HRNR Hornerin |
| Q7LGA3 | HS2ST1 Heparan sulfate 2-O-sulfotransferase 1 |
| Q99714 | HSD17B10 3-hydroxyacyl-CoA dehydrogenase type-2 |
| Q8NBQ5 | HSD17B11 Estradiol 17-beta-dehydrogenase 11 |
| Q53GQ0 | HSD17B12 Estradiol 17-beta-dehydrogenase 12 |
| P51659 | HSD17B4 Peroxisomal multifunctional enzyme type 2 |
| Q3SXM5 | HSDL1 Inactive hydroxysteroid dehydrogenase-like protein |
| Q6YN16 | HSDL2 Hydroxysteroid dehydrogenase-like protein 2 |
| P07900 | HSP90AA1 Heat shock protein HSP 90-alpha |
| P08238 | HSP90AB1 Heat shock protein HSP 90-beta |
| P14625 | HSP90B1 Endoplasmin |
| Q0VDF9 | HSPA14 Heat shock 70 kDa protein 14 |
| P08107 | HSPA1A Heat shock 70 kDa protein 1A/1B |
| P34931 | HSPA1L Heat shock 70 kDa protein 1-like |
| P11021 | HSPA5 78 kDa glucose-regulated protein |
| P17066 | HSPA6 Heat shock 70 kDa protein 6 |
| P11142 | HSPA8 Heat shock cognate 71 kDa protein |
| P38646 | HSPA9 Stress-70 protein, mitochondrial |
| P04792 | HSPB1 Heat shock protein beta-1 |
| Q9NZL4 | HSPBP1 Hsp70-binding protein 1 |
| P10809 | HSPD1 60 kDa heat shock protein, mitochondrial |
| P61604 | HSPE1 10 kDa heat shock protein, mitochondrial |
| Q92598 | HSPH1 Heat shock protein 105 kDa |
| O43719 | HTATSF1 HIV Tat-specific factor 1 |
| Q7Z6Z7 | HUWE1 E3 ubiquitin-protein ligase HUWE1 |
| Q9Y4L1 | HYOU1 Hypoxia up-regulated protein 1 |
| P41252 | IARS Isoleucine--tRNA ligase, cytoplasmic |
| Q9NSE4 | IARS2 Isoleucine--tRNA ligase, mitochondrial |
| O60725 | ICMT Protein-S-isoprenylcysteine O-methyltransferase |
| P14735 | IDE Insulin-degrading enzyme |
| O75874 | IDH1 Isocitrate dehydrogenase [NADP] cytoplasmic |
| P48735 | IDH2 Isocitrate dehydrogenase |
| P50213 | IDH3A Isocitrate dehydrogenase |
| O43837 | IDH3B Isocitrate dehydrogenase [NAD] subunit beta, mitoc |
| P13284 | IF130 Gamma-interferon-inducible lysosomal thiol reducta |
| Q9NZI8 | IGF2BP1 Insulin-like growth factor 2 mRNA-binding protein |
| Q9Y6M1 | IGF2BP2 Insulin-like growth factor 2 mRNA-binding protein |
| O00425 | IGF2BP3 Insulin-like growth factor 2 mRNA-binding protein |
| Q13123 | IK Protein Red |
| Q12905 | ILF2 Interleukin enhancer-binding factor 2 |
| Q12906 | ILF3 Interleukin enhancer-binding factor 3 |
| A1L0T0 | ILVBL Acetolactate synthase-like protein |
| Q16891 | IMMT Mitochondrial inner membrane protein |
| Q9NX62 | IMPAD1 Inositol monophosphatase 3 |
| P12268 | IMPDH2 Inosine-5-monophosphate dehydrogenase 2 |
| Q16352 | INA Alpha-internexin |
| Q9UI26 | IPO11 Importin-11 |
| Q8IEX9 | IPO4 Importin-4 |
| O00410 | IPO5 Importin-5 |
| O95373 | IPO7 Importin-7 |
| O15397 | IPO8 Importin-8 |
| Q96P70 | IPO9 Importin-9 |
| P46940 | IQGAP1 Ras GTPase-activating-like protein IQGAP1 |
| O14654 | IRS4 Insulin receptor substrate 4 |
| Q96CN7 | ISOC1 Isochorismatase domain-containing protein 1 |
| Q96J02 | ITCH E3 ubiquitin-protein ligase Itchy homolog |
| Q9Y287 | ITM2B Integral membrane protein 2B |
| Q8N5M9 | JAGN1 Protein jagunal homolog 1 |
| P14923 | JUP Junction plakoglobin |
| Q15046 | KARS Lysine-tRNA ligase |
| Q96CX2 | KCTD12 BTB/POZ domain-containing protein KCTD12 |
| P24390 | KDELR1 ER lumen protein retaining receptor 1 |
| P33947 | KDELR2 ER lumen protein retaining receptor 2 |
| O43731 | KDELR3 ER lumen protein retaining receptor 3 |
| Q8NB78 | KDM1B Lysine-specific histone demethylase 1B |
| Q06136 | KDSR 3-ketodihydrosphingosine reductase |
| Q07666 | KHDRBS1 KH domain-containing, RNA-binding, signal transduc |
| Q92945 | KHSRP Far upstream element-binding protein 2 |
| Q15397 | KIAA0020 Pumilio domain-containing protein KIAA0020 |
| O75153 | KIAA0664 Clustered mitochondria protein homolog |
| Q2M389 | KIAA1033 WASH complex subunit 7 |
| Q96EK5 | KIAA1279 KIF1-binding protein |

| Accession # | Protein Name |
|---|---|
| Q8N163 | KIAA1967 DBIRD complex subunit KIAA1967 |
| Q8IYS2 | KIAA2013 Uncharacterized protein KIAA2013 |
| P52732 | KIF11 Kinesin-like protein KIF11 |
| Q14807 | KIF22 Kinesin-like protein KIF22 |
| Q99661 | KIF2C Kinesin-like protein KIF2C |
| P33176 | KIF5B Kinesin-1 heavy chain |
| Q07866 | KLC1 Kinesin light chain 1 |
| Q9H0B6 | KLC2 Kinesin light chain 2 |
| P50748 | KNTC1 Kinetochore-associated protein 1 |
| P52294 | KPNA1 Importin subunit alpha-1 |
| P52292 | KPNA2 Importin subunit alpha-2 |
| O00505 | KPNA3 Importin subunit alpha-3 |
| O00629 | KPNA4 Importin subunit alpha-4 |
| O60684 | KPNA6 Importin subunit alpha-7 |
| Q14974 | KPNB1 Importin subunit beta-1 |
| Q5T749 | KPRP Keratinocyte proline-rich protein |
| Q86UP2 | KTN1 Kinectin |
| Q9H9P8 | L2HGDH L-2-hydroxyglutarate dehydrogenase, mitochondrial |
| P11279 | LAMP1 Lysosome-associated membrane glycoprotein 1 |
| P13473 | LAMP2 Lysosome-associated membrane glycoprotein 2 |
| Q6IAA8 | LAMTOR1 Ragulator complex protein LAMTOR1 |
| P28838 | LAP3 Cytosol aminopeptidase |
| Q6PKG0 | LARP1 La-related protein 1 |
| Q71RC2 | LARP4 La-related protein 4 |
| Q92615 | LARP4B La-related protein 4B |
| Q9P2J5 | LARS Leucine--tRNA ligase, cytoplasmic |
| Q15031 | LARS2 Probable leucine--tRNA ligase, mitochondrial |
| Q9Y4W2 | LAS1L Ribosomal biogenesis protein LAS1L |
| Q14739 | LBR Lamin-B receptor |
| P00338 | LDHA L-lactate dehydrogenase A chain |
| P07195 | LDHB L-lactate dehydrogenase B chain |
| Q9Y2U8 | LEMD3 Inner nuclear membrane protein Man1 |
| Q32P28 | LEPRE1 Prolyl 3-hydroxylase 1 |
| O95202 | LETM1 LETM1 and EF-hand domain-containing protein 1, mit |
| Q08380 | LGALS3BP Galectin-3-binding protein |
| Q99538 | LGMN Legumain |
| P18858 | LIG1 DNA ligase 1 |
| P38571 | LIPA Lysosomal acid lipase/cholesteryl ester hydrolase |
| P49257 | LMAN1 Protein ERGIC-53 |
| Q12907 | LMAN2 Vesicular integral-membrane protein VIP36 |
| Q8WVP7 | LMBR1 Limb region 1 protein homolog |
| Q68DH5 | LMBRD2 LMBR1 domain-containing protein 2 |
| Q9BU23 | LMF2 Lipase maturation factor 2 |
| P02545 | LMNA Prelamin-A/C |
| P20700 | LMNB1 Lamin-B1 |
| Q03252 | LMNB2 Lamin-B2 |
| Q9UIQ6 | LNPEP Leucyl-cystinyl aminopeptidase |
| P36776 | LONP1 Lon protease homolog, mitochondrial |
| Q8NF37 | LPCAT1 Lysophosphatidylcholine acyltransferase 1 |
| Q6P1A2 | LPCAT3 Lysophospholipid acyltransferase 5 |
| Q92604 | LPGAT1 Acyl-CoA:lysophosphatidylglycerol acyltransferase |
| P42704 | LRPPRC Leucine-rich PPR motif-containing protein, mitocho |
| Q8N1G4 | LRRC47 Leucine-rich repeat-containing protein 47 |
| Q96AG4 | LRRC59 Leucine-rich repeat-containing protein 59 |
| Q9UFC0 | LRWD1 Leucine-rich repeat and WD repeat-containing prote |
| Q8ND56 | LSM14A Protein LSM14 homolog A |
| Q9BX40 | LSM14B Protein LSM14 homolog B |
| P48449 | LSS Lanosterol synthase |
| P09960 | LTA4H Leukotriene A-4 hydrolase |
| Q96GA3 | LTV1 Protein LTV1 homolog |
| O95232 | LUC7L3 Luc7-like protein 3 |
| P07948 | LYN Tyrosine-protein kinase Lyn |
| Q9UPN3 | MACF1 Microtubule-actin cross-linking factor 1, isoforms |
| P43366 | MAGEB1 Melanoma-associated antigen B1 |
| O15479 | MAGEB2 Melanoma-associated antigen B2 |
| O60732 | MAGEC1 Melanoma-associated antigen C1 |
| Q9UBF1 | MAGEC2 Melanoma-associated antigen C2 |
| Q9Y5V3 | MAGED1 Melanoma-associated antigen D1 |
| Q9UNF1 | MAGED2 Melanoma-associated antigen D2 |
| Q96A72 | MAGOHB Protein mago nashi homolog 2 |
| Q9H0U3 | MAGT1 Magnesium transporter protein 1 |
| P33908 | MAN1A1 Mannosyl-oligosaccharide 1,2-alpha-mannosidase IA |
| O00754 | MAN2B1 Lysosomal alpha-mannosidase |
| Q9Y2E5 | MAN2B2 Epididymis-specific alpha-mannosidase |
| P46821 | MAP1B Microtubule-associated protein 1B |
| Q02750 | MAP2K1 Dual specificity mitogen-activated protein kinase |
| P36507 | MAP2K2 Dual specificity mitogen-activated protein kinase |
| P27816 | MAP4 Microtubule-associated protein 4 |
| P28482 | MAPK1 Mitogen-activated protein kinase 1 |
| P27361 | MAPK3 Mitogen-activated protein kinase 3 |
| Q15691 | MAPRE1 Microtubule-associated protein RP/EB family member |
| Q15555 | MAPRE2 Microtubule-associated protein RP/EB family member |
| Q9NX47 | MARCH5 E3 ubiquitin-protein ligase MARCH5 |
| P56192 | MARS Methionine--tRNA ligase, cytoplasmic |
| Q96GX5 | MASTL Serine/threonine-protein kinase greatwall |
| P43243 | MATR3 Matrin-3 |
| Q7Z434 | MAVS Mitochondrial antiviral-signaling protein |
| Q96N66 | MBOAT7 Lysophospholipid acyltransferase 7 |
| Q8IVS2 | MCAT Malonyl-CoA-acyl carrier protein transacylase, mit |
| Q9HCC0 | MCCC2 Methylcrotonoyl-CoA carboxylase beta chain, mitoch |
| Q8NI22 | MCFD2 Multiple coagulation factor deficiency protein 2 |
| P49736 | MCM2 DNA replication licensing factor MCM2 |
| P25205 | MCM3 DNA replication licensing factor MCM3 |
| P33991 | MCM4 DNA replication licensing factor MCM4 |
| P33992 | MCM5 DNA replication licensing factor MCM5 |
| Q14566 | MCM6 DNA replication licensing factor MCM6 |
| P33993 | MCM7 DNA replication licensing factor MCM7 |
| Q9BTE3 | MCMBP Mini-chromosome maintenance complex-binding protei |
| Q9ULC4 | MCTS1 Malignant T-cell-amplified sequence 1 |
| Q14676 | MDC1 Mediator of DNA damage checkpoint protein 1 |
| P40926 | MDH2 Malate dehydrogenase, mitochondrial |
| P23368 | ME2 NAD-dependent malic enzyme, mitochondrial |

| Accession # | Protein Name |
|---|---|
| O00470 | MEIS1 Homeobox protein Meisl |
| O14770 | MEIS2 Homeobox protein Meis2 |
| Q7L2J0 | MEPCE 7SK snRNA methylphosphate capping enzyme |
| Q14696 | MESDC2 LDLR chaperone MESD |
| Q8N6R0 | METTL13 Methyltransferase-like protein 13 |
| Q9H8H3 | METTL7A Methyltransferase-like protein 7A |
| Q9GZY8 | MFF Mitochondrial fission factor |
| O95140 | MFN2 Mitofusin-2 |
| Q6N075 | MFSD5 Major facilitator superfamily domain-containing pr |
| Q8NHS3 | MFSD8 Major facilitator superfamily domain-containing pr |
| O60502 | MGEA5 Bifunctional protein NCOAT |
| O14880 | MGST3 Microsomal glutathione S-transferase 3 |
| Q5JRA6 | MIA3 Melanoma inhibitory activity protein 3 |
| Q9BPX6 | MICU1 Calcium uptake protein 1, mitochondrial |
| Q99797 | MIPEP Mitochondrial intermediate peptidase |
| P46013 | MKI67 Antigen KI-67 |
| Q9BYG3 | MKI67IP MKI67 FHA domain-interacting nucleolar phosphoprot |
| P55196 | MLLT4 Afadin |
| Q96EY8 | MMAB Cob(I)yrinic acid a,c-diamide adenosyltransferase, |
| Q8N4V1 | MMGT1 Membrane magnesium transporter 1 |
| Q96T76 | MMS19 MMS19 nucleotide excision repair protein homolog |
| Q13724 | MOGS Mannosyl-oligosaccharide glucosidase |
| Q9UBU8 | MORF4L1 Mortality factor 4-like protein 1 |
| Q15014 | MORF4L2 Mortality factor 4-like protein 2 |
| Q9HCE1 | MOV10 Putative helicase MOV-10 |
| O00566 | MPHOSPH10 U3 small nucleolar ribonucleoprotein protein MPP10 |
| Q00013 | MPP1 55 kDa erythrocyte membrane protein |
| Q14168 | MPP2 MAGUK p55 subfamily member 2 |
| Q9NZW5 | MPP6 MAGUK p55 subfamily member 6 |
| P25325 | MPST 3-mercaptopyruvate sulfurtransferase |
| P39210 | MPV17 Protein Mpv17 |
| Q567V2 | MPV17L2 Mpv17-like protein 2 |
| Q7Z7H8 | MRPL10 39S ribosomal protein L10, mitochondrial |
| Q13084 | MRPL28 39S ribosomal protein L28, mitochondrial |
| Q9BZE1 | MRPL37 39S ribosomal protein L37, mitochondrial |
| Q9NYK5 | MRPL39 39S ribosomal protein L39, mitochondrial |
| Q9NQ50 | MRPL40 39S ribosomal protein L40, mitochondrial |
| Q9H9J2 | MRPL44 39S ribosomal protein L44, mitochondrial |
| Q9BRJ2 | MRPL45 39S ribosomal protein L45, mitochondrial |
| Q9H2W6 | MRPL46 39S ribosomal protein L46, mitochondrial |
| Q7Z7F7 | MRPL55 39S ribosomal protein L55, mitochondrial |
| Q9Y676 | MRPS18B 28S ribosomal protein S18b, mitochondrial |
| P82650 | MRPS22 28S ribosomal protein S22, mitochondrial |
| Q92552 | MRPS27 28S ribosomal protein S27, mitochondrial |
| Q92665 | MRPS31 28S ribosomal protein S31, mitochondrial |
| P82673 | MRPS35 28S ribosomal protein S35, mitochondrial |
| P82933 | MRPS9 28S ribosomal protein S9, mitochondrial |
| P43246 | MSH2 DNA mismatch repair protein Msh2 |
| P52701 | MSH6 DNA mismatch repair protein Msh6 |
| O43347 | MSI1 RNA-binding protein Musashi homolog 1 |
| Q96DH6 | MSI2 RNA-binding protein Musashi homolog 2 |
| P26038 | MSN Moesin |
| Q9P289 | MST4 Serine/threonine-protein kinase MST4 |
| Q9BUK6 | MSTO1 Protein misato homolog 1 |
| P00395 | MT-CO1 Cytochrome c oxidase subunit 1 |
| P00403 | MT-CO2 Cytochrome c oxidase subunit 2 |
| P03886 | MT-ND1 NADH-ubiquinone oxidoreductase chain 1 |
| P03891 | MT-ND2 NADH-ubiquinone oxidoreductase chain 2 |
| P03905 | MT-ND4 NADH-ubiquinone oxidoreductase chain 4 |
| P03915 | MT-ND5 NADH-ubiquinone oxidoreductase chain 5 |
| O94776 | MTA2 Metastasis-associated protein MTA2 |
| Q13126 | MTAP S-methyl-5-thioadenosine phosphorylase |
| Q9NZJ7 | MTCH1 Mitochondrial carrier homolog 1 |
| Q9Y6C9 | MTCH2 Mitochondrial carrier homolog 2 |
| Q86UE4 | MTDH Protein LYRIC |
| Q9UDX5 | MTFP1 Mitochondrial fission process protein 1 |
| P11586 | MTHFD1 C-1-tetrahydrofolate synthase, cytoplasmic |
| Q6UB35 | MTHFD1L Monofunctional C1-tetrahydrofolate synthase, mitoc |
| P13995 | MTHFD2 Bifunctional methylenetetrahydrofolate dehydrogena |
| P42898 | MTHFR Methylenetetrahydrofolate reductase |
| Q13505 | MTX1 Metaxin-1 |
| O75431 | MTX2 Metaxin-2 |
| Q969V5 | MUL1 Mitochondrial ubiquitin ligase activator of NFKB 1 |
| Q9BQG0 | MYBBP1A Myb-binding protein 1A |
| P35580 | MYH10 Myosin-10 |
| P35749 | MYH11 Myosin-11 |
| P35579 | MYH9 Myosin-9 |
| O14950 | MYL12B Myosin regulatory light chain 12B |
| P60660 | MYL6 Myosin light polypeptide 6 |
| Q96H55 | MYO19 Unconventional myosin-XIX |
| P41227 | NAA10 N-alpha-acetyltransferase 10 |
| Q9BXJ9 | NAA15 N-alpha-acetyltransferase 15, NatA auxiliary subun |
| Q6N069 | NAA16 N-alpha-acetyltransferase 16, NatA auxiliary subun |
| Q14CX7 | NAA25 N-alpha-acetyltransferase 25, NatB auxiliary subun |
| Q86UY6 | NAA40 N-alpha-acetyltransferase 40 |
| Q13765 | NACA Nascent polypeptide-associated complex subunit alp |
| Q4G0N4 | NADKD1 NAD kinase domain-containing protein 1 |
| Q13564 | NAE1 NEDD8-activating enzyme E1 regulatory subunit |
| P54802 | NAGLU Alpha-N-acetylglucosaminidase |
| P43490 | NAMPT Nicotinamide phosphoribosyltransferase |
| P55209 | NAP1L1 Nucleosome assembly protein 1-like 1 |
| Q99733 | NAP1L4 Nucleosome assembly protein 1-like 4 |
| F5HFY4 | NAP1L4b Nucleosome assembly protein 1-like 4 |

| Accession # | Protein Name |
|---|---|
| P54920 | NAPA Alpha-soluble NSF attachment protein |
| P49321 | NASP Nuclear autoantigenic sperm protein |
| Q9H0A0 | NAT10 N-acetyltransferase 10 |
| Q15021 | NCAPD2 Condensin complex subunit 1 |
| Q9BPX3 | NCAPG Condensin complex subunit 3 |
| Q15003 | NCAPH Condensin complex subunit 2 |
| Q09161 | NCBP1 Nuclear cap-binding protein subunit 1 |
| Q9UBB6 | NCDN Neurochondrin |
| Q6PIU2 | NCEH1 Neutral cholesterol ester hydrolase 1 |
| Q969V3 | NCLN Nicalin |
| Q9HCD5 | NCOA5 Nuclear receptor coactivator 5 |
| Q92542 | NCSTN Nicastrin |
| O95299 | NDUFA10 NADH dehydrogenase [ubiquinone] 1 alpha subcomplex |
| Q86Y39 | NDUFA11 NADH dehydrogenase [ubiquinone] 1 alpha subcomplex |
| Q9P0J0 | NDUFA13 NADH dehydrogenase [ubiquinone] 1 alpha subcomplex |
| O95167 | NDUFA3 NADH dehydrogenase |
| P51970 | NDUFA8 NADH dehydrogenase [ubiquinone] 1 alpha subcomplex |
| Q16795 | NDUFA9 NADH dehydrogenase [ubiquinone] 1 alpha subcomplex |
| O14561 | NDUFAB1 Acyl carrier protein, mitochondrial |
| O96000 | NDUFB10 NADH dehydrogenase [ubiquinone] 1 beta subcomplex |
| O43676 | NDUFB3 NADH dehydrogenase |
| O95168 | NDUFB4 NADH dehydrogenase [ubiquinone] 1 beta subcomplex |
| O95169 | NDUFB8 NADH dehydrogenase [ubiquinone] 1 beta subcomplex |
| Q9Y6M9 | NDUFB9 NADH dehydrogenase [ubiquinone] 1 beta subcomplex |
| P28331 | NDUFS1 NADH-ubiquinone oxidoreductase 75 kDa subunit, mit |
| O75306 | NDUFS2 NADH dehydrogenase [ubiquinone] iron-sulfur protei |
| O75489 | NDUFS3 NADH dehydrogenase [ubiquinone] iron-sulfur protei |
| O75251 | NDUFS7 NADH dehydrogenase |
| O00217 | NDUFS8 NADH dehydrogenase [ubiquinone] iron-sulfur protei |
| P49821 | NDUFV1 NADH dehydrogenase |
| P19404 | NDUFV2 NADH dehydrogenase [ubiquinone] flavoprotein 2, mi |
| P07197 | NEFM Neurofilament medium polypeptide |
| Q9UMX5 | NENF Neudesin |
| Q8NBF2 | NHLRC2 NHL repeat-containing protein 2 |
| P55769 | NHP2L1 NHP2-like protein 1 |
| Q9Y221 | NIP7 60S ribosome subunit biogenesis protein NIP7 homol |
| Q9BPW8 | NIPSNAP1 Protein NipSnap homolog 1 |
| O15226 | NKRF NF-kappa-B-repressing factor |
| Q9BYT8 | NLN Neurolysin, mitochondrial |
| P30419 | NMT1 Glycylpeptide N-tetradecanoyltransferase 1 |
| P40261 | NNMT Nicotinamide N-methyltransferase |
| Q13423 | NNT NAD(P) transhydrogenase, mitochondrial |
| Q9Y3T9 | NOC2L Nucleolar complex protein 2 homolog |
| Q8WTT2 | NOC3L Nucleolar complex protein 3 homolog |
| Q9BVI4 | NOC4L Nucleolar complex protein 4 homolog |
| Q5SY16 | NOL9 Polynucleotide 5-hydroxyl-kinase NOL9 |
| Q15155 | NOMO1 Nodal modulator 1 |
| Q5JPE7 | NOMO2 Nodal modulator 2 |
| P69849 | NOMO3 Nodal modulator 3 |
| Q15233 | NONO Non-POU domain-containing octamer-binding protein |
| O00567 | NOP56 Nucleolar protein 56 |
| Q9Y2X3 | NOP58 Nucleolar protein 58 |
| Q8IVI9 | NOSTRIN Nostrin |
| O15118 | NPC1 Niemann-Pick C1 protein |
| P61916 | NPC2 Epididymal secretory protein E1 |
| P55786 | NPEPPS Puromycin-sensitive aminopeptidase |
| P06748 | NPM1 Nucleophosmin |
| O75607 | NPM3 Nucleoplasmin-3 |
| P15559 | NQO1 NAD(P)H dehydrogenase [quinone] 1 |
| P04150 | NR3C1 Glucocorticoid receptor |
| P01111 | NRAS GTPase NRas |
| O43847 | NRD1 Nardilysin |
| Q8IXM6 | NRM Nurim |
| Q15738 | NSDHL Sterol-4-alpha-carboxylate 3-dehydrogenase, decarb |
| P46459 | NSF Vesicle-fusing ATPase |
| Q08J23 | NSUN2 tRNA (cytosine(34)-C(5))-methyltransferase |
| P49902 | NT5C2 Cytosolic purine 5-nucleotidase |
| Q9HOP0 | NT5C3 Cytosolic 5-nucleotidase 3 |
| Q969T7 | NT5C3L Cytosolic 5-nucleotidase III-like protein |
| Q5TFE4 | NT5DC1 5-nucleotidase domain-containing protein 1 |
| Q9H857 | NT5DC2 5-nucleotidase domain-containing protein 2 |
| Q86UY8 | NT5DC3 5-nucleotidase domain-containing protein 3 |
| Q9BV86 | NTMT1 N-terminal Xaa-Pro-Lys N-methyltransferase 1 |
| Q9BSD7 | NTPCR Cancer-related nucleoside-triphosphatase |
| Q02818 | NUCB1 Nucleobindin-1 |
| P80303 | NUCB2 Nucleobindin-2 |
| Q9Y266 | NUDC Nuclear migration protein nudC |
| Q96RS6 | NUDCD1 NudC domain-containing protein 1 |
| Q9BQG2 | NUDT12 Peroxisomal NADH pyrophosphatase NUDT12 |
| Q9NV35 | NUDT15 Probable 8-oxo-dGTP diphosphatase NUDT15 |
| A8MXV4 | NUDT19 Nucleoside diphosphate-linked moiety X motif 19, m |
| O43809 | NUDT21 Cleavage and polyadenylation specificity factor su |
| Q9BW91 | NUDT9 ADP-ribose pyrophosphatase, mitochondrial |
| Q14980 | NUMA1 Nuclear mitotic apparatus protein 1 |
| P57740 | NUP107 Nuclear pore complex protein Nup107 |
| Q8WUM0 | NUP133 Nuclear pore complex protein Nup133 |
| P49790 | NUP153 Nuclear pore complex protein Nup153 |
| O75694 | NUP155 Nuclear pore complex protein Nup155 |
| Q12769 | NUP160 Nuclear pore complex protein Nup160 |
| Q92621 | NUP205 Nuclear pore complex protein Nup205 |
| Q8TEM1 | NUP210 Nuclear pore membrane glycoprotein 210 |
| P35658 | NUP214 Nuclear pore complex protein Nup214 |
| Q8NFH5 | NUP35 Nucleoporin NUP53 |
| Q8NFH4 | NUP37 Nucleoporin Nup37 |
| Q8NFH3 | NUP43 Nucleoporin Nup43 |
| Q9UKX7 | NUP50 Nuclear pore complex protein Nup50 |
| Q7Z3B4 | NUP54 Nucleoporin p54 |
| P37198 | NUP62 Nuclear pore glycoprotein p62 |
| Q9BW27 | NUP85 Nuclear pore complex protein Nup85 |

| Accession # | Protein Name |
|---|---|
| Q99567 | NUP88 Nuclear pore complex protein Nup88 |
| Q8N1F7 | NUP93 Nuclear pore complex protein Nup93 |
| P52948 | NUP98 Nuclear pore complex protein Nup98-Nup96 |
| P61970 | NUTF2 Nuclear transport factor 2 |
| Q9UBU9 | NXF1 Nuclear RNA export factor 1 |
| Q6DKJ4 | NXN Nucleoredoxin |
| P04181 | OAT Ornithine aminotransfemse, mitochondrial |
| Q9NX40 | OCIAD1 OCIA domain-containing protein 1 |
| Q5SWX8 | ODR4 Protein odr-4 homolog |
| Q02218 | OGDH 2-oxoglutarate dehydrogenase, mitochondrial |
| O15294 | OGT UDP-N-acetylglucosamine--peptide N-acetylglucosami |
| Q9NTK5 | OLA1 Obg-like ATPase 1 |
| Q96E52 | OMA1 Metalloendopeptidase OMA1, mitochondrial |
| O60313 | OPA1 Dynamin-like 120 kDa protein, mitochondrial |
| Q9H6K4 | OPA3 Optic atrophy 3 protein |
| Q9UBD5 | ORC3 Origin recognition complex subunit 3 |
| P22059 | OSBP Oxysterol-binding protein 1 |
| Q9BZF1 | OSBPL8 Oxysterol-binding protein-related protein 8 |
| Q96SU4 | OSBPL9 Oxysterol-binding protein-related protein 9 |
| Q96FW1 | OTUB1 Ubiquitin thioestemse OTUB1 |
| Q15070 | OXA1L Mitochondrial inner membrane protein OXA1L |
| P13674 | P4HA1 Prolyl 4-hydroxylase subunit alpha-1 |
| P07237 | P4HB Protein disulfide-isomerase |
| Q9UQ80 | PA2G4 Proliferation-associated protein 2G4 |
| P11940 | PABPC1 Polyadenylate-binding protein 1 |
| Q9H361 | PABPC3 Polyadenylate-binding protein 3 |
| Q13310 | PABPC4 Polyadenylate-binding protein 4 |
| Q86U42 | PABPN1 Polyadenylate-binding protein 2 |
| P68402 | PAFAH1B2 Platelet-activating factor acetylhydrolase IB subu |
| P22234 | PAICS Multifunctional protein ADE2 |
| Q9H074 | PAIP1 Polyadenylate-binding protein-interacting protein |
| Q13177 | PAK2 Serine/threonine-protein kinase PAK 2 |
| Q9NVE7 | PANK4 Pantothenate kinase 4 |
| P51003 | PAPOLA Poly(A) polymerase alpha |
| O43252 | PAPSS1 Bifunctional 3-phosphoadenosine 5-phosphosulfate |
| P09874 | PARP1 Poly [ADP-ribose] polymerase 1 |
| Q96KB5 | PBK Lymphokine-activated killer T-cell-originated prot |
| Q86U86 | PBRM1 Protein polybromo-1 |
| Q15365 | PCBP1 Poly(rC)-binding protein 1 |
| Q15366 | PCBP2 Poly(rC)-binding protein 2 |
| P57721 | PCBP3 Poly(rC)-binding protein 3 |
| Q16822 | PCK2 Phosphoenolpyruvate carboxykinase [GTP], mitochond |
| Q15154 | PCM1 Pericentriolar material 1 protein |
| P22061 | PCMT1 Protein-L-isoaspartate(D-aspartate) O-methyltransf |
| P12004 | PCNA Proliferating cell nuclear antigen |
| Q9UHG3 | PCYOX1 Prenylcysteine oxidase 1 |
| Q8NBM8 | PCYOX1L Prenylcysteine oxidase-like |
| P49585 | PCYT1A Choline-phosphate cytidylyltransferase A |
| Q14690 | PDCD11 Protein RRP5 homolog |
| Q53EL6 | PDCD4 Programmed cell death protein 4 |
| O14737 | PDCD5 Programmed cell death protein 5 |
| O75340 | PDCD6 Programmed cell death protein 6 |
| Q8WUM4 | PDCD6IP Programmed cell death 6-interacting protein |
| Q9H2J4 | PDCL3 Phosducin-like protein 3 |
| Q6L8Q7 | PDE12 2,5-phosphodiesterase 12 |
| P08559 | PDHA1 Pyruvate dehydrogenase E1 component subunit alpha, |
| P11177 | PDHB Pyruvate dehydrogenase E1 component subunit beta, |
| P30101 | PDIA3 Protein disulfide-isomerase A3 |
| P13667 | PDIA4 Protein disulfide-isomerase A4 |
| Q15084 | PDIA6 Protein disulfide-isomerase A6 |
| O00151 | PDLIM1 PDZ and LIM domain protein 1 |
| Q9P0J1 | PDP1 |
| Q9NUG6 | PDRG1 p53 and DNA damage-regulated protein 1 |
| Q29RF7 | PDS5A Sister chromatid cohesion protein PDS5 homolog A |
| O00764 | PDXK Pyridoxal kinase |
| P30086 | PEBP1 Phosphatidylethanolamine-binding protein 1 |
| Q9BY49 | PECR Peroxisomal trans-2-enoyl-CoA reductase |
| Q9UBV8 | PEF1 Peflin |
| Q9BRX2 | PELO Protein pelota homolog |
| Q8IZL8 | PELP1 Proline-, glutamic acid- and leucine-rich protein |
| O00541 | PES1 Pescadillo homolog |
| O96011 | PEX11B Peroxisomal membrane protein 11B |
| Q9Y5Y5 | PEX16 Peroxisomal membrane protein PEX16 |
| P40855 | PEX19 Peroxisomal biogenesis factor 19 |
| PFAS | |
| O15067 | Phosphoribosylformylglycinamidine synthase |
| Q9UHV9 | PFDN2 Prefoldin subunit 2 |
| Q99471 | PFDN5 Prefoldin subunit 5 |
| P17858 | PFKL 6-phosphofructokinase, liver type |
| P08237 | PFKM 6-phosphofructokinase, muscle type |
| Q01813 | PFKP 6-phosphofructokinase type C |
| P07737 | PFN1 Profilin-1 |
| Q96HS1 | PGAM5 Serine/threonine-protein phosphatase PGAM5, mitoch |
| P00558 | PGK1 Phosphoglycerate kinase 1 |
| P07205 | PGK2 Phosphoglycerate kinase 2 |
| P36871 | PGM1 Phosphoglucomutase-1 |
| O95394 | PGM3 Phosphoacetylglucosamine mutase |
| O00264 | PGRMC1 Membrane-associated progesterone receptor componen |
| O15173 | PGRMC2 Membrane-associated progesterone receptor componen |
| P35232 | PHB Prohibitin |
| Q99623 | PHB2 Prohibitin-2 |
| O43175 | PHGDH D-3-phosphoglycerate dehydrogenase |
| Q9BTU6 | PI4K2A Phosphatidylinositol 4-kinase type 2-alpha |
| Q9UBF8 | PI4KB Phosphatidylinositol 4-kinase beta |
| Q13492 | PICALM Phosphatidylinositol-binding clathrin assembly pro |
| Q92643 | PIGK GPI-anchor transamidase |
| Q969N2 | PIGT GPI transamidase component PIG-T |
| Q9H490 | PIGU Phosphatidylinositol glycan anchor biosynthesis cl |
| Q13526 | PIN1 Peptidyl-prolyl cis-trans isomerase NIMA-interacti |
| Q9UG56 | PISD Phosphatidylserine decarboxylase proenzyme |
| Q00169 | PITPNA Phosphatidylinositol transfer protein alpha isofor |
| P48739 | PITPNB Phosphatidylinositol transfer protein beta isoform |
| Q5JRX3 | PITRM1 Presequence protease, mitochondrial |
| P30613 | PKLR Pyruvate kinase isozymes R/L |
| P14618 | PKM Pyruvate kinase isozymes M1/M2 |
| Q99640 | PKMYT1 Membrane-associated tyrosine- and threonine-specif |

| Accession # | Protein Name |
|---|---|
| Q16512 | PKN1 Serine/threonine-protein kinase N1 |
| Q16513 | PKN2 Serine/threonine-protein kinase N2 |
| Q9Y446 | PKP3 Plakophilin-3 |
| Q8NCC3 | PLA2G15 Group XV phospholipase A2 |
| Q8NHP8 | PLBD2 Putative phospholipase B-like 2 |
| P19174 | PLCG1 1-phosphatidylinositol 4,5-bisphosphate phosphodie |
| Q8IV08 | PLD3 Phospholipase D3 |
| Q15149 | PLEC Plectin |
| Q99541 | PLIN2 Perilipin-2 |
| O60664 | PLIN3 Perilipin-3 |
| P53350 | PLK1 Serine/threonine-protein kinase PLK1 |
| Q02809 | PLOD1 Procollagen-lysine, 2-oxoglutarate 5-dioxygenase 1 |
| P13797 | PLS3 Plastin-3 |
| Q10713 | PMPCA Mitochondrial-processing peptidase subunit alpha |
| O75439 | PMPCB Mitochondrial-processing peptidase subunit beta |
| Q9H307 | PNN Pinin |
| Q96AD5 | PNPLA2 Patatin-like phospholipase domain-containing prote |
| Q8TCS8 | PNPT1 Polyribonucleotide nucleotidyltransferase 1, mitoc |
| F8VUJ3 | POC1B-GALNT4 Protein POC1B-GALNT4 |
| Q14181 | POLA2 DNA polymerase alpha subunit B |
| P28340 | POLD1 DNA polymerase delta catalytic subunit |
| Q9Y257 | POLDIP2 Polymerase delta-interacting protein 2 |
| P24928 | POLR2A DNA-directed RNA polymerase II subunit RPB1 |
| P30876 | POLR2B DNA-directed RNA polymerase II subunit RPB2 |
| O00411 | POLRMT DNA-directed RNA polymerase, mitochondrial |
| Q15165 | PON2 Serum paraoxonase/arylesterase 2 |
| Q99575 | POP1 Ribonucleases P/MRP protein subunit POP1 |
| P16435 | POR NADPH--cytochrome P450 reductase |
| Q9H2U2 | PPA2 Inorganic pyrophosphatase 2, mitochondrial |
| Q9NQ55 | PPAN Suppressor of SWI4 1 homolog |
| C9J3F9 | PPAN-P2RY11 Protein PPAN-P2RY11 |
| Q06203 | PPAT Amidophosphoribosyltransferase |
| Q13356 | PPIL2 Peptidyl-prolyl cis-trans isomerase-like 2 |
| P49593 | PPM1F Protein phosphatase 1F |
| O15355 | PPM1G Protein phosphatase 1G |
| Q9Y570 | PPME1 Protein phosphatase methylesterase 1 |
| P62136 | PPP1CA Serine/threonine-protein phosphatase PP1-alpha cat |
| P62140 | PPP1CB Serine/threonine-protein phosphatase PP1-beta cata |
| P36873 | PPP1CC Serine/threonine-protein phosphatase PP1-gamma cat |
| P67775 | PPP2CA Serine/threonine-protein phosphatase 2A catalytic |
| P62714 | PPP2CB Serine/threonine-protein phosphatase 2A catalytic |
| P30153 | PPP2R1A Serine/threonine-protein phosphatase 2A 65 kDa reg |
| P30154 | PPP2R1B Serine/threonine-protein phosphatase 2A 65 kDa reg |
| P63151 | PPP2R2A Serine/threonine-protein phosphatase 2A 55 kDa reg |
| Q15172 | PPP2R5A Serine/threonine-protein phosphatase 2A 56 kDa reg |
| Q13362 | PPP2R5C Serine/threonine-protein phosphatase 2A 56 kDa reg |
| Q14738 | PPP2R5D Serine/threonine-protein phosphatase 2A 56 kDa reg |
| P60510 | PPP4C Serine/threonine-protein phosphatase 4 catalytic s |
| O00743 | PPP6C Serine/threonine-protein phosphatase 6 catalytic s |
| Q9UPN7 | PPP6R1 Serine/threonine-protein phosphatase 6 regulatory |
| Q5H9R7 | PPP6R3 Serine/threonine-protein phosphatase 6 regulatory |
| P50897 | PPT1 Palmitoyl-protein thioesterase 1 |
| Q9UMR5 | PPT2 Lysosomal thioesterase PPT2 |
| O43663 | PRC1 Protein regulator of cytokinesis 1 |
| P42785 | PRCP Lysosomal Pro-X carboxypeptidase |
| Q06830 | PRDX1 Peroxiredoxin-1 |
| P32119 | PRDX2 Peroxiredoxin-2 |
| P30048 | PRDX3 Thioredoxin-dependent peroxide reductase, mitochon |
| Q13162 | PRDX4 Peroxiredoxin-4 |
| P30044 | PRDX5 Peroxiredoxin-5, mitochondrial |
| P30041 | PRDX6 Peroxiredoxin-6 |
| Q9HCU5 | PREB Prolactin regulatory element-binding protein |
| P48147 | PREP Prolyl endopeptidase |
| Q4J6C6 | PREPL Prolyl endopeptidase-like |
| P49643 | PRIM2 DNA primase large subunit |
| P17612 | PRKACA cAMP-dependent protein kinase catalytic subunit a1 |
| P54619 | PRKAG1 5-AMP-activated protein kinase subunit gamma-1 |
| P10644 | PRKAR1A cAMP-dependent protein kinase type I-alpha regulat |
| P13861 | PRKAR2A cAMP-dependent protein kinase type II-alpha regula |
| P31323 | PRKAR2B cAMP-dependent protein kinase type II-beta regulat |
| P05771 | PRKCB Protein kinase C beta type |
| P14314 | PRKCSH Glucosidase 2 subunit beta |
| P78527 | PRKDC DNA-dependent protein kinase catalytic subunit |
| O75569 | PRKRA Interferon-inducible double stranded RNA-dependent |
| Q99873 | PRMT1 Protein arginine N-methyltransferase 1 |
| O60678 | PRMT3 Protein arginine N-methyltransferase 3 |
| O14744 | PRMT5 Protein arginine N-methyltransferase 5 |
| Q9UMS4 | PRPF19 Pre-mRNA-processing factor 19 |
| Q5VTL8 | PRPF38B Pre-mRNA-splicing factor 38B |
| O75400 | PRPF40A Pre-mRNA-processing factor 40 homolog A |
| O94906 | PRPF6 Pre-mRNA-processing factor 6 |
| Q6P2Q9 | PRPF8 Pre-mRNA-processing-splicing factor 8 |
| P48634 | PRRC2A Protein PRRC2A |
| Q9Y520 | PRRC2C Protein PRRC2C |
| P07602 | PSAP Proactivator polypeptide |
| P49768 | PSEN1 Presenilin-1 |
| P49810 | PSEN2 Presenilin-2 |
| O75475 | PSIP1 PC4 and SFRS1-interacting protein |
| P25786 | PSMA1 Proteasome subunit alpha type-1 |
| P25787 | PSMA2 Proteasome subunit alpha type-2 |
| P25788 | PSMA3 Proteasome subunit alpha type-3 |
| P25789 | PSMA4 Proteasome subunit alpha type-4 |
| P28066 | PSMA5 Proteasome subunit alpha type-5 |
| P60900 | PSMA6 Proteasome subunit alpha type-6 |
| O14818 | PSMA7 Proteasome subunit alpha type-7 |
| P20618 | PSMB1 Proteasome subunit beta type-1 |
| P49721 | PSMB2 Proteasome subunit beta type-2 |
| P49720 | PSMB3 Proteasome subunit beta type-3 |
| P28070 | PSMB4 Proteasome subunit beta type-4 |
| P28074 | PSMB5 Proteasome subunit beta type-5 |
| P28072 | PSMB6 Proteasome subunit beta type-6 |
| Q99436 | PSMB7 Proteasome subunit beta type-7 |
| P62191 | PSMC1 26S protease regulatory subunit 4 |
| P35998 | PSMC2 26S protease regulatory subunit 7 |

| Accession # | Protein Name |
|---|---|
| P17980 | PSMC3 26S protease regulatory subunit 6A |
| P43686 | PSMC4 26S protease regulatory subunit 6B |
| P62195 | PSMC5 26S protease regulatory subunit 8 |
| P62333 | PSMC6 26S protease regulatory subunit 10B |
| Q99460 | PSMD1 26S proteasome non-ATPase regulatory subunit 1 |
| O75832 | PSMD10 26S proteasome non-ATPase regulatory subunit 10 |
| O00231 | PSMD11 26S proteasome non-ATPase regulatory subunit 11 |
| Q9UNM6 | PSMD13 26S proteasome non-ATPase regulatory subunit 13 |
| O00487 | PSMD14 26S proteasome non-ATPase regulatory subunit 14 |
| Q13200 | PSMD2 26S proteasome non-ATPase regulatory subunit 2 |
| O43242 | PSMD3 26S proteasome non-ATPase regulatory subunit 3 |
| Q16401 | PSMD5 26S proteasome non-ATPase regulatory subunit 5 |
| Q15008 | PSMD6 26S proteasome non-ATPase regulatory subunit 6 |
| P51665 | PSMD7 26S proteasome non-ATPase regulatory subunit 7 |
| P48556 | PSMD8 26S proteasome non-ATPase regulatory subunit 8 |
| Q06323 | PSME1 Proteasome activator complex subunit 1 |
| Q9UL46 | PSME2 Proteasome activator complex subunit 2 |
| P61289 | PSME3 Proteasome activator complex subunit 3 |
| Q92530 | PSMF1 Proteasome inhibitor PI31 subunit |
| O95456 | PSMG1 Proteasome assembly chaperone 1 |
| Q8WXF1 | PSPC1 Paraspeckle component 1 |
| P26599 | PTBP1 Polypyrimidine tract-binding protein 1 |
| O95758 | PTBP3 Polypyrimidine tract-binding protein 3 |
| Q96EY7 | PTCD3 Pentatricopeptide repeat-containing protein 3, mit |
| P48651 | PTDSS1 Phosphatidylserine synthase 1 |
| Q9BVG9 | PTDSS2 Phosphatidylserine synthase 2 |
| Q9H7Z7 | PTGES2 Prostaglandin E synthase 2 |
| Q15185 | PTGES3 Prostaglandin E synthase 3 |
| Q8N8N7 | PTGR2 Prostaglandin reductase 2 |
| Q9P035 | PTPLAD1 3-hydroxyacyl-CoA dehydratase 3 |
| P18031 | PTPN1 Tyrosine-protein phosphatase non-receptor type 1 |
| Q06124 | PTPN11 Tyrosine-protein phosphatase non-receptor type 11 |
| Q9H3S7 | PTPN23 Tyrosine-protein phosphatase non-receptor type 23 |
| Q6NZI2 | PTRF Polymerase I and transcript release factor |
| Q9Y3E5 | PTRH2 Peptidyl-tRNA hydrolase 2, mitochondrial |
| Q9UHX1 | PUF60 Poly(U)-binding-splicing factor PUF60 |
| Q14671 | PUM1 Pumilio homolog 1 |
| Q96PZ0 | PUS7 Pseudouridylate synthase 7 homolog |
| Q15269 | PWP2 Periodic tryptophan protein 2 homolog |
| Q9NR77 | PXMP2 Peroxisomal membrane protein 2 |
| P32322 | PYCR1 Pyrroline-5-carboxylate reductase 1, mitochondrial |
| Q96C36 | PYCR2 Pyrroline-5-carboxylate reductase 2 |
| P11216 | PYGB Glycogen phosphorylase, brain form |
| P06737 | PYGL Glycogen phosphorylase, liver form |
| P20742 | PZP Pregnancy zone protein |
| Q5XKP0 | QIL1 Protein QIL1 |
| Q96PU8 | QKI Protein quaking |
| P61026 | RAB10 Ras-related protein Rab-10 |
| P62491 | RAB11A Ras-related protein Rab-11A |
| Q15907 | RAB11B Ras-related protein Rab-11B |
| P61106 | RAB14 Ras-related protein Rab-14 |
| Q9NP72 | RAB18 Ras-related protein Rab-18 |
| P62820 | RAB1A Ras-related protein Rab-1A |
| Q9H0U4 | RAB1B Ras-related protein Rab-1B |
| Q9UL25 | RAB21 Ras-related protein Rab-21 |
| Q969Q5 | RAB24 Ras-related protein Rab-24 |
| P61019 | RAB2A Ras-related protein Rab-2A |
| Q8WUD1 | RAB2B Ras-related protein Rab-2B |
| Q15042 | RAB3GAP1 Rab3 GTPase-activating protein catalytic subunit |
| Q9H2M9 | RAB3GAP2 Rab3 GTPase-activating protein non-catalytic subun |
| Q8TBN0 | RAB3IL1 Guanine nucleotide exchange factor for Rab-3A |
| P20339 | RAB5A Ras-related protein Rab-5A |
| P61020 | RAB5B Ras-related protein Rab-5B |
| P51148 | RAB5C Ras-related protein Rab-5C |
| P51149 | RAB7A Ras-related protein Rab-7a |
| P51151 | RAB9A Ras-related protein Rab-9A |
| Q7Z6M1 | RABEPK Rab9 effector protein with kelch motifs |
| P54727 | RAD23B UV excision repair protein RAD23 homolog B |
| Q92878 | RAD50 DNA repair protein RAD50 |
| P78406 | RAE1 mRNA export factor |
| P11233 | RALA Ras-related protein Ral-A |
| Q9UKM9 | RALY RNA-binding protein Raly |
| P62826 | RAN GTP-binding nuclear protein Ran |
| P43487 | RANBP1 Ran-specific GTPase-activating protein |
| P49792 | RANBP2 E3 SUMO-protein ligase RanBP2 |
| P62834 | RAP1A Ras-related protein Rap-1A |
| P61224 | RAP1B Ras-related protein Rap-1b |
| P61225 | RAP2B Ras-related protein Rap-2b |
| Q9Y3L5 | RAP2C Ras-related protein Rap-2c |
| P54136 | RARS Arginine--tRNA ligase, cytoplasmic |
| Q8IY67 | RAVER1 Ribonucleoprotein PTB-binding 1 |
| Q09028 | RBBP4 Histone-binding protein RBBP4 |
| Q16576 | RBBP7 Histone-binding protein RBBP7 |
| Q9NWB1 | RBFOX1 RNA binding protein fox-1 homolog 1 |
| O43251 | RBFOX2 RNA binding protein fox-1 homolog 2 |
| P98175 | RBM10 RNA-binding protein 10 |
| Q8IXT5 | RBM12B RNA-binding protein 12B |
| Q96PK6 | RBM14 RNA-binding protein 14 |
| B0LM41 | RBM14/RBM4 Protein RBM14-RBM4 |
| Q96T37 | RBM15 Putative RNA-binding protein 15 |
| P49756 | RBM25 RNA-binding protein 25 |
| Q9NW13 | RBM28 RNA-binding protein 28 |
| P98179 | RBM3 Putative RNA-binding protein 3 |
| Q14498 | RBM39 RNA-binding protein 39 |
| Q9BWF3 | RBM4 RNA-binding protein 4 |
| Q9BQ04 | RBM4B RNA-binding protein 4B |
| P29558 | RBMS1 RNA-binding motif, single-stranded-interacting pro |
| P38159 | RBMX RNA-binding motif protein, X chromosome |
| Q96E39 | RBMXL1 RNA binding motif protein, X-linked-like-1 |
| Q15293 | RCN1 Reticulocalbin-1 |
| Q14257 | RCN2 Reticulocalbin-2 |
| Q8TC12 | RDH11 Retinol dehydrogenase 11 |
| Q8NBN7 | RDH13 Retinol dehydrogenase 13 |
| Q9HBH5 | RDH14 Retinol dehydrogenase 14 |
| P35241 | RDX Radixin |

| Accession # | Protein Name |
|---|---|
| P46063 | RECQL ATP-dependent DNA helicase Q1 |
| Q00765 | REEP5 Receptor expression-enhancing protein 5 |
| O15258 | RER1 Protein RER1 |
| Q6NUM9 | RETSAT All-trans-retinol 13,14-reductase |
| P35250 | RFC2 Replication factor C subunit 2 |
| P40938 | RFC3 Replication factor C subunit 3 |
| P35249 | RFC4 Replication factor C subunit 4 |
| P40937 | RFC5 Replication factor C subunit 5 |
| Q96AA3 | RFT1 Protein RFT1 homolog |
| Q15382 | RHEB GTP-binding protein Rheb |
| P61586 | RHOA Transforming protein RhoA |
| P08134 | RHOC Rho-related GTP-binding protein RhoC |
| Q8IXI1 | RHOT2 Mitochondrial Rho GTPase 2 |
| Q5UIP0 | RIF1 Telomere-associated protein RIF1 |
| Q6NUQ1 | RINT1 RAD50-interacting protein 1 |
| Q9BVS4 | RIOK2 Serine/threonine-protein kinase RIO2 |
| O43353 | RIPK2 Receptor-interacting serine/threonine-protein kina |
| Q9NWS8 | RMND1 Required for meiotic nuclear division protein 1 ho |
| O00584 | RNASET2 Ribonuclease T2 |
| Q9H920 | RNF121 RING finger protein 121 |
| Q9UBS8 | RNF14 E3 ubiquitin-protein ligase RNF14 |
| Q5VTR2 | RNF20 E3 ubiquitin-protein ligase BRE1A |
| Q9H4A4 | RNPEP Aminopeptidase B |
| P27694 | RPA1 Replication protein A 70 kDa DNA-binding subunit |
| P15927 | RPA2 Replication protein A 32 kDa subunit |
| P62906 | RPL10A 60S ribosomal protein L10a |
| Q02543 | RPL18A 60S ribosomal protein L18a |
| P62750 | RPL23 A 60S ribosomal protein L23a |
| P61254 | RPL26 60S ribosomal protein L26 |
| P62888 | RPL30 60S ribosomal protein L30 |
| P36578 | RPL4 60S ribosomal protein L4 |
| P18124 | RPL7 60S ribosomal protein L7 |
| P62424 | RPL7A 60S ribosomal protein L7a |
| Q6DKI1 | RPL7L1 60S ribosomal protein L7-like 1 |
| P62917 | RPL8 60S ribosomal protein L8 |
| P05387 | RPLP2 60S acidic ribosomal protein P2 |
| P04843 | RPN1 Dolichyl-diphosphooligosaccharide-protein glycosy |
| P04844 | RPN2 Dolichyl-diphosphooligosaccharide-protein glycosy |
| Q9NQG5 | RPRD1B Regulation of nuclear pre-mRNA domain-containing p |
| P46783 | RPS10 40S ribosomal protein S10 |
| P62277 | RPS13 40S ribosomal protein S13 |
| P62244 | RPS15A 40S ribosomal protein S15a |
| P62249 | RPS16 40S ribosomal protein S16 |
| P62269 | RPS18 40S ribosomal protein S18 |
| P15880 | RPS2 40S ribosomal protein S2 |
| P62266 | RPS23 40S ribosomal protein S23 |
| P62847 | RPS24 40S ribosomal protein S24 |
| P62979 | RPS27A Ubiquitin-40S ribosomal protein S27a |
| P23396 | RPS3 40S ribosomal protein S3 |
| P61247 | RPS3A 40S ribosomal protein S3a |
| Q15418 | RPS6KA1 Ribosomal protein S6 kinase alpha-1 |
| Q15349 | RPS6KA2 Ribosomal protein S6 kinase alpha-2 |
| P51812 | RPS6KA3 Ribosomal protein S6 kinase alpha-3 |
| P62241 | RPS8 40S ribosomal protein S8 |
| A6NE09 | RPSAP58 Protein RPSAP58 |
| Q8IZ73 | RPUSD2 RNA pseudouridylate synthase domain-containing pro |
| Q9HB90 | RRAGC Ras-related GTP-binding protein C |
| Q9P2E9 | RRBP1 Ribosome-binding protein 1 |
| P23921 | RRM1 Ribonucleoside-diphosphate reductase large subunit |
| P31350 | RRM2 Ribonucleoside-diphosphate reductase subunit M2 |
| P56182 | RRP1 Ribosomal RNA processing protein 1 homolog A |
| Q5JTH9 | RRP12 RRP12-like protein |
| Q14684 | RRP1B Ribosomal RNA processing protein 1 homolog B |
| O76021 | RSL1D1 Ribosomal L1 domain-containing protein 1 |
| Q92541 | RTF1 RNA polymerase-associated protein RTF1 homolog |
| O95197 | RTN3 Reticulon-3 |
| Q9NQC3 | RTN4 Reticulon-4 |
| Q8WWV3 | RTN4IP1 Reticulon-4-interacting protein 1, mitochondrial |
| Q9Y265 | RUVBL1 RuvB-like 1 |
| Q9Y230 | RUVBL2 RuvB-like 2 |
| Q9NTJ5 | SACM1L Phosphatidylinositide phosphatase SAC1 |
| Q15424 | SAFB Scaffold attachment factor B1 |
| Q14151 | SAFB2 Scaffold attachment factor B2 |
| Q9Y512 | SAMM50 Sorting and assembly machinery component 50 homolo |
| Q9NSI8 | SAMSN1 SAM domain-containing protein SAMSN-1 |
| Q9NR31 | SAR1A GTP-binding protein SAR1a |
| Q9Y6B6 | SAR1B GTP-binding protein SAR1b |
| P49591 | SARS Serine--tRNA ligase, cytoplasmic |
| Q9NP81 | SARS2 Serine--tRNA ligase, mitochondrial |
| O43290 | SART1 U4/U6.U5 tri-snRNP-associated protein 1 |
| Q15020 | SART3 Squamous cell carcinoma antigen recognized by T-ce |
| O14828 | SCAMP3 Secretory carrier-associated membrane protein 3 |
| Q8WTV0 | SCARB1 Scavenger receptor class B member 1 |
| Q14108 | SCARB2 Lysosome membrane protein 2 |
| Q8NBX0 | SCCPDH Saccharopine dehydrogenase-like oxidoreductase |
| O00767 | SCD Acyl-CoA desaturase |
| Q8WVM8 | SCFD1 Sec1 family domain-containing protein 1 |
| O75880 | SCO1 Protein SCO1 homolog, mitochondrial |
| O43819 | SCO2 Protein SCO2 homolog, mitochondrial |
| P22307 | SCP2 Non-specific lipid-transfer protein |
| Q9HB40 | SCPEP1 Retinoid-inducible serine carboxypeptidase |
| O00560 | SDCBP Syntenin-1 |
| Q9BRK5 | SDF4 45 kDa calcium-binding protein |
| P31040 | SDHA Succinate dehydrogenase [ubiquinone] flavoprotein |
| P21912 | SDHB Succinate dehydrogenase [ubiquinone] iron-sulfur s |
| P67812 | SEC11A Signal peptidase complex catalytic subunit SEC11A |
| P55735 | SEC13 Protein SEC13 homolog |
| O15027 | SEC16A Protein transport protein Sec16A |
| O75396 | SEC22B Vesicle-trafficking protein SEC22b |
| Q15436 | SEC23A Protein transport protein Sec23A |
| Q15437 | SEC23B Protein transport protein Sec23B |
| Q9Y6Y8 | SEC23IP SEC23-interacting protein |
| P53992 | SEC24C Protein transport protein Sec24C |
| O94979 | SEC31A Protein transport protein Sec31A |
| P61619 | SEC61A1 Protein transport protein Sec61 subunit alpha isof |

| Accession # | Protein Name |
|---|---|
| Q99442 | SEC62 Translocation protein SEC62 |
| Q9UGP8 | SEC63 Translocation protein SEC63 homolog |
| Q9UBV2 | SEL1L Protein sel-1 homolog 1 |
| Q15019 | SEPT2 Septin-2 |
| Q16181 | SEPT7 Septin-7 |
| Q8NC51 | SERBP1 Plasminogen activator inhibitor 1 RNA-binding prot |
| P30740 | SERPINB1 Leukocyte elastase inhibitor |
| P29508 | SERPINB3 Serpin B3 |
| P35237 | SERPINB6 Serpin B6 |
| P50454 | SERPINH1 Serpin H1 |
| P58004 | SESN2 Sestrin-2 |
| Q01105 | SET Protein SET |
| Q15637 | SF1 Splicing factor 1 |
| Q15459 | SF3A1 Splicing factor 3A subunit 1 |
| Q12874 | SF3A3 Splicing factor 3A subunit 3 |
| O75533 | SF3B1 Splicing factor 3B subunit 1 |
| Q13435 | SF3B2 Splicing factor 3B subunit 2 |
| Q9BWJ5 | SF3B5 Splicing factor 3B subunit 5 |
| P23246 | SFPQ Splicing factor, proline- and glutamine-rich |
| Q9H9B4 | SFXN1 Sideroflexin-1 |
| Q96NB2 | SFXN2 Sideroflexin-2 |
| Q6P4A7 | SFXN4 Sideroflexin-4 |
| O95470 | SGPL1 Sphingosine-1-phosphate lyase 1 |
| O43765 | SGTA Small glutamine-rich tetratricopeptide repeat-cont |
| Q99961 | SH3GL1 Endophilin-A2 |
| Q9Y371 | SH3GLB1 Endophilin-B1 |
| P34896 | SHMT1 Serine hydroxymethyltransferase, cytosolic |
| P34897 | SHMT2 Serine hydroxymethyltransferase, mitochondrial |
| Q9HAT2 | SIAE Sialate O-acetylesterase |
| Q99720 | SIGMAR1 Sigma non-opioid intracellular receptor 1 |
| Q96ST3 | SIN3A Paired amphipathic helix protein Sin3a |
| P42285 | SKIV2L2 Superkiller viralicidic activity 2-like 2 |
| P63208 | SKP1 S-phase kinase-associated protein 1 |
| P41440 | SLC19A1 Folate transporter 1 |
| P43007 | SLC1A4 Neutral amino acid transporter A |
| Q15758 | SLC1A5 Neutral amino acid transporter B(0) |
| P53007 | SLC25A1 Tricarboxylate transport protein, mitochondrial |
| Q9UBX3 | SLC25A10 Mitochondrial dicarboxylate carrier |
| Q02978 | SLC25A11 Mitochondrial 2-oxoglutarate/malate carrier protei |
| O75746 | SLC25A12 Calcium-binding mitochondrial carrier protein Ara1 |
| Q9UJS0 | SLC25A13 Calcium-binding mitochondrial carrier protein Ara1 |
| Q9Y619 | SLC25A15 Mitochondrial ornithine transporter 1 |
| P16260 | SLC25A16 Graves disease carrier protein |
| Q9HC21 | SLC25A19 Mitochondrial thiamine pyrophosphate carrier |
| O43772 | SLC25A20 Mitochondrial carnitine/acylcarnitine carrier prot |
| Q9H936 | SLC25A22 Mitochondrial glutamate carrier 1 |
| Q6NUK1 | SLC25A24 Calcium-binding mitochondrial carrier protein SCaM |
| Q70HW3 | SLC25A26 S-adenosylmethionine mitochondrial carrier protein |
| Q00325 | SLC25A3 Phosphate carrier protein, mitochondrial |
| Q5SVS4 | SLC25A30 Kidney mitochondrial carrier protein 1 |
| Q9H2D1 | SLC25A32 Mitochondrial folate transporter/carrier |
| Q9BSK2 | SLC25A33 Solute carrier family 25 member 33 |
| P12235 | SLC25A4 ADP/ATP translocase 1 |
| Q8TBP6 | SLC25A40 Solute carrier family 25 member 40 |
| P05141 | SLC25A5 ADP/ATP translocase 2 |
| P12236 | SLC25A6 ADP/ATP translocase 3 |
| O14975 | SLC27A2 Very long-chain acyl-CoA synthetase |
| P11166 | SLC2A1 Solute carrier family 2, facilitated glucose trans |
| Q8TAD4 | SLC30A5 Zinc transporter 5 |
| Q6NXT4 | SLC30A6 Zinc transporter 6 |
| Q8NEW0 | SLC30A7 Zinc transporter 7 |
| Q6PML9 | SLC30A9 Zinc transporter 9 |
| O00400 | SLC33A1 Acetyl-coenzyme A transporter 1 |
| Q8TB61 | SLC35B2 Adenosine 3-phospho 5-phosphosulfate transporter |
| Q8IXU6 | SLC35F2 Solute carrier family 35 member F2 |
| Q96QD8 | SLC38A2 Sodium-coupled neutral amino acid transporter 2 |
| P08195 | SLC3A2 4F2 cell-surface antigen heavy chain |
| P30825 | SLC7A1 High affinity cationic amino acid transporter 1 |
| Q9H2G2 | SLK STE20-like serine/threonine-protein kinase |
| Q8WU79 | SMAP2 Stromal membrane-associated protein 2 |
| P28370 | SMARCA1 Probable global transcription activator SNF2L1 |
| P51532 | SMARCA4 Transcription activator BRG1 |
| O60264 | SMARCA5 SWI/SNF-related matrix-associated actin-dependent |
| Q12824 | SMARCB1 SWI/SNF-related matrix-associated actin-dependent |
| Q92922 | SMARCC1 SWI/SNF complex subunit SMARCC1 |
| Q14683 | SMC1A Structural maintenance of chromosomes protein 1A |
| O95347 | SMC2 Structural maintenance of chromosomes protein 2 |
| Q9UQE7 | SMC3 Structural maintenance of chromosomes protein 3 |
| Q9NTJ3 | SMC4 Structural maintenance of chromosomes protein 4 |
| A6NHR9 | SMCHD1 Structural maintenance of chromosomes flexible hin |
| Q16637 | SMN1 Survival motor neuron protein |
| P17405 | SMPD1 Sphingomyelin phosphodiesterase |
| Q9NXE4 | SMPD4 Sphingomyelin phosphodiesterase 4 |
| Q2TAY7 | SMU1 WD40 repeat-containing protein SMU1 |
| Q9H7B4 | SMYD3 SET and MYND domain-containing protein 3 |
| O00161 | SNAP23 Synaptosomal-associated protein 23 |
| O95721 | SNAP29 Synaptosomal-associated protein 29 |
| Q7KZF4 | SND1 Staphylococcal nuclease domain-containing protein |
| O75643 | SNRNP200 U5 small nuclear ribonucleoprotein 200 kDa helicas |
| Q96DI7 | SNRNP40 U5 small nuclear ribonucleoprotein 40 kDa protein |
| P08621 | SNRNP70 U1 small nuclear ribonucleoprotein 70 kDa |
| P09012 | SNRPA U1 small nuclear ribonucleoprotein A |
| P62314 | SNRPD1 Small nuclear ribonucleoprotein Sm D1 |
| Q13573 | SNW1 SNW domain-containing protein 1 |
| Q13596 | SNX1 Sorting nexin-1 |
| O60749 | SNX2 Sorting nexin-2 |
| Q96L92 | SNX27 Sorting nexin-27 |
| Q9Y5X3 | SNX5 Sorting nexin-5 |

| Accession # | Protein Name |
|---|---|
| Q9UNH7 | SNX6 Sorting nexin-6 |
| Q9Y5X1 | SNX9 Sorting nexin-9 |
| P35610 | SOAT1 Sterol O-acyltransferase 1 |
| P04179 | SOD2 Superoxide dismutase |
| P18583 | SON Protein SON |
| Q99523 | SORT1 Sortilin |
| O60271 | SPAG9 C-Jun-amino-terminal kinase-interacting protein 4 |
| Q8NB90 | SPATA5 Spermatogenesis-associated protein 5 |
| Q8NBT2 | SPC24 Kinetochore protein Spc24 |
| Q9HBM1 | SPC25 Kinetochore protein Spc25 |
| Q15005 | SPCS2 Signal peptidase complex subunit 2 |
| Q8N0X7 | SPG20 Spartin |
| Q9H2V7 | SPNS1 Protein spinster homolog 1 |
| P35270 | SPR Sepiapterin reductase |
| P02549 | SPTA1 Spectrin alpha chain, erythrocytic 1 |
| Q13813 | SPTAN1 Spectrin alpha chain, non-erythrocytic 1 |
| Q01082 | SPTBN1 Spectrin beta chain, non-erythrocytic 1 |
| O15269 | SPTLC1 Serine palmitoyltransferase 1 |
| O15270 | SPTLC2 Serine palmitoyltransferase 2 |
| Q14534 | SQLE Squalene monooxygenase |
| P30626 | SRI Sorcin |
| P19623 | SRM Spermidine synthase |
| P61011 | SRP54 Signal recognition particle 54 kDa protein |
| Q9UHB9 | SRP68 Signal recognition particle 68 kDa protein |
| O76094 | SRP72 Signal recognition particle 72 kDa protein |
| Q965B4 | SRPK1 SRSF protein kinase 1 |
| P08240 | SRPR Signal recognition particle receptor subunit alpha |
| Q9Y5M8 | SRPRB Signal recognition particle receptor subunit beta |
| Q9UQ35 | SRRM2 Serine/arginine repetitive matrix protein 2 |
| Q9BXP5 | SRRT Serrate RNA effector molecule homolog |
| O75494 | SRSF10 Serine/arginine-rich splicing factor 10 |
| P84103 | SRSF3 Serine/arginine-rich splicing factor 3 |
| Q16629 | SRSF7 Serine/arginine-rich splicing factor 7 |
| Q13242 | SRSF9 Serine/arginine-rich splicing factor 9 |
| Q04837 | SSBP1 Single-stranded DNA-binding protein, mitochondrial |
| P43307 | SSR1 Translocon-associated protein subunit alpha |
| P51571 | SSR4 Translocon-associated protein subunit delta |
| Q08945 | SSRP1 FACT complex subunit SSRP1 |
| P50502 | ST13 Hsc70-interacting protein |
| Q8N3U4 | STAG2 Cohesin subunit SA-2 |
| Q92783 | STAM Signal transducing adapter molecule 1 |
| O95772 | STARD3NL MLN64 N-terminal domain homolog |
| Q9NQZ5 | STARD7 StAR-related lipid transfer protein 7, mitochondri |
| P42224 | STAT1 Signal transducer and activator of transcription 1 |
| P52630 | STAT2 Signal transducer and activator of transcription 2 |
| P40763 | STAT3 Signal transducer and activator of transcription 3 |
| P42229 | STAT5A Signal transducer and activator of transcription 5 |
| P51692 | STAT5B Signal transducer and activator of transcription 5 |
| O95793 | STAU1 Double-stranded RNA-binding protein Staufen homolo |
| Q13586 | STIM1 Stromal interaction molecule 1 |
| P31948 | STIP1 Stress-induced-phosphoprotein 1 |
| Q9Y6E0 | STK24 Serine/threonine-protein kinase 24 |
| Q13188 | STK3 Serine/threonine-protein kinase 3 |
| Q13043 | STK4 Serine/threonine-protein kinase 4 |
| P16949 | STMN1 Stathmin |
| Q9UJZ1 | STOML2 Stomatin-like protein 2 |
| Q9Y3F4 | STRAP Serine-threonine kinase receptor-associated protei |
| Q96519 | STRBP Spermatid perinuclear RNA-binding protein |
| P46977 | STT3A Dolichyl-diphosphooligosaccharide--protein glycosy |
| Q8TCJ2 | STT3B Dolichyl-diphosphooligosaccharide--protein glycosy |
| Q9UNE7 | STUB1 E3 ubiquitin-protein ligase CHIP |
| O60499 | STX10 Syntaxin-10 |
| Q86Y82 | STX12 Syntaxin-12 |
| Q9P2W9 | STX18 Syntaxin-18 |
| Q13190 | STX5 Syntaxin-5 |
| O43752 | STX6 Syntaxin-6 |
| Q15833 | STXBP2 Syntaxin-binding protein 2 |
| O00186 | STXBP3 Syntaxin-binding protein 3 |
| Q96I99 | SUCLG2 Succinyl-CoA ligase [GDP-forming] subunit beta, mi |
| Q8IWZ8 | SUGP1 SURP and G-patch domain-containing protein 1 |
| O94901 | SUN1 SUN domain-containing protein 1 |
| Q9UH99 | SUN2 SUN domain-containing protein 2 |
| Q9Y5B9 | SUPT16H FACT complex subunit SPT16 |
| O00267 | SUPT5H Transcription elongation factor SPT5 |
| Q7KZ85 | SUPT6H Transcription elongation factor SPT6 |
| O15260 | SURF4 Surfeit locus protein 4 |
| Q15022 | SUZ12 Polycomb protein SUZ12 |
| Q96A49 | SYAP1 Synapse-associated protein 1 |
| Q92797 | SYMPK Symplekin |
| O60506 | SYNCRIP Heterogeneous nuclear ribonucleoprotein Q |
| Q9Y6A5 | TACC3 Transforming acidic coiled-coil-containing protein |
| Q9BSH4 | TACO1 Translational activator of cytochrome c oxidase 1 |
| Q92804 | TAF15 TATA-binding protein-associated factor 2N |
| P37802 | TAGLN2 Transgelin-2 |
| Q13148 | TARDBP TAR DNA-binding protein 43 |
| P26639 | TARS Threonine--tRNA ligase, cytoplasmic |
| Q9BW92 | TARS2 Threonine--tRNA ligase, mitochondrial |
| Q8TC07 | TBC1D15 TBC1 domain family member 15 |
| Q99426 | TBCB Tubulin-folding cofactor B |
| Q9BTW9 | TBCD Tubulin-specific chaperone D |
| Q15813 | TBCE Tubulin-specific chaperone E |
| Q9Y4P3 | TBL2 Transducin beta-like protein 2 |
| Q12788 | TBL3 Transducin beta-like protein 3 |
| Q969Z0 | TBRG4 Protein TBRG4 |
| P23193 | TCEA1 Transcription elongation factor A protein 1 |
| Q13428 | TCOF1 Treacle protein |
| P17987 | TCP1 T-complex protein 1 subunit alpha |
| Q9Y2W6 | TDRKH Tudor and KH domain-containing protein |
| Q9NZ01 | TECR Trans-2,3-enoyl-CoA reductase |
| Q9Y4R8 | TELO2 Telomere length regulation protein TEL2 homolog |
| Q9NXF1 | TEX10 Testis-expressed sequence 10 protein |
| Q00059 | TFAM Transcription factor A, mitochondrial |
| Q92734 | TFG Protein TFG |
| P02786 | TFRC Transferrin receptor protein 1 |

| Accession # | Protein Name |
|---|---|
| P21980 | TGM2 Protein-glutamine gamma-glutamyltransferase 2 |
| Q08188 | TGM3 Protein-glutamine gamma-glutamyltransferase E |
| Q96RS0 | TGS1 Trimethylguanosine synthase |
| Q8IXH7 | TH1L Negative elongation factor C/D |
| Q96FV9 | THOC1 THO complex subunit 1 |
| Q96J01 | THOC3 THO complex subunit 3 |
| P52888 | THOP1 Thimet oligopeptidase |
| Q9Y2W1 | THRAP3 Thyroid hormone receptor-associated protein 3 |
| Q9BV44 | THUMPD3 THUMP domain-containing protein 3 |
| P31483 | TIA1 Nucleolysin TIA-1 isoform p40 |
| Q01085 | TIAL1 Nucleolysin TIAR |
| P62072 | TIMM10 Mitochondrial import inner membrane translocase su |
| Q9Y5L4 | TIMM13 Mitochondrial import inner membrane translocase su |
| Q99595 | TIMM17A Mitochondrial import inner membrane translocase su |
| O60830 | TIMM17B Mitochondrial import inner membrane translocase su |
| O14925 | TIMM23 Mitochondrial import inner membrane translocase su |
| Q5SRD1 | TIMM23B Putative mitochondrial import inner membrane trans |
| O43615 | TIMM44 Mitochondrial import inner membrane translocase su |
| Q3ZCQ8 | TIMM50 Mitochondrial import inner membrane translocase su |
| Q9NPL8 | TIMMDC1 Translocase of inner mitochondrial membmne domain |
| O75663 | TIPRL TIP41-like protein |
| Q6JUT2 | TIRAP3 TIR domain-containing adapter molecule 2 |
| Q86UE8 | TLK2 Serine/threonine-protein kinase tousled-like 2 |
| E9PSI1 | TM9SF1 Transmembrane 9 superfamily member 1 |
| Q99805 | TM9SF2 Transmembrane 9 superfamily member 2 |
| Q9HD45 | TM9SF3 Transmembrane 9 superfamily member 3 |
| Q92544 | TM9SF4 Transmembrane 9 superfamily member 4 |
| P55061 | TMBIM6 Bax inhibitor 1 |
| Q9UM00 | TMCO1 Transmembrane and coiled-coil domain-containing pr |
| Q13445 | TMED1 Transmembrane emp24 domain-containing protein 1 |
| P49755 | TMED10 Transmembrane emp24 domain-containing protein 10 |
| Q15363 | TMED2 Transmembrane emp24 domain-containing protein 2 |
| Q9Y3A6 | TMED5 Transmembrane emp24 domain-containing protein 5 |
| Q9Y3B3 | TMED7 Transmembrane emp24 domain-containing protein 7 |
| Q9BVK6 | TMED9 Transmembrane emp24 domain-containing protein 9 |
| Q9H0G1 | TMEM126A Transmembrane protein 126A |
| Q8IUX1 | TMEM126B Transmembrane protein 126B |
| Q9P0S9 | TMEM14C Transmembrane protein 14C |
| Q9NX00 | TMEM160 Transmembrane protein 160 |
| Q9NX61 | TMEM161A Transmembrane protein 161A |
| Q9HC07 | TMEM165 Transmembrane protein 165 |
| Q86WV6 | TMEM173 Transmembrane protein 173 |
| O14524 | TMEM194A Transmembrane protein 194A |
| Q8N511 | TMEM199 Transmembrane protein 199 |
| Q6UW68 | TMEM205 Transmembrane protein 205 |
| Q9H813 | TMEM206 Transmembrane protein 206 |
| Q96SK2 | TMEM209 Transmembrane protein 209 |
| Q6NUQ4 | TMEM214 Transmembrane protein 214 |
| P57088 | TMEM33 Transmembrane protein 33 |
| Q9NVV0 | TMEM38B Trimeric intracellular cation channel type B |
| Q9BTV4 | TMEM43 Transmembrane protein 43 |
| Q9BTX1 | TMEM48 Nucleoporin NDC1 |
| Q9BXS4 | TMEM59 Transmembrane protein 59 |
| Q6PI78 | TMEM65 Transmembrane protein 65 |
| Q96MH6 | TMEM68 Transmembrane protein 68 |
| Q9BUB7 | TMEM70 Transmembrane protein 70, mitochondrial |
| Q8NBN3 | TMEM87A Transmembrane protein 87A |
| Q5BJF2 | TMEM97 Transmembrane protein 97 |
| P28289 | TMOD1 Tropomodulin-1 |
| Q9NYL9 | TMOD3 Tropomodulin-3 |
| P42166 | TMPO Lamina-associated polypeptide 2, isoform alpha |
| P42167 | TMPO Lamina-associated polypeptide 2, isoforms beta/gam |
| Q6ZXV5 | TMTC3 Transmembrane and TPR repeat-containing protein 3 |
| Q9H3N1 | TMX1 Thioredoxin-related transmembrane protein 1 |
| Q96JJ7 | TMX3 Protein disulfide-isomerase TMX3 |
| Q9H1E5 | TMX4 Thioredoxin-related transmembrane protein 4 |
| Q9C0C2 | TNKS1BP1 182 kDa tankyrase-1-binding protein |
| Q92973 | TNPO1 Transportin-1 |
| O14787 | TNPO2 Transportin-2 |
| Q9Y5L0 | TNPO3 Transportin-3 |
| O60784 | TOM1 Target of Myb protein 1 |
| Q9NS69 | TOMM22 Mitochondrial import receptor subunit TOM22 homolo |
| O96008 | TOMM40 Mitochondrial import receptor subunit TOM40 homolo |
| O94826 | TOMM70A Mitochondrial import receptor subunit TOM70 |
| P11388 | TOP2A DNA topoisomerase 2-alpha |
| Q02880 | TOP2B DNA topoisomerase 2-beta |
| O14656 | TOR1A Torsin-1A |
| Q5JTV8 | TOR1AIP1 Torsin-1A-interacting protein 1 |
| P04637 | TP53 Cellular tumor antigen p53 |
| O43399 | TPD52L2 Tumor protein D54 |
| P06753 | TPM3 Tropomyosin alpha-3 chain |
| P67936 | TPM4 Tropomyosin alpha-4 chain |
| O14773 | TPP1 Tripeptidyl-peptidase 1 |
| P12270 | TPR Nucleoprotein TPR |
| P13693 | TPT1 Tmnslationally-controlled tumor protein |
| Q9ULW0 | TPX2 Targeting protein for Xklp2 |
| Q13595 | TRA2A Transformer-2 protein homolog alpha |
| P62995 | TRA2B Transformer-2 protein homolog beta |
| Q9H4I3 | TRABD TraB domain-containing protein |
| Q15629 | TRAM1 Translocating chain-associated membrane protein 1 |
| Q12931 | TRAP1 Heat shock protein 75 kDa, mitochondrial |
| Q13263 | TRIM28 Transcription intermediary factor 1-beta |
| Q9UPN9 | TRIM33 E3 ubiquitin-protein ligase TRIM33 |
| Q14669 | TRIP12 E3 ubiquitin-protein ligase TRIP12 |
| Q15645 | TRIP13 Pachytene checkpoint protein 2 homolog |
| Q7L0Y3 | TRMT10C Mitochondrial ribonuclease P protein 1 |
| Q7Z4G4 | TRMT11 tRNA (guanine(10)-N2)-methyltransferase homolog |
| Q7Z2T5 | TRMT1L TRMT1-like protein |
| Q8IZ69 | TRMT2A tRNA (uracil-5-)-methyltransferase homolog A |
| P10155 | TROVE2 60 kDa SS-A/Ro ribonucleoprotein |

| Accession # | Protein Name |
|---|---|
| P43897 | TSFM Elongation factor Ts, mitochondrial |
| Q99816 | TSG101 Tumor susceptibility gene 101 protein |
| Q15631 | TSN Translin |
| Q99598 | TSNAX Translin-associated protein X |
| O43657 | TSPAN6 Tetraspanin-6 |
| Q2NL82 | TSR1 Pre-rRNA-processing protein TSR1 homolog |
| Q99614 | TTC1 Tetratricopeptide repeat protein 1 |
| Q6DKK2 | TTC19 Tetratricopeptide repeat protein 19, mitochondrial |
| Q6P3X3 | TTC27 Tetratricopeptide repeat protein 27 |
| Q6PGP7 | TTC37 Tetratricopeptide repeat protein 37 |
| Q5R3I4 | TTC38 Tetratricopeptide repeat protein 38 |
| O95801 | TTC4 Tetratricopeptide repeat protein 4 |
| Q14166 | TTLL12 Tubulin-tyrosine ligase-like protein 12 |
| Q9C0H2 | TTYH3 Protein tweety homolog 3 |
| Q71U36 | TUBA1A Tubulin alpha-1A chain |
| P68363 | TUBA1B Tubulin alpha-1B chain |
| Q9BQE3 | TUBA1C Tubulin alpha-1C chain |
| Q13748 | TUBA3C Tubulin alpha-3C/D chain |
| P68366 | TUBA4A Tubulin alpha-4A chain |
| Q9NY65 | TUBA8 Tubulin alpha-8 chain |
| P07437 | TUBB Tubulin beta chain |
| Q9H4B7 | TUBB1 Tubulin beta-1 chain |
| Q13885 | TUBB2A Tubulin beta-2A chain |
| Q9BVA1 | TUBB2B Tubulin beta-2B chain |
| Q13509 | TUBB3 Tubulin beta-3 chain |
| P04350 | TUBB4A Tubulin beta-4A chain |
| P68371 | TUBB4B Tubulin beta-4B chain |
| Q9BUF5 | TUBB6 Tubulin beta-6 chain |
| Q3ZCM7 | TUBB8 Tubulin beta-8 chain |
| P23258 | TUBG1 Tubulin gamma-1 chain |
| Q9BSJ2 | TUBGCP2 Gamma-tubulin complex component 2 |
| P49411 | TUFM Elongation factor Tu, mitochondrial |
| Q6IBS0 | TWF2 Twinfilin-2 |
| P40222 | TXLNA Alpha-taxilin |
| P10599 | TXN Thioredoxin |
| Q99757 | TXN2 Thioredoxin, mitochondrial |
| O95881 | TXNDC12 Thioredoxin domain-containing protein 12 |
| Q9BRA2 | TXNDC17 Thioredoxin domain-containing protein 17 |
| Q8NBS9 | TXNDC5 Thioredoxin domain-containing protein 5 |
| O43396 | TXNL1 Thioredoxin-like protein 1 |
| Q16881 | TXNRD1 Thioredoxin reductase 1, cytoplasmic |
| P04818 | TYMS Thymidylate synthase |
| Q2T9J0 | TYSND1 Peroxisomal leader peptide-processing protease |
| Q01081 | U2AF1 Splicing factor U2AF 35 kDa subunit |
| P26368 | U2AF2 Splicing factor U2AF 65 kDa subunit |
| O15042 | U2SURP U2 snRNP-associated SURP motif-containing protein |
| P22314 | UBA1 Ubiquitin-like modifier-activating enzyme 1 |
| Q9UBT2 | UBA2 SUMO-activating enzyme subunit 2 |
| P62987 | UBA52 Ubiquitin-60S ribosomal protein L40 |
| A0AVT1 | UBA6 Ubiquitin-like modifier-activating enzyme 6 |
| Q9BSL1 | UBAC1 Ubiquitin-associated domain-containing protein 1 |
| Q5T6F2 | UBAP2 Ubiquitin-associated protein 2 |
| Q14157 | UBAP2L Ubiquitin-associated protein 2-like |
| J3QRK5 | UBBP4 Protein UBBP4 |
| P63279 | UBE2I SUMO-conjugating enzyme UBC9 |
| P68036 | UBE2L3 Ubiquitin-conjugating enzyme E2 L3 |
| P61081 | UBE2M NEDD8-conjugating enzyme Ubc12 |
| P61088 | UBE2N Ubiquitin-conjugating enzyme E2 N |
| Q9C0C9 | UBE2O Ubiquitin-conjugating enzyme E2 O |
| Q7Z7E8 | UBE2Q1 Ubiquitin-conjugating enzyme E2 Q1 |
| Q15386 | UBE3C Ubiquitin-protein ligase E3C |
| Q9UMX0 | UBQLN1 Ubiquilin-1 |
| Q9UHD9 | UBQLN2 Ubiquilin-2 |
| Q9NRR5 | UBQLN4 Ubiquilin-4 |
| P17480 | UBTF Nucleolar transcription factor 1 |
| Q04323 | UBXN1 UBX domain-containing protein 1 |
| P09936 | UCHL1 Ubiquitin carboxyl-terminal hydrolase isozyme L1 |
| P15374 | UCHL3 Ubiquitin carboxyl-terminal hydrolase isozyme L3 |
| Q9Y5K5 | UCHL5 Ubiquitin carboxyl-terminal hydrolase isozyme L5 |
| O94874 | UFL1 E3 UFM1-protein ligase 1 |
| Q16739 | UGCG Ceramide glucosyltransferase |
| Q9NYU2 | UGGT1 UDP-glucose:glycoprotein glucosyltransferase 1 |
| Q6BDS2 | UHRF1BP1 UHRF1-binding protein 1 |
| Q13432 | UNC119 Protein unc-119 homolog A |
| A6NIH7 | UNC119B Protein unc-119 homolog B |
| Q70J99 | UNC13D Protein unc-13 homolog D |
| Q9H3U1 | UNC45A Protein unc-45 homolog A |
| A4D2Q0 | UNC84A SUN domain-containing protein 1 |
| E9PBQ3 | Uncharacterized protein |
| H3BQZ7 | Uncharacterized protein |
| H7C417 | Uncharacterized protein |
| H7C455 | Uncharacterized protein |
| H7C469 | Uncharacterized protein |
| I3L2F9 | Uncharacterized protein |
| Q92900 | UPF1 Regulator of nonsense transcripts 1 |
| Q9BZI7 | UPF3B Regulator of nonsense transcripts 3B |
| Q9NVA1 | UQCC Ubiquinol-cytochrome c reductase complex chaperone |
| P31930 | UQCRC1 Cytochrome b-c1 complex subunit 1, mitochondrial |
| P22695 | UQCRC2 Cytochrome b-c1 complex subunit 2, mitochondrial |
| P47985 | UQCRFS1 Cytochrome b-c1 complex subunit Rieske, mitochondr |
| O14949 | UQCRQ Cytochrome b-c1 complex subunit 8 |
| Q14694 | USP10 Ubiquitin carboxyl-terminal hydrolase 10 |
| P51784 | USP11 Ubiquitin carboxyl-terminal hydrolase 11 |
| P54578 | USP14 Ubiquitin carboxyl-terminal hydrolase 14 |
| Q9Y4E8 | USP15 Ubiquitin carboxyl-terminal hydrolase 15 |
| Q53GS9 | USP39 U4/U6.U5 tri-snRNP-associated protein 2 |
| Q96K76 | USP47 Ubiquitin carboxyl-terminal hydrolase 47 |
| Q86UV5 | USP48 Ubiquitin carboxyl-terminal hydrolase 48 |
| P45974 | USP5 Ubiquitin carboxyl-terminal hydrolase 5 |
| Q93009 | USP7 Ubiquitin carboxyl-terminal hydrolase 7 |
| Q9NQZ2 | UTP3 Something about silencing protein 10 |
| Q9NYH9 | UTP6 U3 small nucleolar RNA-associated protein 6 homolo |

| Accession # | Protein Name |
|---|---|
| P51809 | VAMP7 Vesicle-associated membrane protein 7 |
| Q9P0L0 | VAPA Vesicle-associated membrane protein-associated pro |
| O95292 | VAPB Vesicle-associated membrane protein-associated pro |
| P26640 | VARS Valine-tRNA ligase |
| Q99536 | VAT1 Synaptic vesicle membrane protein VAT-1 homolog |
| P61758 | VBP1 Prefoldin subunit 3 |
| P18206 | VCL Vinculin |
| P55072 | VCP Transitional endoplasmic reticulum ATPase |
| Q96JH7 | VCPIP1 Deubiquitinating protein VCIP135 |
| P21796 | VDAC1 Voltage-dependent anion-selective channel protein |
| P45880 | VDAC2 Voltage-dependent anion-selective channel protein |
| Q9Y277 | VDAC3 Voltage-dependent anion-selective channel protein |
| P08670 | VIM Vimentin |
| Q96GC9 | VMP1 Vacuole membrane protein 1 |
| Q96RL7 | VPS13A Vacuolar protein sorting-associated protein 13A |
| Q9P253 | VPS18 Vacuolar protein sorting-associated protein 18 hom |
| Q96AX1 | VPS33A Vacuolar protein sorting-associated protein 33A |
| Q96QK1 | VPS35 Vacuolar protein sorting-associated protein 35 |
| Q9UN37 | VPS4A Vacuolar protein sorting-associated protein 4A |
| O75351 | VPS4B Vacuolar protein sorting-associated protein 4B |
| Q9UID3 | VPS51 Vacuolar protein sorting-associated protein 51 hom |
| Q99986 | VRK1 Serine/threonine-protein kinase VRK1 |
| Q7Z5K2 | WAPAL Wings apart-like protein homolog |
| P23381 | WARS Tryptophan--tRNA ligase, cytoplasmic |
| Q969T9 | WBP2 WW domain-binding protein 2 |
| O75083 | WDR1 WD repeat-containing protein 1 |
| Q9UNX4 | WDR3 WD repeat-containing protein 3 |
| Q8NI36 | WDR36 WD repeat-containing protein 36 |
| Q15061 | WDR43 WD repeat-containing protein 43 |
| Q9NNW5 | WDR6 WD repeat-containing protein 6 |
| Q9GZS3 | WDR61 WD repeat-containing protein 61 |
| Q9BQA1 | WDR77 Methylosome protein 50 |
| Q6UXN9 | WDR82 WD repeat-containing protein 82 |
| O96028 | WHSC1 Probable histone-lysine N-methyltransferase NSD2 |
| Q5T9L3 | WLS Protein wntless homolog |
| Q9NQW7 | XPNPEP1 Xaa-Pro aminopeptidase 1 |
| Q9NQH7 | XPNPEP3 Probable Xaa-Pro aminopeptidase 3 |
| O14980 | XPO1 Exportin-1 |
| Q9HAV4 | XPO5 Exportin-5 |
| Q96QU8 | XPO6 Exportin-6 |
| O43592 | XPOT Exportin-T |
| P13010 | XRCC5 X-ray repair cross-complementing protein 5 |
| P12956 | XRCC6 X-ray repair cross-complementing protein 6 |
| Q9H0D6 | XRN2 5-3 exoribonuclease 2 |
| P54577 | YARS Tyrosine--tRNA ligase, cytoplasmic |
| P67809 | YBX1 Nuclease-sensitive element-binding protein 1 |
| P07947 | YES1 Tyrosine-protein kinase Yes |
| O95070 | YIF1A Protein YIF1A |
| Q5BJH7 | YIF1B Protein YIF1B |
| P49750 | YLPM1 YLP motif-containing protein 1 |
| Q96TA2 | YME1L1 ATP-dependent zinc metalloprotease YME1L1 |
| Q96MU7 | YTHDC1 YTH domain-containing protein 1 |
| Q9Y5A9 | YTHDF2 YTH domain family protein 2 |
| P31946 | YWHAB 14-3-3 protein beta/alpha |
| P62258 | YWHAE 14-3-3 protein epsilon |
| P61981 | YWHAG 14-3-3 protein gamma |
| Q04917 | YWHAH 14-3-3 protein eta |
| P27348 | YWHAQ 14-3-3 protein theta |
| P63104 | YWHAZ 14-3-3 protein zeta/delta |
| Q8N4Q0 | ZADH2 Zinc-binding alcohol dehydrogenase domain-containi |
| Q8WU90 | ZC3H15 Zinc finger CCCH domain-containing protein 15 |
| Q7Z2W4 | ZC3HAV1 Zinc finger CCCH-type antiviral protein 1 |
| Q9NUD5 | ZCCHC3 Zinc finger CCHC domain-containing protein 3 |
| Q6NZY4 | ZCCHC8 Zinc finger CCHC domain-containing protein 8 |
| Q96KR1 | ZFR Zinc finger RNA-binding protein |
| O75844 | ZMPSTE24 CAAX prenyl protease 1 homolog |
| P17028 | ZNF24 Zinc finger protein 24 |
| O75312 | ZNF259 Zinc finger protein ZPR1 |
| Q5BKZ1 | ZNF326 DBIRD complex subunit ZNF326 |
| Q96F45 | ZNF503 Zinc finger protein 503 |
| Q86UK7 | ZNF598 Zinc finger protein 598 |
| Q15942 | ZYX Zyxin |

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A small molecule ligand having a structure represented by Formula (I):

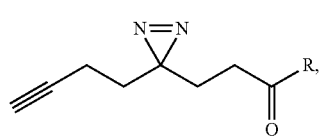

(I)

wherein R is

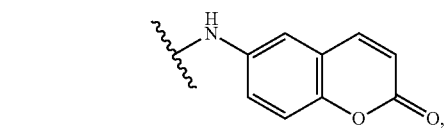

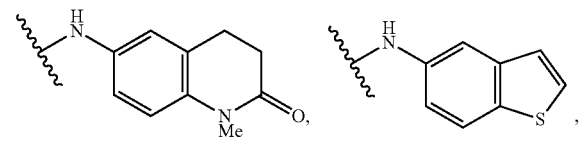

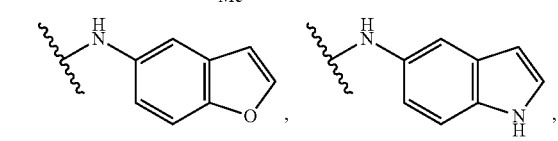

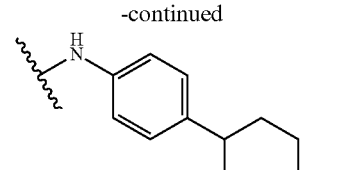

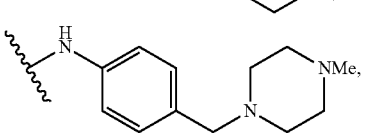

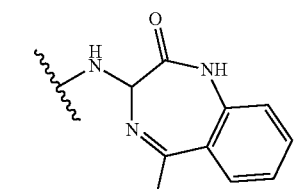

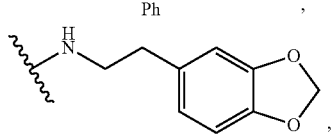

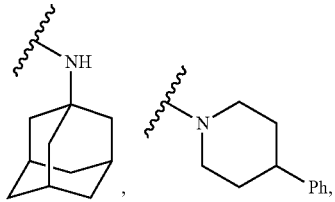

567

-continued

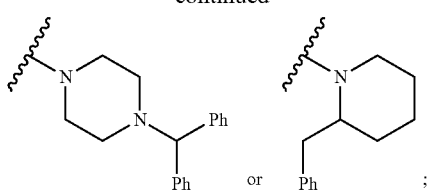

or ;

and wherein the wavy lines \ indicate linkage to the carbonyl group of the structure of Formula (I).

2. A small molecule ligand which binds to a ligand binding site of Cathepsin B (CTSB), the small molecule ligand is, selected from the group consisting of

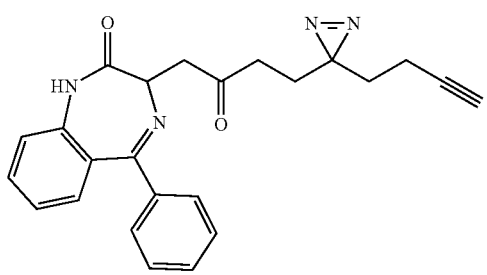

,

568

-continued

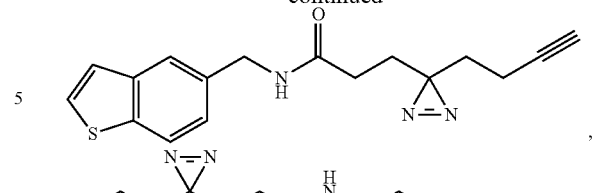

,

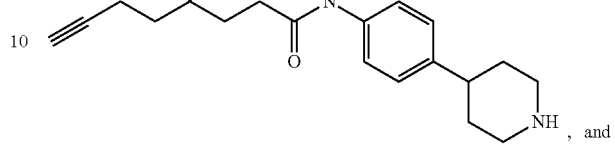

, and

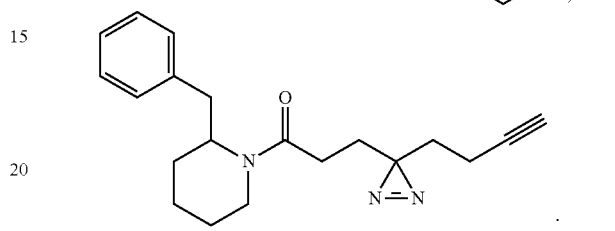

.

3. The small molecule ligand of claim 2, wherein the ligand binding site is defined by the following residues: GQDHCGIESEVVAGIPR of the CTSB protein having the UniProtKB accession number P07858.

* * * * *